US006967198B2

(12) United States Patent
Benedict et al.

(10) Patent No.: US 6,967,198 B2
(45) Date of Patent: Nov. 22, 2005

(54) TRICYCLIC COMPOUNDS PROTEIN KINASE INHIBITORS FOR ENHANCING THE EFFICACY OF ANTI-NEOPLASTIC AGENTS AND RADIATION THERAPY

(75) Inventors: Suzanne Benedict, Carlsbad, CA (US); Michael Bennett, San Diego, CA (US); Sacha Ninkovic, Carlsbad, CA (US); Min Teng, San Diego, CA (US); Yuanjin Rui, San Diego, CA (US); Fen Wang, San Diego, CA (US); Yong Wang, San Diego, CA (US); Jinjiang Zhu, San Diego, CA (US)

(73) Assignee: Agouron Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 10/754,171

(22) Filed: Jan. 9, 2004

(65) Prior Publication Data
US 2005/0075499 A1 Apr. 7, 2005

Related U.S. Application Data
(60) Provisional application No. 60/439,396, filed on Jan. 9, 2003.

(51) Int. Cl.$^7$ ..................... A61K 31/551; C07D 487/02
(52) U.S. Cl. ....................... 514/220; 540/495; 540/488; 514/211
(58) Field of Search ................................. 514/220, 211; 540/495, 488

(56) References Cited

U.S. PATENT DOCUMENTS

| 6,211,164 | B1 | 4/2001 | Luo et al. |
| 6,383,744 | B1 | 5/2002 | Green et al. |
| 6,413,755 | B1 | 7/2002 | Luyten et al. |
| 6,495,541 | B1 | 12/2002 | Webber et al. |
| 2003/0078254 | A1 | 4/2003 | Webber et al. |

FOREIGN PATENT DOCUMENTS

| EP | 1096014 A2 | 5/2001 |
| WO | WO 00/16781 | 3/2000 |
| WO | WO 00/42040 | 7/2000 |
| WO | WO 01/16136 A2 | 3/2001 |
| WO | WO 01/16306 | 3/2001 |
| WO | WO 01/21771 | 3/2001 |
| WO | WO 02/44183 A2 | 6/2002 |
| WO | WO 02/070494 | 9/2002 |

OTHER PUBLICATIONS

Accili, D., "A Kinase In the Life of The β Cell," *Journal of Clinical Investigation*, 2001, pp. 1575–1576, vol. 108, No. 11.
Al–Khodairy, F., et al., "Identification And Characterization Of New Elements Involved In Checkpoint And Feedback Controls In Fission Yeast," *Molecular Biology of the Cell*, 1994, pp. 147–160, vol. 5.

Bagshawe, K., et. al., "Antibody–Directed Enzyme Prodrug Therapy: A Review," *Drug. Development Research*, 1995, pp. 220–230, vol. 34.
Barber, A., et al., "Insulin Rescues Retinal Neurons From Apoptosis By A Phosphatidylinositol 3–Kinase/Akt–Mediated Mechanism That Reduces The Activation Of Caspase–3," *Journal of Biological Chemistry*, 2001, pp. 32814–32821, vol. 276, No. 35.
Bartek, J., et al., "CHK2 Kinase—A busy Messenger," *Nature Reviews Molecular Cell Biology*, 2001, pp. 877–886, vol. 2.
Belsches, A.P., et al., "Role of C–SRC Tyrosine Kinase in EGF–Induced Mitogensis," *Frontiers in Bioscience*, 1997, Electronic Publication 2: D501–D518.
Bertolini, G., et. al., "A New Rational Hypothesis for the Pharmacophore of the Active Metabolite of Lefluonomide, a Potent Immunosuppressive Drug," *Journal of Med. Chem.*, 1997, 2011–2016, 40.
Berven, L., et al., "Cellular Function of p70$^{S6K}$. A Role in Regulation Cell Motility," *Immunology and Cell Biology*, 2000, pp. 447–451, vol. 78, No. 4.
Bishop, A.L., et al., "Rho GTPases and Their Effector Proteins," *Biochem. J.*, 2000, pp. 241–255, vol. 348.
Bjorge, J., et al., "Selected Glimpses Into The Activation And Function Of Src Kinase," *Oncogene*, 2000, pp. 5620–5635, vol. 19, No. 49.
Blume–Jensen, P., et al., "Oncogenic Kinase Signalling," *Nature*, 2001, pp. 355–365, vol. 411, No. 6835.
Bodor, N., "Novel Approaches to the Design of Safer Drugs: Soft Drugs and Site–Specific Chemical Delivery Systems," *Advances in Drug Research*, 1984, pp. 254–331, vol. 13.
Brandon, E., et al., "PKA Isoforms, Neural Pathways, And Behaviour: Making The Connection," *Current Opinion in Neurobiology* 1997, pp. 397–403, vol. 7.

(Continued)

Primary Examiner—Charanjit S. Aulakh
(74) Attorney, Agent, or Firm—Bryan C. Zielinski; Elsa Djuardi; Ye Hua

(57) ABSTRACT

Protein kinase, such as CHK-1, inhibiting tricyclic compounds of the following formula (wherein $R^2$, $R^3$ and $R^4$ are as defined in the specification)

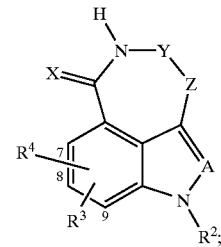

pharmaceutical compositions containing effective amounts of said compounds or their salts are useful as a single agent or in combination with an anti-neoplastic agent or therapeutic radiation having an anti-neoplastic effect for treating diseases or conditions such as cancers.

37 Claims, No Drawings

OTHER PUBLICATIONS

Brazil, D., et al., "Ten Years Of Protein Kinase B Signalling: A Hard Akt To Follow," *Trends in Biochemical Sciences*, 2001, pp. 657–664, vol. 26, No. 11.

Brushia, R.J., et al., "Phosphorylase Kinase: The Complexity of its regulation is Reflected in the Complexity of its Structure," *Frontiers in Bioscience* (Electronic Publication), 1999, pp. D618–D641, vol. 4.

Bundgaard, H., *Design and Application of Prodrugs, Chapter 5, Drug Design Application and Development*, 1991, Harwood Academic Publishers.

Bundgaard, H., et al., *Design of Prodrugs*, 1985, Elsevier Press.

Buolamwini, J., "Cell Cycle Molecular Targets In Novel Anticancer Drug Discovery," *Current Pharmaceutical Design*, 2000, pp. 379–392, vol. 6.

Calautti, E., et al., "Fyn Tyrosine Kinase Is A Downstream Mediator Of Rho/PRK2 Function In Keratinocyte Cell–Cell Adhesion," *Journal of Cell Biology* 2002, pp. 137–148, vol. 156, No. 1.

Cannon, et al., "6–Hydroxy–4–[2–(di–n–Propylamino)ethyl]indole: Synthesis And Dopaminergic Actions," *J. Med. Chem.*, 1984, pp. 386–389, vol. 27.

Carter, C., "Protein Kinase C As A Drug Target: Implications For Drug Or Diet Prevention And Treatment Of Cancer," *Current Drug Targets* 2000, pp. 163–183, vol. 1, No. 2.

Chamoin, S., et al., "The Stille Cross Coupling Reactions On Solid Support. Link To Solution Phase Directed Ortho Metalation. An Ester Linker Approach To Styryl, Biaryl And Heterobiaryl Carboxylic Acids," *Tetrahedron Letters*, 1998, pp. 4175–4178, vol. 39.

Chen, Z., et al., "Map Kinases," *Chemical Reviews*, 2001, pp. 2449–2476, vol. 101, No. 8.

Clerk, A., et al., "Untangling The Web: Specific Signaling From PKC Isoforms To MAPK Cascades," *Circulation Research*, 2001, pp. 847–849, vol. 89, No. 10.

Cobb, M., et al., "Dimerization In MAP–Kinase Signaling," *Trends in Biochemical Sciences*, 2000, pp. 7–9, vol. 25, No. 1.

Cobb, M., et al., "How MAP Kinases Are Regulated," *Journal of Biological Chemistry*, 1995, pp. 14843–14846, vol. 270, No. 25.

Coe, J., et al., "Convenient Preparation Of N–Substituted Indoles By Modified Leimgruber–Batcho Indole Synthesis," *Tetrahedron Letters*, 1996, pp, 6045–6048, vol. 37, No. 34.

Davis, J.D., "The Mitogen–activated Protein Kinase Signal Transduction Pathway," *Journal of Biological Chemistry*, pp. 14553–14556, vol. 17, No. 15.

Deak, M., et al., "Motogen– and Stress–Activated Protein Kinase–1 (MSK1) is Directly Activated by MAPK And SAPK2/p38, And May Mediate Activation Of CREB," *EMBO J.*, 1998, pp. 4426–4441, vol. 17, No. 15.

Deucher, A., et al., "Calcium–Dependent Involucrin Expression Is Inversely Regulated By Protein Kinase C (PKC) α And PKCδ," *Journal of Biological Chemistry*, 2002, pp. 17032–17040, vol. 277, No. 19.

Ellis, L., et al., "Vascular Endothelial Growth Factor In Human Colon Cancer: Biology And Therapeutic Implications," *Oncologist*, 2000, pp. 11–15, vol. 5 (suppl. 1).

Fagnola, M., et al., "Solid–Phase Synthesis Of Indoles Using The Palladium–Catalysed Coupling Of Alkynes With Iodoaniline Derivatives," *Tetrahedron Letters*, 1997, pp. 2307–2310, vol. 38, No. 13.

Fan, et al., "Cellular Effects of Olomoucine in Human Lymphoma Cells Differing in p53 function," *Chemotherapy*, 1999, pp. 437–445, vol. 45.

Flaggs, G., et al., Atm–dependent interactions of a mammalian Chk1 homolog with meiotic chromosomes, *Current Biology*, 1997, pp. 977–986, vol. 7.

Frank, R., "Perspective: Potential New Medical Therapies For Diabetic Retinopathy: Protein Kinase C Inhibitors," *American Journal of Opthalmology*, 2002, pp. 693–698, vol. 133, No. 5.

Friedman, J., "Fat In All Wrong Places," *Nature*, 2002, pp. 268–269 vol. 415, No. 17.

Funder, J., "Aldosterone Action: New Answers, New Questions," *Molecular and Cellular Endocrinology*, 1999, pp. 1–3 vol. 151, Nos. 1–2.

Garcia–Echeverria, C., "Antagonists Of The Src Homology 2 (SH2) Domains Of Grb2, Src, Lck And ZAP–70," *Current Medicinal Chemistry*, 2001, pp. 1589–1604, vol. 8.

Graves, D., et al., "Substrate And Inhibitor Recognition Of Protein Kinases: What Is Known About The Catalytic Subunit Of Phosphorylase Kinase," *Pharmacol. Ther.*, 1999, pp. 143–155, vol. 82, Nos. 2–3.

Greenberg, S., et al., "Role Of PKC And Tyrosine Kinase In Ethanol–Mediated Inhibitor Of LPS–Inducible Nitric Oxide Synthase," *Alcohol*, 1998, pp. 167–175, vol. 16, No. 2.

Greene, T., et al., *Protecting Groups in Organic Synthesis*, $2^{nd}$ ed., John Wiley & Sons, Inc.

Gross, C., et al., "The Protein Kinase C–Related Kinase PRK2 Interacts With The Protein Tyrosine Phosphatase PTB–BL Via A Novel PDZ Domain Binding Motif," *FEBS Letters*, 2001, pp. 101–104, vol. 496, Nos. 2–3.

Halpern, M., et al. "Endogenous c–src As Determinant Of The Tumorigenicity Of src Oncogenes," *Proc. Natl. Acad. Sci. USA*, 1996, pp. 824–827, vol. 92, No. 2.

Harrison's, *Principles of Internal Medicine*, 11 ed, McGraw–Hill Book Company.

Haskell, M., et al., "C–Src Tyrosine Phosphorylation Of Epidermal Growth Factor Receptor, P190 RhoGAP, And Focal Adhesion Kinase Regulates Diverse Cellular Processes," *Chemical Reviews*, 2001, pp. 2425–2440, vol. 101.

Hidalgo, M., et al., "The Rapamycin–Sensitive Signal Transduction Pathway As A Target For Cancer Therapy," *Oncogene*, 2000, pp. 6680–6686, vol. 19, No. 56.

Kamp, T.J., et al., "Regulation of Cardiac L–Type Calciaum Channels by Protein Kinase A and Protein Kinase C," *Circulation Research*, 2000, pp. 1095–1102, vol. 87, No. 12.

Kemp, B., et al., "Dealing With Energy Demand: The AMP–Activated Protein Kinase," *Trends in Biochemical Sciences*, 1999, 22–25, vol. 24, No. 1.

Kilimann, M.W., "Glycogen Storage Disease Due to Phosphorylase Kinase Deficiency," *Protein Dysfunction and Human Genetic Disease*, 1997, Chapter 4, pp. 57–75.

Kumar, C.C., et al., "Drugs Targeted Against Protein Kinases," *Expert. Opin. Emerging Drugs*, pp. 303–315, vol. 6, No. 2.

Larock, R., *Comprehensive Organic Transformations: A Guide To Functional Group Preparations*, $2^{nd}$ ed., 1989, Wiley–VCH Inc.

Lee, J., et al., "Inhibition Of p38 MAP Kinase As A Therapeutic Strategy," *Immunopharmacology* 2000, pp. 185–201, vol. 47, Nos. 2–3.

Leslie, N., et al., "Phosphoinositide–Regulated Kinases And Phosphoinositide Phosphatases," *Chem Rev.* 2001, pp. 2365–2380, vol. 101.

Littke, A., et al., "Versatile Catalysts For The Suzuki Cross-Coupling Of Arylboronic Acids With Aryl And Vinyl Halides And Triflates Under Mild Conditions," *J. Am. Chem. Soc.,* 2000, pp. 4020–4028, vol. 122.

Magnelli, L., et al., "Regulation of p53 Protein Kinase C During Multi–Stage Carcinogenesis," *Journal of Cancer Research and Clinical Oncology,* 1997, pp. 365–369 vol. 123, No. 7.

Majolini, M.B., "Dysregulation of the Protein Tyrosine Kinase LCK in Lymphoproliferative Disorders and in Other Neoplasias," *Leukemia and Lymphoma,* 1999, pp. 245–254 vol. 35, No. 3–4.

Medema, R., et al., "AFX–Like Forkhead Transcription Factors Mediate Cell–Cycle Regulation By Ras And PKB Through p27$^{kip1}$," *Nature,* 2000 pp. 782–787 vol. 404.

Mendel, D.B., "Development of SU5416, A selective Small Molecule Inhibitor of VEGF Receptor Tyrosine Kinase Activity, as an Anti–Angiogenesis Agent," *Anti–Cancer Drug Design,* 2000, pp. 29–41, vol. 15.

Millauer, B., et al., "Dominant–Negative Inhibition of Flk–1 Suppresses the Growth of Many Tumor Types in Vivo," *Cancer Research,* 1996, pp. 1615–1620, vol. 56.

Mohammadi, M., et al., "Crystal Structure of an Angiogenesis Inhibitor Bound to the FGF Receptor Tyrosine Kinase Domain," *EMBO J.* 1998, pp. 5996–5904, vol. 17.

Mohammadi, M., et al., "Identification Of Six Novel Autophosphorylation Sites On Fibroblast Growth Factor Receptor 1 And Elucidation Of Their Importance In Receptor Activation And Signal Transduction," *Molecular Cellular Biology,* 1996, pp. 977–989, vol. 16, No. 3.

Muise–Helmericks, R., et al., "Cyclin D Expression Is Controlled Post–Transcriptionally Via A Phosphatidylinositol 3–Kinase/Akt–Dependent Pathway," *Journal of Biological Chemistry,* 1988, pp. 29864–29872, vol. 273, No. 45.

Narumiya, S., et al., Regulators and Effectors of Small GTPases, Part D, *Methods in Enzymology,* 2000, pp. 273–284, vol. 325.

Nesher, R., et al., "β–Cell Protein Kinases And The Dynamics Of The Insulin Response To Glucose," *Diabetes,* 2002, pp. S68–S73 vol. 51 (Suppl. 1).

Newgard, C., et al., "Organizing Glucose Disposal: Emerging Roles Of The Glycogen Targeting Subunits Of Protein Phosphates–1," *Diabetes,* 2000, pp. 1967–1977, vol. 49.

Newton, A., "Protein Kinase C: Structural And Spatial Regulation By Phosphorylation, Cofactors, And Macromolecular Interactions," *Chem. Rev.,* 2001, pp. 2353–2364, vol. 101.

Nicholson, K., et al., "The Protein Kinas B/Akt Signalling Pathway In Human Malignancy," *Cellular Signalling,* 2002, pp. 381–395, vol. 14, No. 5.

Nomura, M., et al., "Mitogen– And Stress–Activated Protein Kinase 1 Mediates Activation Of Akt By Ultraviolet B Irradiation," *Journal of Biological Chemistry,* 2001, pp. 25558–25567, vol. 276, No. 27.

Nurse, P., "Checkpoint Pathways Come Of Age," *Cell,* 1997, pp. 865–867 vol. 91.

Parast, C., et al., "Characterization And Kinetic Mechanism Of Catalytic Domain Of Human Vascular Endothelial Growth Factor Receptor–2 Tyrosine Kinase (VEGFR2 TK), A Key Enzyme In Angiogenesis," *Biochemistry,* 1988, pp. 16788–16801, vol. 37.

Parekh, D., et al., "New EMBO Member's Review: Multiple Pathways Control Protein Kinase C Phosphorylation," *EMBO J.,* 2000, pp. 496–503, vol. 19, No. 4.

Peng, C.Y., et al., "Mitotic And G2 Checkpoint Control: Regulation of 14–3–3 Protein Binding By Phosphorylation Of Cdc25C On Serine–216," *Science,* 1997, pp. 1501–1505, vol. 277.

Peterson, R., et al., "Kinase Phosphorylation: Keeping It All In The Family," *Current Biology* 1999, pp. R521–R524, vol. 9, No. 14.

Resh, M.D., "Fyn, A Src Family Tyrosine Kinase," *J of Biochemistry & Cell Biology,* pp. 1159–1162, vol. 30, No. 11.

Rhind, N., et al., "Roles Of The Mitotic Inhibitors Wee1 And Mik1 In The $G_2$ DNA Damage And Replication Checkpoints," *Molecular and Cellular Biology,* 2001, pp. 1499–1508, vol. 21, No. 5.

Roovers, et al., "Integrating the MAP Kinase Signal into the G1 Phase Cell Cycle Machinery," *BioEssays,* 2000, pp. 818–826, vol. 22, No. 9.

Rosenzweig, T., et al., "Differential Effects Of Tumor Necrosis Factor–α and δ Mediate Inhibition Of Insulin Receptor Signaling," *Diabetes,* 2002, pp. 1921–1930, vol. 51, No. 6.

Ruderman, N., et al., "Malonyl–CoA, Fuel sensing, and Insulin Resistance," *American Journal of Physiology,* 1999, pp. E1–E18, vol. 276.

Sakamoto, K.M., "Semaxanib SUGEN," *Idrugs,* 2001, pp. 1061–1067, vol. 4, No. 9.

Sanchez, Y., et al., "Conservation Of The Chhk1 Checkpoint Pathway In Mammals: Linkage Of DNA Damage To Cdk Regulation Through Cdc25," *Science,* 1997, pp. 1497–1501, vol. 277, No. 5.

Sebolt–Leopold, JS. "Development Of Anticancer Drugs Targeting The MAP Kinase Pathway," *Oncogene* 2000, pp. 6594–6599, vol. 19.

Shabb, J., "Physiological Substrates Of camp–Dependent Protein Kinase," *Chemical Reviews,* 2001, pp. 2381–2411, vol. 101, No. 8.

Shan, D., et al., "Prodrug Strategies Based On Intramolecular Cyclization Reactions" J. Pharm. Sci. 1997, pp. 765–767 vol. 86, No. 7.

Skalhegg, B.S., et al., "Specificity in the cAMP/PKA Signaling Pathway, Differential Expression, Regulation, and Subcellular Localization of Subunits of PKA," 2000, *Frontiers in bioscience Electronic Publication,* 5:D678–D693.

Sonogashira, K., et al., "A Convenient Synthesis Of Acetylenes: Catalytic Substitutions Of Acetylenic Hydrogen with Bromoalkenes, Iodoarenes, and Bromopyridines," *Tetrahedron Lett.,* 1975, pp. 4467–4470, No. 50.

Still, W., et al., "Rapid Chromatographic Technique For Preparative Separations With Moderate Resolution," *Journal of Organic Chemistry,* 1978, pp. 2923–2925, vol. 43, No. 14.

Strawn, L.M., et al., "Flk–1 as Target for Tumor Growth Inhibition," *Cancer Research,* 1996, pp. 3540–3545, vol. 56.

Strelkov, I.S., "Ser–10 Phosphorylation of Histone H3 and Immediate Early Gene Expression in Oncogene–transformed Mouse Fibroblasts," *Cancer Research,* pp. 75–78, vol. 62, No. 1.

Toker, A., et al., "Cellular Signaling: Pivoting Around PDK–1," *Cell,* 2000, pp. 185–188, vol. 103.

Tortora, G., et al., "Oral Antisense That Targets Protein Kinase A Cooperates With Taxol And Inhibits Tumor Growth, Angiogenesis, And Growth Factor Production," *Clinical Cancer Research,* 2000 pp. 2506–2512, vol. 6.

Tortora, G., et al., "Protein Kinase A Type I: A Target For Cancer Therapy," *Clinical Cancer Research* 2002, pp. 303–304, vol. 8.

Yu, C.F., et al., "ERK regulates the Hepatocyte Growth Factor–mediated Interaction of Gab1 and the Phosphatidylinosital 3–Kinase," *Journal of Biological Chemistry*, 2001, pp. 32552–32558, vol. 276, No. 35.

Vajkoczy, P., "Inhibition of Tumor Growth, Angiogenesis, and Microcirculation by the Novel Flk–1 Inhibitor SU5416 as Assessed by Intravital Multi–fluorescence Videomicroscopy," *Neoplasial*, 1999, pp. 31–41, vol. 1, No. 1.

Venien–Bryan, C., et al., "Three–Dimensional Structure Of Phosphorylase Kinase At 22 A Resolution And Its Complex With Glycogen Phosphorylase b," *Structure*, 2002, pp. 33–41, vol. 10.

Verrey, F., et al., "Pleiotropic Action of Aldosterone in Epithelia mediated by Transcription and Post–transcription Mechanisms," *Kidney International*, 2000, pp. 1277–1282, vol. 57, No. 4.

Walworth, N., "Fission yeast chk1 protein kinase links the rad checkpoint pathway to cdc2," *Nature*, 1993, pp. 368–371, vol. 363.

Webb, C.P., et al., "The Geldanamycins are Potent Inhibitors of the Hepatocyte Growth Factor/Scatter Factor–Met–Urokinase Plasminogen Activator–Plasmin Proteolytic Network," *Cancer Research*, 2000, pp. 342–349, vol. 60, No. 2.

Winert, T., "Enhanced: A DNA Damage Checkpoint Meets The Cell Cycle Engine," *Science*, 1997, pp. 1450–1451, vol. 277.

Wick, et al., "A New Molecular Target of Insulin Action: Regulating the Pivotal PDK1," *Current Drug Targets: Immune, Endocrine and Metabolic Disorders*, pp. 209–221, vol. 1, No. 3.

Yoshiji, et al., "Vascular Endotheliel Growth Factor Is Essential for Initial but not Continued in Vivo Growth of Human Brest Carcinoma Cells," *Cancer Research*, 1997, pp. 3924–3928, vol. 57.

Zhan, X., et al., "Nonreceptor Tyrosine Phosphatases In Cellular Signaling: Regulation Of Mitogen–Activated Protein Kinases," *Chemical Reviews*, 2001, pp. 2477–2496, vol. 101.

Zhang, X., et al., "Trans–1–[(2–Phenylcyclopropyl)methyl] 4–Arylpiperazines: Mixed Dopamine $D_2/D_4$ Receptor Antagonists As Potential Antipsychotic Agents," *J. Med. Chem.*, 2000 pp. 3923–3932, vol. 43.

Zhong, "Ultraviolet B–Induced Phosphorylation Of Histone H3 At Serine 28 Is Mediated By MSK1," *Journal of Biological Chemistry*, 2001, pp. 33213–33219, vol. 276, No. 35.

TRICYCLIC COMPOUNDS PROTEIN KINASE INHIBITORS FOR ENHANCING THE EFFICACY OF ANTI-NEOPLASTIC AGENTS AND RADIATION THERAPY

This application claims priority benefits under 35 U.S.C. § 119(e) of a provisional application Ser. No. 60/439,396, filed Jan. 9, 2003.

FIELD OF THE INVENTION

This invention relates to novel tricyclic compounds of formula I that inhibit protein kinases, preferably CHK-1. The invention further relates to pharmaceutical compositions containing such compounds, and to methods for the treatment of a condition which can be treated by the inhibition of protein kinases, preferably CHK-1, in a mammal by administering effective amounts of such compounds in conjunction with an anti-neoplastic agent, a radiation therapy, or as a single agent.

BACKGROUND OF THE INVENTION

A eukaryotic cell cycle has a carefully regulated progression of phases: initial gap ($G_1$), DNA synthesis (S), secondary gap ($G_2$), and mitosis (M). $G_1$, S and $G_2$ are known as interphase. In $G_1$, the cell, whose biosynthetic pathways were slowed during mitosis, resumes a high rate of RNA and protein biosynthesis. The S phase begins when DNA synthesis starts and ends when the DNA content of the nucleus has been replicated. The cell then enters $G_2$ where again RNA and protein biosynthesis occur. Following $G_2$, the cell enters M phase that begins with nuclear division and ends with the complete division of the cytoplasm into two daughter cells. This marks the beginning of interphase for the new cells. Non-dividing cells exist at $G_0$, a time following mitosis and before DNA synthesis.

Checkpoint enzymes, such as the serine/threonine protein kinase called checkpoint kinase 1 (CHK-1 or p56CHK-1), are responsible for maintaining the order and fidelity of events in the cell cycle. CHK-1 transduces signals from the DNA damage sensory complex to inhibit activation of Cdc2-cyclin B complex which promotes mitotic entry (*Science*, 277, 1501–1505 (1997); *Science*, 277, 1497–1501 (1997)). In eukaryotes, Cdc2 is known as Cdk1 (cyclin-dependent kinase 1). CHK-1 regulates Cdc25, a dual specificity phosphatase that activates Cdc2. Thus, CHK-1 serves as the direct link between the $G_2$ checkpoint and the negative regulation of Cdc2.

Healthy cells have both the $G_1$ and $G_2$ checkpoints and their associated repair processes to ensure viability after treatment of DNA damage (chemotherapy and/or radiation). Cancer cells, however, rely exclusively on the $G_2$ checkpoint and its associated repair processes in order to remain viable and to continue replication. Abrogation of the $G_2$ checkpoint would leave cancer cells with no means to delay progression into mitosis following DNA damage. Inactivation of CHK-1 has been shown to abrogate $G_2$ arrest induced by DNA damage inflicted by either anticancer agents or endogenous DNA damage. In addition, inactivation of CHK-1 results in preferential killing of the resulting DNA damaged, checkpoint defective cells (*Cell*, 91, 865–867 (1997); *Science*, 277, 1450–1451 (1997); *Nature*, 363, 368–371 (1993); *Molec. Biol. Cell*, 5, 147–160 (1994)). Therefore there is a need for small molecule inhibitors of CHK-1 to preferentially abrogate the $G_2$ checkpoint over $G_1$ and to effectively remove the only checkpoint control found in many types of cancers. When administered during the course of a DNA damaging event, such as chemotherapy employing anti-neoplastic agents, radiation therapy, immunotherapies and antiangiogenic therapies, a CHK-1 inhibitor can sensitize cancer cells thereby triggering damage-mediated apoptosis. Therefore there is a need for a combination therapy involving CHK-1 inhibitor in the course of a DNA damaging event.

Since protein kinases are ubiquitous and interrelated, selective modulation of a single kinase, such as CHK-1, or family of kinases may not result in an effective therapeutic treatment. There is therefore a need for small molecule inhibitors to influence one or more targeted protein kinases whose inhibition, taken as a whole, would produce the desired therapeutic treatment. Although kinase selectivity and its relation to generalized toxicity are important, therapeutic efficacy may rely on the inhibition of more than one protein kinase. Chemical core structures that can be suitably appended to interact selectively and potently with targeted protein kinases represent a valuable tool for drug discovery and scientific research. Therefore there is a need for such a core structure as an inhibitor of one or more protein kinases. Whether administered as a single agent or as co-therapy, the protein kinase inhibitors, such as CHK-1 inhibitors, of the present invention could prove beneficial in the treatment of a number of human diseases, such as cancer.

Certain CHK-1 inhibitors have been proposed for cancer therapy (see Sanchez, Y. et. al. (1997) *Science* 277: 1497–1501 and Flaggs, G. et al. (1997) *Current Biology* 7:977–986; U.S. Pat. Nos. 6,413,755, 6,383,744, and 6,211,164; and International Publication Nos. WO 01/16306, WO 01/21771, WO 00/16781, and WO 02/070494).

SUMMARY OF THE INVENTION

An object of the invention is to provide compounds that inhibit the activity of one or more protein kinases, such as CHK-1.

In a general aspect, the invention relates to a protein kinase inhibitor, preferably CHK-1 inhibitor, tricyclic compounds of the Formula I:

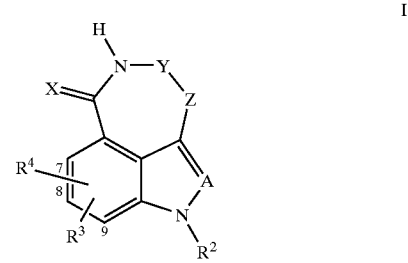

wherein:
X is =O or =S;
A is =CR$^1$— or =N—;
The group —Y—Z— has the formula —O—CH$_2$— or —N=CH—;
R$^1$ is:
(a) (C$_1$–C$_8$)alkyl;
(b) —C(=O)—R$^5$;
(c) —C(=O)—NR$^6$R$^7$; or
(d) R$^{35}$, or R$^{36}$, (C$_2$–C$_8$)alkenyl, or (C$_2$–C$_8$)alkynyl {wherein each of said (C$_2$–C$_8$)alkenyl or (C$_2$–C$_8$) alkynyl is unsubstituted or substituted with one to four substituents independently selected from the group consisting of F, Cl, OH, —NH$_2$, R$^{40}$ and R$^{42}$);

$R^2$ is
(a) H, OH, or $(C_1-C_8)$alkyl;
(b) —C(=O)—$R^8$;
(c) —(C=S)—$R^9$ or —(C=S)—$NR^{10}R^{11}$; or
(d) $R^{38}$ or $R^{39}$;

$R^3$ is
(a) $(C_1-C_8)$alkyl;
(b) —C(=O)—$R^{12}$;
(c) —C(=O)—$NR^{13}R^{14}$;
(d) —$NR^{15}$—C(=O)—$R^{16}$;
(e) —$NR^{17}$—$SO_2R^{18}$;
(f) —$NR^{19}$—$SO_n$—$NR^{20}R^{21}$ {wherein n is 1 or 2};
(g) —$NR^{22}$—(C=S)—$R^{23}$ or —$NR^{22}$—(C=S)—$NR^{23}R^{24}$;
(h) $R^{38}$, $(C_2-C_8)$alkenyl, or $(C_2-C_8)$alkynyl {wherein each of said $R^3$ $(C_2-C_8)$alkenyl or $(C_2-C_8)$alkynyl is unsubstituted or substituted with one to four substituents independently selected from the group consisting of —(C=O)—O—$(C_1-C_8)$alkyl, —O—(C=O)—$(C_1-C_8)$alkyl, —(C=O)—$(C_1-C_8)$alkyl, $R^{40}$, $R^{41}$, and $R^{42}$};
(i) $R^{37}$, —$NH_2$, —NH$((C_2-C_8)$alkenyl), —NH$((C_2-C_8)$alkynyl), —N$((C_1-C_8)$alkyl)$((C_2-C_8)$alkenyl), or —N$((C_1-C_8)$alkyl)$((C_2-C_8)$alkynyl) {wherein each of said $R^{26}$ $(C_2-C_8)$alkenyl or $(C_2-C_8)$alkynyl is unsubstituted or substituted with one to four substituents independently selected from the group consisting of $R^{40}$, $R^{41}$, and $R^{42}$}; or
(j) $R^{38}$;

$R^4$ is selected from the group consisting of H, F, Br, Cl, and $(C_1-C_8)$alkyl;

$R^5$ is selected from the group consisting of H, $(C_1-C_8)$alkyl, $(C_1-C_8)$alkyl-O—, and $R^{36}$;

Each $R^6$ and $R^7$ are independently selected from the group consisting of H, $(C_1-C_8)$alkyl, and $R^{35}$;

$R^8$ is selected from the group consisting of $(C_1-C_8)$alkyl, $(C_2-C_8)$alkenyl, $(C_2-C_8)$alkynyl, —$NH_2$, $R^{36}$, and $R^{37}$;

Each of $R^9$, $R^{10}$ and $R^{11}$ are independently selected from the group consisting of H, $(C_1-C_8)$alkyl, and $R^{36}$;

$R^{12}$ is selected from the group consisting of H, OH, $(C_1-C_8)$alkyl, $(C_1-C_8)$alkyl-O—, and $R^{36}$;

$R^{13}$ is H or $(C_1-C_8)$alkyl;

$R^{14}$ is selected from the group consisting of H, $(C_1-C_8)$alkyl, —$CH_2$—(C=O)—O—$(C_1-C_8)$alkyl, and $R^{36}$;

$R^{15}$ is H or $(C_1-C_8)$alkyl;

$R^{16}$ is selected from the group consisting of H, $(C_1-C_8)$alkyl, $(C_2-C_8)$alkenyl, $(C_2-C_8)$alkynyl, —$NH_2$, $R^{36}$, and $R^{37}$;

wherein said $R^{16}$ $(C_2-C_8)$alkenyl or $(C_2-C_8)$alkynyl is unsubstituted or substituted with one to four substituents independently selected from the group consisting of $R^{40}$;

$R^{17}$ is selected from the group consisting of H, $(C_1-C_8)$alkyl, and $R^{38}$;

$R^{18}$ is $(C_1-C_8)$alkyl or $R^{38}$;

$R^{19}$, $R^{20}$, and $R^{21}$ are independently selected from the group consisting of H, $(C_1-C_8)$alkyl, and $R^{38}$;

$R^{22}$, $R^{23}$ and $R^{24}$ are independently selected from the group consisting of H, $(C_1-C_8)$alkyl, and $R^{36}$;

$R^{25}$ is H or $(C_1-C_8)$alkyl;

$R^{26}$ is selected from the group consisting of —C(=O)—O—C(CH$_3$)$_3$, $(C_1-C_8)$alkyl, —$(CR^{13}R^{15})_t(C_3-C_{10})$cycloalkyl, —$(CR^{13}R^{15})_t(C_2-C_{10})$heterocyclyl, —$(CR^{13}R^{15})_t(C_6-C_{10})$aryl, and —$(CR^{13}R^{15})_t(C_1-C_{10})$heteroaryl; wherein t is an integer from 0 to 2;

or $R^{25}$ and $R^{26}$ may optionally be taken together with the nitrogen to which they are attached to form a 5 to 8-membered heteroaryl or heterocyclyl ring;

$R^{27}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{28}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{29}$ is H or $(C_1-C_8)$alkyl;

$R^{30}$ is $(C_1-C_8)$alkyl, $(C_3-C_{10})$cycloalkyl, $(C_2-C_{10})$heterocyclyl, $(C_6-C_{10})$aryl, or $(C_1-C_{10})$heteroaryl;

or $R^{29}$ and $R^{30}$ may optionally be taken together with the nitrogen to which they are attached to form a 5 to 8-membered heteroaryl or heterocyclyl ring;

$R^{31}$ is H or $(C_1-C_8)$alkyl;

$R^{32}$ is independently selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

or $R^{31}$ and $R^{32}$ may optionally be taken together with the nitrogen to which they are attached to form a 5 to 8-membered heteroaryl or heterocyclyl ring;

$R^{33}$ is $(C_1-C_8)$alkyl, —$(CR^{13}R^{15})_q(C_3-C_{10})$cycloalkyl, —$(CR^{13}R^{15})_q(C_2-C_{10})$heterocyclyl, —$(CR^{13}R^{15})_q(C_3-C_{10})$aryl, or —$(CR^{13}R^{15})_q(C_1-C_{10})$heteroaryl; wherein q is an integer from 0 to 2;

$R^{34}$ is $(C_1-C_8)$alkyl, —$(CR^{13}R^{15})_p(C_3-C_{10})$cycloalkyl, —$(CR^{13}R^{15})_p(C_2-C_{10})$heterocyclyl, —$(CR^{13}R^{15})_p(C_3-C_{10})$aryl, or —$(CR^{13}R^{15})_p(C_1-C_{10})$heteroaryl; wherein p is an integer from 0 to 2;

Each $R^{35}$ is independently selected from the group consisting of H, F, Cl, Br, I, CN, OH, $NO_2$, —$NH_2$, —NH—C(=O)—O—C(CH$_3$)$_3$, and $CF_3$;

Each $R^{36}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{37}$ is independently selected from the group consisting of —$NR^{25}R^{26}$ and $R^{27}$—O—;

$R^{38}$ is $R^{28}$—$SO_n$—; wherein n is 0, 1, or 2 when —$SO_n$— is bonded to $R^{28}$ via an $R^{28}$ carbon atom, or wherein n is 1 or 2 when —$SO_n$— is bonded to $R^{28}$ via an $R^{28}$ ring nitrogen atom;

$R^{39}$ is $R^{29}R^{30}$N—$SO_n$—; wherein n is 1 or 2;

wherein each of said $(C_1-C_8)$alkyl, wherever it occurs in any of said $R^1$(a)–(d), $R^2$(a)–(d), $R^3$(a)–(j), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{37}$, $R^{38}$, and $R^{39}$ is unsubstituted or substituted with one to four substituents independently selected from the group consisting of $(C_2-C_8)$alkenyl and $R^{40}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in said $R^1$(b)–(d), $R^2$(b)–(d), $R^3$(a)–(j), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$, $R^{32}$, $R^{33}$, $R^{34}$, $R^{36}$, $R^{37}$, $R^{38}$, and $R^{39}$ is independently unsubstituted or substituted with one to four substituents independently selected from $R^{40}$;

$R^{40}$ is selected from the group consisting of $(C_1-C_8)$alkyl, $R^{41}$, $R^{42}$, and $R^{43}$;

Each $R^{41}$ is independently selected from the group consisting of F, Cl, Br, I, CN, OH, $NO_2$, $-NH_2$, $-NH-C(=O)-O-C(CH_3)_3$, COOH, $-C(=O)(C_1-C_8)$alkyl, $-C(=O)-O-(C_1-C_8)$alkyl, $-NH-SO_2-(C_1-C_8)$alkyl, $-NH-SO_2-(C_6-C_{10})$aryl and $CF_3$;

Each $R^{42}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{43}$ is independently selected from the group consisting of:
$-NR^{31}R^{32}$; $R^{33}-O-$; and $R^{34}-SO_n-$; wherein n is 0, 1, or 2 when $-SO_n-$ is bonded to $R^{34}$ via an $R^{34}$ carbon atom, or wherein n is 1 or 2 when $-SO_n-$ is bonded to $R^{34}$ via an $R^{34}$ ring nitrogen atom;

wherein each of said $(C_1-C_8)$alkyl, wherever it occurs in any of $R^{40}$ and $R^{41}$ is independently unsubstituted or substituted with one to four substituents independently selected from the group consisting of $R^{44}$ and $R^{45}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{42}$ or $R^{43}$, is independently unsubstituted or substituted with one to four substituents independently selected from the group consisting of $R^{47}$ selected from the group consisting of $(C_1-C_{10})$alkyl, $R^{44}$, and $R^{45}$;

Each $R^{44}$ is independently selected from the group consisting of F, Cl, Br, I, CN, OH, $NO_2$, $-NH_2$, $-CF_3$, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N<[(C_1-C_8)$alkyl$]_2$, $-NH-(C=O)-(C_1-C_8)$alkyl, $R^{37}$, and $R^{38}$;

Each $R^{45}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

wherein each of said $(C_1-C_8)$alkyl wherever it occurs in any of said $R^{44}$ or $R^{45}$ is independently unsubstituted or substituted with one to four substituents independently selected from the group consisting of $R^{46}$ and $R^{47}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{43}$ or $R^{44}$ is independently unsubstituted or substituted with one to four substituents independently selected from the group consisting of $(C_1-C_8)$alkyl, $R^{46}$ and $R^{47}$;

Each $R^{46}$ is independently selected from the group consisting of F, Cl, Br, I, CN, OH, $NO_2$, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N<[(C_1-C_8)$alkyl$]_2$, $-NH-(C=O)-(C_1-C_8)$alkyl, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N>[(C_1-C_8)$alkyl$]_2$, $-NH-(C=O)-(C_1-C_8)$alkyl, $R^{37}$, and $R^{38}$; and Each $R^{47}$ is independently selected from the group consisting of $(C_3-C_{10})$cycloalkyl; $(C_2-C_{10})$heterocyclyl, $(C_8-C_{10})$aryl, and $(C_1-C_{10})$heteroaryl;

or a pharmaceutically acceptable salt thereof.

The invention is also directed to pharmaceutically acceptable prodrugs, pharmaceutically active metabolites, and pharmaceutically acceptable salts of the compounds of Formula I. Pharmaceutically acceptable salts of such active metabolites are also provided. Advantageous methods of making the compounds of the Formula I are also described.

The compounds of this invention include all stereoisomers (e.g., cis and trans isomers) and all optical isomers of compounds of the Formula I (e.g., R and S enantiomers), as well as racemic, diastereomeric and other mixtures of such isomers.

The compounds of the invention may also exist in different tautomeric forms. This invention relates to all tautomers of Formula I.

The compounds of this invention may contain olefin-like double bonds. When such bonds are present the compounds of the invention exist as cis and trans configurations and as mixtures thereof.

In one embodiment, the invention relates to compounds of the Formula I wherein $R^3$ is $(C_1-C_8)$alkyl substituted with one to four substituents independently selected from the group consisting of F, OH, $-NH_2$, $(C_1-C_8)$alkyl-NH—, $(C_3-C_{10})$cycloalkyl, $(C_2-C_{10})$heterocyclyl, $(C_6-C_{10})$aryl, and $(C_6-C_{10})$heteroaryl.

In another embodiment, the invention relates to compounds of the Formula I herein $R^3$ is selected from the group consisting of $(C_2-C_8)$alkenyl, $(C_2-C_8)$alkynyl, $(C_3-C_6)$cycloalkyl, $(C_2-C_{10})$heterocyclyl, phenyl, and $(C_1-C_{10})$heteroaryl; wherein each of said $(C_2-C_8)$alkenyl or $(C_2-C_8)$alkynyl is unsubstituted or substituted with one to three substituents independently selected from the group consisting of F, OH, $-NH_2$, $(C_1-C_8)$alkyl-NH—, $[(C_1-C_8)$alkyl$]_2$>N—, $(C_3-C_{10})$cycloalkyl, $(C_2-C_{10})$heterocyclyl, $(C_6-C_{10})$aryl, and $(C_1-C_{10})$heteroaryl; and wherein each of said $(C_3-C_6)$cycloalkyl, $(C_2-C_{10})$heterocyclyl, phenyl, or $(C_1-C_{10})$heteroaryl is unsubstituted or substituted with one to four substituents independently selected from the group consisting of $(C_1-C_8)$alkyl, F, OH, $-NH_2$, $(C_1-C_8)$alkyl-NH—, $[(C_1-C_8)$alkyl$]_2$>N—, $(C_3-C_{10})$cycloalkyl, $(C_2-C_{10})$heterocyclyl, $(C_6-C_{10})$aryl, and $(C_1-C_{10})$heteroaryl.

In another embodiment the invention relates to compounds of the Formula I wherein $R^3$ is $-C(=O)-NR^{13}R^{14}$ {wherein $R^{13}$ is H or $(C_1-C_8)$alkyl}, wherein said $R^{13}$ $(C_1-C_4)$alkyl is unsubstituted or substituted with one to four substituents independently selected from the group consisting of F, OH, $-NH_2$, $R^{41}$, and $R^{42}$; wherein each of said $R^{36}$ is unsubstituted or substituted with one or two substituents independently selected from the group consisting of $(C_6-C_{10})$aryl, $(C_1-C_{10})$heteroaryl, $(C_2-C_{10})$heterocyclyl, $(C_1-C_8)$alkyl-NH—, and $[(C_1-C_8)$alkyl$]_2$>N—; and wherein each of said $(C_8-C_{10})$aryl substituent is unsubstituted or substituted with one to three substituents independently selected from the group consisting of $(C_1-C_8)$alkyl, F, Cl, $-CF_3$, and OH.

In another embodiment, the invention relates to compounds of the Formula I wherein $R^{16}$ is $(C_1-C_8)$alkyl unsubstituted or substituted with one to four substituents independently selected from the group consisting of OH, $R^{33}-O-$, CN, $-NH_2$, $(C_1-C_8)$alkyl-NH—, $-NH-(CR^{13}R^{15})_t(C_3-C_{10})$cycloalkyl, $-NH-(CR^{13}R^{15})_t(C_2-C_{10})$heterocyclyl, $-NH-(CR^{13}R^{15})_t(C_6-C_{10})$aryl, or $-NH-(CR^{13}R^{15})_t(C_1-C_{10})$heteroaryl-NH— {wherein t is an integer from 0 to 2}, $[(C_1-C_8)$alkyl$]_2$>N—, $[(C_1-C_8)$alkyl$][(C_3-C_{10})$cycloalkyl$]$>N—, $(C_3-C_{10})$cycloalkyl, $(C_2-C_{10})$heterocyclyl, $(C_8-C_{10})$aryl, and $(C_1-C_{10})$heteroaryl; wherein said $R^{33}$ is $(C_1-C_8)$alkyl, $-(CR^{13}R^{15})_q(C_3-C_{10})$cycloalkyl, $-(CR^{13}R^{15})_q(C_2-C_{10})$heterocyclyl, —(CR$^{13}$R$^{15}$)$_q$(C$_8$–C$_{10}$)aryl, or —(CR$^{13}$R$^{15}$)$_q$(C$_1$–C$_{10}$) heteroaryl; and wherein q is an integer from 0 to 2. Within this embodiment, said (C$_3$–C$_{10}$)cycloalkyl substituent wherever it occurs is unsubstituted or substituted with one to four substituents independently selected from the group consisting of (C$_3$–C$_{10}$)cycloalkyl, (C$_2$–C$_{10}$)heterocyclyl, (C$_6$–C$_{10}$) aryl, and (C$_1$–C$_{10}$)heteroaryl. Within this embodiment, said (C$_6$–C$_{10}$)aryl substituent wherever it occurs is unsubstituted or substituted with one to four substituents independently selected from the group consisting of (C$_1$–C$_8$)alkyl, F, Cl, Br, CN, OH, and CF$_3$. Within this embodiment, said said (C$_2$–C$_{10}$)heterocyclyl substituent wherever it occurs is unsubstituted or substituted with one or two substituents independently selected from the group consisting of (C$_1$–C$_8$) alkyl, —(C═O)—(C$_1$–C$_8$)alkyl, —(C═O)—O—(C$_1$–C$_8$) alkyl, —S—(C$_1$–C$_8$)alkyl, F, Br, OH, and CF$_3$.

In another embodiment, the invention relates to compounds of the Formula I wherein R$^3$ is —NR$^{15}$—C(═O)—R$^{16}$; wherein R$^{16}$ is (C$_2$–C$_8$)alkenyl unsubstituted or substituted with one to four substituents independently selected from the group consisting of (C$_3$–C$_{10}$)cycloalkyl, (C$_2$–C$_{10}$) heterocyclyl, (C$_6$–C$_{10}$)aryl, and (C$_1$–C$_{10}$)heteroaryl; wherein said (C$_6$–C$_{10}$)aryl substituent is unsubstituted or substituted with one to four substituents independently selected from the group consisting of (C$_1$–C$_8$)alkyl, F, Cl, Br, CN, OH, and CF$_3$; and wherein said (C$_2$–C$_{10}$) heterocyclyl substituent is unsubstituted or substituted with one or two substituents independently selected from the group consisting of (C$_1$–C$_8$)alkyl, —(C═O)—(C$_1$–C$_8$) alkyl, —(C═O)—O—(C$_1$–C$_8$)alkyl, —S—(C$_1$–C$_8$)alkyl, F, Br, OH, and CF$_3$.

In another embodiment, the invention relates to compounds of the Formula I wherein R$^3$ is —NR$^{15}$—C(═O)—R$^{16}$; wherein R$^{16}$ is (C$_1$–C$_{10}$)heteroaryl unsubstituted or substituted with one or two substituents independently selected from the group consisting of (C$_1$–C$_8$)alkyl, —(C═O)—(C$_1$–C$_8$)alkyl, —S—(C$_1$–C$_8$)alkyl, F, Cl, CN, OH, and CF$_3$. Preferably the R$^{16}$ (C$_1$–C$_{10}$)heteroaryl is pyridinyl.

In another preferred embodiment, the invention relates to compounds of the Formula I wherein R$^3$ is —NR$^{15}$—C(═O)—R$^{16}$; wherein R$^{16}$ is (C$_3$–C$_{10}$)cycloalkyl unsubstituted or substituted with one or two substituents independently selected from the group consisting of (C$_1$–C$_8$)alkyl, F, Cl, CN, OH, NH$_2$, CF$_3$, (C$_2$–C$_{10}$)heterocyclyl, (C$_6$–C$_{10}$)aryl, and (C$_1$–C$_{10}$)heteroaryl; wherein said (C$_6$–C$_{10}$)aryl substituent is unsubstituted or substituted with one to four substituents independently selected from the group consisting of (C$_1$–C$_8$)alkyl, F, Cl, Br, CN, OH, and CF$_3$; and wherein said (C$_2$–C$_{10}$)heterocyclyl substituent is unsubstituted or substituted with one or two substituents independently selected from the group consisting of (C$_1$–C$_8$)alkyl, —(C═O)—(C$_1$–C$_8$)alkyl, —(C═O)—O—(C$_1$–C$_8$)alkyl, —S—(C$_1$–C$_8$)alkyl, F, Br, OH, and CF$_3$. More preferably said R$^{16}$ (C$_3$–C$_{10}$)cycloalkyl is selected from the group consisting of cyclopropyl and cyclohexyl. More preferably said (C$_8$–C$_{10}$) aryl substituents is unsubstituted.

In another preferred embodiment, the invention relates to compounds of the Formula I wherein R$^3$ is —NR$^{15}$—C(═O)—R$^{16}$; wherein R$^{16}$ is (C$_2$–C$_{10}$)heterocyclyl unsubstituted or substituted with one to four substituents independently selected from the group consisting of (C$_1$–C$_8$)alkyl, —(C═O)—(C$_1$–C$_8$)alkyl, —(C═O)—O—(C$_1$–C$_8$)alkyl, F, Cl, CN, OH, and CF$_3$. More preferably said R$^{16}$ (C$_2$–C$_{10}$) heterocyclyl is selected from the group consisting of piperazinyl, piperidinyl, pyrrolidinyl, pyrrolidinonyl, thiadiazolyl, tetrahydroisoquinolinyl, tetrahydronaphthalenyl, and indanyl.

In another preferred embodiment, the invention relates to compounds of the Formula I wherein R$^3$ is —NR$^{15}$—C(═O)—R$^{16}$; wherein R$^{16}$ is phenyl unsubstituted or substituted with one to three substituents independently selected from the group consisting of (C$_1$–C$_8$)alkyl, (C$_1$–C$_8$)alkyl-O—, F, Cl, Br, CN, OH, and CF$_3$.

In another embodiment, the invention relates to compounds of the Formula I wherein R$^1$ is (C$_1$–C$_8$)alkyl substituted with one to two substituents independently selected from the group consisting of F, Cl, —OH, —NH$_2$, (C$_1$–C$_8$) alkyl-NH—, [(C$_1$–C$_8$)alkyl]$_2$>N—, and (C$_1$–C$_8$)alkyl-O—; wherein each of said (C$_1$–C$_8$)alkyl substituent, wherever it occurs, is independently unsubstituted or substituted with one to three substituents independently selected from the group consisting of —NH$_2$, (C$_1$–C$_8$)alkyl-NH—, [(C$_1$–C$_8$) alkyl]$_2$>N—, —O—(C═O)—(C$_1$–C$_8$)alkyl, (C$_2$–C$_{10}$) heterocyclyl, (C$_6$–C$_{10}$)aryl, and (C$_1$–C$_{10}$)heteroaryl.

In another embodiment, the invention relates to compounds of the Formula I wherein R$^1$ is unsubstituted (C$_1$–C$_8$)alkyl; such as methyl or ethyl.

In another embodiment, the invention relates to compounds of the Formula I wherein R$^1$ is (C$_2$–C$_8$)alkenyl or (C$_2$–C$_8$)alkynyl; wherein each of said (C$_2$–C$_8$)alkenyl or (C$_2$–C$_8$)alkynyl is unsubstituted or substituted with one to two substituents independently selected from the group consisting of —NH$_2$, (C$_1$–C$_8$)alkyl-NH—, [(C$_1$–C$_8$)alkyl]$_2$>N—, (C$_2$–C$_{10}$)heterocyclyl, and (C$_1$–C$_{10}$)heteroaryl; wherein each of said (C$_1$–C$_8$)alkyl substituent, wherever it occurs, is independently unsubstituted or substituted with one to three substituents independently selected from the group consisting of —NH$_2$, (C$_1$–C$_8$)alkyl-NH—, [(C$_1$–C$_8$) alkyl]$_2$>N—, —O—(C═O)—(C$_1$–C$_8$)alkyl, (C$_2$–C$_{10}$) heterocyclyl, (C$_8$–C$_{10}$)aryl, and (C$_1$–C$_{10}$)heteroaryl.

In another preferred embodiment, the invention relates to compounds of the Formula I wherein R$^1$ is R$^{38}$ selected from the group consisting of H, Cl, and Br.

In another embodiment, the invention relates to compounds of the Formula I wherein R$^1$ is selected from the group consisting of (C$_3$–C$_6$)cycloalkyl, (C$_2$–C$_{10}$) heterocyclyl, phenyl, and (C$_1$–C$_{10}$)heteroaryl; wherein each of said (C$_2$–C$_{10}$)heterocyclyl, phenyl, or (C$_1$–C$_{10}$)heteroaryl is unsubstituted or substituted with one to three substituents independently selected from the group consisting of (C$_1$–C$_8$) alkyl, F, Cl, —NH$_2$, —OH, (C$_1$–C$_8$)alkyl-NH—, and [(C$_1$–C$_8$)alkyl]$_2$>N—; wherein each of said (C$_1$–C$_8$)alkyl substituent, wherever it occurs, is unsubstituted or substituted with one to three substituents selected from —NH$_2$, (C$_1$–C$_8$)alkyl-NH—, [(C$_1$–C$_8$)alkyl]$_2$>N—, —O—(C═O)—(C$_1$–C$_8$)alkyl, (C$_2$–C$_{10}$)heterocyclyl, (C$_6$–C$_{10}$) aryl, and (C$_1$–C$_{10}$)heteroaryl. Within this embodiment, preferably R$^1$ is phenyl, (C$_2$–C$_{10}$)heterocyclyl or (C$_1$–C$_{10}$) heteroaryl; more preferably phenyl, tetrahydropyridinyl, piperidinyl, pyridinyl, imidazolyl, isoxazolyl, or pyrazolyl. Within this embodiment, preferably R$^1$ is phenyl substituted with one methyl, (C$_2$–C$_{10}$)heterocyclyl substituted with one methyl, or (C$_1$–C$_{10}$)heteroaryl substituted with one methyl; more preferably phenyl substituted with one methyl, tetrahydropyridinyl substituted with one methyl, piperidinyl substituted with one methyl, pyridinyl substituted with one methyl, imidazolyl substituted with one methyl, isoxazolyl substituted with one methyl, or pyrazolyl substituted with one methyl.

In another embodiment, the invention relates to compounds of the Formula I wherein R$^1$ is —C(═O)—R$^5$, and R$^5$ is (C$_1$–C$_8$)alkyl-O— or (C$_2$–C$_{10}$)heterocyclyl, such as morpholinyl; wherein said R$^5$ (C$_2$–C$_{10}$)heterocyclyl is unsubstituted or substituted with (C$_1$–C$_8$)alkyl, such as methyl or ethyl.

In another preferred embodiment, the invention relates to compounds of the Formula I wherein $R^1$ is —C(=O)—$NR^6R^7$; wherein each of said $R^6$ and $R^7$ are independently H or ($C_1$–$C_8$)alkyl; and wherein each of said $R^6$ and $R^7$ ($C_1$–$C_8$)alkyl are unsubstituted or substituted with one to three substituents independently selected from the group consisting of OH, —$NH_2$, ($C_1$–$C_8$)alkyl-NH—, [($C_1$–$C_8$)alkyl]$_2$>N—, ($C_2$–$C_{10}$)heterocyclyl, and ($C_1$–$C_{10}$)heteroaryl.

In another preferred embodiment, the invention relates to compounds of the Formula I wherein $R^2$ is H or ($C_1$–$C_8$)alkyl unsubstituted or substituted with one to four substituents independently selected from the group consisting of OH, —$NH_2$, ($C_1$–$C_8$)alkyl-NH—, [($C_1$–$C_8$)alkyl]$_2$>N—, ($C_2$–$C_{10}$)heterocyclyl, and ($C_1$–$C_{10}$)heteroaryl.

In another embodiment, the invention relates to compounds of the Formula I wherein A is =N—.

In another embodiment, the invention relates to compounds of the Formula I wherein $R^2$ is —C(=O)—$R^8$, wherein $R^8$ is selected from the group consisting of ($C_1$–$C_8$)alkyl, ($C_2$–$C_8$)alkenyl, ($C_2$–$C_8$)alkynyl, —$NH_2$, and $R^{37}$ selected from the group consisting of ($C_1$–$C_8$)alkyl-NH—, [($C_1$–$C_8$)alkyl]$_2$>N—, and ($C_1$–$C_8$)alkyl-O—; wherein each of said $R^8$ and $R^{37}$ ($C_1$–$C_8$)alkyl, wherever it occurs, is independently unsubstituted or substituted with one to four substituents independently selected from $R^{40}$ selected from the group consisting of F, OH, —$NH_2$, ($C_3$–$C_{10}$)cycloalkyl, ($C_2$–$C_{10}$)heterocyclyl, ($C_6$–$C_{10}$)aryl, ($C_1$–$C_{10}$)heteroaryl; ($C_1$–$C_8$)alkyl-NH— and [($C_1$–$C_8$)alkyl]$_2$>N—;

wherein each of said $R^{40}$ ($C_1$–$C_8$)alkyl, wherever it occurs, is independently unsubstituted or substituted with one to four substituents independently selected from $R^{44}$ independently selected from the group consisting of OH, —$NH_2$, ($C_1$–$C_8$)alkyl-NH—, [($C_1$–$C_8$)alkyl]$_2$>N—, and ($C_3$–$C_{10}$)cycloalkyl-NH—;

wherein each of said each of said $R^{40}$ ($C_3$–$C_{10}$)cycloalkyl, ($C_2$–$C_{10}$)heterocyclyl, ($C_6$–$C_{10}$)aryl, or ($C_1$–$C_{10}$)heteroaryl, wherever it occurs, is independently unsubstituted or substituted with one to four substituents independently selected from $R^{47}$ selected from the group consisting of ($C_1$–$C_8$)alkyl, OH, —$NH_2$, ($C_1$–$C_8$)alkyl-NH—, [($C_1$–$C_8$)alkyl]$_2$>N—, and ($C_3$–$C_{10}$)cycloalkyl-NH—; and wherein each of said $R^{47}$ ($C_1$–$C_8$)alkyl, wherever it occurs, is independently unsubstituted or substituted with one to four substituents independently selected from the group consisting of OH, —$NH_2$, ($C_1$–$C_8$)alkyl-NH—, [($C_1$–$C_8$)alkyl]$_2$>N—, and ($C_3$–$C_{10}$)cycloalkyl-NH.

In another embodiment, the invention relates to compounds of the Formula I wherein $R^2$ is —C(=O)—$R^8$, wherein $R^8$ is selected from the group consisting of ($C_3$–$C_6$)cycloalkyl, ($C_2$–$C_{10}$)heterocyclyl, phenyl, or ($C_1$–$C_{10}$)heteroaryl; wherein each of said $R^8$ ($C_3$–$C_6$)cycloalkyl, ($C_2$–$C_{10}$)heterocyclyl, phenyl, or ($C_1$–$C_{10}$)heteroaryl is unsubstituted or substituted with one to four substituents independently selected from $R^{40}$ selected from the group consisting of ($C_1$–$C_8$)alkyl, F, OH, —$NH_2$, ($C_1$–$C_8$)alkyl-NH—, [($C_1$–$C_8$)alkyl]$_2$>N—, ($C_3$–$C_{10}$)cycloalkyl, ($C_2$–$C_{10}$)heterocyclyl, ($C_8$–$C_{10}$)aryl, and ($C_1$–$C_{10}$)heteroaryl; wherein each of said $R^{40}$ ($C_1$–$C_8$)alkyl, wherever it occurs, is independently unsubstituted or substituted with one to four substituents independently selected from $R^{44}$ independently selected from the group consisting of OH, —$NH_2$, ($C_1$–$C_8$)alkyl-NH—, [($C_1$–$C_8$)alkyl]$_2$>N—, and ($C_3$–$C_{10}$)cycloalkyl-NH—; wherein each of said $R^{40}$ ($C_3$–$C_{10}$)cycloalkyl, ($C_2$–$C_{10}$)heterocyclyl, ($C_3$–$C_{10}$)aryl, or ($C_1$–$C_{10}$)heteroaryl is unsubstituted or substituted with one to four substituents independently selected from $R^{47}$ selected from the group consisting of ($C_1$–$C_8$)alkyl, OH, —$NH_2$, ($C_1$–$C_8$)alkyl-NH—, [($C_1$–$C_8$)alkyl]$_2$>N—, and ($C_3$–$C_{10}$)cycloalkyl-NH—; wherein each of said $R^{47}$ ($C_{1–C8}$)alkyl, wherever it occurs, is unsubstituted or substituted with one to four substituents independently selected from the group consisting of OH, —$NH_2$, ($C_1$–$C_8$)alkyl-NH—, [($C_1$–$C_8$)alkyl]$_2$>N—, and ($C_3$–$C_{10}$)cycloalkyl-NH.

In another embodiment, the invention relates to compounds of the Formula I wherein said $R^3$ is on any one of position 7, 8, or 9 of said compound of the formula I. Preferably, the invention relates to compounds of the Formula I wherein said $R^3$ is on position 8 of said compound of the formula I.

In another preferred embodiment, the invention relates to compounds of the Formula I wherein said $R^4$ is on position 7 of said compound of the formula I. More preferably, said $R^3$ is on position 8 of said compound of the formula I and said $R^4$ is on position 7 of said compound of the formula I.

In another embodiment, the invention relates to compounds of the Formula I wherein said $R^4$ is Cl or Br on position 7 of said compound of the formula I.

In another preferred embodiment, the invention relates to compounds of the Formula I wherein said $R^4$ is H on position 7 of said compound of the formula I.

In another preferred embodiment, the invention relates to compounds of the Formula I wherein X is O.

In another preferred embodiment, the invention relates to compounds of the Formula I wherein the group —Y—Z— has the formula —N=CH—.

Preferably the invention relates to compounds of the Formula I selected from the group N-(6-Oxo-2-phenyl-5,6-dihydro-1H-[1,2]diazepino[4,5,6-cd]indol-8-yl)-2-phenyl-acetamide;

2-Cyclohexyl-N-(6-oxo-2-phenyl-5,6-dihydro-1H-[1,2]diazepino[4,5,6-cd]indol-8-yl)-acetamide;

N-(6-Oxo-2-phenyl-5,6-dihydro-1H-[1,2]diazepino[4,5,6-cd]indol-8-yl)-4-phenyl-butyramide;

N-(6-Oxo-2-phenyl-5,6-dihydro-1H-[1,2]diazepino[4,5,6-cd]indol-8-yl)-3-phenyl-propionamide;

3-Fluoro-2-methyl-N-(6-oxo-2-phenyl-5,6-dihydro-1H-[1,2]diazepino[4,5,6-cd]indol-8-yl)benzamide;

2-Fluoro-N-(6-oxo-2-phenyl-5,6-dihydro-1H-[1,2]diazepino[4,5,6-cd]indol-8-yl)-3-trifluoromethyl-benzamide;

N-(6-Oxo-2-phenyl-5,6-dihydro-1H-[1,2]diazepino[4,5,6-cd]indol-8-yl)-2-trifluoromethyl-benzamide;

(1R, 2R)-2-Phenyl-cyclopropanecarboxylic acid (6-oxo-2-phenyl-5,6-dihydro-1H-[1,2]diazepino[4,5,6-cd]indol-8-yl)-amide;

2-(3-Chlorophenyl)-N-(6-oxo-2-phenyl-5,6-dihydro-1H-[1,2]diazepino[4,5,6-cd]indol-8-yl)acetamide;

N-(6-Oxo-2-phenyl-5,6-dihydro-1H-[1,2]diazepino[4,5,6-cd]indol-8-yl)-4-thien-2-ylbutanamide;

1-Acetyl-N-(6-oxo-2-phenyl-5,6-dihydro-1H-[1,2]diazepino[4,5,6-cd]indol-8-yl)piperidine-4-carboxamide;

3-(2-Methylphenyl)-N-(6-oxo-2-phenyl-5,6-dihydro-1H-[1,2]diazepino[4,5,6-cd]indol-8-yl)propanamide;

(2S)-2-Amino-N-(6-oxo-2-phenyl-5,6-dihydro-1H-[1,2]diazepino[4,5,6-cd]indol-8-yl)-4-phenyl-butyramide compound with trifluoro-acetic acid;

(2R)-2-Amino-2-cyclohexyl-N-(6-oxo-2-phenyl-5,6-dihydro-1H-[1,2]diazepino[4,5,6-cd]indol-8-yl)ethanamide trifluoroacetate;

(1R,2R)-2-Phenyl-cyclopropanecarboxylic acid (6-oxo-2-phenyl-5,6-dihydro-1H-[1,2]diazepino[4,5,6-cd]indol-8-yl)-amide;

2-Ethylsulfanyl-N-(6-oxo-2-phenyl-5,6-dihydro-1H-[1,2]
   diazepino[4,5,6-cd]indol-8-yl)-nicotinamide;
(1R,2R)-2-Phenyl-cyclopropanecarboxylic acid (6-oxo-5,6-
   dihydro-1H-[1,2]diazepino[4,5,6-cd]indol-8-yl)-amide;
N-[2-(3-Dimethylaminomethyl-phenyl)-6-oxo-5,6-dihydro-
   1H-[1,2]diazepino[4,5,6-cd]indol-8-yl]-2-fluoro-3-
   trifluoromethyl-benzamide;
6-Oxo-2-phenyl-N-(2-phenylcyclopropyl)-5,6-dihydro-1H-
   [1,2]diazepino[4,5,6-cd]indole-8-carboxamide;
N-[1-(4-Fluorophenyl)ethyl]-6-oxo-2-phenyl-5,6-dihydro-
   1H-[1,2]diazepino[4,5,6-cd]indole-8-carboxamide;
(1R,2R)-2-Phenyl-cyclopropanecarboxylic acid [2-(3-
   dimethylaminomethyl-phenyl)-6-oxo-5,6-dihydro-1H-[1,
   2]diazepino[4,5,6-cd]indol-8-yl]-amide;
(1R,2R)-2-Phenyl-cyclopropanecarboxylic acid [2-(3-
   dimethylaminomethyl-phenyl)-6-oxo-5,6-dihydro-1H-[1,
   2]diazepino[4,5,6-cd]indol-8-yl]-amide (hydrochloric
   salt);
Acetic acid 3-{6-oxo-8-[((1R, 2R)-2-phenyl-
   cyclopropanecarbonyl)-amino]-5,6-dihydro-1H-[1,2]
   diazepino[4,5,6-cd]indol-2-yl}-benzyl ester;
(1R, 2R)-2-Phenyl-cyclopropanecarboxylic acid [2-(3-
   hydroxymethyl-phenyl)-6-oxo-5,6-dihydro-1H-[1,2]
   diazepino[4,5,6-cd]indol-8-yl]-amide;
(2R)-2-Amino-2-cyclohexyl-N-(6-oxo-2-phenyl-5,6-
   dihydro-1H-[1,2]diazepino[4,5,6-cd]indol-8-yl)-
   acetamide (hydrochloric salt);
N-[1-(4-Hydroxyphenyl)ethyl]oxo-2-phenyl-5,6-dihydro-
   1H-[1,2]diazepino[4,5,6-cd]indole-8-carboxamide;
2,3-Difluoro-N-(6-oxo-2-phenyl-5,6-dihydro-1H-[1,2]
   diazepino[4,5,6-cd]indol-8-yl)-benzamide;
(1R,2R)-2-Phenyl-cyclopropanecarboxylic acid (6-oxo-5,6-
   dihydro-1H-[1,2]diazepino[4,5,6-cd]indol-8-yl)-amide;
N-(4-Fluorobenzyl)-6-oxo-2-phenyl-5,6-dihydro-1H-[1,2]
   diazepino[4,5,6-cd]indole-8-carboxamide;
(1R,2R)-2-Phenyl-cyclopropanecarboxylic acid [2-(3-
   cyclobutylaminomethyl-phenyl)-6-oxo-5,6-dihydro-1H-
   [1,2]diazepino[4,5,6-cd]indol-8-yl]-amide(hydrochloric
   salt);
(1R,2R)-2-Phenyl-cyclopropanecarboxylic acid [6-oxo-2-
   (3-pyrrolidin-1-ylmethyl-phenyl)-5,6-dihydro-1H-[1,2]
   diazepino[4,5,6-cd]indol-8-yl]-amide(hydrochloric salt);
N-(6-Oxo-2-phenyl-5,6-dihydro-1H-[1,2]diazepino[4,5,6-
   cd]indol-8-yl)-(1,2-trans)-2-[6-(trifluoromethyl)pyridin-
   3-yl]cyclopropanecarboxamide trifluoroacetate;
(2R)-2-Amino-N-(6-oxo-2-phenyl-5,6-dihydro-1H-[1,2]
   diazepino[4,5,6-cd]indol-8-yl)-2-phenyl-acetamide
   (hydrochloric salt);
(2R)-2-Amino-N-(6-oxo-2-phenyl-5,6-dihydro-1H-[1,2]
   diazepino[4,5,6-cd]indol-8-yl)-3-phenyl-propionamide
   (hydrochloric salt);
(3E)-4-Phenyl-but-3-enoic acid (6-oxo-2-phenyl-5,6-
   dihydro-1H-[1,2]diazepino[4,5,6-cd]indol-8-yl)-amide;
2-Indan-2-yl-N-(6-oxo-2-phenyl-5,6-dihydro-1H-[1,2]
   diazepino[4,5,6-cd]indol-8-yl)-acetamide;
(1,2-trans)-2-(4-Fluoro-phenyl)-cyclopropanecarboxylic
   acid (6-oxo-2-phenyl-5,6-dihydro-1H-[1,2]diazepino[4,5,
   6-cd]indol-8-yl)-amide;
(1,2-trans)-2-Pyridin-3-yl-cyclopropanecarboxylic acid
   (6-oxo-2-phenyl-5,6-dihydro-1H-[1,2]diazepino[4,5,6-
   cd]indol-8-yl)-amide (hydrochloric salt);
(1,2-trans)-2-(3-Methoxy-phenyl)-cyclopropanecarboxylic
   acid (6-oxo-2-phenyl-5,6-dihydro-1H-[1,2]diazepino[4,5,
   6-cd]indol-8-yl)-amide;
2-Indan-2-yl-(6-oxo-5,6-dihydro-1-[1,2]diazepino[4,5,6-cd]
   indol-8-yl)-acetamide;
(2R)-2-Hydroxy-N-(6-oxo-2-phenyl-5,6-dihydro-1H-[1,2]
   diazepino[4,5,6-cd]indol-8-yl)-2-phenylethanamide;
(1,2-trans)-2-Pyridin-2-yl-cyclopropanecarboxylic acid
   (6-oxo-2-phenyl-5,6-dihydro-1H-[1,2]diazepino[4,5,6-
   cd]indol-8-yl)-amide acetic acid;
(1,2-trans)-2-(1H-Imidazol-4-yl)-cyclopropanecarboxylic
   acid (6-oxo-2-phenyl-5,6-dihydro-1H-[1,2]diazepino[4,5,
   6-cd]indol-8-yl)-amide acetic acid;
(2R)-Piperidine-2-carboxylic acid (6-oxo-2-phenyl-5,6-
   dihydro-1H-[1,2]diazepino[4,5,6-cd]indol-8-yl)-amide
   (hydrochloric salt);
(2S)-2-Amino-3-cyano-N-(6-oxo-2-phenyl-5,6-dihydro-
   1H-[1,2]diazepino[4,5,6-cd]indol-8-yl)-propionamide
   acetic acid;
(2R)-2-amino-3-(4-hydroxyphenyl)-N-(6-oxo-2-phenyl-5,
   6-dihydro-1H-[1,2]diazepino[4,5,6-cd]indol-8-yl)
   propanamide (hydrochloric salt);
(1R,2R)-6-Oxo-8-[(2-phenyl-cyclopropanecarbonyl)-
   amino]-5,6-dihydro-1H-[1,2]diazepino[4,5,6-cd]indole-
   2-carboxylic acid methyl ester,
(2R)-3-(4-Hydroxyphenyl)-2-(methylamino)-N-(6-oxo-2-
   phenyl-5,6-dihydro-1H-[1,2]diazepino[4,5,6-cd]indol-8-
   yl)propanamide (hydrochloric salt);
(2R)-2-Amino-3-(4-fluorophenyl)-N-(6-oxo-2-phenyl-5,6-
   dihydro-1H-[1,2]diazepino[4,5,6-cd]indol-8-yl)
   propanamide (hydrochloric salt);
(1R,2R)-6-Oxo-8-[(2-phenyl-cyclopropanecarbonyl)-
   amino]-5,6-dihydro-1H-[1,2]diazepino[4,5,6-cd]indole-
   2-carboxylic acid methylamide;
(1R,2R)-6-Oxo-8-[(2-phenyl-cyclopropanecarbonyl)-
   amino]-5,6-dihydro-1H-[1,2]diazepino[4,5,6-cd]indole-
   2-carboxylic acid (2-hydroxy-ethyl)-amide;
(1R,2R)-6-Oxo-8-[(2-phenyl cyclopropanecarbonyl)-
   amino]-5,6-dihydro-1H-[1,2]diazepino[4,5,6-cd]indole-
   2-carboxylic acid (2-dimethylamino-ethyl)-amide;
(2R)-2-Amino-2-(4-hydroxyphenyl)-N-(6-oxo-2-phenyl-5,
   6-dihydro-1H-[1,2]diazepino[4,5,6-cd]indol-8-yl)
   ethanamide (hydrochloric salt);
(1,2-trans)-2-(4-Hydroxy-phenyl)-cyclopropanecarboxylic
   acid (6-oxo-5,6-dihydro-1-[1,2]diazepino[4,5,6-cd]indol-
   8-yl)-amide;
(1,2-trans)-2-(4-Hydroxy-phenyl)-cyclopropanecarboxylic
   acid (6-oxo-2-phenyl-5,6-dihydro-1-[1,2]diazepino[4,5,
   6]indol-8-yl)-amide;
(1R,2R)-2-Phenyl-cyclopropanecarboxylic acid (2-ethyl-
   oxo-5,6-dihydro-1H-[1,2]diazepino[4,5,6-cd]indol-8-yl)-
   amide;
(1R,2R)-2-Phenyl-cyclopropanecarboxylic acid (2-chloro-
   6-oxo-5,6-dihydro-1H-[1,2]diazepino[4,5,6-cd]indol-8-
   yl)-amide;
(1,2-trans)-2-(3-Bromo-phenyl)-cyclopropanecarboxylic
   acid (6-oxo-5,6-dihydro-1H-[1,2]diazepino[4,5,6-cd]
   indol-8-yl)-amide;
(1,2-trans)-2-(3-Hydroxy-phenyl)-cyclopropanecarboxylic
   acid (6-oxo-5,6-dihydro-1-[1,2]diazepino[4,5,6]indol-8-
   yl)-amide;
2-(3,4-Dihydroisoquinolin-2(1H)-yl)-N-(6-oxo-2-phenyl-5,
   6-dihydro-1H-[1,2]diazepino[4,5,6-cd]indol-8-yl)
   acetamide;
(1R,2R)-2-Phenyl-cyclopropanecarboxylic acid (2-bromo-
   oxo-5,6-dihydro-1H-[1,2]diazepino[4,5,6-cd]indol-8-yl)-
   amide;
(1R,2R)-2-Phenyl-cyclopropanecarboxylic acid [6-oxo-2-
   (1,2,3,6-tetrahydro-pyridin-4-yl)-5,6-dihydro-1H-[1,2]
   diazepino[4,5,6-cd]indol-yl]-amide (hydrochloric salt);
(1R,2R)-N-(6-Oxo-2-pyridin-4-yl-5,6-dihydro-1H-[1,2]
   diazepino[4,5,6-cd]indol-8-yl)-2-
   phenylcyclopropanecarboxamide;
N-(6-Oxo-2-pyridin-4-yl-5,6-dihydro-1H-[1,2]diazepino[4,
   5,6-cd]indo-8-yl)-(1,2-trans)-2-pyridin-3-
   ylcyclopropanecarboxamide;

N-(6-Oxo-2-pyridin-3-yl-5,6-dihydro-1H-[1,2]diazepino[4,5,6-cd]indol-8-yl)-(1,2-trans)-2-pyridin-3-ylcyclopropanecarboxamide;

(1R,2R)-N-(6-Oxo-2-pyridin-3-yl-5,6-dihydro-1H-[1,2]diazepino[4,5,6-cd]indol-8-yl)-2-phenylcyclopropanecarboxamide;

(1R,2R)-2-Phenyl-cyclopropanecarboxylic acid [2-(3-dimethylamino-prop-1-ynyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-dimethylamino-propyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-dimethylamino-propenyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-methylamino-prop-1-ynyl)-6-oxo-5,6-dihydro-1H-[1,2]diazepino[4,5,6-cd]indol-8-yl]-amide (hydrochloric salt);

(1,2-trans)-2-Pyridin-3-yl-cyclopropanecarboxylic acid [2-(3-methylamino-prop-1-ynyl)-6-oxo-5,6-dihydro-1H-[1,2]diazepino[4,5,6-cd]indol-8-yl]-amide (dihydrochloric salt);

(2R)-2-Amino-2-cyclohexyl-N-[2-(3-methylamino-prop-1-ynyl)-6-oxo-5,6-dihydro-1H-[1,2]diazepino[4,5,6-cd]indol-8-yl]-acetamide (dihydrochloric salt);

(1,2-trans)-N-[1-(2-Hydroxyethyl)-6-oxo-5,6-dihydro-1H-[1,2]diazepino[4,5,6-cd]indol-8-yl]-2-phenylcyclopropanecarboxamide;

(1R,2R)-2-Phenyl-cyclopropanecarboxylic acid (2-dimethylaminomethyl-6-oxo-5,6-dihydro-1H-[1,2]diazepino[4,5,6-cd]indol-8-yl)-amide;

(1R,2R)-2-Phenyl-cyclopropanecarboxylic acid [1-(2-amino-ethyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-morpholin-4-yl-prop-1-ynyl)-6-oxo-5,6-dihydro-1H-[1,2]diazepino[4,5,6-cd]indol-8-yl]-amide;

(1R,2R)-2-Phenyl-cyclopropanecarboxylic acid [6-oxo-2-(3-pyrrolidin-1-yl-prop-1-ynyl)-5,6-dihydro-1H-[1,2]diazepino[4,5,6-cd]indol-8-yl]-amide; and (1R,2R)-2-Phenyl-cyclopropanecarboxylic acid [1-(2-amino-ethyl)-2-chloro-6-oxo-5,6-dihydro-1H-[1,2]diazepino[4,5,6-cd]indol-8-yl]-amide;

(1R,2R)-2-Phenyl-cyclopropanecarboxylic acid [2-(1H-imidazol-2-yl)-6-oxo-5,6-dihydro-1H-[1,2]diazepino[4,5,6-cd]indol-8-yl]-amide;

(1R,2R)-2-Phenyl-cyclopropanecarboxylic acid (2-cyano-6-oxo-5,6-dihydro-1H-[1,2]diazepino[4,5,6-cd]indol-8-yl)-amide; and (1R,2R)-2-Phenyl-cyclopropanecarboxylic acid [2-(1H-imidazol-2-yl)-6-oxo-5,6-dihydro-1H-[1,2]diazepino[4,5,6-cd]indol-8-yl]-amide; or the pharmaceutically acceptable salts or solvates thereof.

Other preferred compounds are selected from the group consisting of

3-Fluoro-2-methyl-N-(6-oxo-2-phenyl-5,6-dihydro-1H-[1,2]diazepino[4,5,6-cd]indol-8-yl)-benzamide;

2-Fluoro-N-(6-oxo-2-phenyl-5,6-dihydro-1H-[1,2]diazepino[4,5,6-cd]indol-8-yl)-3-trifuoromethyl-benzamide;

N-(6-Oxo-2-phenyl-5,6-dihydro-1H-[1,2]diazepino[4,5,6-cd]indol-8-yl)-4-thien-2-ylbutanamide;

(1R,2R)-2-Phenyl-cyclopropanecarboxylic acid (6-oxo-2-phenyl-5,6-dihydro-1H-[1,2]diazepino[4,5,6-cd]indol-8-yl)-amide;

(1R,2R)-2-Phenyl-cyclopropanecarboxylic acid [2-(3-dimethylaminomethyl-phenyl)-6-oxo-5,6-dihydro-1H-[1,2]diazepino[4,5,6-cd]indol-8-yl]-amide;

Acetic acid 3-{6-oxo-8-[((1R, 2R)-2-phenyl-cyclopropanecarbonyl)-amino]-5,6-dihydro-1H-[1,2]diazepino[4,5,6-cd]indol-2-yl}-benzyl ester;

(1R,2R)-2-Phenyl-cyclopropanecarboxylic acid [2-(3-hydroxymethyl-phenyl)-6-oxo-5,6-dihydro-1H-[1,2]diazepino[4,5,6-cd]indol-8-yl]-amide;

(2R)-2-Amino-2-cyclohexyl-N-(6-oxo-2-phenyl-5,6-dihydro-1H-[1,2]diazepino[4,5,6-cd]indol-yl)-acetamide;

(1R,2R)-2-Phenyl-cyclopropanecarboxylic acid (6-oxo-5,6-dihydro-1H-[1,2]diazepino[4,5,6-cd]indol-8-yl)-amide;

(1R,2R)-2-Phenyl-cyclopropanecarboxylic acid [2-(3-cyclobutylaminomethyl-phenyl)-6-oxo-5,6-dihydro-1H-[1,2]diazepino[4,5,6-cd]indol-8-yl]-amide;

(1R,2R)-2-Phenyl-cyclopropanecarboxylic acid [6-oxo-2-(3-pyrrolidin-1-ylmethyl-phenyl)-5,6-dihydro-1H-[1,2]diazepino[4,5,6-cd]indol-8-yl]-amide;

2-Indan-2-yl-N-(6-oxo-2-phenyl-5,6-dihydro-1H-[1,2]diazepino[4,5,6-cd]indol-8-yl)-acetamide;

(1,2-trans)-2-(4-Fluoro-phenyl)-cyclopropanecarboxylic acid (6-oxo-2-phenyl-5,6-dihydro-1H-[1,2]diazepino[4,5,6-cd]indol-8-yl)-amide;

(2R)-2-Amino-3-(4-hydroxyphenyl)-N-(6-oxo-2-phenyl-5,6-dihydro-1H-[1,2]diazepino[4,5,6-cd]indol-8-yl) propanamide;

(1R,2R)-6-Oxo-8-[(2-phenyl-cyclopropanecarbonyl)-amino]-5,6-dihydro-1H-[1,2]diazepino[4,5,6-cd]indole-2-carboxylic acid methyl ester;

(1R,2R)-6-Oxo-8-[(2-phenyl-cyclopropanecarbonyl)-amino]-5,6-dihydro-1H-[1,2]diazepino[4,5,6-cd]indole-2-carboxylic acid methylamide;

(1R,2R)-6-Oxo-8-[(2-phenyl-cyclopropanecarbonyl)-amino]-5,6-dihydro-1H-[1,2]diazepino[4,5,6-cd]indole-2-carboxylic acid (2-hydroxy-ethyl)-amide;

(1R,2R)-6-Oxo-8-[(2-phenyl-cyclopropanecarbonyl)-amino]-5,6-dihydro-1H-[1,2]diazepino[4,5,6-cd]indole-2-carboxylic acid (2-hydroxy-ethyl)-amide;

(2R)-2-Amino-2-(4-hydroxyphenyl)-N-(6-oxo-2-phenyl-5,6-dihydro-1H-[1,2]diazepino[4,5,6-cd]indol-8-yl) ethanamide;

(1,2-trans)-2-(4-Hydroxy-phenyl)cyclopropanecarboxylic acid (6-oxo-5,6-dihydro-1H-[1,2]diazepino[4,5,6-cd]indol-8-yl)-amide;

(1,2-trans)-2-(4-Hydroxy-phenyl)-cyclopropanecarboxylic acid (6-oxo-2-phenyl-5,6-dihydro-1-[1,2]diazepino[4,5,6]indol-8-yl)-amide;

(1R,2R)-2-Phenyl-cyclopropanecarboxylic acid (2-ethyl-oxo-5,6-dihydro-1H-[1,2]diazepino[4,5,6-cd]indol-8-yl)-amide;

(1R,2R)-2-Phenyl-cyclopropanecarboxylic acid (2-ethyl-6-oxo-5,6-dihydro-1H-[1,2]diazepino[4,5,6-cd]indol-8-yl)-amide;

2-(3,4-Dihydroisoquinolin-2(1H)-yl)-N-(6-oxo-2-phenyl-5,6-dihydro-1H-[1,2]diazepino[4,5,6-cd]indol-8-yl) acetamide;

2-(3,4-Dihydroisoquinolin-2(1H)-yl)-N-(6-oxo-2-phenyl-5,6-dihydro-1H-[1,2]diazepino[4,5,6-cd]indol-8-yl) acetamide;

(1R,2R)-2-Phenyl-cyclopropanecarboxylic acid [6-oxo-2-(1,2,3,6-tetrahydro-pyridin-4-yl)-5,6-dihydro-1H-[1,2]diazepino[4,5,6-cd]indol-8-yl]-amide;

(1R,2R)-N-(6-Oxo-2-pyridin-4-yl-5,6-dihydro-1H-[1,2]diazepino[4,5,6-cd]indol-8-yl)-2-phenylcyclopropanecarboxamide;

(1R,2R)-N-(6-Oxo-2-pyridin-3-yl-5,6-dihydro-1H-[1,2]diazepino[4,5,6-cd]indol-8-yl)-2-phenylcyclopropanecarboxamide;

(1R,2R)-2-Phenyl-cyclopropanecarboxylic acid [2-(3-dimethylamino-prop-1-ynyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-dimethylamino-propenyl)-6-oxo-5,6-dihydro-1H-[1,2]diazepino[4,5,6-cd]indol-8-yl]-amide;

(1R,2R)-2-Phenyl-cyclopropanecarboxylic acid [2-(3-methylamino-prop-1-ynyl)-6-oxo-5,6-dihydro-1H-[1,2]diazepino[4,5,6-cd]indol-8-yl]-amide;

(2R)-2-Amino-2-cyclohexyl-N-[2-(3-methylamino-prop-1-ynyl)-oxo-5,6-dihydro-1H-[1,2]diazepino[4,5,6-cd]indol-8-yl]-acetamidede;

(1R,2R)-2-Phenyl-cyclopropanecarboxylic acid (2-hydroxymethyl-6-oxo-5,6-dihydro-1H-[1,2-cd]diazepino[4,5,6]indol-8-yl)-amide;

(1R,2R)-2-Phenyl-cyclopropanecarboxylic acid [6-oxo-2-(3-pyrrolidin-1-yl-prop-1-ynyl)-5,6-dihydro-1H-[1,2]diazepino[4,5,6-cd]indol-8-yl]-amide;

(1R,2R)-2-Phenyl-cyclopropanecarboxylic acid [2-(1H-imidazol-2-yl)-oxo-5,6-dihydro-1H-[1,2]diazepino[4,5,6-cd]indol-8-yl]-amide;

(1R,2R)-2-Phenyl-cyclopropanecarboxylic acid (2-cyano-6-oxo-5,6-dihydro-1H-[1,2]diazepino[4,5,6-cd]indol-8-yl)-amide; and (2R)-2-Amino-2-(4-hydroxyphenyl)-N-(6-oxo-2-phenyl-5,6-dihydro-1H-[1,2]diazepino[4,5,6-cd]indol-8-yl)ethanamide hydrochloride; or the pharmaceutically acceptable salts or solvates thereof.

Other preferred compounds of formula I are selected from the group consisting of:

2-Fluoro-N-(6-oxo-2-phenyl-5,6-dihydro-1H-[1,2]diazepino[4,5,6-cd]indol-8-yl)-3-trifluoromethyl-benzamide;

N-(6-Oxo-2-phenyl-5,6-dihydro-1H-[1,2]diazepino[4,5,6-cd]indol-8-yl)-4-thien-2-ylbutanamide;

(1R, 2R)-2-Phenyl-cyclopropanecarboxylic acid [2-(3-hydroxymethyl-phenyl)-6-oxo-5,6-dihydro-1H-[1,2]diazepino[4,5,6-cd]indol-8-yl]-amide;

(2R)-2-Amino-2-cyclohexyl-N-(6-oxo-2-phenyl-5,6-dihydro-1H-[1,2]diazepino[4,5,6-cd]indol-8-yl)-acetamide(hydrochloride);

6-Oxo-2-phenyl-N-[(1R)-1-phenylethyl]-5,6-dihydro-1H-[1,2]diazepino[4,5,6-cd]indole-8-carboxamide;

(1R,2R)-2-Phenyl-cyclopropanecarboxylic acid (6-oxo-5,6-dihydro-1H-[1,2]diazepino[4,5,6-cd]indol-8-yl)-amide;

(2R)-2-Hydroxy-N-(6-oxo-2-phenyl-5,6-dihydro-1H-[1,2]diazepino[4,5,6-cd]indol-8-yl)-2-phenylethanamide;

(1,2-trans)-2-Pyridin-2-yl)-cyclopropanecarboxylic acid (6-oxo-2-phenyl-5,6-dihydro-1H-[1,2]diazepino[4,5,6-cd]indol-8-yl)-amide (acetic acid salt);

(1,2-trans)-2-(1H-Imidazol-4-yl)-cyclopropanecarboxylic acid (6-oxo-2-phenyl-5,6-dihydro-1H-[1,2]diazepino[4,5,6-cd]indol-8-yl)-amide (acetic acid salt);

(2R)-Piperidine-2-carboxylic acid (6-oxo-2-phenyl-5,6-dihydro-1H-[1,2]diazepino[4,5,6-cd]indol-8-yl)-amide (hydrochloric salt);

(2R)-2-Amino-3-(4-hydroxyphenyl)-N-(6-oxo-2-phenyl-5,6-dihydro-1H-[1,2]diazepino[4,5,6-cd]indol-8-yl)propanamide hydrochloride;

(1R,2R)-6-Oxo-[(2-phenyl-cyclopropanecarbonyl)-amino]-5,6-dihydro-1H-[1,2]diazepino[4,5,6-cd]indole-2-carboxylic acid (2-dimethylamino-ethyl)-amide;

Example 182: (1,2-trans)-2-(4-Hydroxy-phenyl)-cyclopropanecarboxylic acid (6-oxo-2-phenyl-5,6-dihydro-1-[1,2]diazepino[4,5,6]indol-8-yl)-amide;

(1R,2R)-2-Phenyl-cyclopropanecarboxylic acid (2-ethyl-6-oxo-5,6-dihydro-1H-[1,2]diazepino[4,5,6-cd]indol-8-yl)-amide;

(1R,2R)-N-(6-Oxo-2-pyridin-3-yl-5,6-dihydro-1H-[1,2]diazepino[4,5,6-cd]indol-8-yl)-2-phenylcyclopropanecarboxamide; and (1R,2R)-2-Phenyl-cyclopropanecarboxylic acid [1-(2-amino-ethyl)-2-chloro-6-oxo-5,6-dihydro-1H-[1,2]diazepino[4,5,6-cd]indol-8-yl]-amide; or the pharmaceutically acceptable salts or solvates thereof.

In another embodiment, the invention also relates to compounds of the Formula I that are selective for CHK-1 over CHK-2 with selectivity ratio between about 5 folds and about 5000 folds; preferably between about 50 folds and about 1000 folds; and more preferably between about 70 folds and about 830 folds. Within this embodiment, the more preferred compounds are selected from the group consisting of:

2-Fluoro-N-(6-oxo-2-phenyl-5,6-dihydro-1H-[1,2]diazepino[4,5,6-cd]indol-8-yl)-3-trifluoromethyl-benzamide;

N-(6-Oxo-2-phenyl-5,6-dihydro-1H-[1,2]diazepino[4,5,6-cd]indol-8-yl)-2-trifluoromethyl-benzamide;

N-(6-Oxo-2-phenyl-5,6-dihydro-1H-[1,2]diazepino[4,5,6-cd]indol-8-yl)-4-thien-2-ylbutanamide;

N-[2-(3-Dimethylaminomethyl-phenyl)-6-oxo-5,6-dihydro-1H-[1,2]diazepino[4,5,6-cd]indol-8-yl]-2-fluoro-3-trifluoromethyl-benzamide;

(2R)-2-Amino-2-cyclohexyl-N-(6-oxo-2-phenyl-5,6-dihydro-1H-[1,2]diazepino[4,5,6-cd]indol-8-yl)-acetamide(hydrochloride);

(1R,2R)-2-Phenyl-cyclopropanecarboxylic acid (6-oxo-5,6-dihydro-1H-[1,2]diazepino[4,5,6-cd]indol-8-yl)-amide;

(1R,2R)-6-Oxo-8-[(2-phenyl-cyclopropanecarbonyl)-amino]-5,6-dihydro-1H-[1,2]diazepino[4,5,6-cd]indole-2-carboxylic acid (2-dimethylamino-ethyl)-amide;

(2R)-2-Amino-2-(4-hydroxyphenyl)-N-(6-oxo-2-phenyl-5,6-dihydro-1H-[1,2]diazepino[4,5,6-cd]indol-8-yl)ethanamide hydrochloride;

(1,2-trans)-2-(4-Hydroxy-phenyl)-cyclopropanecarboxylic acid (6-oxo-2-phenyl-5,6-dihydro-1-[1,2]diazepino[4,5,6]indol-8-yl)-amide; and (1R,2R)-2-Phenyl-cyclopropanecarboxylic acid (2-ethyl-6-oxo-5,6-dihydro-1H-[1,2]diazepino[4,5,6-cd]indol-8-yl)-amide; or the pharmaceutically acceptable salts or solvates thereof.

Another embodiment of the invention is a compound selected from the group consisting of:

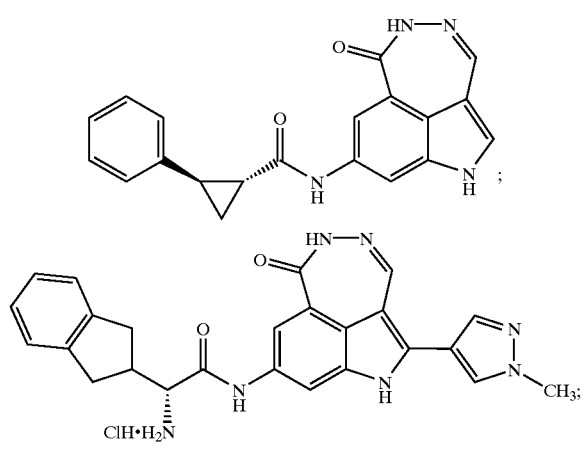

-continued
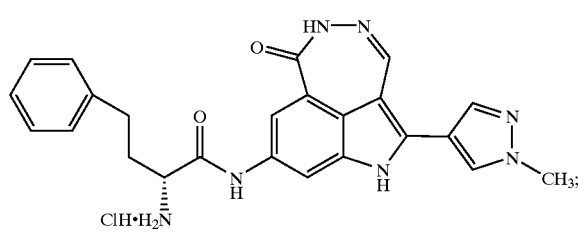
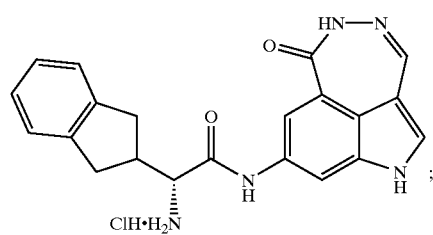
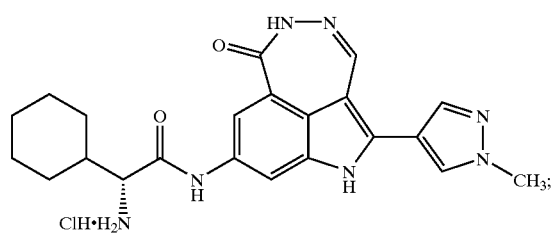
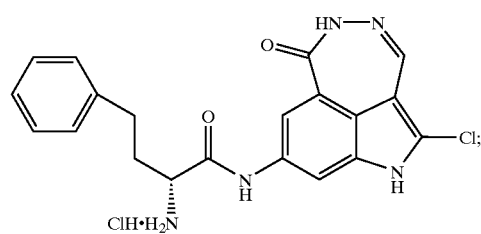
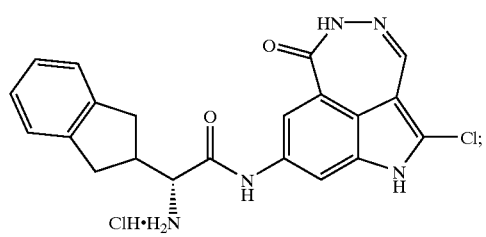
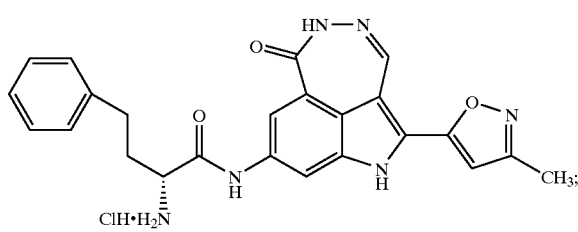
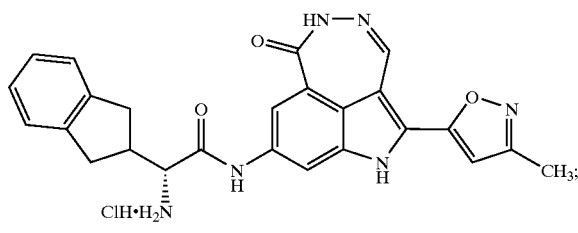
and
-continued
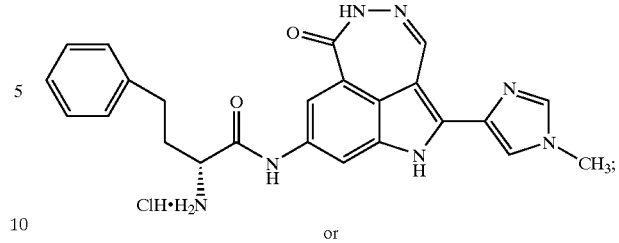
or
a pharmaceutically acceptable salt or solvate thereof.
Another embodiment of the invention is a compound, which is:
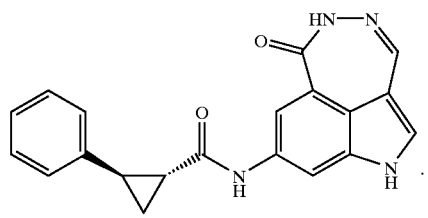
Another embodiment of the invention is a compound, which is:
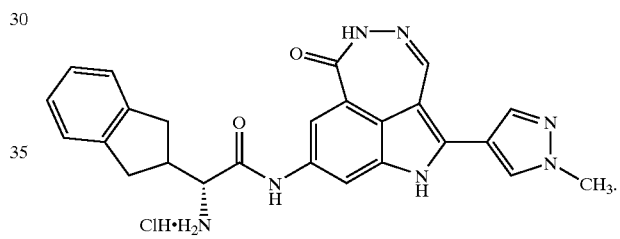
Another embodiment of the invention is a compound, which is:
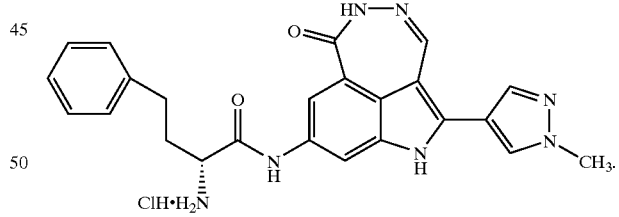
Another embodiment of the invention is a compound, which is:
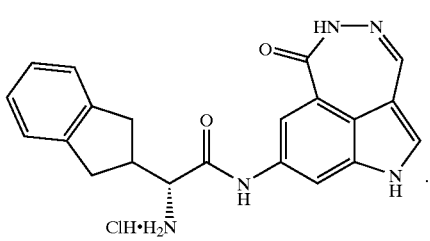

Another embodiment of the invention is a compound, which is:

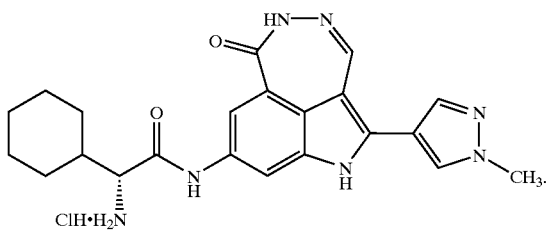

Another embodiment of the invention is a compound, which is:

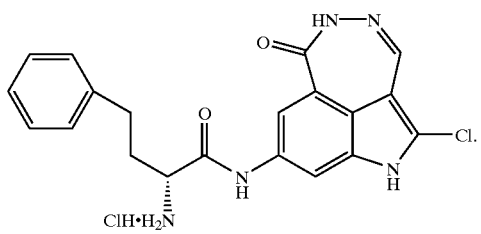

Another embodiment of the invention is a compound, which is:

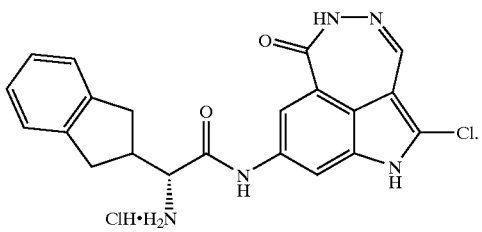

Another embodiment of the invention is a compound, which is:

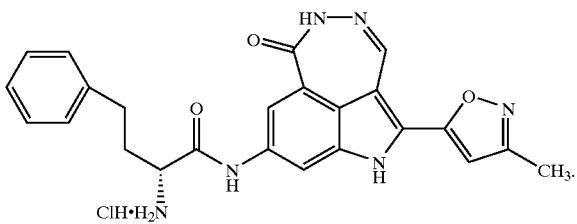

Another embodiment of the invention is a compound, which is:

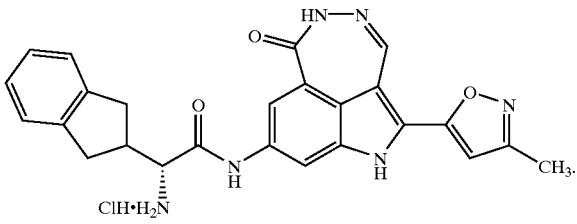

Another embodiment of the invention is a compound, which is:

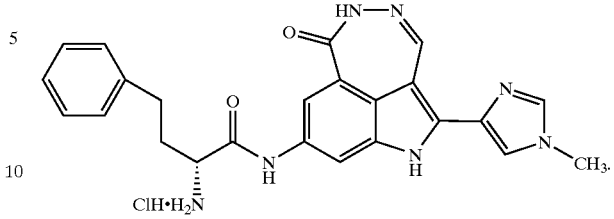

Another object of the invention is to provide a composition for the treatment of neoplasms, and for enhancing the antineoplastic effects of anti-neoplastic agents and therapeutic radiation.

In an embodiment, the invention relates to a composition containing a compound of the Formula I, a pharmaceutically acceptable salt, solvate, or prodrug thereof and an anti-neoplastic agent as a combined preparation for the simultaneous, separate or sequential use in treating a neoplasm.

In another embodiment, the invention relates to a composition containing a compound of the Formula I, a pharmaceutically acceptable salt, solvate, or prodrug thereof and an anti-neoplastic agent as a combined preparation for the simultaneous, separate or sequential use in treating a neoplasm wherein the anti-neoplastic agent is selected from the group consisting of alkylating agents, antibiotics and plant alkaloids, hormones and steroids, synthetic agents having anti-neoplastic activity, antimetabolites and biological molecules having anti-neoplastic activity.

In another embodiment, the invention relates to a composition containing a compound of the Formula I, a pharmaceutically acceptable salt, solvate, or prodrug thereof and an anti-neoplastic agent as a combined preparation for the simultaneous, separate or sequential use in treating a neoplasm wherein the anti-neoplastic agent is selected from the group consisting of Ara-c, VP-16, cis-platin, adriamycin, 2-chloro-2-deoxyadenosine, 9-(3-D-arabinosyl-2-fluoroadenine, carboplatin, gemcitabine, camptothecin, paclitaxel, BCNU, 5-fluorouracil, irinotecan, and doxorubicin.

Another object of the invention is to provide a method for the treatment of neoplasms.

In an embodiment, the invention relates to a method for treating a neoplasm which comprises administering to a mammal in need thereof, an anti-neoplastic agent in combination with a compound of the Formula I, a pharmaceutically acceptable salt, solvate, or prodrug thereof.

In another embodiment, the invention relates to a method for treating a neoplasm which comprises administering to a mammal in need thereof, an anti-neoplastic agent in combination with a compound of the Formula I, a pharmaceutically acceptable salt, solvate, or prodrug thereof, wherein the anti-neoplastic agent is selected from the group consisting of Ara-c, VP-16, cis-platin, adriamycin, 2-chloro-2-deoxyadenosine, 9-p-D-arabinosyl-2-fluoroadenine, carboplatin, gemcitabine, camptothecin, paclitaxel, BCNU, 5-fluorouracil, irinotecan, and doxorubicin. In another embodiment, more than one anti-neoplastic agents may be used in combination with a compound of the Formula I, the pharmaceutically acceptable salts, solvates, or prodrugs thereof.

Another object of the invention is to provide methods for enhancing the anti-neoplastic effect of therapeutic radiation.

In an embodiment, the invention relates to a method for treating a neoplasm which comprises administering to a mammal in need thereof, therapeutic radiation having an anti-neoplastic effect in combination with a compound of the Formula I, a pharmaceutically acceptable salt, solvate, or prodrug thereof.

Another object of the invention is to provide methods for enhancing the antineoplastic effect of an anti-neoplastic agent.

In an embodiment, the invention relates to a method for enhancing the anti-neoplastic effect of an anti-neoplastic agent in a mammal which comprises administering to a mammal in need thereof, a compound of the Formula I, a pharmaceutically acceptable salt, solvate, or prodrug thereof, in combination with an antineoplastic agent. The antineoplastic agents include alkylating agents, antibiotics and plant alkaloids, hormones and steroids, synthetic agents having anti-neoplastic activity, antimetabolites and biological molecules having anti-neoplastic activity. Specific anti-neoplastic agents include Ara-c, VP-16, cis-platin, adriamycin, 2-chloro-2-deoxyadenosine, 9-β-D-arabinosyl-2-fluoroadenine, carboplatin, gemcitabine, camptothecin, paclitaxel, BCNU, 5-fluorouracil, irinotecan, and doxorubicin.

In another embodiment, the invention relates to a method for enhancing the anti-neoplastic effect of therapeutic radiation in a mammal which comprises administering to a mammal in need thereof, a compound of the Formula I, a pharmaceutically acceptable salt, solvate, or prodrug thereof, in combination with therapeutic radiation having an anti-neoplastic effect.

Another object of the invention is to provide a method for the treatment of a condition which can be treated by the inhibition of protein kinases. In one embodiment of the invention, the protein kinases are selected from the group consisting of Checkpoint kinase 1 (CHK-1), Checkpoint kinase 2 (CHK-2), Cyclin dependent kinase 1 (CDK1), Serum and glucocorticoid regulated kinase (SGK), Adenosine 5'-monophosphate (AMP)-activated protein kinase (AMPK), Lymphoid T cell tyrosine kinase (LCK), Mitogen activated protein kinase-2 (MAPK-2), Mitogen- and stress-activated protein kinase 1 (MSK1), Rho kinase (ROCK-II), P70 S6 kinase (p70S6K), cAMP (adenosine 3', 5' cyclic monophosphate)-dependent protein kinase (PKA), Mitogen activated protein kinase (MAPK), Mitogen activated protein kinase-1 (MAPK-1), Protein kinase C-related kinase 2 (PRK2), 3'-Phosphoinositide dependent kinase 1 (PDK1), Fyn kinase (FYN), Protein kinase C (PKC), Protein Kinase C Beta 2 (PKCβII), Protein Kinase C Gamma (PKCγ), Vascular endothelial growth factor receptor 2 (VEGFR-2), Fibroblast growth factor receptor (FGFR), Phosphorylase kinase (PHK), Wee1 kinase (Wee1), and Protein Kinase B (PKB). Preferably, the protein kinases are selected from the group consisting of Checkpoint kinase 1 (CHK-1), Checkpoint kinase 2 (CHK-2), Mitogen activated protein kinase (MAPK), Mitogen activated protein kinase-1 (MAPK-1), Mitogen activated protein kinase-2 (MAPK-2), Vascular endothelial growth factor receptor 2 (VEGFR-2), Fibroblast growth factor receptor (FGFR), Phosphorylase kinase (PHK), Protein Kinase B alpha (PKBα), and Wee1 kinase (Wee1).

In an embodiment, the invention relates to a method for the treatment of a condition which can be treated by the inhibition of protein kinases in a mammal, including a human, comprising administering to a mammal in need thereof, a compound of the Formula I, a pharmaceutically acceptable salt, solvate, or prodrug thereof.

In another embodiment, said condition which can be treated by the inhibition of protein kinases is selected from the group consisting of connective tissue disorders, inflammatory disorders, immunology/allergy disorders, infectious diseases, respiratory diseases, cardiovascular diseases, eye diseases, metabolic diseases, central nervous system (CNS) disorders, liver/kidney diseases, reproductive health disorders, gastric disorders, skin disorders and cancers.

Other aspects, advantages, and preferred features of the invention will become apparent from the detailed description below.

DETAILED DESCRIPTION AND PREFERRED EMBODIMENTS OF THE INVENTION

For purposes of the present invention, as disclosed and claimed herein, the following terms and abbreviations are defined as follows:

Unless otherwise indicated, the term "wherever it occurs" refers to any occurrence of any functional groups (such as $R^1$, $R^2$ or any substituents thereof), including any occurrence of any component of any functional groups referred to herein (e.g., the "$(C_1-C_8)$alkyl component of $(C_1-C_8)$alkyl-O—).

Unless otherwise indicated, the term "$(C_1-C_8)$alkyl" as well as the $(C_1-C_8)$alkyl component of other terms referred to herein (e.g., the "$(C_1-C_8)$alkyl component of $(C_1-C_8)$ alkyl-O—), may be linear or branched (such as methyl, ethyl, n-propyl, isopropyl, n-butyl, iso-butyl, secondary-butyl, tertiary-butyl).

Unless otherwise indicated, the term "$(C_2-C_8)$alkenyl" means straight or branched hydrocarbon radical, substituent, moiety, or sub-moiety referred to herein having 2 to 8 carbon atoms having at least one double bond including, but not limited to ethenyl, 1-propenyl, 2-propenyl (allyl), iso-propenyl, 2-methyl-1-propenyl, 1-butenyl, or 2-butenyl.

Unless otherwise indicated, the term "$(C_2-C_8)$alkynyl" is used herein to mean straight or branched hydrocarbon radical, substituent, moiety, or sub-moiety referred to herein having 2 to 8 carbon atoms having one triple bond including, but not limited to, ethynyl (—C≡C—H), propynyl (—CH$_2$—C≡C—H or —C≡C—CH$_3$), or butynyl (—CH$_2$—CH$_2$—C≡C—H, or —CH$_2$—C≡C—CH$_3$, or —C≡C—CH$_2$CH$_3$).

Unless otherwise indicated, the term "$(C_3-C_{10})$ cycloalkyl" refers to a non-aromatic, saturated or partially saturated, monocyclic or fused, Spiro or unfused bicyclic or tricyclic hydrocarbon radical, substituent, moiety, or sub-moiety referred to herein containing a total of from 3 to 10 carbon atoms, preferably 5–8 ring carbon atoms. Exemplary $(C_3-C_{10})$cycloalkyls include monocyclic rings having from 3–7, preferably 3–6, carbon atoms, such as cyclopropyl, cyclobutyl, cyclopentyl, cyclohexyl, cycloheptyl and the like. Illustrative examples of $(C_3-C_{10})$cycloalkyl are derived from, but not limited to, the following:

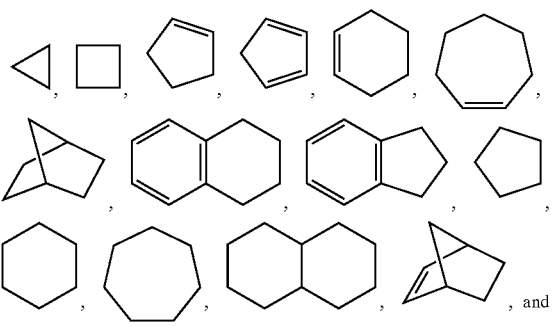, and

Unless otherwise indicated, the term "$(C_2-C_{10})$ heterocyclyl" refers to a non-aromatic, saturated or partially saturated, monovalent, monocyclic or fused, spiro or unfused bicyclic or tricyclic radical, substituent, moiety, or sub-moiety referred to herein containing a total of from 2 to 10 ring carbon atoms and 1 to 5 ring heteroatoms selected from nitrogen, oxygen and sulfur. Illustrative examples of $(C_2-C_{10})$heterocyclyl include azetidinyl, pyrrolidyl, piperidyl, piperazinyl, morpholinyl, chromenyl, tetrahydro-2H-1,4-thiazinyl, tetrahydrofuryl, dihydrofuryl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicyclo[3.2.1]octyl, azabicyclo[3.3.1]nonyl, azabicyclo[4.3.0]nonyl, oxabicyclo[2.2.1]heptyl, 1,5,9-triazacyclododecyl, and the like. Additional illustrative examples of $(C_2-C_{10})$heterocyclyl are derived from, but not limited to, the following:

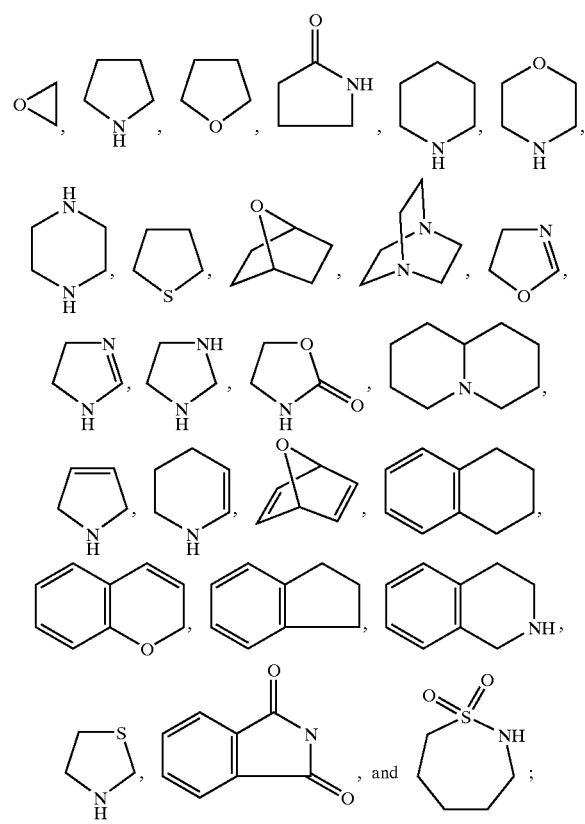

unless otherwise indicated, the foregoing $(C_2-C_{10})$ heterocycyl can be C-attached or N-attached where such is possible. For instance, piperidyl can be piperid-1-yl (N-attached) or piperid-2-yl (C-attached).

Unless otherwise indicated, the term "$(C_6-C_{10})$aryl" refers to an aromatic, monovalent, monocyclic or fused or unfused bicyclic or tricyclic radical, substituent, moiety, or sub-moiety referred to herein containing a total of from 6 to 10 ring carbon atoms. Illustrative examples of $(C_6-C_{10})$aryl are derived from, but not limited to, the following:

Unless otherwise indicated, the term "$(C_6-C_{10})$ heteroaryl" refers to an aromatic, monovalent monocyclic, fused or unfused bicyclic or tricyclic radical, substituent, moiety, or sub-moiety referred to herein containing a total of from 1 to 10 ring carbon atoms and 1 to 5 ring heteroatoms selected from nitrogen, oxygen and sulfur. Illustrative examples of $(C_1-C_{10})$heteroaryl include, but not limited to, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl. Further examples of $(C_1-C_{10})$heteroaryl are derived from, but not limited to, the following:

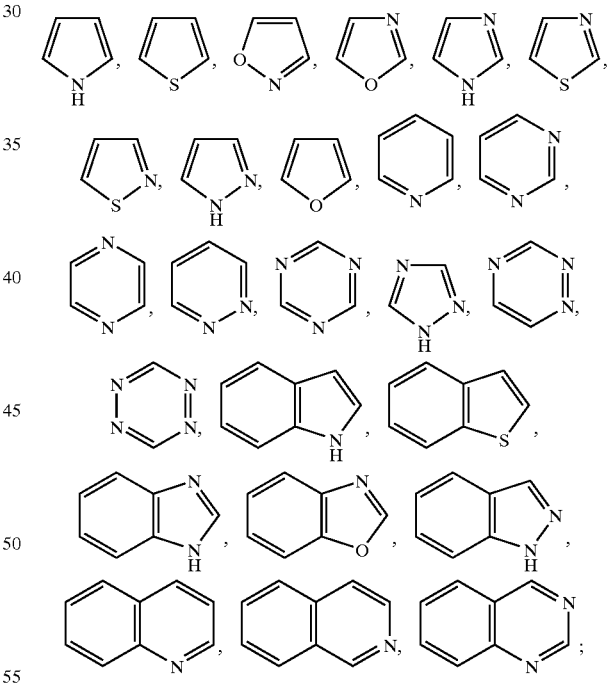

unless otherwise indicated, the foregoing $(C_1-C_{10})$ heteroaryl can be C-attached or N-attached where such is possible. For instance, pyridyl can be pyrid-1-yl (N-attached) or pyrid-3-yl (C-attached).

Unless otherwise indicated, the term "$((C_3-C_{10})$cycloalkyl)$((C_1-C_8)$alkyl)>N—" refers to a radical, substituent, moiety, or sub-moiety referred to herein having the formula:

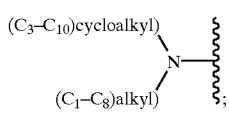

wherein the terms "$(C_3-C_{10})$cycloalkyl" and "$(C_1-C_8)$alkyl" are as defined above.

Unless otherwise indicated, the term "$((C_6-C_{10})$aryl$)((C_1-C_{10})$alkyl$)>N$—" refers to a radical, substituent, moiety, or sub-moiety referred to herein having the formula:

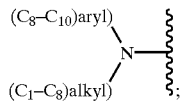

wherein the terms "$((C_6-C_{10})$aryl" and "$(C_1-C_8)$alkyl" are as defined above.

Unless otherwise indicated, the term "$(C_1-C_{10})$heteroaryl-NH—" refers to a radical, substituent, moiety, or sub-moiety referred to herein having the formula:

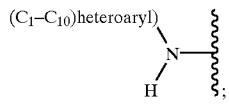

wherein the term "$(C_1-C_{10})$heteroaryl" is as defined above and wherein said $(C_1-C_{10})$heteroaryl is bonded to the —NH— via a ring $(C_1-C_{10})$heteroaryl carbon atom.

Unless otherwise indicated, the term "$(C_2-C_{10})$heterocyclyl-NH—" refers to a radical, substituent, moiety, or sub-moiety referred to herein having the formula:

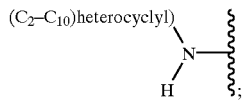

wherein the term "$(C_2-C_{10})$heterocyclyl" is as defined above and wherein said $(C_2-C_{10})$heterocyclyl is bonded to the —NH— via a ring $(C_2-C_{10})$heterocyclyl carbon atom.

The term "a pharmaceutically acceptable salt" refers to a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

The term "prodrug", as used herein, refers to a metabolic precursor of a compound of the Formula I (or a salt thereof that is pharmaceutically acceptable. A prodrug may be inactive when administered to a subject but is converted in vivo to an active compound of the Formula I. The term "active metabolite", as used herein, refers to a metabolic product of a compound of the Formula I that is pharmaceutically acceptable and effective. Prodrugs and active metabolites of compounds of the Formula I may be determined using techniques known in the art. Prodrugs and active metabolites of a compound may be identified using routine techniques known in the art. See, e.g., Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs, Drug Design and Development* (Krogsgaard-Larsen, et al., eds., Harwood Academic Publishers, (1991)).

The CHK-1 inhibitor of the present invention may be administered in combination with other anti-neoplasm therapies including anti-neoplastic agents and radiation therapy.

The term "in combination with" means that the compound of Formula I may be administered shortly before, shortly after, concurrently, or any combination of before, after, or concurrently, with such other anti-neoplasm therapies. Thus, the compound and the anti-neoplastic agent may be administered simultaneously as either as a single composition or as two separate compositions or sequentially as two separate compositions. Likewise, the compound and radiation therapy may be administered simultaneously, separately or sequentially. The compound may be administered in combination with more than one anti-neoplasm therapy. In a preferred embodiment, the compound may be administered from 2 weeks to 1 day before any chemotherapy, or 2 weeks to 1 day before any radiation therapy. In another preferred embodiment, the CHK-1 inhibitor may be administered during anti-neoplastic chemotherapies and radiation therapies. If administered following such chemotherapy or radiation therapy, the CHK-1 inhibitor may be given within 1 to 14 days following the primary treatments. The CHK-1 inhibitor may also be administered chronically or semi-chronically, over a period of from about 2 weeks to about 5 years. One skilled in the art will recognize that the amount of CHK-1 inhibitor to be administered in accordance with the present invention in combination with other antineoplastic agents or therapies is that amount sufficient to enhance the anti-neoplasm effects of anti-neoplastic agents or radiation therapies or that amount sufficient to induce apoptosis or cell death along with the anti-neoplastic or radiation therapy and/or to maintain an antiangiogenic effect. Such amount may vary, among other factors, depending upon the size and the type of neoplasia, the concentration of the compound in the therapeutic formulation, the specific anti-neoplasm agents used, the timing of the administration of the CHK-1 inhibitors relative to the other therapies, and the age, size and condition of the patient.

The term "protein kinases", as used herein, refers to enzymes that catalyze the phosphorylation of hydroxy groups on tyrosine, serine and threonine residues of proteins. The consequences of this seemingly simple activity are staggering; cell growth, differentiation and proliferation, i.e., virtually all aspects of cell life in one way or another depend on the protein kinase activity. Furthermore, abnormal protein kinase activity has been related to a host of disorders, ranging from relatively non-life threatening diseases such as psoriasis to extremely virulent diseases such as glioblastoma (brain cancer). The protein kinases can be conveniently broken down into two major classes, the protein tyrosine kinases (PTKs) and the serine-threonine kinases (STKs). In addition, a third class of dual specificity kinases which can phosphorylate both tyrosine and serine-threonine residues is known. Examples of protein kinases and their isoforms contemplated within this invention include, but are not limited to, Checkpoint kinase 1 (CHK-1), Checkpoint kinase 2 (CHK-2), Cyclin dependent kinase 1 (CDK1), Serum and glucocorticoid regulated kinase (SGK), Adenosine 5'-monophosphate (AMP)-activated protein kinase (AMPK), Lymphoid T cell tyrosine kinase (LCK), Mitogen activated protein kinase-2 (MAPK-2), Mitogen- and stress-activated protein kinase 1 (MSK1), Protein Kinase B (PKB), Protein Kinase B alpha (PKBα), Rho kinase (ROCK-II), P70 S6 kinase (p70S6K), cAMP (adenosine 3',5' cyclic monophosphate)-dependent protein kinase (PKA), Mitogen activated protein kinase-1 (MAPK-1), Protein kinase C-related kinase 2 (PRK2), 3'-Phosphoinositide dependent kinase 1 (PDK1), Fyn kinase (FYN), Protein kinase C (PKC), Protein Kinase C Beta 2 (PKCβII), Protein Kinase C Gamma (PKCγ), Vascular endothelial growth factor receptor 2 (VEGFR-2), Fibroblast growth factor receptor (FGFR), Phosphorylase kinase (PHK), Wee1 kinase (Wee1), and Protein Kinase B (PKB).

Checkpoint kinase 2 (CHK-2) acts as a cell cycle checkpoint controller in response to DNA damage. CHK-2 is a downstream effector of ATM which phosphorylates p53 protein and affects cell cycle progression from $G_1$ to the S phase. CHK-2 activation also affects S phase progression. In addition along with CHK-1, CHK-2 influences $G_2$/M transition and plays a role in apoptosis if the damage cannot be repaired. CHK-2 could play a role in sensitizing cancer cells to DNA-damaging therapies. CHK-2 may also play a role as a tumor suppressor. Bartek, J. et al. (2001) *Nature Reviews, Molecular Cell biology* 2:877–886.

Cyclin dependent kinase 1 (CDK1) is also known as Cdc2 in yeast cells. The cell cycle directs specific events that control growth and proliferation of cells. The cyclin B/Cdk1 complex promotes entry into mitosis. Cyclin B1 overexpression has been found in 90% of colorectal carcinomas Since the cell cycle is dysregulated in human cancers, modulation of CDK activity is a possible therapy. Olomoucine, a CDK inhibitor, has been shown to inhibit cellular proliferation in human cancer cells. In lymphoma cells, olomoucine arrests the cell cycle in both the $G_1$ and $G_2$ phases by inhibiting cyclin E/CDK2 and cyclin B/CDK1. Buolamwini, J. K. (2000) *Current Pharmaceutical Design* 6:379–392; Fan, S., et al. (1999) *Chemotherapy* 45:437–445.

Serum and glucocorticoid regulated kinase (SGK) is rapidly and highly regulated by corticosteroids in A6 cells at the mRNA and protein levels. SGK is also induced by aldosterone in the kidney of adrenalectomized rats. SGK is activated by 3'-phosphoinositide dependent kinase 1 (PDK1). SGK might play a critical role in aldosterone target cells and may be physiologically important in the early response to aldosterone. Aldosterone receptor antagonists have recently shown great promise in clinical trials for patients with heart failure. The ability to mediate the physiological responses to aldosterone may likewise prove beneficial. See Leslie, N. R. et. al. (2001) *Chemical Reviews* 101(8):2365–2380; Funder, J. W. (1999) *Molecular and Cellular Endocrinology* 151(1–2):1–3; Verrey, F., et. al. (2000) *Kidney International* 57(4):1277–1282.

Adenosine 5'-monophosphate (AMP)-activated protein kinase (AMPK) isoform α2 (AMPK α2) is present in high concentrations in skeletal muscle, heart, and liver while the α1 isoform is widely distributed. AMPK, probably the α2 isoform, phosphorylates acetyl-CoA carboxylase β isoform (ACCβ) and inactivates it under conditions electrical stimulation or exercise. In rat skeletal muscle, malonyl-CoA is regulated by ACCβis and involved in the regulatory mechanism of transferring long chain fatty acids into the mitochondria where they are oxidized. AMPK could therefore be linked to obesity and/or insulin resistance, and modulation of AMPK could be potentially beneficial in the treatment of these diseases. AMPK inhibits enzymes involved in glycogen and cholesterol synthesis. It is a possible regulatory enzyme that in response to adenosine 5'-triphosphate (ATP) depletion, reduces further ATP consumption by initiating cellular adjustments that are directed toward maintaining ATP levels. In addition, AMPK has been linked to transcription, regulation of creatinine kinase, apoptosis, and glucose transport See Kemp, B. E. et al. (1999) *Trends in Biochemical Sciences* 24(1):22–25; Friedman, J. (2002) *Nature* 415(6869):268–269; Ruderman, N. B., et. al. (1999) *American Journal of Physiology* 276 (1, Pt 1):E1–E18.

Lymphoid T cell tyrosine kinase (LCK) is a cytosolic non-receptor tyrosine kinase and a T-lymphocyte member of the Src family. LCK has been implicated in early phase T-cell receptor activation by antigens and plays a critical role in T-cell mediated immune responses. Upon activation by autophosphorylation, LCK phosphorylates T-cell receptor ξ-chains which can then recruit a second cytoplasmic protein-tyrosine kinase ZAP-70 to promote T-cell activation. Inhibitors could be used for the treatment of rheumatoid arthritis, diseases related to immune response and T-cell based leukemias and lymphomas. See Garcia-Echeverria, C. (2001) *Current Medicinal Chemistry* 8(13):1589–1604; Majolini, M. B. et. al. (1999) *Leukemia & Lymphoma* 35(3/4):245–254.

Mitogen- and stress-activated protein kinase 1 (MSK1) is activated on stimulation of the Ras-mitogen activated protein kinase (MAPK) pathway and also by the p38 stress kinase pathway. Both pathways are implicated in tumorigenesis. Stimulation of the Ras-MAPK signal transduction pathway by growth factors or phorbol esters results in phosphorylation of histone H3. MSK1 has been shown to mediate epidermal growth factor (EGF) or TPA (12-O-tetradecanoylphorbol-13-acetate, a phorbol ester) induced phosphorylation of H3. There is evidence that persistent activation of Ras-MAPK pathway and MSK1 resulting in elevated phosphorylated H3 levels may contribute to aberrant gene expression observed in oncogene-transformed cells. Inhibition of MSK1 suppressed the induction of c-fos (proto-oncogene) and uPA genes in parental and oncogene-transformed cells. Both c-fos and uPA are involved in tumor invasion and metastasis. See Strelkov, I., et al. (2002) *Cancer Research* 62(1):75–78; Zhong, S., et al. (2001) *Journal of Biological Chemistry* 276(36):33213–33219; Nomura, M., et. al. (2001) *Journal of Biological Chemistry* 276(27);25558–25567.

Rho kinase (ROCK-II) is also known as ROKα. By inhibiting ROCK-II, one could potentially influence Rho GTPases which act as molecular controls that regulate many essential cellular processes, including actin dynamics, cell-cycle progression, and cell adhesion. The in vitro and in vivo biological effects of Y-27632, a specific inhibitor of ROCK, have been described in the literature and include lowering blood pressure in hypertensive rats, inhibition of Rho-induced formation of stress fibers and focal adhesions, and inhibition of tumor growth. See Narumiya, S., et. al(2000) *Methods in Enzymology* 325 (Regulators and Effectors of Small GTPases, Part D): 273–284 (and associated references listed therein); Bishop, et al. (2000) *Biochem. J.* 348: 241–255.

P70 S6 kinase (p70$^{S6G}$) is found as two isoforms-one cytoplasmic and the other in the nucleus. They are similar except for N-terminus, and both are called p70$^{S6K}$ or S6K1. A second functional homologue S6K2 was also identified. P70$^{S6K}$ is a downstream target of the lipid kinase phosphoinositide 3-OH kinase (PI(3)K). P70$^{S6K}$ is implicated in cell cycle control and neuronal cell differentiation. P70$^{S6K}$ may also function in regulating cell motility which could influence tumor metastases, the immune response, and tissue repair. Along with PKB/Akt, p70$^{S6K}$ is a crucial effector in oncogenic protein-tyrosine kinase (PTK) signaling. P70$^{S6K}$ may be a more potent kinase for BAD than PKB/Akt (see above) in response to insulin growth factor 1 (IGF-1) stimulation. P70$^{S6K}$ may therefore play an important anti-apoptotic role. See Blume-Jensen, P., et. al. (2001) *Nature* 411(6835):355–365; Accili, D. (2001) *Journal of Clinical Investigation* 108(11):1575–1576; Hidalgo, M., et. al. (2000) *Oncogene* 19(56):6680–6686; Berven, L., et al. (2000) *Immunology and Cell Biology* 78(4):447–451.

cAMP (adenosine 3',5' cyclic monophosphate)-dependent protein kinase (PKA) is involved in a wide range of physiological responses following interaction with cAMP. cAMP is a second messenger that regulates many different cellular activities such as gene transcription, cell growth and differentiation, ion channel conductivity, and release of neurotransmitters. The cAMP/PKA interaction acts as a major regulatory mechanism in mammals, and PKA has been shown phosphorylate a myriad of physiological substrates. PKA has two major isoforms-PKAI and PKAII. PKAI inhibitors have shown enhancing effects when used in combination certain cytotoxic cancer therapies. Antisense oligonucleotides targeting the PKAI subunit RIα have shown enhanced anti-tumor effects when combined with Taxol. Glucagon activates PKA and PKA may influence insulin response along with calmodulin-dependent protein kinase and protein kinase C. PKA is involved in regulating cardiac L-type calcium channels, and modulation of the implicated regulatory pathways may prove useful in the treatment of heart disease. In addition, dysfunctional T-cells isolated from HIV patients have been restored by the addition of PKAI antagonists. See Skalhegg, B. S., et. al. (2000) *Frontiers in Bioscience* [Electronic Publication] 5:D678–D693; Brandon, E. P., et. al. (1997) *Current Opinion in Neurobiology* 7(3):397–403; Nesher, R. et al.(2002) *Diabetes* 51(Suppl. 1): S68–S73; Shabb, J. B. (2001) *Chemical Reviews* 101(8):2381–2411; Kamp, T. J., et. al. (2000) *Circulation Research* 87(12);1095–1102; Tortora, G., et. al. (2002) *Clinical Cancer Research* 8:303–304; Tortora, G., et. al. (2000) *Clinical Cancer Research* 6:2506–2512.

Mitogen activated protein kinase (MAPK) is also known as ERK. In tumorigenesis, ras oncogenes transmit extracellular growth signals. The MAPK pathway is an important signaling route between membrane-bound ras and the nucleus. A phosphorylation cascade involving three key kinases is involved. They are Raf, MEK (MAP kinase kinase) and MAPK/ERK Raf isoforms phosphorylate and activate isoforms MEK1 and MEK2. MEK1 and 2 are dual specificity kinases that in turn phosphorylate and activate the MAPK isoforms MAPK1/ERK1 and MAPK2/ERK2. In fibroblasts, MAPK1/ERK1 and MAPK2/ERK2 are both strongly activated by growth factors and by tumor-promoting phorbol esters. MAPK1/ERK1 and MAPK2/ERK2 are also involved with glucose regulation, neurotransmitter regulation, and secetagogue regulation (in endocrine tissues). The MAPK pathway has also been linked to the induction of cyclin D1 mRNA and thus linked to G1 phase of cell cycle. See Webb, C. P., et. al. (2000) *Cancer Research* 60(2), 342–349; Roovers, K., et. al. (2000) *BioEssays* 22(9): 818–826; Chen, Z., et al. (2001) *Chemical Reviews* 101(8): 2449–2476; Lee, J. C., et al. (2000) *Immunopharmacology* 47(2–3):185–201, Sebolt-Leopold J. S. (2000) *Oncogene* 19:6594–599; Cheng, F. Y., et. al. (2001) *Journal of Biological Chemistry* 276(35):32552–32558; Cobb, M. H., et al. (2000) Trends in Biochemical Sciences 25(1):7–9; Cobb, M. H., et. al. (1995) *Journal of Biological Chemistry* 270(25): 14843–14846; Deak, M., et al. (1998) *EMBO Journal* 17(15):4426–4441; Davis, J. D. (1993) *Journal of Biological Chemistry* 268(20):14553–14556.

cSrc (also known as p60 c-src) is cytosolic, non-receptor tyrosine kinase. c-Src is involved in the transduction of mitogenic signals from a number of polypeptide growth factors such as epidermal growth factor (EGF) and platelet-derived growth factor (PDGF). c-Src is over expressed in mammary cancers, pancreatic cancers, neuroblastomas, and others. Mutant c-Src has been identified in human colon cancer. c-Src phosphorylates a number of proteins that are involved in regulating cross-talk between the extracellular matrix and the cytoplasmic actin cytoskeleton. Modulation cSrc activity could have implications in diseases relating to cell proliferation, differentiation and death. See Bjorge, J. D., et. al. (2000) *Oncogene* 19(49):5620–5635; Halpern, M. S., et. al. (1996) *Proc. Natl. Acad. Sci. U.S.A.* 93(2), 824–7; Belsches, A. P., et. al. (1997) *Frontiers in Bioscience* [Electronic Publication] 2:D501–D518; Zhan, X., et. al (2001) *Chemical Reviews* 101:2477–2496; Haskell, M. D., et. al. (2001) *Chemical Reviews* 101:2425–2440;

Protein kinase C-related kinase 2 (PRK2) is regulated by the G-protein Rho. PRK2 is found in regions of large actin turnover. Endogenous PRK2 kinase activity increases with keratinocyte differentiation and is associated with keratinocyte cell-cell adhesion and Fyn kinase activation. See Gross, C., et. al. (2001) *FEBS Letters* 496(2,3):101–104; Calautti, E., et. al. (2002) *Journal of Cell Biology* 156(1): 137–148.

3'-Phosphoinositide dependent kinase 1 (PDK1) phosphorylates and activates members of the AGC (cAMP-dependent, cGMP-dependent, and protein kinase C) kinase family that are activated downstream of phosphoinositide 3-kinase (PI3K). PI3K becomes active through insulin stimulation. PDK1 activates a number of protein kinases and therefore can be connected to the regulation of a number of insulin specific events. PDK1 phosphorylation and activation of PKCξ is necessary for insulin-dependent GLUT4 translocation. Insulin-induced GLUT4 translocation is physiologically related to the actin-based cytoskeleton. Disturbances in actin filaments have been linked to loss of insulin effect on glucose transport and decreased translocation of GLUT4. See Wick, K. L., et. al. (2001) *Current Drug Targets: Immune, Endocrine and Metabolic Disorders* 1(3): 209–221; Peterson, R. T., et. al. (1999) *Current Biology* 9(14):R521–R524; Toker, A., et al. (2000) *Cell* 103(2): 185–188; Leslie, N. R. (2001) *Chem. Rev.* 101: 2365–2380.

Fyn kinase (FYN) is a member of the Src family of tyrosine kinases. Fyn has been implicated in positive control of keratinocyte cell-cell adhesion. Adhesion plays a crucial function in establishment and maintenance of organized tissues. Fyn knockout and transgenic mice established that Fyn participates in T cell receptor (TCR) signaling. Overexpression of the fyn(T) transgene produces T cells with enhanced responsiveness to TCR signaling. Conversely, expression of an inactive kinase form is inhibitory. Fyn may be an appropriate target for treatment of autoimmune diseases. Fyn-/-mice are hypersensitive to alcohol which suggests that Fyn might be a target for the treatment of alcoholism. Alteration of Fyn levels may also aid in the treatment of skin disorders. Fyn has been implicated in the regulation of programmed cell death, and Fyn-/-mice exhibit reduced apoptosis. See also PRK2. See Calautti, E., et. al. (2002) *Journal of Cell Biology* 156(1):137–148; Resh, M. D. (1998) *Journal of Biochemistry & Cell Biology* 30(11): 1159–1162.

Vascular endothelial growth factor receptor 2 (VEGFR-2) is also known as FLK-1 and as KDR (kinase insert domain receptor). Other VEGF receptor tyrosine kinases include VEGFR-1(FIt-1) and VEGFR-3 (FIt-4). Angiogenesis or the development of new vasculature is central to the process by which solid tumors grow. The degree of vasculaturization has been linked with increased potential for metastasis. VEGFR-2, expressed only on endothelial cells, binds the potent angiogenic growth factor VEGF and mediates the subsequent signal transduction. Inhibition of VEGF-R2 activity has resulted in decreased angiogenesis and tumor growth in in vivo models, and inhibitors of VEGFR-1 are currently in clinical trials for the treatment of cancer. See Strawn, et al.,(1996) *Cancer Research* 56:3540–3545; Millauer, et al.,(1996) *Cancer Research* 56:1615–1620; Sakamoto, K. M. (2001) *IDrugs* 4(9):1061–1067; Ellis, L. M., et. al. (2000) *Oncologist* 5(Suppl. 1):11–15; Mendel, D. B., et. al (2000) *Anti-Cancer Drug Design* 15:29–41; Kumar, C. C. et. al. (2001) *Expert Opin. Emerging Drugs* 6(2):303–315; Vajkoczy, P., et. al (1999) *Neoplasia* 1(1): 31–41.

Fibroblast growth factor receptor (FGFR) binds the angiogenic growth factors aFGF and bFGF and mediates subsequent intracellular signal transduction. Growth factors such as bFGF may play a critical role in inducing angiogenesis in solid tumors that have reached a certain size. FGFR is expressed in a number of different cell types throughout the body and may or may not play important roles in normal physiological processes in adult humans. Systemic administration of a small-molecule inhibitor of FGFR has been reported to block bFGF-induced angiogenesis in mice. See Yoshiji, et al., (1997) *Cancer Research* 57: 3924–3928; Mohammad, et. al., (1998) *EMBO Journal* 17:5996–5904.

Phosphorylase kinase (PHK) activates glycogen phosphorylase. The primary consequence of this activation is to release glucose 1-phosphate from glycogen. Conversion to glycogen is the major means by which glucose is stored in mammals. Intracellular glycogen stores are used to maintain blood-glucose homeostasis during fasting and are a source of energy for muscle contraction. In Vivo, PHK is phosphorylated by cAMP-dependent protein kinase (PKA) which increases the specific activity of PHK. Both Type 1 and 2 diabetics show reduced glycogen levels in liver and muscle cells. Glycogen levels are tightly regulated by hormones and metabolic signaling. Kinase inhibitors that could augment intracellular glycogen levels may prove beneficial in the treatment of diabetes. See Brushia, R. J., et. al. (1999) *Frontiers in Bioscience [Electronic Publication]* 4:D618–D641; Newgard, C. B., et. al. (2000) *Diabetes* 49:1967–1977; Venien-Bryan, C., et. al. (2002) *Structure* 10:33–41; Graves, D., et. al. (1999) *Pharmacol Ther.* 82: (2–3)143–155; Kilimann, M. W. (1997) *Protein Dysfunction and Human Genetic Disease*, Chapter 4:57–75.

Wee1 kinase (Wee1) along with Mik1 kinase has been shown to phosphorylate Cdc2. Phosphorylation of Cdc2 has been shown to prevent mitotic entry. Wee1 may play an important role the normal growth cycle of cells and may be implicated in cell-cycle checkpoint control. Rhind, N., et. al. (2001) *Molecular and Cellular Biology* 21(5):1499–1508.

Protein Kinase B (PKB) is also known as Akt. There are three very similar isoforms known as PKB $\alpha$, $\beta$ and $\gamma$ (or Akt 1, 2, and 3). Ultraviolet irradiation in the 290–320 nM range has been associated with the harmful effects of sunlight. This irradiation causes activation of PKB/Akt and may be implicated in tumorigenesis. Over expressed PKB/Akt has been shown in ovarian, prostate, breast & pancreatic cancers. PKB/Akt is also involved in cell cycle progression. PKB/Akt promotes cell survival in a number of ways. It phosphorylates the proapoptotic protein, BAD, so that it is unable to bind and inactivate the antiapoptotic protein. Bcl-xl. PKB/Akt also serves to inhibit apoptosis by inhibiting caspase 9 and forkhead transcription factor and by activating IkB kinase. See Barber, A. J. (2001) *Journal of Biological Chemistry* 276(35):32814–32821; Medema, R. H., et al. (2000) *Nature* 404:782–787; Muise-Helmericks, R. C., et. al (1998) *Journal of Biological Chemistry* 273(45): 29864–29872; Nomura, M., et. al. (2001) *Journal of Biological Chemistry* 276(27): 2558–25567; Nicholson, K. M., et. al. (2002) Cellular Signaling 14(5): 381–395; Brazil, D. P., et al. (2001) *Trends in Biochemical Sciences* 26(11): 657–664. Leslie, N. R. (2001) *Chem Rev* 101: 2365–2380.

Protein kinase C (PKC) classical isoforms are designated $\alpha, \beta 1, \beta 2$ and $\gamma$ and all are $Ca^{2+}$ dependent. PKC isoforms are involved in signal transduction pathways linked to a number of physiological responses including membrane transport, cellular differentiation and proliferation, organization of cytoskeletal proteins and gene expression. Tumor promoting phorbol esters activate classical PKC isoforms and antisense oligonucleotides can block this activation. PKC isoforms are often over expressed in various cancers. PKC inhibitors have been shown to reverse p-glycoprotein-mediated multi-drug resistance and can increase intracellular concentrations of other anti-cancer agents. In myocytes, PKC isoforms have been implicated in certain cardiac pathologies. PKC-$\gamma$ is highly expressed in brain and spinal cord and is primarily localized in dendrites and neuron cell bodies. PKC-$\beta$2 is involved in cell proliferation and overexpression increases sensitivity to cancer. PKC$\beta$ inhibitors are a potential new therapy for diabetic retinopathy with clinical trials ongoing. See Magnelli, L., et. al. (1997) *Journal of Cancer Research and Clinical Oncology* 123(7):365–369; Clerk, A, et al (2001) *Circulation Research* 89(10): 847–849; Carter, C. (2000) Current Drug Targets1(2):163–183; Greenberg, S., et. al. (1998) *Alcohol* 16(2);167–175; Rosenzweig, T., et. al. (2002) Diabetes 51(6):1921–1930; Deucher, A., et. al. (2002) *Journal of Biological Chemistry* 277(19): 17032–17040; Frank, R. N. (2002) *American Journal of Ophthalmology* 133(5):693–698; Parekh, D., et. al. (2000) *EMBO Journal* 19(4):496–503; Newton, A. C. (2001) *Chem. Rev.* 101:2353–2364.

The term "treating" or "treated", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Connective tissue disorders" as used herein refers to disorders such as degenerative cartilage loss following traumatic joint injury, osteoarthritis, osteoporosis, Paget's disease, loosening of artificial joint implants, periodontal disease and gingivitis.

"Destruction of articular cartilage" as used herein refers to connective tissue disorders resulting in articular cartilage destruction, preferably joint injury, reactive arthritis, acute pyrophosphate arthritis (pseudogout), psoriatic arthritis, or juvenile rheumatoid arthritis, more preferably osteoarthritis.

"Inflammatory disorders" as used herein refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

"Immunology/allergy disorders" as used herein refers to disorders such as organ transplant toxicity, allergic reactions, allergic contact hypersensitivity, autoimmune disorders such as those disorders associated with granulomatous inflammation/tissue remodeling (such as asthma), immunosuppression and sarcoid.

"Infectious diseases," including those mediated by viruses, bacteria, fungi or mycobacterial infection, as used herein refers to disorders such as septic arthritis, AIDS, fever; Prion diseases, myasthenia gravis, Malaria, sepsis, hemodynamic shock and septic shock.

"Respiratory diseases" as used herein refers to disorders such as chronic obstructive pulmonary disease (including emphysema), acute respiratory distress syndrome, asthma, hyperoxic alveolar injury and idiopathic pulmonary fibrosis and other fibrotic lung diseases.

"Cardiovascular diseases" as used herein refers to disorders such as atherosclerosis including atherosclerotic plaque rupture; aortic aneurysm including abdominal aortic aneurysm and brain aortic aneurysm; congestive heart failure; myocardial and cerebral infarction; stroke; cerebral ischemia; coagulation and acute phase response; left ventricular dilation; post ischemic reperfusion injury; angiofibromas; hemangiomas; and restenosis.

"Eye diseases" as used herein refers to disorders such as aberrant angiogenesis, ocular angiogenesis, ocular inflammation, keratoconus, Sjogren's syndrome, myopia, ocular tumors, corneal graft rejection, corneal injury, neovascular glaucoma, corneal ulceration, corneal scarring, macular degeneration (including "Age Related Macular Degeneration (ARMD) including both wet and dry forms), proliferative vitreoretinopathy and retinopathy of prematurity.

"Metabolic diseases" as used herein refers to disorders such as diabetes (including non-insulin dependent diabetes mellitus, diabetic retinopathy, insulin resistance, diabetic ulceration).

"Central Nervous System" (CNS) disorders as used herein refers to disorders such as head trauma, spinal cord injury, Inflammatory diseases of the central nervous system, neurodegenerative disorders (acute and chronic), Alzheimer's disease, demyelinating diseases of the nervous system, Huntington's disease, Parkinson's disease, peripheral neuropathy, pain, cerebral amyloid angiopathy, nootropic or cognition enhancement, amyotrophic lateral sclerosis, multiple sclerosis, migraine, depression and anorexia.

"Liver/Kidney diseases" as used herein refers to disorders such as nephrotic syndromes such as glomerulonephritis and glomerular disease of the kidney, proteinuria, cirrhosis of the liver and interstitial nephritis.

"Reproductive Health disorders" as used herein refers to disorders such as endometriosis, contraception (male/female), dysmenorrhea, dysfunctional uterine bleeding, premature rupture of fetal membranes and abortifactant.

"Gastric disorders" as used herein refers to disorders such as colonic anastomosis and gastric ulcers.

"Skin disorders" as used herein refers to disorders such as skin aging, pressure sores, psoriasis, eczema, dermatitis, radiation damage, tissue ulceration, decubital ulcers, epidermolysis bullosa, abnormal wound healing (topical and oral formulations), burns and scleritis.

"Cancers" as used herein refers to disorders such as solid tumor cancer including colon cancer, breast cancer, lung cancer and prostrate cancer, tumor invasion, tumor growth tumor metastasis, cancers of the oral cavity and pharynx (lip, tongue, mouth, pharynx), esophagus, stomach, small intestine, large intestine, rectum, liver and biliary passages, pancreas, larynx, lung, bone, connective tissue, skin, cervix uteri, corpus endometrium, ovary, testis, bladder, kidney and other urinary tissues, eye brain and central nervous system, thyroid and other endocrine gland, Hodgkin's disease, non-Hodgkin's lymphomas, multiple myeloma and hematopoietic malignancies including leukemias and lymphomas including lymphocytic, granulocytic and monocytic.

The following reaction Schemes illustrate the preparation of the compounds of the present invention. Unless otherwise indicated each of A, the group —Y—Z—, X, $R^1$, $R^2$, $R^3$, and $R^4$ in the reaction Schemes and the discussion that follows are defined as above.

SCHEME 1

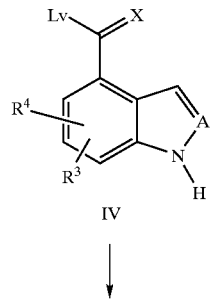

IV

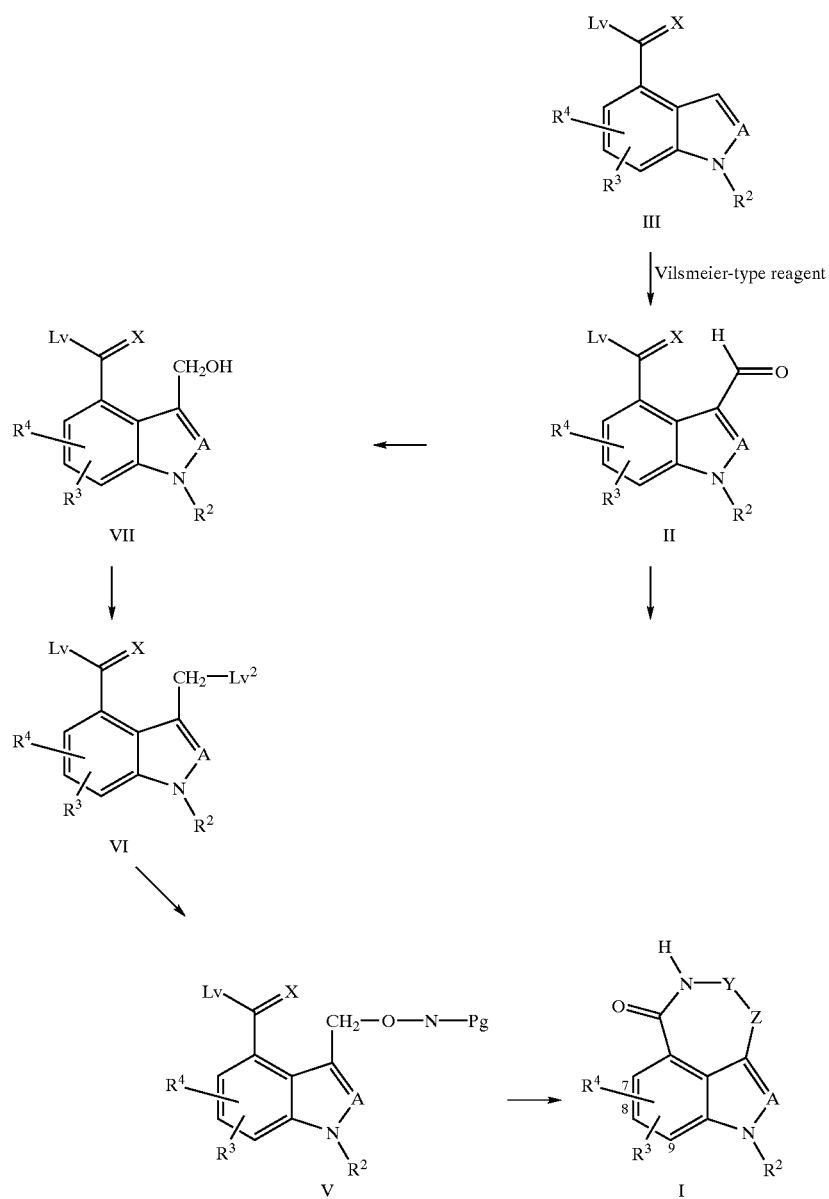
SCHEME 2
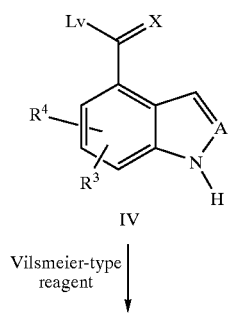

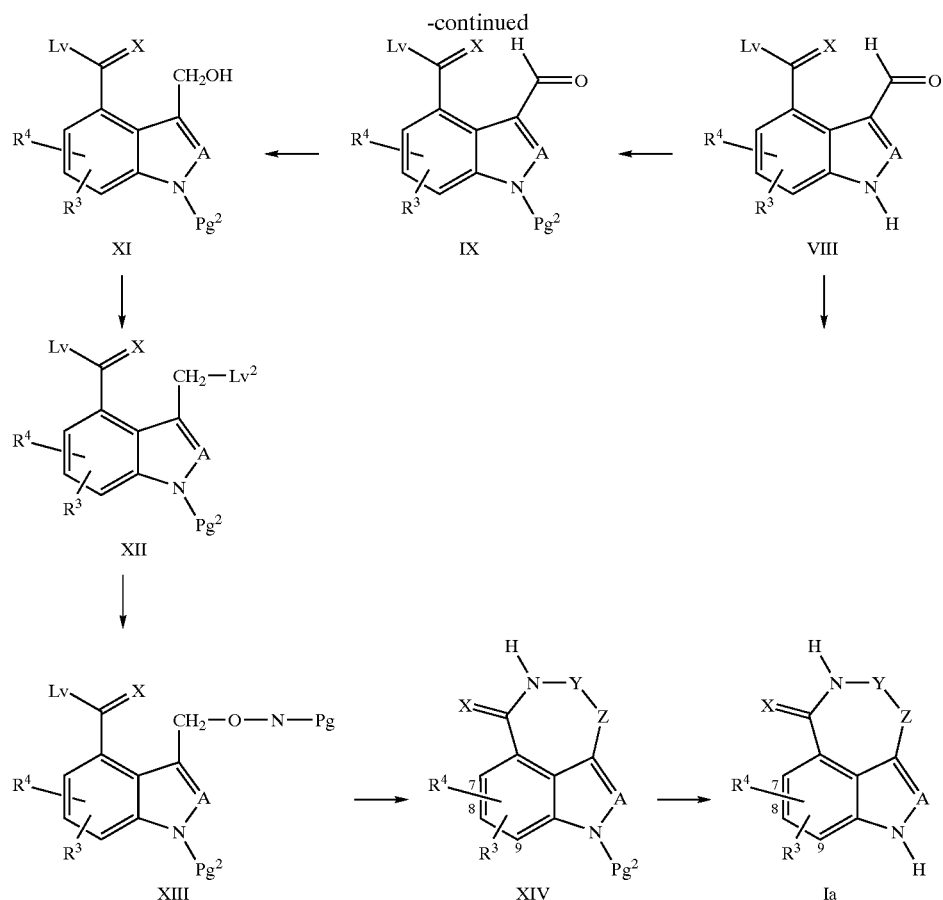
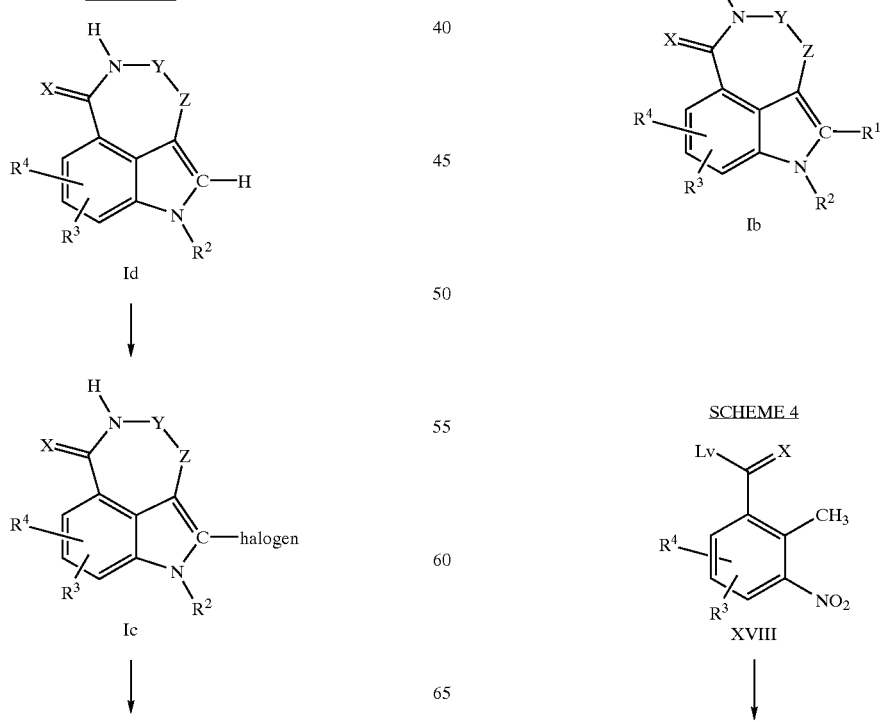
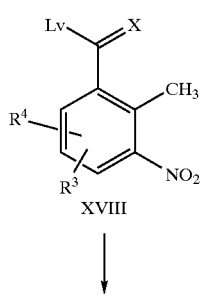

-continued
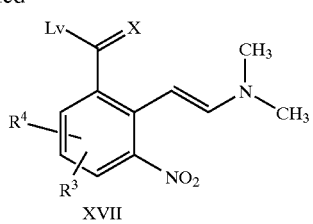
XVII
↓
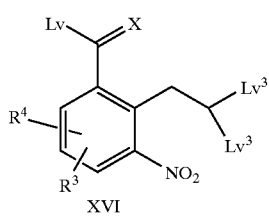
XVI
↓
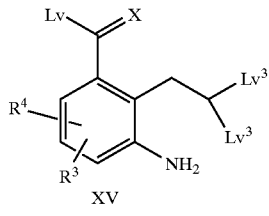
XV
↓
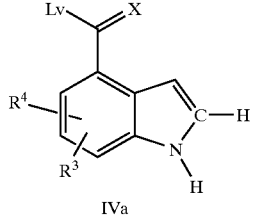
IVa
SCHEME 5
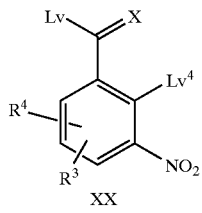
XX
↓
-continued
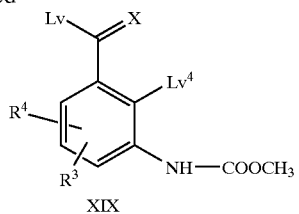
XIX
↓
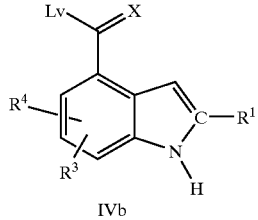
IVb
SCHEME 6
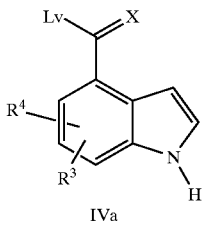
IVa
↓
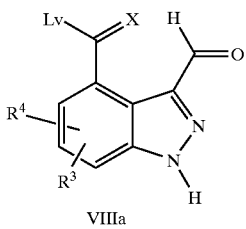
VIIIa
↓
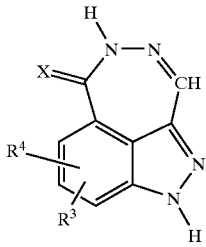
Ie
↓

-continued

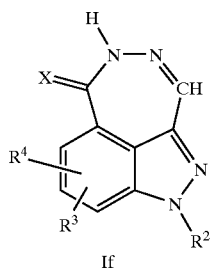

If

Scheme 1 refers to the preparation of compounds of the formula I. Referring to Scheme 1, a compound of formula I, wherein the group —Y—Z— has the formula —N=CH— and $R^2$ is other than hydrogen, can be prepared by reacting a compound of the formula II, wherein $R^2$ is other than hydrogen and wherein Lv is a leaving group, with hydrazine in a solvent. Suitable Lv leaving groups include methoxy, ethoxy, or benzyloxy, preferably methoxy. Suitable solvents include alcohols (such as ethanol), preferably methanol. The aforesaid reaction can be conducted at a temperature of about 25° C. to about 90° C., preferably about 65° C. The aforesaid reaction can be conducted for a time period of about 5 minutes to about 24 hours, preferably about 0.5 hour Compounds of formula II, wherein $R^2$ is other than hydrogen and wherein Lv is as described above, can be prepared by reacting a compound of the formula III, wherein $R^2$ is other than hydrogen and wherein Lv is as described above, with a Vilsmeier-type formylating reagent in a solvent. Suitable Vilsmeier-type formylating reagents include $POCl_3$ and DMF or $(CF_3SO_2)_2O$ and DMF; preferably $POCl_3$ and DMF. Suitable solvents include chloroform, dioxane, tetrahydrofuran, dimethylformamide, or methylene chloride; preferably methylene chloride. The aforesaid reaction can be conducted at a temperature of about 0° C. to about 25° C., preferably about 0° C. during the reagent addition then allowing the reaction mixture to warm to 23° C. over about 0.5 hour. The aforesaid reaction can be conducted for a time period of about 5 minutes to about 24 hours, preferably about 0.5 hour.

Compounds of formula III, wherein $R^2$ is other than hydrogen and wherein Lv is as described above, can be prepared reacting a compound of formula IV, wherein Lv is as described above, with a compound of formula:

wherein $Lv^1$ is a leaving group, such as halo, preferably bromo or chloro, in the presence of a suitable base in a polar solvent. Suitable bases include alkoxide bases (such as sodium methoxide, sodium ethoxide, or potassium tert-butoxide); hydride bases (such as sodium hydride); or carbonate bases (such as potassium carbonate or cesium carbonate); preferably potassium carbonate. Suitable polar solvents include tetrahydrofuran, dimethylformamide, dimethyl sulfoxide, or alcohols (such as ethanol), preferably dimethylformamide. The aforesaid reaction can be conducted at a temperature of about 0° C. to about 100° C., preferably about 80° C. The aforesaid reaction can be conducted for a time period of about 0.5 hour to about 72 hours, preferably about 24 hours.

A compound of formula I, wherein the group —Y—Z— is —O—$CH_2$— and wherein $R^2$ is other than hydrogen, can be prepared by reacting a compound of formula V, wherein $R^2$ is other than hydrogen, wherein Pg is a protecting group, and Lv is as described above, with a Pg deprotecting agent.

Suitable Pg includes phthaloyl, tert-butoxycarbonyl, benzyloxycarbonyl, or ethoxycarbonyl; preferably phthaloyl. Suitable Pg deprotecting agents include hydrazine, trifluoroacetic acid, hydrochloric acid, hydrogen chloride, hydrogen bromide in acetic acid, or hydrogen gas and Pd catalyst; preferably hydrazine. Acidic reactions can be neutralized after deprotection with a suitable base including tertiary amines (such as triethylamine or diisopropylethylamine) or carbonate bases (such as potassium carbonate); preferably triethylamine. Suitable solvents include dimethylformamide, methylene chloride, chloroform, or alcohol, (such as methanol), preferably methanol. The aforesaid reaction can be conducted at a temperature of about 20° C. to about 130° C., preferably about 65° C. The aforesaid reaction can be conducted for a time period of about 0.5 hours to about 48 hours, preferably about 2 hours.

A compound of formula V, wherein $R^2$ is other than hydrogen, wherein Pg is a protecting group, and Lv is as described above, can be prepared by reacting a compound of formula VI, wherein $R^2$ is other than hydrogen, $Lv^2$ is a leaving group and Lv is as described above, with a compound of formula

in the presence of a base in a solvent. Suitable $Lv^2$ leaving groups include halo, toluenesulfonyl, methanesulfonyl, trifluoromethanesulfonyl, or Mitsunobu-type reaction adducts. Suitable compounds of formula Pg—N—OH include N-hydroxyphthalimide, tert-butyl N-hydroxylcarbamate, N-hydroxyurethane, or benzyl N-hydroxycarbamate. Suitable bases include sodium hydride, 1,8-diazabicyclo[5.4.0]undec-7-ene, pyridine, tertiary amines (such as diisopropylethylamine or triethylamine) or carbonate bases (such as sodium carbonate); preferably sodium carbonate. Suitable solvents include dimethylformamide, dimethylsulfoxide, tetrahydrofuran, methylene chloride, chloroform, or alcohol (such as methanol); preferably dimethylsulfoxide. The aforesaid reaction can be conducted at a temperature of about −25° C. to about 80° C., preferably about 23° C. The aforesaid reaction can be conducted for a time period of about 5 minutes to about 48 hours, preferably about 20 hours.

A compound of formula VI, wherein $R^2$ is other than hydrogen and $Lv^2$ and Lv are as described above, can be prepared by reacting a compound of formula VII, wherein $R^2$ is other than hydrogen and Lv is as described above, with an $Lv^2$ producing agent, in a solvent. Suitable $Lv^2$ producing agents include $(C_6H_5)_3P$ and $CCl_4$; $(C_6H_5)_3P$ and $PBr_3$; para-$CH_3C_6H_4SO_2Cl$; $CH_3SO_2Cl$; $(CF_3SO_2)_2O$; or Mitsunobu-type reagents (such as diethyl azodicarboxylate and $(C_6H_5)_3P$); preferably $(C_6H_5)_3P$ and $CCl_4$. Suitable solvents include methylene chloride, chloroform, tetrahydrofuran, carbon tetrachloride, benzene, or toluene; preferably methylene chloride. The aforesaid reaction can be conducted at a temperature of about −25° C. to about 80° C., preferably about 23° C. The aforesaid reaction can be conducted for a time period of about 5 minutes to about 24 hours, preferably about 20 hours.

A compound of formula VII, wherein $R^2$ is other than hydrogen and Lv is as described above, can be prepared by reacting a compound of formula II, wherein $R^2$ is other than hydrogen and Lv is as described above, with a reducing agent in a solvent. Suitable reducing agents include sodium borohydride, lithium borohydride, zinc borohydride, diborane, borane complexes, triacetoxyborohydride, sodium cyanoborohydride, or lithium cyanoborohydride; preferably sodium borohydride. Suitable solvents include alcohol (such as methanol), tetrahydrofuran, a mixture of methanol and anhydrous HCl, or a mixture of methanol and acetic acid; preferably methanol. The aforesaid reaction can be conducted at a temperature of about 0° C. to about 50° C., preferably about 23° C. The aforesaid reaction can be conducted for a time period of about 5 minutes to about 24 hours, preferably about 15 minutes.

Scheme 2 refers to the preparation of compounds of the formula Ia, which is a compound of formula I wherein $R^2$ is hydrogen. Referring to Scheme 2, a compound of formula Ia, wherein the group —Y—Z— has the formula —N═CH—, can be prepared by reacting a compound of the formula VIII, wherein Lv is a leaving group, as described above, with hydrazine in a solvent The reaction condition is as described above in the description for Scheme 1 for the preparation of a compound of formula I from a compound of formula II.

Compounds of formula VIII, wherein Lv is as described above, can be prepared by reacting a compound of the formula IV, wherein Lv is as described above, with a Vilsmeier reagent in a solvent. The reaction condition is as described above in the description for Scheme 1 for the preparation of compounds of formula II from a compound of formula III.

A compound of formula Ia, wherein the group —Y—Z— is —O—CH$_2$—, can be prepared by reacting a compound of formula XIV, wherein Pg$^2$ is a protecting group, with a Pg$^2$ deprotecting agent in a solvent. Suitable Pg$^2$ protecting groups include tert-butoxycarbonyl, benzyloxycarbonyl, or 2-(trimethylsilyl)ethoxymethyl; preferably tert-butoxycarbonyl. Suitable Pg$^2$ deprotecting agents include trifluoroacetic acid, hydrochloric acid, hydrogen chloride, hydrogen bromide in acetic acid, hydrogen gas and Pd catalyst, or tetrabutylammonium fluoride; preferably trifluoroacetic acid. Suitable solvents include methylene chloride, chloroform, dioxane, dimethylformamide, or alcohol (such as methanol); preferably methylene chloride. The aforesaid reaction can be conducted at a temperature of about 20° C. to about 80° C., preferably about 23° C. The aforesaid reaction can be conducted for a time period of about 15 minutes to about 48 hours, preferably about 2 hours.

A compound of formula XIV, wherein Pg$^2$ is as described above, can be prepared by reacting a compound of formula XIII, wherein Pg is a protecting group as described in the compound of formula V of Scheme 1, and Pg$^2$ and Lv are as described above, with a Pg deprotecting agent. The reaction condition is as described above in the description for Scheme 1 for the preparation of a compound of formula I from a compound of formula V.

A compound of formula XIII, wherein Pg$^2$, Lv and Lv$^2$ are as described above, can be prepared by reacting a compound of formula XII, wherein Pg$^2$, Lv and Lv$^2$ are as described above, with a compound of formula

Pg—N—OH wherein Pg is as described above, in the presence of a base in a solvent. The reaction condition is as described above in the description for Scheme 1 for the preparation of a compound of formula V from a compound of formula VI.

A compound of formula XII, wherein Pg$^2$, Lv$^2$ and Lv are as described above, can be prepared by reacting a compound of formula XI, wherein Pg$^2$ and Lv are as described above, with an Lv$^2$ producing agent, in a solvent. The reaction condition is as described above in the description for Scheme 1 for the preparation of a compound of formula VI from a compound of formula VII.

A compound of formula XI, wherein Pg$^2$ and Lv are as described above, can be prepared by reacting a compound of formula IX, wherein Pg$^2$ and Lv are as described above, with a reducing agent in a solvent. The reaction condition is as described above in the description for Scheme 1 for the preparation of a compound of formula VII from a compound of formula II.

A compound of formula IX, wherein Pg$^2$ and Lv are as described above, can be prepared by reacting a compound of formula VIII, wherein Lv is as described above, with a Pg$^2$ protecting agent in the presence of a suitable base in a solvent. Suitable Pg$^2$ protecting agents include di-tert-butyl dicarbonate, benzyl chloroformate, or 2-(trimethylsilyl)ethoxymethyl chloride; preferably di-tert-butyl dicarbonate. Suitable bases include hydride bases (such as sodium hydride, lithium hydride, or potassium hydride); preferably sodium hydride. Suitable solvents include tetrahydrofuran or dimethylformamide; preferably tetrahydrofuran. The aforesaid reaction can be conducted at a temperature of about 0° C. to about 60° C., preferably about 23° C. The aforesaid reaction can be conducted for a time period of about 15 minutes to about 24 hours, preferably about 1 hour.

Scheme 3 refers to the preparation of a compound of the formula Ib, which is a compound of the formula I wherein A is ═CR$^1$—. Referring to Scheme 3, a compound of formula Ib, can be prepared by reacting a compound of the formula Ic, wherein halogen is selected from bromo or iodo, with a coupling reagent of the formula:

R$^1$—M wherein M is a H or metal, in the presence of palladium and copper catalysts in a solvent. Suitable metals include boron and tin, preferably boron. Suitable coupling reagents include Stille coupling reagent (see Chamoin, S., Houldsworth, S., Snieckus, V. *Tetrahedron Lett.* 1998, 39, 4175–4178 incorporated herein by reference), Suzuki coupling reagent (see Littke, A. F., Chaoyang, D., Fu, G. C. *J. Am. Chem. Soc.* 2000, 122, 4020–4028 incorporated herein by reference), or Sonogashira coupling reagent (see Sonogashira, K., Tohda, Y., Hagihara, N. *Tetrahedron Lett.* 1975, 16, 44467–4470 incorporated herein by reference); preferably Suzuki coupling reagent or Stile coupling reagent. Suitable palladium and copper catalysts include Pd(C$_6$H$_5$)$_3$P)$_4$, Pd(dba)$_2$, Pd(P(C$_6$H$_5$)$_3$)Cl$_2$ and CuI. Suitable solvents include dimethylformamide or tetrahydrofuran; preferably dimethylformamide. The aforesaid reaction can be conducted at a temperature of about 22° C. to about 110° C., preferably about 90° C. The aforesaid reaction can be conducted for a time period of about 5 minutes to about 48 hours, preferably about 2 hours.

Some compounds of the formula Ib, such as those wherein R$^1$ is a substituted alkyne (for example methylaminopropynyl) may need additional steps requiring the use of a protecting group (for example tert-butoxycarbonyl). These protection groups and their removal processes are well known in the art and can be found in Greene and Wuts, *Protecting Groups in Organic Synthesis*, (John Wiley & Sons, 2$^{nd}$ Ed). Furthermore, compounds of the Ib, such as those wherein R$^1$, R$^2$ or R$^3$ is a substituted alkyl, alkynyl, aromatic or vinyl are subjected to additional standard chemical transformations (for example catalytic hydrogenation, OsO$_4$/NMMO/NaIO$_4$ oxidative cleavage, mesylation/displacement, reductions and reductive amination). These processes are also well known in the art and can be found in Larock, R. C., *Comprehensive Organic Transformations* (Wiley-VCH, 2$^{nd}$ Ed.).

A compound of formula Ib, wherein A is ═CR$^1$— and R$^1$ is —(C═O)—O—(C$_1$–C$_6$)alkyl, can be prepared by reacting a compound of the formula Ic, wherein halogen is selected from bromo or iodo, with carbon monoxide in the presence of a palladium catalyst, a base, and a compound of the formula H—O—($C_1$-$C_6$)alkyl (depending on the —($C_1$-$C_6$)alkyl part of the desired $R^1$) in a solvent. Suitable palladium catalysts include Pd(dppf)$Cl_2$. Suitable bases include tertiary amine bases such as triethylamine. Suitable compounds of the formula H—O—($C_1$-$C_6$)alkyl include methanol, ethanol, or propanol. Suitable solvents include dimethylformamide or tetrahydrofuran; preferably dimethylformamide. The aforesaid reaction can be conducted at a temperature of about 22° C. to about 110° C., preferably about 85° C. The aforesaid reaction can be conducted for a time period of about 30 minutes to about 48 hours, preferably about 16 hours.

A compound of formula Ib, wherein A is =$CR^1$— and $R^1$ is —(C=O)—NH—($C_1$-$C_6$)alkyl or —(C=O)—NH—($C_1$-$C_6$)alkyl-OH or —(C=O)—NH—($C_1$-$C_6$)alkyl-N($CH_3$)$_2$ or —(C=O)-1-(4-N-methylpiperazine) can be prepared by reacting a compound of the formula Ic, wherein halogen is selected from bromo or iodo, with carbon monoxide in the presence of a palladium catalyst, a base, and a compound of the formula $H_2N$—($C_1$-$C_6$)alkyl or $H_2N$—($C_1$-$C_6$)alkyl-OH or $H_2N$—($C_1$-$C_6$)alkyl-N($CH_3$)$_2$ or N-methylpiperazine (depending on the —($C_1$-$C_6$)alkyl part of the desired $R^1$) in a solvent. Suitable palladium catalysts include Pd(dppf)$Cl_2$. Suitable bases include tertiary amine bases such as triethylamine. Suitable compounds of the formulas $H_2N$—($C_1$-$C_6$)alkyl or $H_2N$—($C_1$-$C_6$)alkyl-OH or $H_2N$—($C_1$-$C_6$)alkyl-N($CH_3$)$_2$ or N-methylpiperazine include 2-aminoethanol, N,N-dimethylethylenediamine, methylamine N-methylpiperazine Suitable solvents include dimethylformamide or toluene; preferably dimethylformamide. The aforesaid reaction can be conducted at a temperature of about 22° C. to about 110° C., preferably about 85° C. The aforesaid reaction can be conducted for a time period of about 30 minutes to about 48 hours, preferably about 16 hours.

A compound of formula Ic, wherein halogen is bromo or iodo, can be prepared by reacting a compound of formula Id with a suitable halogenating agent in a solvent. Suitable halogenating agents include N-bromosuccinimide or N-iodosuccinimide; preferably N-bromosuccinimide. Suitable solvents include tetrahydrofuran or dimethylformamide, preferably dimethylformamide. The aforesaid reaction can be conducted at a temperature of about 0° C. to about 75° C., preferably about 22° C. The aforesaid reaction can be conducted for a time period of about 5 minutes to about 24 hours, preferably about 1 hour.

A compound of formula Ic, wherein halogen is chloro, can be prepared by reacting a compound of formula Id with a suitable chlorinating agent in a solvent. Suitable chlorinating agents include N-chlorosuccinimide Suitable solvents include tetrahydrofuran or dimethylformamide; preferably dimethylformamide. The aforesaid reaction can be conducted at a temperature of about 0° C. to about 75° C., preferably about 45° C. The aforesaid reaction can be conducted for a time period of about 5 minutes to about 24 hours, preferably about 1 hour.

Scheme 4 refers to the preparation of a compound of the formula IVa, which is a compound of formula IV of Scheme 1, wherein A is =CH—. Referring to Scheme 4, a compound of formula IVa, wherein Lv is as described above, can be prepared by reacting a compound of formula XV, wherein Lv is as described above and each of $Lv^3$ is a leaving group, with a suitable acid in a polar protic solvent (see Coe, J. W., Vetelino, M. G., Bradlee, M. J., *Tetrahedron Lett.* (1996), 37, 6045–6047 incorporated herein by reference). Suitable $Lv^3$ leaving groups include methoxy or ethoxy, preferably methoxy. Suitable acids include HCl, $H_2SO_4$, para toluenesulfonic acid, camphorsulfonic acid, or Lewis acids; preferably HCl. Suitable polar protic solvents include alcohols (such as methanol or ethanol), preferably methanol. The aforesaid reaction can be conducted at a temperature of about 0° C. to about 100° C., preferably about 65° C. The aforesaid reaction can be conducted for a time period of about 5 minutes to about 24 hours, preferably about 1 hour.

A compound of formula XV, wherein Lv and $Lv^3$ are as described above, can be prepared by reacting a compound of formula XVI, wherein Lv and $Lv^3$ are as described above, with a reducing agent in a polar solvent. Suitable reducing agents include catalytic transfer reagents such as hydrazine hydrate, ammonium formate, ammonium chloride, cyclohexene, or hydrogen gas in the presence of catalysts [such as Pd on carbon (see Coe, J. W., Vetelino, M. G., Bradlee, M. J. *Tetrahedron Lett.* (1996), 37, 6045–6047 incorporated herein by reference), Ru, Rh, Raney nickel, or Pt]; HCl or acetic acid in the presence of In, Fe, Sn, or Zn; HCl/$SnCl_2$;$SnCl_2$.2$H_2O$; $Bu_3SnH$/AIBN; or $Fe_3(CO)_{12}$; preferably $SnCl_2$.2$H_2O$ or hydrogen gas in the presence of Pd on carbon or Raney nickel. Suitable polar solvents include alcohols (such as methanol or ethanol), preferably methanol. The aforesaid reaction can be conducted at a temperature of about 0° C. to about 100° C., preferably about 23° C. Where hydrogen gas is used the reaction pressure can be 1 to 4 atm, preferably 1 atm. The aforesaid reaction can be conducted for a time period of about 2 hours to about 48 hours, preferably about 24 hours.

A compound of formula XVI, wherein Lv and $Lv^3$ are as described above, can be prepared by reacting a compound of formula XVII, wherein Lv is as described above, with a suitable acid in an anhydrous polar protic solvent of formula $Lv^3$—H. Suitable acids include HCl, $H_2SO_4$, or para toluenesulfonic acid, preferably HCl. Alternatively, HCl can be generated in situ by using an HCl generating agent such as TMS-Cl or acetyl chloride, preferably TMS-Cl, in an anhydrous polar protic solvent such as methanol. Suitable anhydrous polar protic solvents of formula $Lv^3$—H include anhydrous alcohols (such as methanol or ethanol), preferably anhydrous methanol. The aforesaid reaction can be conducted at a temperature of about 23° C. to about 78° C., preferably about 65° C. The aforesaid reaction can be conducted for a time period of about 30 minutes to about 48 hours, preferably about 24 hours.

A compound of formula XVII, wherein Lv is as described above, can be prepared by reacting a compound of formula XVIII, wherein Lv is as described above, with a compound of formula

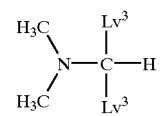

wherein each of $Lv^3$ is as described above, in a polar solvent. Suitable compounds of formula $(CH_3)_2$—N—CH—(LV)$_2$ include dimethylformamide-dimethylacetal. Suitable polar solvents include dimethylformamide, toluene, or alcohol (such as ethanol), preferably dimethylformamide. The aforesaid reaction can be conducted at a temperature of about 22° C. to about 150° C., preferably about 110° C. The aforesaid reaction can be conducted for a time period of about 15 minutes to about 24 hours, preferably about 6 hours.

Compounds of formula $(CH_3)_2$—NCH—$(Lv^3)_2$ are commercially available.

Compounds of the formula XVII, wherein Lv is as described above, are commercially available or alternatively can be made by methods well known to those skilled in the art.

Scheme 5 refers to preparation of a compound of the formula IVb, which is a compound of formula IV of Scheme 1, wherein A is =CR$^1$—. Referring to Scheme 5, a compound of formula IVb can be prepared by reacting a compound of the formula XIX, wherein Lv is as described above and Lv$^4$ is a leaving group, with a suitable substituted alkyne of formula

wherein M$^1$ is H or metal (such as Sn or B), preferably H or Sn, in the presence of a metal catalyst in a polar solvent. Suitable Lv$^4$ leaving groups include halo preferably bromo or iodo. Suitable metal catalysts Include palladium or copper catalysts (See Fagnola, M. C., et. al. *Tetrahedron Lett.* (1997), 38, 2307–2310 incorporated herein by reference). Suitable polar solvents include dimethylformamide, dioxane, dimethylsulfoxide, or mixtures thereof, preferably a mixture of dimethylformamide and dioxane. The aforesaid reaction can be conducted at a temperature of about 22° C. to about 120° C., preferably about 90° C. The aforesaid reaction can be conducted for a time period of about 5 minutes to about 24 hours, preferably about 8 hours.

Compounds of formula M$^1$—C≡C—R$^1$ are commercially available or can be made by methods well known to those skilled in the art.

A compound of formula XIX, wherein Lv and Lv$^4$ are as described above, can be prepared by reacting a compound of formula XX, wherein Lv and Lv$^4$ are as described above, with a reducing agent in the presence of (CH$_3$CO)$_2$O in a polar solvent. Suitable reducing agents include hydrogen gas in the presence of catalysts such as Pd/C (see Coe, J. W., Vetelino, M. G., Bradlee, M. J. *Tetrahedron Lett.*(1996), 37, 6045–6047 incorporated herein by reference), Rd, Raney nickel, or Pt; acetic acid in the presence of In, Fe, or Zn; SnCl$_2$; or Fe$_3$(CO)$_{12}$; preferably hydrogen gas in the presence of Pd/C; or acetic acid in the presence of Fe. Suitable polar solvents include dimethylformamide, methanol, ethanol, or acetic acid; preferably methanol or acetic acid. The aforesaid reaction can be conducted at a temperature of about 20° C. to about 100° C., preferably about 22° C. Where hydrogen gas is used the reaction pressure can be 1 to 4 atm, preferably 1 atm. The aforesaid reaction can be conducted for a time period of about 2 hours to about 48 hours, preferably about 24 hours.

Compounds of the formula XX are commercially available or can be made by methods well known to those skilled in the art.

Scheme 6 refers to preparation of a compound of the formula If, which is a compound of formula I of Scheme 1, wherein the group —Y—Z— has the formula —N═CH—, A is ═N—, and R$^2$ is other than hydrogen. Referring to Scheme 6, a compound of formula If can be prepared by reacting a compound of the formula Ie, which is a compound of formula I of Scheme 1, wherein the group —Y—Z— has the formula —N═CH—, A is ═N—, and R$^2$ is hydrogen, with a compound of formula

wherein Lv$^1$ is a leaving group, such as halo, preferably bromo or chloro, in the presence of a suitable base in a polar solvent. The reaction condition is as described above in the description for Scheme 1 for the preparation of compounds of formula III from a compound of formula IV.

Compounds of formula Ie can be prepared by reacting a compound of the formula VIIIa, which is a compound of formula VII of Scheme 2, wherein A is ═N— and Lv is as described above, with hydrazine in a solvent. The reaction condition is as described above in the description for Scheme 1 for the preparation of a compound of formula I from a compound of formula II.

Compounds of formula VIIIa can be prepared by reacting a compound of the formula IVa, which is a product of Scheme 4, with a nitrous acid producing agent in the presence of an acid in a solvent. Suitable nitrous acid producing agents include NaNO$_2$, KNO$_2$, isoamyl nitrite, or tertbutyl nitrite; preferably NaNO$_2$. Suitable acids include acetic acid or aqueous HCl; preferably acetic acid. Suitable solvents include acetic acid, benzene, dimethylformamide, toluene, or alcohols (such as methanol), preferably acetic acid. The aforesaid reaction can be conducted at a temperature of about 0° C. to about 30° C., preferably about 0° C. warming to 23° C. The aforesaid reaction can be conducted for a time period of about 5 minutes to about 24 hours, preferably about 1 hour.

Within the invention it is understood that a compound of Formula I may exhibit the phenomenon of tautomerism and that the formula drawings within this specification represent only one of the possible tautomeric forms. It is to be understood that the invention encompasses any tautomeric form which modulates and/or inhibits kinase activity and is not to be limited merely to any one tautomeric form utilized within the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, Formula I is intended to cover solvated as well as unsolvated forms of the identified structures. For example. Formula I include compounds of the indicated structure in both hydrated and non-hydrated forms. Other examples of solvates include the structures in combination with isopropanol, ethanol, methanol, DMSO, ethyl acetate, acetic acid, or ethanolamine.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyrovic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The pharmaceutically acceptable salts of the compound of Formula I can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

The compound of Formula I may be used in combination with conventional anti-neoplasm therapies to treat mammals, especially humans, with neoplasia. The procedures for conventional anti-neoplasm therapies, including chemotherapies using anti-neoplastic agents and therapeutic radiation, are readily available, and routinely practiced in the art, e.g., see Harrison's *Principles Of Internal Medicine*, (11$^{th}$ edition, McGraw-Hill Book Company).

Neoplasia is characterized by abnormal growth of cells which often results in the invasion of normal tissues, e.g., primary tumors or the spread to distant organs, e. g., metastasis. The treatment of any neoplasia by conventional non-surgical anti-neoplasm therapies may be enhanced by the present invention. Such neoplastic growth includes but not limited to primary tumors, primary tumors that are incompletely removed by surgical techniques, primary tumors which have been adequately treated but which are at high risk to develop a metastatic disease subsequently, and an established metastatic disease.

Specifically, the CHK-1 inhibitor of Formula I above may enhance the anti-neoplasm effects of an anti-neoplastic agent. The wide variety of available anti-neoplastic agents are contemplated for combination therapy in accordance with present invention. In a preferred embodiment, antineoplastic agents that assert their cytotoxic effects by activating programmed cell death or apoptosis may be used in combination with the described CHK-1 inhibitor. The anti-neoplastic agents contemplated in accordance with the present invention include, but are not limited to alkylating agents, including busulfan, chlorambucil, cyclophosphamide, iphosphamide, melphalan, nitrogen mustard, streptozocin, thiotepa, uracil nitrogen mustard, triethylenemelamine, temozolomide, and SARCnu; antibiotics and plant alkaloids including actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, VM-26, and VP-16-213; hormones and steroids including 5α-reductase inhibitor, aminoglutethimide, anastrozole, bicalutamide, chlorotrianisene, DES, dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, SERM3, tamoxifen, testolactone, testosterone, triamicnolone, and zoladex; synthetics including all-trans retinoic acid, BCNU (carmustine), CBDCA carboplatin (paraplatin), CCNU (lomustine), cis-diaminedichloroplatinum (cisplatin), dacarbazine, gliadel, hexamethylmelamine, hydroxyurea, levamisole, mitoxantrone, o, p'-DDD (lysodren, mitotane), oxaliplatin, porfimer sodium, procarbazine, GleeVec; antimetabolites including chlorodeoxyadenosine, cytosine arabinoside, 2'-deoxycoformycin, fludarabine phosphate, 5-fluorouracil, 5-FUDR, gemcitabine, camptothecin, 6-mercaptopurine, methotrexate, MTA, and thioguanine; and biologics including alpha interferon, BCG, G-CSF, GM-CSF, interleukin-2, herceptin; and the like.

In a preferred embodiment of the invention, the anti-neoplastic agent is selected from the group consisting of alkylating agents, antibiotics and plant alkaloids, hormones and steroids, synthetic agents having anti-neoplastic activity, antimetabolites and biological molecules having anti-neoplastic activity.

In a preferred embodiment of the invention the antineoplastic agent is selected from the group consisting of Ara-c, VP-16, cis-platin, adriamycin, 2-chloro-2-deoxyadenosine, 9-β-D-arabinosyl-2-fluoroadenine, carboplatin, gemcitabine, camptothecin, paclitaxel, BCNU, 5-fluorouracil, irinotecan, and doxorubicin; more preferably gemcitabine.

All the neoplastic conditions treatable with such anti-neoplastic agents may be treated in accordance with the present invention by using a combination of the compound of Formula I with one or more anti-neoplastic agents. The anti-neoplastic agents assert their cytotoxicity or anti-neoplasm effects in a variety of specific neoplastic conditions. For example, Ara-c is normally used for treatment of childhood-null acute lymphoid leukemia (ALL), thymic ALL, B-cell ALL, acute myeloid leukemia, acute granulocytic leukemia and its variants, non-Hodgkins lymphoma, myelomonocytoid leukemia, acute megakaryocytoid leukemia and Burkitt's lymphoma, Adult-B-ALL, acute myeloid leukemia, chronic lymphoid leukemia, chronic myeloid leukemia, and T cell leukemia. VP-16 is normally used for treatment of testicular carcinoma, small and large non-small cell lung carcinoma, Hodgkin's lymphoma, non-Hodgkin's lymphoma, choriocarcinoma, Ewing's sarcoma, and acute granulocytic leukemia. Cis-platin can be employed for treatment of testicular carcinoma, germ cell tumors, ovarian carcinomas, prostate cancer, lung cancer, sarcomas, cervical cancer, endometrial cancer, gastric cancer, breast cancer, and cancer of the head and neck. 2-Chloro-2-deoxyadenosine and 9-β-D-arabinosyl-2-fluoroadenine can be used to treat chronic lymphoid leukemia, lymphomas and hairy cell leukemia. Doxorubicin can be used to treat acute granulocytic leukemia and its variants, ALL, breast cancer, bladder cancer, ovarian cancer, thyroid cancer, lung cancer, Hodgkin's lymphoma, non-Hodgkin's lymphoma, sarcomas, gastric carcinoma, prostate cancer, endometrial cancer, Wilm's tumor and neuroblastoma.

Clinical effects of anti-neoplastic agents in all neoplastic conditions treatable with antineoplastic agents including the ones discussed above may be potentiated by use of a combination therapy with the identified CHK-1 inhibitor in accordance with the present invention.

The CHK-1 inhibitor identified in the present invention may also enhance the antineoplasm effects of radiation therapy. Usually, radiation can be used to treat the site of a solid tumor directly or administered by brachytherapy implants. The various types of therapeutic radiation which are contemplated for combination therapy in accordance with the present invention may be those used in the treatment of cancer which include, but are not limited to X-rays, gamma radiation, high energy electrons and High LET (Linear Energy Transfer) radiation such as protons, neutrons, and alpha particles. The ionizing radiation may be employed by techniques well known to those skilled in the art. For example, X-rays and gamma rays are applied by external and/or interstitial means from linear accelerators or radioactive sources. High-energy electrons may be produced by linear accelerators. High LET radiation is also applied from radioactive sources implanted interstitially.

The specific dosage amount of a compound of the Formula I, a pharmaceutically acceptable salt, solvate, or prodrug thereof being administered to obtain therapeutic or inhibitory effects may be determined in a manner known in the art according to the particular circumstances surrounding the case, including, e.g., the specific agent being administered, the route of administration, the condition being treated, and the subject or host being treated. An exemplary total daily dose of a compound of the Formula I, which may be administered in single or multiple doses, contains a dosage level of from about 0.01 mg/kg body weight to about 50 mg/kg body weight.

The compounds of the Formula I of the invention may be administered by any of a variety of suitable routes, such as orally, rectally, transdermally, subcutaneously, intravenously, intramuscularly, or intranasally. The compounds of the Formula I are preferably formulated into compositions suitable for the desired routes before being administered.

A pharmaceutical composition or preparation according to the invention comprises an effective amount of a compound of the Formula I, optionally one or more other active agents, and a pharmaceutically acceptable carrier, such as a diluent or excipient for the agent; when the carrier serves as a diluent, it may be a solid, semi-solid, or liquid material acting as a vehicle, excipient, or medium for the active ingredient(s). Compositions according to the invention may be made by admixing the active ingredient(s) with a carrier, or diluting it with a carrier, or enclosing or encapsulating it within a carrier, which may be in the form of a capsule, sachet, paper container, or the like. Exemplary ingredients, in addition to one or more compounds of the Formula I and any other active ingredients, include Avicel (microcrystalline cellulose), starch, lactose, calcium sulfate dihydrate, terra alba, sucrose, talc, gelatin, agar, pectin, acacia, magnesium stearate, stearic acid, peanut oil, olive oil, glyceryl monostearate, Tween 80 (polysorbate 80), 1,3-butanediol, cocoa butter, beeswax, polyethylene glycol, propylene glycol, sorbitan monostearate, polysorbate 60, 2-octyldodecanol, benzyl alcohol, glycine, sorbic acid, potassium sorbate, disodium hydrogen phosphate, sodium chloride, and water.

The compositions may be prepared in any of a variety of forms suitable for the desired mode of administration. For example, pharmaceutical compositions may be prepared in the form of tablets, pills, powders, lozenges, sachets, cachets, elixirs, suspensions, emulsions, solutions, syrups, aerosols (as solids or in liquid media), ointments (e.g., containing up to 10% by weight of a compound of the Formula I), soft-gel and hard-gel capsules, suppositories, sterile injectable solutions, sterile packaged powders, and the like.

Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation can be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. A compound of Formula I may be dissolved in DMSO and diluted with water. The composition may also be in the form of a solution of a salt form of the active ingredient in an appropriate aqueous vehicle such as water or isotonic saline or dextrose solution.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, hydroxypropylmethyl-cellulose, sodium carboxymethylcellulose, methyl cellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insulator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, the active agent is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

The compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD cosolvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The compounds of the Formula I, a pharmaceutically acceptable salt, solvate, or prodrug thereof are useful as anti-angiogenesis agents and as agents for modulating and/or inhibiting the activity of protein kinases, thus providing treatments for cancer or other diseases associated with cellular proliferation mediated by protein kinases.

Therapeutically effective amounts of the agents of the invention may be used to treat diseases mediated by modulation or regulation of protein kinases. An effective amount is intended to mean that amount of an agent that, when administered to a mammal in need of such treatment, is sufficient to effect treatment for a disease mediated by the activity of one or more kinases. Thus, e.g., a therapeutically effective amount of a compound of the Formula I, a pharmaceutically acceptable salt, solvate, or prodrug thereof is a quantity sufficient to modulate, regulate, or inhibit the activity of one or more kinases such that a disease condition which is mediated by that activity is reduced or alleviated.

Biochemical and Biological Evaluation

Enzyme Assays

CHK-1 Construct for Assay

As previously detailed in European Patent Application No. 1 096 014 A2 (filed Oct. 31, 2000), the C-terminally His-tagged kinase domain of human CHK-1 (KH289), amino acid residues 1–289, can be expressed using the baculovirus/insect cell system. This construct has been shown to possess catalytic activity approximately 10-fold greater than full length CHK-1. The Bac-to-Bac system (Life Technologies) can be used to generate recombinant baculovirus for the expression of KH289 as per instructions. Recombinant viruses can be confirmed by PCR for the presence of CHK-1 cDNA insertion. Protein expression can be confirmed by SDS-PAGE or Western blot with CHK-1 polyclonal antibodies. Sf9 insect cells (Invitrogen, Carlsbad, Calif., USA) can be used for initial amplification of recombinant virus stock. High titer stocks of recombinant viruses can be generated by 2 to 3 rounds of amplification using Sf21 insect cells. Hi-S insect cells (Invitrogen, Carlsbad, Calif., USA) can be used for protein production. Both Sf9 and Hi-S cell lines can be adapted to grow in insect medium containing 1% Fetal Bovine Serum (Life Technologies, Grand Island, N.Y., USA). The viral stock was stored at 10° C. and used for large-scale protein production within 2 months to avoid viral instability. For protein production, infected Hi-S cells can be harvested by centrifugation and stored at −80° C. From these cells, 6X-His tagged KH289 (identified by SDS-PAGE) can be obtained after purification and can be flash-frozen in liquid $N_2$ and stored at −80° C. Maintaining salt concentration around 500 mM NaCl including 5% glycerol was found to be crucial for preventing aggregation of CHK-1 proteins during purification and storage.

CHK-1 Assay

As previously detailed in European Patent Application No. 1 096 014 A2 (filed Oct. 31, 2000), the enzymatic activity of a kinase can be measured by its ability to catalyze the transfer of a phosphate residue from a nucleoside triphosphate to an amino acid side chain in a selected protein target. The conversion of ATP to ADP generally accompanies the catalytic reaction. Herein, a synthetic substrate peptide, Syntide-2, having amino acid sequence PLARTLS-VAGLPGKK can be utilized. The production of ADP from ATP that accompanies phosphoryl transfer to the substrate can be coupled to oxidation of NADH using phosphoenolpyruvate (PEP) through the actions of pyruvate kinase (PK) and lactic dehydrogenase (LDH). The oxidation of NADH can be monitored by following the decrease of absorbance at 340 nm (e340=6.22 cm-1 mM-1) using a HP8452 spectrophotometer. Typical reaction solutions contained: 4 mM PEP, 0.15 mM NADH, 28 units of LDH/mL, 16 units of PK/mL, 3 mM DTT, 0.125 mM Syntide-2, 0.15 mM ATP and 25 mM $MgCl2$ in 50 mM TRIS pH 7.5; 400 mM NaCl. Assays can be initiated with 10 nM of kinase domain of CHK-1, KH289. Ki values can be determined by measuring initial enzyme activity in the presence of varying concentrations of inhibitors. The data can be analyzed using Enzyme Kinetic and Kaleidagraph software.

The Ki values (nM) for the compounds of the invention are as follows:

| | |
|---|---|
| Example 1 | 159 |
| Example 2 | 4 |
| Example 3 | 1.7 |
| Example 4 | 0.473 |
| Example 5 | 20 |
| Example 6 | 0.029 |
| Example 7 | 0.042 |
| Example 8 | 0.195 |
| Example 9 | 0.325 |
| Example 10 | 0.829 |
| Example 11 | 0.0096 |
| Example 12 | 0.007 |
| Example 13 | 0.008 |
| Example 14 | 0.007 |
| Example 15 | 0.01 |
| Example 16 | 0.008 |
| Example 17 | 0.013 |
| Example 18 | 0.014 |
| Example 19 | 0.313 |
| Example 20 | 0.058 |
| Example 21 | 0.045 |
| Example 22 | 0.118 |
| Example 23 | 0.023 |
| Example 24 | 0.025 |
| Example 25 | 0.0047 |
| Example 26 | 0.022 |
| Example 27 | 0.33 |
| Example 28 | 0.0028 |
| Example 29 | 0.043 |
| Example 30 | 0.147 |
| Example 31 | 0.0074 |
| Example 32 | 0.0071 |
| Example 34 | 0.007 |
| Example 35 | 0.0103 |
| Example 36 | 0.0016 |
| Example 37 | 0.021 |
| Example 38 | 0.0037 |
| Example 39 | 0.008 |
| Example 40 | 0.000964 |
| Example 41 | 0.000805 |
| Example 42 | 0.0048 |
| Example 43 | 0.012 |
| Example 44 | 0.0077 |
| Example 45 | 0.00043 |
| Example 46 | 0.0027 |
| Example 47 | 0.000359 |
| Example 48 | 0.0031 |
| Example 49 | 0.142 |
| Example 50 | 0.0017 |
| Example 51 | 1.5 |
| Example 52 | 0.013 |
| Example 53 | 0.03 |
| Example 54 | 0.0016 |
| Example 55 | 0.078 |
| Example 56 | 0.033 |
| Example 57 | 0.054 |
| Example 58 | 0.182 |
| Example 60 | 0.0039 |
| Example 61 | 0.000151 |
| Example 62 | 0.017 |
| Example 63 | 0.359 |
| Example 64 | 0.123 |
| Example 65 | 0.347 |
| Example 66 | 0.0018 |
| Example 67 | 0.00095 |
| Example 68 | 0.029 |

| | |
|---|---|
| Example 70 | 0.132 |
| Example 71 | 2 |
| Example 72 | 0.038 |
| Example 73 | 0.0028 |
| Example 74 | 2.4 |
| Example 75 | 0.0028 |
| Example 76 | 0.041 |
| Example 77 | 0.011 |
| Example 78 | 0.006 |
| Example 79 | 0.0038 |
| Example 80 | 0.153 |
| Example 81 | 0.422 |
| Example 82 | 0.0077 |
| Example 83a | 0.0013 |
| Example 83b | 0.000587 |
| Example 84 | 1.5 |
| Example 85 | 0.000398 |
| Example 86 | 0.000336 |
| Example 87 | 0.0053 |
| Example 88 | 0.044 |
| Example 89 | 0.0129 |
| Example 90 | 0.028 |
| Example 91 | 0.000569 |
| Example 92 | 0.023 |
| Example 93 | 0.006 |
| Example 94 | 0.095 |
| Example 95 | 0.011 |
| Example 96 | 0.0047 |
| Example 97 | 0.0027 |
| Example 98 | 0.018 |
| Example 99 | 0.222 |
| Example 100 | 0.000738 |
| Example 101 | 0.139 |
| Example 102 | 1.6 |
| Example 103 | 0.004 |
| Example 104 | 0.0133 |
| Example 105 | 0.291 |
| Example 106 | 0.027 |
| Example 107 | 0.446 |
| Example 108 | 0.005 |
| Example 109 | 0.411 |
| Example 110 | 0.293 |
| Example 111 | 0.000605 |
| Example 112 | 0.000573 |
| Example 113 | 0.0029 |
| Example 114 | 0.0012 |
| Example 115 | 0.002 |
| Example 116 | 0.012 |
| Example 117 | 1.5 |
| Example 118 | 7 |
| Example 119 | 12.7 |
| Example 120 | 0.002 |
| Example 121 | 0.000196 |
| Example 122 | 0.072 |
| Example 123 | 0.06 |
| Example 124 | 0.000743 |
| Example 125 | 0.001 |
| Example 126 | 0.0032 |
| Example 127 | 0.021 |
| Example 128 | 0.0015 |
| Example 129 | 0.03 |
| Example 130 | 1.8 |
| Example 131 | 0.223 |
| Example 132 | 0.0054 |
| Example 133 | 0.0027 |
| Example 134 | 0.0015 |
| Example 135 | 0.0028 |
| Example 136 | 0.0032 |
| Example 137 | 0.048 |
| Example 138 | 0.012 |
| Example 139 | 0.0032 |
| Example 140 | 0.0063 |
| Example 141 | 0.028 |
| Example 142 | 0.644 |
| Example 143 | 0.000517 |
| Example 144 | 1.6 |
| Example 145 | 0.646 |
| Example 146 | 1.1 |
| Example 147 | 0.061 |
| Example 160 | 0.000115 |
| Example 161 | 0.083 |
| Example 162 | 0.077 |
| Example 163 | 0.106 |
| Example 164 | 0.039 |
| Example 165 | 0.056 |
| Example 167 | 0.0028 |
| Example 168 | 0.002 |
| Example 169 | 0.000358 |
| Example 170 | 0.000553 |
| Example 171 | 0.000625 |
| Example 172 | 0.078 |
| Example 173 | 0.034 |
| Example 174 | 0.007 |
| Example 175 | 0.000318 |
| Example 176 | |
| Example 177 | 0.13 |
| Example 178 | 0.01 |
| Example 179 | 0.045 |
| Example 180 | 0.241 |
| Example 181 | 0.000376 |
| Example 182 | 0.000478 |
| Example 183 | 0.391 |
| Example 184 | 0.048 |
| Example 185 | 1.3 |
| Example 186 | 0.000352 |
| Example 187 | 0.143 |
| Example 188 | 0.019 |
| Example 189 | 0.019 |
| Example 190 | 0.0001 |
| Example 191 | 0.0058 |
| Example 192 | |
| Example 193 | |
| Example 194 | |
| Example 195 | 0.582 |
| Example 196 | 0.061 |
| Example 197 | 0.072 |
| Example 198 | 0.006 |
| Example 199 | 0.14 |
| Example 200 | 0.019 |
| Example 201 | 0.231 |
| Example 202 | 0.0032 |
| Example 203 | 0.0013 |
| Example 204 | 0.000664 |
| Example 206 | 0.000114 |
| Example 219 | 0.016 |
| Example 220 | 0.00082 |
| Example 221 | 0.035 |
| Example 222 | 0.0092 |
| Example 223 | 0.273 |
| Example 224 | 0.319 |
| Example 225 | 0.000219 |
| Example 226 | 0.0018 |
| Example 227 | 1.4 |
| Example 228 | 0.03 |
| Example 229 | 0.21 |
| Example 230 | 0.021 |
| Example 231 | 0.0019 |
| Example 232 | 0.000102 |
| Example 233 | 0.000121 |
| Example 235 | 0.0022 |
| Example 236 | 0.000064 |
| Example 237 | 0.000068 |
| Example 238 | 0.0013 |
| Example 239 | 0.000529 |
| Example 240 | 0.0036 |
| Example 249 | 0.0091 |
| Example 250 | 0.031 |
| Example 251 | 0.01 |
| Example 252 | 3 |
| Example 253 | 0.0002 |
| Example 254 | 0.0009 |
| Example 255 | 0.14 |
| Example 256 | 0.78 |
| Example 257 | 0.27 |
| Example 258 | 0.01 |
| Example 259 | 0.99 |
| Example 260 | 0.42 |
| Example 261 | 2 |

-continued

| | |
|---|---|
| Example 262 | 0.3 |
| Example 263 | 0.43 |
| Example 264 | 0.48 |
| Example 265 | 0.73 |
| Example 266 | 0.29 |
| Example 267 | 0.78 |
| Example 268 | 0.01 |
| Example 269 | 0.15 |
| Example 270 | 0.79 |
| Example 271 | 1.2 |
| Example 272 | 0.2 |
| Example 273 | 0.46 |
| Example 274 | 2 |
| Example 275 | 7 |
| Example 276 | 4.5 |
| Example 277 | 0.55 |
| Example 278 | 0.47 |

VEGF-R2 Construct for Assay

This construct determines the ability of a test compound to inhibit tyrosine kinase activity. A construct (VEGF-R2Δ50) of the cytosolic domain of (human) vascular endothelial growth factor receptor 2 (VEGF-R2) lacking the 50 central residues of the 68 residues of the kinase insert domain can be expressed in a baculovirus/insect cell system. Of the 1356 residues of full-length VEGF-R2, VEGF-R2Δ50 contains residues 806–939 and 990–1171, and also one point mutation (E990V) within the kinase insert domain relative to wild-type VEGF-R2. Autophosphorylation of the purified construct can be performed by incubation of the enzyme at a concentration of 4 $\mu$M in the presence of 3 mM ATP and 40 mM MgCl$_2$ in 100 mM HEPES, pH 7.5, containing 5% glycerol and 5 mM DTT, at 4° C. for 2 hours. After autophosphorylation, this construct has been shown to possess catalytic activity essentially equivalent to the wild-type autophosphorylated kinase domain construct. See Parast et al. (1998) Biochemistry 37:16788–16801.

VEGF-R2 Assay

Coupled Spectrophotometric (FLVK-P) Assay

The production of ADP from ATP that accompanies phosphoryl transfer can be coupled to oxidation of NADH using phosphoenolpyruvate (PEP) and a system having pyruvate kinase (PK) and lactic dehydrogenase (LDH). The oxidation of NADH can be monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2Δ50 can be the following: 1 mM PEP; 250 $\mu$M NADH; 50 units of LDH/mL; 20 units of PK/mL; 5 mM DTT; 5.1 mM poly($E_4Y_1$); 1 mM ATP; and 25 mM MgCl$_2$ in 200 mM HEPES, pH 7.5. Assay conditions for unphosphorylated VEGF-R2Δ50 can be the following: 1 mM PEP; 250 $\mu$M NADH; 50 units of LDH/mL; 20 units of PK/mL; 5 mM DTT; 20 mM poly($E_4Y_1$); 3 mM ATP; and 60 mM MgCl$_2$ and 2 mM MnCl$_2$ in 200 mM HEPES, pH 7.5. Assays can be initiated with 5 to 40 nM of enzyme. Enzyme percentage inhibition values can be determined by measuring enzyme activity in the presence of 0.05 $\mu$M test compound. The data can be analyzed using Enzyme Kinetic and Kaleidagraph software.

FGFR

FGF-R1 Construct for Assay

The intracellular kinase domain of (human) FGF-R1 can be expressed using the baculovirus vector expression system starting from the endogenous methionine residue 456 to glutamate 766, according to the residue numbering system of Mohammadi, et al. (1996) *Mol. Cell. Biol.* 16:977–989. In addition, the construct also has the following 3 amino acid substitutions: L457V, C488A, and C584S.

FGF-R Assay

The spectrophotometric assay can be carried out as described above for VEGF-R2, except for the following changes in concentration: FGF-R=50 nM, ATP=2 mM, and poly(E4Y1)=15 mM. $K_i$ values can be determined by measuring enzyme activity in the presence of varying concentrations of test compounds.

PHK

Phosphorylase Kinase Construct for Assay

The truncated catalytic subunit (gamma subunit) of phosphorylase kinase (amino acids 1–298) can be expressed in *E. coli* and isolated from inclusion bodies. Phosphorylase kinase can then be refolded and stored in glycerol at −20° C.

Phosphorylase Kinase Assay

In the assay, the purified catalytic subunit can be used to phosphorylate phosphorylase b using radiolabled ATP. Briefly, 1.5 mg/ml of phosphorylase b can be incubated with 10 nM phosphorylase kinase in 10 mM MgCl$_2$, 50 mM Hepes pH 7.4, at 37° C. The reaction can be started with the addition of ATP to 100 uM and incubated for 15 min at 25° C. or 37° C. The reaction can be terminated and proteins can be precipitated by the addition of TCA to 10% final concentration. The precipitated proteins can be isolated on a 96 well Millipore MADP NOB filter plate. The filter plate can be extensively washed with 20% TCA, and dried. Scintilation fluid can be then added to the plate and incorporated radiolabel can be counted on a Wallac microbeta counter. The % inhibition of phosphoryl transfer from ATP to phosphorylase b in the presence of 10 $\mu$M of compound can then be measured.

CHK-2 Assay

CHK-2 enzyme can be obtained from Upstate Group, Inc. and is an N-terminal, GST-tagged and C-terminal His-tagged fusion protein corresponding to amino acids 5–543 of human CHK-2 as confirmed by mass tryptic fingerprinting, expressed in *E. coli*; Mr~87 kDa. The assay condition for CHK-2 can be as described above for CHK-1, except that the enzyme CHK2 (0.059 $\mu$M) can be utilized in place of KH289. Further, no NaCl can be added.

CDK-1 Assay

CDK-1/cyclin B, active complex can be obtained from Upstate Group, Inc. and is a C-terminal, His-tagged CDK-1 and an N-terminal GST-tagged-cyclin B as confirmed by mass tryptic fingerprinting and protein sequencing, produced individually in Sf21 cells and then complexed in vitro. The assay condition for CDK-1 can be as described above for CHK-1, except that the enzyme complex CDK-1/cyclin B (0.2 $\mu$M) can be utilized in place of KH289, and Histone-H1 (Upstate USA, Inc.) (0.059 $\mu$M) can be utilized as a substrate in place of Syntide-2. Further, no NaCl can be added.

WEE-1 Assay

Delfia$^{(R)}$ Assay Protocol for WEE-1

WEE-1 enzyme can be obtained from Upstate Group, Inc. and is an N-terminal, GST-tagged fusion protein to full length rat WEE-1, expressed in *E. coli*; Mr~100 kDa. This kinase assay can be carried out on coated poly (Glu-Tyr) 4:1 (random copolymer) 96-well filter plates (NoAb Diagnostics). The assay volume can be 100 μl per well plus 2 μl DMSO (control) or 2 μl of compound in DMSO. Buffer A can be 10% glycerol, 20 mM TRIS (pH7.5), 10 mM $MgCl_2$, 50 mM NaCl and 5 mM DTT. The plates can be prepared by automation.

To an appropriate well can be added either 2 μl of DMSO (control) or 2 μl of compound in DMSO. To the positive control wells can be added 30 μl of 0.5M EDTA. To each well can be added 50 μl ATP in Buffer A such that the ATP assay concentration can be 33 μM. To start the reaction, 50 μl Wee1 in Buffer A can be added to each well such that the Wee1 assay concentration can be 0.1 ng/μl. The plate can be can be mixed by shaking and then allowed to remain at room temperature for 30 minutes. To stop the reaction, the plate can be washed once with Delfia Wash on an EL405 plate washer. To each well can be added 100 μl of EuPY in Delfia$^{(R)}$ assay buffer such that the EuPY assay concentration can be 0.0149 ng/μl. The plate can be allowed to sit for 1 hours or overnight. The plate can be washed once again with Delfia$^{(R)}$ Wash (EL405 plate washer), and allowed to dry. To each well can be added 100 μl of Delfia $^{(R)}$ Enhancement solution and the plate can be allowed to sit for 10 minutes. The plate can be read on Wallac's Victor fluorescence reader (Europium Protocol). $K_i$ values can be determined by measuring enzyme activity in the presence of varying concentrations of test compounds.

SGK Assay

SGK (human) (Upstate Group, Inc., KINASEPROFILER™) (5–10 mU) can be incubated with 8 mM MOPS pH7.0, 0.2 mM EDTA, 30 μM Crosstide, 10 mM MgAcetate and [γ-$^{33}$P-ATP] (Specific activity approximately 500 cpm/pmol, concentration as required) to form a final reaction volume of 25 μl. Compounds can be tested at 1 μM. The reaction can be initiated by the addition of $Mg^{2+}$ [γ-$^{33}$P-ATP]. The ATP concentration can be 10 μM. After incubation for 40 minutes at room temperature, the reaction can be stopped by the addition of 5 μl of a 3% phosphoric acid solution. 10 μl of the reaction can then be spotted onto a P30 filtermat and washed three times for 5 minutes in 50 mM phosphoric acid and once in methanol prior to drying and scintillation counting. Results represent an average of two experiments and enzymatic activity can be expressed as a percentage of that in control incubations without test compounds.

AMPK Assay

AMPK (rat) (Upstate Group, Inc., KINASEPROFILER™) (5–10 mU) can be incubated with 50 mM Hepes pH7.4, 1 mM DTT, 0.02% Brij35, 200 μM AMP, 200 μM AMARAASAAALARRR, 10 mM MgAcetate and [γ-$^{33}$P-ATP](Specific activity approximately 500 cpm/pmol, concentration as required) to form a final reaction volume of 25 μl. Compounds can be tested at 1 μM. The reaction can be initiated by the addition of $Mg^{2+}$ [γ-$^{33}$P-ATP]. The ATP concentration can be 10 μM. After incubation for 40 minutes at room temperature, the reaction can be stopped by the addition of 5 μl of a 3% phosphoric acid solution. 10 μl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

LCK Assay

LCK (human) (Upstate Group, Inc., KINASEPROFILER™) (5–10 mU) can be incubated with 50 mM Tris pH7.5, 0.1 mM EGTA, 0.1 mM NaVanadate, 250 □M KVEKIGEGTYGVVYK (CDC2 peptide), 10 mM MgAcetate and [γ-$^{33}$P-ATP] (Specific activity approximately 500 cpm/pmol, concentration as required) to form a final reaction volume of 25 μl. Compounds can be tested at 1 μM. The reaction can be initiated by the addition of $Mg^{2+}$ [γ-$^{33}$-ATP]. The ATP concentration can be 10 μM. After incubation for 40 minutes at room temperature, the reaction can be stopped by the addition of 5 μl of a 3% phosphoric acid solution. 10 μl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

MAPK2 Assay

MAPK2 (mouse) (Upstate Group, Inc., KINASEPROFILER™) (5–10 mU) can be incubated with 25 mM Tris pH 7.5, 0.02 mM EGTA, 0.33 mg/ml myelin basic protein, 10 mM MgAcetate and [γ-$^{33}$P-ATP] (Specific activity approximately 500 cpm/pmol, concentration as required) to form a final reaction volume of 25 μl. Compounds can be tested at 1 μM. The reaction can be initiated by the addition of $Mg^{2+}$ [γ-$^{33}$P-ATP]. The ATP concentration can be 10 μM. After incubation for 40 minutes at room temperature, the reaction can be stopped by the addition of 5 μl of a 3% phosphoric acid solution. 10 μl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

MSK1 Assay

MSK1 (human) (Upstate Group, Inc., KINASEPROFILER™) (5–10 mU) can be incubated with 8 mM MOPS pH7.0, 0.2 mM EDTA, 30 pM Crosstide, 10 mM MgAcetate and [γ-$^{33}$P-ATP] (Specific activity approximately 500 cpm/pmol, concentration as required) to form a final reaction volume of 25 μl. Compounds can be tested at 1 μM. The reaction can be initiated by the addition of $Mg^{2+}$ [γ-$^{33}$P-ATP]. The ATP concentration can be 10 μM. After incubation for 40 minutes at room temperature, the reaction can be stopped by the addition of 5 μl of a 3% phosphoric acid solution. 10 μl of the reaction can then be spotted onto a P30 filtermat and washed three times for 5 minutes in 50 mM phosphoric acid and once in methanol prior to drying and scintillation counting. Results represent an average of two experiments and enzymatic activity can be expressed as a percentage of that in control incubations without test compound.

PKBα Assay

PKBα (human) (Upstate Group, Inc., KINASEPROFILER™) (5–10 mU) can be incubated with 8 mM MOPS pH7.0, 0.2 mM EDTA, 30 μM Crosstide, 10 mM MgAcetate and [γ-$^{33}$P-ATP] (Specific activity approximately 500 cpm/pmol, concentration as required) to form a final reaction volume of 25 μl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 50 mM phosphoric acid and once in methanol prior to drying and scintillation counting. Results represent an average of two experiments and enzymatic activity can be expressed as a percentage of that in control incubations without test compound.

ROCKII Assay

ROCKII (rat) (Upstate Group, Inc., KINASEPROFILER™) (5–10 mU) can be incubated with 50 mM Tris pH7.5, 0.1 mM EGTA, 30 □M KEAKEKRQEQIAKRRRLSSLRASTSKSGGSQK, 10 mM MgAcetate and [ψ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

p70 S6K Assay p70S6K (human) (Upstate Group, Inc., KINASEPROFILER™) (5–10 mU) can be incubated with 8 mM MOPS pH7.0, 0.2 mM EDTA, 100 µM KKRNRTLTV, 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

PKA Assay

PKA (bovine) (Upstate Group, Inc., KINASEPROFILER™) (5–10 mU) can be incubated with 8 mM MOPS pH7.0, 0.2 mM EDTA, 30 µM LRRASLG (Kemptide), 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 50 mM phosphoric acid and once in methanol prior to drying and scintillation counting. Results represent an average of two experiments and enzymatic activity can be expressed as a percentage of that in control incubations without test compound.

MAPK1 Assay

MAPK1 (human) (Upstate Group, Inc., KINASEPROFILER™) (5–10 mU) can be incubated with 25 mM Tris pH7.5, 0.02 mM EGTA, 1 mM synthetic peptide, 10 mM MgAcetate and [γ-$^{33}$P-ATP) (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

cSRC Assay cSRC (human) (Upstate Group, Inc., KINASEPROFILER™) (5–10 mU) can be incubated with 8 mM MOPS pH7.0, 0.2 mM EDTA, 250 µM KVEKIGEG-TYGVVYK (CDC2 peptide), 10 mM MgAcetate and [γ-$^{33}$P-ATP](Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution, 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

PRK2 Assay

PRK2 (human) (Upstate Group, Inc., KINASEPROFILER™) (5–10 mU) can be incubated with 50 mM Tris pH7.5, 0.1 mM EGTA, 0.1% µ-mercaptoethanol, 30 µM AKRRRLSSLRA, 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

PDK1 Assay

PDK1 (human) (Upstate Group, Inc., KINASEPROFILER™) (5–10 mU) can be incubated with 50 mM Tris pH7.5, 100 µM KTFCGTPEYLAPEVRRE-PRILSEEEQEMFRDFDYIADWC (PDKtide), 0.1% β-mercaptoethanol, 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

FYN Assay

FYN (human) (Upstate Group, Inc., KINASEPROFILER™) (5–10 mU) can be incubated with 50 mM Tris pH7.5, 0.1 mM EGTA, 0.1 mM NaVanadate, 250 µM KVEKIOEGTYGVVYK (CDC2 peptide), 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

PKCβII (human) (Upstate Group, Inc., KINASEPROFILER™) (5–10 mU) can be incubated with 20 mM Hepes pH7.4, 0.03% Triton X-100, 0.1 mM CaCl$_2$, 0.1 mg/ml phosphatidylserine, 10 µg/ml diacylglycerol, 0.1 mg/ml histone H1, 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$ [γ-$^{33}$P-ATP]]. The ATP concentration can be 10 µM. After incubation for 40 minutes at room temperature, the reaction can be stopped by the addition of 5 µl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

PKCγ Assay

PKCγ (human) (Upstate Group, Inc., KINASEPROFILER™) (5–10 mU) can be incubated with 20 mM Hepes pH7.4, 0.03% Triton X-100, 0.1 mM CaCl$_2$, 0.1 mg/ml phosphatidylserine, 10 µg/ml diacylglycerol, 0.1 mg/ml histone H1, 10 mM MgAcetate and [γ-$^{33}$P-ATP] (Specific activity approximately 500 cpm/pmol, concentration as required) to form a final reaction volume of 25 µl. Compounds can be tested at 1 µM. The reaction can be initiated by the addition of Mg$^{2+}$[γ-$^{33}$P-ATP]. The ATP concentration can be 10 µM. After incubation for 40 minutes at room temperature, the reaction can be stopped by the addition of 5 γl of a 3% phosphoric acid solution. 10 µl of the reaction can then be spotted onto a P30 filtermat and washed three times for 5 minutes in 75 mM phosphoric acid and once in methanol prior to drying and scintillation counting. Results represent an average of two experiments and enzymatic activity can be expressed as a percentage of that in control incubations without test compound.

Whole Cell Checkpoint Abrogation Assay

Chk1 Mitotic Index ELISA Assay

To examine the in vitro effects of Chk1 inhibitory compounds, an ELISA assay can be designed to monitor the abrogation of DNA damage-induced checkpoint control. The assay can be based on the trapping and detection of mitotic cells following DNA damage-induced arrest. Phosphorylation of Histone H3 on serine 10 has been shown to correlate with mitosis and therefore can be required for chromosome condensation; consequently a mitosis specific phospho-epitope on Histone H3 can be used as a signal for checkpoint abrogation.

CA46 (lymphoma) cells can be treated with a DNA damaging agent, such as camptothecin (Sigma), at 50 nM for 8 hours to induce DNA damage. The control compound or Chk1 inhibitor can be then added at increasing concentrations with Nocodazole (Sigma) at 0.1 µg/ml and plates can be incubated for 16 hours. Control cells, where only Chk1 inhibitors can be added, can be prepared as well to assure that the inhibitors alone have no effect on the cell cycle. The cells can be then harvested, washed with PBS, and crude acid extraction can be performed. Pellets can be resuspended in 80 µl of Acid Extraction Buffer (10 mM Hepes pH 7.9, 1.5 mM MgCl$_2$, 10 mM KCl, 0.5 mM DTT, 1.5 mM PMSF, 0.4N sulfuric acid), vortexed briefly, and incubated for 30 minutes on ice. Samples can be then centrifuged and 75 µl of the supernatant can be transferred to a 96 well flat-bottom plate (VWR 3596). Next 15 µl Neutralizing Cocktail (# of samples×(10 µl 10N NaOH+5 µl 1M Tris Base) can be added to each well, and after mixing, 5 µl of this can be transferred to another 96 well plate with 100 µl 50 mM Tris base (pH 9.6) in each well. Samples can be dried overnight. The wells can be then washed with 200 µl ELISA wash buffer (PBS with 20 mM Tris pH 7.5, 0.05% Tween 20) 5 times and blocked with 200 µl blocking buffer (PBS with 20 mM Tris pH 7.5, 0.05% Tween 20, 3.5% Dry milk, 1.5% BSA. pH to 7.5 after preparation) for 1 hour at room temperature. Following wash and block, anti-phospho Histone H3 antibodies (Upstate USA, Inc., rabbit polyclonal) can be added at 0.5 µg/ml in block (100 µl per well) and incubated for 2 hours at room temperature. Wells can be washed again to remove unbound primary antibody and 100 µl alkaline phosphatase conjugated secondary antibodies at 0.3 mg/ml (Pierce, goat anti-rabbit IgG (HOURS+L)) in block can be added for 1 hour at room temp. Wells can be washed 5 times to remove unbound secondary antibody, and washed again 3 times with PBS alone to remove detergents. Then 100 µl alkaline phosphatase substrate (Pierce 1–Step pNPP) can be added to wells. Plates can be protected from light and incubated at room temp for 1 hour. The OD can be read on Molecular Devices Vmax Kinetic Microplate Reader at 405 nm. The ratio of the OD (optical density) of a compound treated sample to the Nocodazole only treated sample (about 100% mitotic or abrogation) can be expressed in a percentage, and quantifies the percent abrogation of the checkpoint. The concentration at which a compound causes 50% abrogation of the checkpoint can be called the $EC_{50}$. The raw OD values can be graphed in Excel, and an $EC_{50}$ value can be generated using Kaleidograph software. Strong signal results from Nocodazole only treated cells, and equals 100% mitosis in this assay. Camptothecin+Nocodazole treated control samples have low signal, signifying no mitosis and therefore, no checkpoint abrogation. When potent Chk1 inhibitors are added to Camptothecin treated cells with Nocodazole, a high signal can be generated (generally in a dose dependent manner), due to the checkpoint abrogation activity caused by the combination treatment.

The examples above illustrate compounds according to Formula I and assays that may readily be performed to determine their activity levels against the various kinase complexes. It will be apparent that such assays or other suitable assays known in the art may be used to select an inhibitor having a desired level of activity against a selected target.

The exemplary compounds described above may be formulated into pharmaceutical compositions according to the following general examples.

Parenteral Composition

To prepare a parenteral pharmaceutical composition suitable for administration by injection, 100 mg of a water-soluble salt of a compound of Formula I or II may be dissolved in DMSO and then mixed with 10 mL of 0.9% sterile saline. The mixture may be incorporated into a dosage unit form suitable for administration by injection.

Oral Composition

To prepare a pharmaceutical composition for oral delivery, 100 mg of a compound of Formula I or II may be mixed with 750 mg of lactose. The mixture may be incorporated into an oral dosage unit for, such as a hard gelatin capsule, which may be suitable for oral administration.

The starting materials used in the examples are commercially available and/or can be prepared by techniques known in the art. Freebases and salts of prepared starting materials and intermediates were used interchangeably and are indicated. Freebases were prepared by addition of a tertiary base to the salt followed by silica gel chromatography of the resulting freebase if necessary. Salts were prepared by adding an equivalent amount of the appropriate acid to the freebase in a slurry or solution.

The preparation of specific preferred compounds of the invention is described in detail in the following examples. The artisan will recognize that the chemical reactions described may be readily adapted to prepare a number of other kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) distilled from calcium hydride and N,N-dimethylformamide (DMF) were purchased from Aldrich in Sure seal bottles and used as received. All solvents were purified using standard methods readily known to those skilled in the art, unless otherwise indicated.

The reactions set forth below were done generally under a positive pressure of argon or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with an iodine chamber, UV, p-anisaldehyde spray reagent or phosphomolybdic acid reagent (Aldrich Chemical 20 wt % in ethanol), ninhydrin reagent, and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ or $MgSO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 µm) and a silica gel: crude material ratio of about 20:1 to 50:1 unless otherwise stated. Hydrogenation was done at the pressure indicated in the examples or at atmospheric pressure. $^1$H-NMR spectra were recorded on a Bruker instrument operating at 300 M Hz, 400 M Hz or 500 M Hz and $^{13}$C-NMR spectra were recorded operating at 75 M Hz. NMR spectra were obtained as $CDCl_3$ solutions (reported in ppm), using chloroform as the reference standard (7.25 ppm and 77.00 ppm) or DMSO-$D_6$ (2.50 ppm and 39.51 ppm) or or $CD_3OD$ (3.4 ppm and 4.8 ppm and 49.3 ppm), or internal tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

The starting materials used in the examples are commercially available and/or can be prepared by techniques known in the art. Freebases and salts of prepared starting materials and intermediates were used interchangeably and are indicated. Freebases were prepared by addition of a tertiary base to the salt followed by silica gel chromatography of the resulting freebase if necessary. Salts were prepared by adding an equivalent amount of the appropriate acid to the freebase in a slurry or solution.

The following abbreviations may be used herein: $Et_2O$ (diethyl ether); DMF (N,N-dimethylformamide); DMSO (dimethylsulfoxide); MeOH (methanol); EtOH (ethanol); EtOAc (ethyl acetate); THF (tetrahydrofuran); Ac (acetyl); Me (methyl); Et (ethyl); and Ph (phenyl).

EXAMPLES

Example 1

7-Pyridin-3-yl-1,5-dihydro-[1,2]diazepino[4,5,6-cd]indol-6-one

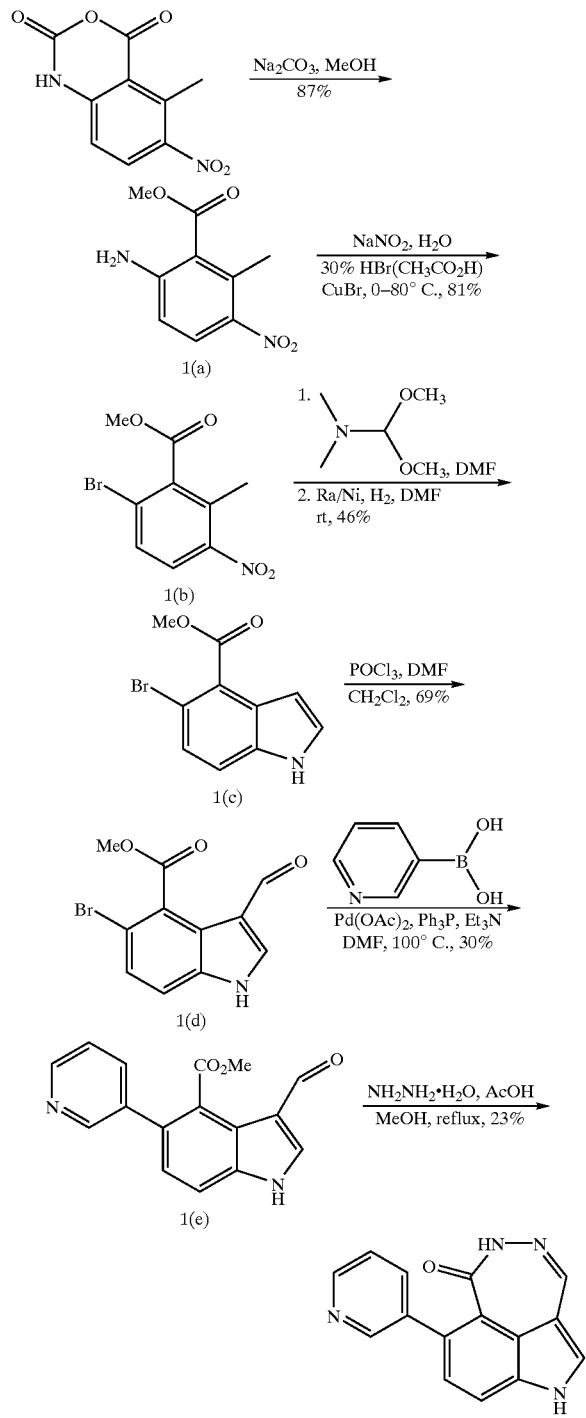

Step 1. Preparation of 6-Amino-2-methyl-3-nitro-benzoic Acid Methyl Ester 1(a)

5-Methyl-6-nitro-1H-benzo[d][1,3]oxazine-2,4-dione (8 g, 36.0 mmol) prepared from 2-Amino-6-methyl-benzoic acid (Aldrich) as described by Abood, N. A., et al. (1997) Bioorganic & Med. Chem. Lett. 7: 2105–2108 and sodium carbonate (3.82, 36.0 mmol) were stirred in methanol (180 mL, 0.1 M) at 0° C. for 0.5 hours and then at ambient temperature for 3 hours. Strongly acidic ion-exchange resin (Dowex® 50 WX4-200) was added until neutral pH and the solution was filtered. The solvent was removed under reduced pressure and silica gel chromatography (60:40 hexane/ethyl acetate) afforded Intermediate 1(a) (6.59 g) in 87% yield.

$^1$H-NMR (d$_6$-DMSO): δ 7.88 (d, 1H, J=9.1 Hz), 6.65 (d, 1H, J=9.2 Hz), 6.55 (s, 2H), 3.86 (s, 3H), 2.38 (s, 3H).

LCMS: (M−H$^+$) 209.1

Step 2. Preparation of 6-Bromo-2-methyl-3-nitro-benzoic Acid Methyl Ester 1(b)

Intermediate 1(a) (0.29 g, 1.38 mmol) was added to an ice-cold solution of HBr (30% in acetic acid, 1.6 mL) and water (3.0 mL). Sodium nitrite (0.103 g, 1.5 mmol) in water (2.0 mL) was added dropwise and the mixture stirred at 0° C. for 0.5 hours. Excess nitric acid was destroyed by the addition of urea. The diazonium salt solution was added to a mixture of CuBr (0.6 g, 4.18 mmol), HBr (30% in acetic acid, 3.5 mL) and water (5.0 mL) at 35° C. and the reaction mixture was heated at 80° C. for 1.5 hours. The resulting precipitate was filtered and washed with water to afford Intermediate 1(b) (0.307 g) in 81% yield.

$^1$H-NMR (d$_6$-DMSO): δ 7.99 (d, 1H, J=8.8 Hz), 7.85 (d, 1H, J=8.8 Hz), 3.94 (s, 3H), 2.39 (s, 3H).

Step 3. Preparation of 5-Bromo-1H-indole-4-carboxylic Acid Methyl Ester 1(c)

Intermediate 1(b) (2.6 g, 9.5 mmol) was dissolved in anhydrous N,N-dimethylformamide (0.5 M, 20 mL). N,N-Dimethylformamide dimethyl acetal (3.0 eq, 3.8 mL, 28.5 mmol) was added under an argon atmosphere at ambient temperature with stirring. The mixture was heated at 130° C. for 5 hours and cooled to ambient temperature. N,N-Dimethylformamide and the unreacted N,N-dimethylformamide dimethyl acetal was removed under reduced pressure (35° C., c.a. 5 mm Hg). Toluene (~50 mL) was added and the volatiles removed under vacuum. The crude enamine was dissolved in N,N-dimethylformamide (0.2 M, 50 mL) followed by the addition of Ra/Ni (~300 mg). The reaction mixture was stirred under hydrogen atmosphere for 7 hours, filtered over celite and concentrated. Silica gel chromatography (80:20 hexane/ethyl acetate) afforded Intermediate 1(c) (1.1 g) in 46% yield.

$^1$H-NMR (d$_6$-DMSO): δ 11.54 (s, 1H), 7.51 (d, 1H, J=1.8 Hz), 7.49 (dd, 1H, J=8.5, 0.8 Hz), 7.33 (dd, 1H, J=8.7 Hz), 6.50–6.47 (m, 1H), 3.92 (s, 3H).

LCMS: (M+H$^+$) 252.1

Step 4. Preparation of 5-Bromo-3-formyl-1H-indole-4-carboxylic Acid Methyl Ester 1(d)

A premixed Vilsmeier reagent consisting of POCl$_3$ (0.53 mL, 5.7 mmol) in N,N-dimethylformamide (1.2 mL, 15.6 mmol) was added dropwise at 0° C., to Intermediate 1(c) (0.66 g, 2.6 mmol) in anhydrous CH$_2$Cl$_2$ (13 mL, 0.2 M) with vigorous stirring. The mixture was stirred for 0.5 hours at ambient temperature, quenched with aqueous sodium acetate (2.0 M, 10 ml) and neutralized with solid Na$_2$CO$_3$. The mixture was partitioned between ethyl acetate (50 mL) and H$_2$O (10 mL). The layers were separated and the aqueous layer was extracted with ethyl acetate (1×20 mL). The organic layers were combined, washed with brine, dried over Na$_2$SO$_4$ and concentrated to give Intermediate 1(d) (0.51 g) in 69% yield.

$^1$H-NMR (d$_6$-DMSO): δ 12.54 (s, 1H), 9.80 (s, 1H), 8.43 (s, 1H), 7.59–7.48 (m, 2H), 3.91 (s, 3H).

LCMS: (M+H$^+$) 306.0

Step 5. Preparation of 3-Formyl-5-pyridin-3-yl-1H-indole-4-arboxylic Acid Methyl Ester 1(e)

A solution of Intermediate 1(d) (0.05 g, 0.18 mmol), 3-boronic acid pyridine (0.034 g, 0.27 mmol), palladium (II) acetate (0.004 g, 0.0018 mmol), triphenylphosphine (0.009 g, 0.035 mmol) and triethylamine (0.08 mL, 0.55 mmol) in N,N-dimethylformamide (0.7 mL, 0.25 M) was heated at 100° C. for 96 hours. The reaction mixture was cooled and filtered through celite, providing after column chromatography Intermediate 1(e) (0.015 g) in 30% yield.

LCMS: (M+H$^+$) 281.1

Step 6. Preparation of Title Compound: 7-Pyridin-3-yl-1,5-dihydro-[1,2]diazepino[4,5,6-cd]indol-6-one A solution of Intermediate 1(e) (0.015 g, 0.054 mmol), hydrazine (0.008 mL, 0.135 mmol) and acetic acid (0.020 mL, 2%) in anhydrous methanol (1.0 mL, 0.05 M) was heated at 80° C. for 24 hours. The reaction mixture was cooled at ambient temperature and the title compound (0.0035 g) was obtained after a preparative HPLC purification in 23% yield.

$^1$H-NMR (d$_6$-DMSO): δ 12.03 (s, 1H), 9.97 (s, 1H), 8.69 (s, 1H), 8.65 (d, 1H, J=4.6 Hz), 8.09 (d, 1H, J=8.3 Hz), 7.77 (d, 1H, J=2.7 Hz), 7.76–7.68 (m, 1H), 7.61 (d, 1H, J=8.4 Hz), 7.54 (s, 1H), 7.01 (d, 1H, J=8.4 Hz).

LCMS: (M+H$^+$) 263.1

Example 2

8-Amino-1,5-dihydro-[1,2]diazepino[4,5,6-cd]indol-8-one (Hydrochloric Salt)

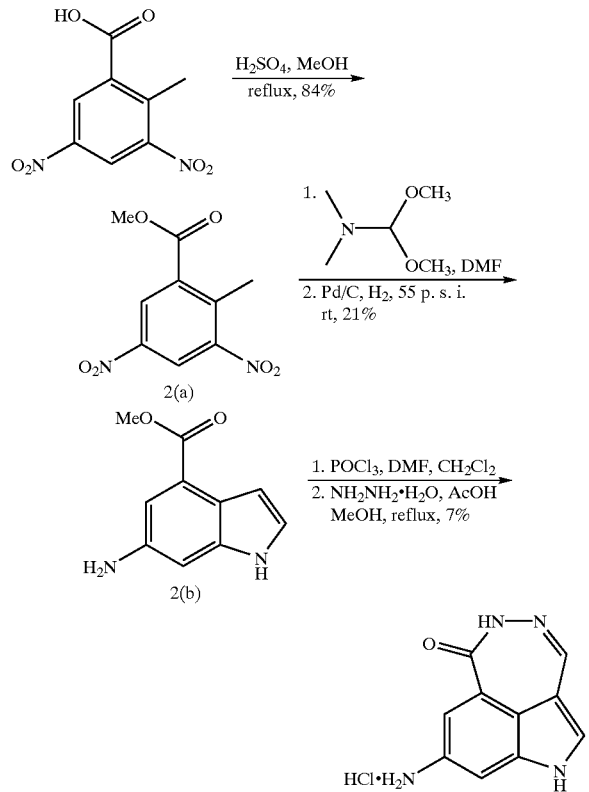

Step 1. Preparation of 2-Methyl-3,5-dinitro-benzoic Acid Methyl Ester 2(a)

Concentrated sulfuric acid (0.5 mL) was added slowly at ambient temperature with stirring to 2-methyl-3,5-dinitrobenzoic acid (5.22 g, 23.06 mmol) in anhydrous methanol (200 mL). After refluxing overnight under an argon atmosphere, the reaction was determined to be about 50% complete. Toluene (100 mL) was used to azeotrope the H$_2$O generated from the reaction, and fresh anhydrous methanol (300 mL) and H$_2$SO$_4$ (0.5 mL) were added and the mixture was again refluxed overnight under an argon atmosphere at which point the volatile components were reduced in vacuo. Ethyl acetate and 5% aqueous NaOH were added with stirring, and the product was extracted into the ethyl acetate. The ethyl acetate was then washed twice each with 5% aqueous NaOH and saturated aqueous NaHCO$_3$, once with brine and dried with Na$_2$SO$_4$ to give Intermediate 2(a) (4.65 g, 19.37 mmol) as a white solid in 84% yield.

Step 2. Preparation of 6-Amino-1H-indole-4-carboxylic Acid Methyl Ester 2(b)

Using a modification of the procedure described by Coe, J. W., et al. (1996) Tetrahedron Letters 37(34):6045–6048, Intermediate 2(a) (268 mg, 1.12 mmol) was dissolved in anhydrous N,N-dimethylformamide (0.56 mL) and N,N-dimethylformamide dimethyl acetal (0.445 mL, 3.35 mmol) was added under an Ar atmosphere with stirring. The mixture was heated at 120° C. overnight at which point the unreacted N,N-dimethylformamide dimethyl acetal was removed under vacuum (35–40° C., c.a. 5 mm Hg). To the resulting red enamine was added anhydrous N,N-dimethylformamide (c.a. 10 mL) and 10% palladium on carbon (230 mg) and the mixture was hydrogenated at 55 p.s.i. for 5 hours. The Pd catalyst was filtered through diatomaceous earth and H$_2$O was added to the filtrate. The aqueous component was then extracted multiple times with ethyl acetate and the combined extracts were dried with Na$_2$SO$_4$, filtered, and the volatile components were removed in vacuo to give the crude Intermediate 2(90 mg) as a brown glass. Purification was carried out by eluting through a silica plug with 20% ethyl acetate and 20% ethanol in hexane giving Intermediate 2(b) (45 mg, 0.24 mmol) as a brown solid in 21% yield.

Step 3. Preparation of Title Compound: 8-Amino-1,5-dihydro-[1,2]diazepino[4,5,6-cd]indol-6-one (Hydrochloric Salt)

With ice bath cooling under argon, to Intermediate 2(b) (45 mg, 0.24 mmol) in anhydrous CH$_2$Cl$_2$ (0.3 mL) and N,N-dimethylformamide (0.3 mL) was added dropwise a premixed Vilsmeier reagent (0.1 mL) consisting of POCl$_3$ (0.47 mL) in N,N-dimethylformamide (0.77 mL). After removing the ice bath, the mixture was stirred for 0.5 hours at which point the reaction was again cooled in an ice bath and an additional Vilsmeier reagent (0.1 mL) was added. Following removal of the ice bath, the reaction was stirred 0.5 hours and then poured onto ice. Ethyl acetate was added followed by aqueous saturated NaHCO$_3$. The product was then extracted into ethyl acetate, washed with brine, dried with Na$_2$SO$_4$, and filtered to give (by LCMS) di-N-formylated 3-formyl-1H-indole-4-carboxylic acid methyl ester (37 mg, 0.13 mmol) as a brown glass which was then dissolved in anhydrous methanol (2.2 mL). Acetic acid (0.022, 0.384 mmol) and H$_2$NNH$_2$·H$_2$O (0.038 mL, 0.78 mmol) were added, and the mixture was refluxed for 2 hours. After removing the volatile components in vacuo, the crude product was dissolved in H$_2$O and filtered, the water was lyophilized and the resulting yellow glass (36 mg) was chromatographed on silica gel eluting with 10% methanol in CH$_2$Cl$_2$. Fractions judged pure were pooled, and the product in methanol was acidified with 1M HCl. The volatile components were removed in vacuo using acetonitrile to azeotrope remaining water affording the title compound (4 mg, 0.016 mmol) as a brown solid in 7% yield.

$^1$H NMR (d$_6$-DMSO): δ 11.99 (s, 1H), 10.40 (s, 1H), 7.70 (s, 1H), 7.55 (s, 1H), 7.52–7.41 (m, 2H).

HRMS (MALDI M+H$^+$) Calcd for $C_{10}H_8N_4O$: 201.0771. Found: 201.0776.

Alternative Method for the Preparation of Intermediate 2(b) Hydrochloride:

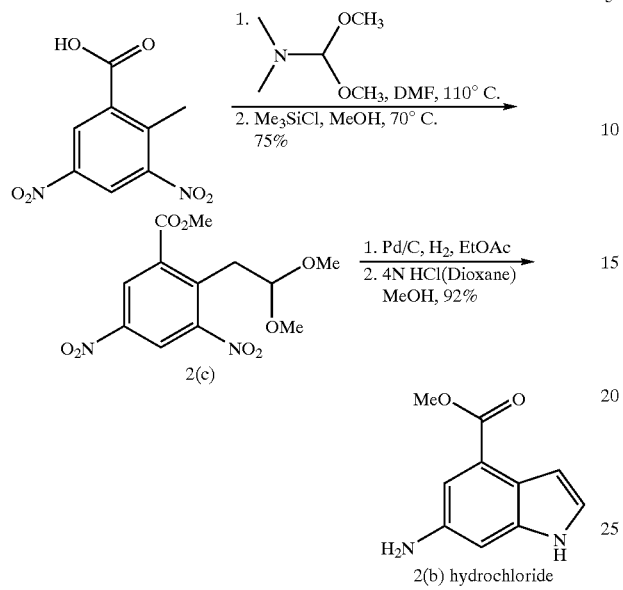

2(b) hydrochloride

Step 4. Preparation of 2-(2,2-Dimethoxy-ethyl)-3,5-dinitro-benzoic Acid Methyl Ester 2(c)

[Attn; 2-(2-Dimethylamino-vinyl)-3,5-dinitro-benzoic acid methyl ester generated during (first step of Step 4) enamine formation could lead to explosive decompositionl] 2-Methyl-3,5-dinitro-benzoic acid (100 g, 0.442 mol) was dissolved in anhydrous N,N-dimethylformamide (1 M, 400 mL). N,N-Dimethylformamide dimethyl acetal (188 mL, 1.33 mol) was added under an argon atmosphere over 10 min at ambient temperature with stirring. The mixture was heated at 110° C. for 5 hours behind a shield, and cooled at ambient temperature. N,N-Dimethylformamide and the unreacted N,N-dimethylformamide dimethyl acetal were removed under reduced pressure (35° C., c.a. 5 mm Hg). Toluene (~50 mL) was added and the volatiles removed under vacuum. 2-(2-Dimethylamino-vinyl)-3,5-dinitro-benzoic acid methyl ester, isolated as a dark red solid, was mixed with anhydrous methanol (880 mL) and chlorotrimethylsilane (140 mL, 1.10 mol) was added over 10 min. The solution was heated at reflux (oil bath 67–70° C.) under argon for 20 hours, cooled to ambient temperature, and the volume of the mixture was reduced under vaccuum to approximately 100 mL. The precipitated solid was collected by filtration and washed with cold methanol (100 mL). The dark brown solid was dried under vacuum, triturated with acetone (100 mL), again collected by filtration and washed with diethyl ether (150 mL) to afford Intermediate 2(c) (79 g). The mother liquor from the first precipitation and the various triturations were combined and concentrated. Additional Intermediate 2(c) (21 g) was then recrystallized from cyclohexane/ethyl acetate (9:1) providing a second batch. Again the resulting mother liquor was reduced in vacuo and a third batch of Intermediate 2(c) (4 g) was recrystallized from acetone/H$_2$O (6:4). The combined yield for all three batches of Intermediate 2(c) (104 g) was 75%.

Step 5. Preparation of 6-Amino-1H-indole-4-carboxylic Acid Methyl Ester Hydrochloride 2(b)

Intermediate 2(c) (20 g, 63.6 mmol) was dissolved in anhydrous ethyl acetate (350 mL) and 10% palladium on carbon (7.4 g, 6.36 mmol) was added under argon. The mixture was hydrogenated at 1 atm until the reaction was judged complete by LCMS. The Pd catalyst was removed by filtering through diatomaceous earth, and the filtrate was reduced in vacuo. The crude 3,5-diamino-2-(2,2-dimethoxy-ethyl)-benzoic acid methyl ester was dissolved in anhydrous methanol (40 ml), and 4.0 M HCl in dioxane (160 mL) was added. The mixture was stirred at ambient temperature for one hour. The precipitated solid was collected by filtration and washed with CH$_2$Cl$_2$ and diethyl ether and dried under vacuum to produce Intermediate 2(b) (hydrochloride) (11.85 g) as a gray solid. The filtrate was concentrated and more Intermediate 2(b) hydrochloride (1.48 g) was precipitated. The combined yield for both batches of Intermediate 2(b) (13.33 g) was 92%

Example 3

N-(6-Oxo-5,6-dihydro-1H-[1,2]diazepino[4,5,6-cd]indol-8-yl)-acetamide

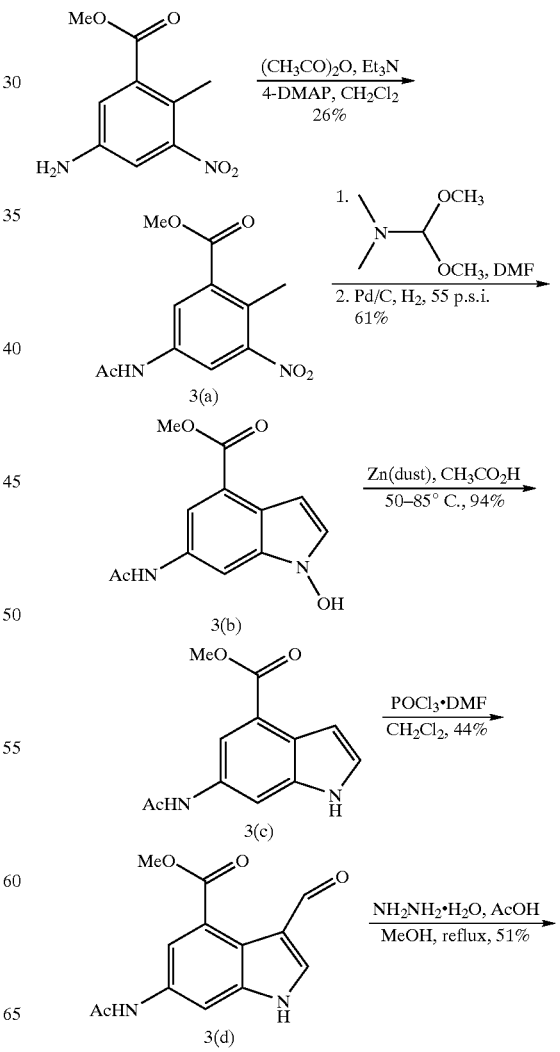

-continued

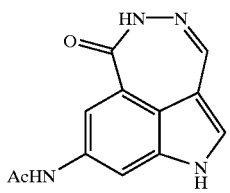

Step 1. Preparation of 5-Acetylamino-2-methyl-3-nitro-benzoic Acid Methyl Ester 3(a)

To 5-amino-2-methyl-3-nitro-benzoic acid methyl ester (428 mg, 2.04 mmol), prepared as described by Cannon et al. (1984) J. Med. Chem. 27:386–389, in $CH_2Cl_2$ (4 mL) was added triethylamine (1.71 mL, 12.2 mmol), acetic anhydride (0.77 mL, 8.14 mmol) and 4-(dimethylamino)pyridine (30 mg, 0.25 mmol) with stirring at ambient temperature. After stirring overnight, LCMS indicated a mixture of mono and diacetylated products. Saturated aqueous $NaHCO_3$ was added, and the mixture was again allowed to stir overnight. Additional $CH_2Cl_2$ was added, and the layers were separated. The organic layer was reduced and ethyl acetate was added. The organic layer was washed with saturated aqueous $NaHCO_3$, with $H_2O$, with saturated aqueous $KHSO_4$, with brine, dried ($Na_2SO_4$), filtered and evaporated to an oil which was then re-dissolved in a minimal amount of ethyl acetate. Hexane was added and the resulting precipitate was isolated as tan solids (469 mg) which were then purified on silica gel, eluting with 1:2 ethyl acetate:hexane followed by 1:1 ethyl acetate:hexane, to afford Intermediate 3(a) (133 mg, 0.53 mmol) as a cream solid in 26% yield. (5-diacetylamino-2-methyl-3-nitro-benzoic acid methyl ester (248 mg, 0.84 mmol) was also isolated.)

$^1$H NMR ($d_6$-DMSO): δ 10.46 (br s, 1H, exchanges), 8.34 (s, 1H), 8.14 (s, 1H), 3.89 (s, 3H), 2.43 (s, 3H), 2.08 (s, 3H).

LCMS: (M–H)$^-$ 251.3.

Step 2. Preparation of 6-Acetylamino-1-hydroxy-1H-indole-4-carboxylic Acid Methyl Ester 3(b)

To Intermediate 3(a) (117 mg, 0.46 mmol) in anhydrous N,N-dimethylformamide (0.5 mL) was added, under an Ar atmosphere with stirring, N,N-dimethylformamide dimethyl acetal (0.185 mL, 1.39 mmol). The mixture was heated at 120° C. for 5–6 hours at which point the unreacted N,N-dimethylformamide dimethyl acetal was removed under vacuum (35–40° C., c.a. 5 mm Hg). To the resulting red enamine was added anhydrous N,N-dimethylformamide (c.a. 20 mL), ethyl acetate (10 mL) and 10% palladium on carbon (150 mg). The mixture was hydrogenated at 55 p.s.i. for 4 hours at which point the N,N-dimethylformamide was removed in vacuo, methanol was added, and the Pd catalyst was removed by filtration. Again the volatile components were removed in vacuo. Following diethyl ether trituration, the triturate was evaporated to afford crude Intermediate 3(b) (70 mg, 0.28 mmol) as tan solids in 61% yield which were carried forward without further purification.

LCMS: (M–H)$^-$ 247.3.

Step 3. Preparation of 6-Acetylamino-1H-indole-4-arboxylic Acid Methyl Ester 3(c)

To Intermediate 3(b) (39 mg, 0.16 mmol) in acetic acid (1 mL) was added zinc dust (206 mg, 3.15 mmol) with stirring. The mixture was heated at 50° C. for 0.5 hours and then 65° C. for 0.5 hours during which time the mixture turns green. After cooling to room temperature methanol is added and the mixture is filtered though diatomaceous earth rinsing several times with methanol. Following evaporation the resulting tan solids are triturated with methanol and the volatile components of the triturate are remove in vacuo to afford crude Intermediate 3(c) (35 mg, 0.15 mmol) as tan solids in 94% crude yield which were then carried on without further purification.

LCMS: (M–H)$^-$ 231.2.

Step 4. Preparation of 6-Acetylamino-4-formyl-1H-indole-4-carboxylic Acid Methyl Ester 3(d)

With ice bath cooling under argon, 0.2 mL of a premixed Vilsmeier reagent consisting of $POCl_3$ (0.47 mL) in N,N-dimethylformamide (0.77 mL) was added in two equal portions to Intermediate 3(c) (35 mg, 0.15 mmol) in 1:1 $CH_2Cl_2$: N,N-dimethylformamide (1 mL). After 0.5 hours the reaction was quenched with water and extracted with ethyl acetate. The aqueous layer was then basified to about pH 8 with 5% aqueous NaOH and extracted again with ethyl acetate. The combined ethyl acetate extracts were dried with $Na_2SO_4$, filtered and evaporated to give Intermediate 3(d) (19 mg, 0.07 mmol) as yellow solids in 44% crude yield which were then carried on without further purification.

LCMS: (M–H)$^-$ 259.3.

Step 5. Preparation of Title Compound: N-(6-oxo-5,6-dihydro-1H-[1,2]diazepino[4,5,6-cd]indol-8-yl)-acetamide To Intermediate 3(d) (19 mg, 0.07 mmol) in anhydrous methanol (2.0 mL) was added acetic acid (0.006 mL, 0.1 mmol) and $H_2NNH_2 \cdot H_2O$ (11 mg, 0.22 mmol) and the mixture was refluxed for about 1 hour after which the volatile components were removed in vacuo and the resulting yellow glass was redissolved in methanol. Following recrystallization from methanol/diethyl ether, the title compound (9 mg, 0.04 mmol) was obtained as a yellow powder in 51% yield.

$^1$H NMR ($d_6$-DMSO): δ 11.60 (br s, 1H, exchanges), 10.10 (s, 1H, exchanges), 9.90 (s, 1H, exchanges), 8.00 (s, 1H), 7.45 (br s, 2H), 7.30 (s, 1H), 1.90 (s, 3H).

LCMS: (M+H$^+$) 243.1, (M+Na$^+$) 265.1.

Example 4

2,2,2-Trifluoro-N-(6-oxo-5,6-dihydro-1H-[1,2]diazepino[4,5,6-cd]indol-8-yl)-acetamide

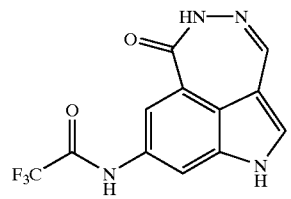

With stirring, trifluoroacetic anhydride (0.032 mL, 0.23 mmol) was added dropwise to triethylamine (0.088 mL, 0.63 mmol) and the title compound of Example 2 (freebase) (43 mg, 0.21 mmol) in N,N-dimethylformamide (2 mL). After 2.5 hours, additional trifluoroacetic anhydride (0.032 mL, 0.23 mmol) was added to drive the reaction to completion at which point diethyl ether was added to precipitate brown solids (25 mg), which were discarded. The triturate was reduced in volume and subjected to preparative HPLC (MetaChem Metasil AQ C18 reverse-phase 10 μm, 120A, 250×21.2 mm column eluting with $CH_3CN/0.1\%$ TFA in $H_2O$ at a flowrate of 20 mL/min using a gradient of 5–95% $CH_3CN$ over 20 min) affording, after isolation, the title compound (3.7 mg, 0.01 mmol) as a brown solid in 6% yield.

$^1$H NMR ($d_6$-DMSO): δ 12.01 (s, 1H), 11.41 (s, 1H), 10.40 (s, 1H), 8.15 (s, 1H), 7.91 (s, 1H), 7.78 (s, 1H), 7.61 (s, 1H)

LCMS: (M–H)$^-$ 295.2.

Example 5

7-Amino-2-phenyl-1,5-dihydro-[1,2]diazepino[4,5,6-cd]indol-6-one

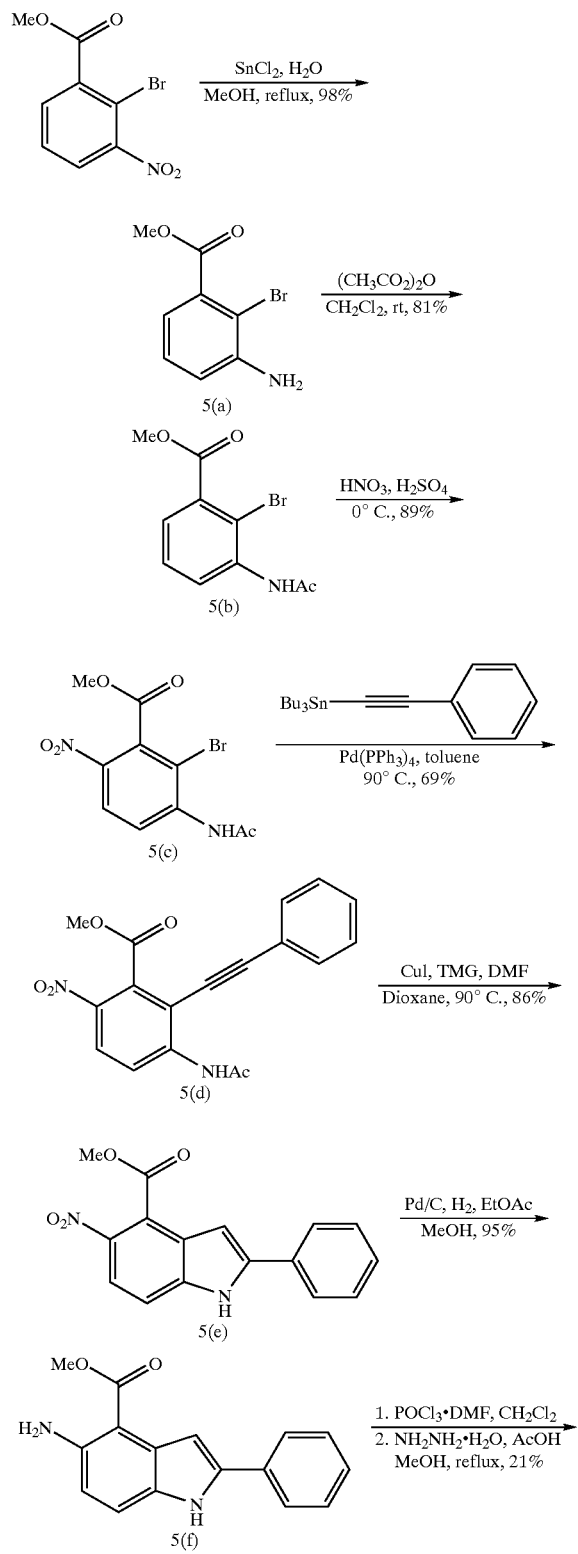

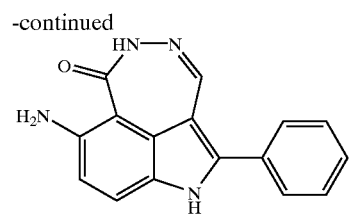

Step 1. Preparation of 3-Amino-2-bromo-benzoic Acid Methyl Ester 5(a)

2-Bromo-3-nitro-benzoic acid methyl ester (12.9 g, 49.5 mmol) (prepared from 2-amino-3-nitro-benzoic acid as described by Webber E. S., et al., see patent application number WO 01/16136 A2) and $SnCl_2$ (42 g, 223 mmol) were refluxed in methanol (225 mL, 0.2 M) and $H_2O$ (5.3 g, 243 mmol) for 2 hours. After cooling at ambient temperature, diatomaceous earth (20 g) and dichloromethane (1 L) were added followed with 3N aqueous sodium hydroxide (150 mL) with vigorous stirring. The mixture was filtered and the organic phase was washed with saturated aqueous sodium chloride. The organic solution was dried over sodium sulfate, filtered and all volatiles were removed under reduced pressure to afford Intermediate 5(a) (11.4 g) in 98% yield.

$^1$H-NMR ($d_6$-DMSO): δ 7.12 (dd, 1H, J=8.1, 7.5 Hz). 6.93 (dd, 1H, J=8.1, 1.6 Hz), 6.80 (dd, 1H, J=7.4, 1.6 Hz), 5.57 (s, 2H), 3.81 (s, 3H).

Step 2. Preparation of 3-Acetylamino-2-bromo-benzoic Acid Methyl Ester 5(b)

Intermediate 5(a) (2.21 g, 9.6 mmol) and acetic anhydride (1.82 mL, 19.2 mmol) were stirred in $CH_2Cl_2$ (100 mL, 0.1 M) at 22° C. for 24 hours. Volatiles were removed in vacuo and silica gel chromatography afforded Intermediate 5(b) (2.08 g) in 79% yield.

$^1$H-NMR ($d_6$-DMSO): δ 9.58 (s, 1H), 7.70 (dd, 1H, J=6.9, 2.7 Hz), 7.50–7.41 (m, 2H), 3.86 (s, 3H), 2.09 (s, 3H).

LCMS: (M+H$^+$) 272.0, 274.0

Step 3. Preparation of 3-Acetylamino-2-bromo-6-nitro-benzoic Acid Methyl Ester 5(c)

Intermediate 5(b) (1.0 g, 3.7 mmol) was nitrated in a manner analogous to step 1 of Example 2. Intermediate 5(c) (1.0 g, 89%) was obtained after silica gel chromatography.

$^1$H-NMR ($d_6$-DMSO): δ 9.83 (s, 1H), 8.3 (d, 1H, J=9.0 Hz), 8.15 (d, 1H, J=9.0 Hz), 3.93 (s, 3H), 2.20 (s, 3H).

LCMS: (M+H$^+$) 315.0, 317.0

Step 4. Preparation of 3-Acetylamino-6-nitro-2-phenylethynyl-benzoic Acid Methyl Ester 5(d)

Intermediate 5(c) (0.85 g, 2.7 mmol) was acetylated in a manner analogous to step 3 of Example 6 to afford Intermediate 5(d) (0.4 g, 44%) after silica gel chromatography.

$^1$H-NMR ($d_6$-DMSO): δ 9.93 (s, 1H), 8.32–8.25 (m, 2H), 7.65–7.59 (m, 2H), 7.53–7.47 (m, 3H), 3.97 (s, 3H), 2.25 (s, 3H).

LCMS: (M−H$^+$) 337.1

Step 5. Preparation of 5-Nitro-2-phenyl-1H-indole-4-carboxylic Acid Methyl Ester 5(e)

Intermediate 5(d) (0.096 g, 0.28 mmol), copper iodide (0.076 g, 0.4 mmol), N,N,N,N-tetramethylguanidine (0.36 mL, 2.8 mmol) were stirred in a mixture of dimethylformamide/dioxane (1:4, 2 mL, 0.15 M) at 90° C. for 2 hours. The reaction mixture was cooled to ambient temperature and poured into ethyl acetate (30 mL). The organic layer was washed subsequently with a saturated ammonium chloride solution (3×5 mL), $H_2O$ (2×5 mL), saturated aqueous sodium chloride solution (2×5 mL), dried over sodium sulfate, filtered and volatiles removed in vacuo.

Silica gel chromatography afforded Intermediate 5(e) (0.073 g) in 86% yield.

$^1$H-NMR (d$_6$-DMSO): δ 12.50 (s, 1H), 7.98–7.88 (m, 3H), 7.69–7.40 (m, 4H), 7.13 (broad s, 1H), 3.97 (s, 3H).

LCMS: (M–H$^+$) 295.1

Step 6. Preparation of 5-Amino-2-phenyl-1H-indole-4-carboxylic Acid Methyl Ester 5(f)

In an analogous manner to that of the preparation of Example 2 (step 5), Intermediate 5(e) (0.072 g, 0.24 mmol) was hydrogenated to afford Intermediate 5(f) (0.06 g, 95%).

$^1$H-NMR (d$_6$-DMSO): δ 11.68 (s, 1H), 7.86 (d, 2H, J=7.4 Hz), 7.52–7.43 (m, 3H), 7.31 (dd, 1H, J=7.4, 7.2 Hz), 7.20 (s, 1H), 6.83 (d, 1H, J=8.5 Hz), 3.94 (s, 3H).

LCMS: (M+H$^+$) 235.1

Step 7. Preparation of Title Compound: 7-Amino-2-phenyl-1,5-dihydro-[1,2]diazepino[4,5,6-cd]indol-6-one Carried out analogously to steps 4 and 5 of Example 3, Intermediate 5(f) (0.055 g, 0.21 mmol) was formylated and cyclized to provide the title compound (0.012 g, 21%).

$^1$H-NMR (d$_6$-DMSO): δ 12.17 (s, 1H), 8.32 (s, 1H), 7.95–7.84 (m, 3H), 7.74 (d, 1H, J=1.8 Hz), 7.55–7.47 (m, 2H), 7.42 (d, 1H. J=8.6 Hz), 7.37 (dd, 1H, J=7.4, 7.3 Hz), 5.91 (s, 2H).

LCMS: (M+H$^+$) 277.1

Example 6

N-(6-Oxo-2-phenyl-5,6-dihydro-1H-[1,2]diazepino[4,5,6-cd]indol-8-yl-acetamide

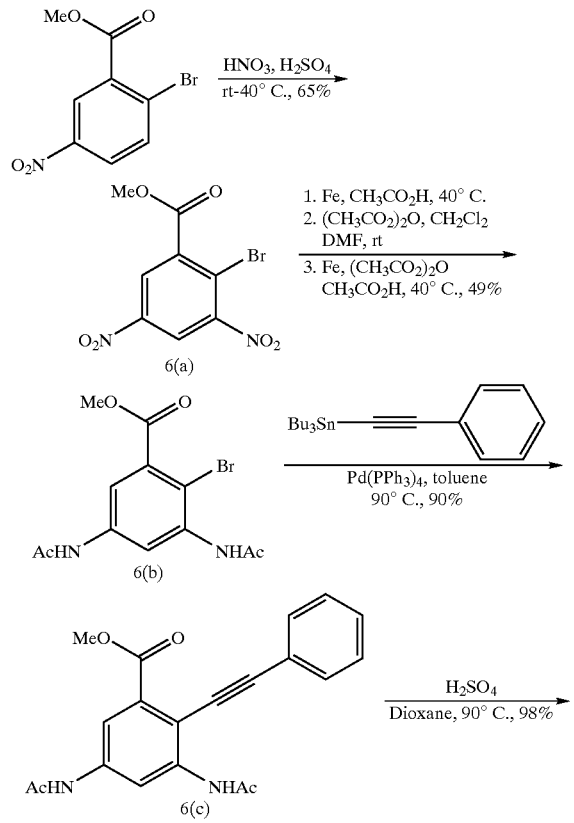

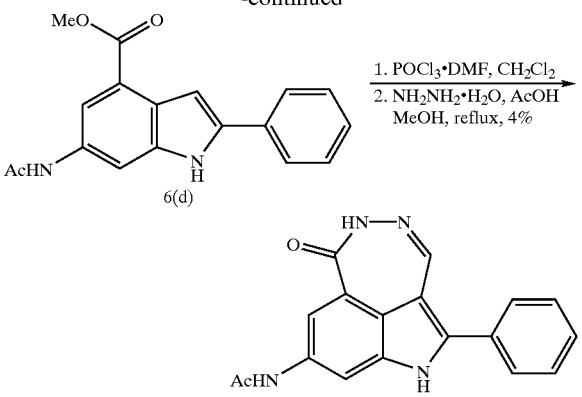

Step 1. Preparation of 2-Bromo-3,5-dinitro-benzoic Acid Methyl Ester 6(a)

Concentrated sulfuric acid (20 mL) was slowly added to 2-bromo-5-nitro-benzoic acid methyl ester (20.52 g, 78.91 mmol) with stirring. After a few minutes, fuming nitric acid (20 mL) was added and the mixture was capped and heated at 40° C. for approximately 60 hours at which point the flask was cooled to ambient temperature, carefully opened, and the reaction was poured onto ice water and ethyl acetate. The product was extracted into ethyl acetate and washed twice with H$_2$O, twice with saturated aqueous NaHCO$_3$, brine, dried (Na$_2$SO$_4$), and filtered to afford Intermediate 6(a) (15.64 g, 51.26 mmol) as a cream solid in 65% yield.

$^1$H NMR (d$_6$-DMSO): δ 9.07 (s, 1H), 8.73 (s, 1H), 3.98 (s, 3H).

LCMS: (M-CO$_2$CH$_3$)$^−$ 245.1, 247.1.

Step 2. Preparation of 3,5-Bis-acetylamino-2-bromo-benzoic Acid Methyl Ester 6(b)

To acetic acid (250 mL) at room temperature was added Intermediate 6(a) (15.49 g, 50.79 mmol). The mixture was placed in an oil bath at 40° C. for c.a. 10 min and stirred vigorously under an Ar atmosphere until the solution went clear. Iron powder (25.34 g, 453.72 mmol) was added and the mixture was heated at 40° C. for c.a. 6 hours. The mixture was filtered through diatomaceous earth, rinsing with methanol. The combined filtrate and rinses were evaporated to give orange solids, which were determined to be a mixture of products (13.2 g) resulting from incomplete reduction of the nitro groups. This mixture (13.1 g) in CH$_2$Cl$_2$ (48 mL) and N,N-dimethylformamide (5 mL) was then treated with acetic anhydride (36 mL, 382 mmol) and stirred overnight under an Ar atmosphere. The CH$_2$Cl$_2$ was evaporated and the mixture was partitioned between ethyl acetate and saturated aqueous NaHCO$_3$. The aqueous layer was extracted twice with ethyl acetate and the combined extracts were washed successively with 1:1 H$_2$O:saturated aqueous NaHCO$_3$ (multiple washings), 0.5 M aqueous HCl (X2), saturated aqueous NaHCO$_3$ (X2) and brine. The ethyl acetate solution was then dried (Na$_2$SO$_4$), filtered and evaporated to give yellow solids, which were then triturated with diethyl ether (c.a. 75 mL) to give a mixture of acetylated products (11.4 g) as a yellow solids. A portion of this mixture of acetylated products (5.5 g) in acetic acid (17.4 mL) was then treated with acetic anhydride (16.5 mL, 174 mmol) and iron powder (9.74 g, 174 mmol) and heated at 40° C. under an Ar atmosphere overnight. Methanol was then added and the reaction was stirred at room temperature for c.a. 1.5 hours. Then 9:1 CH$_2$Cl$_2$:methanol was added, and the mixture was filtered through diatomaceous earth, rinsing with 9:1 CH$_2$Cl$_2$:methanol. The combined filtrate and rinses were evaporated and again methanol was added and the mixture was stirred c.a. 0.5 hours after which the methanol was evaporated. Ethyl acetate was added followed by hexane to precipitate orange solids (6.9 g) which were collected. Silica gel chromatography eluting with 1:1 acetone:hexane which afforded, after isolation, Intermediate 6(b) (4.1 g, 12.46 mmol) as a cream solid in 49% yield.

Step 3. Preparation of 3,5-Bis-acetylamino-2-phenylethynyl-benzoic Acid Methyl Ester 6(c)

With stirring, argon was bubbled into anhydrous toluene (18 mL) containing Intermediate 6(b) (1.08 g, 3.29 mmol). Tributyl-phenylethynyl-stannane (1.73 mL, 4.94 mmol) and tetrakis(triphenylphosphine) palladium(0) (310 mg, 0.28 mmol) were added sequentially and more Ar was bubbled into the reaction. After capping tightly, the mixture was heated at 90° C. overnight under an argon atmosphere. After cooling to ambient temperature, $H_2O$, and saturated aqueous $KHSO_4$ were added and the product was extracted into ethyl acetate and isolated. Following silica gel chromatography eluting with 2:3 acetone:hexane, fractions judged pure were pooled. Intermediate 6(c) (1.14 g, 3.25 mmol) was isolated, found to be contaminated by approximately 5–10% triphenylphosphine oxide, and carried on to the next step without further purification.

$^1$H NMR ($d_6$-DMSO): δ 10.30 (s, 1H), 9.50 (s, 1H), 8.23 (s, 1H), 8.08 s, 1H), 7.63–7.51 (m, 2H, contaminated by $Ph_3PO$), 7.50–7.38 (m, 3H, contaminated by $Ph_3PO$), 3.90 (s, 3H), 2.17 (s, 3H), 2.05 (s, 3H).

LCMS: $(M+H^+)$ 351.1, $(M+Na^+)$ 373.1, $(M-H^-)$ 349.1.

Step 4. Preparation of 6-Acetylamino-2-phenyl-1H-indole-4-carboxylic Acid Methyl Ester 6(d)

To the impure Intermediate 6(c) (853 mg, 2.4 mmol) is added concentrated sulfuric acid (15 mL). After stirring 0.5 hours, the mixture is carefully poured onto methanol (30 mL) with vigorous swirling. Ethyl acetate (c.a. 300 mL) and $H_2O$ (c.a. 100 mL) are added. The aqueous layer is extracted three times with ethyl acetate, and the combined extracts are washed with saturated aqueous $NaHCO_3$ until the evolution of $CO_2$ ceases. The product in ethyl acetate is then washed with brine, dried ($Na_2SO_4$), filtered and volatile components evaporated to afford crude Intermediate 6(d) (790 mg, c.a. 2.4 mmol) as a yellow powder which was carried on without further purification.

$^1$H NMR ($d_6$-DMSO): δ 11.75 (s, 1H, exchanges), 10.07 (s, 1H, exchanges), 8.33 (s, 1H), 7.90–7.80 (m, 3H), 7.66–7.23 (m, 4H, partially obscured), 3.93 (s, 3H), 2.07 (s, 3H).

LCMS: $(M+H^+)$ 309.1, $(M+Na^+)$ 331.1, $(M-H)^-$ 307.1.

Step 5. Preparation of Title Compound: N-(6-Oxo-2-phenyl-5,6-dihydro-1H-[1,2]diazepino[4,5,6-cd]indol-8-yl-acetamide Crude Intermediate 6(d) (312 mg, c.a. 1 mmol) in N,N-dimethylformamide (2 mL) and $CH_2Cl_2$ (5 mL) was treated with Vilsmeier reagent (0.9 mL) in a manner similar to that described for Example 3, step 4. After removal of the $CH_2Cl_2$, adjusting the pH to c.a. 8 with 1N NaOH and removal of the volatile components in vacuo, the yellow solids were triturated with ethyl acetate and methanol. The triturate was evaporated to afford the crude 6-acetylamino-3-formyl-2-phenyl-1H-indole-4-carboxylic acid methyl ester (405 mg) as a yellow solid contaminated with salts from the aqueous quench. In a procedure similar to that described for Example 3, step 5, anhydrous methanol (15 mL), acetic acid (0.084 mL, 1.47 mmol) and $H_2NNH_2 \cdot H_2O$ (0.147 mL, 3.03 mmol) were then added and the mixture was refluxed for 2 hours. The volatile components were evaporated and the resulting solids were triturated with methanol to dissolve the product while leaving behind most of the insoluble solids. The triturate was evaporated, and this process was repeated. The second triturate was evaporated to give yellow solids (70 mg) enriched in product which were then subjected to silica gel chromatography eluting with hexane:ethyl acetate:ethanol (4:1:1) to give the title compound (12 mg, 0.04 mmol) after isolation as a yellow powder in approximately 4% overall yield.

$^1$H NMR ($d_6$-DMSO): δ 12.10 (s, 1H, exchanges), 10.33 (s, 1H, exchanges), 10.06(s, 1H, exchanges), 8.17 (s, 1H), 7.70–7.43 (m, 7H), 2.05 (s, 3H).

LCMS: $(M+H^+)$ 319.1, $(M+Na^+)$ 341.1, $(M-H)^-$ 317.

Alternative Method for the Preparation of Intermediate 6(b).

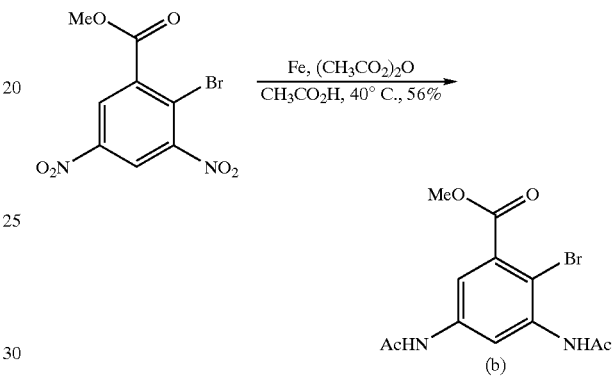

To acetic acid (10 mL) at room temperature was added acetic anhydride (10.0 mL, 106 mmol), iron powder (5.5 g, 98 mmol) and Intermediate 6(a) (3.0 g, 9.8 mmol). The mixture was placed in an oil bath at 43° C. and stirred vigorously under argon for 48 hours. The thick slurry goes from orange to tan in color. Additional acetic acid (2 mL), acetic anhydride (2 mL, 21.2 mmol), and iron powder (1.0 g, 17.9 mmol) were added, and the mixture was stirred at 43° C. for an additional 24 hours whereupon the mixture was poured into 10% methanol in $CH_2Cl_2$ (300 mL) and filtered though diatomaceous earth. The filtrate was concentrated and ethyl acetate (300 mL) and $H_2O$ (300 mL) were added. The product was extracted into ethyl acetate and washed twice with $H_2O$, twice with brine, dried ($MgSO_4$), and filtered. Following recrystallization from hot ethyl acetate (10 mL), collection by filtration and subsequent washing of the solids with $CH_2Cl_2$ (5 mL) and diethyl ether (30 mL), Intermediate 6(b) (1.8 g, 5.47 mmol) was obtained as a white solid in 56% yield.

Example 7

8-Amino-2-phenyl-1,5-dihydro-[1,2]diazepino[4,5,6-cd]indol-6-one

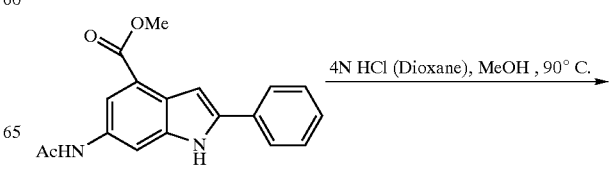

-continued

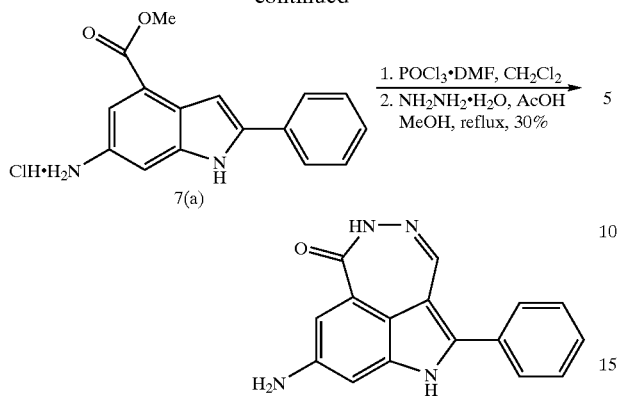

Step 1. Preparation of 6-Amino-2-phenyl-1H-indole-4-carboxylic Acid Methyl Ester (Hydrochloric Salt) Salt 7(a)

Intermediate 6(d) of Example 6 (9.3 g, 30.2 mmol) and anhydrous 4M HCl in dioxane (160 mL, 604 mmol) were heated in anhydrous methanol (160 mL) at reflux for 3 hours, cooled to ambient temperature and volatiles removed in vacuo. The resulting solid was triturated with ethyl acetate/$CH_2Cl_2$ (1:1, 50 mL) and dried to afford Intermediate 7(a) (8.7 g) in 95% yield.

$^1$H-NMR ($d_6$-DMSO): δ 12.26 (s, 1H), 10.10 (broad, 1H), 7.93 (d, 2H, J=7.7 Hz), 7.71 (d, 2H, J=12.2 Hz), 7.52 (dd, 2H, J=7.7, 7.6 Hz), 7.43–7.36 (m, 2H), 3.96 (s, 3H).

LCMS: (M+H$^+$) 267.2.

Step 2. Preparation of Title Compound: 8-Amino-2-phenyl-1,5-dihydro-[1,2]diazepino[4,5,6-cd]indol-6-one In two steps, analogous to steps 4 and 5 of Example 3, Intermediate 7(a) (8.7 g, 28.7 mmol) was cyclized to afford the title compound (5.47 g, 69%).

$^1$H-NMR ($d_6$-DMSO): δ 11.53 (s, 1H), 10.15 (s, 1H), 7.62–7.40 (m, 6H), 6.98 (d, 1H, J=1.8 Hz), 6.65 (d, 1H, J=1.8 Hz), 5.21 (s, 2H).

LCMS: (M+H$^+$) 277.2.

Example 8

N-(6-oxo-2-phenyl-5,6-dihydro-1H-[1,2]diazepino[4,5,6-cd]indol-8-yl)-succinamic Acid

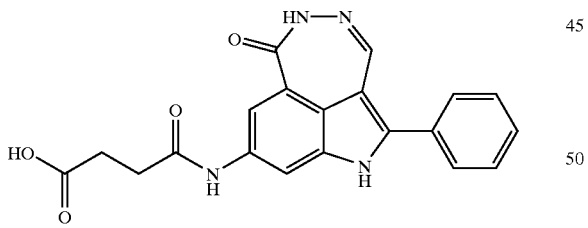

Succinic anhydride (3 eq, 0.022 g) was added to a solution of the title compound of Example 7 (0.02 g, 0.072 mmol) in N,N-dimethylformamide (0.7 M, 1 mL) and methanol (2.5 M, 0.3 mL). The reaction mixture was stirred at 22° C. for 24 hours and concentrated under reduced pressure. The yellow solid was triturated with methanol (1.0 mL) and collected by filtration. Following washes with methanol (4 mL) and diethyl ether (5.0 mL), the title compound (21 mg) was obtained in 77% yield.

$^1$H-NMR ($d_6$-DMSO): δ 12.03 (s, 1H), 10.31 (s, 1H), 10.09 (s, 1H), 8.12 (s, 1H), 7.68–7.45 (m, 7H), 2.60–2.53 (m, 4H).

LCMS: (M+H$^+$) 377.1.

Example 9

N-(6-Oxo-2-phenyl-5,6-dihydro-1H-[1,2]diazepino[4,5,6-cd]indol-8-yl)-methanesulfonamide

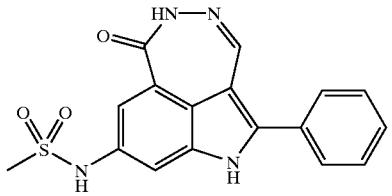

Methanesulfonyl Chloride (1.5 eq, 0.003 g) was added to a solution of the title compound of Example 7 (0.005 g, 0.018 mmol) in $CH_2Cl_2$ (0.045 M, 0.4 mL) and pyridine (0.045 M, 0.4 mL). The mixture was stirred at 22° C. for 24 hours and concentrated under reduced pressure. Silica gel chromatography (triethylamine/methanol/$CH_2Cl_2$; 1:5:94) afforded the title compound (1.7 mg) in 30% yield.

$^1$H-NMR ($d_6$-DMSO): δ 12.15 (s, 1H), 10.40 (s, 1H), 9.71 (s, 1H), 7.70–7.43 (m, 8H), 2.30 (m, 3H).

LCMS: (M+H$^+$) 355.1.

Example 10

1-(6-Oxo-2-phenyl-5,6-dihydro-1H-[1,2]diazepino[4,5,6-cd]indol-8-yl)-pyrrolidine-2,5-dione

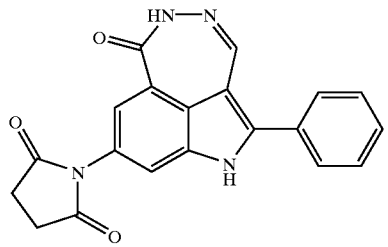

Triethylamine (0.18 mmol, 0.025 mL) and O-(7-azabenzotriazol-1-yl)-N,N,N',N'-tetramethyluronium hexafluorophosphate (0.04 mmol, 0.013 g) were added to a solution of the title compound of Example 8 (0.013 g, 0.036 mmol) in N,N-dimethylformamide (0.05 M, 0.75 mL). The reaction mixture was stirred at 22° C. for 12 hours and concentrated under reduced pressure. The yellow solid was triturated with methanol (3.0 mL), collected by filtration, and washed with methanol (4.0 mL) and diethyl ether (5.0 mL) to afford the title compound (5.8 mg) in 47% yield.

$^1$H-NMR ($d_6$-DMSO): δ 12.38 (s, 1H), 10.44 (s, 1H), 9.71 (s, 1H), 7.74–7.42 (m, 8H), 2.79 (m, 3H).

LCMS: (M+H$^+$) 359.1.

Example 11

2-Methyl-cyclopropanecarboxylic Acid(6-oxo-2-phenyl-5,6-dihydro-1H-[1,2]diazepino[4,5,6-cd]indol-8-yl)-amide

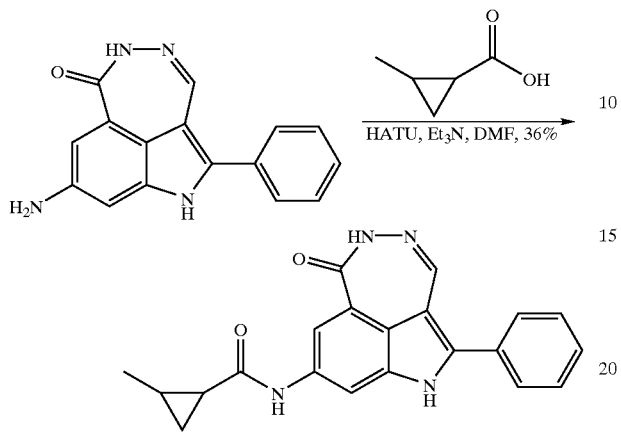

Triethylamine (0.030 mL, 0.22 mmol), the title compound of Example 7 (15 mg, 0.054 mmol) and 2-methyl-cyclopropanecarboxylic acid (6 mg, 0.062 mmol) were stirred in N,N-dimethylformamide (1.0 mL). O-(7-azabenzotriazol-1-yl)-N,N,N',N'-tetramethyluronium hexafluorophosphate (25 mg, 0.065 mmol) was added and the reaction was stirred overnight at which point the volatile components were removed under vacuum. The resulting mixture was purified on silica gel, eluting with 3:2 hexane-:ethyl acetate. The purest fractions were combined and after solvent removal, the resulting solids were triturated with diethyl ether to give the title compound (7 mg, 0.020 mmol) as yellow powder in 36% yield.

$^1$H-NMR (d$_6$-DMSO): δ 12.03 (s, 1H), 10.32 (s, 1H), 10.27 (s, 1H), 8.13 (s, 1H), 7.67–7.48 (m, 7H), 1.54 (m, 1H), 1.11(s, 1H), 1.09 (d, 3H), 1.07 (m, 1H), 1.03 (m, 1H).

LCMS: (M+H$^+$) 359.1, (M+Na$^+$) 381.1.

Example 12

N-(6-Oxo-2-phenyl-5,6-dihydro-1H-[1,2]diazepino[4,5,6-cd]indol-8-yl)-2-tetrazol-1-yl-acetamide

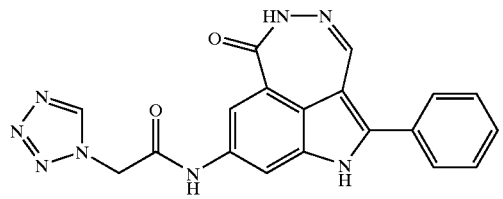

Preparation of example 12 from the title compound of Example 7 (15 mg, 0.054 mmol), tetrazol-1-yl-acetic acid (8 mg, 0.062 mmol), triethylamine (0.030 mL, 0.22 mmol), and O-(7-azabenzotriazol-1-yl)-N,N,N',N'-tetramethyluronium hexafluorophosphate (25 mg, 0.065 mmol) in N,N-dimethylformamide (1.0 mL) was carried out analogously to Example 11. Additional tetrazol-1-yl-acetic acid acid (1.0 mg, 0.008 mmol) and O-(7-azabenzotriazol-1-yl)-N,N,N',N'-tetramethyluronium hexafluorophosphate (3.0 mg, 0.008 mmol) were added after c.a. 18 hours to drive the reaction to completion. Filtration, concentration and recrystallization afforded the title compound (12 mg, 0.031 mmol) as a yellow powder in 58% yield.

$^1$H-NMR (d$_6$-DMSO): δ 12.13 (s, 1H), 10.71 (s, 1H), 10.39 (s, 1H), 9.44 (s, 1H), 8.07 (m, 1H), 7.68–7.47 (m, 7H), 5.05 (s, 2H).

LCMS: (M+H$^+$) 387.2, (M+Na$^+$) 409.1.

Example 13

2-Cyclopentyl-N-(6-oxo-2-phenyl-5,6-dihydro-1H-[1,2]diazepino[4,5,6-cd]indol-8-yl)-acetamide

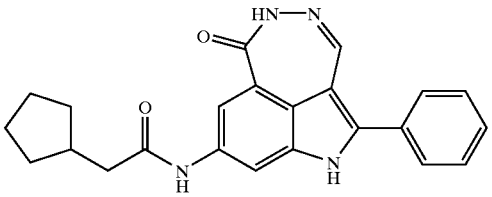

Preparation of example 13 from the title compound of Example 7 (15 mg, 0.054 mmol), cyclopentyl-acetic acid (8 mg, 0.062 mmol), triethylamine (0.030 mL, 0.22 mmol), and O-(7-azabenzotriazol-1-yl)-N,N,N',N'-tetramethyluronium hexafluorophosphate (25 mg, 0.065 mmol) in dimethylformamide (1.0 mL) was carried out analogously to Example 11. Silica gel chromatography (1:1 ethyl acetate:hexane), also in an analogous manner, followed by diethyl ether trituration afforded the title compound (3 mg, 0.008 mmol) as a yellow powder in 14% yield.

$^1$H-NMR (d$_6$-DMSO): δ 12.03 (s, 1H), 10.32 (s, 1H), 9.99 (s, 1H), 8.17 (s, 1H), 7.67–7.49 (m, 7H), 2.33–2.26 (m, 3H), 1.78 (m, 2H), 1.65–1.53 (m, 4H), 1.22 (m, 2H).

LCMS: (M+H$^+$) 387.2, (M+Na$^+$) 409.2.

Example 14

2-Methyl-N-(6-oxo-2-phenyl-5,6-dihydro-1H-[1,2]diazepino[4,5,6-cd]indol-8-yl)-nicotinamide

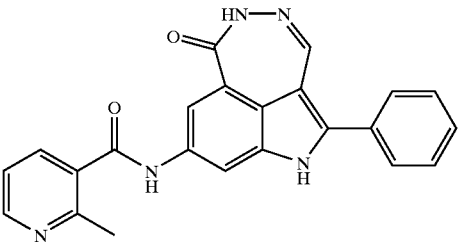

Preparation of example 14 from the title compound of Example 7 (15 mg, 0.054 mmol), 2-methyl-nicotinic acid (9 mg, 0.062 mmol), triethylamine (0.030 mL, 0.22 mmol), and O-(7-azabenzotriazol-1-yl)-N,N,N',N'-tetramethyluronium hexafluorophosphate (25 mg, 0.065 mmol) in N,N-dimethylformamide (1.0 mL) was carried out analogously to Example 11. Silica gel chromatography (ethyl acetate), also in an analogous manner, followed by diethyl ether trituration afforded the title compound (7 mg, 0.018 mmol) as a yellow powder in 33% yield.

$^1$H-NMR (d$_6$-DMSO): δ 12.13 (s, 1H), 10.57 (s, 1H), 10.36 (s, 1H), 8.57 (m, 1H), 8.25 (s, 1H), 7.90 (m, 1H), 7.84 (m, 1H), 7.68 (m, 2H), 7.61–7.50 (m, 4H), 7.34 (m, 1H), 2.60 (s, 3H).

LCMS: (M+H$^+$) 396.2, (M+Na$^+$) 418.1.

Example 15

4,4,4-Trifluoro-N-(6-oxo-2-phenyl-5,6-dihydro-1H-[1,2]diazepino[4,5,6-cd]indol-8-yl)-butyramide

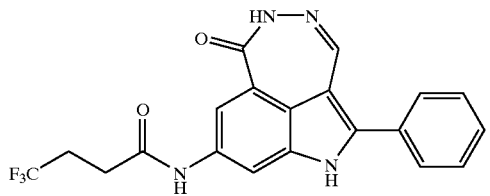

Preparation of example 15 from the title compound of Example 7 (15 mg, 0.054 mmol), 4,4,4-trifluorobutyric acid (9 mg, 0.062 mmol), triethylamine (0.030 mL, 0.22 mmol), and O-(7-azabenzotriazol-1-yl)-N,N,N'N'-tetramethyluronium hexafluorophosphate (25 mg, 0.065 mmol) in N,N-dimethylfomamide (1.0 mL) was carried out analogously to Example 11. Silica gel chromatography (1:1 ethyl acetate:hexane), also in an analogous manner, followed by diethyl ether trituration afforded the title compound (7 mg, 0.017 mmol) as a yellow powder in 32% yield. $^1$H-NMR (d$_6$-DMSO): δ 12.09 (s, 1H), 10.34 (s, 1H), 10.22 (s, 1H), 8.14 (s, 1H), 7.68–7.50 (m, 7H), 2.62 (m, 4H).

LCMS: (M+H$^+$) 401.1, (M+Na$^+$) 423.0.

Example 16

4-Methyl-[1,2,3]thiadiazole-5-carboxylic Acid(6-oxo-2-phenyl-5,6-dihydro-1H-[1,2]diazepino[4,5,6-cd]indol-8-yl)-amide

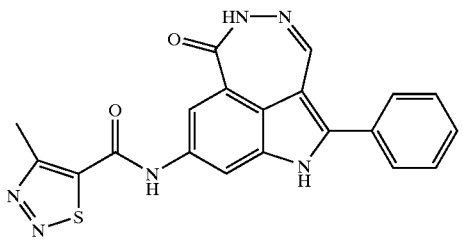

Preparation of example 16 from the title compound of Example 7 (15 mg, 0.054 mmol), 4-methyl-[1,2,3]thiadiazole-5-carboxylic acid (8 mg, 0.062 mmol), triethylamine (0.030 mL, 0.22 mmol), and O-7-azabenzotriazol-1-yl)-N,N,N'N'-tetramethyluronium hexafluorophosphate (25 mg, 0.065 mmol) in N,N-dimethylformamide (1.0 mL) was carried out analogously to Example 11. Additional 4-methyl-[1,2,3]thiadiazole-5-carboxylic acid (1.0 mg, 0.006 mmol) and O-(7-azabenzotriazol-1-yl)-N,N,N'N'-tetramethyluronium hexafluorophosphate (2.0 mg, 0.006 mmol) were added after c.a. 18 hours to drive the reaction to completion. Silica gel chromatography, also in an analogous manner, followed by diethyl ether trituration afforded the title compound (7 mg, 0.017 mmol) as a yellow powder in 32% yield.

$^1$H-NMR (d$_6$-DMSO): δ 12.21 (s, 1H), 10.85 (s, 1H), 10.41 (s, 1H), 8.18 (s, 1H), 7.81 (m, 1H), 7.69 (m, 2H), 7.61–7.51 (m, 4H), 2.85 (s, 3H).

LCMS: (M+H$^+$) 403.1, (M+Na$^+$) 425.0.

Example 17

N-(6-Oxo-2-phenyl-5.6-dihydro-1H-[1,2]diazepino[4,5,6-cd]indol-8-yl-2-phenyl-propionamide

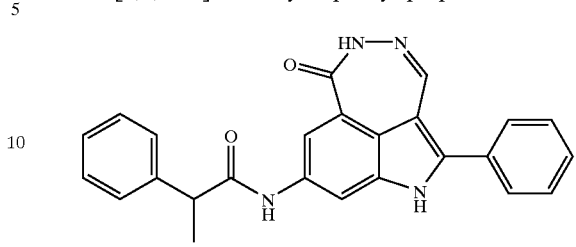

Preparation of example 17 from the title compound of Example 7 (15 mg, 0.054 mmol), 2-phenyl-propionic acid (9 mg, 0.062 mmol), triethylamine (0.030 mL, 0.22 mmol), and O-(7-azabenzotriazol-1-yl)-N,N,N',N'-tetramethyluronium hexafluorophosphate (25 mg, 0.065 mmol) in N,N-dimethylformamide (1.0 mL) was carried out analogously to Example 11. Silica gel chromatography (1:1 ethyl acetate:hexane), also in an analogous manner, followed by diethyl ether trituration afforded the title compound (7 mg, 0.017 mmol) as a yellow powder in 32% yield.

$^1$H-NMR (d$_6$-DMSO): δ 12.08 (s, 1H), 10.33 (s, 1H), 10.21 (s, 1H), 8.16 (s, 1H), 7.64 (m, 3H), 7.59 (m, 2H), 7.55 (m, 2H), 7.43 (m, 2H), 7.37 (m, 2H), 7.32 (m, 1H), 3.31 (quart., 1H), 1.45 (d, 3H).

LCMS: (M+H$^+$) 409.1, (M+Na$^+$) 431.1.

Example 18

N-(6-Oxo-2-phenyl-5,6-dihydro-1H-[1,2]diazepino[4,5,6-cd]indol-8-yl)-2-phenoxy-acetamide

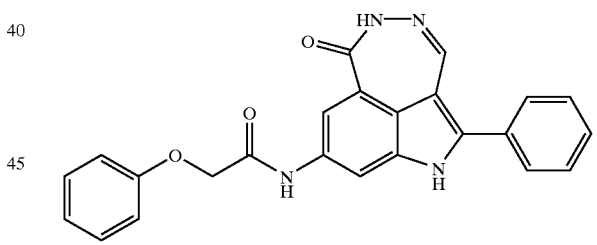

Preparation of example 18 from the title compound of Example 7 (15 mg, 0.054 mmol), phenoxy-acetic acid (9 mg, 0.062 mmol), triethylamine (0.030 mL, 0.22 mmol), and O-(7-azabenzotriazol-1-yl)-N,N,N',N'-tetramethyluronium hexafluorophosphate (25 mg, 0.065 mmol) in N,N-dimethylformamide (1.0 mL) was carried out analogously to Example 11. Silica gel chromatography (1:1 ethyl acetate:hexane increasing to 100% ethyl acetate), also in an analogous manner, followed by diethyl ether trituration afforded the title compound (4.5 mg, 0.011 mmol) as a yellow powder in 20% yield.

$^1$H-NMR (d$_6$-DMSO): δ 12.13 (s, 1H), 10.36 (s, 1H), 10.26 (s, 1H), 8.16 (s, 1H), 7.73 (m, 1H), 7.66 (m, 2H), 7.57 (m, 2H), 7.51 (m, 2H), 7.31 (m, 2H), 7.03 (m, 3H), 4.71 (s., 2H).

LCMS: (M+H$^+$) 411.0, (M+Na$^+$) 433.1.

Example 19

Methyl-[(6-oxo-2-phenyl-5,6-dihydro-1H-[1,2]diazepino[4,5,6-cd]indol-8-ylcarbamoyl)-methyl]-carbamic Acid tert-butyl Ester

Preparation of example 19 from the title compound of Example 7 (hydrochloride) (18 mg, 0.065 mmol), (tert-butoxycarbonyl-methyl-amino)-acetic acid (12 mg, 0.065 mmol), triethylamine (0.012 mL, 0.085 mmol), and O-(7-azabenzotriazol-1-yl)-N,N,N',N'-tetramethyluronium hexafluorophosphate (27 mg, 0.072 mmol) in CH$_2$Cl$_2$ (0.5 mL) and N,N-dimethylformamide (0.5 mL) was carried out analogously to Example 11. Silica gel chromatography (10:9:1 hexane:CH$_2$Cl$_2$:methanol), also in an analogous manner, followed by diethyl ether trituration afforded the title compound (28 mg, 0.063 mmol) as a yellow powder in 96% yield.

$^1$H NMR (CDCl$_3$): δ 9.11 (br s, 1H), 8.38 (br s, 2H), 7.62–7.46 (m, 7H), 7.43 (s, 1H), 4.02 (s, 2H), 3.03 (s, 3H), 1.50 (s, 9H).

LCMS: (M+H$^+$) 448.1, (M+Na$^+$) 470, (M−H$^-$) 446.1.

Example 20

2-Methylamino-N-(6-oxo-2-phenyl-5,6-dihydro-1H-[1,2]diazepino[4,5,6-cd]indol-8-yl)-methyl]-acetamide; Compound with Trifluoro-acetic Acid

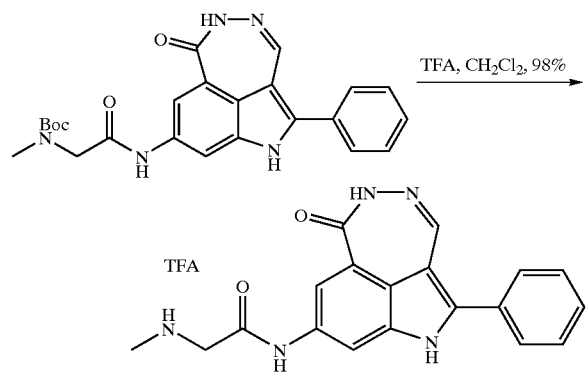

The title compound of Example 19 (19 mg, 0.042 mmol) in CH$_2$Cl$_2$ (0.65 mL) was treated with trifluoroacetic acid (0.45 mL) and allowed to stir for 0.5 hours. The volatile components were removed under vacuum, and diethyl ether was added and evaporated three times to give the title compound (19 mg, 0.041 mmol) as a yellow, orange powder in 98% yield.

$^1$H NMR (d$_4$-methanol): δ 8.15 (s, partially exchanged), 7.68–7.52 (m, 8H), 4.00 (s, 2H), 2.80 (s, 3H).

LCMS: (M+H$^+$) 348.2.

Example 21

N-(6-Oxo-2-phenyl-5,6-dihydro-1H-[1,2]diazepino[4,5,6-cd]indol-8-yl)-butyramide

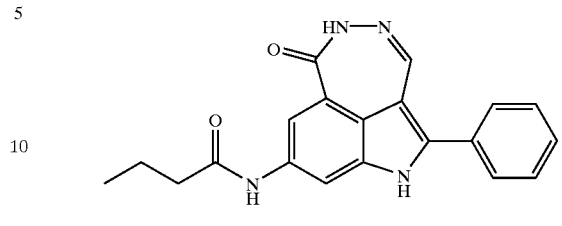

Preparation of example 21 from the title compound of Example 7 (hydrochloride) (22 mg, 0.080 mmol), n-butyric acid (0.007 mL, 0.080 mmol), triethylamine (0.014 mL, 0.10 mmol), and O-(7-azabenzotriazol-1-yl)-N,N,N',N'-tetramethyluronium hexafluorophosphate (32 mg, 0.084 mmol) in CH$_2$Cl$_2$ (0.3 mL) and N,N-dimethylformamide (0.3 mL) was carried out analogously to Example 11. Silica gel chromatography (10:9:1 hexane:CH$_2$Cl$_2$:methanol followed by 9:5:1 CH2Cl$_2$:hexane:methanol), also in an analogous manner, afforded the title compound (14 mg, 0.04 mmol) as a yellow powder in 50% yield.

$^1$H NMR (d$_6$-DMSO): δ 12.05 (s, 1H, exchanges), 10.22 (s, 1H, exchanges), 10.00 (s, 1H, exchanges), 8.15 (s, 1H), 7.39–7.71 (m, 7H), 2.30 (m, 2H)[1], 1.67 (m, 2H)[2], 0.95 (m, 3H)[1]. [1] Becomes triplet upon DCI addition, [2] Becomes quartet upon DCI addition.

LCMS: (M+H$^+$) 347.1, (M+Na$^+$) 369.1.

Example 22

N-(6-Oxo-2-phenyl-5,6-dihydro-1H-[1,2]diazepino[4,5,6-cd]indol-8-yl)-nicotinamide

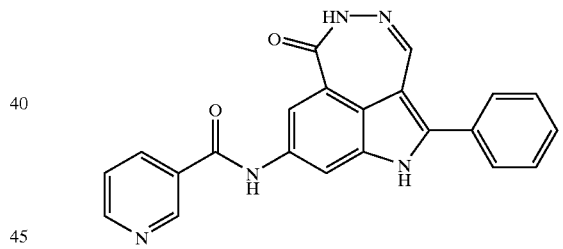

Preparation of example 22 from the title compound of Example 7 (hydrochloride) (21 mg, 0.076 mmol), nicotinic acid (7 mg, 0.076 mmol), triethylamine (0.014 mL, 0.10 mmol), and O-(7-azabenzotriazol-1-yl)-N,N,N,',N'-tetramethyluronium hexafluorophosphate (32 mg, 0.084 mmol) in CH$_2$Cl$_2$ (0.3 mL) and N,N-dimethylformamide (0.3 mL) was carried out analogously to Example 11. Silica gel chromatography (9:1 CH$_2$Cl$_2$:methanol), also in an analogous manner, afforded the title compound (20 mg, 0.052 mmol) as a yellow powder in 69% yield.

$^1$H NMR (d$_6$-DMSO): δ 12.18 (s, 1H, exchanges), 10.59 (s, 1H, exchanges), 10.38 (s, 1H, exchanges), 9.17(s, 1H), 8.80 (s, 1H, partially obscurred, with fine splitting), 8.40–8.26 (m, 2H), 7.91 (s, 1H), 7.73–7.65 (m, 2H), 7.62–7.47 (m, 5H).

$^1$H NMR (d$_6$-DMSO/DCI): δ 9.44 (s, 1H), 9.10 (d, 1H, J=5.0 Hz), 9.00 (d, 1H, J=9.5), 8.32 (s, 1H), 8.15 (dd, 1H, J=7.0, 7.5 Hz), 7.92 (s, 1H), 7.73 (s, 1H, overlapping), 7.68 (s, 1H, overlapping), 7.64–7.50 (m, 4H).

LCMS: (M+H$^+$) 382.1, (M+Na$^+$) 404.1.

Example 23

2-Methyl-N-(6-oxo-2-phenyl-5,6-dihydro-1H-[1,2]diazepino[4,5,6-cd]indol-8-yl)-benzamide

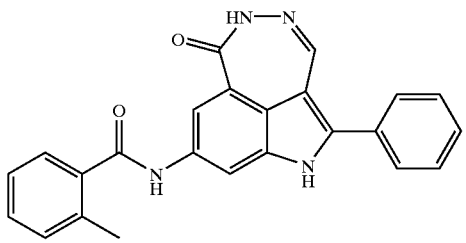

Preparation of example 23 from the title compound of Example 7 (hydrochloride) (22 mg, 0.08 mmol), 2-methylbenzoic acid (11 mg, 0.08 mmol), triethylamine (0.014 mL, 0.10 mmol), and O-(7-azabenzotriazol-1-yl)-N,N,N',N'-tetramethyluronium hexafluorophosphate (33 mg, 0.088 mmol) in $CH_2Cl_2$ (0.3 mL) and N,N-dimethylformamide (0.3 mL) was carried out analogously to Example 11. Silica gel chromatography (8:5:2 $CH_2Cl_2$:hexane:methanol), also in an analogous manner, afforded the title compound (23 mg, 0.058 mmol) as a yellow powder in 73% yield.

$^1$H NMR ($d_6$-DMSO): δ 12.11 (s, 1H, exchanges), 10.42 (s, 1H, exchanges), 10.34 (s, 1H, exchanges), 8.24 (s, 1H), 7.88 (s, 1H), 7.71–7.65 (m, 2H), 7.63–7.45 (m, 3H), 7.43–7.35 (m, 2H), 7.34–7.25 (m, 3H), 2.4 (s, 3H).

LCMS: (M+H$^+$) 395.1, (M+Na$^+$) 417.0.

Example 24

N-(6-Oxo-2-phenyl-5,6-dihydro-1H-[1,2]diazepino[4,5,6-cd]indol-8-yl)-benzamide

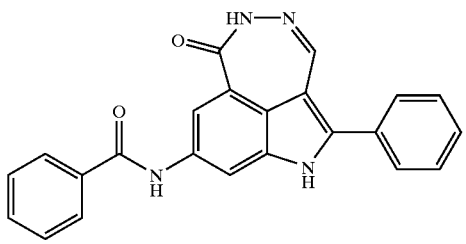

Preparation of example 24 from the title compound of Example 7 (hydrochloride) (23 mg, 0.082 mmol), benzoic acid (11 mg, 0.09 mmol), triethylamine (0.016 mL, 0.115 mmol), and O-(7-azabenzotriazol-1-yl)-N,N,N,',N'-tetramethyluronium hexafluorophosphate (34 mg, 0.090 mmol) in $CH_2Cl_2$ (0.3 mL) and N,N-dimethylformamide (0.3 mL) was carried out analogously to Example 11. Silica gel chromatography (10:9:1 hexane:$CH_2Cl_2$:methanol followed by 8:5:2 $CH_2Cl_2$:hexane:methanol), also in an analogous manner, afforded the title compound (20 mg, 0.053 mmol) as a yellow powder in 64% yield.

$^1$H NMR ($d_6$-DMSO): δ 12.13 (s, 1H), 10.41 (s, 1H), 10.35 (s, 1H), 8.32 (s, 1H), 8.03 (d, 2H, J=8 Hz), 7.94 (s, 1H), 7.70 (s, 1H, overlapping), 7.67 (s, 1H, overlapping), 7.63–7.48 (m, 7H).

LCMS: (M+H$^+$) 381.1, (M+Na$^+$) 403.1.

Example 25

N-(6-Oxo-2-phenyl-5,6-dihydro-1H-[1,2]diazepino[4,5,6-cd]indol-8-yl)-2-phenyl-acetamide

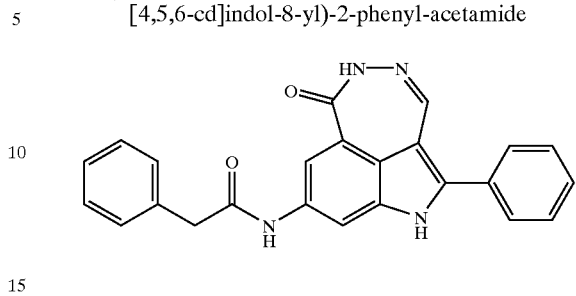

Preparation of example 25 from the title compound of Example 7 (hydrochloride) (20 mg, 0.072 mmol), phenylacetic acid (11 mg, 0.08 mmol), triethylamine (0.014 mL, 0.10 mmol), and O-(7-azabenzotriazol-1-yl)-N,N,N',N'-tetramethyluronium hexafluorophosphate (30 mg, 0.080 mmol) in $CH_2Cl_2$ (0.3 mL) and N,N-dimethylformamide (0.3 mL) was carried out analogously to Example 11. Silica gel chromatography (8:5:2 $CH_2Cl_2$:hexane:methanol), also in an analogous manner, afforded the title compound (27 mg, 0.068 mmol) as a yellow powder in 95% yield.

$^1$H NMR ($d_6$-DMSO): δ 12.08 (s, 1H, exchanges), 10.31 (s, 2H, exchanges), 8.18 (s, 1H), 7.72–7.62 (m, 3H), 7.60–7.45 (m, 4H), 7.41–7.21 (m, 5H), 3.68 (s, 2H).

LCMS: (M+H$^+$) 395.1, (M+Na$^+$) 417.1.

Example 26

N-(6-Oxo-2-phenyl-5,6-dihydro-1H-[1,2]diazepino[4,5,6-cd]indol-8-yl)-2-piperazin-1-yl-acetamide Di-trifluoroacetic Acid Salt

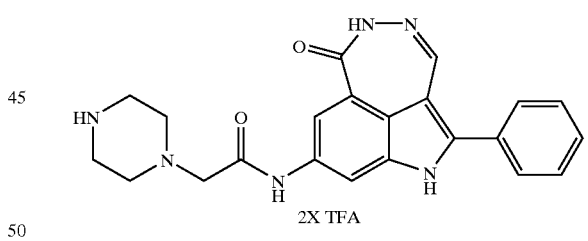

To a suspension of the title compound of Example 27 in dichloromethane (0.3 M, 0.6 mL), was added trifluoroacetic acid (0.3 M, 0.6 mL). The reaction mixture was stirred at 22° C. for 0.5 hours and concentrated under reduced pressure. The solid was triturated with dichloromethane (3.0 mL), collected by filtration, and washed with diethyl ether (5.0 mL) to afford the title compound (9.8 mg) in 95% yield.

$^1$H-NMR ($d_6$-DMSO): δ 12.09 (s, 1H), 10.36 (s, 1H), 9.98 (s, 1H), 8.53 (bs, 2H), 8.16 (d, 1H, J=1.6 Hz), 7.66 (m, 2H), 7.69–7.48 (m, 7H), 3.32 (s, 2H), 3.20 (m, 4H), 2.82 (m, 4H).

HRMS: (M+H$^+$) calcd for $C_{22}H_{23}N_6O_2$, 403.1882, found 403.1902.

Example 27

4-[(6-Oxo-2-phenyl-5,6-dihydro-1H-[1,2]diazepino[4,5,6-cd]indol-8-ylcarbamoyl)-methyl]-piperazine-1-carboxylic Acid tert-butyl Ester

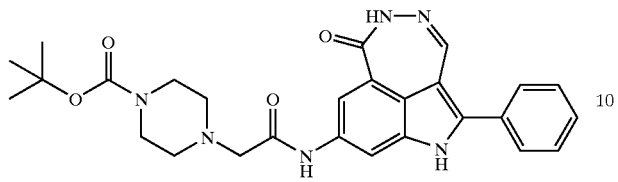

Preparation of example 27 from the title compound of Example 7 (0.025 g, 0.09 mmol), 4-carboxymethyl-piperazine-1 carboxylic acid tert-butyl ester (0.044 g, 0.18 mmol), triethylamine (0.05 mL, 0.4 mmol), and O-(7-azabenzotriazol-1-yl)-N,N,N',N'-tetramethyluronium hexafluorophosphate (38 mg, 0.1 mmol) and N,N-dimethylformamide (0.05 M, 1.8 mL) was carried out analogously to Example 11. Silica gel chromatography (95:5 CH$_2$Cl$_2$/methanol), also in an analogous manner, afforded the title compound (15 mg) as a yellow powder in 33% yield.

$^1$H-NMR (d$_6$-DMSO): δ 12.07 (s, 1H), 10.34 (s, 1H), 9.92 (s, 1H), 8.17 (s, 1H), 7.69–7.64 (m, 3H), 7.61–7.54 (m, 2H), 7.52–7.47 (m, 2H), 3.40 (m, 4H), 3.29 (m buried, 4H), 3.18 (s, 2H).

HRMS: (M+H$^+$) calcd for C$_{29}$H$_{31}$N$_6$O$_4$, 503.2407, found 503.2407.

The starting material 4-Carboxymethyl-piperazine-1-carboxylic acid tert-butyl ester was prepared as follow:

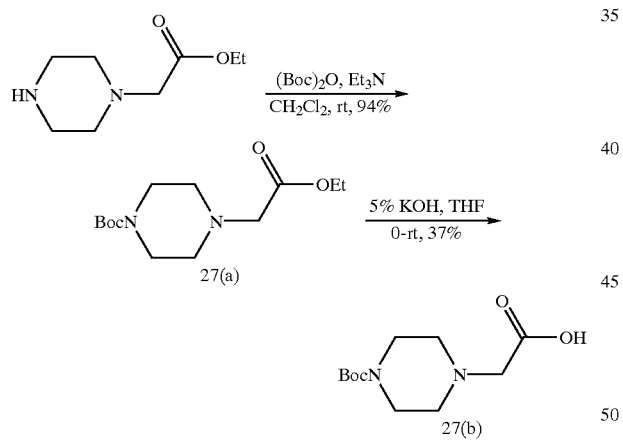

Step 1. Preparation of 4-Methoxycarbonylmethyl-piperazine-1-carboxylic Acid tert-butyl Ester 27(a)

Piperazin-1-yl-acetic acid ethyl ester (2.84 g, 15.7 mmol), triethylamine (7.6 mL, 55.0 mmol) and di-tert-butyl dicarbonate (4.45 g, 20.4 mmol) were stirred in CH$_2$Cl$_2$ (0.3 M, 55 mL) at 22° C. for 24 hours. The volatiles were removed in vacuo and silica gel chromatography (60:40 ethyl acetate/hexanes), afforded Intermediate 27(a) (4.01 g) in 94% yield.

$^1$H-NMR (d$_6$-DMSO): δ 4.08 (q, 2H, J=7.1 Hz), 3.35–3.21 (m, 6H), 2.52–2.41 (m, 4H), 1.39 (s, 9H), 1.18 (t, 7.1 Hz).

$^{13}$C-NMR (d$_6$-DMSO): δ 170.2, 154.2, 79.1, 60.2, 58.6, 52.0, 28.4, 14.5.

Step 2. Preparation of 4-Carboxymethyl-piperazine-1-carboxylic Acid tert-butyl Ester 27(b)

Intermediate 27(a) (3.6 g, 13.2 mmol) and a 5% aqueous KOH solution (90 mL, 80.0 mmol) were stirred in tetrahydrofuran (30 mL, 0.44 M) at 22° C. for 2 hours. The volatiles were removed in vacuo and treatment with strongly acidic Dowex-50™ (WX8-200), elution with ammonium hydroxide (1.0 N), and treatment with Amberlite™ CG-50 afforded Intermediate 27(b) (1.2 g) in 37% yield.

$^1$H-NMR (d$_6$-DMSO): δ 3.35–3.31 (m, 4H), 3.21 (s, 2H), 2.52–2.41 (m, 4H), 1.39 (s, 9H).

Example 28

2-Cyclohexyl-N-(6-oxo-2-phenyl-5,6-dihydro-1H-[1,2]diazepino[4,5,6-cd]indol-8-yl)-acetamide

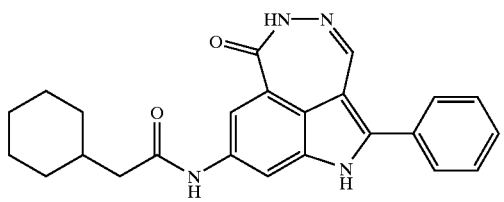

Preparation of example 28 from the title compound of Example 7 (0.025 g, 0.09 mmol), Cyclohexyl-acetic acid (0.015 g, 0.11 mmol), triethylamine (0.05 mL, 0.4 mmol), O-(7-azabenzotriazol-1-yl)-N,N,N',N'-tetramethyluronium hexafluorophosphate (38 mg, 0.1 mmol) and N,N-dimethylformamide (0.05 M, 1.8 mL) was carried out analogously to Example 11. Silica gel chromatography (95:5 CH$_2$Cl$_2$/methanol) also in an analogous manner followed by diethyl ether trituration afforded the title compound (13 mg) as a yellow powder in 36% yield.

$^1$H-NMR (d$_6$-DMSO): δ 12.03 (s, 1H), 10.32 (s, 1H), 9.99 (s, 1H), 8.17 (s, 1H), 7.68–7.45 (m, 7H), 2.20 (d, 2H, J=7.0 Hz), 1.86–1.58 (m, 6H), 1.31–1.10 (m, 3H), 1.10–0.91 (m, 2H).

HRMS: (M+H$^+$) calcd for C$_{24}$H$_{25}$N$_4$O$_2$, 401.1978, found 401.1987.

Example 29

4-(6-Oxo-2-phenyl-5,6-dihydro-1H-[1,2]diazepino[4,5,6-cd]indol-8-ylcarbamoyl)-piperidine-1-arboxylic Acid tert-butyl Ester

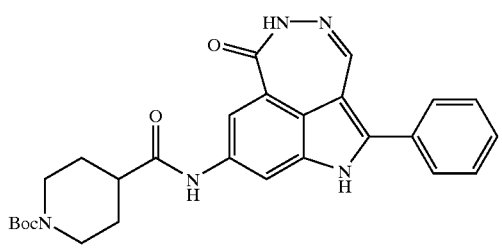

Preparation of example 29 from the title compound of Example 7 (hydrochloride) (22 mg, 0.07 mmol), piperidine-1,4-dicarboxylic acid mono-tert-butyl ester (19 mg, 0.084 mmol), triethylamine (0.015 mL, 0.105 mmol), and O-(7-azabenzotriazol-1-yl)-N,N,N',N'-tetramethyluronium hexafluorophosphate (32 mg, 0.084 mmol) in CH$_2$Cl$_2$ (0.3 mL) and N,N-dimethylformamide (0.3 mL) was carried out analogously to Example 11. Silica gel chromatography (8:5:2 CH$_2$Cl$_2$:hexane:methanol), also in an analogous manner, afforded the title compound (24 mg, 0.049 mmol) as a yellow powder in 70% yield.

¹H NMR (d₆-DMSO): 12.09 (s, 1H); 10.38 (s, 1H), 10.12 (s, 1H), 8.17 (s, 1H), 7.70–7.64 (m, 3H), 7.62–7.54 (m, 2H), 7.53–7.49 (m, 2H), 4.01 (br d, 2H, J=12.06 Hz), 2.86–2.72 (m, 2H), 1.81 (br d, 2H, J=13:00 Hz), 1.58–1.44 (m, 2H), 1.42 (s, 9H), 1.40 (m, 1H, partially obscured).

LCMS: (M–H)⁻ 486.2.

Example 30

4-[(6-Oxo-2-phenyl-5,6-dihydro-1H-[1,2]diazepino [4,5,6-cd]indol-8-ylcarbamoyl)-methyl]-piperidine-1-carboxylic Acid tert-butyl Ester

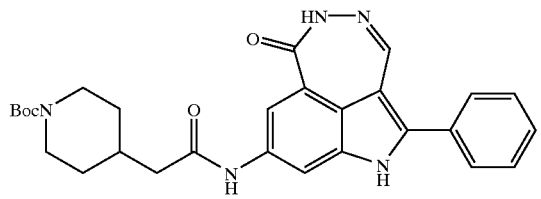

Preparation of example 30 from the title compound of Example 7 (hydrochloride) (22 mg, 0.07 mmol), 4-carboxymethyl-piperidine-1-carboxylic acid tert-butyl ester (20 mg, 0.084 mmol), triethylamine (0.015 mL, 0.105 mmol), and O-(7-azabenzotriazol-1-yl)-N,N,N',N'-tetramethyluronium hexafluorophosphate (32 mg, 0.084 mmol) in CH₂Cl₂ (0.3 mL) and N,N-dimethylformamide (0.3 mL) was carried out analogously to Example 11. Silica gel chromatography (8:5:2 CH₂Cl₂:hexane:methanol), also in an analogous manner, afforded the title compound (35 mg, 0.070 mmol) as a yellow powder in 100% yield.

¹H NMR (d₆-DMSO): 12.08 (s, 1H), 10.38 (s, 1H), 10.09 (s, 1H), 8.19 (s, 1H), 7.70–7.46 (m, 7H), 3.93 (br d, 2H, J=12.24 Hz), 2.81–2.66 (m, 2H), 2.27 (d, 2H, J=7.16 Hz), 1.96 (br s, 1H), 1.67 (br d, 2H, J=13.94 Hz), 1.40 (s, 9H), 1.17–1.01 (m, 2H).

LCMS: (M+Na⁺) 524.2, (M–H)⁻ 500.1.

Example 31

Piperidine-4-carboxylic acid (6-oxo-2-phenyl-5,6-dihydro-1H-[1,2]diazepino[4,5,6-cd]indol-8-yl)-amide Compound with Trifluoro-acetic Acid

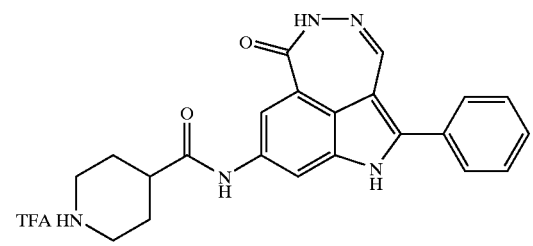

Preparation of example 31 from the title compound of Example 29 (20 mg, 0.041 mmol) and 45% TFA in CH₂Cl₂ (1 mL) was carried out analogously to Example 20. Isolation, also in an analogous manner, afforded the title compound (20 mg, 0.040 mmol) as a yellow powder in 97% yield.

¹H NMR (d₄-methanol): 8.03 (s, 1H), 7.56–7.31 (m, 7H), 3.43–3.32 (m, 2H), 3.01–2.90 (m, 2H), 2.61 (m, 1H), 2.04–1.78 (m, 4H).

LCMS: (M+H⁺) 388.1

Example 32

N-(6-Oxo-2-phenyl-5,6-dihydro-1H-[1,2]diazepino [4,5,6-cd]indol-8-yl)-2-piperidin-4-yl-acetamide; Compound with Trifluoro-acetic Acid

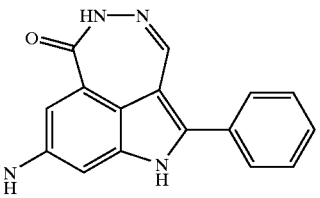

Preparation of example 32 from the title compound of Example 30 (31 mg, 0.062 mmol) and 45% TFA in CH₂Cl₂ (1 mL) was carried out analogously to Example 20. Isolation, also in an analogous manner, afforded the title compound (29 mg, 0.056 mmol) as a yellow powder in 91% yield.

¹H NMR (d₄-methanol): δ 8.20 (s, 1H), 7.70–7.50 (m, 7H), 3.50–3.40 (m, 2H, partially obscurred), 3.10 (dd, 2H, J=9.0, 9.2 Hz), 2.45 (d, 2H, J=7.2 Hz), 2.25 (br m, 1H), 2.0–2.11 (m, 2H), 1.68–1.45 (m, 2H).

LCMS: (M+H⁺) 402.2

Example 33 tert-butyl (1S)-1-cyclohexyl-2-oxo-2-[(6-oxo-2-phenyl-5.6-dihydro-1H-[1,2]diazepino[4,5,6-cd] indol-8-yl)amino]ethylcarbamate

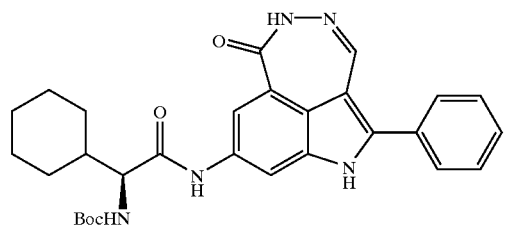

Preparation of example 33 from the title compound of Example 7 (35 mg, 0.13 mmol), (2S)-[(tert-butoxycarbonyl) amino](cyclohexyl)ethanoic acid (39 mg, 0.15 mmol), triethylamine (0.073 mL, 0.52 mmol), and O-(7-azabenzotriazol-1-yl)-N,N,N',N'-tetramethyluronium hexafluorophosphate (58 mg, 0.15 mmol) in N,N-dimethylformamide (2.0 mL) was carried out analogously to Example 11 except that after 24 hours additional (2S)-[(tert-butoxycarbonyl)amino](cyclohexyl)ethanoic acid (17 mg, 0.065 mmol) and O-(7-azabenzotriazol-1-yl)-N,N,N',N'-tetramethyluronium hexafluorophosphate (25 mg, 0.065 mmol) were added to drive the reaction to completion. Silica gel chromatography (1:1 ethyl acetate:hexane), also in an analogous manner, followed by diethyl ether trituration afforded the title compound (45 mg, 0.087 mmol) as a yellow powder in 67% yield.

¹H-NMR (d₆-DMSO): δ 12.08 (s, 1H), 10.38 (s, 1H), 10.13 (s, 1H), 8.14 (s, 1H), 7.71–7.44 (m, 6H), 6.90 (m, 1H), 3.95 (m, 1H), 1.78–1.44 (m, 5H), 1.43–1.24 (m, 10H, contains singlet at 1.39), 1.23–1.02 (m, 5H).

LCMS: (M+H)⁻ 514.1.

Example 34

(2S)-2-amino-2-cyclohexyl-N-(6-oxo-2-phenyl-5,6-dihydro-1H-[1,2]diazepino[4,5,6-cd]indol-8-yl)ethanamide Trifluoroacetate

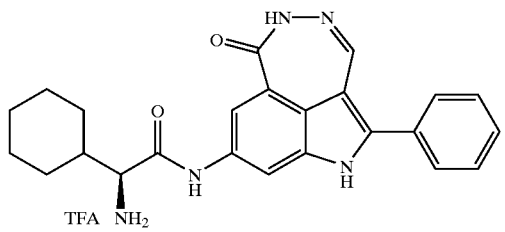

Preparation of example 34 from the title compound of Example 33 (40 mg, 0.078 mmol), and 1:1 TFA/CH$_2$Cl$_2$ (5 mL) was carried out analogously to Example 20. Isolation, also in an analogous manner, included a further trituration with methanol/diethyl ether and afforded the title compound (10 mg, 0.019 mmol) as an orange/yellow powder in 24% yield.

$^1$H NMR (d$_6$-DMSO): δ 12.19 (s, 1H), 10.60 (s, 1H), 10.44 (s, 1H), 8.25 (br s, 3H), 8.11 (s, 1H), 7.71–7.46 (m, 7H), 3.69 (m, 1H), 1.93–1.52 (m, 6H), 1.29–0.97 (m, 5H).

LCMS: (M+H$^+$) 415.1.

Example 35

3-Fluoro-N-(6-oxo-2-phenyl-5,6-dihydro-1H-[1,2]diazepino[4,5,6-cd]indol-8-yl)-benzamide

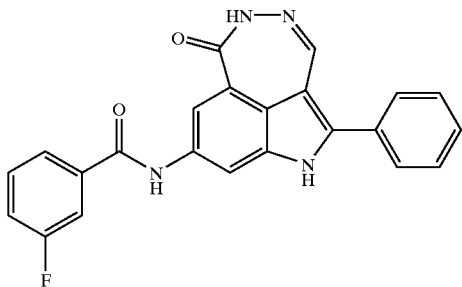

Preparation of example 35 from the title compound of Example 7 (0.025 g, 0.09 mmol), 3-Fluoro-benzoic acid (0.015 g, 0.11 mmol), triethylamine (0.05 mL, 0.4 mmol), O-(7-azabenzotriazol-1-yl)-N,N,N',N'-tetramethyluronium hexafluorophosphate (38 mg, 0.1 mmol) and N,N-dimethylformamide (0.05 M, 1.8 mL) was carried out analogously to Example 11. Silica gel chromatography (95:5 CH$_2$Cl$_2$/methanol), also in an analogous manner, afforded the title compound (15 mg) as a yellow powder in 42% yield.

$^1$H-NMR (d$_6$-DMSO): δ 12.18 (s, 1H), 10.47 (s, 1H), 10.40 (s, 1H), 8.31 (d, 1H, J=1.3 Hz), 7.92 (d, 1H, J=1.5 Hz), 7.90–7.81 (m, 2H), 7.72–7.41 (m, 8H).

HRMS: (M+H$^+$) calcd for C$_{23}$H$_{16}$N$_4$O$_2$F, 399.1257, found 399.1257.

Example 36

N-(6-Oxo-2-phenyl-5,6-dihydro-1H-[1,2]diazepino[4,5,6-cd]indol-8-yl)-4-phenyl-butyramide

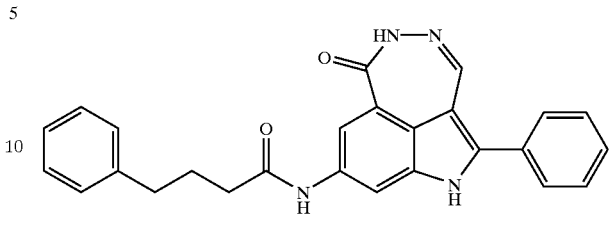

Preparation of example 36 from the title compound of Example 7 (0.030 g, 0.11 mmol), 4-Phenyl-butyric acid (0.027 g, 0.16 mmol), triethylamine (0.077 mL, 0.44 mmol), O-(7-azabenzotriazol-1-yl)-N,N,N',N'-tetramethyluronium hexafluorophosphate (63 mg, 0.16 mmol) and N,N-dimethylformamide (0.05 M, 2.0 mL) was carried out analogously to Example 11. Silica gel chromatography (95:5 CH$_2$Cl$_2$/methanol) afforded the title compound (15 mg) as a yellow powder in 33% yield.

$^1$H-NMR (d$_6$-DMSO): δ 12.06 (s, 1H), 10.35 (s, 1H), 10.06 (s, 1H), 8.18 (d, 1H, J=1.5 Hz), 7.69–7.46 (m, 7H), 7.33–7.16 (m, 5H), 2.64 (dd, 2H, J=7.4, 7.0 Hz), 2.35 (m, 5H), 1.97–1.86 (m, 2H).

HRMS: (M+H$^+$) calcd for C$_{26}$H$_{23}$N$_4$O$_2$, 423.1821, found 423.1826.

Anal. Calcd. for C$_{26}$H$_{22}$N$_4$O$_2$.0.2 H$_2$O: C, 73.29; H, 5.30; N, 13.15. Found: C, 73.33; H, 5.28; N, 13.23.

Example 37

1-Methyl-piperidine-4-carboxylic Acid (6-oxo-2-phenyl-5,6-dihydro-1H-[1,2]diazepino[4,5,6-cd]indol-8-yl)-amide; 2,2,2-trifluoro-acetic Acid Salt

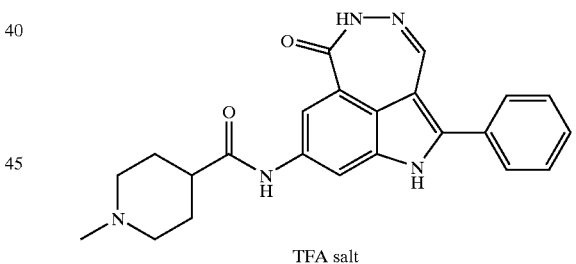

Preparation of example 37 from the title compound of Example 7 (0.030 g, 0.11 mmol), 1-Methyl-piperidine-4-carboxylic acid (0.023 g, 0.16 mmol), triethylamine (0.077 mL, 0.44 mmol), O-(7-azabenzotriazol-1-yl)-N,N,N',N'-tetramethyluronium hexafluorophosphate (63 mg, 0.16 mmol) and N,N-dimethylformamide (0.05 M, 2.0 mL) was carried out analogously to Example 11. HPLC purification afforded the title compound (23 mg) as a yellow powder in 41% yield.

$^1$H-NMR (d$_6$-DMSO): δ 12.10 (s, 1H), 10.39 (s, 1H), 10.23 (s, 1H), 9.17 (bs, 1H), 8.12 (d, 1H, J=1.5 Hz), 7.69–7.47 (m, 7H), 3.05–2.93 (m, 2H), 2.80 (d, 3H), 2.65–2.48 (buried m, 1H), 2.10–2.01 (m, 2H), 1.92–1.80 (m, 2H).

HRMS: (M+H$^+$) calcd for C$_{23}$H$_{24}$N$_5$O$_2$, 402.1930, found 402.1937.

Example 38

N-(6-Oxo-2-phenyl-5,6-dihydro-1H-[1,2]diazepino[4,5,6-cd]indol-8-yl)-3-phenyl-propionamide

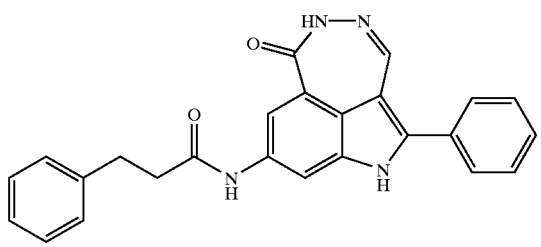

Preparation of example 38 from the title compound of Example 7 (0.030 g, 0.11 mmol), 3-Phenyl-propionic acid (0.025 g, 0.16 mmol), triethylamine (0.077 mL, 0.44 mmol), O-(7-azabenzotriazol-1-yl)-N,N,N',N'-tetramethyluronium hexafluorophosphate (63 mg, 0.16 mmol) and N,N-dimethylformamide (0.05 M, 2.0 mL) was carried out analogously to Example 11. Silica gel chromatography (95:5 CH$_2$Cl$_2$/methanol) afforded the title compound (15 mg) as a yellow powder in 34% yield.

$^1$H-NMR (d$_6$-DMSO): δ 12.09 (s, 1H), 10.38 (s, 1H), 10.36 (s, 1H), 10.13 (s, 1H), 8.15 (d, 1H, J=1.5 Hz), 7.68–7.46 (m, 11H), 7.31 (d, 2H, J=8.4 Hz), 7.24 (d, 1H, J=8.2 Hz), 3.65 (s, 2H), 3.45 (s, 2H).

HRMS: (M+H$^+$) calcd for C$_{25}$H$_{21}$N$_4$O$_2$, 409.1665, found 409.1683.

Example 39

6-Oxo-2-phenyl-5,6-dihydro-1H-[1,2]diazepino[4,5,6-cd]indole-8-carboxylic Acid Methyl Ester

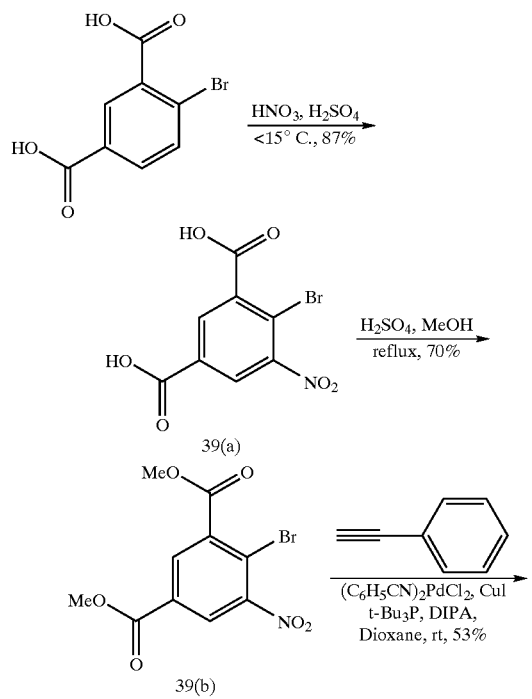

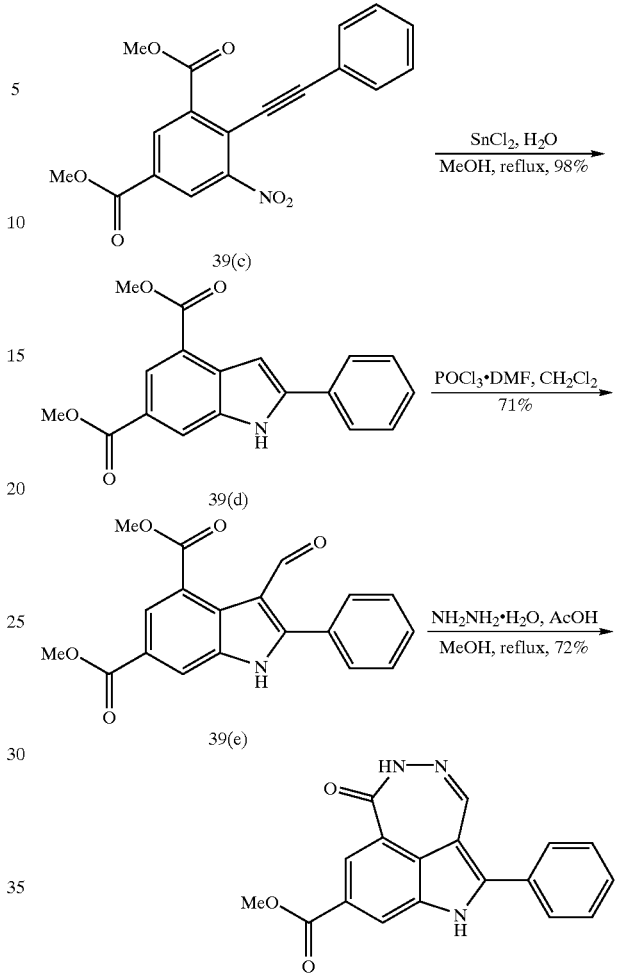

Step 1. Preparation of 4-bromo-nitroisophthalic Acid 39(a)

To a 3-L 4-neck round-bottomed flask equipped with a mechanical stirrer, thermometer, 250-mL addition funnel and charged with concentrated H$_2$SO$_4$ (577 mL), was added 4-bromoisophthalic acid (75.0 g, 306 mmol). The white suspension was cooled to ice-bath temperature and a nitrating reagent (pre-prepared by the careful addition of H$_2$SO$_4$ (169 mL) to HNO$_3$ (107 mL)) was slowly added while maintaining an internal reaction temperature of less than 15° C. When addition was complete, the ice-bath was removed and the suspension stirred overnight at room temperature. After approximately 14 hours, the flask was placed in an ice-bath and crushed ice was added to quench the excess nitrating reagent while maintaining an internal temperature less than 40° C. The cream-colored suspension was filtered, and the solids were collected by filtration and washed with a small volume of ice-cold water. The solids were dissolved in methanol and the volatile components were evaporated. The resulting solids were dried at 60° C. in a vacuum oven overnight to afford Intermediate 39(a) (79.6 g) in 87% yield.

$^1$H NMR (d$_4$-methanol): δ 8.47 (d, 1H, J=1.8 Hz), 8.39 (d, 1H, J=1.8 Hz).

LCMS: (M–H) 289.

Step 2. Preparation of Dimethyl 4-bromo-5-nitroisophthalate 39(b)

To a solution of Intermediate 39(a) (77.6 g, 267 mmol) in methanol (500 mL) was added concentrated H$_2$SO$_4$ (10 mL). The reaction flask was heated in an oil bath at reflux with stirring for approximately 8 hours at which point LC/MS analysis indicated consumption of starting material. The mixture was allowed to cool to room temperature and white solids began to crystallize in the flask. After sitting overnight, the crystals were collected by filtration and washed with water until the pH of the filtrate was neutral. The crystals (51.9 g) were dried in an Abderhalden drying apparatus over refluxing acetone. The mother liquor was concentrated to provide a second crop (7.58 g) which was combined with the first to afford Intermediate 39(b) (59.4 g) in 70% yield.

$^1$H NMR (d$_6$-DMSO): δ 8.62 (s, 1H), 8.45 (s, 1H), 3.95 (s, 3H), 3.93 (s, 3H).

Step 3. Preparation of Dimethyl 5-nitro-4-phenylethynyl) isophthalate 39(c)

A flask containing 1,4-dioxane (16 mL) was purged with nitrogen. CuI (0.12 g, 0.628 mmol) and bis(benzonitrile) dichloropalladium(II) (0.361 g, 0.942 mmol) were added in portions. Tri-tert-butylphosphine (7.83 mL, 1.88 mmol) was added as a 0.24 M solution in 1,4-dioxane via syringe. The solution was allowed to stir for approximately 5 min at which point diisopropylamine (2.65 mL, 18.9 mmol) was added via syringe. Intermediate 39(b) (5.00 g, 15.7 mmol) was added in one solid portion followed by phenylacetylene (2.08 mL, 18.9 mmol). A precipitate formed immediately. The reaction was capped and stirred at room temperature overnight. The mixture was filtered through diatomaceous earth which was subsequently washed with ethyl acetate to recover any trapped product. The combined filtrate and washings were concentrated and dissolved in a minimal amount of hot ethyl acetate. Hexane was added to recrystallize brown needles which were collected by filtration and further washed with hexane. The needles (4.5 g) were dried in a vacuum oven at 60° C. overnight. The mother liquor was concentrated and subjected to silica gel chromatography (10–30% ethyl acetate/hexanes) to yield an additional 1.2 g of a dark brown solid which was combined with the first batch to afford Intermediate 39(c) (5.7 g) in 53% yield.

$^1$H NMR (CDCl$_3$): δ 8.73 (d, 1H, J=1.5 Hz), 8.65 (d, 1H, J=1.8 Hz), 7.61–7.64 (m, 2H), 7.37–7.46 (m, 3H), 4.03 (s, 3H), 4.00 (s, 3H).

LCMS: (M+H) 340.

Step 4. Preparation of Dimethyl 2-phenyl-1H-indole-4,6-dicarboxylate 39(d)

To Intermediate 39(c) (6.37 g, 18.8 mmol) was added anhydrous methanol (120 mL). To the resulting slurry was added Tin(II) chloride (35.6 g, 188 mmol), and the reaction flask was refluxed for 55 hours. Methanol was removed under reduced pressure and the resulting residue was suspended in a small volume of ethyl acetate. Dichloromethane was then added such that the resulting concentration was approximately 95% dichloromethane: 5% ethyl acetate. This suspension was then filtered through a short silica gel plug. The filtrate was concentrated and purified twice by flash silica gel chromatography (5–40% ethyl acetate/ dichloromethane) to obtain 3.1 g of Intermediate 39(d) in 53% yield.

$^1$H NMR (d$_6$-DMSO): δ 12.35 (s, 1H), 8.37 (s, 1H), 8.28 (s, 1H), 7.98–8.00 (m, 2H), 7.47–7.60 (m, 4H), 3.99 (s, 3H), 3.93 (s, 3H).

LCMS: (M+H) 310.

Step 5. Preparation of Dimethyl 3-formyl-2-phenyl-1H-indole-4,6-dicarboxylate 39(e)

To a solution of Intermediate 39(d) (0.052 g, 0.17 mmol) in anhydrous N,N-dimethylformamide (2 mL) at room temperature was added POCl$_3$ (0.2 mL, 2.1 mmol). The resulting violet solution was stirred for 1 hour at room temperature. The mixture was poured into saturated aqueous sodium carbonate (15 mL) and extracted with ethyl acetate. The organic layer was dried over sodium sulfate, concentrated, and purified by silica gel chromatography (33% ethyl acetate/hexanes) to give Intermediate 39(e) (0.0404 g) in 71% yield.

$^1$H NMR (d$_6$-DMSO): δ 13.00 (s, 1H), 9.95 (s, 1H), 8.21 (s, 1H), 7.94 (s, 1H), 7.85–7.75(m, 2H), 7.70–7.55 (m, 3H), 3.90 (s, 3H), 3.86 (s, 3H).

LCMS: (M+H) 338, (M−H) 336.

Step 6. Preparation of Title Compound: 6-Oxo-2-phenyl-5, 6-dihydro-1H-[1,2]diazepino[4,5,6-cd]indole-8-carboxylic Acid Methyl Ester To a solution of Intermediate 39(e) (1.39 g, 4.12 mmol) in anhydrous methanol (70 mL) was added anhydrous hydrazine (0.19 mL, 6.18 mmol). The mixture was refluxed overnight. After cooling, the yellow precipitate was collected by filtration and washed with ice-cold methanol. After drying under vacuum at 60° C. overnight, the title compound (1.06 g) was obtained as a bright yellow solid in 72% yield.

$^1$H-NMR (d$_6$-DMSO): δ 12.58 (s, 1H), 10.54 (s, 1H), 8.13 (d, 1H, J=1.3 Hz), 8.07 (d, 1H, J=1.3 Hz), 7.77–7.67(m, 2H), 7.65–7.54 (m, 3H), 7.52 (s, 1H), 3.88 (s, 3H).

LCMS: (M+H$^+$) 320.3

Example 40

3-Fluoro-2-methyl-N-(6-oxo-2-phenyl-5,6-dihydro-1H-[1,2]diazepino[4,5,6-cd]indol-8-yl)-benzamide

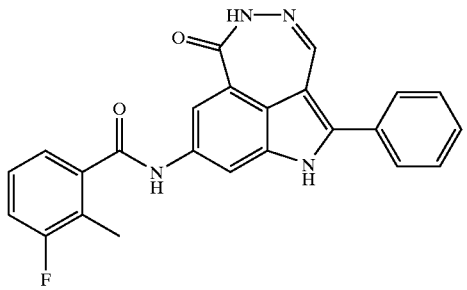

Preparation of example 40 from the title compound of Example 7 (0.030 g, 0.11 mmol), 3-Fluoro-2-methyl-benzoic acid (0.025 g, 0.16 mmol), triethylamine (0.077 mL, 0.44 mmol), O-(7-azabenzotriazol-1-yl)-N,N,N',N'-tetramethyluronium hexafluorophosphate (63 mg, 0.16 mmol) and N,N-dimethylformamide (0.05 M, 2.0 mL) was carried out analogously to Example 11. Silica gel chromatography (95:5 CH$_2$Cl$_2$/methanol) afforded the title compound (14 mg) as a yellow powder in 33% yield.

$^1$H-NMR (d$_6$-DMSO): δ 12.15 (s, 1H), 10.55 (s, 1H), 10.39 (s, 1H), 8.23 (d, 1H, J=1.5 Hz), 7.84 (d, 1H, J=1.4 Hz), 7.72–7.48 (m, 6H), 7.39–7.27 (m, 3H), 2.31 (s, 3H).

LCMS: (M−H$^-$) 411.0.

Example 41

2-Fluoro-N-(6-oxo-2-phenyl-5,6-dihydro-1H-[1,2]diazepino[4,5,6-cd]indol-8-yl)-3-trifluoromethyl-benzamide

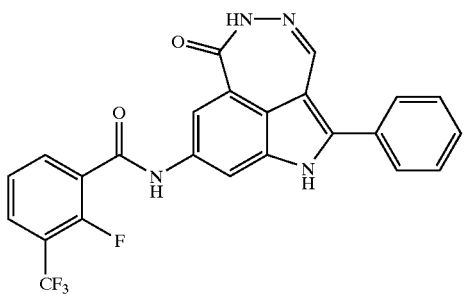

Preparation of example 41 from the title compound of Example 7 (0.1 g, 0.36 mmol), 2-Fluoro-3-trifluoromethyl-benzoic acid (0.113 g, 0.54 mmol), triethylamine (0.2 mL, 1.45 mmol), O-(7-azabenzotriazol-1-yl)-N,N,N',N'-tetramethyluronium hexafluorophosphate (0.207 g, 0.54 mmol) and N,N-dimethylformamide (0.1 M, 3.6 mL) was carried out analogously to Example 11. Silica gel chromatography (95:5 $CH_2Cl_2$/methanol) afforded the title compound (0.147 g) as a yellow powder in 87% yield.

$^1$H-NMR ($d_6$-DMSO): δ 12.20 (s, 1H), 10.81 (s, 1H), 10.43 (s, 1H), 8.24 (d, 1H, J=1.5 Hz), 8.05–7.93 (m, 2H), 7.79 (d, 1H, J=1.4 Hz), 7.72–7.67 (m, 2H), 7.62–7.49 (m, 5H).

HRMS: (M+H$^+$) calcd for $C_{24}H_{15}N_4O_2F_4$, 467.1131, found 467.1119.

Anal. Calcd. for $C_{24}H_{14}N_4O_2F_4 \cdot 0.2H_2O$: C, 61.33; H, 3.09; N, 11.92; F, 16.17. Found: C, 61.17; H, 3.09; N, 11.93; F, 16.65.

Example 42

N-(6-Oxo-2-phenyl-5,6-dihydro-1H-[1,2]diazepino[4,5,6-cd]indol-8-yl)-2-trifluoromethyl-benzamide

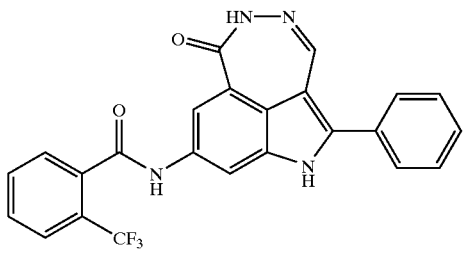

Preparation of example 42 from the title compound of Example 7 (0.1 g, 0.36 mmol), 2-Trifluoromethyl-benzoic acid (0.103 g, 0.54 mmol), triethylamine (0.2 mL, 1.45 mmol), O-(7-azabenzotriazol-1-yl)-N,N,N',N'-tetramethyluronium hexafluorophosphate (0.207 g, 0.54 mmol) and N,N-dimethylformamide (0.1 M, 3.6 mL) was carried out analogously to Example 11. Silica gel chromatography (95:5 $CH_2Cl_2$/methanol) afforded the title compound (0.075 g) as a yellow powder in 46% yield.

$^1$H-NMR ($d_6$-DMSO): δ 12.14 (s, 1H), 10.71 (s, 1H), 10.40 (s, 1H), 8.17 (d, 1H, J=1.4 Hz), 7.89–7.66 (m, 7H), 7.62–7.49 (m, 4H).

HRMS: (M+H$^+$) calcd for $C_{24}H_{16}N_4O_2F_3$, 449.1225, found 449.1223.

Example 43

N-(6-Oxo-2-phenyl-5,6-dihydro-1H-[1,2]diazepino[4,5,6-cd]indol-8-yl)-3-trifluoromethyl-benzamide

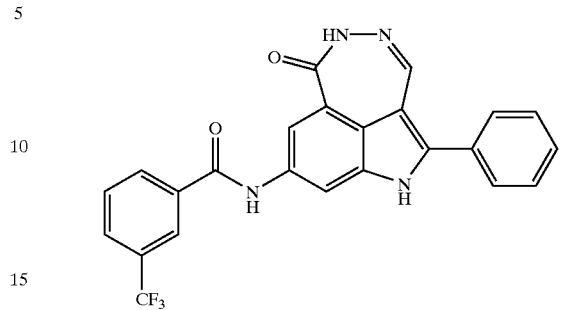

Preparation of example 43 from the title compound of Example 7 (0.03 g, 0.11 mmol), 3-Trifluoromethyl-benzoic acid (0.031 g, 0.16 mmol), triethylamine (0.078 mL, 0.43 mmol), O-(7-azabenzotriazol-1-yl)-N,N,N',N'-tetramethyluronium hexafluorophosphate (0.062 g, 0.11 mmol) and N,N-dimethylformamide (0.05 M, 2.0 mL) was carried out analogously to Example 11. Silica gel chromatography (95:5 $CH_2Cl_2$/methanol) afforded the title compound (0.030 g) as a yellow powder in 61% yield.

$^1$H-NMR ($d_6$-DMSO): δ 12.20 (s, 1H), 10.62 (s, 1H), 10.42 (s, 1H), 8.39–8.30 (m, 3H), 7.98 (d, 1H, J=7.4 Hz), 7.91 (d, 1H, J=1.6 Hz), 7.80 (dd, 1H, J=7.7, 7.5 Hz), 7.69 (d, 2H, J=7.2 Hz), 7.62–7.48 (m, 4H).

HRMS: (M+H$^+$) calcd for $C_{24}H_{15}N_4O_2F_3$, 449.1225, found 449.1229.

Example 44

3-Chloro-N-(6-oxo-2-phenyl-5,6-dihydro-1H-[1,2]diazepino[4,5,6-cd]indol-8-yl)-benzamide

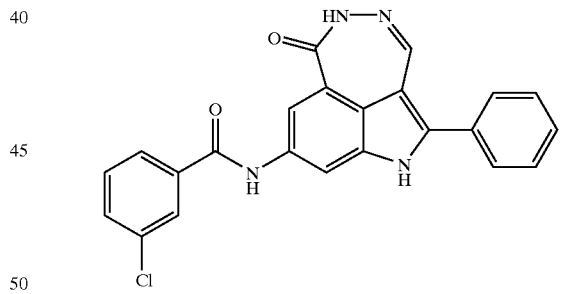

Preparation of example 44 from the title compound of Example 7 (0.03 g, 0.11 mmol), 3-Chloromethyl-benzoic acid (0.025 g, 0.16 mmol), triethylamine (0.078 mL, 0.43 mmol), O-(7-azabenzotriazol-1-yl)-N,N,N',N'-tetramethyluronium hexafluorophosphate (0.062 g, 0.11 mmol) and N,N-dimethylformamide (0.05 M, 2.0 mL) was carried out analogously to Example 11. Silica gel chromatography (95:5 $CH_2Cl_2$/methanol) afforded the title compound (0.015 g) as a yellow powder in 33% yield.

$^1$H-NMR ($d_6$-DMSO): δ 12.18 (s, 1H), 10.50 (s, 1H), 10.41 (s, 1H), 8.32 (d, 1H, J=1.5 Hz), 8.09 (s, 1H), 7.98 (d, 1H, J=7.8 Hz), 7.91 (d, 1H, J=1.6 Hz), 7.72–7.65 (m, 3H), 7.62–7.47 (m, 5H).

HRMS: (M+H$^+$) calcd for $C_{23}H_{16}N_4O_2Cl$, 415.0962, found 415.0981.

Example 45

(1R,2R)-2-Phenyl-cyclopropanecarboxylic Acid (6-oxo-2-phenyl-5,6-dihydro-1H-[1,2]diazepino[4,5,6-cd]indol-8-yl)-amide; and
(1S,2S)-2-Phenyl-cyclopropanecarboxylic Acid (6-oxo-2-phenyl-5,6-dihydro-1H-[1,2]diazepino[4,5,6-cd]indol-8-yl)-amide

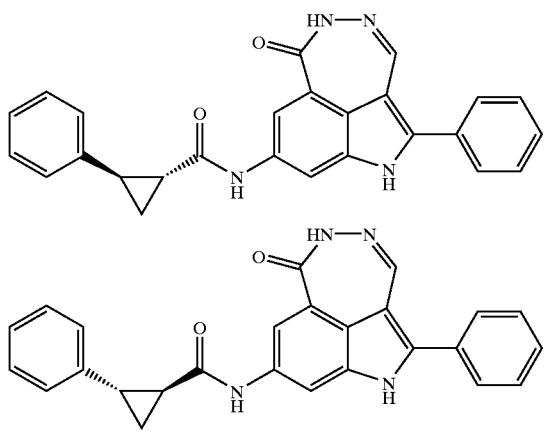

Preparation of example 45 from the title compound of Example 7 (30 mg, 0.11 mmol), ±trans-2-phenyl-1-cyclopropanecarboxylic acid (26 mg, 0.16 mmol), triethylamine (0.076 mL, 0.55 mmol), and O-(7-azabenzotriazol-1-yl)-N,N,N',N'-tetramethyluronium hexafluorophosphate (62 mg, 0.16 mmol) in N,N-dimethylformamide (1.0 mL) was carried out analogously to Example 11. Silica gel chromatography (1:1 ethyl acetate:hexane), also in an analogous manner, followed by trituration with ethyl acetate/diethyl ether afforded the title compound (6.5 mg, 0.015 mmol) (mixture of trans diastereomers) as a yellow powder in 14% yield.

$^1$H-NMR (d$_6$-DMSO): δ 12.09 (s, 1H), 10.44 (s, 1H), 10.37 (s, 1H), 8.17 (s, 1H), 7.71–7.44 (m, 7H), 7.35–7.25 (m, 2H), 7.24–7.10 (m, 3H), 2.39 (m, 1H), 2.10 (m, 1H), 1.52 (m, 1H), 1.38 (m, 1H).

LCMS: (M+H)$^-$ 419.1.

Example 46

2-(3-Chlorophenyl)-N-(6-oxo-2-phenyl-5,6-dihydro-1H-[1,2]diazepino[4,5,6-cd]indol-8-yl)acetamide

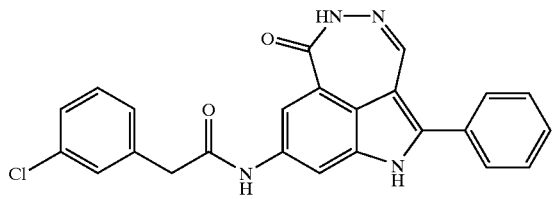

Preparation of example 46 from the title compound of Example 7 (30 mg, 0.11 mmol), (3-chlorophenyl)acetic acid (28 mg, 0.16 mmol), triethylamine (0.076 mL, 0.55 mmol), and O-(7-azabenzotriazol-1-yl)-N,N,N',N'-tetramethyluronium hexafluorophosphate (62 mg, 0.16 mmol) in N,N-dimethylformamide (1.5 mL) was carried out analogously to Example 11. Silica gel chromatography (1:1 ethyl acetate:hexane), also in an analogous manner, followed by methanol trituration afforded the title compound (6.5 mg, 0.015 mmol) as a yellow powder in 14% yield.

$^1$H-NMR (d$_6$-DMSO): δ 12.10 (s, 1H), 10.39 (s, 1H), 10.17 (s, 1H), 8.16 (s, 1H), 7.70–7.18 (m, 11H), 3.69 (s, 1H), 3.50 (s, 1H).

LCMS: (M+H)$^-$ 427.1.

Example 47

N-(6-Oxo-2-phenyl-5,6-dihydro-1H-[1,2]diazepino[4,5,6-cd]indol-8-yl)-4-thien-2-ylbutanamide

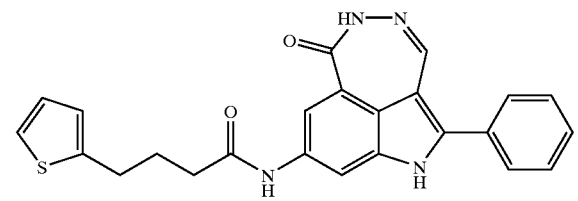

Preparation of example 47 from the title compound of Example 7 (30 mg, 0.11 mmol), 4-thien-2-ylbutanoic acid (24 mg, 0.16 mmol), triethylamine (0.076 mL, 0.55 mmol), and O-(7-azabenzotriazol-1-yl)-N,N,N',N'-tetramethyluronium hexafluorophosphate (62 mg, 0.16 mmol) in N,N-dimethylformamide (1.5 mL) was carried out analogously to Example 11. Silica gel chromatography (3% methanol in CH$_2$Cl$_6$ increasing to 6% methanol in CH$_2$Cl$_2$), also in an analogous manner, followed by methanol trituration afforded the title compound (6.5 mg, 0.015 mmol) as a yellow powder in 14% yield.

$^1$H-NMR (d$_6$-DMSO): δ 12.07 (s, 1H), 10.38 (s, 1H), 10.09 (s, 1H), 8.18 (s, 1H), 7.69–7.61 (m, 3H), 7.60–7.53 (m, 2H), 7.52–7.45 (m, 2H), 7.33 (m, 1H), 6.96 (m, 1H), 6.89 (m, 1H), 2.86 (t, 2H, J=7.53 Hz), 2.40 (t, 2H, J=7.35 Hz), 2.02–1.89 (m, 2H).

LCMS: (M+H)$^-$ 427.1.

Example 48

1-Acetyl-N-(6-oxo-2-phenyl-5,6-dihydro-1H-[1.2]diazepino[4,5,6-cd]indol-8-yl)piperidine-4-carboxamide

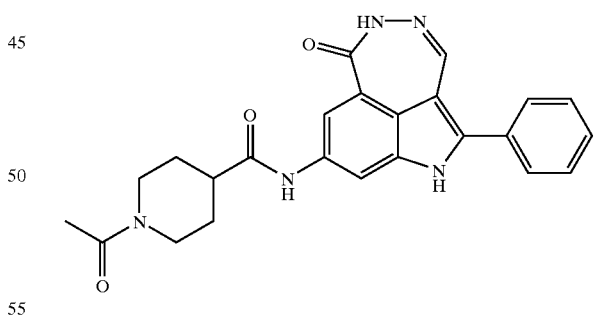

Preparation of example 48 from the title compound of Example 7 (30 mg, 0.11 mmol), 1-acetylpiperidine-4-carboxylic acid (28 mg, 0.16 mmol), triethylamine (0.076 mL, 0.55 mmol), and O-(7-azabenzotriazol-1-yl)-N,N,N',N'-tetramethyluronium hexafluorophosphate (62 mg, 0.16 mmol) in N,N-dimethylformamide (1.5 mL) was carried out analogously to Example 11. Silica gel chromatography (3% methanol in CH$_2$Cl$_2$ increasing to 6% methanol in CH$_2$Cl$_2$), also in an analogous manner, followed by methanol trituration afforded the title compound (12 mg, 0.028 mmol) as a yellow powder in 25% yield.

¹H-NMR (d₆-DMSO): δ 12.07 (s, 1H), 10.37 (s, 1H), 10.10, s, 1H), 8.17 (s, 1H), 7.72–7.43 (m, 7H), 4.41 (d, 1H, J=15.07 Hz), 3.87 (d, 1H, J=14.13 Hz), 3.07 (t, 1H, J=12.81 Hz), 2.65–2.53 (m, 2H, partially obscured), 2.02 (s, 3H), 1.76–1.90 (m, 2H), 1.70–1.37 (m, 2H).

LCMS: (M+H⁺) 430.1, (M+Na⁺) 452.1.

Example 49

6-Oxo-2-phenyl-5,6-dihydro-1H-[1,2]diazepino[4,5,6-cd]indole-8-carboxylic Acid, Potassium Salt

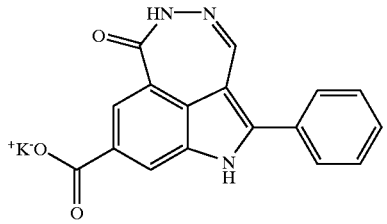

To the title compound of Example 39 (3.0 g, 9.39 mmol) was added DMSO (20 mL). To this semi-suspension was added 2N KOH (19 mL, 37.8 mmol). The solution turned a deep red color and was stirred for approximately 1.5 hours at room temperature. The reaction was purified by preparative HPLC (5–60% CH₃CN/H₂O) over 60 minutes. Fractions containing the product were lyophilized to afford the title compound (0.8 g) as an orange solid in 25% yield.

¹H-NMR (d₆-DMSO): δ 12.21 (s, 1H), 10.12 (s, 1H), 8.16 (d, 1H, J=1.0 Hz), 8.01 (d, 1H, J=1.0 Hz), 7.73–7.65 (m, 2H), 7.62–7.46 (m, 3H), 7.44 (s, 1H).

LCMS: (M+H⁺) 306.1

Example 50

3-(2-Methylphenyl)-N-(6-oxo-2-phenyl-5,6-dihydro-1H-[1,2]diazepino[4,5,6-cd]indol-8-yl)propanamide

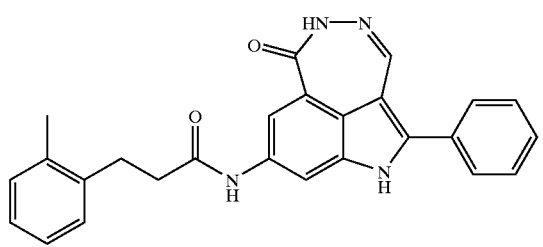

Preparation of example 50 from the title compound of Example 7 (30 mg, 0.11 mmol), 3-(2-methylphenyl)propanoic acid (27 mg, 0.16 mmol), triethylamine (0.076 mL, 0.55 mmol), and O-(7-azabenzotriazol-1-yl)-N,N,N',N'-tetramethyluronium hexafluorophosphate (62 mg, 0.16 mmol) in N,N-dimethylformamide (1.5 mL) was carried out analogously to Example 11. Silica gel chromatography (3% methanol in CH₂Cl₂ increasing to 5% methanol in CH₂Cl₂), also in an analogous manner, followed by methanol trituration afforded the title compound (6 mg, 0.014 mmol) as a yellow powder in 13% yield.

¹H-NMR (d₆-DMSO): δ 12.08 (s, 1H), 10.37 (s, 1H), 10.10 (s, 1H), 8.20 (s, 1H), 7.72–7.42 (m, 7H), 7.26–7.05 (m, 4H), 2.96–2.87 (m, 2H), 2.64–2.55 (m, 2H, partially obscured), 2.32 (s, 3H).

LCMS: (M+H)⁻ 421.1.

Example 51

N-(6-Oxo-2-phenyl-5,6-dihydro-1H-[1,2]diazepino[4,5,6-cd]indol-8-yl)-3-(1-trityl-1H-Imidazol-4-yl)-propionamide

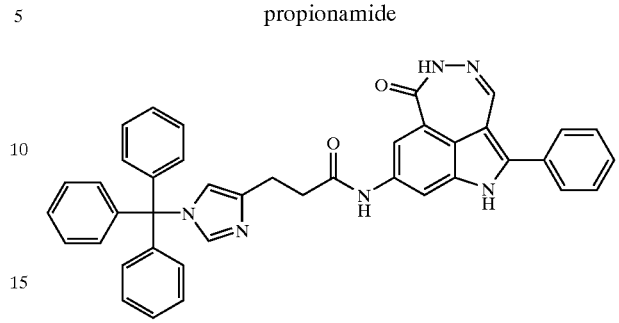

Preparation of example 51 from the title compound of Example 7 (hydrochloride) (31 mg, 0.10 mmol), 3-(1-Trityl-1H-imidazol-4-yl)-propionic acid (46 mg, 0.12 mmol), triethylamine (0.021 mL, 0.15 mmol), and O-(7-azabenzotriazol-1-yl)-N,N,N',N'-tetramethyluronium hexafluorophosphate (46 mg, 0.12 mmol) in CH₂Cl₂ (0.4 mL) and N,N-dimethylformamide (0.4 mL) was carried out analogously to Example 11. Silica gel chromatography (3% triethylamine in 5:4:1 hexane:CH₂Cl₂:methanol), also in an analogous manner, afforded the title compound (40 mg, 0.062 mmol) as a yellow powder in 62% yield.

¹H NMR (CDCl₃/d₄-methanol): δ 8.21 (s, 1H), 7.65–7.25 (m, 15H, partially obscurred), 7.10–7.02 (m, 8H), 6.65 (s, 1H), 2.99–2.89 (m, 2H), 2.71–2.62 (m, 2H).

LCMS: (M+H⁺) 641.2.

Example 52

3-(1H-imidazol-4-yl)-N-(6-oxo-2-phenyl-5,6-dihydro-1H-[1,2]diazepino[4,5,6-cd]indol-8-yl)-propionamide; Compound with Trifluoro-acetic Acid

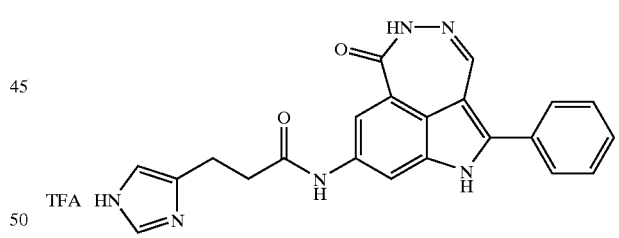

Preparation of example 52 from the title compound of Example 51 (32 mg, 0.050 mmol) and 45% TFA in CH₂Cl₂ (1 mL) was carried out analogously to Example 20. (Deprotection of trityl group was effected using the same conditions as for tert-butoxycarbonyl deprotection.) Isolation, also in an analogous manner, additionally included recrystallization from methanol/ethyl acetate and diethyl ether to afford the title compound (16 mg, 0.031 mmol) as a yellow powder in 62% yield.

¹H NMR (d₆-DMSO): 13.95 (br s, 1H), 12.10 (s, 1H), 10.40 (s, 1H), 10.20 (s, 1H), 8.83 (s, 1H), 8.13 (s, 1H), 7.70–7.63 (m, 3H), 7.62–7.47 (m, 5H), 7.38 (s, 1H), 3.02–2.93 (m, 2H), 2.78–2.70 (m, 2H).

LCMS: (M+H⁺) 399.2.

Example 53

[(S)-1-(6-Oxo-2-phenyl-5,6-dihydro-1H-[1,2]diazepino[4,5,6-cd]indol-8-ylcarbamoyl)-3-phenyl-propyl]-carbamic Acid tert-butyl Ester

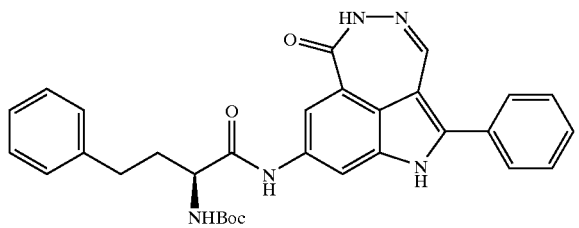

Preparation of example 53 from the title compound of Example 7 (hydrochloride) (31 mg, 0.10 mmol), (S)-2-tert-Butoxycarbonylamino-4-phenyl-butyric acid (34 mg, 0.12 mmol), triethylamine (0.021 mL, 0.15 mmol), and O-(7-azabenzotriazol-1-yl)-N,N,N',N'-tetramethyluronium hexafluorophosphate (46 mg, 0.12 mmol) in CH$_2$Cl$_2$ (0.4 mL) and N,N-dimethylformamide (0.4 mL) was carried out analogously to Example 11. Silica gel chromatography, (5:4:1 hexane:CH$_2$Cl$_2$:methanol), also in an analogous manner, afforded the title compound (40 mg, 0.074 mmol) as a yellow powder in 74% yield.

$^1$H NMR (d$_6$-DMSO): 12.11 (s, 1H), 10.40 (s, 1H), 10.17 (s, 1H), 8.40 (br s, 1H), 8.16 (s, 1H), 7.71–7.45 (m, 6H), 7.35–7.15 (m, 6H), 4.06 (m, 1H), 2.77–2.53 (m, 2H, partially obscured), 1.92 (m, 2H), 1.42 (s, 9H).

LCMS: (M+H$^+$) 538.1, (M+Na$^+$) 560.2, (M–H)$^-$ 536.0.

Example 54

(2S)-2-Amino-N-(6-oxo-2-phenyl-5,6-dihydro-1H-[1,2]diazepino[4,5,6-cd]indol-8-yl)-4-phenyl-butyramide; Compound with Trifluoro-acetic Acid

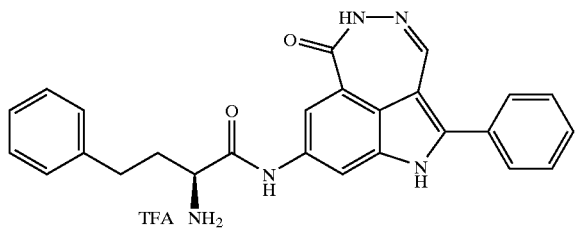

Preparation of example 54 from the title compound of Example 53 (30 mg, 0.056 mmol) and 45% TFA in CH$_2$Cl$_2$ (1 mL) was carried out analogously to Example 20. Isolation, also in an analogous manner, afforded the title compound (26 mg, 0.047 mmol) as a yellow powder in 84% yield.

$^1$H NMR (d$_6$-DMSO): δ 12.22 (s, 1H), 10.71 (s, 1H), 10.47 (s, 1H), 8.38 (br s, 3H), 8.13 (s, 1H), 7.72–7.66 (m, 2H), 7.64–7.49 (m, 4H), 7.36–7.28 (m, 2H), 7.27–7.19 (m, 4H), 4.05 (br s, 1H), 2.77–2.65 (m, 2H), 2.21–2.09 (m, 2H).

LCMS: (M+H$^+$) 438.2, (M+Na$^+$) 460.1, (M–H)$^-$ 436.1.

Example 55

N-Methyl-6-oxo-2-phenyl-5,6-dihydro-1H-[1,2]diazepino[4,5,6-cd]indole-8-carboxamide

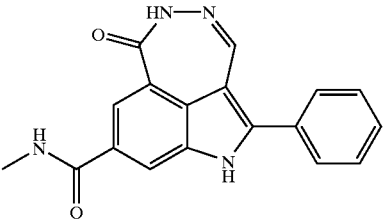

To a solution of the title compound of Example 49 (0.058 g, 0.17 mmol) in DMSO (4 mL) was added triethylamine (0.069 mL, 0.5 mmol), and O-(7-azabenzotriazol-1-yl)-N,N,N',N'-tetramethyluronium hexafluorophosphate (0.084 g, 0.22 mmol). After approximately 5 min, 2.0 M methylamine in tetrahydrofuran (0.5 mL, 0.25 mmol) was added and the solution was stirred for 2 hours. The mixture was purified using preparative HPLC (20–100% CH$_3$CN/H$_2$O containing 0.1% HOAc). The pure fractions were combined and lyophilized to afford the title compound (0.0036 g) in 6.7% yield.

$^1$H-NMR (d$_6$-DMSO): δ 12.46 (s, 1H), 10.45 (s, 1H), 8.58 (s, 1H), 8.20–7.90(m, 2H), 7.85–7.35 (m, 6H), 2.79 (s, 3H).

LCMS: (M+H$^+$) 319.1.

Example 56

N-[2-(1H-imidazol-4-yl)ethyl]-6-oxo-2-phenyl-5,6-dihydro-1H-[1,2]diazepino[4,5,6-cd]indole-8-carboxamide

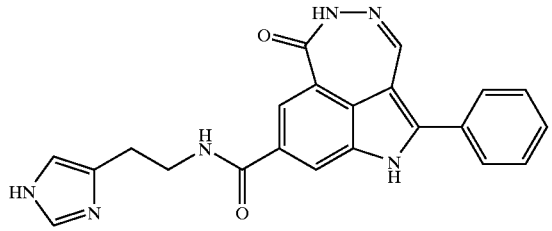

Preparation of example 56 from the title compound of Example 49 (0.0956 g, 0.28 mmol), 2-(1H-imidazol-4-yl)ethylamine dihydrochloride (0.0618 g, 0.34 mmol), triethylamine (0.2 mL, 1.4 mmol), and O-(7-azabenzotriazol-1-yl)-N,N,N',N'-tetramethyluronium hexafluorophosphate (0.129 g, 0.34 mmol) in DMSO (6 mL) was carried out analogously to Example 58. Preparative HPLC (10–80% CH$_3$CN/H$_2$O), also in an analogous manner, afforded the title compound (0.0021 g) in 18% yield.

$^1$H-NMR (d$_6$-DMSO): δ 12.48 (s, 1H), 10.49 (s, 1H), 8.77 (t, 1H, J=5.7 Hz), 8.08 (s, 1H), 8.01 (s, 1H), 7.75–7.66(m, 2H), 7.64–7.54 (m, 5H), 7.51 (s, 1H), 6.85 (s, 1H), 3.55–3.45 (m, 2H), 2.84–2.73 (t, 2H, J=7.2 Hz).

LCMS: (M+H$^+$) 399.1

Anal. Calcd. for C$_{22}$H$_{18}$N$_6$O$_2$.0.60 HCl.0.75 H$_2$O: C, 60.91; H, 4.67; N, 19.37. Found: C, 60.74; H, 4.74; N, 19.48.

Example 57

4-Dimethylamino-N-(6-oxo-2-phenyl-5,6-dihydro-1H-[1,2]diazepino[4,5,6-cd]indol-8-yl)-butyramide (Hydrochloric Salt)

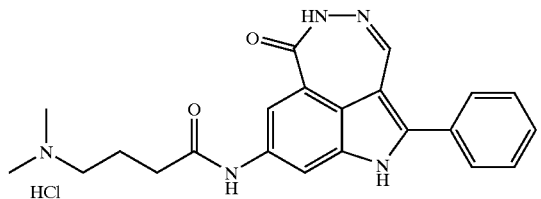

Preparation of example 57 from the title compound of Example 7 (hydrochloride) (27 mg, 0.086 mmol), 4-dimethylamino-butyric acid(hydrochloride)(17 mg, 0.104 mmol), triethylamine (0.036 mL, 0.258 mmol), and O-(7-azabenzotriazol-1-yl)-N,N,N',N'-tetramethyluronium hexafluorophosphate (40 mg, 0.104 mmol) in CH$_2$Cl$_2$ (0.3 mL) and N,N-dimethylformamide (0.3 mL) was carried out analogously to Example 11. Silica gel chromatography (2% triethylamine in 9:1 CH$_2$Cl$_2$:methanol) of the freebase afforded, after acidification with HCl, the title compound (18 mg, 0.042 mmol) as a yellow powder in 49% yield.

$^1$H NMR (d$_6$-DMSO): δ 12.10 (s, 1H), 10.39 (s, 1H), 10.21 (s, 1H), 9.60 (br s, 1H, HCl), 8.13 (s, 1H), 7.69–7.46 (m, 7H), 3.15–3.04 (m, 2H), 2.80 (s, 6H, with fine splitting), 2.45 (t, 2H, partially obscurred), 2.02–1.90 (m, 2H).

LCMS: (M+H$^+$) 390.2.

Example 58

6-Oxo-2-phenyl-N-(2-pyridin-2-ylethyl)-5,6-dihydro-1H-[1,2]diazepino[4,5,6-cd]indole-8-carboxamide

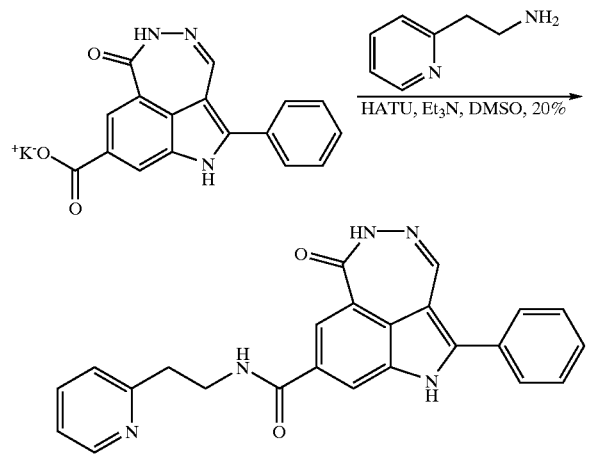

To a solution of the title compound of Example 49 (0.0548 g, 0.16 mmol) in DMSO (1.8 mL) was added triethylamine (0.0268 mL, 0.192 mmol), and O-(7-azabenzotriazol-1-yl) N,N,N',N'-tetramethyluronium hexafluorophosphate (0.0669 g, 0.176 mmol). After approximately 5 min, 2-pyridin-2-ylethylamine (0.0215 g, 0.176 mmol) was added and the solution was allowed to stir overnight. The product was purified using preparative HPLC (5–35% CH$_3$CN/H$_2$O). The pure fractions were combined and lyophilized to afford the title compound (0.013 g) as a yellow powder in 20% yield.

$^1$H NMR (d$_6$-DMSO): δ 10.37 (s, 1H), 8.74 (s, 1H), 8.51 (d, 1H, J=3.0 Hz), 8.01 (d, 2H, J=11 Hz), 7.49–7.71 (m, 7H), 7.20–7.29 (m, 2H), 3.62 (d, 1H, J=4.9 Hz), 3.02 (t, 1H, J=6.4 Hz).

LCMS: (M+H) 410.

Example 59 tert-Butyl (1R)-cyclohexyl-2-oxo-2-[(6-oxo-2-phenyl-5,6-dihydro-1H-[1,2]diazepino[4,5,6-cd]indol-4-yl)amino]ethylcarbamate

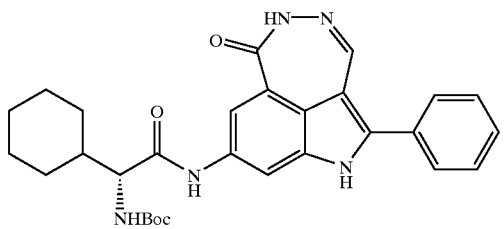

Preparation of example 59 from the title compound of Example 7 (70 mg, 0.25 mmol), (2R)-[(tert-butoxycarbonyl)amino](cyclohexyl)ethanoic acid (98 mg, 0.38 mmol), triethylamine (0.139 mL, 1.0 mmol), and O-(7-azabenzotriazol-1-yl)-N,N,N',N'-tetramethyluronium hexafluorophosphate (144 mg, 0.38 mmol) in N,N-dimethylformamide (2.0 mL) was carried out analogously to Example 11 except that after 24 hours additional (2R)-[(tert-butoxycarbonyl)amino](cyclohexyl)ethanoic acid (32 mg, 0.13 mmol) and O-(7-azabenzotriazol-1-yl)-N,N,N',N'-tetramethyluronium hexafluorophosphate (48 mg, 0.13 mmol) were added to drive the reaction to completion. Silica gel chromatography (1:1 ethyl acetate:hexane), also in an analogous manner, followed by diethyl ether trituration afforded the title compound (90 mg, 0.17 mmol) as a yellow powder in 70% yield.

$^1$H-NMR (d$_6$-DMSO): δ 12.09 (s, 1H), 11.43 (s, 1H), 10.39 (s, 1H), 10.14 (s, 1H), 8.16 (s, 1H), 7.70–7.64 (m, 3H), 7.61–7.54 (m, 2H), 7.53–7.46 (m, 2H), 3.96 (m, 1H), 1.79–1.49 (m, 6H), 1.41–1.29 (m, 14H, contains singlet at 1.38).

LCMS: (M+H)$^-$ 514.2.

Example 60

(2R)-2-Amino-2-cyclohexyl-N-(6-oxo-2-phenyl-5,6-dihydro-1H-[1,2]diazepino[4,5,6-cd]indol-8-yl)ethanamide Trifluoroacetate

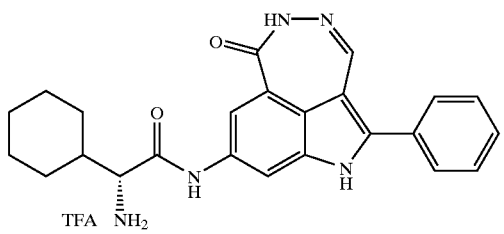

Preparation of example 60 from the title compound of Example 59 (90 mg, 0.17 mmol), and 1:1 TFA/CH$_2$Cl$_2$ (5 mL) was carried out analogously to Example 20. Isolation, also in an analogous manner, included a further trituration with methanol/diethyl ether and afforded the title compound (70 mg, 0.013 mmol) as an orange/yellow powder in 78% yield.

¹H-NMR (d₆-DMSO): δ 12.22 (s, 1H), 10.63 (s, 1H), 10.47 (s, 1H), 8.22 (br s, 2H), 8.14 (s, 1H), 7.72–7.66 (m, 3H), 7.64–7.49 (m, 4H), 3.72 (m, 1H), 1.91–1.59 (m, 6H), 1.29–1.14 (m, 5H, partially obscured by diethyl ether).

LCMS: (M+H⁺) 416.2, (M+Na⁺) 438.2.

Example 61

(1R,2R)-2-Phenyl-cyclopropanecarboxylic Acid (6-oxo-2-phenyl-5,6-dihydro-1H-[1,2]diazepino[4,5,6-cd]indol-8-yl)-amide

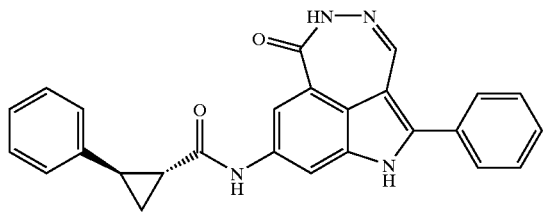

Preparation of example 61 from the title compound of Example 7 (198 mg, 0.72 mmol), (1R,2R)-2-phenylcyclopropanecarboxylic acid (175 mg, 1.08 mmol; as described by. A. Thurkauf, et al., *J. Med. Chem.* 43, 3923–3932, (2000)), triethylamine (0.401 mL, 2.88 mmol), and O-(7-azabenzotriazol-1-yl)-N,N,N',N'-tetramethyluronium hexafluorophosphate (411 mg, 1.08 mmol) in N,N-dimethylformamide (10.0 mL) was carried out analogously to Example 11. Silica gel chromatography (3% methanol in CH₂Cl₂), also in an analogous manner, followed by collection on a frit and subsequent washing with diethyl ether afforded the title compound (86 mg, 0.20 mmol) as a yellow powder in 28% yield.

¹H-NMR (d₆-DMSO): δ 12.09 (s, 1H), 10.44 (s, 1H), 10.37 (s, 1H), 8.16 (d, 1H, J=1.6 Hz), 7.69–7.63 (m, 3H), 7.60–7.46 (m, 4H), 7.34–7.17 (m, 5H), 2.44–2.35 (m, 1H), 2.13–2.05 (m, 1H), 1.55–1.46 (m, 1H), 1.42–1.34 (m, 1H).

LCMS: (M+H⁺) 421.1.

Alternative Method for the Preparation of Example 61

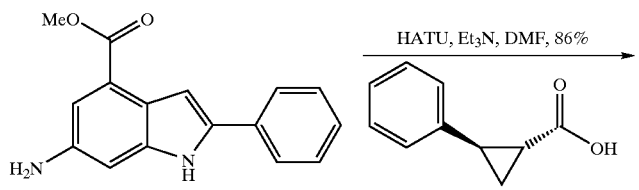

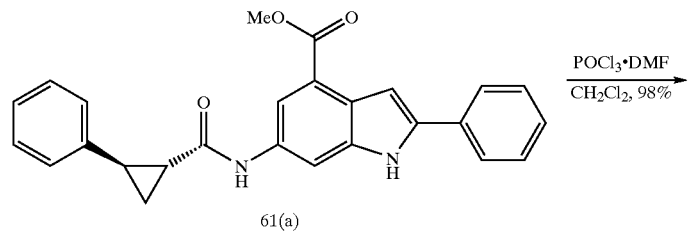

61(a)

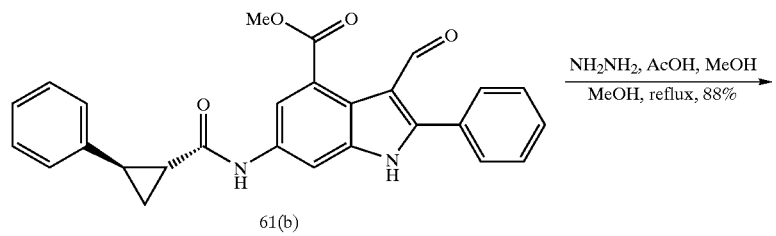

61(b)

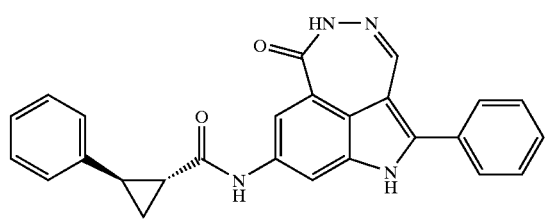

Step 1. Preparation of 2-Phenyl-6-[((1 R,2R)-2-phenyl-cyclopropanecarbonyl)-amino]-1H-indole-4-carboxylic Acid Methyl Ester 61(a)

Preparation from Intermediate 7(a) (3.83 g, 12.64 mmol), (1 R,2R)-2-phenyl-cyclopropanecarboxylic acid (2.27 mg, 13.97 mmol), triethylamine (3.52 mL, 25.28 mmol), and O-(7-azabenzotriazol-1-yl)-N,N,N',N'-tetramethyluronium hexafluorophosphate (5.31 g, 13.97 mmol) in CH$_2$Cl$_2$ (6.5 mL) and N,N-dimethylformamide (6.5 mL) was carried out analogously to Example 11. Extractive work-up from ethyl acetate and saturated aqueous NaHCO$_3$ afforded the crude product as an oil in N,N-dimethylformamide. Diethyl ether (c.a. 500 mL) and CH$_2$Cl$_2$ (80 mL) were added and the mixture was capped and stirred vigorously overnight whereupon the oil was converted to greenish tan solids which were collected by filtration and washed with diethyl ether, methanol, and water. The filtrate was evaporated to an oil and water was added to precipitate a second batch of solids which was also collected by filtration and also washed with methanol and water. Both batches of precipitated and washed solids were combined to give 4.18 g of desired product. In addition, the final filtrate was evaporated and subjected to silica gel chromatography eluting with 1:1 hexane:acetone to give a small amount of additional product (0.275 mg). The combined batches afforded Intermediate 61(a) (4.46 g, 10.86 mmol) as a tan solid in 86% yield.

Step 2. Preparation of 3-formyl-2-phenyl-6-[((1R,2R)-2-phenyl-cyclopropanecarbonyl)-amino]-1H-indole-4-carboxylic Acid Methyl Ester 61(b)

Intermediate 61(a) (4.02 g, 9.79 mmol) was dissolved in CH$_2$Cl$_2$ (80 mL) and treated with Vilsmeier reagent (2.94 mL) in a manner similar to that described in step 4 of Example 3. After c.a. 10 min stirring at ice bath temperature followed by 10 min at room temperature, the volume of CH$_2$Cl$_2$ was reduced under vacuum. With ice bath cooling and stirring, Na$_2$CO$_3$ (c.a. 1.2 g) in H$_2$O (10 mL) was added as a paste to the reaction. Additional H$_2$O (20 mL) was then added to the still cool reaction. Methanol (c.a. 100 mL) was added and the reaction was allowed to warm to room temperature, still stirring, whereup the slow evolution of gas was observed. After 4 hours, the volume of the mixture was reduced under vacuum, and CH$_2$Cl$_2$ was added to adjust the solvent composition to approximately 4:1 CH$_2$Cl$_2$:methanol. Precipitated Na$_2$CO$_3$ was then removed by filtration, and the volume of filtrate was reduced under vacuum leaving mostly methanol as the solvent. Ethyl acetate was added and mixture was then dried (Na$_2$SO$_4$) and filtered and evaporated to give yellow solids. Silica gel chromatography (eluting with 4:1 hexane:acetone increasing to 1:1 hexane:acetone) afforded Intermediate 61(b) (4.2 g, 9.64 mmol) as a yellow powder in c.a. 98% yield.

Step 3. Preparation of Title Compound: (1R,2R)-2-Phenyl-cyclopropanecarboxylic Acid (6-oxo-2-phenyl-5,6-dihydro-1H-[1,2]diazepino[4,5,6-cd]indol-8-yl)-amide Intermediate 61(b) (4.1 g, 9.41 mmol) acetic acid (0.78 mL, 13.63 mmol) and H$_2$NNH$_2$H$_2$O (1.37 mL, 28.23 mmol) in anhydrous methanol (100 mL) were refluxed in manner similar to that described for Example 3, step 5. The resulting precipitate was collected by filtration and washed with a minimum amount of methanol affording the title compound (3.5 g, 8.28 mmol) as a yellow powder in 88% yield.

Example 62

(1S,2S)-2-Phenyl-cyclopropanecarboxylic Acid (6-oxo-2-phenyl-5,6-dihydro-1H-[1,2]diazepino[4,5,6-cd]indol-8-yl)-amide

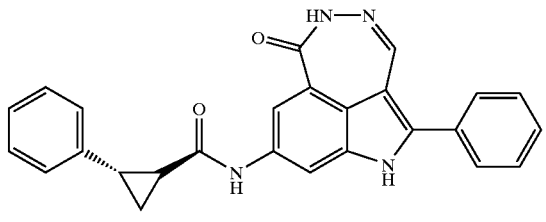

Preparation of example 62 from the title compound of Example 7 (79 mg, 0.28 mmol), (1S,2S)-2-phenylcyclopropanecarboxylic acid (60 mg, 0.37 mmol; as described by A. Thurkauf, et al., *J. Med. Chem.* 43, 3923–3932, (2000)), triethylamine (0.160 mL, 1.14 mmol), and O-(7-azabenzotriazol-1-yl)-N,N,N',N'-tetramethyluronium hexafluorophosphate (141 mg, 0.37 mmol) in N,N-dimethylformamide (10.0 mL) was carried out analogously to Example 11. Silica gel chromatography (5% methanol in CH$_2$Cl$_2$), also in an analogous manner, followed by trituration with methanol afforded the title compound (26 mg, 0.06 mmol) as a yellow powder in 22% yield.

$^1$H-NMR (d$_6$-DMSO): δ 12.10 (s, 1H), 10.44 (s, 1H), 10.37 (s, 1H), 8.17 (s, 1H), 7.72–7.43 (m, 7H), 7.35–7.26 (m, 2H), 7.24–7.17 (m, 3H), 2.40 (m, 1H), 2.10 (m, 1H), 1.52 (m, 1H), 1.38 (m, 1H).

LCMS: (M+H$^+$) 421.3, (M+Na$^+$) 423.2.

Example 63

6-Oxo-2-phenyl-N-[2-(1H-tetraazol-5-yl)ethyl]-5,6-dihydro-1H-[1,2]diazepino[4,5,6-cd]indol-8-carboxamide

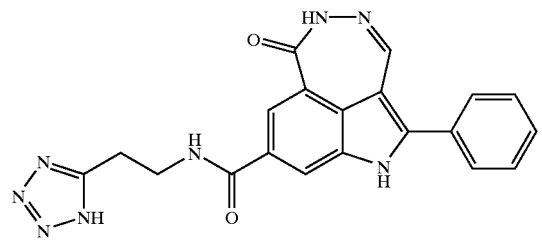

Preparation of example 63 from the title compound of Example 49 (0.0989 g, 0.288 mmol), 2-(1H-tetraazol-5-yl) ethylamine (0.072 g, 0.317 mmol), triethylamine (0.0883 mL, 0.634 mmol), and O-(7-azabenzotriazol-1-yl)-N,N,N', N'-tetramethyluronium hexafluorophosphate (0.121 g, 0.317 mmol) in DMSO (2 mL) was carried out analogously to Example 58. Preparative HPLC (25–80% CH$_3$CN/H$_2$O), also in an analogous manner, afforded the title compound (0.002 g) in 1.7% yield.

$^1$H NMR (d$_6$-DMSO): δ 12.50 (s, 1H), 10.49 (s, 1H), 8.83 (t, 1H, J=4.9 Hz), 8.05 (s, 1H), 7.98 (s, 1H), 7.70 (d, 2H, J=7.6 Hz), 7.51–7.62 (m, 4H), 3.64 (q, 2H, J=6.1 Hz), 3.14 (t, 2H, J=6.8 Hz).

HRMS calculated for C$_{20}$H$_{17}$N$_8$O$_2$ 401.1474 (M+H), found 401.1476.

Example 64

N-[2-(4-Morpholinyl)ethyl]-6-oxo-2-phenyl-5,6-dihydro-1H-[1,2]diazepino[4,5,6-cd]indole-8-carboxamide

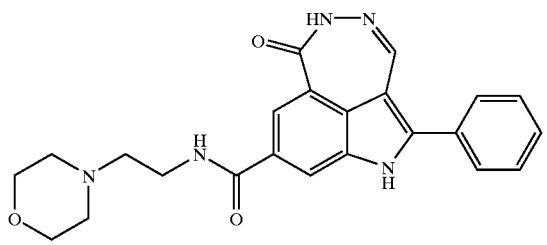

Preparation of example 64 from the title compound of Example 49 (0.0991 g, 0.289 mmol), 2-morpholin-4-ylethylamine (0.041 g, 0.317 mmol), triethylamine (0.0483 mL, 0.347 mmol), and O-(7-azabenzotriazol-1-yl)-N,N,N',N'-tetramethyluronium hexafluorophosphate (0.121 g, 0.317 mmol) in DMSO (2 mL) was carried out analogously to Example 58. Preparative HPLC (10–80% $CH_3CN/H_2O$), also in an analogous manner, afforded the tte compound (0.018 g) in 15% yield.

$^1$H NMR ($d_6$-DMSO): δ 12.48 (s, 1H), 10.49 (s, 1H), 8.62 (t, 1H, J=5.3 Hz), 8.07 (s, 1H), 8.00 (s, 1H), 7.70 (d, 2H, J=6.8 Hz), 7.51–7.62 (m, 4H), 3.57 (t, 4H, J=4.3 Hz), 3.37–3.43 (m, 2H), 2.41 (br s, 6H).

HRMS calculated for $C_{23}H_{24}N_5O_3$ 418.1879 (M+H), found 418.1858.

Example 65

6-Oxo-N-[3-2-oxo-1-pyrrolidinyl)propyl]-2-phenyl-5,6-dihydro-1H-[1,2]diazepino[4,5,6-cd]indole-8-carboxamide

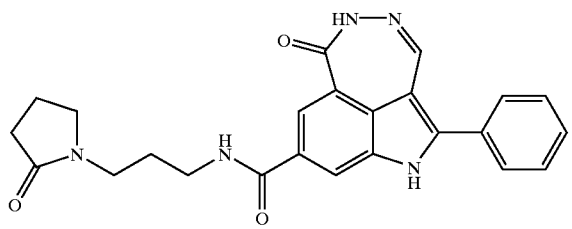

Preparation of example 65 from the title compound of Example 49 (0.109 g, 0.319 mmol), 1-(3-aminopropyl)pyrrolidin-2-one (0.05 g, 0.351 mmol), triethylamine (0.0534 mL, 0.383 mmol), and O-(7-azabenzotriazol-1-yl)-N,N,N',N'-tetramethyluronium hexafluorophosphate (0.133 g, 0.351 mmol) in DMSO (2 mL) was carried out analogously to Example 58. Preparative HPLC (10–80% $CH_3CN/H_2O$), also in an analogous manner, afforded the title compound (0.035 g) in 26% yield.

$^1$H NMR ($d_6$-DMSO): δ 12.54 (s, 1H), 10.51 (s, 1H), 8.66 (s, 1H), 8.08 (s, 1H), 8.01 (s, 1H), 7.70 (d, 2H, J=7.2 Hz), 7.53–7.62 (m, 4H), 3.23–3.37 (m, 6H), 2.21 (t, 2H, J=7.9 Hz), 1.89–1.96 (m, 2H), 1.72 (t, 2H, J=6.8 Hz).

HRMS calculated for $C_{24}H_{24}N_5O_3$ 430.1879 (M+H), found 430.1899.

Example 66

2-Ethylsulfanyl-N-(6-oxo-2-phenyl-5,6-dihydro-1H-[1,2]diazepino[4,5,6-cd]indol-8-yl)-nicotinamide

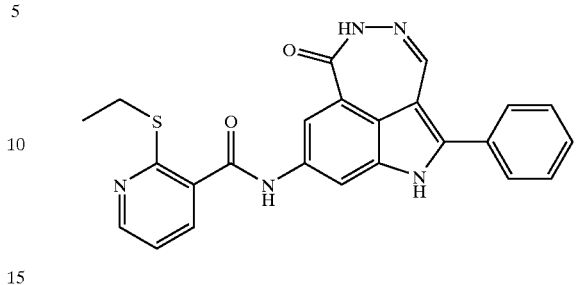

Preparation of example 66 from the title compound of Example 7 (hydrochloride) (30 mg, 0.096 mmol), 2-ethylsulfanyl-nicotinic acid (22 mg, 0.12 mmol), triethylamine (0.020 mL, 0.14 mmol), and O-(7-azabenzotriazol-1-yl)-N,N,N',N'-tetramethyluronium hexafluorophosphate (46 mg, 0.12 mmol) in $CH_2Cl_2$ (0.4 mL) and N,N-dimethylformamide (0.4 mL) was carried out analogously to Example 11. Silica gel chromatography (pre-rinsed silica with 3% triethylamine in ethyl acetate, eluted with 3% triethylamine in 19:6:1 ethyl acetate:hexane:methanol), also in an analogous manner, afforded the title compound (7 mg, 0.016 mmol) as a yellow powder in 17% yield.

$^1$H NMR ($d_6$-DMSO): δ 12.15 (s, 1H), 10.60 (s, 1H), 10.39 (s, 1H), 8.59 (s, 1H, with fine splitting), 8.22 (s, 1H), 7.95 (m, 1H), 7.82 (s, 1H), 7.72–7.48 (m, 6H), 7.25 (m, 1H), 3.21–3.10 (m, 2H, partially obscured), 1.35–1.23 (m, 3H).

LCMS: (M+H$^+$) 442.3, (M+Na$^+$) 464.1.

Example 67

(1R,2R)-2-Phenyl-cyclopropanecarboxylic Acid (6-oxo-5,6-dihydro-1H-[1,2]diazepino[4,5,6-cd]indol-8-yl)-amide; and (1S,2S)-2-Phenyl-cyclopropanecarboxylic Acid (6-oxo-5,6-dihydro-1H-[1,2]diazepino[4,5,6-cd]indol-8-yl)-amide

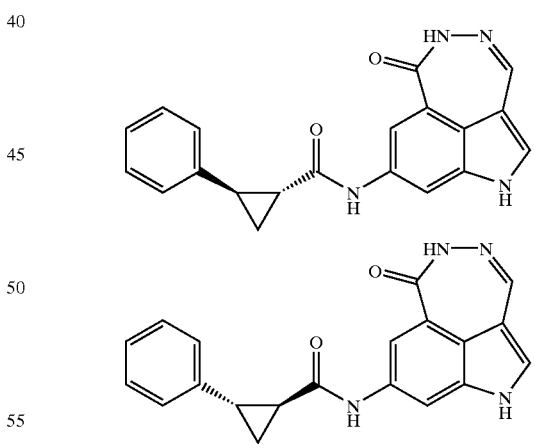

Preparation of example 67 from the title compound of Example 2 (freebase) (21 mg, 0.105 mmol), ±trans-2-phenyl-1-cyclopropanecarboxylic acid (20 mg, 0.126 mmol), triethylamine (0.044 mL, 0.315 mmol), and O-(7-azabenzotriazol-1-yl)-N,N,N',N'-tetramethyluronium hexafluorophosphate (48 mg, 0.126 mmol) in $CH_2Cl_2$ (0.3 mL) and N,N-dimethylformamide (0.3 mL) was carried out analogously to Example 11. Silica gel chromatography (5:4:1 hexane:$CH_2Cl_2$:methanol followed by 9:1 $CH_2Cl_2$:methanol), also in an analogous manner, afforded the title compound (20 mg, 0.058 mmol) (mixture of trans diastereomers) as a yellow powder in 55% yield.

$^1$H NMR (d$_6$-DMSO): δ 11.72 (s, 1H), 10.38 (s, 1H), 10.25 (s, 1H), 8.13 (s, 1H), 7.56 (s, 1H, overlapping), 7.55 (s, 1H, overlapping), 7.46 (s, 1H), 7.37–7.13 (m, 5H), 2.39 (m, 1H), 2.10 (m, 1H), 1.51 (m, 1H), 1.39 (m, 1H).

LCMS: (M+H$^+$) 345.4, (M+Na$^+$) 367.3.

Example 68

8-(3-Chloro-benzylamino)-2-phenyl-1,5-dihydro-[1,2]diazepino[4,5,6-cd]indol-6-one

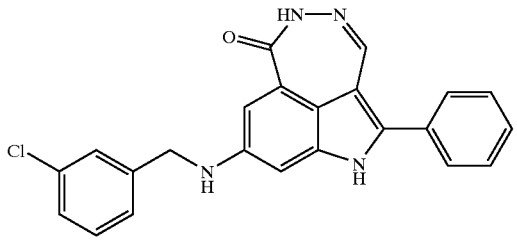

To the title compound of Example 7 (hydrochloride) (40 mg, 0.13 mmol), and triethylamine (0.053 mL, 0.38 mmol) in N,N-dimethylformamide (0.9 mL) was added 1-bromomethyl-3-chloro-benzene (0.17 mL, 0.13 mmol) dropwise with stirring. After stirring overnight, the mixture was chromatographed on silica eluting with 2:1 hexane:ethyl acetate to afford, after isolation, the title compound (36 mg, 0.090 mmol) as a yellow powder in 71% yield.

$^1$H NMR (d$_6$-DMSO): δ 11.59 (s, 1H, exchanges), 10.22 (s, 1H, exchanges), 7.60–7.27 (m, 10H), 7.08 (s, 1H), 6.60 (t, 1H, J=4.9 Hz, exchanges), 6.45 (s, 1H), 4.36 (m, 2H).

LCMS: (M+H$^+$) 401.3, 403.3.

Anal. Calcd. for $C_{23}H_{17}N_4OCl·0.3\ H_2O$: C, 67.99; H, 4.37; N, 13.79.

Found; C, 67.98; H, 4.35; N, 13.58.

Example 69

8-[Bis-(3-chloro-benzyl)-amino]-2-phenyl-1,5-dihydro-[1,2]diazepino[4,5,6-cd]indol-6-one

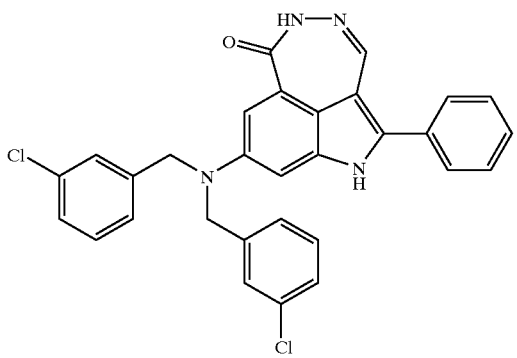

The title compound (7 mg, 0.013 mmol) was isolated as a yellow powder in 10% yield as a by-product from the synthesis outlined in Example 68.

$^1$H NMR (d$_4$-methanol): δ 7.51–7.31 (m, 6H), 7.25–7.10 (m, 9H), 6.64 (s, 1H), 4.64 (s, 4H).

LCMS: (M+H$^+$) 525.3.

Example 70

N-[2-(Dimethylamino)ethyl]-6-oxo-2-phenyl-5,6-dihydro-1H-[1,2]diazepino[4,5,6-cd]indole-8-carboxamide Trifluoroacetate

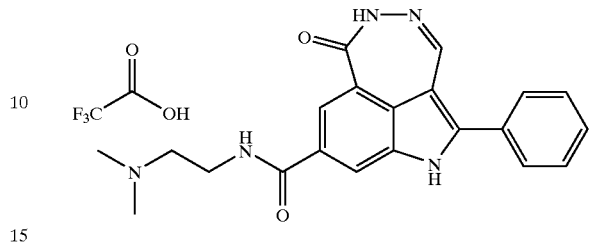

Preparation of example 70 from the title compound of Example 49 (0.08 g, 0.23 mmol), N,N-dimethylethane-1,2-diamine (0.0247 g, 0.28 mmol), triethylamine (0.17 mL, 1.2 mmol), and O-(7-azabenzotriazol-1-yl)-N,N,N',N'-tetramethyluronium hexafluorophosphate (0.106 g, 0.28 mmol) in DMSO (6 mL) was carried out analogously to Example 76. Preparative HPLC (20–100% CH$_3$CN/H$_2$O containing 0.1% trifluoroacetic acid) also in an analogous manner afforded the title compound (0.0076 g) in 6.8% yield.

$^1$H NMR (d$_6$-DMSO): δ 12.53 (s, 1H), 10.54 (s, 1H), 9.30 (s, 1H), 8.84 (t, 1H, J=5.5 Hz), 8.12 (s, 1H), 8.04 (s, 1H), 7.75–7.67(m, 2H), 7.66–7.53 (m, 3H), 7.52 (s, 1H), 3.62 (m, 2H), 3.39 (m, 2H), 2.86 (s, 6H).

LCMS: (M+H$^+$) 376.1

HRMS: $C_{21}H_{21}N_5O_2$·H: 376.1774. Found: 376.1785.

Example 71a (S)-2-Dimethylamino-N-(6-oxo-2-phenyl-5,6-dihydro-1H-[1,2]diazepino[4,5,6-cd]indol-8-yl)-3-phenyl-propionamide (Hydrochloric Salt)

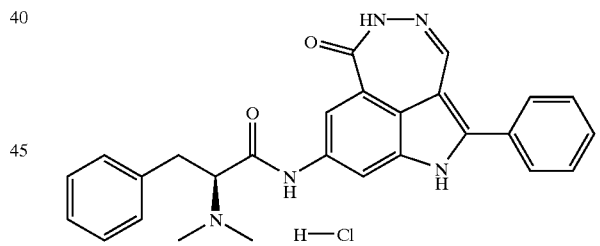

Preparation from the title compound of Example 7 (hydrochloride) (40 mg, 0.128 mmol), (S)-2-Dimethylamino-3-phenyl-propionic acid (30 mg, 0.154 mmol), triethylamine (0.071 mL, 0.512 mmol), and O-(7-azabenzotriazol-1-yl)-N,N,N',N'-tetramethyluronium hexafluorophosphate (59 mg, 0.154 mmol) in CH$_2$Cl$_2$ (0.4 mL) and N,N-dimethylformamide (0.4 mL) was carried out analogously to Example 11. Silica gel chromatography (elute with 1.5% triethylamine in CH$_2$Cl$_2$ followed by 1.5% triethylamine in 9:1 CH$_2$Cl$_2$:methanol), also in an analogous manner, afforded the freebase of the title compound (46 mg, 0.10 mmol) in three separate batches for a combined 80% yield. Two of the batches were carried on to Examples 71b and 71c respectively. To the third batch (8 mg, 0.018 mmol) was added tetrahydrofuran and 1.2 equivalents of HCl in dioxane (from a 4M stock solution). After evaporation, trituration with diethyl ether and 1:1 CH$_2$Cl$_2$:hexane gave the title compound (6 mg, 0.012 mmol) as a yellow powder in 67% yield for the salt formation.

$^1$H NMR (d$_6$-DMSO): δ 12.25 (s, 1H, exchanges), 10.76 (br s, 2H, exchanges), 10.42 (s, 1H, exchanges), 7.95 (s, 1H), 7.72–7.45 (m, 7H), 7.35–7.16 (m, 5H), 4.28 (m, 1H), 3.05–2.90 (m, 6H).

LCMS (freebase): (M+H$^+$) 452.3, (M+Na$^+$) 474.3.

Example 71b (S)-2-Dimethylamino-N-(6-oxo-2-phenyl-5,6-dihydro-1H-[1,2]diazepino[4,5,6-cd]indol-4-yl)-3-phenyl-propionamide

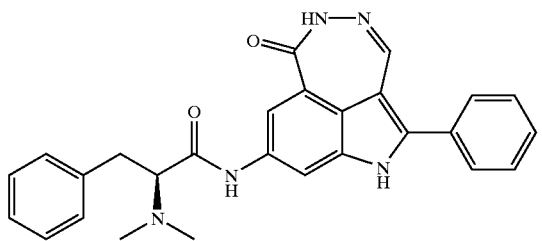

One batch of freebase (S)-2-Dimethylamino-N-(6-oxo-2-phenyl-5,6-dihydro-1H-[1,2]diazepino[4,5,6-cd]indol-8-yl)-3-phenyl-propionamide (13 mg, 0.029 mmol) from Example 71a was triturated with 1:1 diethyl ether:hexane to give the purified title compound (12 mg, 0.027 mmol) as a yellow powder in 93% yield for the trituration.

Example 71c (S)-2-Dimethylamino-N-(6-oxo-2-phenyl-5,6-dihydro-1H-[1,2]diazepino[4,6,5-cd]indol-8-yl)-3-phenyl-propionamide; Compound with (2R,3R)-2,3-dihydroxy-succinic Acid

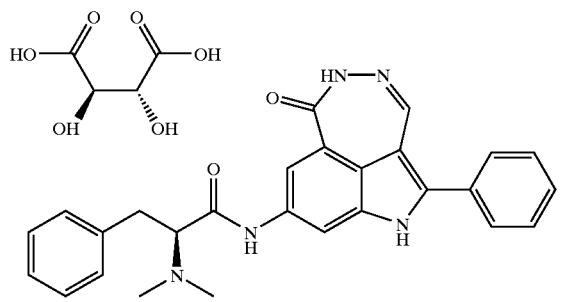

One batch of freebase (S)-2-Dimethylamino-N-6-oxo-2-phenyl-5,6-dihydro-1H-[1,2]diazepino[4,5,6-cd]indol-8-yl)-3-phenyl-propionamide (22 mg, 0.049 mmol) from Example 71a was triturated with 1:1 diethyl ether:hexane giving purified material (20 mg, 0.044 mmol). A portion (10 mg, 0.022 mmol) was then dissolved in a small amount of c.a. 1:1 tetrahydrofuran:methanol and treated with L-tartaric acid (3.3 mg, 0.022 mmol). The volatile components of the resulting clear solution were removed under a stream of argon. To the resulting yellow oil was added diethyl ether plus one drop of methanol giving a fine yellow precipitate which was isolated by decanting most of the liquid and subsequent high vacuum romoval of the remaining volatile components to afford the title compound as a tartrate salt (13 mg, 0.022 mmol) in quantitative yield.

Example 72

N-(2-{4-[(methylamino)methyl]phenyl}-6-oxo-5,6-dihydro-1H-[1,2]diazepino[4,5,6-cd]indol-8-yl) acetamide Trifluoroacetate

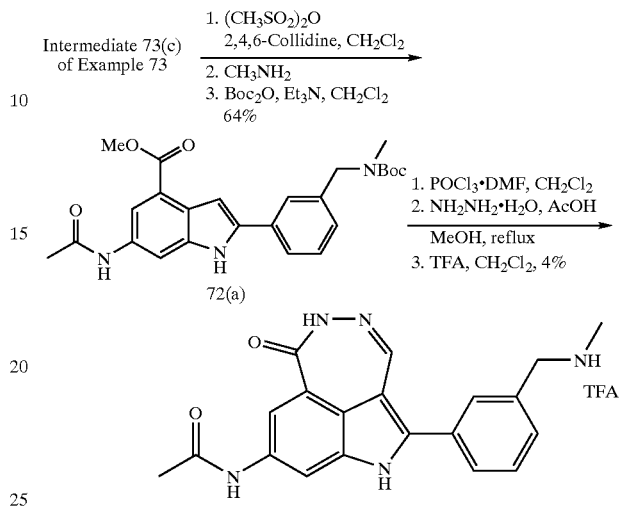

Step 1. Preparation of Methyl 6-(acetylamino)-2-(3-([{[(1,1-dimethylethyl)oxy]carbonyl}(methyl)amino]methyl}phenyl)-1H-indole-4-carboxylate 72(a)

With stirring, to Intermediate 73(c) of Example 73 (54 mg, 0.16 mmol) in CH$_2$Cl$_2$ (2.5 mL) is added 2,4,6-trimethylpyridine (0.11 mL, 0.80 mmol) followed by methanesulfonic anhydride (42 mg, 0.23 mmol). After 3.5 hours, additional methanesulfonic anhydride (7 mg, 0.04 mmol) is added, and the mixture is stirred for an additional 1 hour whereupon methylamine in tetrahydrofuran (2.0 mL, 2.0 M) is added, and the reaction is stirred overnight at room temperature. Following evaporation of the volatile components, CH$_2$Cl$_2$ (2.0 mL), triethylamine (0.064 mL, 0.46 mmol), and di-tert-butyl dicarbonate (50 mg, 0.23 mmol) are added and the reaction is stirred for 2.5 hours whereupon, after removal of the volatile components, the crude product was purified by silica gel chromatography eluting with 1:1 ethyl acetate:hexane to afford Intermediate 72(a) (46 mg, 0.10 mmol) in 64% yield.

Step 2. Preparation of Title Compound: N-(2-{4-[(Methylamino)methyl]phenyl}-6-oxo-5,6-dihydro-1H-[1,2]diazepino[4,5,6-cd]indol-8-yl)acetamide Trifluoroacetate In a manner similar to that described for Example 3, step 4, Intermediate 72(a) (45 mg, 0.10 mmole), in CH$_2$Cl$_2$ (1.5 mL) was treated with a premixed Vilsmeier reagent consisting of POCl$_3$ (0.021 mL, 0.23 mmol) and N,N-dimethylformamide (0.05 mL, 0.65 mmol). After 2 h, 2 N sodium acetate in water was added, and the crude 3-formylated product was isolated by extractive work up using ethyl acetate. After evaporation of the volatile components, methanol (1.5 mL), H$_2$NNH$_2$·H$_2$O (0.015 mL, 0.31 mmol) and acetic acid (0.010 mL, 0.17 mmol) were added, and the mixture was heated in a 70° C. oil bath for 45 min. Purification was effected using silica gel chromatography eluting with 3:2 ethyl acetate:hexane. The protected intermediate, 1,1-dimethylethyl {4-[8-(acetylamino)-6-oxo-5,6-dihydro-1H-[1,2]diazepino[4,5,6-cd]indol-2-yl] phenyl}methyl(methyl)carbamate, was treated with 1:1 TFA/CH$_2$Cl$_2$ (5 mL) analogously to Example 20. Isolation afforded the title compound (2 mg, 0.004 mmol) in 4% yield.

LCMS: (M+H$^+$) 362.3.

Example 73

N-[2-(3-Dimethylaminomethyl-phenyl)-6-oxo-5,6-dihydro-1H-[1,2]diazepino[4,5,6-cd]indol-8-yl]-2-fluoro-3-trifluoromethyl-benzamide

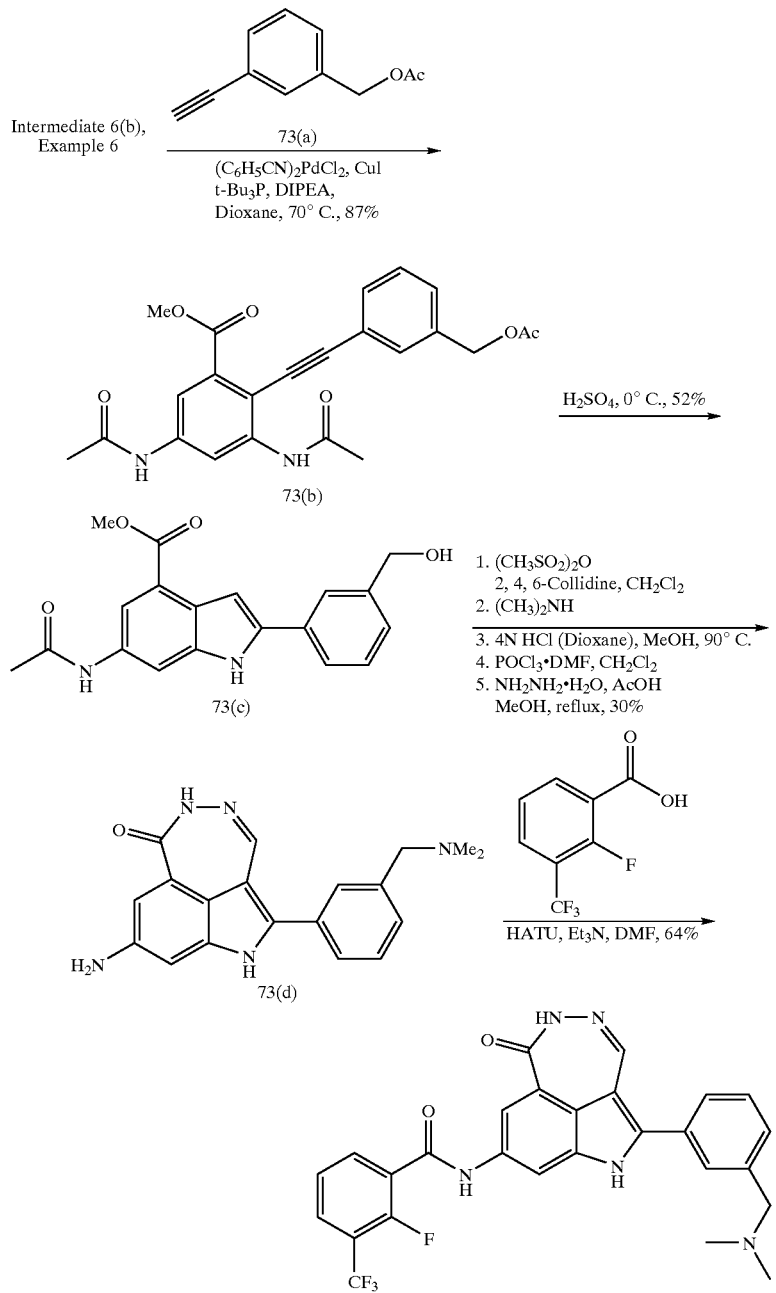

Step 1. Preparation of 2-(3-Acetoxymethyl-phenylethynyl)-3,5-bis-acetylamino-benzoic Acid Methyl Ester 73(b)

A mixture of $(C_6H_5CN)_2PdCl_2$ (0.8 g, 2 mmol), CuI (0.267 g, 1.4 mmol), and tri-tert-butyl-phosphane (1.05 mL, 4 mmol) in dioxane (35 mL, 2.0 M) was stirred at 22° C. for 0.25 hours. Diisopropylamine (17.1 mL, 122 mmol), Intermediate 6(b) of Example 6 (23 g, 69.9 mmol), acetic acid 3-ethynyl-benzyl ester (17 g, 98.0 mmol) (see below for preparation) and N,N-dimethylformamide (35 mL, 2.0 M) were added sequentially. The reaction mixture stirred at 70° C. for 16 hours. Ethyl acetate (300 mL) was added and the salts were filtered through diatomaceous earth. The solvent was removed under reduced pressure, and the resulting solid was triturated with ethyl acetate (25 mL), dichloromethane (50 mL) and diethyl ether (25 mL). The precipitate was collected by filtration and washed with 5% dichloromethane in diethyl ether (100 mL) to afford, after drying, Intermediate 73(b) (25.7 g) in 87% yield as a white powder.

$^1$H-NMR (d$_6$-DMSO): δ 10.35 (s, 1H), 9.54 (s, 1H), 8.21 (d, 1H, J=2.1 Hz), 8.08 (d, 1H, J=2.1 Hz), 7.58–7.38 (m, 4H), 5.12 (s, 2H), 3.90 (s, 3H), 2.17 (s, 3H), 2.09 (s, 3H), 2.07 (s, 3H).

LCMS: (M−H$^+$) 421.3

For step 1, compound 73(a) (acetic acid 3-ethynyl-benzyl ester) was prepared as follows:
Step 1a–1c.

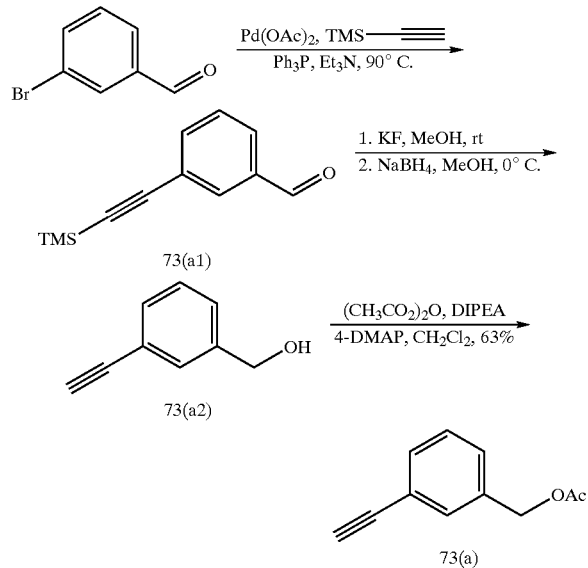

Step 1a: Preparation of Crude 3-trimethylsilanylethynyl-benzaldehyde 73(a1)

3-Bromobenzaldehyde (30 g, 162 mmol), ethynyl-trimethylsilane (30 mL, 211 mmol), triphenylphosphine (2.13 g, 8 mmol), palladium (II) acetate (0.91 g, 4 mmol) and triethylamine (540 mL, 0.3 M) were heated at 90° C. for 5 hours, after cooling to ambient temperature, the mixture was filtered. The filtrate was evaporated, and the residue was subjected to silica gel chromatography (hexane to 4:96 diethyl ether/hexane) to afford 3-trimethylsilanylethynyl-benzaldehyde 73(a1).

Step 1b: Preparation of Crude (3-ethynyl-phenyl)-methanol 73(a2)

To 3-trimethylsilanylethynyl-benzaldehyde 73(a1) from step 1a in methanol (540 mL, 0.3 M) was added KF (18.8 g, 324 mmol), and the resulting mixture stirred at 22° C. for 6 hours. After cooling to 0° C., NaBH$_4$ (6.13 g, 162 mmol) was carefully added over 0.5 hours. Aqueous saturated NH$_4$Cl was carefully added and the volatiles were removed in vacuo. Ethyl acetate (200 mL) was added, and the organic phase was washed with water and a saturated aqueous NaCl solution, dried over MgSO$_4$ and filtered. The volatiles were removed in vacuo to afford crude (3-ethynyl-phenyl)-methanol 73(a2).

Step 1c: Preparation of Acetic Acid 3-ethynyl-benzyl 73(a)

Crude (3-ethynyl-phenyl)-methanol 73(a2) from step 1b, acetic anhydride (20 mL, 21 mmol), diisopropylethylamine (85 mL, 486 mmol) and 4-dimethylamino-pyridine (0.3963.2 mmol) were stirred in CH$_2$Cl$_2$ (540 mL, 0.3 M) for 0.5 hours. Aqueous saturated NH$_4$Cl (100 mL) was carefully added and the organic phase washed with brine, dried over MgSO$_4$ and filtered. The volatiles were removed in vacuo to afford, after silica gel chromatography (hexanes to 12:88 diethyl ether/hexanes), acetic acid 3-ethynyl-benzyl (a) (17.83 g) in 63% yield.

$^1$H-NMR (d$_6$-DMSO): δ 7.32–7.01 (m, 4H), 4.85 (s, 2H), 4.01 (s, 1H), 1.89 (s, 3H).

Step 2. Preparation of 6-Acetylamino-2-3-hydroxymethyl-phenyl)-1H-indole-4-carboxylic Acid Methyl Ester 73(c)

In a manner analogous to Step 4 of Example 6, Intermediate 73(b) (24 g, 56.8 mmol) was cyclized to Intermediate 73(c) (10.1 g) in 52% yield.

$^1$H-NMR (d$_6$-DMSO): δ 11.89 (s, 1H), 10.16 (s, 1H), 8.35 (s, 1H), 7.89 (bs, 2H), 7.51 (d, 1H, J=7.9 Hz), 7.49 (dd, 1H, J=7.7, 7.5 Hz), 7.33 (bs, 2H), 5.37 (dd, 1H, J=5.8, 5.7 Hz), 4.64 (d, 2H, J=5.65 Hz), 3.99 (s, 3H), 2.13 (s, 3H).

LCMS: (M+H$^+$) 339.0

Step 3. Preparation of 8-Amino-2-(3-dimethylaminomethyl-phenyl)-1,5-dihydro-[1,2]diazepino [4,5,6-cd]indol-6-one 73(d)

To a solution of Intermediate 73(c) (1 g, 3 mmol) in dichloromethane (0.1 M, 30 mL) was added 2,4,6-Collidine (1.56 mL, 12 mmol) followed by (CH$_3$SO$_2$)$_2$O (0.62 g, 3.6 mmoL). After stirring for 2 hours, dimethylamine (5.6 M solution in ethanol, 2.6 mL, 15 mmol) was added and the reaction mixture stirred for 24 hours at 22° C. The volatiles were removed in vacuo, and the crude mixture was dissolved in methanol (15 mL). Anhydrous 4M HCl in dioxane (15 mL, 60 mmol) was carefully added, and the solution heated at 90° C. for 2.5 hours. After cooling at 22° C., the volatiles were removed in vacuo and the crude 6-amino-2-(3-dimethylaminomethyl-phenyl)-1H-indole-4-carboxylic acid methyl ester was formylated and cyclized in a manner analogous to steps 4 and 5 of Example 3. Silica gel chromatography (90:10 to 75:25 CH$_2$Cl$_2$/2M ammonia in isopropyl alcohol) provided Intermediate 73(d) (0.3 g, 0.9 mmol) in 30% yield.

$^1$H-NMR (d$_6$-DMSO): δ 11.54 (s, 1H), 10.15 (s, 1H), 7.55–7.32 (m, 5H), 6.98 (d, 1H, J=1.3 Hz), 6.65 (d, 1H, J=1.4 Hz), 5.2 (bs, 2H), 3.49 (b, 2H), 2.20 (bs, 6H).

LCMS: (M+H$^+$) 334.2

Step 4. Preparation of Title Compound: N-[2-(3-Dimethylaminomethyl-phenyl)-6-oxo-5,6-dihydro-1H-[1,2] diazepino[4,5,6-cd]indol-8-yl]-2-fluoro-3-trifluoromethyl-benzamide Preparation from Intermediate 73(d) (0.11 g, 0.4 mmol), 2-Fluoro-3-trifluoromethyl-benzoic acid (0.103 g, 0.6 mmol), triethylamine (0.183 mL, 1.6 mmol), O-(7-azabenzotriazol-1-yl)-N,N,N',N'-tetramethyluronium hexafluorophosphate (0.188 g, 0.6 mmol) and N,N-dimethylformamide (0.2 M, 1.7 mL) was carried out analogously to Example 11. Silica gel chromatography (90:10 to 80:20 CH$_2$Cl$_2$/2M ammonia in isopropyl alcohol) afforded the title compound (0.11 g) as a yellow powder in 64% yield.

$^1$H-NMR (d$_6$-DMSO): δ 12.26 (s, 1H), 10.84 (s, 1H), 10.51 (s, 1H), 9.62 (b, 1H), 8.29 (d, 1H, J=1.4 Hz), 8.08–7.94 (m, 2H), 7.85–7.53 (m, 7H), 4.39 (s, 2H), 2.73 (s, 6H).

LCMS: (M+H$^+$) 524.2.

Example 74

Methyl 1-[3-(methylamino)propyl]-6-oxo-2-phenyl-5,6-dihydro-1H-[1,2]diazepino[4,5,6-cd]indole-6-carboxylate trifluoroacetate

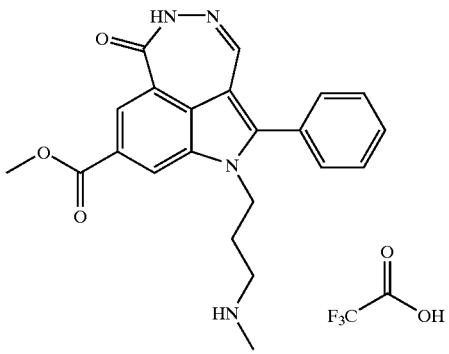

To a solution of the title compound from Example 39 (0.32 g, 1 mmol) in anhydrous DMSO (10 mL) was added NaH (60% suspension in mineral oil) (0.088 g, 2.2 mmol). The mixture was allowed to stir for 5 min whereupon 1,2-dibromopropane (0.24 g, 1,2 mmol) was added. The mixture was allowed to stir overnight at room temperature at which point a 2M solution of methylamine in methanol (4 mL, 8 mmol) was added. The mixture was subjected to preparative HPLC (20–50% $CH_3CN/H_2O$ containing 0.1% trifluoroacetic acid). The purest fractions were combined and lyophilized to afford the title compound (0.0209 g) in 4.1% yield.

$^1$H NMR ($d_6$-DMSO): δ 10.61 (s, 1H), 8.39 (d, 1H, J=1.0 Hz), 8.22 (d, 1H, J=1.0 Hz), 7.70–7.55(m, 5H), 7.07 (s, 1H), 4.41 (t, 2H, J=7.2 Hz), 3.92 (s, 3H), 2.80–2.60 (broad, 2H), 2.43 (s, 3H), 1.95–1.75 (m, 2H).

LCMS: (M+H$^+$) 391.2

HRMS: $C_{22}H_{22}N_4O3.H$: 391.1770. Found: 391.1768.

Example 75

6-Oxo-2-phenyl-N-((1,2-trans)-2-phenylcyclopropyl)-5,6-dihydro-1H-[1,2]diazepino[4,5,6-cd]indole-8-carboxamide

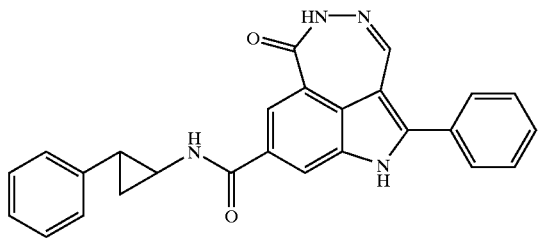

Preparation of example 75 from the title compound of Example 49 (0.34 g, 1 mmol), ±(1,2-trans)-2-phenylcyclopropylamine hydrochloride (0.2 g, 1.2 mmol), triethylamine (0.28 mL, 2 mmol), and O-(7-azabenzotriazol-1-yl)-N,N,N',N'-tetramethyluronium hexafluorophosphate (0.46 g, 1.2 mmol) in DMSO (10 mL) was carried out analogously to Example 76. Preparative HPLC (20–100% $CH_3CN/H_2O$ containing 0.1% trifluoroacetic acid), also in an analogous manner, afforded the title compound (0.0145 g) in 3.5% yield.

$^1$H NMR ($d_6$-DMSO): δ 12.46 (s, 1H), 10.47 (s, 1H), 8.88 (d, 1H, J=4.4 Hz), 8.10 (d, 1H, J=1.4 Hz), 8.02 (d, 1H, J=1.4 Hz), 7.75–7.66(m, 2H), 7.64–7.53(m, 3H), 7.51 (s, 1H), 7.32–7.25 (m, 2H), 7.23–7.10 (m, 3H), 3.08 (m, 1H), 2.11 (m, 1H), 1.41 (m, 1H), 1.23 (m, 1H).

LCMS: (M+H$^+$) 421.1.

Example 76

N-(2-Hydroxy-2-phenylethyl)-6-oxo-2-phenyl-5,6-dihydro-1H-[1,2]diazepino[4,5,6-cd]indole-8-carboxamide

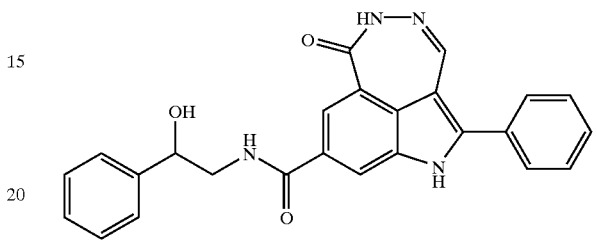

To a solution of the title compound of Example 49 (0.105 g, 0.306 mmol) in DMSO (2 mL) was added triethylamine (0.085 mL, 0.612 mmol), and O-(7-azabenzotriazol-1-yl)-N,N,N',N'-tetramethyluronium hexafluorophosphate (0.232 g, 0.612 mmol). After approximately 5 min, 2-amino-1-phenylethanol (0.084 g, 0.612 mmol) was added, and the mixture was stirred overnight. The mixture was subjected to preparative HPLC (20–100% $CH_3CN/H_2O$ containing 0.1% trifluoroacetic acid), and the purest fractions were combined and lyophilized to afford the title compound (0.018 g) as a yellow powder in 14% yield.

$^1$H NMR ($d_6$-DMSO): δ 12.47 (s, 1H), 10.45 (s, 1H), 8.68 (t, 1H, J=4.5 Hz), 8.09 (s, 1H), 8.01 (s, 1H), 7.71 (d, 2H, J=6.8 Hz), 7.51–7.62 (m, 4H), 7.24–7.41 (m, 5H), 4.80–4.84 (m, 1H), 3.46–3.54 (m, 2H).

HRMS calculated for $C_{25}H_{21}N_4O_3$ 425.1614 (M+H), found 425.1633.

Example 77

6-Oxo-2-phenyl-N-[3-(trifluoromethyl)benzyl]-5,6-dihydro-1H-[1,2]diazepino[4,5,6-cd]indole-8-carboxamide

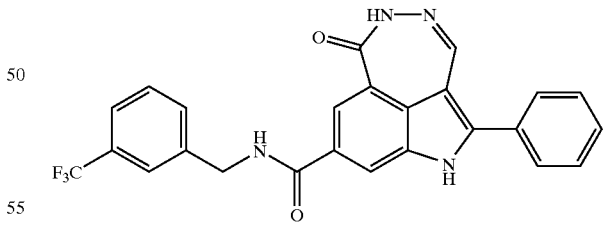

Preparation of example 77 from the title compound of Example 49 (0.1 g, 0.291 mmol), 3-(trifluoromethyl)benzylamine (0.102 g, 0.582 mmol), triethylamine (0.081 mL, 0.582 mmol), and O-(7-azabenzotriazol-1-yl)-N,N,N',N'-tetramethyluronium hexafluorophosphate (0.221 g, 0.582 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.024 g) as a yellow powder in 18% yield.

¹H NMR (d₆-DMSO): δ 12.49 (s, 1H), 10.48 (s, 1H), 9.33 (t 1H, J=6.0 Hz), 8.14 (s, 1H), 8.06 (s, 1H), 7.52–7.72 (m, 10H), 4.58 (d, 3H, J=5.7 Hz).

HRMS calculated for $C_{25}H_{18}N_4O_2F_3$ 463.1382 (M+H), found 463.1391.

Example 78

6-Oxo-2-phenyl-N-(1-phenylethyl)-5,6-dihydro-1H-[1,2]diazepino[4,5,6-cd]indole-8-carboxamide

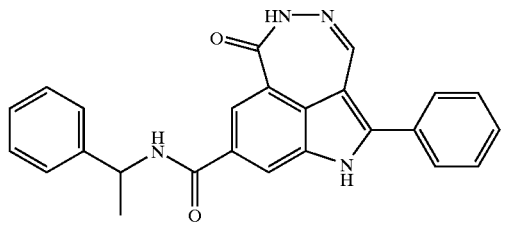

Preparation of example 78 from the title compound of Example 49 (0.103 g, 0.3 mmol), 1-phenylethylamine (0.0727 g, 0.6 mmol), triethylamine (0.084 mL, 0.6 mmol), and O-(7-azabenzotriazol-1-yl)-N,N,N',N'-tetramethyluronium hexafluorophosphate (0.228 g, 0.6 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0081 g) as a yellow powder in 6.6% yield.

¹H NMR (d₆-DMSO): δ 12.44 (s, 1H), 10.46 (s, 1H), 9.03 (d, 1H, J=7.9 Hz), 8.14 (s, 1H), 8.03 (s, 1H), 7.71 (d, 2H, J=7.2 Hz), 7.51–7.62 (m, 4H), 7.41 (d, 2H, J=7.6 Hz), 7.32 (t, 2H, J=7.6 Hz), 7.22 (t, 1H, J=7.2 Hz), 5.16–5.25 (m, 1H), 1.51 (d, 3H, J=6.8 Hz).

HRMS calculated for $C_{25}H_{21}N_4O_2$ 409.1665 (M+H), found 409.1679.

Example 79

N-[1-(4-Fluorophenyl)ethyl]-6-oxo-2-phenyl-5,6-dihydro-1H-[1,2]diazepino[4,5,6-cd]indole-8-carboxamide

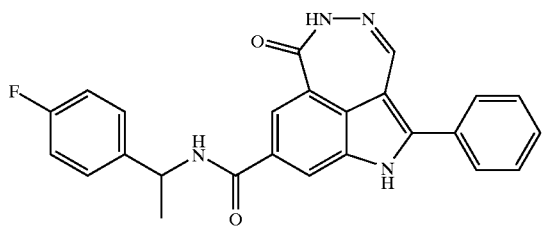

Preparation of example 79 from the title compound of Example 49 (0.0979 g, 0.285 mmol), 1-(4-fluorophenyl)ethylamine (0.0793 g, 0.57 mmol), triethylamine (0.079 mL, 0.57 mmol), and O-(7-azabenzotriazol-1-yl)-N,N,N',N'-tetramethyluronium hexafluorophosphate (0.217 g, 0.57 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0043 g) as a yellow powder in 3.5% yield.

¹H NMR (d₆-DMSO): δ 12.44 (s, 1H), 10.47 (s, 1H), 9.03 (d, 1H, J=7.9 Hz), 8.13 (s, 1H), 8.02 (s, 1H), 7.71 (d, 2H, J=6.8 Hz), 7.51–7.62 (m, 4H), 7.42–7.47 (m, 2H), 7.12–7.18 (m, 2H), 5.15–5.24 (m, 1H), 1.50 (d, 3H, J=7.2 Hz).

HRMS calculated for $C_{25}H_{20}N_4O_2F$ 427.1570 (M+H), found 427.1584.

Example 80

N-(2,3-Dihydro-1H-inden-1-yl)-6-oxo-2-phenyl-5,6-dihydro-1H-[1,2]diazepino[4,5,6-cd]indole-8-carboxamide

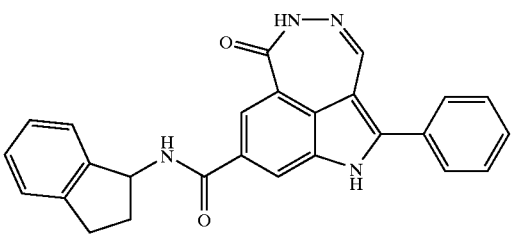

Preparation of example 80 from the title compound of Example 49 (0.1 g, 0.291 mmol), 2,3-dihydro-1H-inden-1-ylamine (0.0775 g, 0.582 mmol), triethylamine (0.081 mL, 0.582 mmol), and O-(7-azabenzotriazol-1-yl)-N,N,N',N'-tetramethyluronium hexafluorophosphate (0.221 g, 0.582 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0045 g) as a yellow powder in 3.7% yield.

¹NMR (d₆-DMSO): δ 12.45 (s, 1H), 10.45 (s, 1H), 9.01 (d, 1H, J=8.3 Hz), 8.15 (s, 1H), 8.09 (s, 1H), 7.71 (d, 2H, J=6.8 Hz), 7.51–7.62 (m, 4H), 7.18–7.28 (m, 4H), 5.56–5.64 (m, 1H), 2.79–3.06 (m, 2H), 1.98–2.46 (m, 2H).

HRMS calculated for $C_{25}H_{20}N_4O_2F$ 427.1570 (M+H), found 427.1584.

Example 81

6-Oxo-2-phenyl-N-(1,2,3,4-tetrahydronaphthalen-1-yl)-5,6-dihydro-1H-[1,2]diazepino[4,5,6-cd]indole-8-carboxamide

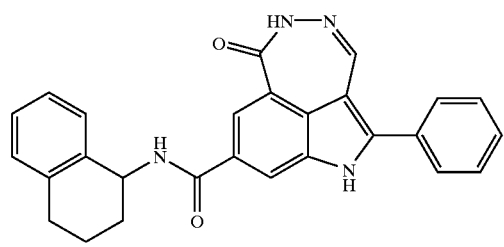

Preparation of example 81 from the title compound of Example 49 (0.103 g, 0.3 mmol), 1,2,3,4-tetrahydronaphthalen-1-ylamine (0.0883 g, 0.6 mmol), triethylamine (0.084 mL, 0.6 mmol), and O-(7-azabenzotriazol-1-yl)-N,N,N',N'-tetramethyluronium hexafluorophosphate (0.228 g, 0.6 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0136 g) as a yellow powder in 10% yield.

¹H NMR (d₆-DMSO): δ 12.44 (s, 1H), 10.44 (s, 1H), 9.01 (d, 1H, J=8.7 Hz), 8.15 (s, 1H), 8.09 (s, 1H), 7.71 (d, 2H,

J=6.8 Hz), 7.51–7.62 (m, 4H), 7.10–7.23 (m, 4H), 5.23–5.30 (m, 1H), 2.75–2.81 (m, 2H), 1.96–2.01 (m, 2H), 1.74–1.90 (m, 2H).

HRMS calculated for $C_{27}H_{23}N_4O_2$ 435.1821 (M+H), found 435.1810.

Example 82

N-[1-Methyl-1-(4-methylphenyl)ethyl]-6-oxo-2-phenyl-5,6-dihydro-1H-[1,2]diazepino[4,5,6-cd]indole-8-carboxamide

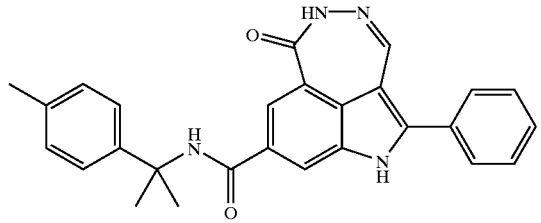

Preparation of example 82 from the title compound of Example 49 (0.103 g, 0.3 mmol), 1-methyl-1-(4-methylphenyl)ethylamine (0.0895 g, 0.6 mmol), triethylamine (0.084 mL, 0.6 mmol), and O-(7-azabenzotriazol-1-yl)-N,N,N',N'-tetramethyluronium hexafluorophosphate (0.228 g, 0.6 mmol) in DMSO (2 mL) was carried out analogously to Example 76. Preparative HPLC (20–100% $CH_3CN/H_2O$ containing 0.1% trifluoroacetic acid, also in an analogous manner, afforded the title compound (0.0304 g) as a yellow powder in 23% yield.

$^1$H NMR ($d_6$-DMSO): δ 12.41 (s, 1H), 10.45 (s, 1H), 8.60 (s, 1H), 8.05 (s, 1H), 7.94 (s, 1H), 7.70 (d, 2H, J=6.80 Hz), 7.51–7.62 (m, 4H), 7.26 (d, 2H, J=8.3 Hz), 7.08 (d, 2H, J=7.9 Hz), 2.25 (s, 3H), 1.67 (s, 6H).

HRMS calculated for $C_{27}H_{25}N_4O_2$ 437.1978 (M+H), found 437.1987.

Example 83a (1R,2R)-2-Phenyl-cyclopropanecarboxylic Acid [2-(3-dimethylaminomethyl-phenyl)-6-oxo-5,6-dihydro-1H-[1,2]diazepino[4,5,6-cd]indol-8-yl]-amide

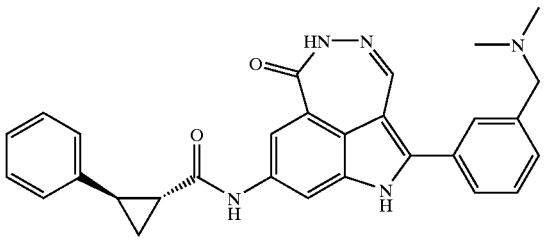

Preparation of example 83a from Intermediate 73(d) of Example 73 (0.11 g, 0.33 mmol), (1R,2R)-2-phenyl-cyclopropanecarboxylic acid (0.08 g, 0.5 mmol), triethylamine (0.183 mL, 1.32 mmol), O-(7-azabenzotriazol-1-yl)-N,N,N',N'-tetramethyluronium hexafluorophosphate (0.188 g, 0.5 mmol) and N,N-dimethylformamide (0.2 M, 1.7 mL) was carried out analogously to Example 11. Silica gel chromatography (90:10 to 80:20 $CH_2Cl_2$/2M ammonia in isopropyl alcohol) afforded the title compound (0.12 g) as a yellow powder in 76% yield.

Example 83b (1R,2R)-2-Phenyl-cyclopropanecarboxylic Acid [2-(3-dimethylaminomethyl-phenyl)-6-oxo-5,6-dihydro-1H-[1,2]diazepino[4,5,6-cd]indol-8-yl]-amide HCl Salt

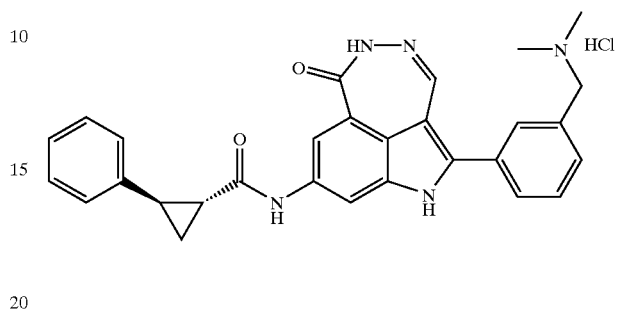

The title compound of Example 83a (0.075 g, 0.16 mmol) in dichloromethane (1.0 mL) was treated with 4M HCl in dioxane (0.043 mL, 0.17 mmol). After concentrating to dryness, the title compound (0.08 g) was obtained in quantitative yield.

$^1$H-NMR ($d_6$-DMSO): δ 12.19 (s, 1H), 10.48 (s, 1H), 10.44 (s, 1H), 10.02 (b, 1H), 8.20 (d, 1H, J=1.5 Hz), 7.84 (s, 1H), 7.76 (d, 1H, J=7.4 Hz), 7.71–7.59 (m, 4H), 7.34–7.17 (m, 5H), 4.38 (d, 1H, J=5.0 Hz), 2.78 (d, 6H, J=4.6 Hz), 2.45–2.37 (m, 1H), 2.14–2.07 (m, 1H), 1.56–1.47 (m, 1H), 1.42–1.35 (m, 1H).

HRMS: (M+H$^+$) calcd for $C_{29}H_{28}N_5O_2$, 478.2243, found 478.2261.

Example 84

N-(2-Hydroxymethyl-6-oxo-5,6-dihydro-1H-[1,2]diazepino[4,5,6-cd]indol-8-yl)-acetamide

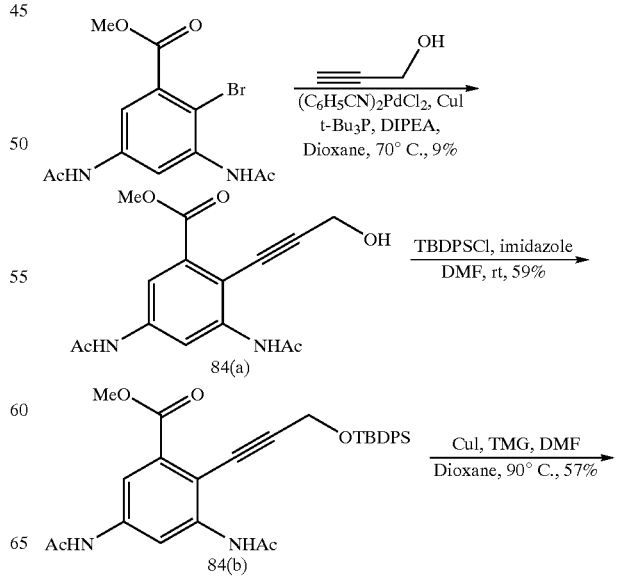

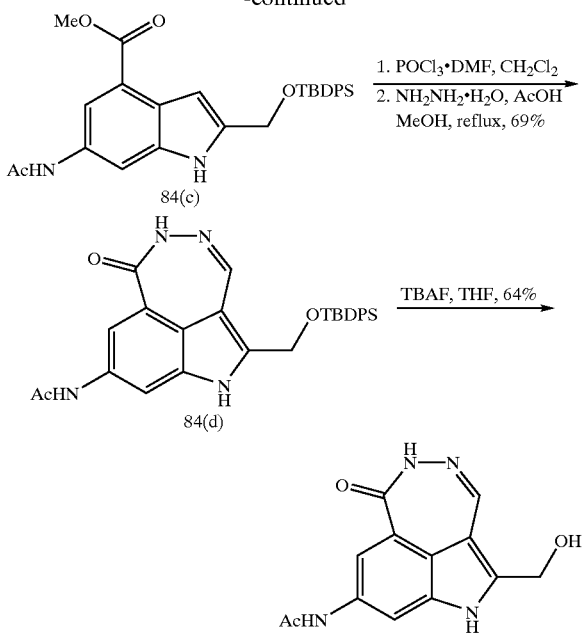

Step 1. Preparation of 3,5-Bis-acetylamino-2-(3-hydroxy-prop-1-ynyl)-benzoic Acid Methyl Ester 84(a)

Intermediate 6(b) (10 g, 30.4 mmol) of Example 6 and propargyl alcohol were reacted in a manner analogous to step 1 of Example 73. Intermediate 84(a) (0.85 g) was obtained in 9% yield.

$^1$H-NMR (d$_6$-DMSO): δ 10.29 (s, 1H), 9.11 (s, 1H), 8.30 (s, 1H), 8.00 (s, 1H), 5.34 (t, 1H, J=5.84 Hz), 4.38 (d, 2H, J=5.84 Hz), 3.83 (s, 3H), 2.13 (s, 3H), 2.05 (s, 3H).

Step 2. Preparation of 3,5-Bis-acetylamino-2-[3-(tert-butyl-diphenyl-silanyloxy)-prop-1-ynyl]-benzoic Acid Methyl Ester 84(b)

Chloro-tert-butyl-diphenyl-silane (1.3 g, 2 mmol), imidazole (0.54 g, 7.9 mmol) and Intermediate 84(a) (0.48 g, 1.6 mmol) were stirred in N,N-dimethylformamide (0.2 M, 15 mL) for 0.5 hours at 22° C. Methanol was added, the volatiles removed in vacuo, and ethyl acetate (50 mL) was added. The organic phase was washed with 1N aqueous HCl, brine, dried over MgSO$_4$, filtered, and the volatiles removed in vacuo. Silica gel chromatography (80:20 ethyl acetate/hexanes) afforded Intermediate 84(b) (0.5 g) in 59% yield.

$^1$H-NMR (d$_6$-DMSO): δ 10.31 (s, 1H), 9.18 (s, 1H), 8.25 (d, 1H, J=1.8 Hz), 8.00 (d, 1H, J=1.8 Hz), 7.74–7.68 (m, 4H), 7.50–7.41 (m, 6H), 4.67 (s, 2H), 3.81 (s, 3H), 2.05 (s, 6H), 1.01 (s, 9H).

LCMS: (M–H$^+$) 541.1

Step 3. Preparation of 6-Acetylamino-2-(tert-butyl-diphenyl-silanyloxymethyl)-1H-indole-4-carboxylic Acid Methyl Ester 84(c)

In a manner analogous to step 5 of Example 5, from Intermediate 84(b) (0.46 g, 0.84 mmol) was reacted to provide Intermediate 84(c) (0.24 g) in 57% yield.

$^1$H-NMR (d$_6$-DMSO): δ 11.36 (s, 1H), 10.04 (s, 1H), 8.25 (s, 1H), 7.78 (d, 1H, J=1.5 Hz), 7.74–7.66 (m, 4H), 7.50–7.41 (m, 6H), 6.72 (s, 1H), 4.85 (s, 2H), 3.87 (s, 3H), 2.06 (s, 3H), 1.03 (s, 9H).

LCMS: (M–H$^+$) 499.1

Step 4. Preparation of N-[2-tert-Butyl-diphenyl-silanyloxymethyl)-6-oxo-5,6-dihydro-1H-[1,2]diazepino[4,5,6-cd]indol-8-yl]-acetamide 84(d)

In a manner analogous to steps 4 and 5 of Example 3, Intermediate 84(c) (0.2 g, 0.4 mmol) was formylated and cyclized to provide Intermediate 84(d) (0.14 g) in 69% yield.

LCMS: (M–H$^+$) 509.1.

Step 5. Preparation of Title Compound: N-(2-Hydroxymethyl-6-oxo-5,6-dihydro-1H-[1,2]diazepino[4,5,6-cd]indol-8-yl)-acetamide To a solution of Intermediate 84(d) (0.085 g, 0.17 mmol) in tetrahydrofuran (0.1 M, 1.6 mL) was added a 1M solution of tetra-butyl ammonium fluoride in tetrahydrofuran (0.184 mL, 0.18 mmol). The mixture was stirred at 22° C. for 2 hours, and the yellow solid was collected by filtration and washed with methanol (5.0 mL) and diethyl ether (5.0 mL) to afford the title compound (0.029 g) in 64% yield.

$^1$H-NMR (d$_6$-DMSO): δ 11.74 (s, 1H), 10.17 (s, 1H), 10.02 (s, 1H), 8.04 (d, 1H, J=1.3 Hz), 7.54 (s, 1H), 7.53 (s, 1H), 5.47 (dd, 1H. J=5.5, 5.5 Hz), 4.68 (d, 2H, J=5.4 Hz).

LCMS: (M+H$^+$) 273.1.

HRMS: (M+H$^+$) calcd for $C_{13}H^{13}N_4O_3$, 273.1001, found 273.0988.

Example 85

Acetic acid 346-oxo-8-[((1R,2R)-2-phenyl-cyclopropanecarbonyl)-amino]-5,6-dihydro-1H-[1,2]diazepino[4,5,6-cd]indol-2-yl)-benzyl Ester

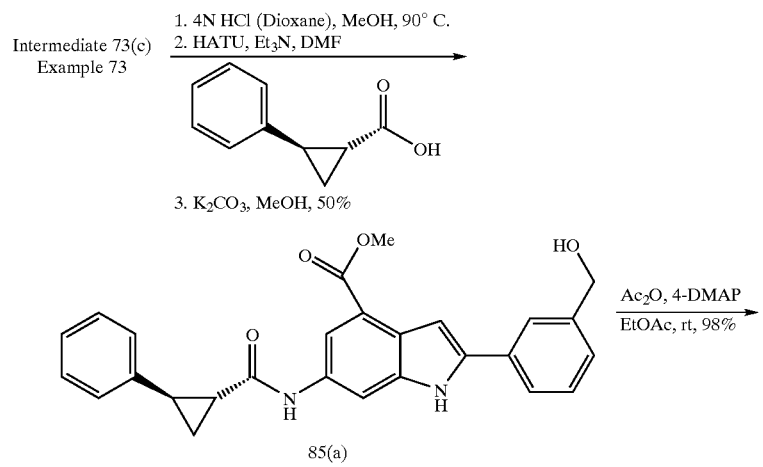

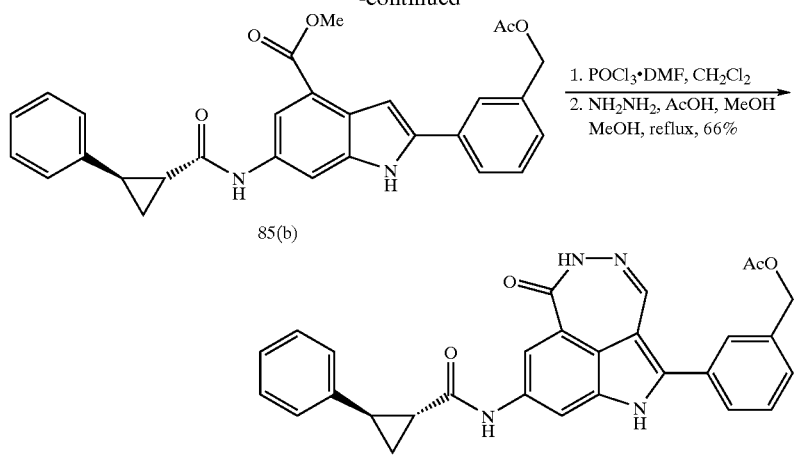

85(b)

Step 1. Preparation of 2-(3-Hydroxymethyl-phenyl)-6-[(1R, 2R)(2-phenyl-cyclopropanecarbonyl)-amino]-1H-indole-4-carboxylic Acid Methyl Ester 85(a)

Intermediate 73(c) from Example 73 (1.8 g, 5 mmol) was dissolved in methanol (22 mL). 4M HCl in dioxane (22 mL, 75 mmol) was carefully added, and the solution was heated at 90° C. for 1 hour. After cooling to 22° C., the volatiles were removed in vacuo giving 6-amino-2-(3-hydroxymethyl-phenyl)-1H-indole-4-carboxylic acid methyl ester which was then combined with (1R,2R)-2-phenyl-cyclopropanecarboxylic acid (2 g, 12.5 mmol), triethylamine (3.5 mL, 25 mmol), and O-(7-azabenzotriazol-1-yl)-N,N,N',N'-tetramethyluronium hexafluorophosphate (4.7 g, 12.5 mmol) in N,N-dimethylformamide (0.2 M, 25 mL) and stirred at 22° C. for 12 hours. Volatiles were removed in vacuo and the crude mixture dissolved in methanol (25 mL, 0.2 M) was treated with $K_2CO_3$ (1.38 g, 10 mmol) for 1 hour at 22° C. Excess $K_2CO_3$ was removed by filtration, and acetic acid (2 drops) was added to the filtrate. Following filtrate evaporation, the residue was subjected to silica gel chromatography (90:10 to 100:0 ethyl acetate/hexane) which provided Intermediate 85(a) (1.1 g. 2.5 mmol) in 50% yield.

$^1$H-NMR (d$_6$-DMSO): δ 11.83 (s, 1H), 10.41 (s, 1H), 8.25 (s, 1H), 7.90 (s, 1H), 7.84 (s, 1H), 7.75 (d, 1H, J=7.9 Hz), 7.43 (dd, 1H, J=7.7, 7.5 Hz), 7.35–7.17 (m, 7H), 5.30 (dd, 1H, J=5.8, 5.6 Hz), 4.59 (d, 2H, J=5.4 Hz), 2.45–2.36 (m, 1H), 2.14–2.07 (m, 1H), 1.58–1.47 (m, 1H), 1.42–1.34 (m, 1H).

HRMS: (M+H$^+$) calcd for $C_{27}H_{25}N_2O_4$, 441.1828, found 441.1814.

Step 2. Preparation of 2-(3-Acetoxymethyl-phenyl)-6-[(1R, 2R)-(2-phenyl-cyclopropanecarbonyl)-amino]-1H-indole-4-carboxylic acid methyl ester 85(b)

To a suspension of Intermediate 85(a) (1.1 g, 2.3 mmol) in ethyl acetate (22 mL, 0.1 M) was added 4-(dimethylamino)-pyridine (0.28 g, 2.3 mmol) and acetic anhydride (0.47 g, 4.6 mmol). The mixture was stirred at 22° C. for 1 h, and the volatiles were removed in vacuo. Silica gel chromatography (70:30 to 100:0 ethyl acetate/Hexanes) provided Intermediate 85(b) (1.1 g, 2.3 mmol) in quantitative yield.

$^1$H-NMR (d$_6$-DMSO): δ 11.85 (s, 1H), 10.43 (s, 1H), 8.26 (s, 1H), 7.92–7.81 (m, 3H), 7.49 (dd, 1H, J=7.7, 7.6 Hz), 7.37–7.13 (m, 7H), 5.15 (s, 2H), 3.92 (s, 3H), 2.45–2.36 (m, 1H), 2.14–2.07 (m, 1H), 1.58–1.47 (m, 1H), 1.42–1.34 (m, 1H).

HRMS: (M+H$^+$) calcd for $C_{29}H_{27}N_2O_5$, 483.1920, found 483.1945.

Step 3. Preparation of Title Compound: Acetic Acid 3-{6-oxo-8-[((1 R, 2R)-2-phenyl-cyclopropanecarbonyl)-amino]-5,6-dihydro-1H-[1,2]diazepino[4,5,6-cd]indol-2-yl}-benzyl Ester In a manner analogous to steps 4 and 5 of Example 3, Intermediate 85(b) (0.75 g, 1.56 mmol) was formylated and cyclized. Purification by silica gel chromatography (40:60 to 100:0 ethyl acetate/Hexanes) afforded the title compound (0.505 g, 1.03 mmol) as a yellow powder in 66% yield.

$^1$H-NMR (d$_6$-DMSO): δ 12.13 (s, 1H), 10.44 (s, 1H), 10.39 (s, 1H), 8.16 (d, 1H, J=1.5 Hz), 7.68–7.45 (m, 6H), 7.34–7.17 (m, 5H), 5.18 (s, 2H), 2.50–2.34 (m, 1H), 2.14–2.07 (m, 4H), 1.58–1.47 (m, 1H), 1.43–1.35 (m, 1H).

HRMS: (M+H$^+$) calcd for $C_{29}H_{25}N_4O_4$, 493.1876, found 493.1882.

Anal. Calcd. for $C_{29}H_{24}N_4O_4 \cdot 0.4H_2O$: C, 69.70; H, 5.00; N, 11.21. Found: C, 69.71; H, 5.03; N, 11.33.

Example 86

(1 R, 2R)-2-Phenyl-cyclopropanecarboxylic Acid [2-(3-hydroxymethyl-Phenyl)-6-oxo-5,6-dihydro-1H-[1,2]diazepino[4,5,6-cd]indol-8-yl]-amide

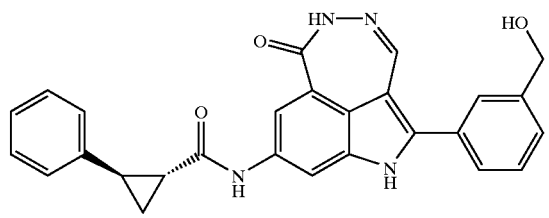

The title compound of Example 85 (0.288 g, 0.58 mmol) and $K_2CO_3$ (0.161 g, 1.17 mmol) were stirred in methanol (0.2 M, 1.7 mL) and tetrahydrofuran (0.2 M, 1.7 mL) for 1.5 hours at 22° C. After the solution was filtered and acidified with two drops of glacial acetic acid, the volatiles were removed in vacuo. Silica gel chromatography (40:60 to 0:100 hexane/ethyl acetate) afforded the title compound (0.26 g) as a yellow powder in 95% yield.

$^1$H-NMR (d$_6$-DMSO): δ 12.11 (s, 1H), 10.43 (s, 1H), 10.36 (s, 1H), 8.15 (d, 1H, J=1.0 Hz), 7.64 (d, 1H, J=1.0 Hz), 7.61 (s, 1H), 7.55–7.17 (m, 9H), 5.35 (dd, 1H, J=5.8, 5.6

Hz), 4.60 (d, 2H, J=5.6 Hz), 2.45–2.36 (m, 1H), 2.14–2.07 (m, 1H), 1.58–1.47 (m, 1H), 1.42–1.34 (m, 1H).

LCMS: (M–H$^+$) 449.1.

Anal. Calcd. for $C_{27}H_{22}N_4O_3$.0.1 $CH_2Cl_2$.0.1 $C_2H_5O_2CCH_3$: C, 70.61; H, 4.96; N, 11.98. Found: C, 70.01; H, 4.95; N, 11.95.

Example 87

N-(2,4-Difluorobenzyl)-6-oxo-2-phenyl-5,6-dihydro-1H-[1,2]diazepino[4,5,6-cd]indole-8-carboxamide

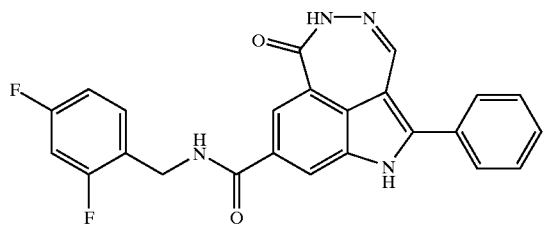

Preparation of example 87 from the title compound of Example 49 (0.102 g, 0.297 mmol), 2,4-difluorobenzylamine (0.085 g, 0.594 mmol), triethylamine (0.083 mL, 0.594 mmol), and O-(7-azabenzotriazol-1-yl)-N,N,N',N'-tetramethyluronium hexafluorophosphate (0.226 g, 0.594 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0044 g) as a yellow powder in 3.4% yield.

$^1$H NMR (d$_6$-DMSO): δ 12.48 (s, 1H), 10.48 (s, 1H), 9.20 (t, 1H, J=5.5 Hz), 8.13 (s, 1H), 8.05 (s, 1H), 7.71 (d, 2H, J=7.2 Hz), 7.52–7.62 (m, 4H), 7.40–7.47 (m, 1H), 7.16–7.25 (m, 1H), 7.03–7.10 (m, 1H), 4.49 (d, 2H, J=5.3 Hz).

HRMS calculated for $C_{24}H_{17}N_4O_2F_2$ 431.1320 (M+H), found 431.1324.

Example 88

4-[2-(6-Oxo-2-phenyl-5,6-dihydro-1H-[1,2]diazepino[4,5,6-cd]indol-8-ylcarbamoyl)-ethyl]-piperidine-1-carboxylic Acid tert-butyl Ester

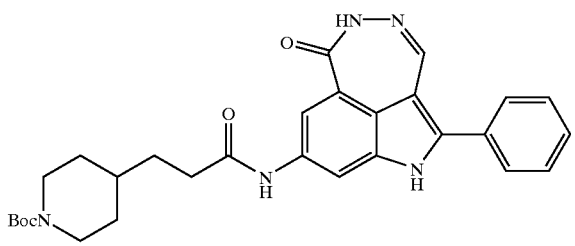

Preparation of example 88 from the title compound of Example 7 (hydrochloride) (44 mg, 0.141 mmol), 4-(2-carboxy-ethyl)-piperidine-1-carboxylic acid tert-butyl ester (43 mg, 0.169 mmol), triethylamine (0.059 mL, 0.423 mmol), and O-(7-azabenzotriazol-1-yl)-N,N,N',N'-tetramethyluronium hexafluorophosphate (64 mg, 0.169 mmol) in $CH_2Cl_2$ (0.4 mL) and N,N-dimethylformamide (0.4 mL) was carried out analogously to Example 11. Silica gel chromatography (eluted with 8:5:2 $CH_2Cl_2$:hexane:methanol), also in an analogous manner, afforded the title compound (62 mg, 0.120 mmol) as a yellow powder in 85% yield.

$^1$H NMR (d$_6$-DMSO): δ 12.15 (s, 1H), 10.37 (s, 1H), 10.06 (s, 1H), 8.20 (s, 1H), 7.70–7.46 (m, 7H), 3.96–3.87 (m, 2H), 2.75–2.63 (m, 2H), 2.42–2.34 (m, 2H), 1.72–1.55 (m, 5H), 1.40 (s, 9H), 1.06–0.98 (m, 2H).

LCMS: (M+H$^+$) 416.3, (M+Na$^+$) 538.3.

Example 89

(E)-N-(6-Oxo-2-phenyl-5,6-dihydro-1H-[1,2]diazepino[4,5,6-cd]indol-8-yl)-3-phenyl-acrylamide

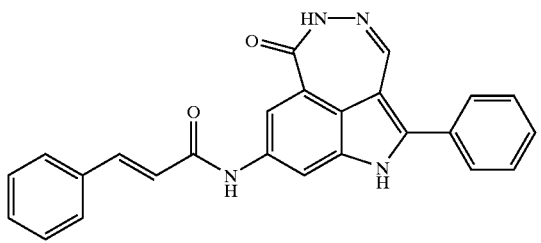

Preparation of example 89 from the title compound of Example 7 (hydrochloride) (40 mg, 0.128 mmol), (E)-3-phenyl-acrylic acid (23 mg, 0.154 mmol), triethylamine (0.054 mL, 0.384 mmol), and O-(7-azabenzotriazol-1-yl)-N,N,N',N'-tetramethyluronium hexafluorophosphate (59 mg, 0.154 mmol) in $CH_2Cl_2$ (0.4 mL) and N,N-dimethylformamide (0.4 mL) was carried out analogously to Example 11. Silica gel chromatography (eluted with 2:1 hexane:acetone), also in an analogous manner, after a final trituration with methanol afforded the title compound (47 mg, 0.116 mmol) as a yellow powder in 90% yield.

$^1$H NMR (d$_6$-DMSO): δ 12.14 (s, 1H), 10.43 (s, 1H), 10.40 (s, 1H), 8.38 (s, 1H), 7.71–7.40 (m, 13H), 6.87 (d, 1H, J=16.2 Hz).

LCMS: (M+H$^+$) 407.1, (M+Na$^+$) 429.0, (M–H$^-$) 405.2.

Anal. Calcd. for $C_{25}H_{18}N_4O_2$.2.7 $H_2O$: C, 65.98; H, 5.18; N, 12.31.

Found: C, 65.62; H, 4.63; N, 12.10.

Example 90

(2E,4E)-Hexa-2,4-dienoic Acid (6-oxo-2-phenyl-5,6-dihydro-1H-[1,2]diazepino[4,5,6-cd]indol-8-yl)-amide

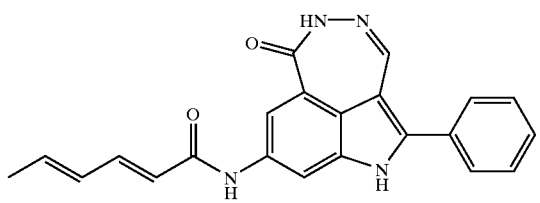

Preparation of example 90 from the title compound of Example 7 (hydrochloride) (41 mg, 0.131 mmol), (2E,4E)-hexa-2,4-dienoic acid (18 mg, 0.157 mmol), triethylamine (0.055 mL, 0.393 mmol), and O-(7-azabenzotriazol-1-yl)-N,N,N',N'-tetramethyluronium hexafluorophosphate (60 mg, 0.157 mmol) in $CH_2Cl_2$ (0.4 mL) and N,N-dimethylformamide (0.4 mL) was carried out analogously to Example 11. Silica gel chromatography (eluted with 2:1 hexane:acetone), also in an analogous manner, after a final trituration with methanol afforded the title compound (8 mg, 0.022 mmol) as a yellow powder in 16% yield.

¹H NMR (d₆-DMSO): δ 12.13 (s, 1H), 10.38 (s, 1H), 10.21 (s, 1H), 8.30 (s, 1H), 7.71–7.48 (m, 7H), 7.15 (m, 1H), 6.38–6.07 (m, 3H), 1.84 (d, 3H, J=5.8 Hz).

LCMS: (M+H⁺) 371.1, (M+Na⁺) 393.0.

Example 91

(2R)-2-Amino-2-cyclohexyl-N-(6-oxo-2-phenyl-5,6-dihydro-1H-[1,2]diazepino[4,5,6-cd]indol-8-yl)-acetamide(Hydrochloride)

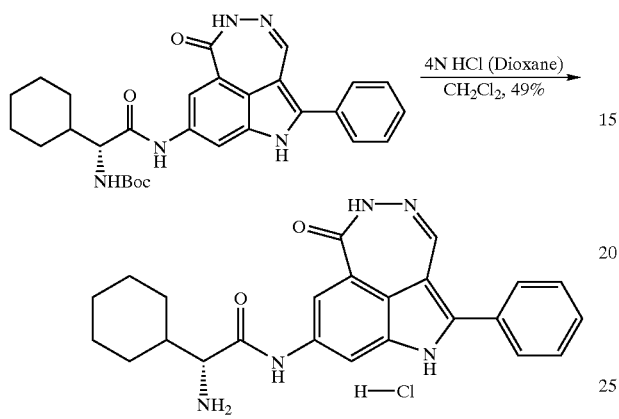

The title compound of Example 59 (210 mg, 0.41 mmol) was treated with 4M HCl in dioxane and allowed to stir tightly capped as a slurry for about 4 hours after which the volatile components were evaporated and diethyl ether was added and evaporated several times. The resulting solids were dissolved in methanol, precipitated with diethyl ether, and collected to afford the title compound (161 mg, 0.36 mmol) as a yellow powder in 87% yield.

¹H NMR (d₆-DMSO): δ 12.27 (s, 1H), 10.83 (s, 1H), 10.44 (s, 1H), 8.36 (br s, 2H), 8.13 (s, 1H), 7.78–7.64 (m, 3H), 7.63–7.48 (m, 4H), 3.81 (br s, 1H), 1.91–1.58 (m, 6H), 1.31–1.00 (m, 5H).

LCMS: (M+H⁺) 416.1,(M+Na⁺) 438.2.

Anal. Calcd. for $C_{24}H_{25}N_5O_2 \cdot 1.5$ HCl·2.0 $H_2O$: C, 56.94; H, 6.07; N, 13.84.

Found: C, 57.20; H, 6.01; N, 13.57.

Example 92

N-(6-Oxo-2-phenyl-5,6-dihydro-1H-[1,2]diazepino[4,5,6-cd]indol-8-yl)-3-piperidin-4-yl-propionamide; Compound with Trifluoro-acetic Acid

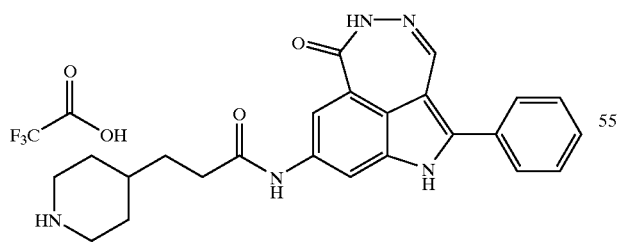

Preparation of example 92 from title compound of Example 88 (52 mg, 0.101 mmol) and 45% TFA in $CH_2Cl_2$ (1 mL) was carried out analogously to Example 20. Isolation, also in an analogous manner, afforded the title compound 50 mg, 0.084 mmol) as a yellow powder in 82% yield.

¹H NMR (d₆-DMSO): δ 12.07 (s, 1H), 10.38 (s, 1H), 10.09 (s, 1H), 8.45 (br s, 1H), 8.17 (s, 1H), 7.70–7.44 (m, 7H), 3.31–3.20 (m, 2H, partially obscurred), 2.93–2.76 (m, 2H), 2.41–2.31 (m, 2H), 1.91–1.76 (m, 2H), 1.64–1.49 (m, 3H), 1.38–1.19 (m, 2H).

Anal. Calcd. for $C_{24}H_{25}N_5O_2 \cdot 1.5$ TFA·0.8 $H_2O$: C, 53.64; H, 4.75; N, 11.58.

Found: C, 53.59; H, 4.74; N, 11.55.

Example 93

6-Oxo-2-phenyl-N-[(1R)-1-phenylethyl]-5,6-dihydro-1H-[1,2]diazepino[4,5,6-cd]indole-8-carboxamide

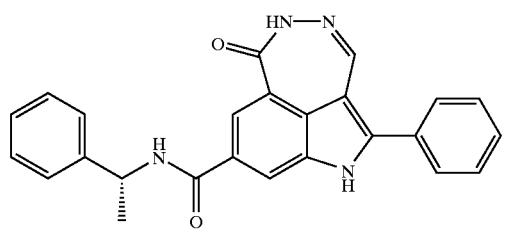

Preparation of example 93 from the title compound of Example 49 (0.105 g, 0.306 mmol), (1R)-1-phenylethylamine (0.0742 g, 0.612 mmol), triethylamine (0.085 mL, 0.612 mmol), and O-(7-azabenzotriazol-1-yl)-N,N,N',N'-tetramethyluronium hexafluorophosphate (0.233 g, 0.612 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0235 g) as a yellow powder in 19% yield.

¹H NMR (d₆-DMSO): δ 12.44 (s, 1H), 10.46 (s, 1H), 9.03 (d, 1H, J=7.9 Hz), 8.14 (s, 1H), 8.04 (s, 1H), 7.70 (d, 2H, J=6.8 Hz), 7.51–7.62 (m, 4H), 7.42 (d, 2H, J=7.2 Hz), 7.30–7.36 (m, 2H), 7.20–7.24 (m, 1H), 5.16–5.25 (m, 1H), 1.50 (d, 3H, J=7.2 Hz).

HRMS calculated for $C_{25}H_{21}N_4O_2$ 409.1665 (M+H), found 409.1666.

Example 94

6-Oxo-2-phenyl-N-[(1S)-1-phenylethyl]-5,6-dihydro-1H-[1,2]diazepino[4,5,6-cd]indole-8-carboxamide

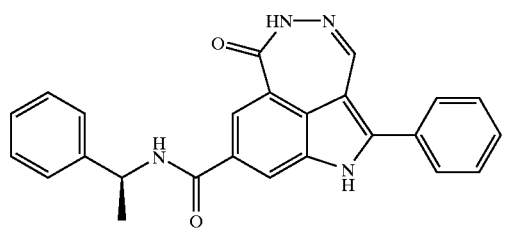

Preparation of example 94 from the title compound of Example 49 (0.0976 g, 0.284 mmol), (1S)-1-phenylethylamine (0.0688 g, 0.568 mmol), triethylamine (0.079 mL, 0.568 mmol), and O-(7-azabenzotriazol-1-yl)-N,N,N',N'-tetramethyluronium hexafluorophosphate (0.216 g, 0.568 mmol) in DMSO (2 mL) was carried out analogously to Example 76. Preparative HPLC (20–100%

CH₃CN/H₂O containing 0.1% trifluoroacetic acid), also in an analogous manner, afforded the title compound (0.0197 g) as a yellow powder in 17% yield.

¹H NMR (d₆-DMSO): δ 12.44 (s, 1H), 10.46 (s, 1H), 9.04 (d, 1H, J=7.9 Hz), 8.14 (s, 1H), 8.03 (s, 1H), 7.70 (d, 2H, J=8.3 Hz), 7.51–7.62 (m, 4H), 7.42 (d, 2H, J=7.2 Hz), 7.30–7.36 (m, 2H), 7.20–7.24 (m, 1H), 5.16–5.25 (m, 1H), 1.50 (d, 3H, J=7.2 Hz).

HRMS calculated for C₂₅H₂₁N₄O₂ 409.1665 (M+H), found 409.1666.

Example 95

N-[1-(4-Chlorophenyl)ethyl]-6-oxo-2-phenyl-5,6-dihydro-1H-[1,2]diazepino[4,5,6-cd]indole-8-carboxamide

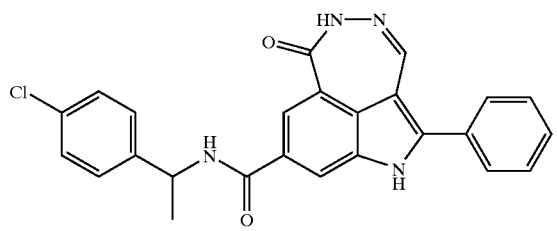

Preparation of example 95 from the title compound of Example 49 (0.104 g, 0.303 mmol), 1-(4-chlorophenyl)ethylamine (0.0943 g, 0.606 mmol), triethylamine (0.084 mL, 0.606 mmol), and O-(7-azabenzotriazol-1-yl)-N,N,N',N'-tetramethyluronium hexafluorophosphate (0.23 g, 0.606 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0025 g) as a yellow powder in 1.9% yield.

¹H NMR (d₆-DMSO): δ 12.45 (s, 1H), 10.47 (s, 1H), 9.06 (d, 1H, J=7.9 Hz), 8.14 (s, 1H), 8.03 (s, 1H), 7.70 (d, 2H, J=7.9 Hz), 7.51–7.62 (m, 4H), 7.38–7.44 (m, 4H), 5.13–5.22 (m, 1H), 1.49 (d, 3H, J=7.2 Hz).

HRMS calculated for C₂₅H₂₀N₄O₂Cl 443.1275 (M+H), found 443.1265.

Example 96

N-[1-(4-Hydroxyphenyl)ethyl]-6-oxo-2-phenyl-5,6-dihydro-1H-[1,2]diazepino[4,5,6-cd]indole-8-carboxamide

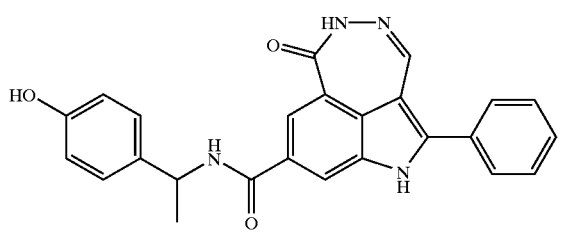

Preparation of example 96 from the title compound of Example 49 (0.104 g, 0.303 mmol), 1-(4-hydroxyphenyl)ethylamine (0.0831 g, 0.606 mmol), triethylamine (0.084 mL, 0.606 mmol), and O-(7-azabenzotriazol-1-yl)-N,N,N',N'-tetramethyluronium hexafluorophosphate (0.23 g, 0.606 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0205 g) as a yellow powder in 16% yield.

¹H NMR (d₆-DMSO): δ 12.42 (s, 1H), 10.45 (s, 1H), 9.21 (br s, 1H), 8.91 (d, 1H, J=8.3 Hz), 8.11 (s, 1H), 8.02 (s, 1H), 7.70 (d, 2H, J=6.8 Hz), 7.51–7.61 (m, 4H), 7.21 (d, 2H, J=8.3 Hz), 6.71 (d, 2H, J=8.3 Hz), 5.08–5.16 (m, 1H), 1.46 (d, 3H, J=7.2 Hz).

HRMS calculated for C₂₅H₂₁N₄O₃ 425.1614 (M+H), found 425.1626.

Example 97

2,3-Difluoro-N-(6-oxo-2-phenyl-5,6-phenyl-dihydro-1H-[1,2]diazepino[4,5,6-cd]indol-8-yl)-benzamide

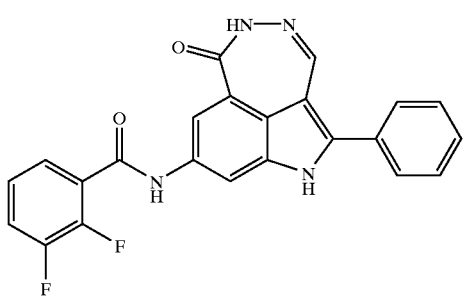

Preparation of example 97 from the title compound of Example 7 (hydrochloride) (40 mg, 0.128 mmol), 2,3-difluoro-benzoic acid (24 mg, 0.154 mmol), triethylamine (0.054 mL, 0.384 mmol), and O-(7-azabenzotriazol-1-yl)-N,N,N',N'-tetramethyluronium hexafluorophosphate (59 mg, 0.154 mmol) in CH₂Cl₂ (0.4 mL) and N,N-dimethylformamide (0.4 mL) was carried out analogously to Example 11. Silica gel chromatography (eluted with 2:1 hexane:acetone increasing to 1:1 hexane:acetone), also in an analogous manner, afforded the title compound (24 mg, 0.058 mmol) as a yellow powder in 45% yield.

¹H NMR (d₆-DMSO): δ 12.20 (s, 1H), 10.72 (s, 1H), 10.42 (s, 1H), 8.24 (s, 1H), 7.81 (s, 1H). 7.72–7.45 (m, 8H), 7.37 (m, 1H).

LCMS: (M+H⁺) 417.0, (M+Na⁺) 439.1.

Example 98

2,3-Dimethyl-N-(6-oxo-2-phenyl-5,6-dihydro-1H-[1,2]diazepino[4,5,6-cd]indol-8-yl)-benzamide

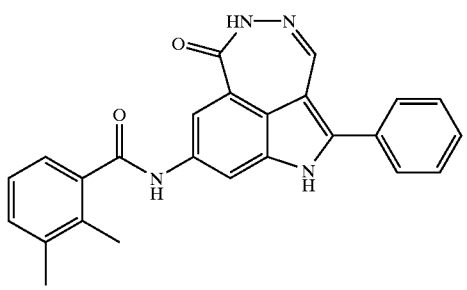

Preparation of example 98 from the title compound of Example 7 (hydrochloride) (42 mg, 0.134 mmol), 2,3- dimethyl-benzoic acid (24 mg, 0.161 mmol), triethylamine (0.056 mL, 0.402 mmol), and O-(7-azabenzotriazol-1-yl)-N,N,N',N'-tetramethyluronium hexafluorophosphate (61 mg, 0.161 mmol) in CH$_2$Cl$_2$ (0.4 mL) and N,N-dimethylformamide (0.4 mL) was carried out analogously to Example 11. The mixture was stirred as a thick slurry and additional 2,3-dimethyl-benzoic acid (12 mg, 0.08 mmol) and O-(7-azabenzotriazol-1-yl)-N,N,N',N'-tetramethyluronium hexafluorophosphate (30 mg, 0.08 mmol) were added after 48 hours to drive the reaction to completion. The mixture was filtered to collect the solids which were then washed with methanol. After drying the solids under high vacuum, the title compound (32 mg, 0.078 mmol) was obtained as a yellow powder in 58% yield.

$^1$H NMR (d$_6$-DMSO): δ 12.14 (s, 1H), 10.47 (s, 1H), 10.39 (s, 1H), 8.25 (s, 1H), 7.86 (m, 1H), 7.72–7.66 (m, 2H), 7.63–7.49 (m, 4H), 7.33–7.25 (m, 2H), 7.21 (m, 1H), 2.31 (s, 3H), 2.29 (s, 3H).

LCMS: (M+H$^+$) 409.1, (M+Na$^+$) 431.1.

Example 99

3-Fluoro-2-methyl-N-(6-oxo-5,6-dihydro-1H-[1,2]diazepino[4,5,6-cd]indol-8-yl)-benzamide

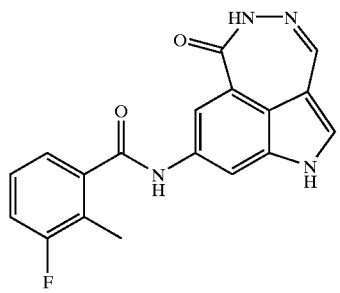

Preparation of example 99 from title compound of Example 2 (21 mg, 0.105 mmol), 3-fluoro-2-methyl-benzoic acid (19 mg, 0.126 mmol), triethylamine (0.044 mL, 0.315 mmol), and O-(7-azabenzotriazol-1-yl)-N,N,N',N'-tetramethyluronium hexafluorophosphate (48 mg, 0.126 mmol) in CH$_2$Cl$_2$ (0.2 mL) and N,N-dimethylformamide (0.2 mL) was carried out analogously to Example 11. The mixture was stirred as a thick slurry and additional 3-fluoro-2-methyl-benzoic acid (11 mg, 0.07 mmol) and O-(7-azabenzotriazol-1-yl)-N,N,N',N'-tetramethyluronium hexafluorophosphate (27 mg, 0.07 mmol) were added after 24 hours to drive the reaction to completion. Purification, also in an analogous manner, except that it required two successive silica gel chromatographies (both eluted with 0.2:1 hexane:acetone increasing to 1:1 hexane:acetone) afforded the title compound (14 mg, 0.042 mmol) as a yellow powder in 40% yield.

$^1$H NMR (d$_6$-DMSO): δ 11.79 (s, 1H), 10.50 (s, 1H), 10.25 (s, 1H), 8.20 (s, 1H), 7.78 (s, 1H), 7.60 (s, 1H), 7.49 (s, 1H), 7.46–7.17 (m, 3H), 2.30 (s, 3H).

LCMS: (M+H$^+$) 337.1, (M+Na$^+$) 359.1.

Example 100

(1R,2R)-2-Phenyl-cyclopropanecarboxylic Acid (6-oxo-5,6-dihydro-1H-[1,2]diazepino[4,5,6-cd]indol-8-yl)-amide

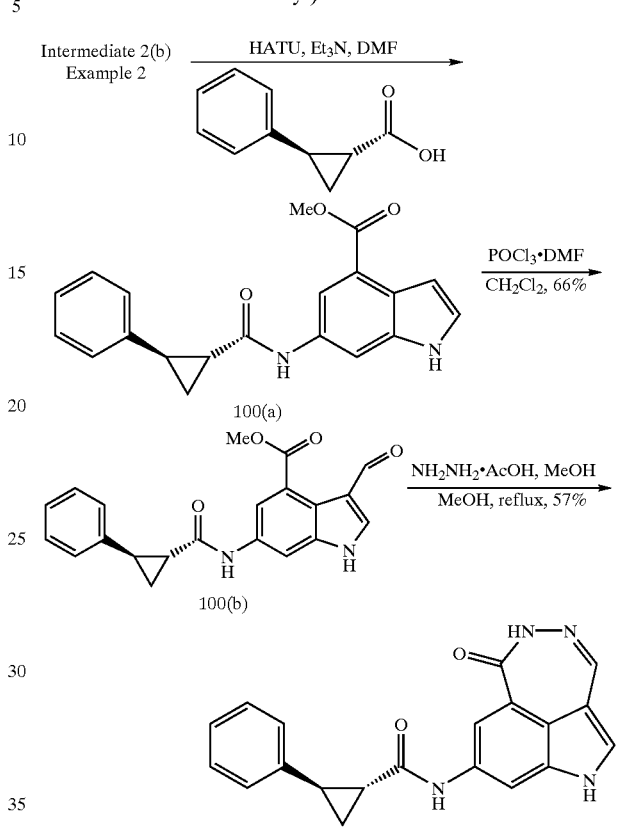

Step 1. Preparation of 6-[((1R,2R)-2-Phenyl-cyclopropanecarbonyl)-amine]-1H-indole-4-carboxylic Acid Methyl Ester 100(a)

Preparation of intermediate 100(a) from Intermediate 2(b) of Example 2 (111 mg, 0.49 mmol), (1R,2R)-2-phenyl-cyclopropanecarboxylic acid (119 mg, 0.73 mmol), triethylamine (0.273 mL, 1.96 mmol), and O-(7-azabenzotriazol-1-yl)-N,N,N',N'-tetramethyluronium hexafluorophosphate (278 mg, 0.73 mmol) in CH$_2$Cl$_2$ (0.4 mL) and N,N-dimethylformamide (0.4 mL) was carried out analogously to Example 11. Extractive work-up from ethyl acetate and saturated aqueous NaHCO$_3$ afforded crude Intermediate 100(a) (222 mg) as a tan solid which was carried on without purification.

Step 2. Preparation of 3-Formyl-6-[((1R,2R)-2-phenyl-cyclopropanecarbonyl)-amino]-1H-indole-4-carboxylic Acid Methyl Ester 100(b)

Intermediate 100(a) (214 mg) was dissolved in CH$_2$Cl$_2$ (3 mL) and N,N-dimethylformamide (0.2 mL) and treated with Vilsmeier reagent (0.147 mL) in a manner similar to that described for Example 3, Step 4. Upon addition, an immediate precipitate formed causing a thick slurry. Additional CH$_2$Cl$_2$ (5.0 mL) and N,N-dimethylformamide (0.2 mL) was added to facilitate stirring. Additional Vilsmeier reagent (0.147 mL) was also added. After c.a. 10 min, hexane was added, and the solids were allowed to settle. After decanting the supernatant, additional hexane was added and the trituration was repeated-discarding both triturates. To the remaining solids, methanol (8 mL) was added along with K$_2$CO$_3$ (750 mg, 5.43 mmol) and H$_2$O (4 mL), and the mixture was allowed to stir. After c.a. 30 min, ethyl acetate was added and the K₂CO₃/H₂O aggregates were removed by decanting the product away in solution. The solvents were then reduced in volume, additional ethyl acetate was added, and the product was subjected to extractive work-up to afford Intermediate 100(b) (117 mg, 0.32 mmol) as a brownish powder in about a 66% combined, crude yield over steps 1 and 2.

Step 3. Preparation of Title Compound: (1R, 2R)-2-Phenyl-cyclopropanecarboxylic Acid (6-oxo-5,6-dihydro-1H-[1,2]diazepino[4,5,6-cd]indol-8-yl)-amide Intermediate 100(b) (105 mg), acetic acid (0.048 mL, 0.84 mmol) and H₂NNH₂.H₂O (0.084 mL, 1.74 mmol) in anhydrous methanol (4.4 mL) were refluxed in manner similar to that described for Example 3, Step 5. The crude product was purified on silica gel eluting with 2:1 then 1:1 hexane:acetone to afford the title compound (61 mg, 0.17 mmol) in about a 57% yield for the last step.

¹H NMR (d₆-DMSO): δ 11.74 (s, 1H), 10.38 (s, 1H), 10.23 (s, 1H), 8.13 (s, 1H), 7.60–7.53 (m, 2H), 7.46 (s, 1H), 7.35–7.26 (m, 2H), 7.24–7.15 (m, 3H), 2.38 (m, 1H), 2.08 (m, 1H), 1.50 (m, 1H), 1.36 (m, 1H).

LCMS: (M+H⁺) 345.2, (M+Na⁺) 367.1.

Anal. Calcd. for C₂₀H₁₆N₄O₂.0.6H₂O.0.1 methanol.0.1 CH₂Cl₂: C, 66.13; H, 4.89; N, 15.27.

Found: C, 66.19; H, 5.03; N, 15.07.

Alternative Method for the Preparation of Example 100.

Preparation of example 100 from the title compound of Example 2 (3.0 g, 12.7 mmol), (1R,2R)-2-phenylcyclopropanecarboxylic acid (2.36 g, 14.6 mmol) (prepared as described by A. Thurkauf, et. al. (2000) *J. Med. Chem.* 43:3923–3932), triethylamine (8.8 mL, 63.4 mmol), and O-(7-azabenzotriazol-1-yl)-N,N,N',N'-tetramethyluronium hexafluorophosphate (5.3 g, 14.5 mmol) in N,N-dimethylformamide (30.0 mL, 0.4 M) was carried out analogously to Example 11. Silica gel chromatography (5:50:45 methanol/ethyl acetate/CH₂Cl₂), also in an analogous manner, afforded the title compound (3.67 g, 10.7 mmol) as a yellow powder in 84% yield.

Example 101

N-[2-Hydroxy-2-(3-hydroxyphenyl)ethyl]-6-oxo-2-phenyl-5,6-dihydro-1H-[1,2]diazepino[4,5,6-cd]indole-8-carboxamide

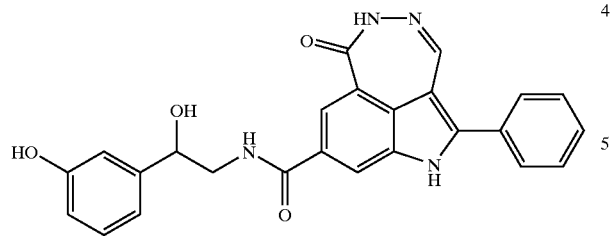

Preparation of example 101 from the title compound of Example 49 (0.238 g, 0.693 mmol), 2-hydroxy-2-(3-hydroxyphenyl)ethylamine hydrochloride (0.264 g, 1.39 mmol), triethylamine (0.29 mL, 2.08 mmol), and O-(7-azabenzotriazol-1-yl)-N,N,N',N'-tetramethyluronium hexafluorophosphate (0.528 g, 1.39 mmol) in DMSO (2 mL) was carried out analogously to Example 76. Preparative HPLC (20–100% CH₃CN/H₂O containing 0.1% trifluoroacetic acid), also in an analogous manner, afforded the title compound (0.0414 g) as a yellow powder in 14% yield.

¹H NMR (d₆-DMSO): δ 12.47 (s, 1H), 10.45 (s, 1H), 9.27 (br s, 1H), 8.68 (t, 1H, J=5.7 Hz), 8.10 (s, 1H), 8.02 (s, 1H), 7.71 (d, 2H, J=7.2 Hz), 7.51–7.62 (m, 4H), 7.08–7.13 (m, 1H), 6.76–6.81 (m, 2H), 6.61–6.64 (m, 1H), 4.70–4.74 (m, 1H).

HRMS calculated for C₂₅H₂₁N₄O₄ 441.1563 (M+H), found 441.1543.

Example 102

Methyl-6-oxo-2-phenyl-1,3,5,6-tetrahydro[1,2]oxazepino[6,5,4-cd]indole-8-carboxylate

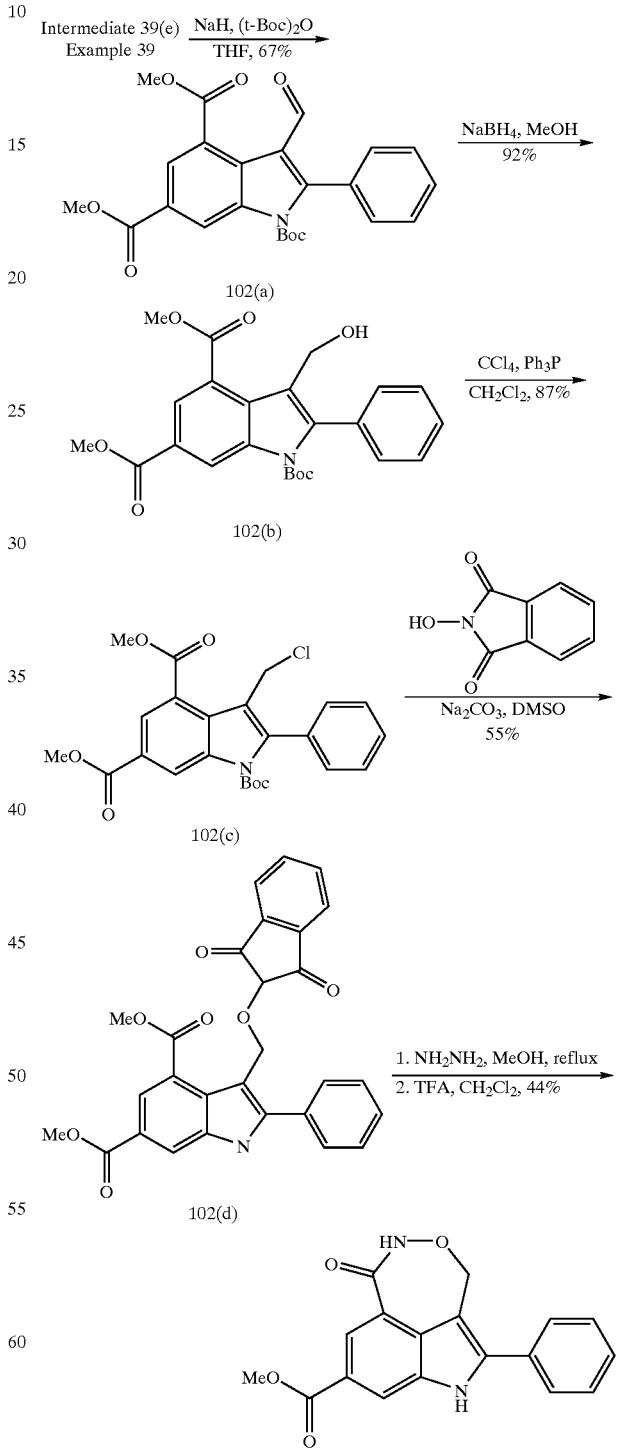

Step 1. Preparation of 1-tert-butyl-4,6-dimethyl-3-formyl-2-phenyl-1H-indole-1,4,6-tricarboxylate 102(a)

To a solution of Intermediate 39(e) of Example 39 (2.25 g, 6.7 mmol), and di-tert-butyl dicarbonate (11.68 g, 54 mmol) in 150 ml of tetrahydrofuran was added a 60% suspension of NaH in mineral oil (1.60 g, 40 mmol). The reaction mixture was stirred at room temperature for 1 hour. Extractive work-up from ethyl acetate and saturated aqueous $NaHCO_3$ followed by silica gel chromatography afforded Intermediate 102(a) (1.97 g), in 67% yield.

$^1$H NMR ($d_6$-DMSO): δ 9.56 (s, 1H), 8.96 (s, 1H), 8.08 (s, 1H), 7.70–7.50 (m, 5H), 3.93 (s, 3H), 3.83 (s, 3H), 1.20 (s, 9H).

Step 2. Preparation of 1-(tert-Butoxycarbonyl)-3-(hydroxymethyl)-6-(methoxycarbonyl)-2-phenyl-1H-indole-4-carboxylic acid 102(b)

Intermediate 102(a) (1.95 g) was dissolved in methanol (200 mL) and $NaBH_4$ (1.70 g) was added and stirred for 15 min. After removing solvent, silica gel chromatography afforded Intermediate 102(b) (1.81 g) in 92% yield.

$^1$H NMR ($d_6$-DMSO): δ 8.97 (d, 1H, J=1.5 Hz), 8.10 (d, 1H, H=1.5 Hz), 7.35–7.55 (m, 5H), 4.61 (t, 1H, J=5.1 Hz), 4.41 (d, 2H, J=5.0 Hz), 3.92 (s, 3H), 3.87 (s, 3H), 1.16 (s, 9H).

Step 3. Preparation of 1-tert-Butyl-4,6-dimethyl-3-chloromethyl)-2-phenyl-1H-indole-1,4,6-tricarboxylate 102(c)

To a solution of intermediate 102(b) (1.68 g, 3.8 mmol) and $CCl_4$ (3.50 g, 23 mmol) in 20 ml of dichloromethane was added $Ph_3P$ (2.42 g, 9.2 mmol). The reaction mixture was stirred at room temperature for 24 hours. The reaction mixture was concentrated, and residue was purified using silica gel chromatography to afford Intermediate 102(c) (1.53 g) in 87% yield.

$^1$H NMR ($d_6$-DMSO): δ 8.97 (d, 1H, J=1.5 Hz), 8.10 (d, 1H, J=1.5 Hz), 7.35–7.55 (m, 5H), 4.61 (t, 1H, J=5.1 Hz), 4.41 (d, 2H, J=5.0 Hz), 3.92 (s, 3H), 3.87 (s, 3H), 1.16 (s, 9H).

Step 4. Preparation of 1-tert-Butyl 4,6-dimethyl 3-([(1,3-dioxo-1,3-dihydro-2H-isoindol-2-yl)oxy]methyl)-2-phenyl-1H-indole-1,4,6-tricarboxylate 102(d)

A mixture of Intermediate 102(c) (0.23 g, 0.5 mmol), N-hydroxyphthalimide (0.24 g, 1.5 mmol) and $Na_2CO_3$ (0.32 g, 3 mmol) was stirred in anhydrous DMSO (10 mL) at room temperature overnight. Extractive work-up from ethyl acetate, followed by silica gel chromatography afforded Intermediate 102(d) (0.16 g) in 55% yield.

$^1$H NMR ($d_6$-DMSO): δ 9.02 (d, 1H, J=1.1 Hz), 8.31 (d, 1H, H=1.1 Hz), 7.75–7.82 (m, 2H), 7.64–7.71(m, 2H), 7.39 (t, 1H, J=7.6 Hz), 7.26 (t, 2H, J=7.6), 7.18 (d, 2H, J=7.8 Hz), 5.32 (s, 2H), 3.94 (s, 3H), 3.92 (s, 3H), 1.11 (s, 9H).

Step 5. Preparation of Title Compound Methyl-6-oxo-2-phenyl-1,3,5,6-tetrahydro[1,2]oxazepino[6,5,4-cd]indole-8-carboxylate A mixture of Intermediate 102(d) (0.15 g, 0.26 mmol) and hydrazine (0.20 g, 6.3 mmol) in methanol (15 mL) was refluxed for 2 hours. After solvent evaporation, the residue was mixed with $CH_2Cl_2$ (15 ml) and trifluoroacetic acid (7.5 ml) and stirred for 2 hours. After solvent removal, the residue was subjected to reverse-phase preparative HPLC affording the title compound (34.8 mg) in 42% yield.

$^1$H NMR ($d_6$-DMSO): δ 12.20 (s, 1H), 11.23 (s, 1H), 8.30 (d, 1H, J=1.2 Hz), 8.21 (d, 1H, H=1.2 Hz), 7.40–7.75 (m, 5H), 5.44 (d, 1H, J=14.7 Hz), 5.22 (d, 1H, J=14.7 Hz), 3.92 (s, 3H).

LCMS ($M^+$+1): 323.0

Example 103

N-(4-Fluorobenzyl)-6-oxo-2-phenyl-5,6-dihydro-1H-[1,2]diazepino[4,5,6-cd]indole-8-carboxamide

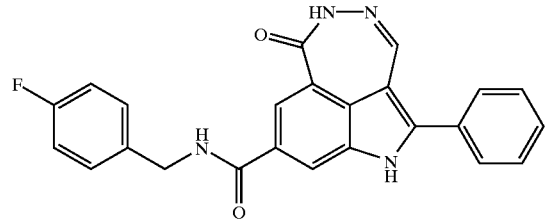

Preparation of example 103 from the title compound of Example 49 (0.108 g, 0.314 mmol), 4-fluorobenzylamine (0.079 g, 0.628 mmol), triethylamine (0.088 mL, 0.628 mmol), and O-(7-azabenzotriazol-1-yl)-N,N,N',N'-tetramethyluronium hexafluorophosphate (0.239 g, 0.628 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0121 g) as a yellow powder in 9.3% yield.

$^1$H NMR ($d_6$-DMSO): δ 12.47 (s, 1H), 10.47 (s, 1H), 9.23 (t, 1H, J=5.9 Hz), 8.13 (s, 1H), 8.05 (s, 1H), 7.71 (d, 2H, J=6.8 Hz), 7.51–7.63 (m, 4H), 7.35–7.40 (m, 2H), 7.12–7.18 (m, 2H), 4.46 (d, 2H, J=5.7 Hz).

HRMS calculated for $C_{24}H_{18}N_4O_2F$ 413.1414 (M+H), found 413.1394.

Example 104

6-Oxo-2-phenyl-N-(2,3,5-trifluorobenzyl)-5,6-dihydro-1H-[1,2]diazepino[4,5,6-cd]indole-8-carboxamide

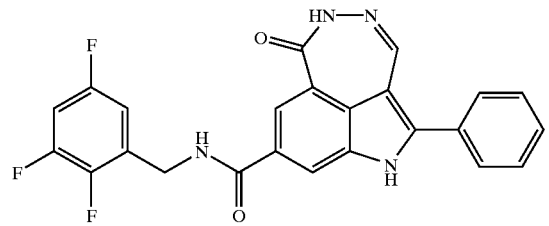

Preparation of example 104 from the title compound of Example 49 (0.101 g, 0.294 mmol), 2,3,5-trifluorobenzylamine (0.0947 g, 0.588 mmol), triethylamine (0.082 mL, 0.588 mmol), and O-(7-azabenzotriazol-1-yl)-N,N,N',N'-tetramethyluronium hexafluorophosphate (0.224 g, 0.588 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.006 g) as a yellow powder in 4.5% yield.

$^1$H NMR ($d_6$-DMSO): δ 12.50 (s, 1H), 10.49 (s, 1H), 9.27 (t, 1H, J=5.9 Hz), 8.13 (s, 1H), 8.05 (s, 1H), 7.71 (d, 2H, J=6.8 Hz), 7.52–7.62 (m, 4H), 7.40–7.48 (m, 1H), 7.05–7.08 (m, 1H), 4.56 (d, 2H, J=4.9 Hz).

HRMS calculated for $C_{24}H_{16}N_4O_2F_3$ 449.1225 (M+H), found 449.1209.

Example 105

N-[3,5-Bis(trifluoromethyl)benzyl]-6-oxo-2-phenyl-5,6-dihydro-1H-[1,2]diazepino[4,5,6-cd]indole-8-carboxamide

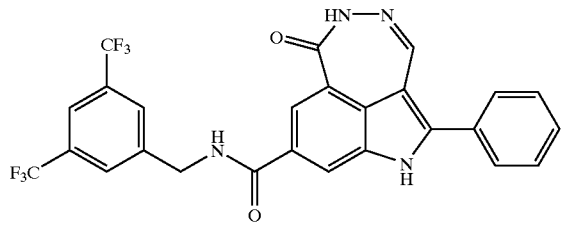

Preparation of example 105 from the title compound of Example 49 (0.101 g, 0.294 mmol), 3,5-bis(trifluoromethyl)benzylamine (0.143 g, 0.588 mmol), triethylamine (0.082 mL, 0.588 mmol), and O-(7-azabenzotriazol-1-yl)-N,N,N',N'-tetramethyluronium hexafluorophosphate (0.224 g, 0.588 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.004 g) as a yellow powder in 2.6% yield.

$^1$H NMR ($d_6$-DMSO): δ 12.50 (s, 1H), 10.50 (s, 1H), 9.37 (t, 1H, J=5.9 Hz), 8.14 (s, 1H), 8.05 (m, 3H), 8.00 (s, 1H), 7.71 (d, 2H, J=8.3 Hz), 7.52–7.62 (m, 4H), 4.67 (d, 2H, J=5.7 Hz).

HRMS calculated for $C_{26}H_{17}N_4O_2F_6$ 531.1256 (M+H), found 531.1272.

Example 106

N-[4-Fluoro-3-trifluoromethyl)benzyl]-oxo-2-phenyl-5,6-dihydro-1H-[1,2]diazepino[4,5,6-cd]indole-8-carboxamide

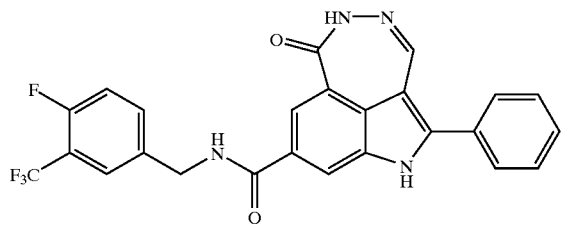

Preparation of example 106 from the title compound of Example 49 (0.105 g, 0.306 mmol), 4-fluoro-3-(trifluoromethyl)benzylamine (0.118 g, 0.612 mmol), triethylamine (0.085 mL, 0.612 mmol), and O-(7-azabenzotriazol-1-yl)-N,N,N',N'-tetramethyluronium hexafluorophosphate (0.233 g, 0.612 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0205 g) as a yellow powder in 14% yield.

$^1$H NMR ($d_6$-DMSO): δ 12.49 (s, 1H), 10.48 (s, 1H), 9.30 (t, 1H, J=5.9 Hz), 8.13 (s, 1H), 8.05 (m, 3H), 7.69–7.75 (m, 4H), 7.45–7.63 (m, 5H), 4.53 (d, 2H, J=5.7 Hz).

HRMS calculated for $C_{25}H_{17}N_4O_2F_4$ 481.1287 (M+H), found 481.1291.

Example 107

N-[(1-Hydroxy-5,7-dimethyl-1,2,3,4-tetrahydronaphthalen-1-yl)methyl]-6-oxo-2-phenyl-5,6-dihydro-1H-[1,2]diazepino[4,5,6-cd]indole-8-carboxamide

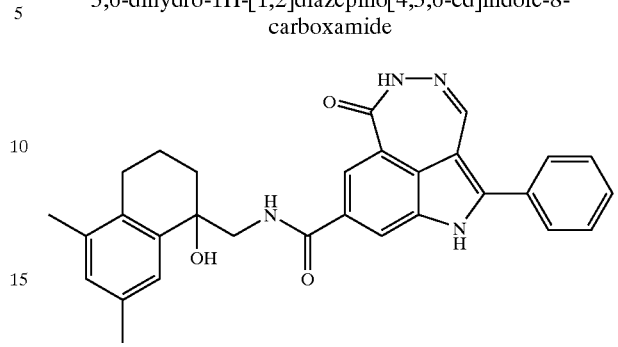

Preparation of example 107 from the title compound of Example 49 (0.104 g, 0.303 mmol), 1-(aminomethyl)-5,7-dimethyl-1,2,3,4-tetrahydronaphthalen-1-ol (0.124 g, 0.606 mmol), triethylamine (0.084 mL, 0.606 mmol), and O-(7-azabenzotriazol-1-yl)-N,N,N',N'-tetramethyluronium hexafluorophosphate (0.23 g, 0.606 mmol) in DMSO (2 mL) was carried out analogously to Example 76. Preparative HPLC (20–100% $CH_3CN/H_2O$ containing 0.1% trifluoroacetic acid) also in an analogous manner afforded the title compound (0.0145 g) as a yellow powder in 9.7% yield.

$^1$H NMR ($d_6$-DMSO): δ 12.47 (s, 1H), 10.48 (s, 1H), 8.48–8.52 (m, 1H), 8.10 (s, 1H), 8.03 (s, 1H), 7.70–7.73 (m, 2H), 7.52–7.62 (m, 4H), 7.25 (s, 1H), 6.86 (s, 1H), 3.66–3.73 (m, 2H), 2.55–2.63 (m, 2H), 2.22 (s, 3H), 2.14 (s, 3H), 1.81–1.98 (m, 4H).

HRMS calculated for $C_{30}H_{29}N_4O_3$ 493.2240 (M+H), found 493.2252.

Example 108

N-[(1R)-1-(1-Naphthyl)ethyl]-6-oxo-2-phenyl-5,6-dihydro-1H-[1,2]diazepino[4,5,6-cd]indole-8-carboxamide

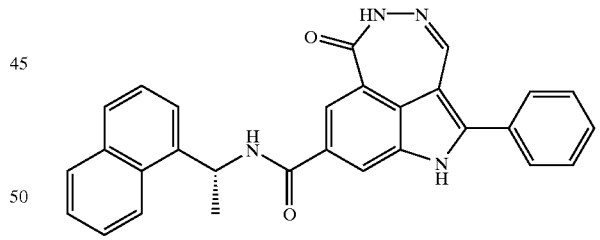

Preparation of example 108 from the title compound of Example 49 (0.105 g, 0.306 mmol), 1-(1-naphthyl)ethylamine (0.105 g, 0.612 mmol), triethylamine (0.085 mL, 0.612 mmol), and O-(7-azabenzotriazol-1-yl)-N,N,N',N'-tetramethyluronium hexafluorophosphate (0.233 g, 0.612 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0161 g) as a yellow powder in 12% yield.

$^1$H NMR ($d_6$-DMSO): δ 12.44 (s, 1H), 10.46 (s, 1H), 9.14 (d, 1H, J=7.9 Hz), 8.17 (s, 1H), 8.05 (s, 1H), 7.87–7.90 (m, 4H), 7.69–7.72 (m, 2H), 7.46–7.63 (m, 7H), 5.34–5.140 (m, 1H), 1.61 (d, 3H, J=6.8 Hz).

Example 109

Diethyl 2-{[(6-oxo-2-phenyl-5,6-dihydro-1H-[1,2]diazepino[4,5,6-cd]indol-8-yl)carbonyl]amino}malonate

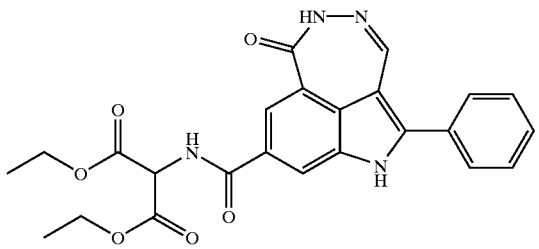

Preparation of example 109 from the title compound of Example 49 (0.106 g, 0.309 mmol), diethyl 2-aminomalonate hydrochloride (0.131 g, 0.618 mmol), triethylamine (0.129 mL, 0.926 mmol), and O-(7-azabenzotriazol-1-yl)-N,N,N',N'-tetramethyluronium hexafluorophosphate (0.235 g, 0.618 mmol) in DMSO (2 mL) was carried out analogously to Example 76. Preparative HPLC (20–100% $CH_3CN/H_2O$ containing 0.1% trifluoroacetic acid), also in an analogous manner, afforded the title compound (0.0064 g) as a yellow powder in 4.5% yield.

$^1$H NMR ($d_6$-DMSO): δ 12.53 (s, 1H), 10.50 (s, 1H), 9.55 (t, 1H, J=7.6 Hz), 8.14 (s, 1H), 8.07 (s, 1H), 7.71–7.73 (m, 2H), 7.52–7.62 (m, 4H), 5.29–5.32 (m. 2H), 4.15–4.25 (m, 4H), 1.23 (t, 6H, J=7.2 Hz).

HRMS calculated for $C_{24}H_{23}N_4O_6$ 463.1618 (M+H), found 463.1606.

Example 110

N-[(1R)-2-Hydroxy-1-phenylethyl]-6-oxo-2-phenyl-5,6-dihydro-1H-[1,2]diazepino[4,5,6-cd]indole-8-carboxamide

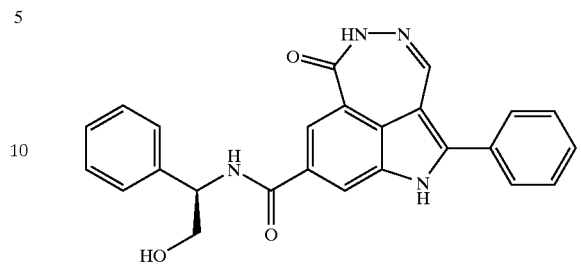

Preparation of example 110 from the title compound of Example 49 (0.17 g, 0.5 mmol), (2R)-2-amino-2-phenylethanol (0.0822 g, 0.6 mmol), triethylamine (0.14 mL, 1 mmol), and O-(7-azabenzotriazol-1-yl)-N,N,N',N'-tetramethyluronium hexafluorophosphate (0.23 g, 0.6 mmol) in DMSO (8 mL) was carried out analogously to Example 76. Preparative HPLC (20–100% $CH_3CN/H_2O$ containing 0.1% trifluoroacetic acid), also in an analogous manner, afforded the title compound (0.0351 g) in 17% yield.

$^1$H NMR ($d_6$-DMSO): δ 12.45 (s, 1H), 10.47 (s, 1H), 8.92 (d, 1H, J=7.9 Hz), 8.17 (s, 1H), 8.04 (s, 1H), 7.75–7.65 (m, 2H), 7.65–7.50 (m, 4H), 7.45–7.37 (m, 2H), 7.37–7.27 (m, 2H), 7.27–7.15 (m, 1H), 5.18–5.01 (m, 1H), 3.83–3.60 (m, 2H).

LCMS: (M+H$^+$) 425.1

Anal. Calcd. for $C_{25}H_{20}N_4O_3$.0.2 trifluoroacetic acid.1.68 $H_2O$: C, 63.88; H, 4.97; N, 11.73. Found: C, 63.86; H, 4.97; N, 11.66.

Example 111

(1R,2R)-2-Phenyl)-cyclopropanecarboxylic Acid [2-(3-cyclobutylaminomethyl-phenyl)-oxo-5,6-dihydro-1H-[1,2]diazepino[4,5,6-cd]indol-8-yl]-amide (Hydrochloric Salt)

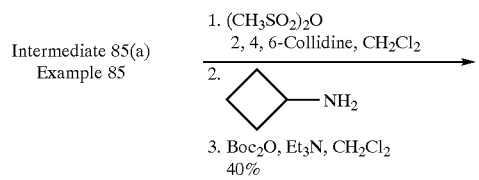

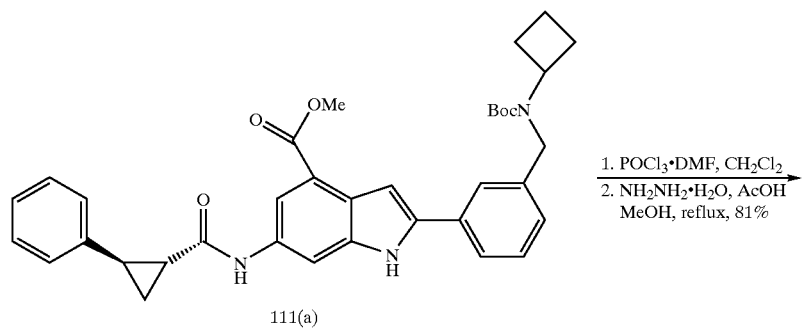

111(a)

-continued

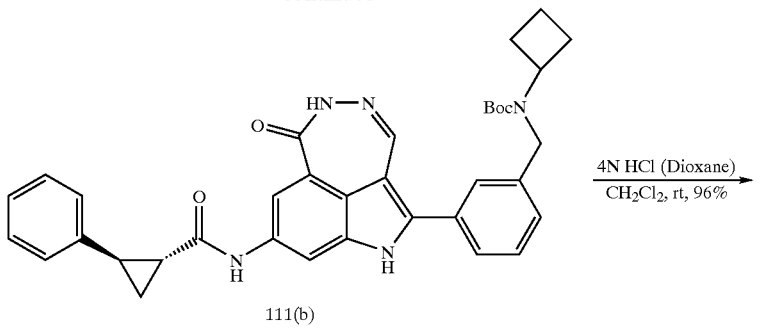

111(b)

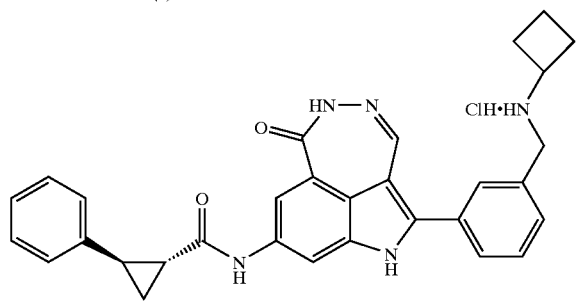

Step 1. Preparation of (1R,2R)-2-{3-[(tert-Butoxycarbonyl-cyclobutyl-amino)-methyl]-phenyl}-6-[(2-phenyl-cyclopropanecarbonyl)-amino]-1H-indole-4-carboxylic Acid Methyl Ester 111(a)

To a suspension of Intermediate 85(a) of Example 85 (0.260 g, 0.6 mmol) in dichloromethane (6.0 mL, 0.1 M) was added 2,4,6-Collidine (0.312 mL, 2.4 mmol) followed by $(CH_3SO_2)_2O$ (0.123 g, 0.7 mmol). After stirring for 1 hour, cyclobutylamine (0.252 mL, 3.0 mmol) was added, and the reaction mixture stirred for 24 hours at 22° C. The volatiles were removed in vacuo and dichloromethane (6.0 mL), triethylamine (3 mmol) and di-tert-butyl dicarbonate (1.2 mmol) were added. The mixture was stirred at 22° C. for 12 hours and volatiles were removed in vacuo. Silica gel chromatography provided Intermediate 111(a) (0.14 g, 0.24 mmol) in 40% yield.

$^1$H-NMR (d$_6$-DMSO): δ 11.82 (s, 1H), 10.42 (s, 1H), 8.27 (s, 1H), 7.89 (d, 1H, J=1.6 Hz), 7.72 (d, 1H, J=8.1 Hz), 7.67 (s, 1H), 7.44 (dd, 1H, J=7.7, 7.6 Hz), 7.36–7.08 (m, 7H), 4.51 (s, 2H), 3.91 (s, 3H), 2.45–2.37 (m, 1H), 2.14–1.95 (m, 5H), 1.62–1.22 (m, 14H).

Step 2. Preparation of (1 R,2R)-Cyclobutyl-(3-{6-oxo-8-[(2-phenyl-cyclopropanecarbonyl)-amino]-5,6-dihydro-1H-[1,2]diazepino[4,5,6-cd]indol-2-yl}-benzyl)-carbamic Acid tert-butyl Ester 111(b)

In a manner analogous to steps 4 and 5 of Example 3, Intermediate 111(a) (0.13 g, 0.22 mmol) was formylated and cyclized. After silica gel chromatography, Intermediate 111 (b) (0.107 g, 0.18 mmol) was obtained as a yellow powder in 81% yield.

$^1$H-NMR (d$_6$-DMSO): δ 12.09 (s, 1H), 10.43 (s, 1H), 10.37 (s, 1H), 8.16 (d, 1H, J=1.2 Hz), 7.63 (d, 1H, J=1.4 Hz), 7.55–7.42 (m, 4H), 7.35–7.16 (m, 6H), 4.53 (s, 2H), 2.45–2.37 (m, 1H), 2.14–1.95 (m, 5H), 1.60–1.23 (m, 14H).

LCMS: (M–H$^+$) 602.2.

Step 3. Preparation of Title Compound: (1R,2R)-2-Phenyl-cyclopropanecarboxylic Acid [2-(3-cyclobutylaminomethyl-phenyl)-6-oxo-5,6-dihydro-1H-[1,2]diazepino[4,5,6-cd]indol-8-yl]-amide (Hydrochloric Salt)

Preparation from Intermediate 111(b) (0.105 g, 0.17 mmol) and 4M HCl in dioxane (1.7 mL) was carried out analogously to Example 91. Isolation, also in an analogous manner, included a further trituration with $CH_2Cl_2$/diethyl ether and afforded the title compound (0.09 g, 0.17 mmol) as an orange/yellow powder in 96% yield.

$^1$H-NMR (d$_6$-DMSO): δ 12.20 (s, 1H), 10.49 (s, 1H), 10.43 (s, 1H), 9.32 (b, 1H), 8.18 (d, 1H, J=1.4 Hz), 7.83 (s, 1H), 7.75–7.58 (m, 5H), 7.35–7.15 (m, 5H), 4.13 (s, 2H), 3.80–3.50 (buried m, 1H), 2.45–2.35 (m, 1H), 2.28–2.08 (m, 5H), 1.88–1.75 (m, 2H), 1.55–1.47 (m, 1H), 1.42–1.34 (m, 1H).

LCMS: (M+H$^+$) 504.2.

HRMS: (M+H$^+$) calcd for $C_{31}H_{30}N_5O_2$, 504.2400, found 504.2378.

Example 112

(1R,2R)-2-Phenyl-cyclopropanecarboxylic Acid [6-oxo-2-(3-pyrrolidin-1-ylmethyl-phenyl)-5,6-dihydro-1H-[1,2]diazepino[4,5,6-cd]indol-8-yl]-amide (Hydrochloric Salt)

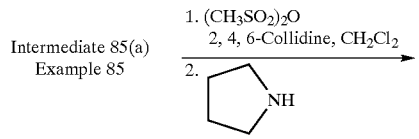

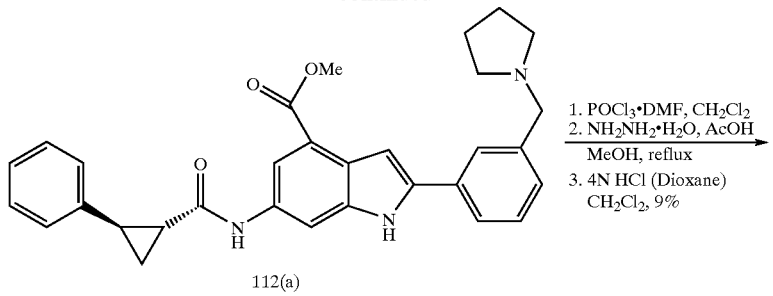

112(a)

1. POCl₃•DMF, CH₂Cl₂
2. NH₂NH₂•H₂O, AcOH
   MeOH, reflux
3. 4N HCl (Dioxane)
   CH₂Cl₂, 9%

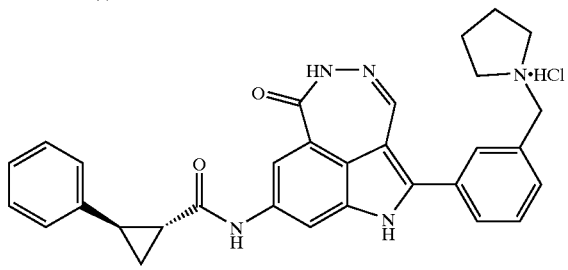

Step 1. Preparation of (1R,2R) 6-[(2-Phenyl-cyclopropanecarbonyl)-amino]-2-(3-pyrrolldin-1-ylmethyl-phenyl)-1H-indole-4-carboxylic Acid Methyl Ester 112(a)

To a suspension of Intermediate 85(a) of Example 85 (0.260 g, 0.6 mmol) in dichloromethane (6.0 mL, 0.1 M) was added 2,4,6-Collidine (0.312 mL, 2.4 mmol) followed by $(CH_3SO_2)_2O$ (0.123 g, 0.7 mmol). After stirring for 1 hour, pyrrolidine (0.252 mL, 3.0 mmol) was added and the reaction mixture stirred for 24 hours at 22° C. Volatiles were removed in vacuo, and the crude Intermediate 112(a) was carried on directly to the next step.

Step 2. Preparation of Title Compound: (1R,2R)-2-Phenyl-cyclopropanecarboxylic Acid [6-oxo-2-(3-pyrrolidin-1-ylmethyl-phenyl)-5,6-dihydro-1H-[1,2]diazepino[4,5,6-cd]indol-8-yl]-amide (Hydrochloric Salt)

In a manner analogous to steps 4 and 5 of Example 3, Intermediate 112(a) (0.42 g, 0.85 mmol) was formylated and cyclized. Silica gel chromatography (90:10:0 to 70:20:10 $CH_2Cl_2$/2.0 M ammonia in isopropyl alcohol/methyl alcohol) and conversion to the HCl salt (4M HCl in dioxane) afforded the title compound (0.04 g, 0.18 mmol) as a yellow-orange powder in 9% yield.

$^1$H-NMR (d$_6$-DMSO): δ 12.20 (s, 1H), 10.55 (s, 1H), 10.49 (s, 1H), 10.43 (b, 1H), 8.19 (d, 1H, J=1.3 Hz), 8.13 (s, 1H), 7.76–7.62 (m, 5H), 7.34–7.16 (m, 5H), 4.45 (d, 2H, J=5.5 Hz), 3.45–3.35 (m, 2H), 3.19–3.07 (m, 2H), 2.45–2.35 (m, 1H), 2.14–1.85 (m, 5H), 1.55–1.47 (m, 1H), 1.42–1.34 (m, 1H).

LCMS: (M+H⁺) 504.2.

HRMS: (M+H⁺) calcd for $C_{31}H_{30}N_5O_2$, 504.2400, found 504.2404.

Example 113

N-(6-Oxo-2-phenyl-5,6-dihydro-1H-[1,2]diazepino[4,5,6-cd]indol-8-yl)-(1,2-trans)-2-[6-(trifluoromethyl)pyridin-3-yl]cyclopropanecarboxamide Trifluoroacetate

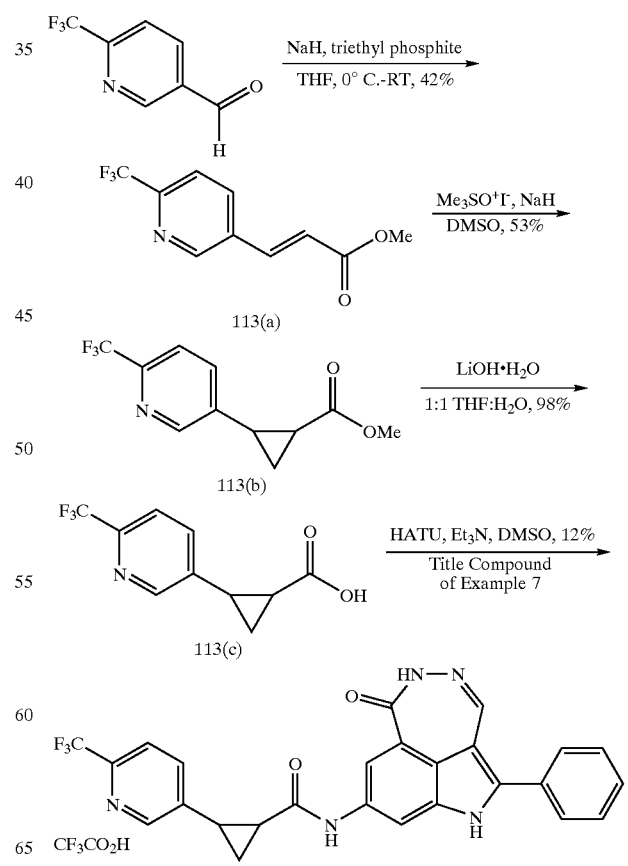

Step 1. Preparation of 3-(6-Trifluoromethyl-pyridin-3-yl)-acrylic Acid Methyl Ester 113(a)

To a solution of triethyl phosphite in anhydrous tetrahydrofuran (25 mL) cooled to 0° C. was added a 60% suspension of sodium hydride in mineral oil (472 mg, 19.7 mmol) in small portions. This mixture was allowed to stir for 30 min at the same low temperature at which point the cooling bath was removed, and the mixture was allowed to warm to room temperature over 60 min. The mixture was cooled again to 0° C. and a solution of 6-trifluoromethyl-3-pyridine carboxaldehyde in anhydrous tetrahydrofuran (20 mL) was added dropwise. The reaction mixture was allowed to warm slowly to room temperature overnight. After 19 hours, the reaction mixture was quenched with water (100 mL) and extracted with ethyl acetate (3×50 mL). The combined organic fractions were dried over anhydrous magnesium sulfate and concentrated to a pale green oil. Purification was carried out using flash silica gel chromatography eluting with 5:95 then 1:9 ethyl acetate:hexane. Pure fractions were combined and concentrated to afford Intermediate 113(a) (1.68 g, 6.85 mmol) as a white solid in 42% yield.

Step 2. Preparation of (1,2-trans)-2-(6-Trifluoromethyl-pyridin-3-yl)-cyclopropanecarboxylic Acid 113(b)

Trimethylsulfoxonium iodide (574 mg, 2.61 mmol) was added to 60% NaH in mineral oil (63 mg, 2.61 mmol), and the flask was purged with nitrogen. Methyl sulfoxide (10 mL) was added slowly over 20 minutes until evolution of hydrogen ceased. To this milky solution was added Intermediate 113(a) (493 mg, 2.01 mmol) in methyl sulfoxide (15 mL) dropwise. The solution was allowed to stir at room temperature overnight. After 26 hours the excess NaH was carefully quenched with water (100 mL). Ethyl ether (100 mL) was added and the layers separated. The aqueous layer was extracted with fresh ethyl ether (3×50 mL). The combined ethereal layers were washed with brine, dried over anhydrous magnesium sulfate and concentrated in vacuo. Flash silica gel chromatography of the crude residue eluting with 1:9 then 1:4 ethyl acetate:hexane gave two pure fractions that upon combining and concentrating under reduced pressure yielded Intermediate 113(b) (275 mg, 1.06 mmol) as white feathers in 53% yield.

Step 3. Preparation of (1,2-trans)-2-[6-(Trifluoromethyl)pyridin-3-yl]cyclopropanecarboxylic Acid 113(c)

To a solution of Intermediate 113(b) (275 mg, 1.06 mmol) in a 1:1 mixture of tetrahydrofuran:water (4 mL) was added lithium hydroxide monohydrate (133 mg, 3.18 mmol). The semi-suspension was allowed to stir at room temperature over 2 days. The reaction mixture was acidified with 2M aqueous hydrochloric acid (c.a. 2 mL). The reaction mixture was then concentrated and lyophilized to obtain Intermediate 113(c) as a white powder containing lithium chloride which was carried on directly without further purification.

Step 4. Preparation of Title Compound: N-(6-Oxo-2-phenyl-5,6-dihydro-1H-[1,2]diazepino[4,5,6-cd]indol-8-yl)-2-[6-trifluoromethyl)pyridin-3-yl]cyclopropanecarboxamide Trifluoroacetate To a solution of Intermediate 113(c) (85 mg, 0.368 mmol) in methyl sulfoxide (2 mL) was added triethylamine (0.056 mL, 0.405 mmol) and O-(7-azabenzotriazol-1-yl)-N,N,N',N'-tetramethyluronium hexafluorophosphate (154 mg, 0.405 mmol). After c.a. 10 min, the title compound of Example 7 (0.102 g, 0.368 mmol) was added. The reaction was capped and stirred overnight at room temperature. The mixture was subjected to preparative HPLC (20–100% acetonitrile/water containing 0.1% trifluoroacetic acid). The pure fractions were combined and lyophilized to afford the title compound (27 mg, 0.045 mmol) as an orange powder in 12% yield.

¹H-NMR (d₆-DMSO): δ 12.11 (b, 1H), 10.50 (b, 1H), 10.39 (b, 1H), 8.71 (b, 1H), 8.15 (b, 2H), 7.90–7.80 (m, 2H), 7.70–7.45 (m, 6H), 2.65–2.55 (m, 1H), 2.27–2.18 (m, 1H), 1.67–1.51 (m, 2H).

LCMS: (M+H⁺) 490.1.

Example 114

(2R)-2-Amino-N-(6-oxo-2-phenyl-5,6-dihydro-1H-[1,2]diazepino[4,5,6-cd]indol-yl)-2-phenyl-acetamide (Hydrochloric Salt)

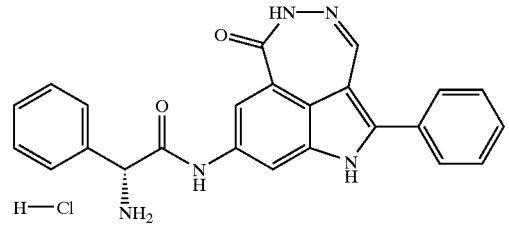

Preparation of example 114 from the impure title compound of Example 117 (90 mg, 0.18 mmol) and 4M HCl in dioxane (10 mL) was carried out analogously to Example 91. Isolation, also in an analogous manner, afforded the title compound (65 mg, 0.10 mmol) as a yellow powder in 71% yield over two steps (including Example 117).

¹H NMR (d₆-DMSO): δ 12.26 (s, 1H, exchanges), 11.08 (s, 1H, exchanges), 10.42 (s, 1H, exchanges), 8.86 (br s, 3H, exchanges), 8.07 (s, 1H), 7.72–7.63 (m, 5H), 7.62–7.41 (m, 7H), 5.22 (m, 1H).

LCMS: (M+H⁺) 410.1, (M+Na⁺) 432.0.

Anal. Calcd. for $C_{24}H_{19}N_5O_2 \cdot 5.6 \cdot HCl \cdot 0.2$ diethyl ether: C, 47.40; H, 4.27; N, 11.14.

Found: C, 47.64; H, 4.21; N, 10.91.

Example 115

(2R)-2-Amino-N-(6-oxo-2-phenyl-5,6-dihydro-1H-[1,2]diazepino[4,5,6-cd]indol-8-yl)-3-phenyl-propionamide (Hydrochloric Salt)

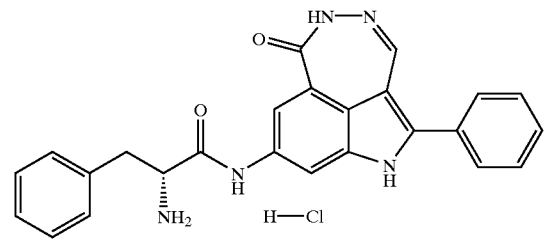

Preparation of example 115 from the title compound of Example 118 (71 mg, 0.136 mmol) and 4M HCl in dioxane (20 mL) was carried out analogously to Example 91. Isolation, also in an analogous manner, afforded the title compound (66 mg, 0.12 mmol) as a yellow powder in 87% yield over two steps (from Example 118).

¹H NMR (d₆-DMSO): δ 12.20 (s, 1H, exchanges), 10.66 (s, 1H, exchanges), 10.44 (s, 1H, exchanges), 8.39 (br s, 3H, exchanges), 8.05 (s, 1H), 7.73–7.46 (m, 7H), 7.39–7.22 (m, 5H), 4.19 (m, 1H), 3.21–3.06 (m, 2H, partially obscured).

LCMS: (M+H⁺) 424.1.

Anal. Calcd. for $C_{25}H_{21}N_5O_2 \cdot 2.8$ HCl·0.1 diethyl ether·0.2 dioxane: C, 57.15; H, 4.83; N, 12.72.

Found: C, 57.33; H, 5.01; N, 12.56.

Example 116

1-Amino-cyclohexanecarboxylic Acid (6-oxo-2-phenyl-5,6-dihydro-1H-[1,2]diazepino[4,5,6-cd]indol-8-yl)-amide (Hydrochloric Salt)

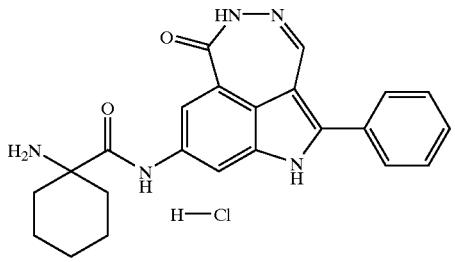

Preparation of example 116 from the title compound of Example 119 (311 mg, 0.062 mmol) and 4M HCl in dioxane (5 mL) was carried out analogously to Example 91. Isolation, also in an analogous manner, included a further trituration with CH$_2$Cl$_2$/hexane and afforded the title compound (29 mg, 0.053 mmol) as an orange/yellow powder in 85% yield.

$^1$H NMR (d$_6$-DMSO): δ 12.29 (s, 1H, exchanges), 10.44 (s, 1H, exchanges), 10.28 (s, 1H, exchanges), 8.36 (br s, 3H, exchanges), 8.11 (s, 1H), 7.81 (s, 1H), 7.74–7.46 (m, 6H), 2.37–2.14 (m, 2H), 1.96–1.35 (m, 8H).

LCMS: (M+H$^+$) 402.2, (M+Na$^+$) 424.1.

Anal. Calcd. for C$_{23}$H$_{23}$N$_5$O$_2$.3.1 HCl.0.1 diethyl ether.0.3 dioxane: C, 53.88; H, 5.42; N, 12.77.

Found: C, 53.86; H, 5.60; N, 12.70.

Example 117

[(R)-(6-Oxo-2-phenyl-5,6-dihydro-1H-[1,2]diazepino[4,5,6-cd]indol-8-ylcarbamoyl)-phenyl-methyl]-carbamic Acid tert-butyl Ester

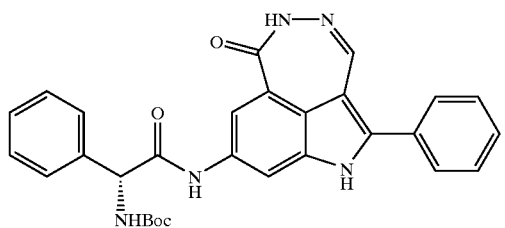

Preparation of example 117 from the the title compound of Example 7 (hydrochloride) (44 mg, 0.141 mmol), (R)-tert-butoxycarbonylamino-phenyl-acetic acid (42 mg, 0.169 mmol), triethylamine (0.059 mL, 0.423 mmol), and O-(7-azabenzotriazol-1-yl)-N,N,N',N'-tetramethyluronium hexafluorophosphate (64 mg, 0.169 mmol) in CH$_2$Cl$_2$ (0.4 mL) and N,N-dimethylformamide (0.4 mL) was carried out analogously to Example 11. Silica gel chromatography (eluted with 1:1 hexane:acetone), also in an analogous manner, afforded the title compound (102 mg) as a yellow powder contaminated with an unknown impurity. The compound was an intermediate and carried on without further purification to Example 91.

$^1$H NMR (d$_6$-DMSO): δ 12.12 (s, 1H), 10.41 (s, 2H), 8.12 (s, 1H), 7.69–7.48 (m, 10H), 7.42–7.27 (m, 3H), 5.36 (d, 1H, J=8.67 Hz), 1.41 (s, 9H).

LCMS: (M−H$^−$) 508.1, (M+H$^+$) 510.2, (M+Na$^+$) 532.2.

Example 118

[(R)-1-(6-Oxo-2-phenyl-5,6-dihydro-1H-[1,2]diazepino[4,5,6-cd]indol-8-ylcarbamoyl)-2-phenyl-ethyl]-carbamic Acid tert-butyl Ester

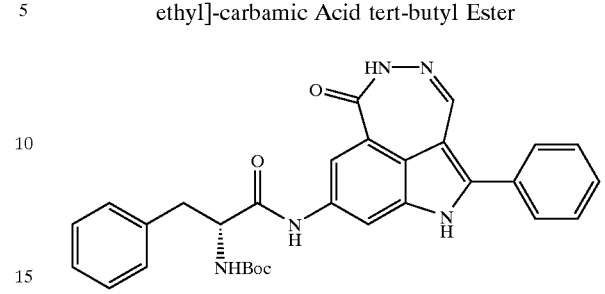

Preparation of example 118 from the title compound of Example 7 (hydrochloride) (43 mg, 0.138 mmol), (R)-tert-butoxycarbonylamino-3-phenyl-propionic acid (44 mg, 0.166 mmol), triethylamine (0.058 mL, 0.414 mmol), and O-(7-azabenzotriazol-1-yl)-N,N,N',N'-tetramethyluronium hexafluorophosphate (63 mg, 0.166 mmol) in CH$_2$Cl$_2$ (0.4 mL) and N,N-dimethylformamide (0.4 mL) was carried out analogously to Example 11. Silica gel chromatography (eluted with 1:1 hexane:acetone), also in an analogous manner, afforded the title compound (80 mg) as a yellow powder contaminated with an unknown impurity. The compound was carried on without further purification to Example 115.

$^1$H NMR (d$_6$-DMSO): δ 12.12 (1H), 10.41 (s, 1H), 10.25 (s, 1H), 8.18 (s, 1H), 7.71–7.48 (m, 7H), 7.38–7.11 (m, 6H), 4.34 (br s, 1H), 3.02 (m, 1H), 2.87 (m, 1H, partially obscured by N,N-dimethylformamide singlet), 1.34 (s, 9H).

LCMS: (M+H$^+$) 524.2, (M+Na$^+$) 546.2.

Example 119

[1-(6-Oxo-2-phenyl-5,6-dihydro-1H-[1,2]diazepino[4,5,6-cd]indol-8-ylcarbamoyl)-cyclohexyl]-carbamic Acid tert-butyl Ester

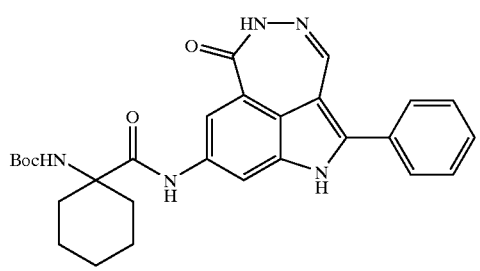

Preparation of example 119 from the title compound of Example 7 (hydrochloride) (45 mg, 0.142 mmol), 1-tert-butoxycarbonylamino-cyclohexanecarboxylic acid (42 mg, 0.171 mmol), triethylamine (0.059 mL, 0.426 mmol), and O-(7-azabenzotriazol-1-yl)-N,N,N',N'-tetramethyluronium hexafluorophosphate (65 mg, 0.171 mmol) in CH$_2$Cl$_2$ (0.4 mL) and N,N-dimethylformamide (0.4 mL) was carried out analogously to Example 11. Silica gel chromatography (eluted with 1:1 hexane:acetone), also in an analogous manner, afforded the title compound (38 mg, 0.076 mmol) as a yellow powder in 53% yield.

¹H NMR (d₆-DMSO): δ 12.08 (s, 1H), 10.37 (s, 1H), 9.59 (s, 1H), 8.14 (s, 1H), 7.70–7.48 (m, 8H), 2.03–1.92 (m, 2H), 1.81–1.71 (m, 2H), 1.47 (m, 5H), 1.40–1.31 (m, 10H).

LCMS: (M+H⁺) 502.1, (M+Na⁺) 524.1.

Example 120

(3E)-4-Phenyl-but-3-enoic Acid (6-oxo-2-phenyl-5,6-dihydro-1H-[1,2]diazepino[4,5,6-cd]indol-8-yl)-amide

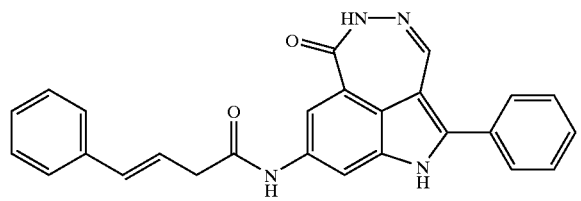

Preparation of example 120 from the title compound of Example 7 (hydrochloride) (44 mg, 0.141 mmol), (E)-4-phenyl-but-3-enoic acid (27 mg, 0.169 mmol), triethylamine (0.059 mL, 0.423 mmol), and O-(7-azabenzotriazol-1-yl)-N,N,N',N'-tetramethyluronium hexafluorophosphate (64 mg, 0.169 mmol) in CH₂Cl₂ (0.4 mL) and N,N-dimethylformamide (0.4 mL) was carried out analogously to Example 11. When the reaction was judged complete, the mixture was filtered to collect the solids which were then washed with methanol. After drying under vacuum, the title compound (41 mg, 0.0.095 mmol) was obtained as a yellow powder in 68% yield.

¹H NMR (d₆-DMSO): δ 12.10, (s, 1H, exchanges), 10.38 (s, 1H, exchanges), 10.22 (s, 1H, exchanges), 8.21 (s, 1H), 7.77–7.63 (m, 3H), 7.60–7.53 (m, 2H), 7.53–7.42 (m, 4H), 7.38–7.30 (m, 2H), 7.24 (m, 1H), 6.57 (d, 1H, J=16.01 Hz), 6.45 (m, 1H).

¹H NMR (d₆-DMSO/DCl): δ 8.20 (s, 1H), 7.75 (s, 1H), 7.71–7.65 (m, 2H), 7.60–7.47 (m, 4H), 7.43–7.37 (m, 2H), 7.38–7.29 (m, 2H), 7.22 (m, 1H), 6.55 (d, 1H, J=16.23 Hz), 6.44 (m, 1H), 3.33 (d, 2H, J=9.09 Hz).

LCMS: (M+H⁺) 421.1, (M+Na⁺) 443.1.

Anal. Calcd. for $C_{26}H_{20}N_4O_2 \cdot 0.1\ H_2O \cdot 0.1$ N,N-dimethylformamide: C, 73.53; H, 4.90; N, 13.37.

Found: C, 73.26; H, 4.50; N, 13.61.

Example 121

2-Indan-2-yl-N-(6-oxo-2-phenyl-5,6-dihydro-1H-[1,2]diazepino[4,5,6-cd]indol-8-yl)-acetamide

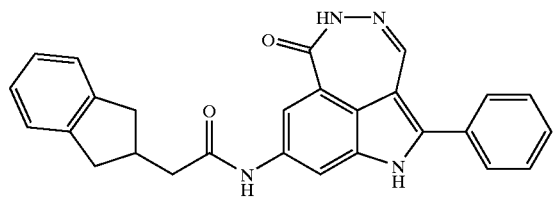

Preparation of example 121 from the title compound of Example 7 (hydrochloride) (41 mg, 0.131 mmol), indan-2-yl-acetic acid (28 mg, 0.157 mmol), triethylamine (0.055 mL, 0.393 mmol), and O-(7-azabenzotriazol-1-yl)-N,N,N',N'-tetramethyluronium hexafluorophosphate (60 mg, 0.157 mmol) in CH₂Cl₂ (0.4 mL) and N,N-dimethylformamide (0.4 mL) was carried out analogously to Example 11. When the reaction was judged complete, the mixture was filtered to collect the solids, which were then washed with methanol. After drying under vacuum, the title compound (45 mg, 0.101 mmol) was obtained as a yellow powder in 77% yield.

¹H NMR (d₆-DMSO): δ 12.08, (s, 1H, exchanges), 10.37 (s, 1H, exchanges), 10.11 (s, 1H, exchanges), 8.20 (s, 1H), 7.70–7.45 (m, 7H), 7.26–7.18 (m, 2H), 7.16–7.08 (m, 2H), 3.07 (dd, 2H, J=7.72, 15.83 Hz), 2.87 (m, 1H), 2.65 (dd, 2H, J=6.59, 15.26 Hz).

LCMS: (M+H⁺) 435.2, (M+Na⁺) 457.1.

Anal. Calcd. for $C_{27}H_{22}N_4O_2 \cdot 0.5\ H_2O$: C, 73.12; H, 5.23; N, 12.63.

Found: C, 72.84; H, 4.99; N, 12.99.

Example 122

N-(6-Oxo-2-phenyl-5,6-dihydro-1H-[1,2]diazepino[4,5,6-cd]indol-8-yl)-2-(toluene-4-sulfonylamino)-benzamide

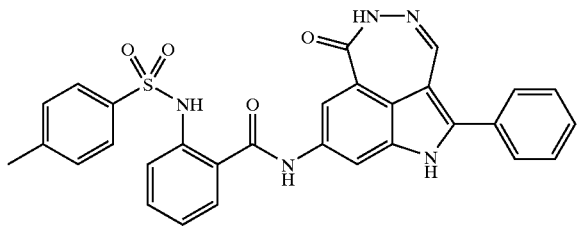

Preparation of example 122 from the title compound of Example 7 (100 mg, 0.362 mmol), 2-(toluene-4-sulfonylamino)-benzoic acid (158 mg, 0.542 mmol), triethylamine (0.201 mL, 1.446 mmol), and O-(7-azabenzotriazol-1-yl)-N,N,N',N'-tetramethyluronium hexafluorophosphate (206 mg, 0.542 mmol) in N,N-dimethylformamide (4.0 mL) was carried out analogously to Example 11. When the reaction was judged complete, N,N-dimethylformamide was evaporated and methanol was added. The mixture was filtered and the solids collected and washed with methanol, dichloromethane and diethyl ether. After drying under vacuum, the title compound (121 mg, 0.220 mmol) was obtained as a yellow powder in 61% yield.

¹H NMR (d₆-DMSO): δ 12.19 (s, 1H), 10.63 (s, 1H), 10.45 (s, 1H), 10.42 (s, 1H), 8.12 (s, 1H), 7.85–7.78 (m, 2H), 7.74–7.67 (m, 2H), 7.64–7.56 (m, 4H), 7.56–7.42 (m, 4H), 7.29–7.20 (m, 3H), 2.27 (s, 3H).

LCMS: (M+H⁺) 550.1; (M–H)⁻ 548.2.

HRMS: (M+H⁺) calcd for $C_{30}H_{24}N_5O_4S$, 550.1549, found 550.1551.

Anal. Calcd. for $C_{30}H_{23}N_5O_4S$, 0.5 H₂O: C, 64.50; H, 4.33; N, 12.54.

Found: C, 64.51; H, 4.20; N, 12.71.

Example 123

6-Oxo-2-phenyl-5,6-dihydro-1H-[1,2]diazepino[4,5,6-cd]indole-8-carboxylic Acid phenethyl-amide

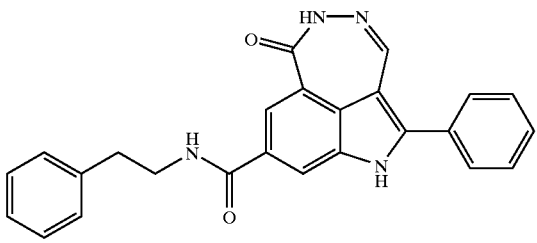

Preparation of example 123 from the title compound of Example 49 (0.17 g, 0.5 mmol), phenethylamine (73 mg, 0.6 mmol), triethylamine (100 mg, 1.0 mmol), and O-(7-azabenzotriazol-1-yl)-N,N,N',N'-tetramethyluronium hexafluorophosphate (0.23 g, 0.6 mmol) in DMSO (8 mL) was carried out analogously to the preparation of Example 76. Preparative HPLC (20–100% $CH_3CN/H_2O$ containing 0.1% trifluoroacetic acid, also in an analogous manner, afforded the title compound (0.021 g) as a yellow powder in 9% yield.

$^1$H NMR ($d_6$-DMSO): δ 12.49 (s, 1H), 10.49 (s, 1H), 8.77 (t, 1H, H=5.5 Hz), 8.07 (s, 1H), 8.00 (s, 1H), 7.10–7.80 (m, 11H), 3.48 (m, 2H), 2.86 (t, 2H, J=7.5 Hz).

LCMS ($M^+$+1): 409.1

Example 124

(1,2-trans)-2-(4-Fluoro-phenyl)-cyclopropanecarboxylic Acid (6-oxo-2-phenyl-5,6-dihydro-1H-[1,2]diazepino[4,5,6-cd]indol-8-yl)-amide

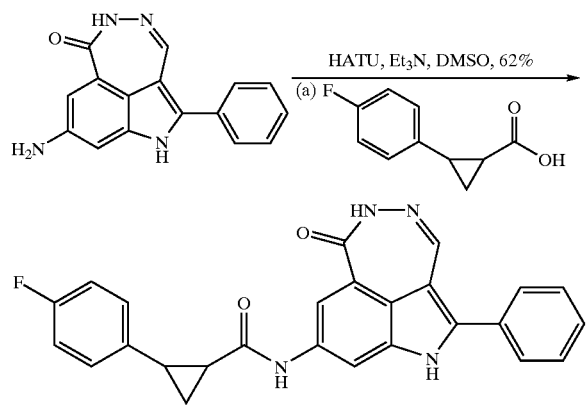

Preparation of example 124 was carried out analogously to the preparation of Example 113 except that (1,2-trans)-2-(4'-fluorophenyl)-cyclopropanecarboxylic acid was used instead of (1,2-trans)-2-(6-trifluoromethyl-pyridin-3-yl)-cyclopropanecarboxylic acid in step 4. (1,2-trans)-2-(4'-Fluorophenyl)-cyclopropanecarboxylic acid was prepared using procedures similar to those described in steps 1–3 of Example 113 except that 4-fluoro-benzaldehyde was used instead of 6-trifluoromethyl-3-pyridine carboxaldehyde. Final HPLC purification, also analogous to Example 113, afforded the title compound (100 mg, 0.228 mmol) as a yellow powder in 62% yield.

$^1$H-NMR ($d_6$-DMSO): δ 12.12 (b, 1H), 10.46 (b, 1H), 10.41 (b, 1H), 8.18 (b, 1H), 7.70–7.45 (m, 7H), 7.30–7.10 (m, 4H), 2.65–2.55 (m, 1H), 2.27–2.18 (m, 1H), 1.67–1.51 (m, 2H).

HRMS: $C_{21}H_{21}N_5O_2$.H: 439.1570. Found: 439.1584.

Example 125

(1,2-trans)-2-Pyridin-3-yl-cyclopropanecarboxylic Acid (6-oxo-2-phenyl-5,6-dihydro-1H-[1,2]diazepino[4,5,6-cd]indol-8-yl)-amide (Hydrochloric Salt)

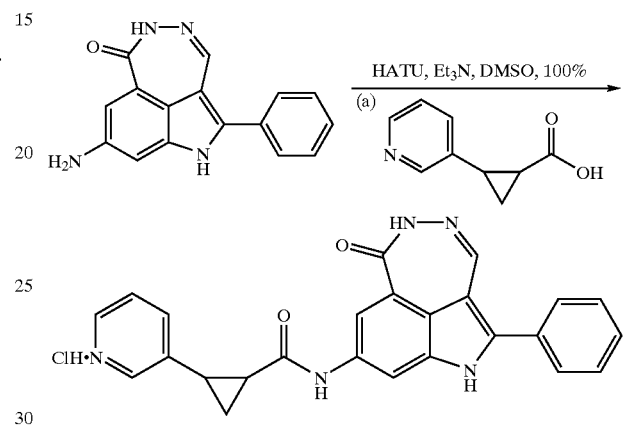

Preparation of example 125 was carried out analogously to the preparation of Example 113 except that (1,2-trans)-2-pyridin-3'-yl-cyclopropanecarboxylic acid was used instead of (1,2-trans)-2-(6-trifluoromethyl-pyridin-3-yl)-cyclopropanecarboxylic acid in step 4. (1,2-trans)-2-Pyridin-3'-yl-cyclopropanecarboxylic acid was prepared using procedures similar to those described in steps 1–3 of Example 113 except that pyridine-3-carbaldehyde was used instead of 6-trifluoromethyl-3-pyridine carboxaldehyde. Final HPLC purification, also analogous to Example 113, afforded the title compound (230 mg, 0.381 mmol) as an orange fluffy solid in quantitative yield.

$^1$H-NMR ($d_6$-DMSO): δ 12.15 (s, 1H), 10.58 (s, 1H), 10.38 (s, 1H), 8.81 (s, 1H), 8.15 (b, 2H), 7.82–7.45 (m, 9H), 2.35–2.25 (m, 1H), 1.70–1.51 (m, 1H), 1.35–1.10 (m, 1H), 0.90–0.65 (m, 1H).

LCMS: ($M+H^+$) 422.1.

Example 126

(1,2-trans)-2-(3-Methoxy-phenyl)-cyclopropanecarboxylic Acid (6-oxo-2-phenyl-5,6-dihydro-1H-[1,2]diazepino[4,5,6-cd]indol-8-yl)-amide

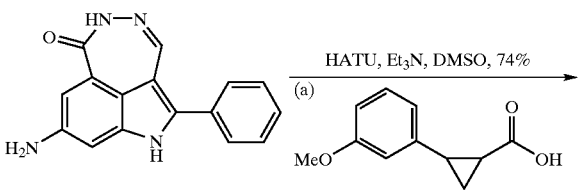

-continued

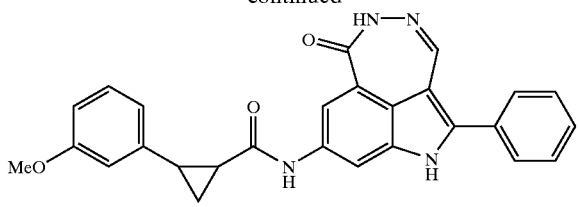

Preparation of example 126 was carried out analogously to the preparation of Example 113 except that (1,2-trans)-2-(3'-methoxyphenyl)-cyclopropanecarboxylic acid was used instead of (1,2-trans)-2-(6-trifluoromethyl-pyridin-3-yl)-cyclopropanecarboxylic acid in step 4. (1,2-trans)-2-(3'-Methoxyphenyl)-cyclopropanecarboxylic acid was prepared using procedures similar to those described in steps 1–3 of Example 113 except that 3-methoxy-benzaldehyde was used instead of 6-trifluoromethyl-3-pyridine carboxaldehyde. Final HPLC purification, also analogous to Example 113, afforded the title compound (132 mg, 0.293 mmol) as a pale orange solid in 74% yield.

$^1$H-NMR (d$_6$-DMSO): δ 12.09 (s, 1H), 10.43 (s, 1H), 10.38 (s, 1H), 8.15 (s, 1H), 7.70–7.40 (m, 7H), 7.25–7.15 (m, 1H), 6.77 (b, 3H), 3.74 (s, 3H), 2.40–2.30 (m, 1H). 2.12–2.05 (m, 1H), 1.55–1.47 (m, 1H), 1.42–1.33 (m, 1H).

LCMS: (M+H$^+$) 451.1.

Example 127

(R)-2-Amino-2-cyclohexyl-(6-oxo-5,6-dihydro-1-[1,2]diazepino[4,5,6-cd]indol-8-yl)-acetamide (Hydrochloric Salt)

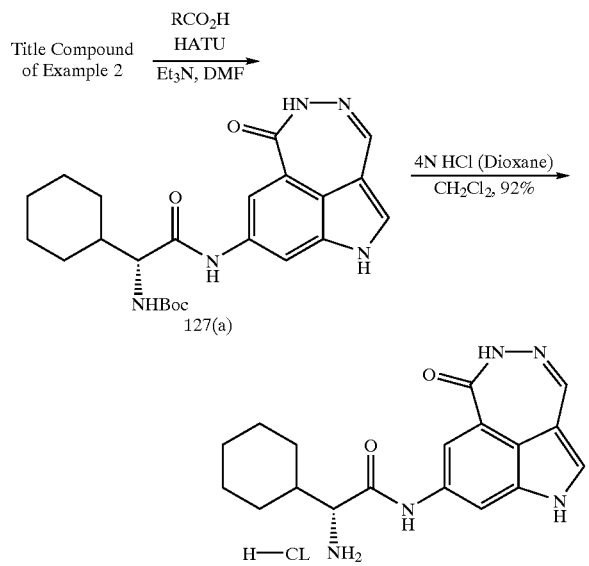

Step 1. Preparation of [(R)-Cyclohexyl-(6-oxo-5,6-dihydro-1H-[1,2]diazepino[4,5,6-cd]indol-8-ylcarbamoyl)-methyl] carbamic Acid tert-butyl Ester 127(a)

Preparation of Intermediate 127(a) from the title compound of Example 2 (105 mg, 0.445 mmol), (R)-tert-butoxycarbonylamino-cyclohexyl-acetic acid (172 mg, 0.668 mmol), triethylamine (0.248 mL, 1.782 mmol), and O-(7-azabenzotriazol-1-yl)-N,N,N',N'-tetramethyluronium hexafluorophosphate (254 mg, 0.668 mmol) in N,N-dimethylformamide (4.0 mL) was carried out analogously to Example 11. Silica gel chromatography (eluted with 1:1 hexane:ethyl acetate), also in an analogous manner, afforded Intermediate 127(a) (110 mg, 0.250 mmol) as a yellow powder in 56% yield.

$^1$H NMR (d$_6$-DMSO): δ 11.71 (d, 1H, J=2.26 Hz), 10.23 (s, 1H), 10.07 (s, 1H), 8.10 (s, 1H), 7.59 (s, 1H), 7.55 (d, 1H, J=2.45 Hz), 7.46 (s, 1H), 6.86 (d, 1H, J=8.85 Hz), 3.92 (dd, 1H, J=8.10, 7.91 Hz), 1.77–1.46 (m, 6H), 1.37 (s, 9H), 1.24–0.93 (m, 5H).

LCMS: (M+H$^+$) 440.1, (M+Na$^+$) 462.2; (M–H)$^-$ 438.2.

Step 2. Preparation of Title Compound: (R)-2-Amino-2-cyclohexyl-(6-oxo-5,6-dihydro-1-[1,2]diazepino[4,5,6-cd]indol-8-yl)-acetamide (Hydrochloric Salt)

Preparation of the title compound from Intermediate 127(a) (66.1 mg, 0.150 mmol) and 4.0 M HCl in dioxane (1.5 mL) was carried out analogously to Example 91. Isolation, also in an analogous manner, afforded the title compound (52.0 mg, 0.138 mmol) as a yellow powder in 92% yield.

$^1$H NMR (d$_6$-DMSO): δ 11.86 (s, 1H), 10.69 (s, 1H), 10.31 (s, 1H), 8.29 (br s, 3H), 8.08 (s, 1H), 7.63 (s, 1H), 7.49 (s, 1H), 3.80–3.69 (m, 1H), 1.93–1.55 (m, 6H), 1.29–0.98 (m, 5H).

LCMS: (M+H$^+$) 340.3, (M+Na$^+$) 362.3.

Example 128

2-Indan-2-yl-(6-oxo-5,6-dihydro-1-[1,2]diazepino[4,5,6-cd]indol-8-yl)-acetamide

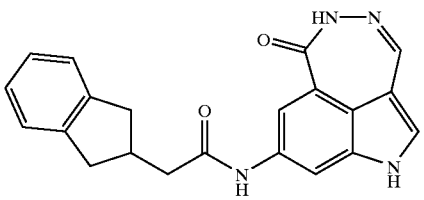

Preparation of example 128 from the title compound of Example 2 (freebase) (88.7 mg, 0.443 mmol), indan-2-yl-acetic acid (117 mg, 0.665 mmol), triethylamine (0.247 mL, 1.774 mmol), and O-(7-azabenzotriazol-1-yl)-N,N,N',N'-tetramethyluronium hexafluorophosphate (253 mg, 0.665 mmol) in N,N-dimethylformamide (4.0 mL) was carried out analogously to Example 11. When the reaction was judged complete, N,N-dimethylformamide was evaporated and methanol was added. The mixture was filtered to collect the solids, which were then washed with methanol, dichloromethane and diethyl ether. After drying under vacuum, the title compound (115 mg, 0.321 mmol) was obtained as a yellow powder in 72% yield.

$^1$H NMR (d$_6$-DMSO): δ 11.71 (s, 1H), 10.23 (s, 1H), 10.05 (s, 1H), 8.15 (s, 1H), 7.58(s, 1H), 7.55 (d, 1H, J=2.26 Hz), 7.46 (s, 1H), 7.26–7.16 (m, 2H), 7.16–7.06 (m, 2H), 3.06 (dd, 2H, J=7.54, 5.54 Hz), 2.92–2.79 (m, 1H), 2.65 (dd, 2H, J=6.59, 6.78 Hz), 2.47 (d, 2H, J=9.80 Hz).

LCMS: (M+H$^+$) 359.1, (M+Na$^+$) 381.0; (M–H)$^-$ 357.2.

Example 129

(1,2-trans)-2-Pyridin-3-yl-cyclopropanecarboxylic Acid (6-oxo-5,6-dihydro-1H-[1,2]diazepino[4,5,6-cd]indol-8-yl)-amide

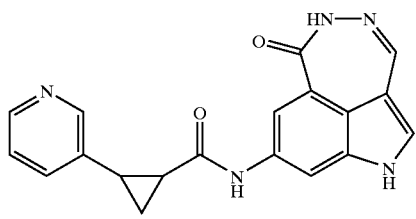

Preparation of example 129 from the title compound of Example 2 (freebase) (200 mg, 1.00 mmol), (1,2-tans)-2-pyridin-3'-yl-cyclopropanecarboxylic acid (see Example 125 for preparation-estimated purity c.a. 75%) (240 mg, c.a. 1.10 mmol), triethylamine (0.550 mL, 3.96 mmol), and O-(7-azabenzotriazol-1-yl)-N,N,N',N'-tetramethyluronium hexafluorophosphate (570 mg, 1.50 mmol) in N,N-dimethylformamide (8.0 mL) was carried out analogously to Example 11. Silica gel chromatography (eluted with 100:10:1 ethyl acetate: methanol: ammonium hydroxide), also in an analogous manner, afforded the title compound (38 mg, 0.110 mmol) as a yellow powder in 11% yield.

$^1$H NMR (d$_6$-DMSO): δ 11.73 (d, 1H, J=2.26 Hz), 10.41 (s, 1H), 10.23 (s, 1H), 8.50 (d, 1H, J=1.88 Hz), 8.41 (dd, 1H, J=3.20, 1.51 Hz), 8.11 (d, 1H, J=1.51 Hz), 7.61–7.48 (m, 3H), 7.45 (s, 1H), 7.32 (dd, 1H, J=5.09, 3.20 Hz), 2.45–2.36 (m, 1H), 2.18–2.05 (m, 1H), 1.58–1.49 (m, 1H), 1.49–1.36 (m, 1H).

LCMS: (M+H$^+$) 346.1; (M−H)$^−$ 344.1.

HRMS: (M+H$^+$) calcd for C$_{19}$H$_{16}$N$_5$O$_2$, 346.1304, found 346.1316.

Example 130

(1,2-trans)-2-(1'-Trityl-1H-imidazol-4'-yl)-cyclopropanecarboxylic Acid (6-oxo-2-phenyl-5,6-dihydro-1H-[1,2]diazepino[4,5,6-cd]indol-8-yl)-amide

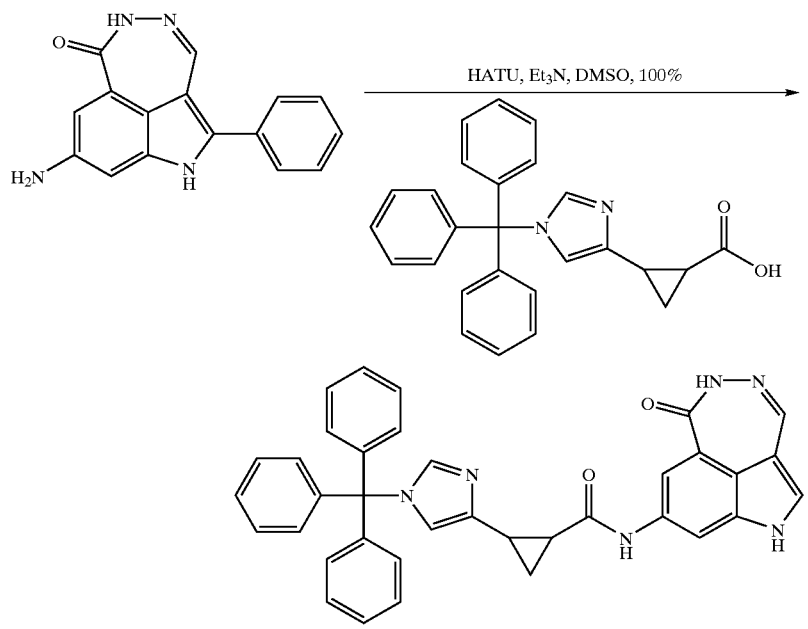

Preparation of example 130 was carried out analogously to the preparation of Example 113 except that (1,2-trans)-2-(1'-trityl-1H-imidazol-4'-yl)-cyclopropanecarboxylic acid was used instead of (1,2-trans)-2-(6-trifluoromethyl-pyridin-3-yl)-cyclopropanecarboxylic acid in step 4. (1,2-trans)-2-(1'-trityl-1H-imidazol-4'-yl)-cyclopropanecarboxylic acid was prepared using procedures similar to those described in steps 1–3 of Example 113 except that 1-trityl-1H-imidazole-4-carbaldehyde was used instead of 6-trifluoromethyl-3-pyridine carboxaldehyde. Final purification consisted of methanol trituration. The resulting solids were isolated by filtration, washed with cold methanol, and dried overnight under vacuum at room temperature to afford the title compound (263 mg, 0.366 mmol) as a yellow powder in quantitative yield.

$^1$H-NMR (d$_6$-DMSO): δ 12.09 (s, 1H), 10.43 (s, 1H), 10.38 (s, 1H), 8.13 (s, 1H), 7.70–7.30 (m, 18H), 7.25 (s, 1H), 7.15–7.05 (m, 6H), 6.87 (s, 1H), 2.35–2.24 (m, 1H), 2.20–2.13 (m, 1H), 1.38–1.23 (m, 2H).

LCMS: (M+H$^+$) 653.3

Example 131

(6-Oxo-5,6-dihydro-1-[1,2]diazepino[4,5,6-]indol-8-yl)-3-(Pyridin-2-yloxy)-benzamide

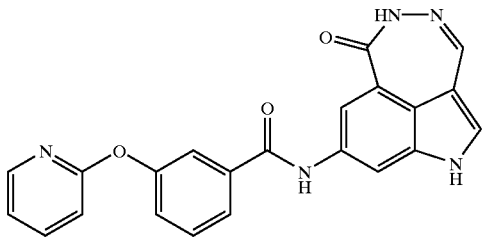

Preparation of example 131 from the title compound of Example 2 (25 mg, 0.125 mmol), 3-(pyridin-2-yloxy)-benzoic acid (88 mg, 0.348 mmol), N,N-diisopropylethylamine (0.19 mL, 1.04 mmol), and O-(7-azabenzotriazol-1-yl)-N,N,N',N'-tetramethyluronium hexafluorophosphate (159 mg, 0.42 mmol) in N,N-dimethylformamide (3 mL) was carried out analogously to Example 11. Silica gel chromatography (eluted with 2% methanol in $CH_2Cl_2$), also in an analogous manner, afforded the title compound (20 mg, 0.05 mmol) as a yellow powder in 40% yield.

$^1$H NMR ($d_6$-Acetone): δ 7.92 (s, 1H), 7.89 (s, 1H), 7.55–7.52 (m, 4H), 7.39 (s, 1H), 7.37 (s, 1H), 7.34 (m, 1H), 7.32–7.24 (m, 2H), 7.15 (m, 1H), 6.95 (m, 1H), 6.93 (m, 1H), 6.77–6.73 (m, 5H), 6.88 (m, 1H).

LCMS: (M+H$^+$) 398.1.

Example 132

N-(6-Oxo-5,6-dihydro-1H-[1,2]diazepino[4,5,6-cd]indol-8-yl)-4-thiophen-2-yl-butyramide

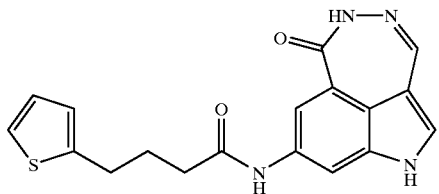

Preparation of example 132 from the title compound of Example 2 (freebase) (200 mg, 1.00 mmol), 4-thiophen-2-yl-butyric acid (187 mg, 1.10 mmol), triethylamine (0.550 mL, 3.96 mmol), and O-(7-azabenzotriazol-1-yl)-N,N,N',N'-tetramethyluronium hexafluorophosphate (570 mg, 1.50 mmol) in N,N-dimethylformamide (8.0 mL) was carried out analogously to Example 11. Silica gel chromatography (eluted with ethyl acetate), also in an analogous manner, afforded the title compound (72 mg, 0.204 mmol) as a yellow powder in 20% yield.

$^1$H NMR ($d_6$-DMSO): δ 11.70 (d, 1H, J=2.07 Hz), 10.22 (s, 1H), 10.03 (s, 1H), 8.13 (d, 1H, J=1.51 Hz), 7.55 (d, 1H, J=1.51 Hz), 7.53 (d, 1H, J=2.45 Hz), 7.45 (s, 1H), 7.31 (dd, 1H, J=4.33, 0.94 Hz), 6.94 (dd, 1H, J=3.39, 1.70 Hz), 6.86 (d, 1H, J=2.83 Hz), 3.84 (t, 2H, J=7.54 Hz), 2.37 (t, 2H, J=7.35 Hz), 1.93 (tt, 2H, J 7.54, 7.35 Hz).

LCMS: (M+H$^+$) 353.2, (M+Na$^+$) 375.2; (M−H)$^−$ 351.2.

HRMS: (M+H$^+$) calcd for $C_{18}H_{17}N_4O_2S$, 353.1072, found 353.1056.

Anal. Calcd. for $C_{18}H_{18}N_4O_2S$: C, 61.35; H, 4.58; N, 15.90.

Found: C, 61.06; H, 4.52; N, 15.71.

Example 133

(2R)-2-Hydroxy-N-(6-oxo-2-phenyl-5,6-dihydro-1H-[1,2]diazepino[4,5,6-cd]indol-8-yl)-2-phenylethanamide

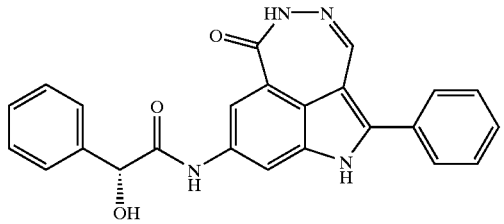

Preparation of example 133 from the title compound of Example 7 (hydrochloride) (46 mg, 0.147 mmol), (2R)-hydroxy(phenyl)ethanoic acid (27 mg, 0.177 mmol), triethylamine (0.061 mL, 0.44 mmol), and O-(7-azabenzotriazol-1-yl)-N,N,N',N'-tetramethyluronium hexafluorophosphate (67 mg, 0.177 mmol) in $CH_2Cl_2$ (0.4 mL) and N,N-dimethylformamide (0.4 mL) was carried out analogously to Example 11. Silica gel chromatography (eluted with 3:1:1 hexane:ethyl acetate:ethanol), also in an analogous manner, followed by two successive triturations (ethyl acetate/diethyl ether then methanol/diethyl ether) afforded the title compound (34 mg, 0.082 mmol) as a yellow powder in 56% yield.

$^1$H NMR ($d_6$-DMSO): δ 12.12, (s, 1H), 10.38 (s, 1H), 10.16 (s, 1H), 8.14 (s, 1H), 7.81 (s, 1H), 7.70–7.64 (m, 2H), 7.61–7.45 (m, 6H), 7.42–7.26 (m, 3H), 6.35 (br s, 1H, partially exchanged), 5.13 (s, 1H).

LCMS: (M−H)$^−$ 409.2.

Example 134

(1,2-trans)-2-Pyridin-2-yl-cyclopropanecarboxylic Acid (6-oxo-2-phenyl-5,6-dihydro-1H-[1,2]diazepino[4,5,6-cd]indol-8-yl-amide (Acetic Acid Salt)

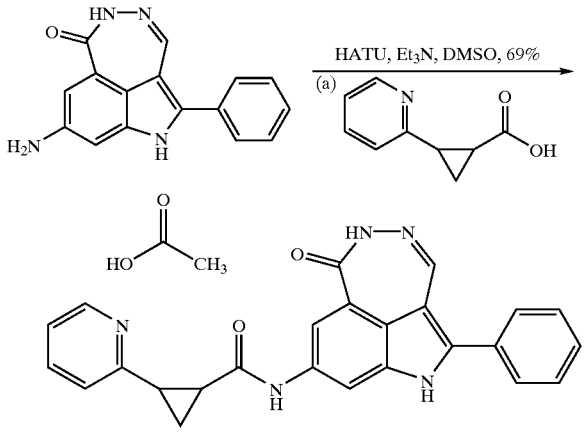

Preparation of example 134 was carried out analogously to the preparation of Example 113 except that (1,2-trans)-2-pyridin-2'-yl-cyclopropanecarboxylic acid was used instead of (1,2-trans)-2-(6-trifluoromethyl-pyridin-3-yl)-cyclopropanecarboxylic acid in step 4. (1,2-trans)-2-Pyridin-2'-yl-cyclopropanecarboxylic acid was prepared using procedures similar to those described in steps 1–3 of Example 113 except that pyridine-2-carbaldehyde was used instead of 6-trifluoromethyl-3-pyridine carbaldehyde. Final HPLC purification, also in an analogous manner but using 0.1% acetic acid instead of 0.1% TFA, afforded the title compound (107 mg, 0.254 mmol) as a greenish-yellow solid in 69% yield.

$^1$H-NMR (d$_6$-DMSO): δ 12.09 (s, 1H), 10.43 (s, 1H), 10.38 (s, 1H), 8.15 (s, 1H), 7.70–7.40 (m, 7H), 7.25–7.15 (m, 1H), 6.77 (b, 3H), 3.74 (s, 3H), 2.40–2.30 (m, 1H), 2.12–2.05 (m, 1H), 1.55–1.47 (m, 1H), 1.42–1.33 (m, 1H).

LCMS: (M+H$^+$) 422.1.

Example 135

(1,2-trans-2-(1H-Imidazol-4-yl)-cyclopropanecarboxylic Acid (6-oxo-2-phenyl-5,6-dihydro-1H-[1,2]diazepino[4,5,6-cd]indol-8-yl)-amide (Acetic Acid Salt)

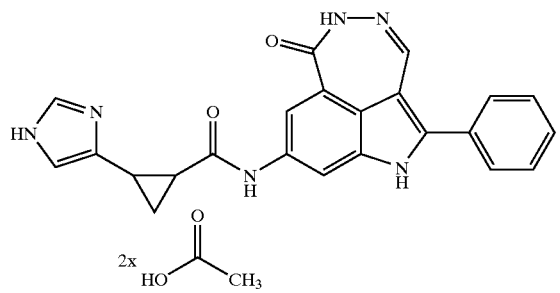

Preparation of example 135 was carried out by suspending the title compound of Example 130 (260 mg, 0.398 mmol) in anhydrous dichloromethane (5 mL) and adding anhydrous trifluoroacetic acid (5 mL) at room temperature. After 30 minutes, the mixture was concentrated and subjected to preparative HPLC, in a manner analogous to Example 134, to afford the title compound (72 mg, 0.175 mmol) as a fluffy yellow solid in 44% yield.

$^1$HNMR (d$_6$-DMSO): δ 12.09 (s, 1H), 10.43 (s, 1H), 10.37 (s, 1H), 8.15 (s, 1H), 7.97 (b, 1H), 7.70–7.45 (m, 7H), 7.13 (b, 1H), 2.40–2.30 (m, 1H), 2.12–2.04 (m, 1H), 1.45–1.33 (m, 2H).

LCMS: (M+H$^+$) 422.1.

Example 136

(2R)-Piperidine-2-carboxylic Acid (6-oxo-2-phenyl-5,6-dihydro-1H-[1,2]diazepino[4,5,6-cd]indol-8-yl)-amide (Hydrochloric Salt)

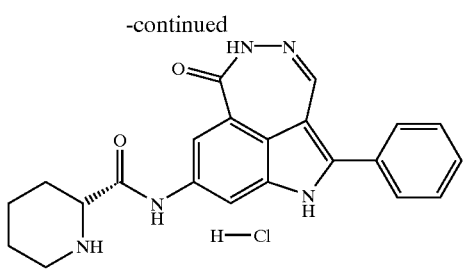

Step 1. Preparation of (2R)-2-(6-Oxo-2-phenyl-5,6-dihydro-1H-[1,2]diazepino[4,5,6-cd]indol-8-ylcarbamoyl)-piperidine-1-carboxylic Acid tert-Butyl Ester 136(a)

Preparation of Intermediate 136(a) from the title compound of Example 7 (0.11 g, 0.4 mmol), (2R)-piperidine-1,2-dicarboxylic acid 1-tert-butyl ester (0.143 g, 0.6 mmol), triethylamine (0.3 mL, 2 mmol), O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 136(a) (0.21 g) as a yellow powder in 88% yield.

$^1$H-NMR (d$_6$-DMSO): δ 12.09 (s, 1H), 10.40 (s, 1H), 10.11 (s, 1H), 8.10 (s, 1H), 7.74–7.44 (m, 7H), 4.64–4.55 (m, 1H), 3.83 (d, 1H, J=12.25 Hz), 3.35–3.20 (buried m, 1H), 2.20–2.05 (m, 1H), 1.80–1.50 (m, 3H), 1.45–1.25 (bs, 11H).

LCMS: (M+H$^+$) 488.2.

Step 2. Preparation of Title Compound: (2R)-Piperidine-2-carboxylic Acid (6-oxo-2-phenyl-5,6-dihydro-1H-[1,2]diazepino[4,5,6-cd]indol-8-yl)-amide (Hydrochloric Salt)

Preparation of the title compound from Intermediate 136(a) (0.16 g, 0.33 mmol) and 4M HCl in dioxane (1.6 mL, 6.6 mmol) was carried out analogously to Example 91. Isolation, also in an analogous manner, included a further trituration with CH$_2$Cl$_2$/diethyl ether and afforded the title compound (0.137 g) as an orange/yellow powder in 96% yield.

$^1$H-NMR (d$_6$-DMSO): δ 12.31 (s, 1H), 10.90 (s, 1H), 10.45 (s, 1H), 9.26 (b, 1H), 8.80–8.75 (m, 1H), 8.11 (s, 1H), 7.76–7.46 (m, 7H), 3.95–3.81 (m, 1H), 3.35–3.25 (m, 1H), 3.10–2.92 (m, 1H), 2.36–2.26 (m, 1H), 1.76–1.51 (m, 5H).

LCMS: (M+H$^+$) 388.1.

Example 137

(2S)-Piperidine-2-carboxylic Acid (6-oxo-2-phenyl-5,6-dihydro-1H-[1,2]diazepino[4,5,6-cd]indol-8-yl)-amide (Hydrochloric Salt)

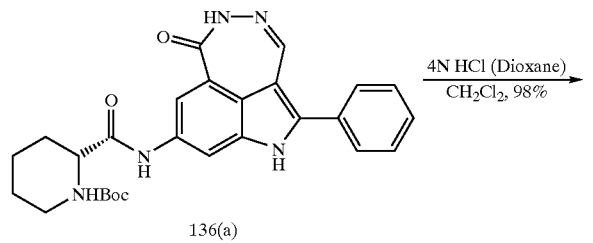

136(a)

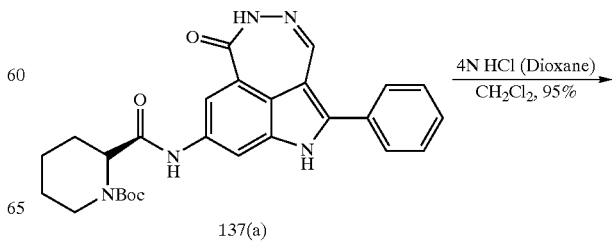

137(a)

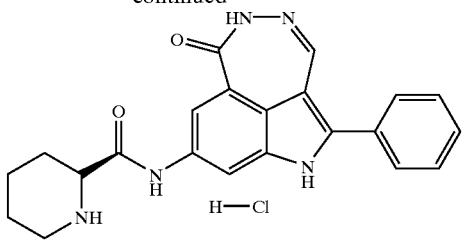

Step 1. Preparation of (2S)-2-(6-Oxo-2-phenyl-5,6-dihydro-1H-[1,2]diazepino[4,5,6-cd]indol-8-ylcarbamoyl)-piperidine-1-carboxylic Acid tert-butyl Ester 137(a)

Preparation of Intermediate 137(a) from the title compound of Example 7 (0.138 g, 0.5 mmol), (2S)-Piperidine-1,2-dicarboxylic acid 1-tert-butyl ester (0.143 g, 0.6 mmol), triethylamine (0.3 mL, 2 mmol), O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 137(a) (0.20 g) as a yellow powder in 84% yield.

$^1$H-NMR (d$_6$-DMSO): δ 12.09 (s, 1H), 10.40 (s, 1H), 10.11 (s, 1H), 8.10 (s, 1H), 7.74–7.44 (m, 7H), 4.64–4.55 (m, 1H), 3.83 (d, 1H, J=12.25 Hz), 3.35–3.20 (buried m, 1H), 2.20–2.05 (m, 1H), 1.80–1.50 (m, 3H), 1.45–1.25 (bs, 11H).

LCMS: (M+H$^+$) 488.1.

Step 2. Preparation of Title Compound: (2S)-Piperidine-2-carboxylic Acid (6-oxo-2-phenyl-5,6-dihydro-1H-[1,2]diazepino[4,5,6-cd]indol-8-yl)-amide (Hydrochloric Salt)

Preparation of the title compound from Intermediate 137(a) (0.16 g, 0.33 mmol) and 4M HCl in dioxane (1.6 mL, 6.6 mmol) was carried out analogously to Example 91. Isolation, also in an analogous manner, included a further trituration with CH$_2$Cl$_2$/diethyl ether and afforded the title compound (0.132 g) as an orange/yellow powder in 95% yield.

$^1$H-NMR (d$_6$-DMSO): δ 12.31 (s, 1H), 10.90 (s, 1H), 10.45 (s, 1H), 9.26 (b, 1H), 8.80–8.75 (m, 1H), 8.11 (s, 1H), 7.76–7.46 (m, 7H), 3.95–3.81 (m, 1H), 3.35–3.25 (m, 1H), 3.10–2.92 (m, 1H). 2.36–2.26 (m, 1H), 1.76–1.51 (m, 5H).

LCMS: (M+H$^+$) 388.2.

Step 1. Preparation of (2S, 4R)-4-Hydroxy-2-(6-oxo-2-phenyl-5,6-dihydro-1H-[1,2]diazepino[4,5,6-cd]indol-ylcarbamoyl)-pyrrolidine-1-carboxylic Acid tert-Butyl Ester 138(a)

Preparation of Intermediate 138(a) from the title compound of Example 7 (0.138 g, 0.5 mmol), (2S, 4R)-4-hydroxy-pyrrolidine-1,2-dicarboxylic acid 1-tert-butyl ester (0.144 g, 0.6 mmol), triethylamine (0.3 mL, 2 mmol), and O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded intermediate 138(a) (0.127 g) as a yellow powder in 52% yield.

$^1$H-NMR (d$_6$-DMSO): δ 12.19 (s, 1H), 10.46 (s, 1H), 10.28 (s, 1H), 8.29 (s, 0.8H, major rotamer), 8.29 (s, 0.2H, minor rotamer), 7.75–7.51 (m, 7H), 4.50–4.35 (m, 2H), 3.60–3.30 (m, 3H), 2.30–2.17 (m, 1H), 2.10–1.90 (m, 1H), 1.48 (s, 2H, minor rotamer), 1.34 (s, 2H, major rotamer).

LCMS: (M+H$^+$) 490.1.

Step 2. Title Compound: (2S,4R)-4-hydroxy-pyrrolidine-2-carboxylic Acid (6-oxo-2-phenyl-5,6-dihydro-1H-[1,2]diazepino[4,5,6-cd]indol-8-yl)-amide (Hydrochloric Salt)

Preparation of the title compound from Intermediate 138(a) (0.105 g, 0.21 mmol) and 4M HCl in dioxane (1 mL, 4.2 mmol) was carried out analogously to Example 91. Isolation, also in an analogous manner, included a further trituration with CH$_2$Cl$_2$/diethyl ether and afforded the title compound (0.065 g) as an orange/yellow powder in 71% yield.

$^1$H-NMR (d$_6$-DMSO): δ 12.33 (s, 1H), 10.93 (s, 1H), 10.44 (s, 1H), 10.10–9.95 (m, 1H), 8.90–8.45 (m, 1H), 8.08 (s, 1H), 7.75–7.45 (m, 7H), 4.75–4.35 (m, 3H), 3.45–3.30 (m, 1H), 3.20–3.10 (m, 1H), 2.50–2.35 (m, 1H), 2.10–1.95 (m, 1H).

LCMS: (M+H$^+$) 390.1.

Example 138

(2S, 4R)-4-Hydroxy-pyrrolidine-2-carboxylic Acid (6-oxo-2-phenyl-5,6-dihydro-1H-[1,2]diazepino[4,5,6-cd]indol-8-yl)-amide (Hydrochloric Salt)

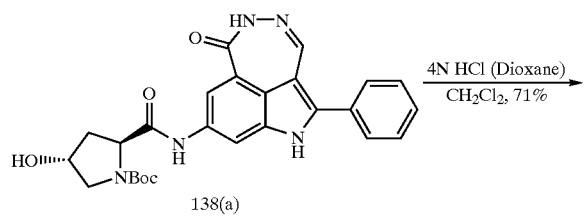

Example 139

(2S)-2-Amino-3-cyano-N-(6-oxo-2-phenyl-5,6-dihydro-1H-[1,2]diazepino[4,5,6-cd]indol-8-yl)-propionamide Acetic Acid Salt

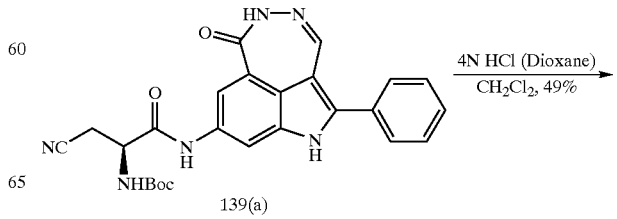

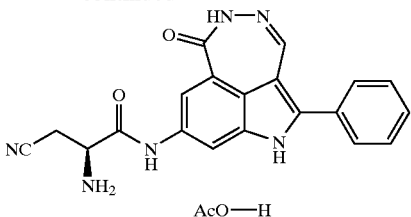

Step 1. Preparation of (1S)-[2-Cyano-1-(6-oxo-2-phenyl-5,6-dihydro-1H-[1,2]diazepino[4,5,6-cd]indol-8-ylcarbamoyl)-ethyl]-carbamic Acid tort-Butyl Ester 139(a)

Preparation of Intermediate 139(a) from the title compound of Example 7 (0.138 g, 0.5 mmol), (2S)-2-tert-butoxycarbonylamino-3-cyano-propionic acid (0.134 g, 0.6 mmol), triethylamine (0.3 mL, 2 mmol), O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 139(a) (0.094 g) as a yellow powder in 40% yield.

$^1$H-NMR (d$_6$-DMSO): δ 12.15 (s, 1H), 10.42 (s, 1H), 10.37 (s, 1H), 8.11 (s, 1H), 7.75–7.48 (m, 8H), 4.55–4.40 (m, 1H), 3.02 (dd, 1H, J=17.1, 4.9 Hz), 2.85 (dd, 1H, J=17.0, 9.0 Hz), 1.43 (s, 9H).

LCMS: (M+H$^+$) 473.2.

Step 2. Preparation of Title Compound: (2S)-2-Amino-3-cyano-N-(6-oxo-2-phenyl-5,6-dihydro-1H-[1,2]diazepino[4,5,6-cd]indol-yl)-propionamide Acetic Acid Salt Preparation of the title compound from Intermediate 139(a) (0.084 g, 0.18 mmol) and 4M HCl in dioxane (0.9 mL, 3.6 mmol) was carried out analogously to Example 91. A preparative HPLC afforded the title compound (0.038 g) as an orange/yellow powder in 49% yield.

$^1$H-NMR (d$_6$-DMSO): δ 12.31 (s, 1H), 10.50 (s, 1H), 10.35 (bs, 1H), 8.24 (s, 1H), 7.80–7.55 (m, 7H), 3.84 (dd, 1H, J=7.0, 6.9 Hz), 2.99 (dd, 1H, J=16.8, 5.7 Hz), 2.85 (dd, 1H, J=16.6, 7.2 Hz), 2.73 (s, 6H).

LCMS: (M+H$^+$) 373.1.

Example 140

(2S)-N-(6-Oxo-2-phenyl-5,6-dihydro-1H-[1,2]diazepino[4,5,6-cd]indol-8-yl)-2-pyrrolidin-2-yl-acetamide (Hydrochloric Salt)

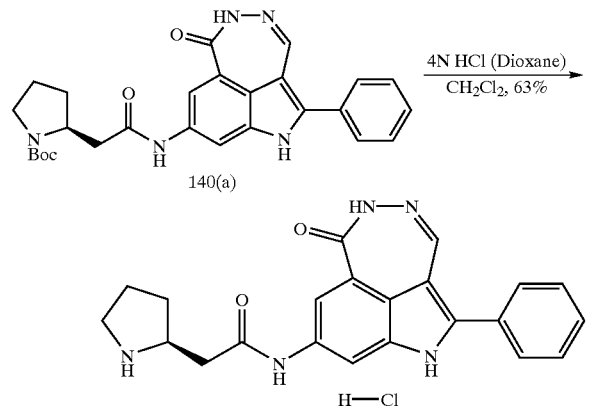

Step 1. Preparation of (2S)-2-[(6-Oxo-2-phenyl-5,6-dihydro-1H-[1,2]diazepino[4,5,6-cd]indol-ylcarbamoyl)-methyl]-pyrrolidine-1-carboxylic Acid tert-butyl Ester 140(a)

Preparation of Intermediate 140(a) from the title compound of Example 7 (0.138 g, 0.5 mmol), (2S)-2-carboxymethyl-pyrrolidine-1-carboxylic acid tert-butyl ester (0.143 g, 0.6 mmol), triethylamine (0.3 mL, 2 mmol), and o-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 140(a) (0.155 g) as a yellow powder in 64% yield.

$^1$H-NMR (d$_6$-DMSO): δ 12.09 (s, 1H), 10.39 (s, 1H), 10.17 and 10.10 (2s, 1H, minor and major rotamer), 8.20 (s, 1H), 7.75–7.45 (m, 7H), 4.10 (s, 1H), 4.20–4.05 (m, 1H), 3.50–3.25 (m, 2H), 2.10–1.75 (m, 4H), 1.40 and 1.29 (2s, 9H, minor and major rotamer).

LCMS: (M–Boc+H$^+$) 388.2.

Step 2. Preparation of Title Compound: (2S)-N-(6-Oxo-2-phenyl-5,6-dihydro-1H-[1,2]diazepino[4,5,6-cd]indol-8-yl)-2-pyrrolidin-2-yl-acetamide (Hydrochloric Salt)

Preparation of the title compound from Intermediate 140(a) (0.1 g, 0.20 mmol) and 4M HCl in dioxane (1 mL, 4.2 mmol) was carried out analogously to Example 91. Isolation, also in an analogous manner, included a further trituration with CH$_2$Cl$_2$/diethyl ether and afforded the title compound (0.055 g) as an orange/yellow powder in 63% yield. major rotamer; $^1$H-NMR (d$_6$-DMSO): δ 12.23 (s, 1H), 10.48 (s, 1H), 10.41 (s, 1H), 9.25–9.10 (m, 1H), 8.95–8.80 (m, 1H), 8.11 (s, 1H), 7.75–7.45 (m, 7H), 4.10 (buried m, 1H), 3.90–3.75 (m, 1H), 3.25–3.15 (m, 2H), 2.95–2.85 (m, 2H), 2.25–1.55 (m, 5H). minor rotamer; $^1$H-NMR (d$_6$-DMSO): δ 12.31 (s, 1H), 10.92 (s, 1H), 10.45 (s, 1H), 9.85–9.75 (m, 1H), 8.75–8.60 (m, 1H), 3.35–3.25 (m, 2H).

LCMS: (M+H$^+$) 388.2.

Example 141

(3R)-1,2,3,4-Tetrahydro-isoquinoline-3-carboxylic Acid (6-oxo-5,6-dihydro-1H-[1,2]diazepino[4,5,6-cd]indol-8-yl)-amide (Hydrochloric Salt)

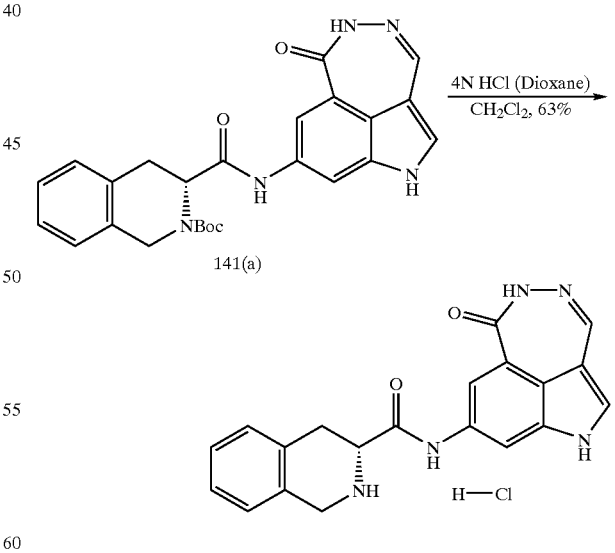

Step 1. Preparation of (3R) 3-(6-Oxo-5,6-dihydro-1H-[1,2]diazepino[4,5,6-cd]indol-8-ylcarbamoyl)-3,4-dihydro-1H-isoquinoline-2-carboxylic Acid tert-butyl Ester 141(a)

Preparation of intermediate 141(a) from the title compound of Example 2 (0.1 g, 0.5 mmol), (3R)-3,4-dihydro-1H-isoquinoline-2,3-dicarboxylic acid 2-tert-butyl ester (0.103 g, 0.6 mmol), triethylamine (0.3 mL, 2 mmol), O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 141(a) (0.094 g) as a yellow powder in 41% yield.

$^1$H-NMR (d$_6$-DMSO): δ 11.72 (bs, 1H), 10.25 (s, 1H), 10.14 (bs, 1H), 8.09 and 7.96 (2s, 1H, major and minor rotamer), 7.57 (s, 2H), 7.47 (s, 1H), 7.30–7.10 (m, 4H), 4.75–4.60 (m, 1H), 4.48–4.34 (m, 1H), 3.40–3.00 (m, 3H), 1.47 (s, 3H), 1.31 (s, 6H).

LCMS: (M–H$^+$) 458.3.

Step 2. Preparation of Title Compound: (3R)-1,2,3,4-Tetrahydro-isoquinoline-3-carboxylic Acid (6-oxo-5,6-dihydro-1H-[1,2]diazepino[4,5,6-cd]indol-8-yl)-amide (Hydrochloric Salt)

Preparation of the title compound from Intermediate 141(a) (0.094 g, 0.20 mmol) and 4M HCl in dioxane (1 mL, 4.2 mmol) was carried out analogously to Example 91. Isolation, also in an analogous manner, included a further trituration with CH$_2$Cl$_2$/diethyl ether and afforded the title compound (0.051 g) as an orange/yellow powder in 63% yield.

$^1$H-NMR (d$_6$-DMSO): δ 11.98 (s, 1H), 11.08 (s, 1H), 10.32 (s, 1H), 9.93 (b, 1H), 9.64 (b, 1H), 8.09 (s, 1H), 7.74 (s, 1H), 7.64 (s, 1H), 7.51 (s, 1H), 7.29 (s, 5H), 4.50–4.10 (buried m, 3H), 3.53 (dd, 1H, J=16.4, 4.0 Hz), 3.14 (dd, 1H, J=16.8, 12.06 Hz).

LCMS: (M+H$^+$) 360.1.

Example 142

(2S, 4R)-4-Benzyloxy-pyridine-2-carboxylic Acid (6-oxo-5,6-dihydro-1H-[1,2]diazepino[4,5,6-cd]indol-8-yl)-amide (Hydrochloric Salt)

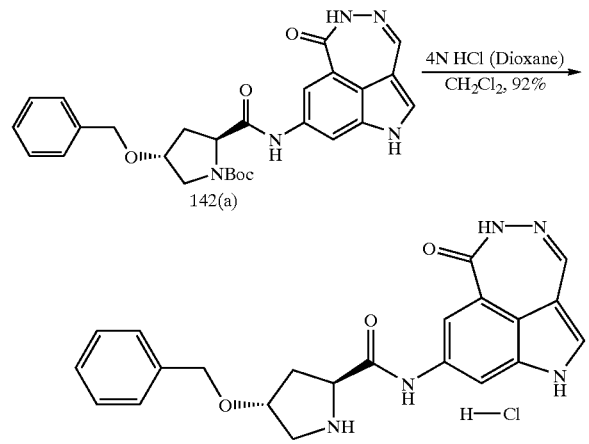

Step 1. Preparation of (2S, 4R) 4-Benzyloxy-2-(6-oxo-5,6-dihydro-1H-[1,2]diazepino[4,5,6-cd]indol-8-ylcarbamoyl)-pyrrolidine-1-carboxylic Acid tert-Butyl Ester 142(a)

Preparation of intermediate 142(a) from the title compound of Example 2 (0.1 g, 0.5 mmol), (2S, 4R)-4-benzyloxy-pyrrolidine-1,2-dicarboxylic acid 1-tert-butyl ester (0.103 g, 0.6 mmol), triethylamine (0.3 mL, 2 mmol), O-(7-azabenzotriazol-1-yl)-N,N,N',N'-tetramethyluronium hexafluorophosphate (0.23 g, 0.63 mmol) and N,N-dimethylformamide (0.1 M, 5 mL) was carried out analogously to Example 11. Silica gel chromatography afforded Intermediate 142(a) (0.126 g) as a yellow powder in 50% yield.

$^1$H-NMR (d$_6$-DMSO): δ 11.76 (s, 1H), 10.26 (s, 1H), 10.18 (s, 1H), 8.18 and 8.10 (s, 1H, rotamers), 7.60 (s, 1H), 7.58 (s, 1H), 7.48 (s, 1H), 7.42–7.26 (m, 5H), 4.53 (s, 2H), 4.39–4.26 (m, 1H), 4.22 (bs, 1H), 3.54 (bs, 2H), 3.32 (s, 2H), 1.27 (s, 6H).

LCMS: (M–H$^+$) 502.2.

Step 2. Preparation of Title Compound: (2S, 4R)-4-Benzyloxy-pyrrolidine-2-carboxylic Acid (6-oxo-5,6-dihydro-1H-[1,2]diazepino[4,5,6-cd]indol-8-yl)-amide (Hydrochloric Salt)

Preparation of the title compound from Intermediate 142(a) (0.106 g, 0.21 mmol) and 4M HCl in dioxane (1 mL, 4.2 mmol) was carried out analogously to Example 91. Isolation, also in an analogous manner, included a further trituration with CH$_2$Cl$_2$/diethyl ether and afforded the title compound (0.085 g) as an orange/yellow powder in 92% yield.

$^1$H-NMR (d$_6$-DMSO): δ 11.96 (s, 1H), 10.94 (s, 1H), 10.33 (s, 1H), 10.12 (b, 1H), 8.89 (b, 1H), 8.06 (s, 1H), 7.70 (s, 1H), 7.64 (s, 1H), 7.51 (s, 1H), 7.45–7.28 (m, 7H), 4.40 (b, 2H), 3.47 (b, 2H), 2.80–2.65 (m, 1H), 2.15–2.01 (m, 1H).

LCMS: (M+H$^+$) 404.2.

Example 143

(2R)-2-Amino-3-(4-hydroxyphenyl)-N-(6-oxo-2-phenyl-5,6-dihydro-1H-[1,2]diazepino[4,5,6-cd]indol-8-yl)propanamide Hydrochloride

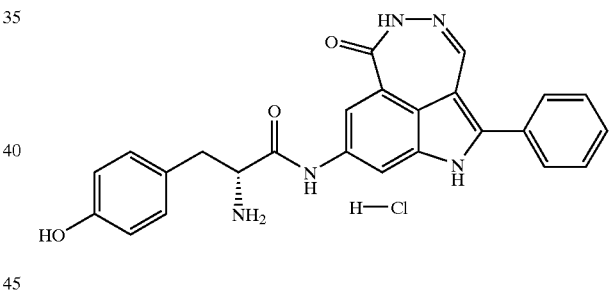

Preparation of example 143 from title compound of Example 150 (64 mg, 0.119 mmol), and 4M HCl in dioxane (5 mL) was carried out analogously to Example 91. Isolation, also in an analogous manner, included freebasing with triethylamine and subsequent silica gel chromatography eluting with 3:1:1 hexane:ethyl acetate:ethanol. With ice bath cooling, the purified freebase in CH$_2$Cl$_2$ (5 mL) was treated with 4M HCl in dioxane (0.1 mL). After removal of the volatile components, the title compound (32 mg, 0.067 mmol) was obtained as an orange/yellow powder in 57% yield.

$^1$H NMR (d$_6$-DMSO): δ 12.25 (s, 1H, exchanges), 10.71 (s, 1H, exchanges), 10.45 (s, 1H, exchanges), 9.44 (br s, 1H, exchanges), 8.45–8.31 (br m, 2H, exchanges), 8.08 (s, 1H), 7.76–7.45 (m, 7H), 7.09 (d, 2H, J=8 Hz), 6.72 9d, 2H, J=8 Hz), 4.13 (m, 1H), 3.19–2.97 (m, 2H).

LCMS: (M+H$^+$) 440.0, (M–H)$^-$ 438.2.

Example 144

(S)-1-Methyl-pyrrolidine-2-carboxylic Acid (6-oxo-5,6-dihydro-1-[1,2]diazepino[4,5,6-]indol-8-yl)-amide

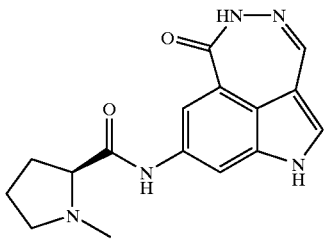

Preparation of example 144 from the title compound of Example 2 (190 mg, 0.95 mmol), N-methylproline (129 mg, 1.47 mmol), triethylamine (0.19 mL, 1.43 mmol), and O-(7-azabenzotriazol-1-yl)-N,N,N',N'-tetramethyluronium hexafluorophosphate (470 mg, 1.3 mmol) in N,N-dimethylformamide (5 mL) was carried out analogously to Example 11. Silica gel chromatography (eluted with 10% methanol in $CH_2Cl_2$), also in an analogous manner, afforded title compound (100 mg, 0.32 mmol) as a yellow powder in 34% yield.

$^1$H NMR ($d_6$-DMSO): 11.83 (s, 1H), 10.33 (s, 1H), 9.96 (s, 1H), 8.24 (s, 1H), 7.73 (s, 1H), 7.65 (s, 1H), 7.55 (s, 1H), 3.20 (m, 1H), 3.03 (m, 1H), 2.63 (m, 1H), 2.23 (m, 1H), 1.91–1.88 (m, 3H).

Anal. Calcd for $C_{16}H_{17}N_5O_2$·0.2 $H_2O$: C, 61.02; H, 5.57; N, 22.24. Found: C, 60.83; H, 5.29; N, 22.23.

LCMS: (M+H$^+$) 312.1.

Example 145

(2R)-5-Oxo-pyrrolidine-2-carboxylic Acid (6-oxo-5,6-dihydro-1-[1,2]diazepino[4,5,6]indol-8-yl)-amide

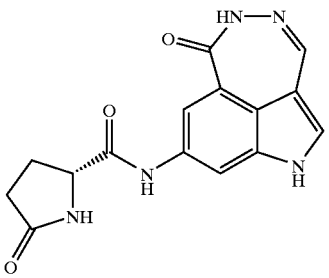

Preparation of example 145 from the title compound of Example 2 (freebase) (190 mg, 0.95 mmol), (R)-(+)-pyrrolidonecarboxylic acid (167 mg, 1.29 mmol), triethylamine (0.25 mL, 1.77 mmol), and O-(7-azabenzotriazol-1-yl)-N,N,N',N'-tetramethyluronium hexafluorophosphate (538 mg, 1.42 mmol) in N,N-dimethylformamide (5 mL) was carried out analogously to Example 11. The mixture was concentrated and the residue was triturated with methanol. The resulting solids were then collected by filtration and washed with methanol to give the title compound (220 mg, 0.57 mmol) as a yellow powder in 60% yield.

$^1$H NMR ($d_6$-DMSO): 11.79 (s, 1H), 10.27 (s, 1H), 10.20 (s, 1H), 8.11 (s, 1H), 7.91 (s, 1H), 7.62 (s, 1H), 7.59 (s, 1H), 7.49 (s, 1H), 4.21 (m, 1H), 2.36 (m, 1H), 2.24–2.16 (m, 2H), 2.03 (m, 1H).

Anal. Calcd for $C_{15}H_{13}N_5O_3$·1 $H_2O$: C, 54.71; H, 4.59; N, 21.27. Found: C, 54.51; H, 4.68; N, 21.05.

LCMS: (M+H$^+$) 312.2.

Example 146

N-(6-Oxo-5,6-dihydro-1H-[1,2]diazepino[4,5,6-cd]indol-8-yl)-3-piperidin-4-yl-acrylamide Acetic Acid Salt

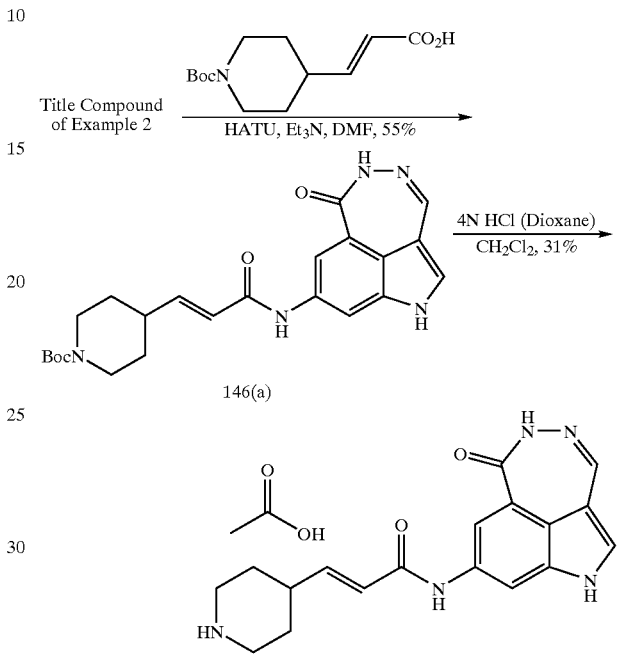

Step 1. Preparation of 4-[2-(6-Oxo-5,6-dihydro-1H-[1,2]diazepino[4,5,6-cd]indol-8-ylcarbamoyl)-vinyl]-piperidine-1-carboxylic Acid tert-butyl Ester 146(a)

Preparation of intermediate 146(a) from the title compound of Example 2 (freebase) (49 mg, 0.245 mmol), 4-(2-carboxy-vinyl)-piperidine-1-carboxylic acid tert-butyl ester (99 mg, 0.39 mmol), triethylamine (0.069 mL, 0.49 mmol), and O-(7-azabenzotriazol-1-yl)-N,N,N',N'-tetramethyluronium hexafluorophosphate (148 mg, 0.39 mmol) in N,N-dimethylformamide (3 mL) was carried out analogously to Example 11. Silica gel chromatography (eluted with 10% methanol in $CH_2Cl_2$), also in an analogous manner, afforded Intermediate 146(a) (58 mg, 0.13 mmol) as a yellow powder in 55% yield.

Step 2. Preparation of Title Compound: N-(6-Oxo-5,6-dihydro-1H-[1,2]diazepino[4,5,6-cd]indol-8-yl)-3-piperidin-4-yl-acrylamide Acetic Acid Salt Preparation of the title compound from Intermediate 146(a) (58 mg, 0.13 mmol) in $CH_2Cl_2$ (2 mL) and 4M HCl in dioxane (2 mL) was carried out analogously to Example 91. After concentration, the residue was purified by preparative HPLC (Peeke Scientific, HI-Q C18 reverse phase 5u, 100A, 250×21.2 mm column) eluting with $CH_3CN$ and 0.1% acetic acid in water at a flow rate of 20 mL/min using a gradient of 5–95% $CH_3CN$ over 40 min to give the title compound (16 mg, 0.04 mmol) as a pale yellow powder in 31% yield.

$^1$H NMR ($d_6$-DMSO): 11.55 (s, 1H), 10.00 (s, 1H), 9.91 (s, 1H), 8.00 (s, 1H), 7.32 (d, J=8 Hz, 2H), 7.22 (s, 1H), 6.50 (m, 1H), 5.82 (m, 1H), 2.77–2.74 (m, 2H), 2.03 (m, 1H), 1.65–1.53 (m, 2H), 1.29–1.28 (m, 2H), 1.10–1.02 (m, 2H).

LCMS: (M+H$^+$) 337.

Example 147

8-tert-Butoxycarbonylamino-6-oxo-5,6-dihydro-1H-[1,2]diazepino[4,5,6-cd]indole-2-carboxylic Acid Methyl Ester

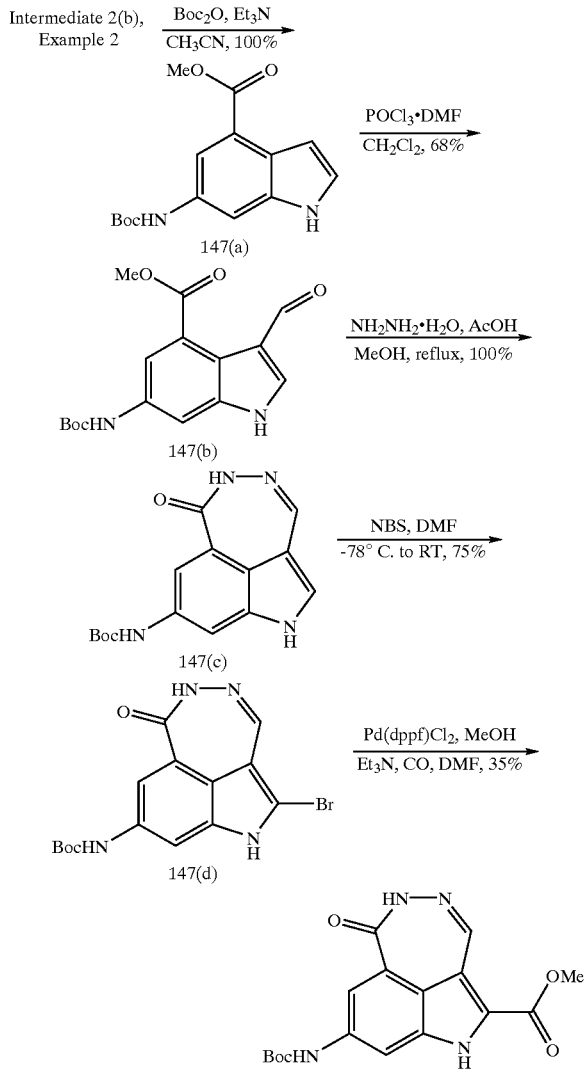

Step 1. Preparation of 6-tert-Butoxycarbonylamino-1H-indole-4-carboxylic Acid Methyl Ester 147(a)

Triethylamine (17.1 mL, 123 mmol) was added slowly to Intermediate 2(b) of Example 2 (hydrochloride) (27.5 g, 121 mmol) cooled to 0° C. in 400 ml anhydrous CH$_3$CN. After 0.5 hours, di-tert-butyl dicarbonate (26.76 g, 123 mmol) in anhydrous CH$_3$CN (50 mL) was added, and the mixture was allowed to stir at room temperature for 24 h at which point volatile components were removed in vacuo. Ethyl acetate (500 mL) and H$_2$O (500 mL) were added, and the aqueous layer was extracted with ethyl acetate (4×120 mL). The combined ethyl acetate extracts were washed with H$_2$O (2×170 mL) and brine (100 mL) and allowed to dry over Na$_2$SO$_4$. Following filtration, the volatile components were removed in vacuo to afford Intermediate 147(a) (35.1 g, 121 mmol) as a brown solid in quantitative yield.

$^1$H NMR (d$_6$-DMSO): δ 12.28 (s, 1H), 9.43 (s, 1H), 7.91 (br s, 1H), 7.89 (s, 1H), 7.42 (t, 1H, J=2.73 Hz), 6.83 (t, 1H, J=2.17 Hz), 3.89 (s, 3H), 1.50 (s, 9H).

LCMS: (M+Na$^+$) 313.1; (M−H)$^-$ 289.2.

Anal. Calcd. for C$_{15}$H$_{18}$N$_2$O$_4$: C, 62.06; H, 6.25; N, 9.65. Found: C, 62.08; H, 6.30; N, 9.59.

Step 2. Preparation of 6-tert-Butoxycarbonylamino-3-formyl-1H-indole-4-carboxylic Acid Methyl Ester 147(b)

A premixed Vilsmeier reagent consisting of phosphorus oxychloride (33.67 mL, 3624 mmol) in N,N-dimethylformamide (81.40 mL) was added dropwise at 0° C. to Intermediate 147(a) (33.87 g, 116 mmol) stirring in anhydrous CH$_2$Cl$_2$ (584 mL). The mixture was stirred for 1 hour at room temperature, quenched with aqueous 2.0 M sodium acetate (700 ml) at 0° C. and neutralized with solid Na$_2$CO$_3$. A solid formed and the mixture was partitioned between ethyl acetate (4000 mL) and H$_2$O (2000 mL). The layers were separated and the aqueous layer was extracted with ethyl acetate (4×500 mL). The organic layers were combined, washed with brine, dried over Na$_2$SO$_4$, filtered, and concentrated. Methanol (3500 mL) was added to the residue followed by K$_2$CO$_3$ (70 g). The mixture was stirred at room temperature for 16 hours at which point volatile components were removed in vacuo. Ethyl acetate (500 mL) and H$_2$O (500 mL) were added. The entire mixture was then filtered and the insoluble solids were collected and dried under vacuum to afford Intermediate 147(b) (14.35 g, 45.1 mmol) as a white solid. The aqueous layer was again extracted with ethyl acetate (4×120 mL), and the ethyl acetate extracts were combined, washed with H$_2$O (2×170 mL), brine and allowed to dry over Na$_2$SO$_4$. Following filtration, the volatile components were removed in vacuo to afford additional Intermediate 147(b) (10.74 g, 33.8 mmol) as a white solid. The combined yield for the two batches was 68%.

$^1$H NMR (d$_6$-DMSO): δ 12.28 (s, 1H), 10.09 (s, 1H), 9.60 (s, 1H), 8.23 (d, 1H, J=3.01 Hz), 7.96 (d, 1H, J=1.32 Hz), 7.65 (d, 1H, J=1.88 Hz), 3.84 (s, 3H), 1.50 (s, 9H).

LCMS: (M+H$^+$) 319, (M+Na$^+$) 341.1; (M−H)$^-$ 317.1

Step 3. Preparation of (6-Oxo-5,6-dihydro-1H-[1,2]diazepino[4,5,6-cd]indol-8-yl)-carbamic Acid tert-butyl Ester 147(c)

Acetic acid (7.89 ml) was added to Intermediate 147(b) (25.1 g, 78.9 mmol) in anhydrous methanol (789 ml). The suspension was stirred at room temperature for 10 minutes and H$_2$NNH$_2$.H$_2$O (21.43 mL, 395 mmol) was added. The mixture was stirred at room temperature for another 10 minutes, heated at 70° C. for 0.5 hours and cooled to room temperature. The volatile components were removed in vacuo and the residual oil was triturated with methanol and toluene to afford Intermediate 147(c) (23.6 g, 78.9 mmol) as a yellow powder in quantitative yield.

$^1$H NMR (d$_6$-DMSO): δ 11.63 (s, 1H), 10.19 (s, 1H), 9.45 (s, 1H), 7.76 (s, 1H), 7.62 (s, 1H), 7.51 (d, 1H, J=2.07 Hz), 7.44 (s, 1H), 1.49 (s, 9H).

LCMS: (M+H$^+$) 301.1, (M+Na$^+$) 323.1; (M−H)$^-$ 299.1.

Anal. Calcd. for C$_{15}$H$_{16}$N$_4$O$_3$.0.5 H$_2$O: C, 59.10; H, 5.46; N, 18.38.

Found: C, 59.49; H, 5.43: N, 17.97.

Step 4. Preparation of (2-Bromo-6-oxo-5,6-dihydro-1H-[1,2]diazepino[4,5,6-cd]indol-8-yl)carbamic Acid tert-butyl Ester 147(d)

Intermediate 147(c) (1.00 g, 3.33 mmol) was dissolved in anhydrous N,N-dimethylformamide (15 ml) and cooled to −78° C. N-Bromosuccinimide (0.564 g, 3.17 mmol) in anhydrous N,N-dimethylformamide (3.5 ml) was added dropwise over 2 min. The reaction mixture was allowed to warm to room temperature and stirred for 1 hour. Additional N-bromosuccinimide (0.337 g, 2.00 mmol) in N,N-dimethylformamide (c.a. 1.5 mL) was then added in portions over a 0.5 hours period to drive the reaction to completion.

The reaction mixture was poured into H₂O (70 mL), and a dark solid precipitated. The solid was collected by filtration and dried under vacuum to give Intermediate 147(d) (0.95 g, 2.51 mmol) as dark solid in 75% yield.

¹H NMR (d₆-DMSO): δ 12.54 (s, 1H), 10.47 (s, 1H), 9.57 (s, 1H), 7.77 (s, 1H), 7.71 (d, 1H, J=1.70 Hz), 7.31 (s, 1H), 1.53 (s, 9H).

LCMS: (M+H⁺) 379.0, 381.0, (M+Na⁺) 401.0, 403.0; (M−H)⁻ 377.1, 379.1.

Anal. Calcd. for C₁₅H₁₅BrN₄O₃: C, 47.51; H, 3.99; N, 14.77.

Found: C, 47.42; H, 3.99; N, 14.51.

Step 5. Preparation of Title Compound: 8-tert-Butoxycarbonylamino-6-oxo-5,6-dihydro-1H-[1,2] diazepino[4,5,6-cd]indole-2-carboxylic Acid Methyl Ester Intermediate 147(d) (0.200 g, 0.529 mmol), triethylamine (0.147 mL, 1.06 mmol) and anhydrous methanol (2 mL) in anhydrous N,N-dimethylformamide (2 ml) were purged with Ar. [1,1'-Bis(diphenylphosphino)ferrocene] dichloropalladium (II) (86.4 mg, 0.106 mmol) was added and CO was bubbled into the reaction mixture for 5 minutes. The reaction was then sealed and heated at 85° C. for 16 hours. The mixture was filtered through a thin pack of diatomaceous earth and the filtrate reduced in vacuo. Silica gel chromatography (eluted with 1:1 ethyl acetate:hexane) afforded the title compound (66 mg, 0.184 mmol) as a yellow powder in 35% yield.

¹H NMR (d₆-DMSO): δ 12.42 (s, 1H), 10.80 (s, 1H), 9.69 (s, 1H), 8.14 (s, 1H) 7.91 (s, 1H), 7.76 (s, 1H), 3.92 (s, 3H), 1.49 (s, 9H).

LCMS: (M+H⁺) 359.1, (M+Na⁺) 381.2; (M−H) 357.0.

Example 148

1-Amino-N-(6-oxo-2-phenyl-5,6-dihydro-1H-[1,2] diazepino[4,5,6-cd]indol-8-yl)-2,3-dihydro-1H-indene-1-carboxamide Hydrochloride

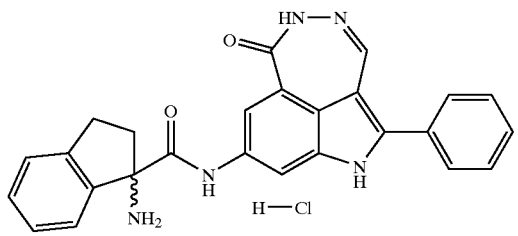

Preparation of example 148 from title compound of Example 149 (52 mg, 0.097 mmol), and 4M HCl in dioxane (5 mL) was carried out analogously to Example 91. Isolation, also in an analogous manner, afforded the title compound (46 mg, 0.097 mmol) as a yellow powder in quantitative yield.

¹H NMR (d₆-DMSO): δ 12.42 (s, 1H), 10.60 (s, 1H), 10.20 (s, 1H), 9.05–8.86 (m, 3H), 8.23 (s, 1H), 7.90–7.73 (m, 3H), 7.72–7.57 (m, 6H), 7.55–7.41 (m 2H), 3.42 (m, 1H), 3.31 (m, 1H), 3.08 (m, 1H), 2.55 (m, 1H, partially obscured).

LCMS: (M+H⁺) 436.2, 419.2.

Example 149

1,1-Dimethylethyl 1-{[(6-oxo-2-phenyl-5,6-dihydro-1H-[1,2]diazepino[4,5,6-cd]indol-8-yl)amino] carbonyl}-2,3-dihydro-1H-inden-1-ylcarbamate

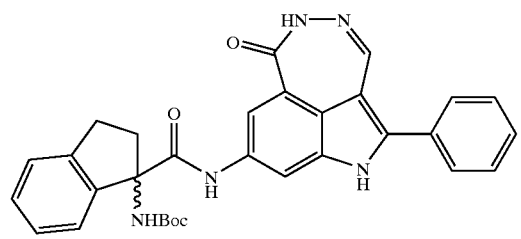

Preparation of example 149 from the title compound of Example 7 (hydrochloride) (52 mg, 0.17 mmol), 1-({[(1,1-dimethylethyl)oxy]carbonyl}amino)-2,3-dihydro-1H-indene-1-carboxylic acid (72 mg, 0.26 mmol), triethylamine (0.071 mL, 0.51 mmol), and O-(7-azabenzotriazol-1-yl)-N,N,N',N'-tetramethyluronium hexafluorophosphate (99 mg, 0.26 mmol) in CH₂Cl₂ (0.4 mL) and N,N-dimethylformamide (0.4 mL) was carried out analogously to Example 11. Silica gel chromatography (eluted with 1:1 hexane:acetone), also in an analogous manner, afforded the title compound (63 mg, 0.12 mmol) as a yellow powder in 69% yield.

¹H NMR (d₆-DMSO): δ 12.05 (s, 1H), 10.36 (s, 1H), 10.01 (m, 1H), 8.09 (m, 1H), 7.87–7.74 (m, 2H), 7.70–7.62 (m, 2H), 7.63–7.53 (m, 2H), 7.52–7.47 (m, 2H), 7.31–7.22 (m, 3H), 3.08–2.95 (m, 3H), 2.09 (m, 1H), 1.40 (m, 9H).

LCMS: (M−H)⁻ 534.0.

Example 150

1,1-Dimethylethyl (1R)-1-[(4-hydroxyphenyl) methyl]-2-oxo-2-[(6-oxo-2-phenyl-5,6-dihydro-1H-[1,2]diazepino[4,5,6-cd]indol-8-yl)amino] ethylcarbamate

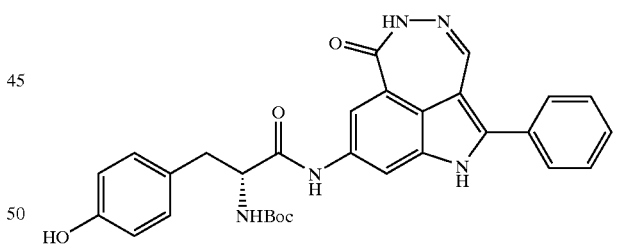

Preparation of example 150 from the title compound of Example 7 (hydrochloride) (44 mg, 0.144 mmol), (2R)-2-({[(1,1-dimethylethyl)oxy]carbonyl}amino)-3-(4-hydroxyphenyl)propanoic acid (46 mg, 0.173 mmol), triethylamine (0.060 mL, 0.43 mmol), and O-(7-azabenzotriazol-1-yl)-N,N,N',N'-tetramethyluronium hexafluorophosphate (66 mg, 0.173 mmol) in CH₂Cl₂ (0.4 mL) and N,N-dimethylformamide (0.4 mL) was carried out analogously to Example 11. Silica gel chromatography (eluted with 1:1 hexane:acetone), also in an analogous manner, afforded the title compound (74 mg, 0.137 mmol) as a yellow powder in 95% yield.

¹H NMR (d₆-DMSO): δ 12.11 (s, 1H), 10.41 (s, 1H), 10.20 (s, 1H), 9.20 (s, 1H), 8.17 (s, 1H), 7.71–7.45 (m, 7H), 7.14 (d, 2H, J=8.50 Hz), 6.68 (d, 2H, J=8.40 Hz), 4.24 (m, 1H), 2.94 (m, 1H), 2.72 (m, 1H), 1.35 (s, 9H).

LCMS: (M−H)⁻ 538.1.

Example 151

1,1-Dimethylethyl (1R)-1-[(4-hydroxyphenyl)methyl]-2-oxo-2-[(6-oxo-2-phenyl-5,6-dihydro-1H-[1,2]diazepino[4,5,6-cd]indol-8-yl)amino]ethyl (methyl)carbamate

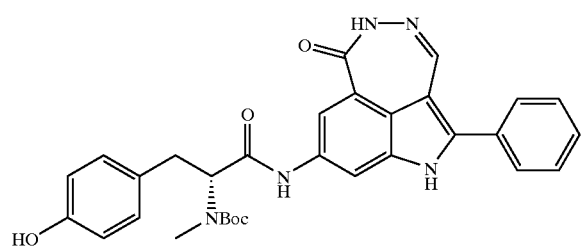

Preparation of example 151 from the title compound of Example 7 (hydrochloride) (40 mg, 0.128 mmol), (2R)-2-[{[(1,1-dimethylethyl)oxy]carbonyl}(methyl)amino]-3-(4-hydroxyphenyl)propanoic acid (57 mg, 0.192 mmol), triethylamine (0.054 mL, 0.384 mmol), and O-(7-azabenzotriazol-1-yl)-N,N,N',N'-tetramethyluronium hexafluorophosphate (73 mg, 0.192 mmol) in CH₂Cl₂ (0.4 mL) and N,N-dimethylformamide (0.4 mL) was carried out analogously to Example 11. Additional (2R)-2-[{[(1,1-dimethylethyl)oxy]carbonyl}(methyl)amino]-3-(4-hydroxyphenyl)propanoic acid (14 mg, 0.047 mmol) and O-(7-azabenzotriazol-1-yl)-N,N,N',N'-tetramethyluronium hexafluorophosphate (18 mg, 0.047 mmol) were added after 24 hours to drive the reaction to completion. Silica gel chromatography (eluted with 1:1 hexane:acetone), also in an analogous manner, afforded the title compound (55 mg, 0.099 mmol) as a yellow powder in 78% yield.

¹H NMR (d₆-DMSO) multiple: δ 12.10 (br s, 1H), 10.38 (br s, 1H), 9.20 (m, 1H), 8.13 (m, 1H), 7.72–7.63 (m, 3H), 7.61–7.43 (m, 4H), 7.09–7.00 (m, 2H), 6.72–6.62 (m, 2H), 4.82–4.60 (m, 1H), 3.19–3.08 (m, 1H), 2.93–2.85 (m, 1H), 2.80–2.62 (m, 3H), 1.37–1.21 (m, 9H).

LCMS: (M+H⁺) 554.2, (M+Na⁺) 576.2 (M−H)⁻ 552.0.

Example 152

1,1-Dimethylethyl (1R)-1-[(4-fluorophenyl)methyl]-2-oxo-2-[(6-oxo-2-phenyl-5,6-dihydro 1H-[1,2]diazepino[4,5,6-cd]indol-8-yl)amino]ethylcarbamate

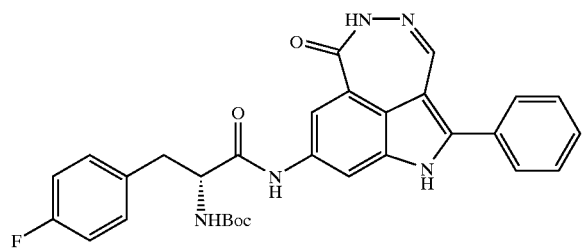

Preparation of example 152 from the title compound of Example 7 (hydrochloride) (40 mg, 0.128 mmol), (2R)-2-({[(1,1-dimethylethyl)oxy]carbonyl}amino)-3-(4-fluorophenyl)propanoic acid (54 mg, 0.192 mmol), triethylamine (0.054 mL, 0.384 mmol), and O-(7-azabenzotriazol-1-yl)-N,N,N',N'-tetramethyluronium hexafluorophosphate (73 mg, 0.192 mmol) in CH₂Cl₂ (0.4 mL) and N,N-dimethylformamide (0.4 mL) was carried out analogously to Example 11. Silica gel chromatography (eluted with 1:1 hexane:acetone), also in an analogous manner, afforded the title compound (61 mg, 0.113 mmol) as a yellow powder in 88% yield.

¹H NMR (d₆-DMSO): δ 12.12 (s, 1H), 10.42 (s, 1H), 10.25 (s, 1H), 8.18 (s, 1H), 7.71–7.46 (m, 7H), 7.42–7.34 (m, 2H), 7.21–7.09 (m, 3H), 4.41 (m, 11H), 3.03 (m, 1H), 2.85 (m 1H), 1.34 (s, 9H).

LCMS: (M−H)⁻ 540.2.

Example 153

1,1-Dimethylethyl (1R)-1-(4-hydroxyphenyl)-2-oxo-2-[(6-oxo-2-phenyl-5,6-dihydro-1H-[1,2]diazepino[4,5,6-cd]indol-8-yl)amino]ethylcarbamate

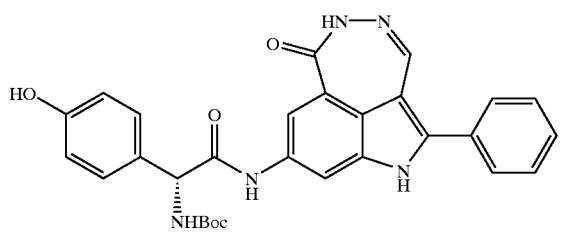

Preparation of example 153 from the title compound of Example 7 (hydrochloride) (42 mg, 0.134 mmol), (2R)-({[(1,1-dimethylethyl)oxy]carbonyl}amino)(4-hydroxyphenyl)ethanoic acid (54 mg, 0.202 mmol), triethylamine (0.056 mL, 0.402 mmol), and O-(7-azabenzotriazol-1-yl)-N,N,N',N'-tetramethyluronium hexafluorophosphate (77 mg, 0.202 mmol) in CH₂Cl₂ (0.4 mL) and N,N-dimethylformamide (0.4 mL) was carried out analogously to Example 11. Additional (2R)-({[(1,1-dimethylethyl)oxy]carbonyl}amino)(4-hydroxyphenyl)ethanoic acid (27 mg, 0.10 mmol) and O-(7-azabenzotriazol-1-yl)-N,N,N',N'-tetramethyluronium hexafluorophosphate (39 mg, 0.10 mmol) were added after 24 hours to drive the reaction to completion. Silica gel chromatography (eluted with 1:1 hexane:acetone), also in an analogous manner, afforded the title compound (48 mg, 0.091 mmol) as a yellow powder in 68% yield.

¹H NMR (d₆-DMSO): δ 12.11 (s, 1H), 10.40 (s, 1H), 10.30 (s, 1H), 9.46 (s, 1H), 8.12 (s, 1H), 7.71–7.48 (m, 7H), 7.33–7.27 (m, 2H), 6.80–6.69 (m, 2H), 5.22 (m, 1H), 1.41 (s, 1H).

LCMS: (M+H⁺) 526.2.

Example 154

1,1-Dimethylethyl (1R)-1-(naphthalen-2-ylmethyl)-2-oxo-2-[(6-oxo-2-phenyl-5,6-dihydro-1H-[1,2]diazepino[4,5,6-cd]indol-8-yl)amino]ethylcarbamate

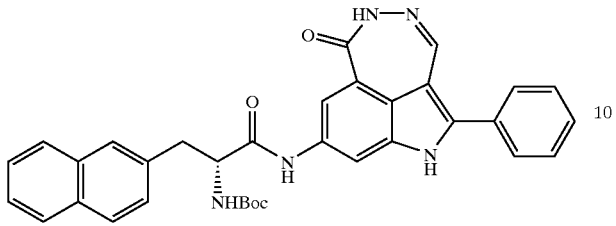

Preparation of example 154 from the title compound of Example 7 (hydrochloride) (40 mg, 0.128 mmol), (2R)-2-({[(1,1-dimethylethyl)oxy]carbonyl}amino)-3-naphthalen-2-ylpropanoic acid (58 mg, 0.192 mmol), triethylamine (0.054 mL, 0.384 mmol), and O-(7-azabenzotriazol-1-yl)-N,N,N',N'-tetramethyluronium hexafluorophosphate (73 mg, 0.192 mmol) in $CH_2Cl_2$ (0.4 mL) and N,N-dimethylformamide (0.4 mL) was carried out analogously to Example 11. Silica gel chromatography (eluted with 1:1 hexane:acetone), also in an analogous manner, afforded the title compound (69 mg, 0.120 mmol) as a yellow powder in 94% yield.

$^1$H NMR ($d_6$-DMSO): δ 12.12 (s, 1H), 10.41 (s, 1H), 10.31 (s, 1H), 8.18 (s, 1H), 7.90–7.81 (m, 4H), 7.71–7.66 (m, 3H), 7.62–7.56 (m, 3H), 7.54–7.46 (m, 4H), 7.23 (d, 1H, J=8.1 Hz), 4.46 (m, 1H), 3.23 (m, 1H), 3.02 (m, 1H), 1.30 (s, 9H).

LCMS: (M–H)$^-$ 572.2.

Example 155

1,1-Dimethyl (1R)-1-[(4-hydroxyphenyl)methyl]-2-oxo-2-[(6-oxo-5,6-dihydro-1H-[1,2]diazepino[4,5,6-cd]indol-8-yl)amino]ethylcarbamate

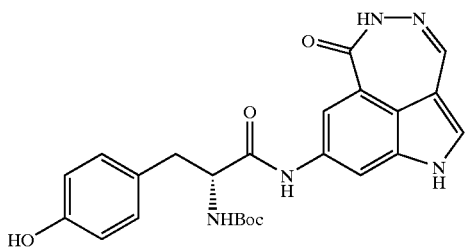

Preparation of example 155 from the title compound of Example 2 (71 mg, 0.30 mmol), (2R)-2-({[(1,1-dimethylethyl)oxy]carbonyl}amino)-3-(4-hydroxyphenyl)propanoic acid (121 mg, 0.45 mmol), triethylamine (0.125 mL, 0.9 mmol), and O-(7-azabenzotriazol-1-yl)-N,N,N',N'-tetramethyluronium hexafluorophosphate (171 mg, 0.45 mmol) in $CH_2Cl_2$ (0.5 mL) and N,N-dimethylformamide (0.5 mL) was carried out analogously to Example 11. Purification, also in an analogous manner (eluted with 1:1 hexane:acetone) afforded the title compound (100 mg, 0.22 mmol) as a yellow powder in 72% yield.

$^1$H NMR ($d_6$-DMSO): δ 11.75 (s, 1H), 10.26 (s, 1H), 10.13 (s, 1H), 9.19 (s, 1H), 8.16 (s, 1H), 7.61–7.56 (m, 2H), 7.14 (d, 2H, J=8.10 Hz), 7.04 (d, 1H, J=8.48 Hz), 6.66 (d, 2H, J=8.10 Hz), 4.22 (m, 1H), 3.08 (m, 1H), 2.87 (m, 1H), 1.34 (s, 9H).

LCMS: (M+H$^+$) 464.2, (M+Na$^+$) 486.2.

Example 156

1,1-Dimethylethyl (1R)-1-[(4-hydroxyphenyl)methyl]-2-oxo-2-[(6-oxo-5,6-dihydro-1H-[1,2]diazepino[4,5,6-cd]indol-8-yl)amino]ethyl(methyl)carbamate

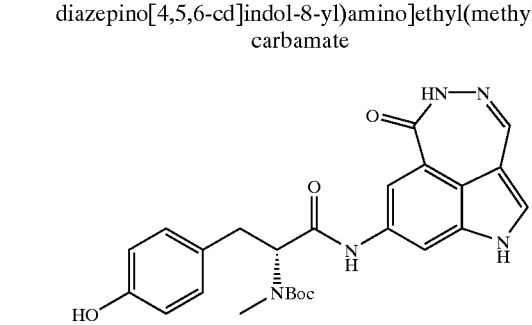

Preparation of example 156 from the title compound of Example 2 (74 mg, 0.31 mmol), (2R)-2-[{[(1,1-dimethylethyl)oxy]carbonyl}(methyl)amino]-3-(4-hydroxyphenyl)propanoic acid (138 mg, 0.47 mmol), triethylamine (0.130 mL, 0.93 mmol), and O-(7-azabenzotriazol-1-yl)-N,N,N',N'-tetramethyluronium hexafluorophosphate (179 mg, 0.47 mmol) in $CH_2Cl_2$ (0.5 mL) and N,N-dimethylformamide (0.5 mL) was carried out analogously to Example 11. Purification, also in an analogous manner (eluted with 1:1 hexane:acetone) afforded the title compound (131 mg, 0.27 mmol) as a yellow powder in 88% yield.

$^1$H NMR ($d_6$-DMSO): δ 11.77 (s, 1H), 10.26 (s, 1H), 9.21 (s, 1H), 8.12 (m, 1H), 7.65 (d, 1H, J=1.32 Hz), 7.58 (d, 1H), J=2.26 Hz), 7.48 (s, 1H), 7.07 (d, 2H, J=8.29 Hz), 6.73–6.64 (m, 2H), 4.75 (m, 1H), 3.12 (m, 1H), 2.86–2.65 (m, 4H, partially obscured by N,N-dimethylformamide), 1.35–1.25 (m, 9H).

LCMS: (M+H$^+$) 478.3, (M+Na$^+$) 500.3.

Example 157

1,1-Dimethylethyl (1R)-1-[(4-fluorophenyl)methyl]-2-oxo-2-[(6-oxo-5,6-dihydro-1H-[1,2]diazepino[4,5,6-cd]indol-8-yl)amino]ethylcarbamate

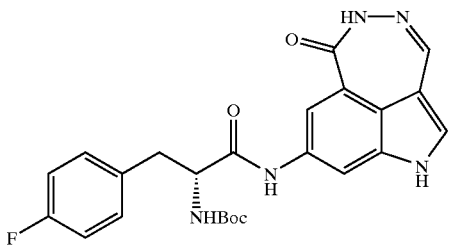

Preparation of example 157 from the title compound of Example 2 (80 mg, 0.34 mmol), (2R)-2-({[(1,1-dimethylethyl)oxy]carbonyl}amino)-3-(4-fluorophenyl)propanoic acid (145 mg, 0.51 mmol), triethylamine (0.142 mL, 1.02 mmol), and O-(7-azabenzotriazol-1-yl)-N,N,N',N'-tetramethyluronium hexafluorophosphate (193 mg, 0.51 mmol) in $CH_2Cl_2$ (0.5 mL) and N,N-dimethylformamide (0.5 mL) was carried out analogously to Example 11. Purification, also in an analogous manner (eluted with 1:1 hexane:acetone) afforded the title compound (56 mg, 0.12 mmol) as a yellow powder in 35% yield.

¹H NMR (d₆-DMSO): δ 11.73 (s, 1H), 10.24 (s, 1H), 10.16 (s, 1H), 8.10 (s, 1H), 7.55 (s, 1H with fine splitting), 7.45 (s, 1H), (7.38–7.29 (m, 2H), 7.16–7.04 (m, 3H), 4.25 (m, 1H), 2.97 (m, 1H), 2.79 (m, 1H), 1.30 (s, 9H).

LCMS: (M+H⁺) 466.2, (M+Na⁺) 488.3.

Example 158

1,1-Dimethylethyl (1R)-1-(naphthalen-2-ylmethyl)-2-oxo-2-[(6-oxo-5,6-dihydro-1H-[1,2]diazepino[4,5,6-cd]indol-8-yl)amino]ethylcarbamate

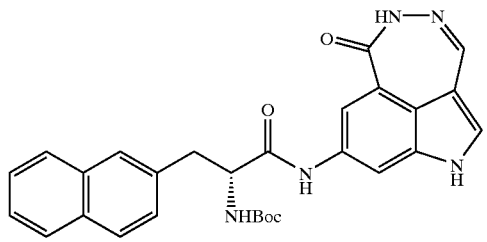

Preparation of example 158 from the title compound of Example 2 (76 mg, 0.32 mmol), (2R)-2-({[(1,1-dimethylethyl)oxy]carbonyl}amino)-3-naphthalen-2-ylpropanoic acid (145 mg, 0.48 mmol), triethylamine (0.134 mL, 0.96 mmol), and O-(7-azabenzotriazol-1-yl)-N,N,N',N'-tetramethyluronium hexafluorophosphate (182 mg, 0.48 mmol) in CH₂Cl₂ (0.5 mL) and N,N-dimethylformamide (0.5 mL) was carried out analogously to Example 11. Purification, also in an analogous manner (eluted with 1:1 hexane:acetone) afforded the title compound (67 mg, 0.13 mmol) as a yellow powder in 42% yield.

¹H NMR (d₆-DMSO): δ 11.76 (br s, 1H), 10.27 (s, 1H), 10.27 (br s, 1H), 8.15 (s, 1H), 7.90–7.79 (m, 4H), 7.62–7.42 (m, 5H), 7.21 (d, 1H, J=7.73 Hz), 4.43 (m, 1H), 3.18 (m, 1H), 3.02 (m, 1H), 1.29 (s, 9H).

LCMS: (M+H⁺) 498.2, (M+Na⁺) 520.2.

Example 159

1,1-Dimethylethyl (1R)-2-oxo-2-[(6-oxo-5,6-dihydro-1H-[1,2]diazepino[4,5,6-cd]indol-8-yl)amino]-1-{[(phenylmethyl)oxy]methyl}ethylcarbamate

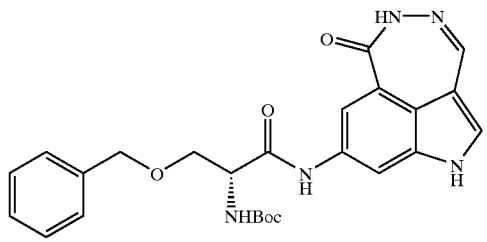

Preparation of example 159 from the title compound of Example 2 (97 mg, 0.41 mmol), (2R)-2-({[(1,1-dimethylethyl)oxy]carbonyl}amino)-3-[(phenylmethyl)oxy]propanoic acid (182 mg, 0.62 mmol), triethylamine (0.171 mL, 1.23 mmol), and O-(7-azabenzotriazol-1-yl)-N,N,N',N'-tetramethyluronium hexafluorophosphate (236 mg, 0.62 mmol) in CH₂Cl₂ (0.5 mL) and N,N-dimethylformamide (0.5 mL) was carried out analogously to Example 11. Purification, also in an analogous manner (eluted with 1:1 hexane:acetone) afforded the title compound (40 mg, 0.083 mmol) as a yellow powder in 20% yield.

¹H NMR (d₆-DMSO): δ 11.78 (br s, 1H), 10.29 (s, 1H), 10.22 (s, 1H), 8.14 (s, 1H), 7.65 (s, 1H), 7.61 (s, 1H, with fine splitting), 7.75 (s, 1H), 7.38–7.26 (m, 4H), 7.08 (d, 1H, J=6.02 Hz), 4.54 (s, 2H), 4.42 (m, 1H), 3.74–3.63 (m, 2H), 1.42 (s, 9H).

LCMS: (M+H⁺) 478.3, (M+Na⁺) 500.2.

Example 160

(1R,2R)-6-Oxo-8-[(2-phenyl-cyclopropanecarbonyl)-amino]-5,6-dihydro-1H-[1,2]diazepino[4,5,6-cd]indole-2-carboxylic Acid Methyl Ester

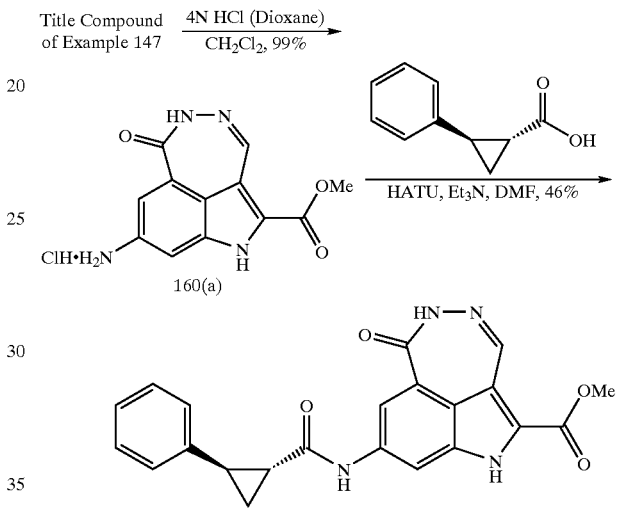

Step 1. Preparation of 8-Amino-6-oxo-5,6-dihydro-1H-[1,2]diazepino[4,5,6-cd]indole-2-carboxylic Acid Methyl Ester (Hydrochloric Salt) 160(a)

Preparation of intermediate 160(a) from the title compound of Example 147 (45.0 mg, 0.125 mmol) and 4.0 M HCl in dioxane (0.32 mL) was carried out analogously to Example 91. Isolation, also in an analogous manner, afforded Intermediate 160(a) (36.9 mg, 0.125 mmol) as a yellow powder in 99% yield.

Step 2. Preparation of Title Compound: (1R,2R)-6-Oxo-8-[(2-phenyl-cyclopropanecarbonyl)-amino]-5,6-dihydro-1H-[1,2]diazepino[4,5,6-cd]indole-2-carboxylic Acid Methyl Ester Preparation of the title compound from Intermediate 160(a) (36.9 mg, 0.125 mmol), (1R,2R)-2-phenyl-cyclopropanecarboxylic acid (22.0 mg, 0.136 mmol), triethylamine (0.175 mL, 1.26 mmol), and O-(7-azabenzotriazol-1-yl)-N,N,N',N'-tetramethyluronium hexafluorophosphate (72.0 mg, 0.189 mmol) in N,N-dimethylformamide (2.0 mL) was carried out analogously to Example 11. Silica gel chromatography (eluted with 1:1 ethyl acetate:hexane), also in an analogous manner, included a further trituration with methanol and ether and afforded the title compound (23 mg, 0.0572 mmol) as a yellow powder in 46% yield.

¹H NMR (d₆-DMSO): δ 12.53 (s, 1H), 10.83 (s, 1H), 10.58 (s, 1H), 8.23 (d, 1H, J=1.51 Hz), 8.15 (s, 1H), 7.76 (d, 1H, J=1.51 Hz), 7.37–7.25 (m, 2H), 7.25–7.14 (m, 3H), 3.93 (s, 3H), 2.45–2.35 (m, 1H), 2.15–2.05 (m, 1H), 1.58–1.47 (m, 1H), 1.45–1.33 (m, 1H).

LCMS: (M+H⁺) 403.3, (M+Na⁺) 425.1; (M−H)⁻ 401.0.
HRMS: (M+H⁺) calcd for $C_{22}H_{19}N_4O_4$, 403.1406, found 403.1413.

Example 161

(2-Methylcarbamoyl-6-oxo-5,6-dihydro-1H-[1,2]diazepino[4,5,6-cd]indol-8-yl)-carbamic Acid tert-butyl Ester

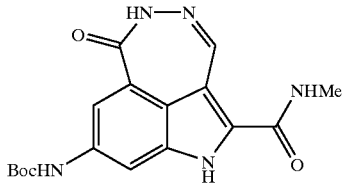

Preparation of example 161 was carried out in a manner analogous to step 5 of Example 147, except that methylamine hydrochloride was substituted for methanol. Thus CO was bubbled through a mixture of Intermediate 147(d) from Example 147 (200 mg, 0.529 mmol), triethylamine (0.29 mL, 2.11 mmol), methylamine hydrochloride (71 mg, 1.06 mmol), and 1,1'-bis(diphenylphosphino)ferrocenedichloropalladium (II) (86 mg, 0.106 mmol). Reaction conditions, work up and silica gel chromatography (eluted with 46:4:25 dichloromethane: methanol: ethyl acetate) were also carried out in an analogous manner and afforded the title compound (55 mg, 0.154 mmol) in 29% yield.

$^1$H NMR (d$_6$-DMSO): δ 12.01 (s, 1H), 10.55 (s, 1H), 9.58 (s, 1H), 8.33–8.25 (m, 1H) 7.98 (s, 1H), 7.80 (s, 1H), 7.71 (d, 1H, J=1.51 Hz), 2.81 (d, 3H, J=4.52 Hz), 1.48 (s, 9H).

LCMS: (M+H⁺) 358.3, (M+Na⁺) 380.1; (M−H³¹) 356.1.

Example 162

[2-(2-Hydroxy-ethylcarbamoyl)-6-oxo-5,6-dihydro-1H-[1,2]diazepino[4,5,6-cd]indol-8-yl]-carbamic Acid tert-butyl Ester

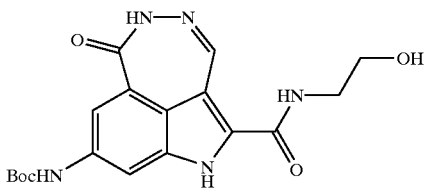

Preparation of example 162 was carried out in a manner analogous to step 5 of Example 147, except that 2-aminoethanol was substituted for methanol, and chromatography was not required. Thus CO was bubbled through a mixture of Intermediate 147(d) from Example 147 (60 mg, 0.16 mmol), triethylamine (0.044 mL, 0.32 mmol), 2-aminoethanol (19 mg, 0.32 mmol), and 1,1'-bis(diphenylphosphino)ferrocenedichloropalladium (II) (26 mg, 0.032 mmol) in N,N-dimethylformamide (3.0 mL). After the reaction was complete, the mixture was filtered through diatomaceous earth. The filtrate was concentrated, and methanol was added. The resulting solids were collected by filtration and washed with methanol, dichloromethane and diethyl ether. After drying under vacuum, the title compound (24 mg, 0.062 mmol) was obtained as a yellow powder in 39% yield.

$^1$H NMR (d$_6$-DMSO): δ 12.08 (s, 1H), 10.56 (s, 1H), 9.58 (s, 1H), 8.30 (t, 1H, J=5.84 Hz) 8.06 (s, 1H), 7.79 (s, 1H), 7.74 (s, 1H), 4.80 (br s, 1H), 3.60–3.48 (m, 2H), 3.38 (m, 2H, partially obscured), 1.48 (s, 9H).

LCMS: (M+H⁺) 388.1, (M+Na⁺) 410.1.

Example 163

(1,2-trans)-2-trans)-2-Piperidin-4-yl-cyclopropanecarboxylic Acid (6-oxo-5,6-dihydro-1H-[1,2]diazepino[4,5,6-cd]indol-8-yl)-amide (Acetic Acid Salt)

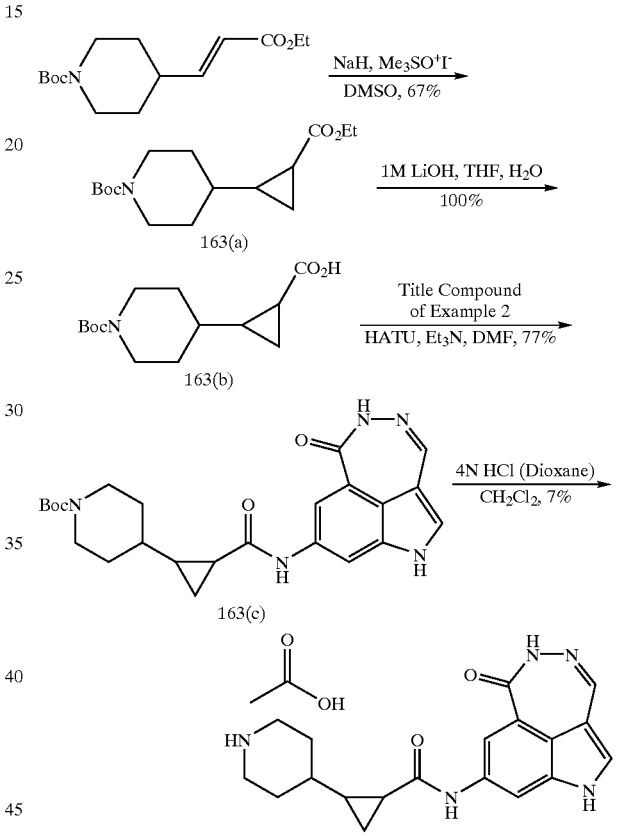

Step 1. Preparation of 4-((1,2-trans)-2-Ethoxycarbonyl-cyclopropyl)-piperidine-1-carboxylic Acid tert-butyl Ester 163(a)

To a mixture of NaH (303 mg, 7.57 mmol) and trimethylsulfoxonium iodide (1.67 g, 7.57 mmol) was added dimethyl sulfoxide (10 mL). After stirring for 30 min, a solution of 4-(2-ethoxycarbonyl-vinyl)-piperidine-1-carboxylic acid tert-butyl ester in dimethyl sulfoxide (5 mL) was added dropwise. After stirring overnight, ethyl acetate and water were added to the mixture. The aqueous layer was extracted with ethyl acetate several times. The combined organic layers were dried over Na$_2$SO$_4$, filtered, and concentrated. The residue was purified by silica gel chromatography eluting with 10% ethyl acetate/hexane to give Intermediate 163(a) (1.16 g, 67%).

Step 2. Preparation of 4-((1,2-trans)-2-Carboxy-cyclopropyl)-piperidine-1-carboxylic Acid tert-butyl Ester 163(b)

To a mixture of Intermediate 163(a) (555 mg, 1.87 mmol) in 3:1 tetrahydrofuran-H$_2$O (12 mL) was added aqueous 1M LiOH (5.61 mL). The resulting mixture was stirred overnight. The mixture was then acidified with 1M HCl to pH 1 and extracted with several times with ethyl acetate. The combined organic layers was then washed with brine and concentrated to give Intermediate 163(b) (515 mg, 1.87 mmol) in quantitative yield which was carried on without further purification.

Step 3. Preparation of 4-[(1,2-trans)-2-(6-Oxo-5,6-dihydro-1H-[1,2]diazepino[4,5,6-cd]indol-8-ylcarbamoyl)-cyclopropyl]-piperidine-1-carboxylic Acid tert-butyl Ester 163(c)

Preparation of Intermediate 163(c) from the title compound of Example 2 (freebase) (374 mg, 1.87 mmol), Intermediate 163(b) (500 mg, 1.87 mmol), triethylamine (0.31 mL, 2.24 mmol), and O-(7-azabenzotriazol-1-yl)-N,N,N',N'-tetramethyluronium hexafluorophosphate (782 mg, 2.06 mmol) in N,N-dimethylformamide (10 mL) was carried out analogously to Example 11. Silica gel chromatography (eluted with 40% acetone in hexane), also in an analogous manner, afforded Intermediate 163(c) as a yellow powder (649 mg, 1.44 mmol) in 77% yield.

Step 4. Preparation of Title Compound: (1,2-trans)-2-Piperidin-4-yl-cyclopropanecarboxylic Acid (6-oxo-5,6-dihydro-1-[1,2]diazepino[4,5,6]indol-8-yl)amide (Acetic Acid Salt)

Preparation of the title compound from Intermediate 163(c) (603 mg, 1.34 mmol) in $CH_2Cl_2$ (10 mL) and 4M HCl in dioxane (10 mL) was carried out analogously to Example 91. After concentration, the crude product was purified by preparative HPLC in a manner analogous to Example 146, Step 2, to give the title compound as a pale yellow powder (37 mg, 0.09 mmol) in 7% yield.

$^1$H NMR ($d_6$-DMSO): 11.71 (s, 1H), 10.26 (s, 1H), 10.23 (s, 1H), 8.11 (s, 1H), 7.55 (d, J=8 Hz, 2H), 7.46 (s, 1H), 3.05–3.03 (m, 2H), 2.51 (m, 1H), 1.65–1.53 (m, 3H), 1.29–1.28 (m, 2H), 1.10 (m, 1H), 0.99 (m, 1H), 0.96 (m, 1H), 0.73 (m, 1H).

LCMS: (M+H$^+$) 352.

Example 164

(6-Oxo-2-vinyl-5,6-dihydro-1H-[1,2]diazepino[4,5,6-cd]indol-8-yl)-carbamic Acid tert-butyl Ester

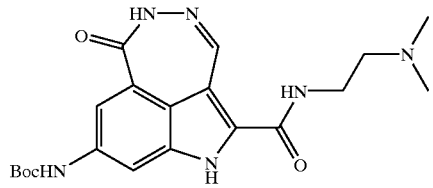

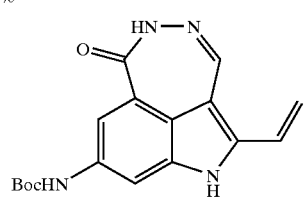

Under an argon atmosphere, Intermediate 147(d) of Example 147 (0.250 g, 0.661 mmol), tributyl-vinyl-tin (0.420 g, 1.32 mmol) and tetrakis(triphenylphosphine) palladium(0) (38 mg, 0.033 mmol) in anhydrous N,N-dimethylformamide (5 mL) were heated at 85° C. for 16 hours. The reaction was filtered through a thin pack of diatomaceous earth, and the filtrate concentrated in vacuo. Silica gel chromatography (eluted with 1:4 ethyl acetate: dichloromethane) afforded the title compound (0.18 g, 0.552 mmol) as a yellow powder in 84% yield.

$^1$H NMR ($d_6$-DMSO): δ 11.80 (s, 1H), 10.32 (s, 1H), 9.51 (s, 1H), 7.72–7.62 (m, 3H), 7.05 (dd, 1H, J=11.87, 6.59 Hz), 5.89 (d, 1H, J=17.33 Hz), 5.43 (d, 1H, J=11.11 Hz), 1.49 (s, 9H).

LCMS: (M+H$^+$) 327.2, (M+Na$^+$) 349.1.

Example 165

[2-(2-Dimethylamino-ethylcarbamoyl)-6-oxo-5,6-dihydro-1H-[1,2]diazepino[4,5,6-cd]indol-8-yl]-carbamic Acid tert-butyl Ester Preparation of example 165 was carried out in a manner analogous to step 5 of Example 147, except that N,N-dimethylethylenediamine was substituted for methanol. Thus CO was bubbled through a mixture of Intermediate 147(d) from Example 147 (1.5 g, 3.97 mmol), triethylamine (1.1 mL, 7.92 mmol), N,N-dimethylethylenediamine (0.7 g, 7.94 mmol) and 1,1'-bis(diphenylphosphino)ferrocenedichloropalladium (II) (0.65 g, 0.796 mmol) in N,N-dimethylformamide (30.0 mL). Reaction conditions, work up and silica gel chromatography (eluted with 46:4:25 dichloromethane: methanol: ethyl acetate) were also carried out in an analogous manner and afforded the title compound (1.25 g, 3.02 mmol) in 76% yield.

$^1$H NMR ($d_6$-DMSO): δ 10.55 (s, 1H), 9.59 (s, 1H), 8.25 (t, 1H, J=5.65, 4.71 Hz) 8.06 (s, 1H), 7.80 (s, 1H), 7.74 (s, 1H), 3.45–3.37 (m, 2H, partially obscured), 2.42 (t 2H, J=6.59, 6.41 Hz), 2.20 (s, 6H), 1.49 (s, 9H).

LCMS: (M+H$^+$) 415.3, (M+Na$^+$) 437.1; (M–H)$^-$ 413.1.

Example 166

(2R,3R)-2-Phenyl-pyrrolidine-3-carboxylic Acid (6-oxo-5,6-dihydro-1H-[1,2]diazepino[4,5,6-cd]indol-8-yl)-amide (Hydrochloric Salt)

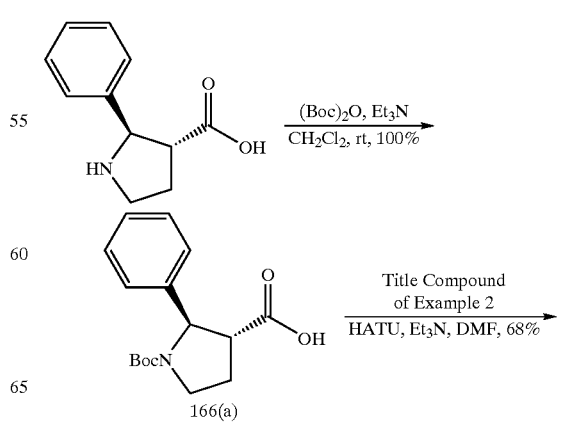

195
-continued

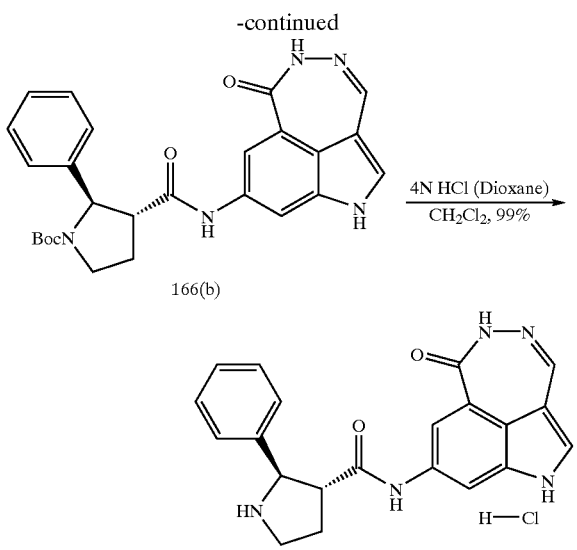

Step 1. Preparation of 2-Phenyl-pyrrolidine-1,3-dicarboxylic Acid 1-tert-butyl Ester 166(a)

To a suspension of (2R,3R)-3-phenylpyrrolidine-2-arboxylic acid (100 mg, 0.556 mmol) in dioxane (2 mL) and H$_2$O (2 mL) was added triethylamine followed by di-tert-butyl dicarbonate (127 mg, 0.583 mmol). The resulting mixture was stirred overnight. The mixture was then partitioned between ethyl acetate and 0.1 M HCl. The combined organic layers were dried over anhydrous Na$_2$SO$_4$, filtered, and concentrated to give Intermediate 166(a) (162 mg, 0.56 mmol) in 100% yield which was carried on without purification.

Step 2. Preparation of 3-(6-Oxo-5,6-dihydro-1H-[1,2]diazepino[4,5,6-cd]indol-8-ylcarbamoyl)-2-phenyl-pyrrolidine-1-carboxylic Acid tert-butyl Ester 166(b)

Preparation of intermediate 166(b) from the title compound of Example 2 (300 mg, 1.0 mmol), Intermediate 166(a) (162 mg, 0.56 mmol), triethylamine (0.15 mL, 1.1 mmol), and O-(7-azabenzotriazol-1-yl)-N,N,N',N'-tetramethyluronium hexafluorophosphate (254 mg, 0.667 mmol) in N,N-dimethylformamide (10 mL) was carried out analogously to Example 11. Silica gel chromatography (eluted with 40% acetone in hexane), also in an analogous manner, afforded Intermediate 166(b) as a yellow powder (180 mg, 0.38 mmol) in 68% yield.

Step 3. Preparation of Title Compound: (2R,3R)-2-Phenyl-pyrrolidine-3-carboxylic Acid (6-oxo-5,6-dihydro-1H-[1,2]diazepino[4,5,6-cd]indol-8-yl)-amide (Hydrochloric Salt)

Preparation of the title compound from Intermediate 166(b) (180 mg, 0.38 mmol) in CH$_2$Cl$_2$ (5 mL) and 4M HCl in dioxane (5 mL) was carried out analogously to Example 91. The solids were collected by filtration and washed with diethyl ether to give the title compound as a pale yellow powder (154 mg, 0.37 mmol) in 99% yield.

$^1$H NMR (d$_6$-DMSO): 12.03 (s, 1H), 10.72 (s, 1H), 10.46 (s, 1H), 10.20 (br s, 1H), 9.24 (brs, 1H), 8.17 (s, 1H), 7.79 (d, J=4.0 Hz, 1H), 7.69 (d, J=4.0 Hz, 1H), 7.58–7.52 (m, 5H), 7.48 (m, 1H), 4.43 (m, 1H), 3.77 (q, J=8.0 Hz, 1H), 3.75 (m, 1H), 3.59 (m, 1H), 2.66 (m, 1H), 2.62 (m, 1H).

LCMS: (M+H$^+$) 374.2.

196

Example 167

(2R)-3-(4-Hydroxyphenyl)-2-(methylamino)-N-(6-oxo-2-phenyl-5,6-dihydro-1H-[1,2]diazepino[4,5,6-cd]indol-8-yl)propanamide Hydrochloride

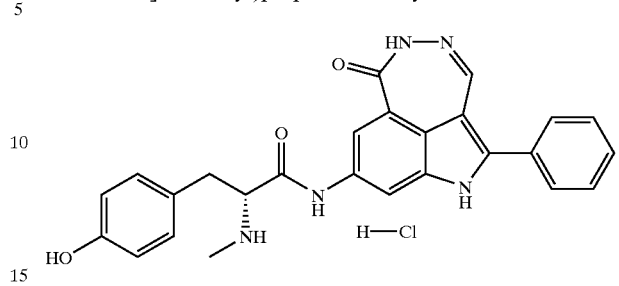

Preparation of example 167 from the title compound of Example 151 (47 mg, 0.085 mmol) and 4M HCl in dioxane (10 mL) was carried out analogously to Example 91. Isolation, also in an analogous manner, included freebasing with triethylamine and subsequent silica gel chromatography eluting with 3:1:1 hexane:ethyl acetate:ethanol. With ice bath cooling, the purified freebase in CH$_2$Cl$_2$ (10 mL) was treated with 4M HCl in dioxane (0.1 mL). After removal of the volatile components, the title compound (20 mg, 0.041 mmol) was obtained as an orange/yellow powder in 48% yield.

$^1$H NMR (d$_6$-DMSO): δ 12.21 (s, 1H), 10.70 (s, 1H), 10.43 (s, 1H), 9.44–9.06 (m, 1H), 8.02 (s, 1H), 7.72–7.64 (m, 2H), 7.61–7.54 (m, 3H), 7.53–7.47 (m, 2H) 7.05 (d, 2H, J=8.0 Hz), 6.65 (d, 2H, J=8.0 Hz), 4.09 (m, 1H), 3.40–3.31 (m, 2H), 3.16 (dd, 1H, J=6.07, 13.90 Hz), 3.07 (dd, 1H, J=7.58, 13.89 Hz), 2.55 (s, 3H).

LCMS: (M+H$^+$) 454.1, (M+Na$^+$) 476.1.

Example 168

(2R)-2-Amino-3-(4-fluorophenyl)-N-(6-oxo-2-phenyl-5,6-dihydro-1H-[1,2]diazepino[4,5,6-cd]indol-8-yl)propanamide Hydrochloride

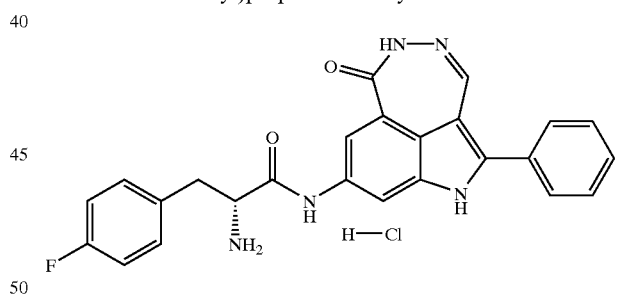

Preparation of example 168 from the title compound of Example 152 (49 mg, 0.091 mmol) and 4M HCl in dioxane (10 mL) was carried out analogously to Example 91. Isolation, also in an analogous manner, included freebasing with triethylamine and subsequent silica gel chromatography eluting with 3:1:1 hexane:ethyl acetate:ethanol. With ice bath cooling, the purified freebase in CH$_2$Cl$_2$ (10 mL) was treated with 4M HCl in dioxane (0.1 mL). After removal of the volatile components, the title compound (21 mg, 0.044 mmol) was obtained as an orange/yellow powder in 49% yield.

$^1$H NMR (d$_6$-DMSO): δ 12.26 (s, 1H), 10.83 (s, 1H), 10.46 (s, 1H), 8.48 (br s, 3H), 8.08 (s, 1H), 7.73–7.48 (m, 7H), 7.40–7.30 (m, 2H), 7.24–7.13 (m, 2H), 4.22 (m, 1H), 3.24 (m, 1H), 3.13 (m, 1H).

LCMS: (M+H$^+$) 442.1, (M+Na$^+$) 464.1.

Example 169

(1R,2R)-6-Oxo-8-[(2-phenyl-cyclopropanecarbonyl)-amino]-5,6-dihydro-1H-[1,2]diazepino[4,5,6-cd]indole-2-carboxylic Acid Methylamide

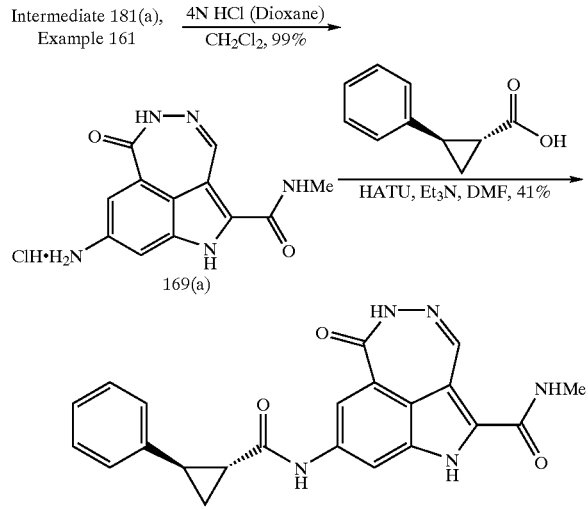

Step 1. Preparation of 8-Amino-6-oxo-5,6-dihydro-1H-[1,2]diazepino[4,5,6-cd]indole-2-carboxylic Acid Methylamide (Hydrochloric Salt) 169(a)

Preparation of intermediate 169(a) from 161(a) of Example 161 (55.0 mg, 0.154 mmol) and 4.0 M HCl in dioxane (0.77 mL) was carried out analogously to Example 91. Isolation, also in an analogous manner, afforded Intermediate 169(a) (45.0 mg, 0.154 mmol) as a yellow powder in 99% yield.

$^1$H NMR (d$_6$-DMSO): δ 12.46 (s, 1H), 10.71 (s, 1H), 8.54 (m, 1H), 8.05 (s, 1H), 7.43 (s, 1H), 7.34 (s, 1H), 2.81 (s, 3H).

LCMS: (M+H$^+$) 258.1; (M–H)$^-$ 256.1.

Step 2. Preparation of Title Compound: (1R,2R)-6-Oxo-8-[(2-phenyl-cyclopropanecarbonyl)-amino]-5,6-dihydro-1H-[1,2]diazepino[4,5,6-cd]indole-2-carboxylic Acid Methylamide Preparation of the title compound from Intermediate 169(a) (45.0 mg, 0.154 mmol), (1R,2R)-2-phenyl-cyclopropanecarboxylic acid (59.4 mg, 0.231 mmol), triethylamine (0.086 mL, 0.616 mmol), and O-(7-azabenzotriazol-1-yl)-N,N,N',N'-tetramethyluronium hexafluorophosphate (87.8 mg, 0.231 mmol) in N,N-dimethylformamide (2.0 mL) was carried out analogously to Example 11. When the reaction was judged complete, N,N-dimethylformamide was evaporated and methanol was added. The mixture was filtered to collect the solids, which were washed with methanol and diethyl ether. After drying under vacuum, the title compound (25.0 mg, 0.0623 mmol) was obtained as a yellow powder in 41% yield.

$^1$H NMR (d$_6$-DMSO): 612.13 (s, 1H), 10.60 (s, 1H), 10.51 (s, 1H), 8.36 (d, 1H, J=4.52 Hz), 8.17 (s, 1H), 8.01 (s, 1H), 7.70 (s, 1H), 7.37–7.25 (m, 2H), 7.25–7.14 (m, 3H), 2.83 (d, 3H, J=4.52 Hz), 2.45–2.35 (m, 1H), 2.14–2.04 (m, 1H), 1.57–1.47 (m, 1H), 1.45–1.33 (m, 1H).

LCMS: (M+H$^+$) 402.1, (M+Na$^+$) 424.1.

HRMS: (M+H$^+$) calcd for C$_{22}$H$_{20}$N$_5$O$_3$, 402.1566, found 402.1551.

Example 170

(1R,2R)-6-Oxo-8-[(2-phenyl-cyclopropanecarbonyl)-amino]-5,6-dihydro-1H-[1,2]diazepino[4,5,6-cd]indole-2-carboxylic Acid (2-hydroxy-ethyl)-amide

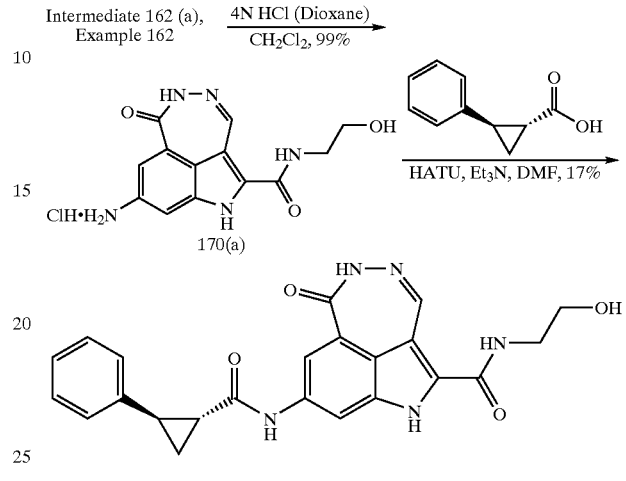

Step 1. Preparation of 8-Amino-6-oxo-5,6-dihydro-1H-[1,2]diazepino[4,5,6-cd]indole-2-carboxylic Acid (2-hydroxy-ethyl)-amide (Hydrochloric Salt) 170(a)

Preparation of intermediate 170(a) from intermediate 162 (a) of Example 162 (80.0 mg, 0.206 mmol) and 4.0 M HCl in dioxane (1.10 mL) was carried out analogously to Example 91. Isolation, also in an analogous manner, afforded Intermediate 170(a) (66.7 mg, 0.206 mmol) as a yellow powder in 99% yield.

LCMS: (M+H$^+$) 288.2.

Step 2. Preparation of Title Compound: (1R,2R)-6-Oxo-8-[(2-phenyl-cyclopropanecarbonyl)-amino]-5,6-dihydro-1H-[1,2]diazepino[4,5,6-cd]indole-2-carboxylic Acid (2-hydroxy-ethyl)-amide Preparation of the title compound from Intermediate 170(a) (66.7 mg, 0.206 mmol), (1R,2R)-2-phenyl-cyclopropanecarboxylic acid (46.0 mg, 0.284 mmol), triethylamine (0.143 mL, 1.03 mmol), and O-(7-azabenzotriazol-1-yl)-N,N,N',N'-tetramethyluronium hexafluorophosphate (147 mg, 0.387 mmol) in N,N-dimethylformamide (2.0 mL) was carried out analogously to Example 11. The reaction mixture was reduced in volume and subjected to preparative HPLC (H1-Q C18 reverse-phase 5 uM, 100A, 150×20 column eluting with CH$_3$CN/0.1% acetic acid in H$_2$O at a flowrate of 20 ml/min using a gradient of 20–60% CH$_3$CN over 30 min) to afford the title compound (15 mg, 0.0348 mmol) as a yellow powder in 17% yield.

$^1$H NMR (d$_6$-DMSO): δ 12.19 (s, 1H), 10.61 (s, 1H), 10.52 (s, 1H), 8.36 (t, 1H, J=5.65 Hz), 8.18 (d, 1H, J=1.70 Hz), 8.09 (s, 1H), 7.70 (d, 1H, J=1.70 Hz), 7.35–7.26 (m, 2H), 7.25–7.16 (m, 3H), 4.82 (t, 1H, J=5.46 Hz), 3.54 (dd, 2H, J=5.84, 5.65 Hz), 3.43–3.32 (m, 2H), 2.45–2.35 (m, 1H), 2.14–2.04 (m, 1H), 1.57–1.47 (m, 1H), 1.44–1.33 (m, 1H).

LCMS: (M+H$^+$) 432.0, (M+Na$^+$) 454.0.

HRMS: (M+H$^+$) calcd for C$_{23}$H$_{22}$N$_5$O$_4$, 432.1672, found 432.1648.

Example 171

(1R,2R)-6-Oxo-8-[(2-phenyl-cyclopropanecarbonyl)-amino]-5,6-dihydro-1H-[1,2]diazepino[4,5,6-cd]indole-2-carboxylic Acid (2-dimethylamino-ethyl)-amide

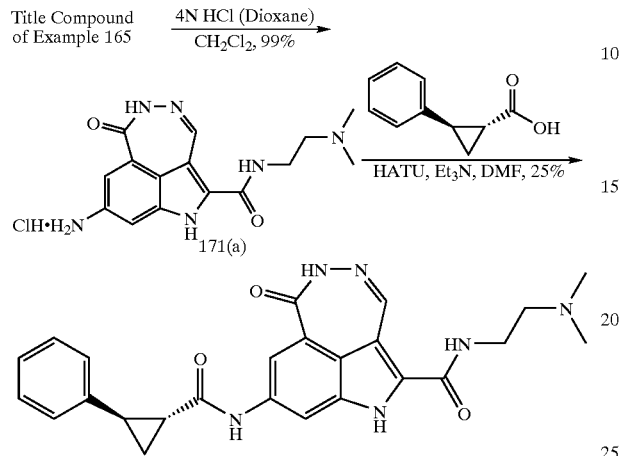

Step 1. Preparation of 8-Amino-6-oxo-5,6-dihydro-1H-[1,2]diazepino[4,5,6-cd]indole-2-carboxylic Acid (2-dimethylamino-ethyl)-amide; Dihydrochloride 171(a)

Preparation of intermediate 171(a) from the title compound of Example 165 (55.0 mg, 0.133 mmol) and 4.0 M HCl in dioxane (0.66 mL) was carried out analogously to Example 91. Isolation, also in an analogous manner, afforded Intermediate 171(a) (51.3 mg, 0.132 mmol) as a yellow powder in 99% yield.

LCMS: (M+H$^+$) 315.2.

Step 2. Preparation of Title Compound: (1R,2R)-6-Oxo-8-[(2-phenyl-cyclopropanecarbonyl)-amino]-5,6-dihydro-1H-[1,2]diazepino[4,5,6-cd]indole-2-carboxylic Acid (2-dimethylamino-ethyl)-amide Preparation of the title compound from Intermediate 171(a) (51.3 mg, 0.132 mmol), (1R,2R)-2-phenyl-cyclopropanecarboxylic acid (24.0 mg, 0.148 mmol), triethylamine (0.074 mL, 0.535 mmol), and O-(7-azabenzotriazol-1-yl)-N,N,N',N'-tetramethyluronium hexafluorophosphate (76.0 mg, 0.200 mmol) in N,N-dimethylformamide (2.0 mL) was carried out analogously to Example 11. The reaction mixture was reduced in volume and subjected to preparative HPLC (H1-Q C18 reverse-phase 5 uM, 100A, 150×20 column eluting with CH$_3$CN/0.1% acetic acid in H$_2$O at a flowrate of 20 mL/min using a gradient of 20–60% CH$_3$CN over 30 min) to afford the title compound (15 mg, 0.0328 mmol) as a yellow-green powder in 25% yield.

$^1$H NMR (d$_6$-DMSO): δ 10.63 (s, 1H), 10.53 (s, 1H), 8.71 (br s, 1H), 8.20 (d, 1H, J=1.13 Hz), 8.06 (s, 1H), 7.70 (d, 1H, J=0.94 Hz), 7.37–7.26 (m, 2H), 7.26–7.15 (m, 3H), 3.70–3.60 (m, 2H), 3.22–3.11 (m, 2H), 2.76 (s, 6H), 2.42–2.32 (m, 1H), 2.16–2.04 (m, 1H), 1.58–1.46 (m, 1H), 1.46–1.33 (m, 1H).

LCMS: (MH$^+$) 459.1, (M+Na$^+$) 481.1.

HRMS: (M+H$^+$) calcd for C$_{25}$H$_{27}$N$_6$O$_3$, 459.2145, found 459.2151.

Example 172

(1,2-trans)-2-(3-Morpholin-4-ylmethyl-phenyl)-cyclopropanecarboxylic Acid (6-oxo-5,6-dihydro-1-[1,2]diazepino[4,5,6]indol-8-yl)-amide

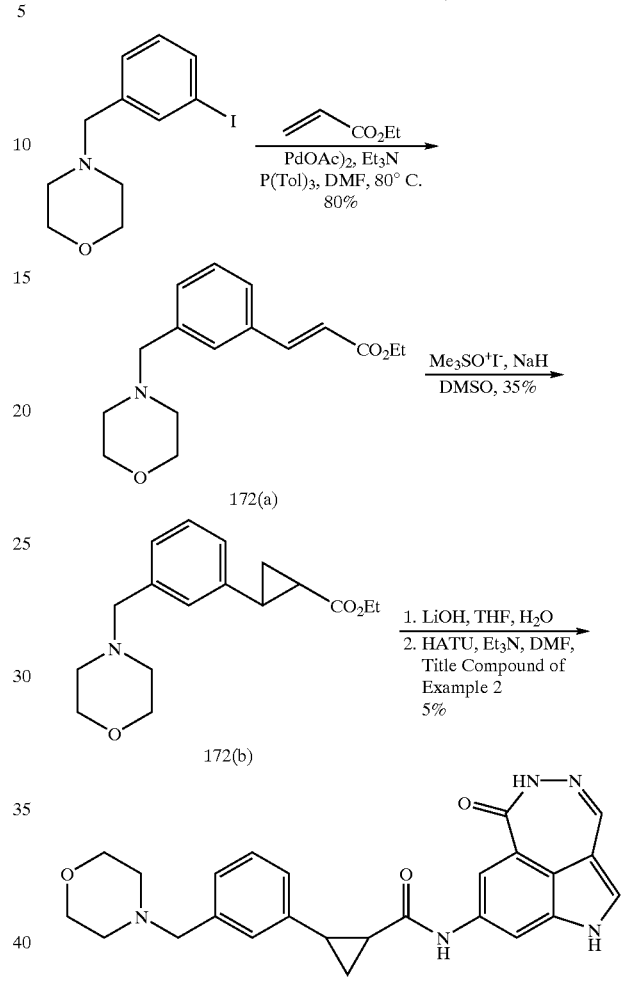

Step 1. Preparation of 3-(3-Morpholin-4-ylmethyl-phenyl)-acrylic Acid Ethyl Ester 172(a)

To a solution of 4-(3-iodo-benzyl)-morpholine (3.44 g, 11.4 mmol) in N,N-dimethylformamide (20 mL) was added triethylamine (1.7 mL, 12.5 mmol), ethyl acrylate (4.1 mL, 45.4 mmol), tri-o-tolylphosphine (346 mg, 1.14 mmol) and palladium (II) acetate (127 mg, 0.57 mmol). The mixture was heated at 80° C. overnight. After concentration, the mixture was chromatographed on silica gel to afford Intermediate 172(a) as a colorless oil (2.37 g, 9.1 mmol) in 80% yield.

Step 2. Preparation of (1,2-trans)-2-(3-Morpholin-4-ylmethyl-phenyl)-cyclopropanecarboxylic Acid Ethyl Ester 172(b)

Preparation of intermediate 172(b) from Intermediate 172(a) (472 mg, 1.81 mmol), NaH (94 mg, 2.35 mmol) and trimethylsulfoxonium iodide (517 mg, 2.35 mmol) was carried out analogously to step 1 of Example 181. After workup, the residue was purified by silica gel chromatography, eluting with 40% ethylacetate/hexane, to give Intermediate 172(b) as a colorless oil (175 mg, 0.64 mmol) in 35% yield.

Step 3. Preparation of Title Compound (1,2-trans)-2-(3-Morpholin-4-ylmethyl-phenyl)-cyclopropanecarboxylic Acid (6-oxo-5,6-dihydro-1H-[1,2]diazepino[4,5,6-cd]indol-8-yl)-amide To a solution of Intermediate 172(b) (175 mg, 0.64 mmol) in tetrahydrofuran (2 mL) was added 1 M aqueous LiOH (3.8 mL, 3.8 mmol). The resulting mixture was stirred overnight whereupon mixture was acidified to pH 2 and extracted with ethyl acetate. Concentration of the organic layer gave crude 2-(3-morpholin-4-ylmethyl-phenyl)-cyclopropanecarboxylic acid which was combined with the title compound from Example 2 (227 mg, 0.756 mmol), triethylamine (0.32 mL, 2.27 mmol), and O-(7-azabenzotriazol-1-yl)-N,N,N',N'-tetramethyluronium hexafluorophosphate (345 mg, 0.907 mmol) in N,N-dimethylformamide (5 mL). After was stirring overnight, the volatile components were removed under vacuum, and the residue was purified by silica gel chromatography to give the title compound as yellow solid (15 mg, 0.03 mmol) in 5% yield.

$^1$H NMR (CD$_3$OD): δ 8.30 (s, 1H), 7.69 (s, 1H), 7.61 (s, 2H), 7.51–7.28 (m, 4H), 3.84 (s, 4H), 3.66 (s, 2H), 2.61 (s, 4H), 2.45 (m, 1H), 2.21 (m, 1H), 1.76 (m, 1H), 1.53 (m, 1H).

LCMS: (M+H$^+$) 444.2

Example 173

(1,2-trans)-2-[3-(4-Methyl-piperazin-1-yl)-phenyl] cyclopropanecarboxylic Acid (6-oxo-5,6-dihydro-1H-[1,2]diazepino[4,5,6-cd]indol-8-yl)-amide

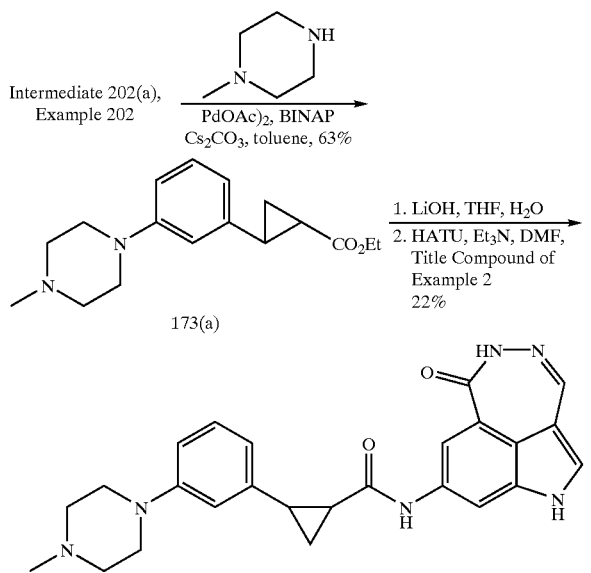

Step 1. Preparation of 2-[3-(4-Methyl-piperazin-1-yl)-phenyl]-cyclopropanecarboxylic Acid Ethyl Ester 173(a)

To a solution of Intermediate 202(a) of Example 202 (165 mg, 0.616 mmol) in toluene (4 mL) was added 2,2'-bis (diphenylphosphino)-1,1'-binaphthyl (34.5 mg, 0.055 mmol), 4-methylpiperazine (0.082 mL, 0.74 mmol), Cs$_2$CO$_3$ (281 mg, 0.862 mmol) and Pd(OAc)$_2$ (8.3 mg, 0.037 mmol). The mixture was refluxed overnight. The brown mixture was then filtered and the filter cake was washed with ethyl acetate. After concentrating the filtrate, the residue was purified by silica gel chromatography, eluting with 2–5% MeOH/CH$_2$Cl$_2$, to afford Intermediate 173(a) as a colorless oil (111 mg, 0.39 mmol) in 63% yield.

Step 2. Preparation of Title Compound: (1,2-trans)-2-[3-(4-Methyl-piperazin-1-yl)-phenyl]-cyclopropanecarboxylic Acid (6-oxo-5,6-dihydro-1H-[1,2]diazepino[4,5,6-cd]indol-8-yl)-amide In a manner similar to that described for step 3 of Example 172, Intermediate 173(a) was treated with 1 M aqueous LiOH to give crude 2-[3-(4-methyl-piperazin-1-yl)-phenyl]-cyclopropanecarboxylic acid. Crude 2-[3-(4-methyl-piperazin-1-yl)-phenyl]-cyclopropanecarboxylic acid was coupled to the title compound of Example 2 (71 mg, 0.3 mmol) also in a manner similar to that described for step 3 of Example 172. Extractive work-up from ethyl acetate and saturated aqueous NaHCO$_3$ afforded the crude product, which was purified by silica gel chromatography, eluting with 3% MeOH\CH$_2$Cl$_2$, to furnish the title compound (38 mg, 0.086 mmol) in 22% yield.

$^1$H NMR (d$_6$-DMSO): δ 11.70 (s, 1H), 10.38 (s, 1H), 10.23 (s, 1H), 8.13 (s, 1H), 7.59 (s, 1H), 7.56 (s, 1H), 7.47 (s, 1H), 7.13 (m, 1H), 6.79–6.74 (m, 2H), 6.58 (m, 1H), 3.22–3.12 (m, 4H), 2.51–2.47 (m, 4H), 2.33 (m, 1H), 2.27 (s, 3H), 2.08 (m, 1H), 1.46 (m, 1H), 1.36 (m, 1H).

LCMS: (M+H$^+$) 443.2

Example 174

(1,2-trans)-2-(3-Morpholin-4-yl-phenyl)-cyclopropanecarboxylic Acid (6-oxo-5,6-dihydro-1H-[1,2]diazepino[4,5,6-cd]indol-8-yl)-amide

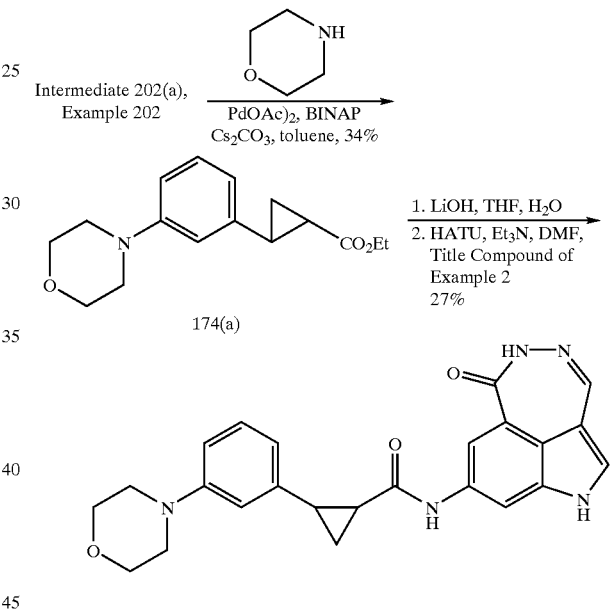

Step 1. Preparation of 2-[3-Morpholin-4-yl)-phenyl]-cyclopropanecarboxylic Acid Ethyl Ester 174(a)

Preparation of intermediate 174(a) from Intermediate 202(a) of Example 202 (239 mg, 0.892 mmol), 2,2'-bis (diphenylphosphino)-1,1'-binaphthyl (50 mg, 0.081 mmol), morpholine (0.12 mL, 1.34 mmol), Cs$_2$CO$_3$ (407 mg, 1.25 mmol) and Pd(OAc)$_2$ (12 mg, 0.054 mmol) in toluene (5 mL) was carried analogously to Example 173. After concentration, the residue was purified by silica gel chromatography, eluting with 1–2% MeOH/CH$_2$Cl$_2$ to afford Intermediate 174(a) as a colorless oil (84 mg, 0.31 mmol) in 34% yield.

Step 2. Preparation of Title Compound: (1,2-trans)-2-(3-Morpholin-4-yl-phenyl)-cyclopropanecarboxylic Acid (6-oxo-5,6-dihydro-1H-[1,2]diazepino[4,5,6-cd]indol-8-yl)-amide Preparation of the title compound was carried out analogously to step 3 of Example 172 except that Intermediate 174(a) was used instead of Intermediate 172(b). The title compound was obtained in 27% yield.

$^1$H NMR (d$_6$-DMSO): δ 10.37 (d, 1H, J=2.26 Hz), 10.24 (s, 1H), 8.24 (d, 1H, J=1.88 Hz), 7.58 (d, 1H, J=1.51 Hz), 7.56 (d, 1H, J=3.30 Hz), 7.47 (s, 1H), 7.15 (t, J=8.0 Hz, 1H), 6.79–6.77 (m, 2H), 6.61 (d, 1H, J=8.0 Hz), 3.74–3.72 (m, 4H), 2.23 (m, 1H), 2.07 (m, 1H), 1.46 (m, 1H), 1.38 (m, 1H).

LCMS: (M+H$^+$) 430.2

Example 175

(2R)-2-Amino-2-(4-hydroxyphenyl)-N-(6-oxo-2-phenyl-5,6-dihydro-1H-[1,2]diazepino[4,5,6-cd]indol-8-yl)ethanamide Hydrochloride

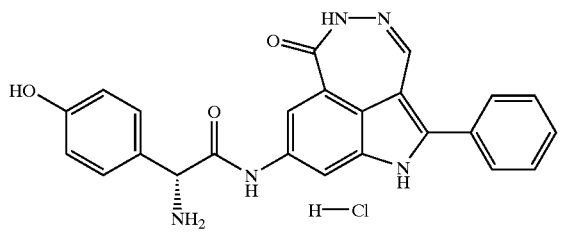

Preparation of example 175 from the title compound of Example 153 (38 mg, 0.072 mmol) and 4M HCl in dioxane (10 mL) was carried out analogously to Example 91. Isolation, also in an analogous manner, included freebasing with triethylamine and subsequent silica gel chromatography eluting with 3:1:1 hexane:ethyl acetate:ethanol. With ice bath cooling, the purified freebase in CH$_2$Cl$_2$ (10 mL) was treated with 4M HCl in dioxane (0.1 mL). After removal of the volatile components, the title compound (20 mg, 0.043 mmol) was obtained as an orange/yellow powder in 60% yield.

$^1$H NMR (d$_6$-DMSO): δ 12.23 (s, 1H), 10.82 (s, 1H), 10.45 (s, 1H), 8.71 (br s, 3H), 8.10 (s, 1H), 7.75–7.65 (m, 3H), 7.63–7.49 (m, 4H), 7.43 (d, 2H, J=8.47 Hz), 6.86 (d, 2H, J=8.47 Hz), 5.02 (m, 1H).

LCMS: (M+H$^+$) 426.2.

Example 176

(2R)-2-Amino-3-naphthalen-2-yl-N-(6-oxo-2-phenyl-5,6-dihydro-1H-[1,2]diazepino[4,5,6-cd]indol-8-yl)propanamide Hydrochloride

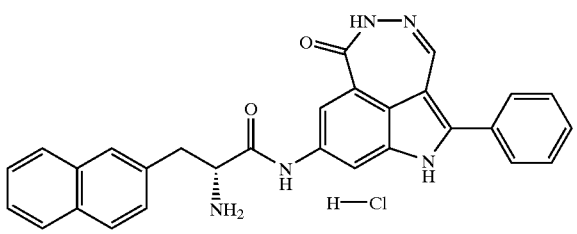

Preparation of example 176 from the title compound of Example 154 (59 mg, 0.103 mmol) and 4M HCl in dioxane (10 mL) was carried out analogously to Example 91. Isolation, also in an analogous manner afforded the title compound (52 mg, 0.102 mmol) as an orange/yellow powder in 99% yield.

$^1$H NMR (d$_6$-DMSO): δ 12.24 (s, 1H), 10.82 (s, 1H), 10.44 (s, 1H), 8.43 (br s, 3H), 8.07 (s, 1H), 7.93–7.81 (m, 5H), 7.71–7.45 (m, 9H), 4.32 (br s, 1H), 3.44 (m, 1H, partially obscured), 3.28 (m, 1H).

LCMS: (M+H$^+$) 474.2, (M+Na$^+$) 496.3.

Example 177

(2R)-2-Amino-N-(6-oxo-5,6-dihydro-1H-[1,2]diazepino[4,5,6-cd]indol-8-yl)-3-[(phenylmethyl)oxy]propanamide Hydrochloride

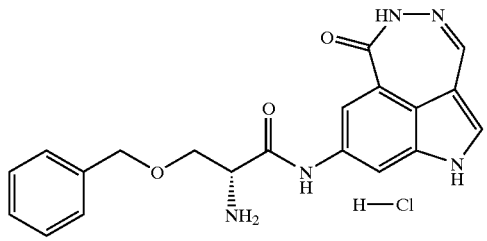

Preparation of example 177 from the title compound of Example 159 (35 mg, 0.072 mmol) and 4M HCl in dioxane (10 mL) was carried out analogously to Example 91. Isolation, also in an analogous manner afforded the title compound (30 mg, 0.072 mmol) as an orange/yellow powder in 100% yield.

$^1$H NMR (d$_6$-DMSO): δ 11.89 (s, 1H), 10.75 (s, 1H), 10.32 (s, 1H), 8.45 (br s, 3H), 8.06 (s, 1H), 7.63 (s, 2H), 7.50 (s, 1H), 7.38–7.26 (m, 5H), 4.59 (dd, 2H, J=12.25, 17.33 Hz), 4.24 (br s, 1H), 3.89 (d, 2H, J=4.15 Hz, partially obscured).

LCMS: (M+H$^+$) 378.2, (M+Na$^+$) 400.1.

Example 178

(2R)-2-Amino-3-(4-hydroxyphenyl)-N-(6-oxo-5,6-dihydro-1H-[1,2]diazepino[4,5,6-cd]indol-8-yl)propanamide Hydrochloride

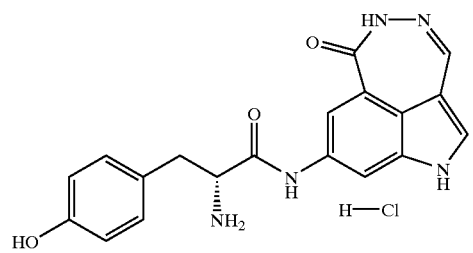

Preparation of example 178 from the title compound of Example 155 (90 mg, 0.194 mmol) and 4M HCl in dioxane (10 mL) was carried out analogously to Example 91. Isolation, also in an analogous manner afforded the title compound (56 mg, 0.140 mmol) as an orange/yellow powder in 72% yield.

$^1$H NMR (d$_6$-DMSO): δ 11.89 (s, 1H), 10.70 (s, 1H), 10.30 (s, 1H), 9.38 (br s, 1H), 8.34 (br s, 3H), 8.03 (s, 1H), 7.62 (s, 1H), 7.58 (s, 1H), 7.49 (s, 1H), 7.08 (d, 2H, J=8.29 Hz), 6.70 (d, 2H, J=8.29 Hz), 4.11 (br s, 1H), 2.93–3.15 (m, 2H).

LCMS:(M+Na$^+$) 386.5, (M−H)$^-$ 362.4.

Example 179

(2R)-2-Amino-3-naphthalen-2-yl-N-(6-oxo-5,6-dihydro-1H-[1,2]diazepino[4,5,6-cd]indol-8-yl) propanamide Hydrochloride

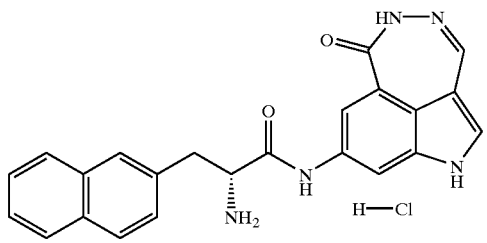

Preparation of example 179 from the title compound of Example 158 (57 mg, 0.115 mmol) and 4M HCl in dioxane (10 mL) was carried out analogously to Example 91. Isolation, also in an analogous manner afforded the title compound (48 mg, 0.111 mmol) as an orange/yellow powder in 97% yield.

$^1$H NMR (d$_6$-DMSO): δ 11.88 (s, 1H), 10.82 (s, 1H), 10.30 (s, 1H), 8.43 (br s, 3H), 8.04 (s, 1H), 7.93–7.78 (m, 4H), 7.64–7.57 (m, 2H), 7.54–7.45 (m, 4H), 4.32 (br s, 1H), 3.22–3.46 (m, 2H, partially obscured).

LCMS: (M+H$^+$) 398.5, (M+Na$^+$) 420.4.

Example 180

2-(1,1'-Biphenyl-4-yl)-N-(6-oxo-5,6-dihydro-1H-[1,2]diazepino[4,5,6-cd]indol-8-yl)acetamide

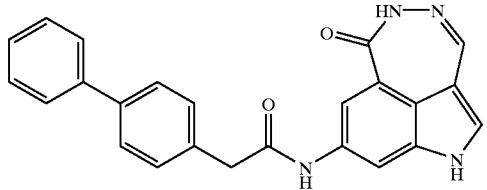

Preparation of example 180 from the title compound of Example 2 (75 mg, 0.38 mmol), 1,1'-biphenyl-4-ylacetic acid (93 mg, 0.44 mmol), triethylamine (0.16 mL, 1.15 mmol), and O-(7-azabenzotriazol-1-yl)-N, N,N',N'-tetramethyluronium hexafluorophosphate (167 mg, 0.44 mmol) in CH$_2$Cl$_2$ (1.0 mL) and N,N-dimethylformamide (1.0 mL) was carried out analogously to Example 11. Silica gel chromatography was performed twice eluting both times with 1:1 hexane:acetone and the purest fractions were combined, evaporated, and the resulting solids triturated with methanol to afford the title compound (5 mg, 0.012 mmol) as a yellow powder in 3% yield.

$^1$H NMR (d$_6$-DMSO): δ11.74 (s, 1H), 10.35 (s, 1H), 10.25 (s, 1H), 8.14 (s, 1H), 7.69–7.54 (m, 6H), 7.51–7.33 (m, 6H), 3.69 (s, 2H).

LCMS: (M+H$^+$) 395.4, (M+Na$^-$) 417.4.

Example 181

(1,2-trans)-2-(4-Hydroxy-phenyl)-cyclopropanecarboxylic Acid (6-oxo-5,6-dihydro-1H-[1,2]diazepino[4,5,6-cd]indol-8-yl)-amide

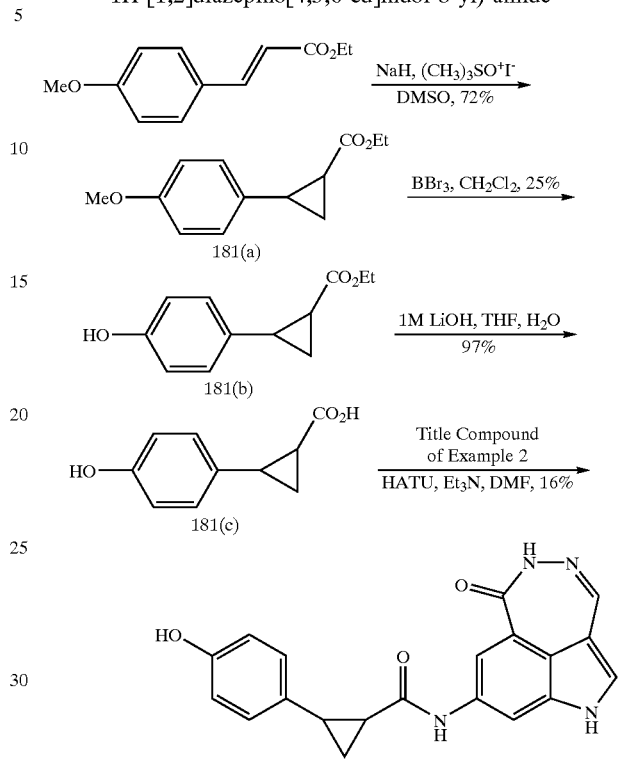

Step 1. Preparation of (1,2-trans)-2-(4-Methoxy-phenyl)-cyclopropanecarboxylic Acid Ethyl Ester 181(a)

To a mixture of NaH (200 mg, 5.0 mmol) and trimethylsulfoxonium iodide (1.1 g, 5.0 mmol) was added DMSO (10 mL). After stirring for 30 min, a solution of 3-(4-methoxyphenyl)-acrylic acid ethyl ester (400 mg, 1.92 mmol) in DMSO (5 mL) was added drop wise. After stirring overnight, the mixture was partitioned between ethyl acetate and water. The aqueous layer was re-extracted with ethyl acetate, and the combined organic layers were dried over Na$_2$SO$_4$ and concentrated. Purification by silica gel chromatography eluting with 10% ethyl acetate in hexane gave Intermediate 181(a) (318 mg, 1.44 mmol) in 72% yield.

Step 2. Preparation of (1,2-trans)-2-(4-Hydroxy-phenyl)-cyclopropanecarboxylic Acid Ethyl Ester 181(b)

To a stirred solution of Intermediate 181(a) (318 mg, 1.45 mmol) in CH$_2$Cl$_2$ (8 mL) at −78° C. was added 1M BBr$_3$ in CH$_2$Cl$_2$ (1.7 mL). The resulting mixture was then warmed to 23° C. and stirred for 30 min. The mixture was quenched with saturated aqueous NaHCO$_3$ and extracted with CH$_2$Cl$_2$. The organic layer was dried over anhydrous Na$_2$SO$_4$, filtered, concentrated, and subjected to silica gel chromatography eluting with 15% ethyl acetate in hexane to afford Intermediate 181(b) as a colorless oil (75 mg, 0.364 mmol) in 25% yield.

Step 3. Preparation of (1,2-trans)-2-(4-Hydroxy-phenyl)-cyclopropanecarboxylic Acid 181(c)

To a stirred solution of Intermediate 181(b) (75 mg, 0.36 mmol) in tetrahydrofuran (2.5 mL) was added aqueous 1M LiOH (2.5 mL). The resulting mixture was stirred at 23° C. for 12 hours. The mixture was then acidified with 1M HCl to pH 1 and extracted with ethyl acetate. The organic layer was then washed with brine and concentrated to give Intermediate 181(c) (63 mg, 0.35 mmol) in 97% yield which was carried on without further purification.

Step 4. Preparation of Title Compound: (1,2-trans)-2-(4-Hydroxy-phenyl)-cyclopropanecarboxylic Acid (6-oxo-5,6-dihydro-1H-[1,2]diazepino[4,5,6-cd]indol-8-yl)amide Preparation of the title compound from the title compound of Example 2 (66 mg, 0.278 mmol), Intermediate 181(c) (62 mg, 0.348 mmol), triethylamine (0.073 mL, 0.52 mmol), and O-(7-azabenzotriazol-1-yl)-N,N,N',N'-tetramethyluronium hexafluorophosphate (159 mg, 0.42 mmol) in N,N-dimethylformamide (2 mL) was carried out analogously to Example 11. Silica gel chromatography (eluted with 2% methanol in CH$_2$Cl$_2$), also in an analogous manner, afforded the title compound (20 mg, 0.056 mmol) as a yellow powder in 16% yield.

$^1$H NMR (d$_6$-DMSO): 12.09 (s, 1H), 10.38 (s, 1H), 10.37 (s, 1H), 9.26 (br s, 1H), 8.16 (s, 1H), 7.65–7.67 (m, 2H), 7.58 (t, J=8.0 Hz, 1H), 7.50 (s, 1H), 7.00 (d, J=8.0 Hz, 2H), 6.70 (d, J=8.0 Hz, 2H), 2.33 (m, 1H), 1.98 (m, 1H), 1.43 (m, 1H), 1.24 (m, 1H).

LCMS: (M+H$^+$) 361.3.

Example 182

(1,2-trans)-2-(4-Hydroxy-phenyl)-cyclopropanecarboxylic Acid (6-oxo-2-phenyl-5,6-dihydro-1-[1,2]diazepino[4,5,6]indol-8-yl)-amide

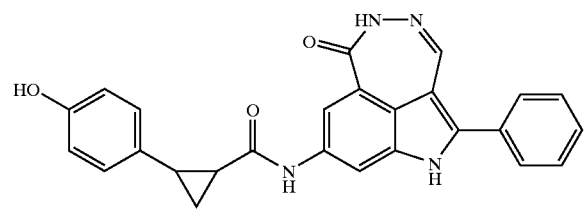

Preparation of example 182 from the title compound of Example 7 (35 mg, 0.127 mmol), Intermediate 181(c) of Example 181 (66 mg, 0.372 mmol), triethylamine (0.062 mL, 0.45 mmol), and O-(7-azabenzotriazol-1-yl)-N,N,N',N'-tetramethyluronium hexafluorophosphate (156 mg, 0.41 mmol) in N,N-dimethylformamide (3 mL) was carried out analogously to Example 11. Silica gel chromatography (eluted with 2% methanol in CH$_2$Cl$_2$), also in an analogous manner, gave the title compound (32 mg, 0.073 mmol) as a yellow powder in 20% yield.

$^1$H NMR (d$_4$-methanol): 8.04 (s, 1H), 7.44 (s, 1H), 7.35 (s, 1H), 7.34 (s, 1H), 6.91 (d, J=9.0 Hz, 2H), 6.62 (d, J=9.0 Hz, 2H), 2.31 (m, 1H), 1.87 (m, 1H), 1.43 (m, 1H), 1.24 (m, 1H).

LCMS: (M+H$^+$) 437.4.

Example 183

(2-Ethyl-6-oxo-5,6-dihydro-1H-[1,2]diazepino[4,5,6-cd]indol-8-yl)-carbamic Acid tert-butyl Ester Title Compound of Example 164 →[Pd/C, H$_2$, DMF, MeOH][69%]

Palladium (10% on activated carbon) (0.23 g, 0.198 mmol) was added to a solution of the title compound of Example 164 (0.65 g, 1.99 mmol) in 1:10 N,N-dimethylformamide: methanol (11 mL). The reaction mixture was purged with H$_2$ and stirred at room temperature under H$_2$ (1 atm.) for 5 hours. The palladium was filtered and the volatile components were removed in vacuo. The resulting residue was dissolved in methanol and loaded onto a silica gel plug. The plug was then loaded onto a silica gel column and eluted with 1.2:1 dichloromethane: ethyl acetate to afford the title compound (0.45 g, 1.37 mmol) as a yellow solid in 69% yield.

$^1$H NMR (d$_6$-DMSO): δ 11.54 (s, 1H), 10.05 (s, 1H), 9.37 (s, 1H), 7.63 (s, 1H), 7.58 (s, 1H), 7.44 (s, 1H), 2.80 (dd, 2H, J=7.35, 7.54 Hz), 1.48 (s, 9H), 1.23 (t, 3H, J=7.54 Hz).

LCMS: (M+H$^+$) 329.5, (M+Na$^+$) 351.5; (M–H) 327.4.

Example 184

4-(8-tert-Butoxycarbonylamino-6-oxo-5,6-dihydro-1H-[1,2]diazepino[4,5,6-cd]indol-2-yl)-3,6-dihydro-2H-pyridine-1-carboxylic Acid tert-butyl Ester

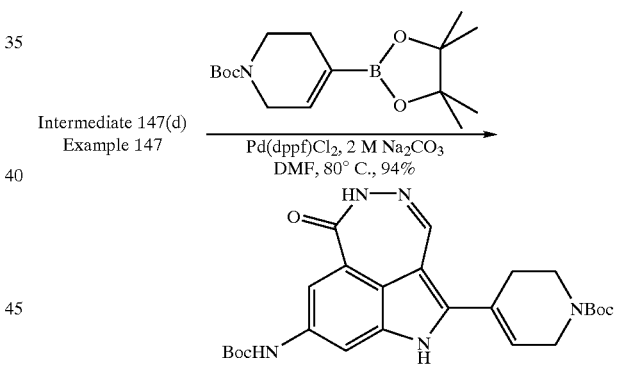

Under an argon atmosphere, 2.0 M aqueous Na$_2$CO$_3$ (0.66 mL) was added to a mixture of Intermediate 147(d) of Example 147 (100 mg, 0.265 mmol), 4-(4,4,5,5-tetramethyl-[1,3,2]dioxaborolan-2-yl)-3,6-dihydro-2H-pyridine-1-carboxylic Acid tert-butyl Ester (122 mg, 0.395 mmol) and [1,1'-bis(diphenylphosphino)ferrocene]dichloropalladium (II) (10.8 mg, 0.013 mmol) in anhydrous N,N-dimethylformamide (5 ml). The mixture was heated at 80° C. for 16 hours. The reaction was filtered through a thin pack of diatomaceous earth, and the volatile components were removed in vacuo. Silica gel chromatography (eluted with 1:1 ethyl acetate:hexane) afforded the title compound (120 mg, 0.249 mmol) as a yellow powder in 94% yield.

$^1$H NMR (d$_6$-DMSO): δ 11.62 (s, 1H), 10.22 (s, 1H), 9.46 (s, 1H), 7.69 (s, 1H), 7.65 (d, 1H, J=1.70 Hz), 7.49 (s, 1H), 6.16 (s, 1H), 4.06 (s, 2H), 3.56 (t, 2H, J=5.65, 4.90 Hz), 3.31 (m, 2H, partially obscured), 1.49 (s, 9H), 1.44 (s, 9H).

LCMS: (M+H$^+$) 482.5, (M+Na$^+$) 504.5; (M–H)$^-$ 480.5.

HRMS: (M+H⁺) calcd for $C_{25}H_{32}N_5O_5$, 482.2403, found 482.2417.

The 4-(4,4,5,5-tetramethyl-[1,3,2]dioxaborolan-2-yl)-3,6-dihydro-2H-pyridine-1-carboxylic acid tert-butyl ester starting material was prepared according to Eastwood, P. R. (2000) Tetrahedron Letters 41(19):3705–3708 from trifluoromethanesulfonic acid 1-tert-butoxycarbonyl-1,2,3,6-tetrahydropyridin-4-yl ester which in turn was prepared according to the procedure outlined by Barrow, J. C. et. al.(2000) J. Med. Chem. 43(14) 2703–2718.

Example 185

8-Amino-2-(1,2,3,6-tetrahydro-pyridin-4-yl)-1,5-dihydro-[1,2]diazepino[4,5,6-cd]indol-6-one

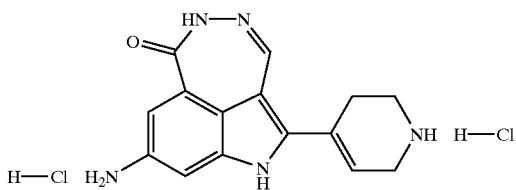

Preparation of example 185 from the title compound of Example 184 (20 mg, 0.042 mmol) and 4.0 M HCl in dioxane (0.1 mL) was carried out analogously to Example 91. Isolation, also in an analogous manner, afforded the title compound (14.7 mg, 0.042 mmol) as a yellow powder in 99% yield.

¹H NMR (d₆-DMSO): δ 12.20 (br s, 1H), 10.46 (s, 1H), 9.14 (s, 3H), 7.57 (s, 1H), 7.36 (s, 2H), 6.22 (s, 1H), 3.83 (s, 2H), 3.36 (s, 2H), 2.74 (s, 2H).

LCMS: (M+Na⁺) 304.3; (M–H)⁻ 280.2.

HRMS: (M+H⁺) calcd for $C_{15}H_{16}N_5O$, 282.1355, found 282.1349.

Example 186

(1R,2R)-2-Phenyl-cyclopropanecarboxylic Acid (2-ethyl-6-oxo-5,6-dihydro-1H-[1,2]diazepino[4,5,6-cd]indol-8-yl)-amide

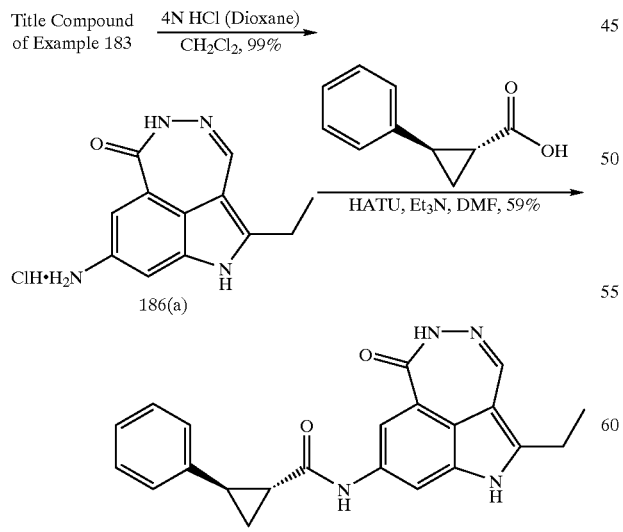

Step 1. Preparation of 8-Amino-2-ethyl-1,5-dihydro-[1,2]diazepino[4,5,6-cd]indol-6-one (Hydrochloric Salt) 186(a)

Preparation of intermediate 186(a) from the title compound of Example 183 (120 mg, 0.366 mmol) and 4.0 M HCl in dioxane (0.92 mL) was carried out analogously to Example 91. Isolation, also in an analogous manner, afforded Intermediate 186(a) (95.5 mg, 0.366 mmol) as a yellow powder in 99% yield.

LCMS: (M+H⁺) 229.1.

Step 2. Preparation of Title Compound: (1R,2R)-2-Phenyl-cyclopropanecarboxylic Acid (2-ethyl-6-oxo-5,6-dihydro-1H-[1,2]diazepino[4,5,6-cd]indol-8-yl)-amide Preparation of the title compound from Intermediate 186(a) (95.5 mg, 0.366 mmol), (1R,2R)-2-phenyl-cyclopropanecarboxylic acid (65.0 mg, 0.401 mmol), triethylamine (0.510 mL, 3.66 mmol), and O-(7-azabenzotriazol-1-yl)-N,N,N',N'-tetramethyluronium hexafluorophosphate (210 mg, 0.552 mmol) in N,N-dimethylformamide (4.0 mL) was carried out analogously to Example 11. The volatile components were removed in vacuo and the resulting residue was dissolved in methanol and loaded onto a silica gel plug. The plug was then loaded onto a silica gel column and eluted with 1.2:1 dichloromethane: ethyl acetate to afford the title compound (80 mg, 0.215 mmol) as a yellow solid in 59% yield.

¹H NMR (d₆-DMSO): δ 11.63 (s, 1H), 10.31 (s, 1H), 10.09 (s, 1H), 8.00 (d, 1H, J=1.51 Hz), 7.52 (d, 1H, J=1.51 Hz), 7.45 (s, 1H), 7.34–7.24 (m, 2H), 7.24–7.13 (m, 3H), 2.81 (q, 2H, J=7.54 Hz), 2.41–2.31 (m, 1H), 2.11–2.00 (m, 1H), 1.53–1.43 (m, 1H), 1.40–1.29 (m, 1H), 1.23 (t, 3H, J=7.54 Hz).

LCMS: (M+H⁺) 373.1.

HRMS: (M+H⁺) calcd for $C_{22}H_{21}N_4O_2$, 371.1665, found 373.1672.

Example 187

(2-Chloro-6-oxo-5,6-dihydro-1H-[1,2]diazepino[4,5,6-cd]indol-8-yl)-carbamic Acid tert-butyl Ester Intermediate 147(c), Example 147 → NCS, DMF, 50° C., 90%

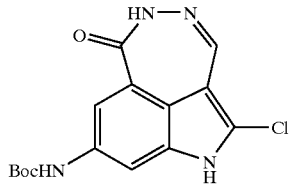

N-Chlorosuccinimide (0.47 g, 3.52 mmol) was added to a solution of Intermediate 147(c) of Example 147 (1.00 g, 3.33 mmol) in anhydrous N,N-dimethylformamide (10 ml) and anhydrous chloroform (6.5 mL). The reaction was heated at 50° C. for 3 hours at which point the volatile components were removed in vacuo. The resulting residue was dissolved in methanol and loaded onto a silica gel plug. The plug was then loaded onto a silica gel column and eluted with 23:2:50 dichloromethane: methanol: ethyl acetate to afford the tide compound (1 g, 2.99 mmol) as a yellow solid in 90% yield.

¹H NMR (d₆-DMSO): δ 12.52 (s, 1H), 10.41 (s, 1H), 9.51 (s, 1H), 7.70 (s, 1H), 7.66 (s, 1H), 7.32 (s, 1H), 1.47 (s, 9H).

LCMS: (M+H⁺) 335.1, (M+Na⁺) 357.0; (M–H)⁻ 333.0.

Example 188

(1,2-trans)-2-Pyridin-3-yl-cyclopropanecarboxylic Acid (2-ethyl-6-oxo-5,6-dihydro-1H-[1,2]diazepino[4,5,6-cd]indol-8-yl)-amide

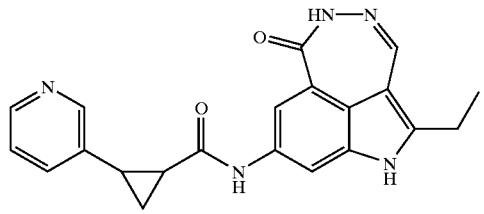

Preparation of example 188 from Intermediate 186(a) of Example 186 (90 mg, 0.341 mmol), crude (1,2-trans)-2-pyridin-3-yl-cyclopropanecarboxylic acid (see Example 125 for preparation-estimated purity c.a. 75%) (79.5 mg, c.a. 0.341 mmol), triethylamine (0.237 mL, 1.73 mmol), and O-(7-azabenzotriazol-1-yl)-N,N,N',N'-tetramethyluronium hexafluorophosphate (194 mg, 0.510 mmol) in N,N-dimethylformamide (4.0 mL) was carried out analogously to Example 11. The volatile components were removed in vacuo, and the resulting residue was dissolved in methanol and loaded onto a silica gel plug. The plug was then loaded onto a silica gel column and eluted with 50:3 dichloromethane: methanol to afford the title compound (75 mg, 0.201 mmol) as a yellow solid in 59% yield.

$^1$H NMR (d$_6$-DMSO): δ 11.65 (s, 1H), 10.36 (s, 1H), 10.11 (s, 1H), 8.51 (d, 1H, J=1.88 Hz), 8.42 (dd, 1H, J=1.32, 1.32 Hz), 8.01 (d, 1H, J=1.70 Hz), 7.57 (dt, 1H, J=7.91, 1.88 Hz), 7.53 (d, 1H, J=1.70 Hz), 7.47 (s, 1H), 7.33 (dd, 1H, J=4.90, 4.71 Hz), 2.82 (q, 2H, J=7.54 Hz), 2.47–2.38 (m, 1H), 2.17–2.08 (m, 1H), 1.58–1.49 (m, 1H), 1.49–1.39 (m, 1H), 1.24 (t, 3H, J=7.54 Hz).

LCMS: (M+H$^+$) 374.2, (M+Na$^+$) 396.0; (M−H)$^−$ 372.0.

HRMS: (M+H$^+$) calcd for C$_{21}$H$_{20}$N$_5$O$_2$, 374.1617, found 374.1620.

Example 189

(R)-2-Amino-2-cyclohexyl-N-(2-ethyl-6-oxo-5,6-dihydro-1H-[1,2]diazepino[4,5,6-cd]indol-8-yl)-acetamide (Hydrochloride Salt)

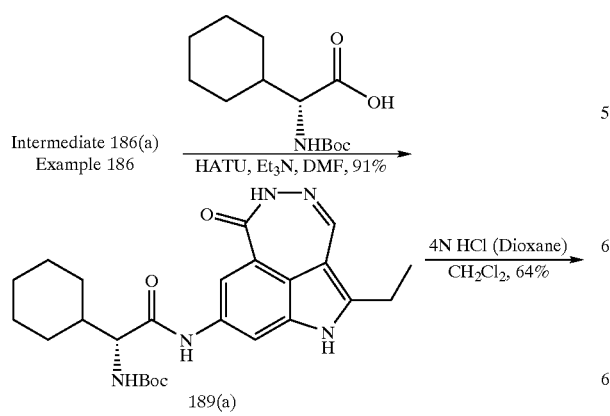

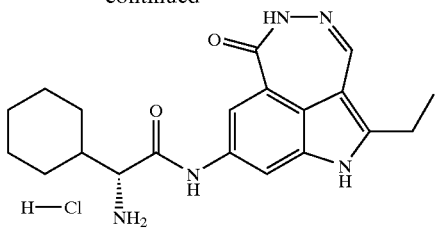

Step 1. Preparation of (R)-[Cyclohexyl-(2-ethyl-6-oxo-5,6-dihydro-1H-[1,2]diazepino[4,5,6-cd]indol-8-ylcarbamoyl)-methyl]-carbamic Acid tert-butyl Ester 189(a)

Preparation of intermediate 189(a) from Intermediate 186(a) of Example 186 (90 mg, 0.341 mmol), (R)-tert-butoxycarbonylamino-cyclohexyl-acetic acid (88 mg, 0.342 mmol), triethylamine (0.237 mL, 1.73 mmol), and O-(7-azabenzotriazol-1-yl)-N,N,N',N'-tetramethyluronium hexafluorophosphate (194 mg, 0.510 mmol) in N,N-dimethylformamide (4.0 mL) was carried out analogously to Example 11. The volatile components were removed in vacuo, and the resulting residue was dissolved in methanol and loaded onto a silica gel plug. The plug was then loaded onto a silica gel column and eluted with 1.2:1 dichloromethane: ethyl acetate to afford Intermediate 189(a) (146 mg, 0.313 mmol) as a yellow solid in 91% yield.

$^1$H NMR (d$_6$-DMSO): δ 11.64 (s, 1H), 10.12 (s, 1H), 10.02 (s, 1H), 7.99 (s, 1H), 7.54 (s, 1H), 7.47 (s, 1H), 6.87 (d, 1H, J=7.72 Hz), 3.92 (t, 1H, J=8.48 Hz), 2.82 (q, 2H, J=7.54 Hz), 1.78–1.46 (m, 6H), 1.38 (s, 9H), 1.24 (t, 3H, J=7.54 Hz), 1.19–0.94 (m, 5H).

LCMS: (M+H$^+$) 468.2, (M+Na$^+$) 490.2.

Step 2. Preparation of Title Compound: (R)-2-Amino-2-cyclohexyl-N-(2-ethyl-6-oxo-5,6-dihydro-1H-[1,2]diazepino[4,5,6-cd]indol-8-yl)-acetamide (Hydrochloric Salt)

Preparation of the title compound from Intermediate 189(a) (136 mg, 0.291 mmol) and 4.0 M HCl in dioxane (1.5 mL) was carried out analogously to Example 91. Isolation, also in an analogous manner, afforded the title compound (75 mg, 0.186 mmol) as a yellow powder in 64% yield.

$^1$H NMR (d$_6$-DMSO): δ 11.81 (s, 1H), 10.66 (s, 1H), 10.19 (s, 1H), 8.42–8.20 (m, 3H), 7.98 (s, 1H), 7.59 (s, 1H), 7.50 (s, 1H), 3.82–3.66 (m, 1H), 2.84 (q, 2H, J=7.54 Hz), 1.94–1.53 (m, 6H), 1.30–0.98 (m, 8H).

LCMS: (M+H$^+$) 368.1, (M+Na$^+$) 390.2; (M−H)$^−$ 366.1.

HRMS: (M+H$^+$) calcd for C$_{20}$H$_{26}$N$_5$O$_2$, 368.2087, found 368.2084.

Example 190

(1R,2R)-2-Phenyl-cyclopropanecarboxylic Acid (2-chloro-6-oxo-5,6-dihydro-1H-[1,2]diazepino[4,5,6-cd]indol-8-yl)-amide

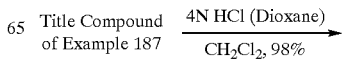

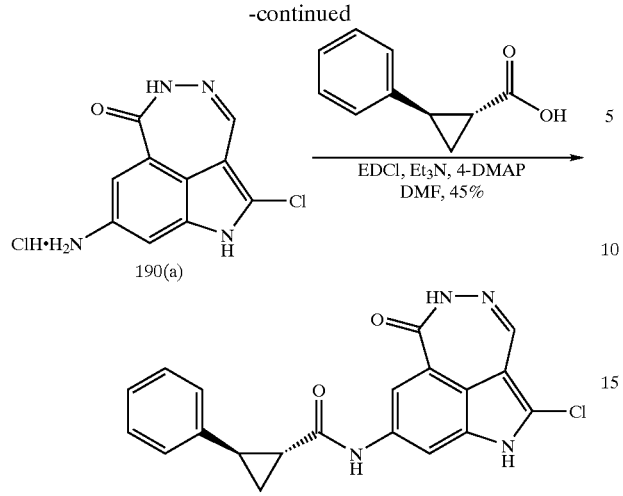
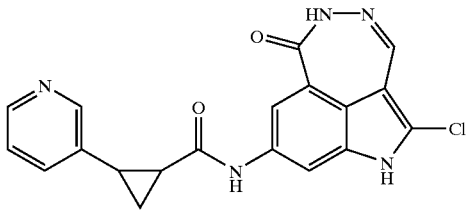

Step 1. Preparation of 8-Amino-2-chloro-1,5-dihydro-[1,2]diazepino[4,5,6-cd]indol-6-one (Hydrochloric Salt) 190(a)

Preparation of intermediate 190(a) from the title compound of Example 187 (0.83 g, 2.48 mmol) and 4.0 M HCl in dioxane (6.2 mL) was carried out analogously to Example 91. Isolation, also in an analogous manner, afforded Intermediate 190(a) (0.66 g, 2.44 mmol) as a yellow powder in 98% yield.

$^1$H NMR (d$_6$-DMSO): δ 12.87 (s, 1H), 10.57 (s, 1H), 7.38 (s, 2H), 7.27 (s, 1H).

LCMS: (M–H)$^-$ 233.1.

Step 2. Preparation of Title Compound: (1R,2R)-2-Phenyl-cyclopropanecarboxylic Acid (2-chloro-6-oxo-5,6-dihydro-1H-[1,2]diazepino[4,5,6-cd]indol-8-yl)-amide Intermediate 190(a) (120 mg, 0.443 mmol), (1R,2R)-2-phenyl-cyclopropanecarboxylic acid (86.0 mg, 0.531 mmol), (3-dimethylamino-propyl)-ethyl-carbodiimide hydrochloride (102 mg, 0.534 mmol), and 4-dimethylaminopyridine (65 mg, 0.533 mmol) were stirred in N,N-dimethylformamide (7.0 mL) at room temperature for 16 h at which point the volatile components were removed in vacuo. The resulting residue was dissolved in methanol and loaded onto a silica gel plug. The plug was then loaded onto a silica gel column and eluted with 1.2:1 dichloromethane: ethyl acetate to afford the title compound (75 mg, 2.99 mmol) as a yellow solid in 45% yield.

$^1$H NMR (d$_6$-DMSO): δ 12.65 (s, 1H), 10.46 (s, 2H), 8.09 (s, 1H), 7.63 (s, 1H), 7.36 (s, 1H), 7.34–7.25 (m, 2H), 7.25–7.12 (m, 3H), 2.44–2.30 (m, 1H), 2.13–2.01 (m, 1H), 1.57–1.44 (m, 1H), 1.44–1.31 (m, 1H).

LCMS: (M–H)$^-$ 377.1.

HRMS: (M+H$^+$) calcd for C$_{20}$H$_{16}$N$_4$O$_2$Cl, 379.0962, found 379.0941.

Example 191

(1,2-trans)-2-Pyridin-3-yl-cyclopropanecarboxylic Acid (2-chloro-6-oxo-5,6-dihydro-1H-[1,2]diazepino[4,5,6-cd]indol-8-yl)-amide Preparation of example 191 from Intermediate 190(a) of Example 190 (120 mg, 0.443 mmol), crude 2-pyridin-3-yl-cyclopropanecarboxylic acid (estimated purity c.a. 75%) (124 mg, c.a. 0.532 mmol), (3-dimethylamino-propyl)-ethyl-carbodiimide hydrochloride (102 mg, 0.534 mmol), and 4-dimethylaminopyridine (65 mg, 0.533 mmol) in N,N-dimethylformamide (7.0 mL) was carried out analogously to Example 190, Step 2. When the reaction was judged complete, the volatile components were removed in vacuo, and the resulting residue was dissolved in methanol and loaded onto a silica gel plug. The plug was then loaded onto a silica gel column and eluted with 50:3 dichloromethane: methanol to afford the title compound (80 mg, 0.210 mmol) as a yellow solid in 48% yield.

$^1$H NMR (d$_6$-DMSO): δ 12.65 (s, 1H), 10.48 (s, 1H), 10.46 (s, 1H), 8.51 (s, 1H), 8.42 (d, 1H, J=3.20 Hz), 8.09 (d, 1H, J=1.13 Hz), 7.63 (d, 1H, J=1.32 Hz), 7.57 (d, 1H, J=7.91 Hz), 7.40–7.28 (m, 2H), 2.47–2.37 (m, 1H), 2.19–2.06 (m, 1H), 1.60–1.50 (m, 1H), 1.50–1.40 (m, 1H).

LCMS: (M+H$^+$) 380.0, (M+Na$^+$) 402.1; (M–H)$^-$ 378.0.

HRMS: (M+H$^+$) calcd for C$_{19}$H$_{15}$N$_5$O$_2$Cl, 380.0914, found 380.0922.

Example 192

N-(6-oxo-5,6-dihydro-1H-[1,2]diazepino[4,5,6-cd]indol-8-yl)-N'-(phenylmethyl)urea

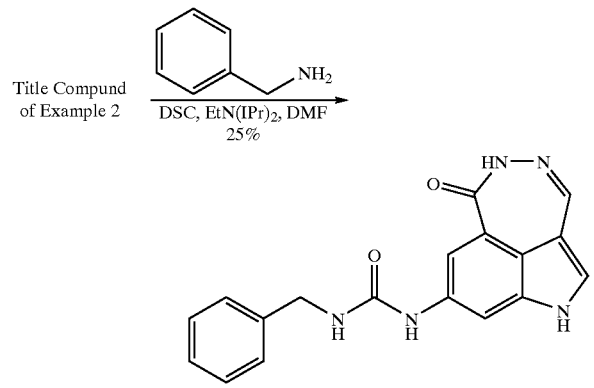

To the title compound of Example 2 (45 mg, 0.19 mmol) and N,N'-disuccinimidyl carbonate (49 mg, 0.19 mmol) was added N,N-dimethylformamide (0.5 mL) and triethylamine (0.084 mL, 0.60 mmol). After 3 to 5 min, benzylamine (0.046 mL, 0.20 mmol) was added, and the reaction was stirred for about an hour. Methylene chloride:methanol (4:1) was added and the resulting solids were removed by trituration. The triturate was loaded onto a silica gel plug and evaporated. The plug was then loaded onto a silica gel column and eluted with hexane:acetone (1:1) and the purest fractions were combined. After solvent removal, the title compound (16 mg, 0.048 mmol) was obtained as brown powder in 25% yield.

$^1$H NMR (d$_6$-DMSO): δ 11.61 (s, 1H, exchanges), 10.19 (s, 1H, exchanges), 8.75 (s, 1H, exchanges), 7.93 (s, 1H), 7.49 (m, 1H), 7.40–7.30 (m, 7H), 6.55 (m, 1H, exchanges), 4.31 (d, 2H, J=5.84 Hz).

LCMS: (M+H$^+$) 334.2, (M+Na$^+$) 356.3

Example 193

(2R)-3-(4-Hydroxyphenyl)-2-(methylamino)-N-(6-oxo-5,6-dihydro-1H-[1,2]diazepino[4,5,6-cd]indol-8-yl)propanamide Hydrochloride

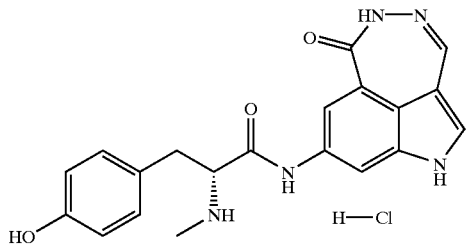

Preparation of example 193 from the title compound of Example 156 (121 mg, 0.25 mmol) and 4M HCl in dioxane (10 mL) was carried out analogously to Example 91. Isolation, also in an analogous manner, afforded the title compound (74 mg, 0.18 mmol) as an orange/yellow powder in 72% yield.

$^1$H NMR (d$_6$-DMSO): major component/conformer: δ 11.89 (s, 1H, exchanges), 10.73 (s, 1H, exchanges), 10.31 (s, 1H, exchanges), 9.36 (br s, 2H, exchanges), 9.11 (br s, 1H, exchanges), 7.99 (s, 1H), 7.64 (s, 1H), 7.56 (s, 1H), 7.50 (s, 1H), 7.06 (d, 2H, J=8.48 Hz), 6.69 (d, 2H, J=8.48 Hz), 4.11 (m, 1H), 3.18 (m, 1H), 3.08 (m, 1H), 2.55 (s, 3H, partially obscurred).

LCMS: (M+H$^+$) 378.0, (M+Na$^+$) 400.1.

Example 194

(2R)-2-Amino-3-(4-fluorophenyl)-N-(6-oxo-5,6-dihydro-1H-[1,2]diazepino[4,5,6-cd]indol-8-yl)propanamide Hydrochloride

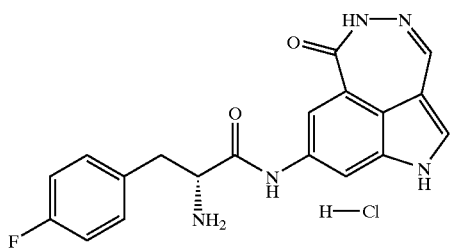

Preparation of example 194 from the title compound of Example 157 (48 mg, 0.10 mmol) and 4M HCl in dioxane (10 mL) was carried out analogously to Example 91. Isolation, also in an analogous manner afforded the title compound (34 mg, 0.08 mmol) as an orange/yellow powder in 80% yield.

$^1$H NMR (d$_6$-DMSO): δ 11.88 (s, 1H, exchanges), 10.72 (s, 1H, exchanges), 10.32 (s, 1H, exchanges), 8.37 (br s, 4H, exchanges), 8.04 (s, 1H), 7.64 (s, 1H), 7.57 (s, 1H), 7.50 (s, 1H), 7.38–7.29 (m, 2H), 7.22–7.14 (m, 2H), 4.19 (m, 1H), 3.26–3.03 (m, 2H).

LCMS: (M+H$^+$) 366.0, (M+Na$^+$) 388.1.

Example 195

N-(6-Oxo-5,6-dihydro-1H-[1,2]diazepino[4,5,6-cd]indol-8-yl)-2-(3H-[1,2,3]triazolo[4,5-b]pyridin-3-yloxy)acetamide

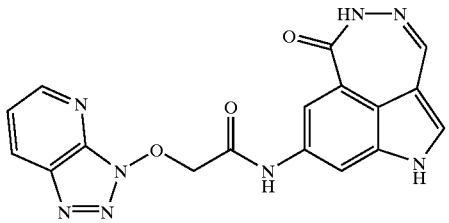

In a manner analogous to that of Example 19, to a stirred suspension of 8-amino-1,5-dihydro-6H-[1,2]diazepino[4,5,6-cd]indol-6-one hydrochloride in anhydrous N,N-dimethylformamide (9 mL) was added bromoacetic acid (168 mg, 1.2 mmol), O-(7-azabenzotriazol-1-yl)-N,N,N',N'-tetramethyluronium hexafluorophosphate (553 mg, 1.4 mmol) and triethylamine The reaction was stirred at room temperature for 16 hours. The volatile components were evaporated and water was added to the residue. The precipitated orange solids were collected by filtration and washed with water and ethyl acetate. After drying, the title compound (158 mg) was obtained as an orange powder in 35% yield.

$^1$H NMR (DMSO-d$_6$) d: 5.28 (1H, s), 7.47 (1H, s), 7.58 (3H, m), 8.09 (1H, d, J=1.77 Hz), 8.63 (1H, dd, J=8.59 Hz), 8.83 (1H, dd, J=4.55 Hz), 10.27 (1H, s), 10.52 (1H, s), 11.77 (1H, s).

LCMS: (M+H$^+$) 377.

Example 196

(1,2-trans)-2-(3-Methoxy-phenyl)-cyclopropanecarboxylic Acid (6-oxo-5,6-dihydro-1H-[1,2]diazepino[4,5,6-cd]indol-8-yl)-amide

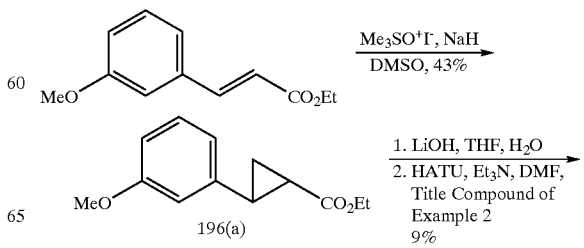

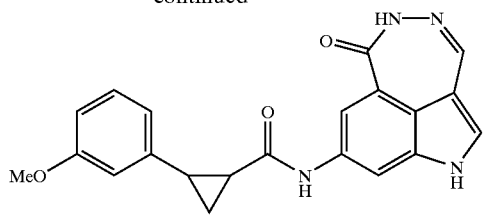

Step 1: Preparation of (1,2-trans)-2-(3-Methoxy-phenyl)-cyclopropanecarboxylic Acid Ethyl Ester 196(a)

Preparation of intermediate 196(a) from NaH (1.04 g, 26 mmol) and trimethylsulfoxonium iodide (5.72 g, 26 mmol), 3-(methoxy-phenyl)-acrylic acid ethyl ester (4.12 g, 20 mmol) in DMSO (30 mL) was carried out analogously to step 2 of Example 113 to afford Intermediate 196(a) (1.89 g, 8.6 mmol) in 43% yield.

Step 2: Preparation of Title Compound: (1,2-trans)-2-(3-Methoxy-phenyl)-cyclopropanecarboxylic Acid (6-oxo-5,6-dihydro-1-[1,2]diazepino[4,5,6-]indol-8-yl)-amide Preparation of the title compound was carried out analogously to step 3 of Example 172 except that Intermediate 196(a) was used instead of Intermediate 172(b). The title compound was obtained in 9% yield.

$^1$H NMR (d$_6$-DMSO): δ 11.85 (d, 1H, J=2.26 Hz), 10.37 (s, 1H), 10.23 (s, 1H), 8.12 (s, 1H), 7.57 (dd, 1H, J=3.20, 1.51 Hz), 7.46 (s, 2H), 7.20 (t, J=8.0 Hz, 1H), 6.77–6.74 (m, 3H), 3.75 (s, 3H), 2.36 (m, 1H), 2.08 (m, 1H), 1.48 (m, 1H), 1.38 (m, 1H).

LCMS: (M+H$^+$) 375.1.

Example 197

4-Acetylamino-N-(6-oxo-5,6-dihydro-1H-[1,2]diazepino[4,5,6-cd]indol-8-yl)-benzamide

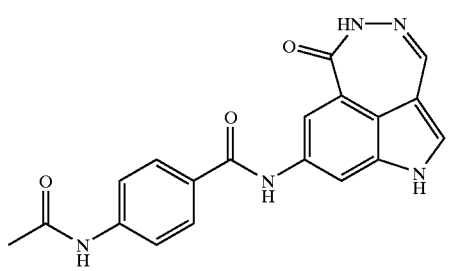

Preparation of example 197 from the title compound of Example 2 (124 mg, 0.525 mmol), 4-acetylamino-benzoic acid (113 mg, 0.631 mmol), (3-dimethylamino-propyl)-ethyl-carbodiimide hydrochloride (120 mg, 0.628 mmol), and 4-dimethylaminopyridine (77 mg, 0.631 mmol) in N,N-dimethylformamide (7.0 mL) was carried out analogously to Example 190, Step 2. When the reaction was judged complete, the volatile components were evaporated and methanol was added. The mixture was filtered to collect the solids, which were then washed with methanol, dichloromethane and diethyl ether. After drying, the title compound (32 mg, 0.0886 mmol) was obtained as a yellow powder in 17% yield.

$^1$H NMR (d$_6$-DMSO): δ 11.79 (d, 1H, J=2.64 Hz), 10.25 (s, 1H), 10.23 (s, 2H), 8.27 (d, 1H, J=1.70 Hz), 7.96 (d, 2H, J=8.67 Hz), 7.85 (d, 1H, J=1.70 Hz), 7.70 (d, 2H, J=8.67 Hz), 7.58 (d, 1H, J=2.64 Hz), 7.48 (s, 1H), 2.09 (s, 3H).

LCMS: (M–H)$^-$ 360.2.

HRMS: (M+H$^+$) calcd for C$_{19}$H$_{16}$N$_5$O$_3$, 362.1253, found 362.1280.

Example 198

(R)-2-Amino-N-(2-chloro-6-oxo-5,6-dihydro-1H-[1,2]diazepino[4,5,6-cd]indol-8-yl)-2-cyclohexyl-acetamide (Hydrochloric Salt)

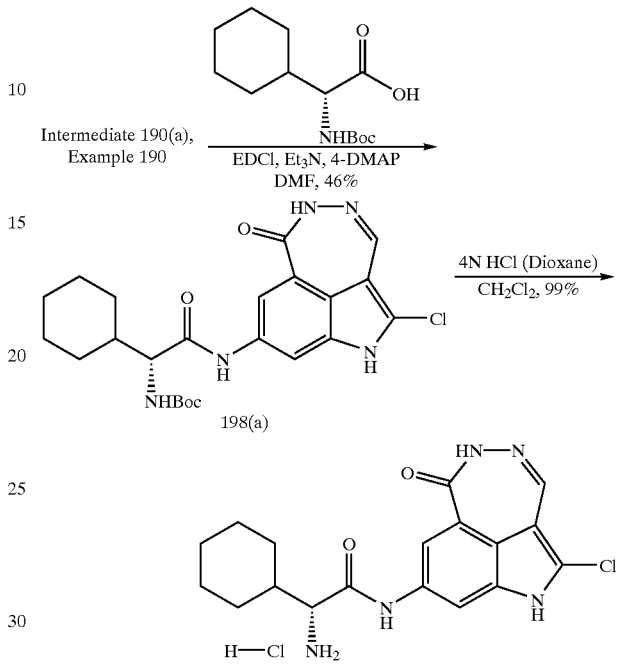

Step 1. Preparation of [(2-Chloro-6-oxo-5,6-dihydro-1H-[1,2]diazepino[4,5,6-cd]indol-8-ylcarbamoyl)-cyclohexyl-methyl]-carbamic Acid tert-butyl Ester 198(a)

Preparation of intermediate 198(a) from Intermediate 190(a) of Example 190 (100 mg, 0.369 mmol), (R)-tert-butoxycarbonylamino-cyclohexyl-acetic acid (114 mg, 0.443 mmol), (3-dimethylamino-propyl)-ethyl-carbodiimide hydrochloride (85 mg, 0.445 mmol), and 4-dimethylaminopyridine (54 mg, 0.443 mmol) in N,N-dimethylformamide (7.0 mL) was carried out analogously to Example 190, Step 2. When the reaction was judged complete, the volatile components were removed in vacuo, and the resulting residue was dissolved in methanol and loaded onto a silica gel plug. The plug was then loaded onto a silica gel column and eluted with 1.2:1 dichloromethane: ethyl acetate to afford Intermediate 198(a) (80 mg, 0.169 mmol) as a yellow solid in 46% yield.

$^1$H NMR (d$_6$-DMSO): δ 12.64 (s, 1H), 10.47 (s, 1H), 10.16 (s, 1H), 8.06 (d, 1H, J=1.51 Hz), 7.66 (d, 1H, J=1.51 Hz), 7.36 (s, 1H), 6.91 (d, 1H, J=9.04 Hz), 3.92 (dd, 1H, J=8.29, 7.91 Hz), 1.78–1.46 (m, 6H), 1.38 (s, 9H), 1.21–0.92 (m, 5H).

LCMS: (M–H)$^-$ 472.1.

Step 2. Preparation of Title Compound: (R)-2-Amino-N-(2-chloro-6-oxo-5,6-dihydro-1H-[1,2]diazepino[4,5,6-cd]indol-8-yl)-2-cyclohexyl-acetamide (Hydrochloric Salt)

Preparation of the title compound from Intermediate 198(a) (75 mg, 0.159 mmol) and 4.0 M HCl in dioxane (0.8 mL) was carried out analogously to Example 91. Isolation, also in an analogous manner, afforded the title compound (65 mg, 0.159 mmol) as a yellow powder in 99% yield.

$^1$H NMR (d$_6$-DMSO): δ 12.81 (s, 1H), 10.77 (s, 1H), 10.53 (s, 1H), 8.30 (br s, 3H), 8.03 (d, 1H, J=1.70 Hz), 7.70

(d, 1H, J=1.70 Hz), 7.39 (s, 1H), 3.73 (m, 1H), 1.93–1.55 (m, 6H), 1.27–1.01 (m, 5H).

LCMS: (M+H$^+$) 374.0; (M−H)$^−$ 372.2.

HRMS: (M+H$^+$) calcd for CH$_{18}$N$_5$O$_2$Cl, 374.1384, found 374.1369.

Example 199

2-(3,4-Dihydro-1H-isoquinolin-2-yl)-N-(6-oxo-5,6-dihydro-1H-[1,2]diazepino[4,5,6-cd]indol-8-yl)-acetamide

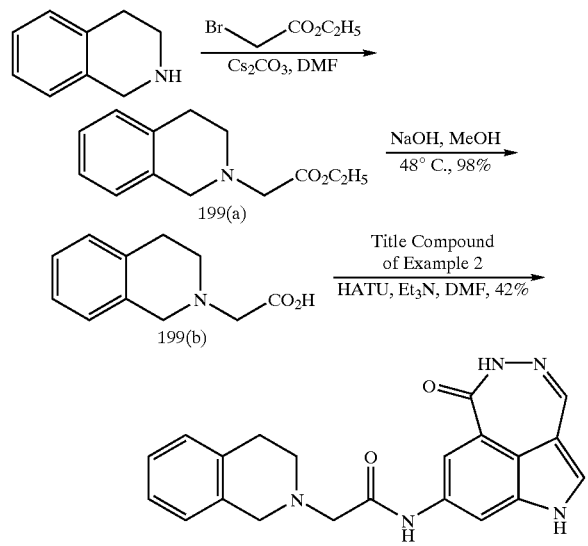

Step 1. Preparation of (3,4-Dihydro-1H-isoquinolin-2-yl)-acetic Acid Ethyl Ester 199(a)

To a solution of 1,2,3,4-tetra-hydroisoquinoline (2.664 g, 20 mmol) and ethyl bromoacetate (3.647 g, 22 mmol) in N,N-dimethylformamide (23 mL), was added Cs$_2$CO$_3$ (7.168 g, 22 mmol) under N$_2$. The mixture was stirred at room temperature for 4 hours. The solvent was removed under reduced pressure, and the remaining residue was subjected to silica gel chromatography, eluting with ethyl acetate/hexanes (33:66) to afford Intermediate 199(a) (3.39 g, 15.5 mmol) as yellow oil in 77% yield.

$^1$H-NMR (CDCl$_3$): δ 7.13–7.09 (m, 3H), 6.99 (t, 1H), 4.22 (q, 2H), 3.84 (s, 2H), 3.44 (s, 2H), 2.94 (s, 4H), 1.29 (t, 3H).

LCMS: (M+H$^+$) 220.3.

Step 2. Preparation of (3,4-Dihydro-1H-isoquinolin-2-yl)-acetic Acid 199(b)

To a suspension of Intermediate 199(a) (1.643 g, 7.5 mmol) in methanol (20 mL) was added 2.5 N NaOH (7.8 mL). The reaction solution was heated at 48° C. and stirred overnight. With cooling, the pH was adjusted to 8 by adding 1M HCl. The volatile components were removed under vacuum, and the resulting mixture was suspended in methanol. After filtration to remove the insoluble solids, the filtrate was evaporated to give Intermediate 199(b) (1.4 g, 7.3 mmol) as white foam in 98% yield.

$^1$H-NMR (d$_6$-DMSO): δ 7.13–7.09 (m, 3H), 7.02 (t, 1H), 3.76 (s, 2H), 3.27 (s, 2H), 2.88–2.82 (m, 4H).

LCMS: (M+H$^+$) 192.2.

Step 3. Preparation of Title Compound: 2-(3,4-Dihydro-1H-isoquinolin-2-yl)-N-(6-oxo-5,6-dihydro-1H-[1,2]diazepino[4,5,6-cd]indol-8-yl)-acetamide Preparation of the title compound from the title compound of Example 2 (185 mg, 0.79 mmol), Intermediate 199(b) (150 mg, 0.79 mmol), triethylamine (0.274 mL, 1.98 mmol), O-(7-azabenzotriazol-1-yl)-N,N,N',N'-tetramethyluronium hexafluorophosphate (330 mg, 0.879 mmol) and N,N-dimethylformamide (3 mL) was carried out analogously to 11. Following evaporation of the volatile components, the resulting residue was triturated with a small amount of N,N-dimethylformamide and water to give the title compound (123.5 mg, 0.331 mmol) as yellow solid in 42% yield.

$^1$H-NMR (d$_6$-DMSO): δ 11.73 (s, 1H). 10.22 (s, 1H), 9.97 (s, 1H), 8.13 (s, 1H), 7.62(s, 1H), 7.55 (s, 1H), 7.45 (s, 1H), 7.12–7.04 (m, 4H), 3.72 (s, 2H), 2.88–2.80 (m, 6H).

LCMS: (M+H$^+$) 374.4

Example 200

2-(1,3-Dihydro-isoindol-2-yl)-N-(6-oxo-5,6-dihydro-1H-[1,2]diazepino[4,5,6-cd]indol-8-yl)-acetamide

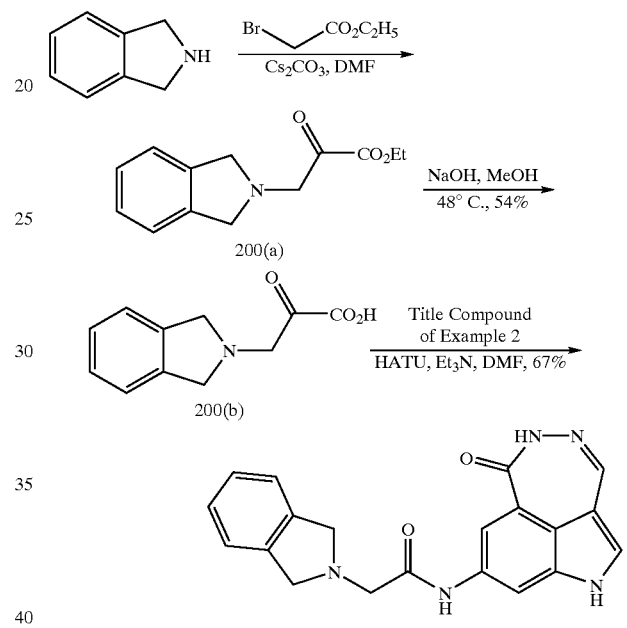

Step 1. Preparation of (1,3-Dihydro-isoindol-2-yl)-acetic Acid Ethyl Ester 200(a)

Into a solution of isoindoline (1.788 g, 15 mmol) and ethyl bromoacetate (2.756 g, 16.5 mmol) in N,N-dimethylformamide (20 mL), was added Cs$_2$CO$_3$ (5.376 g, 16.5 mmol) under N$_2$. The mixture was stirred at room temperature for 4 hours. The solvent was removed under reduced pressure and the resulting mixture was subjected to silica gel chromatography, eluting with 33:66 ethyl acetate-:hexane to afford Intermediate 200(a) (1.14 g, 5.56 mmol) as a yellow oil in 37% yield.

$^1$H-NMR (CDCl$_3$): δ 7.20 (s, 4H), 4.22 (q, 6H), 3.66 (s, 2H), 1.29 (t, 3H).

LCMS: (M+H$^+$) 206.3.

Step 2. Preparation of 1,3-Dihydro-isoindol-2-yl)-acetic Acid 200(b)

To a suspension of Intermediate 200(a) (1.14 g, 5.56 mmol) in methanol (20 mL) was added 2.5 N NaOH (5.78 mL). The reaction solution was heated at 48° C. and stirred overnight. With cooling, the pH was adjusted to 8 by adding 1M HCl. The volatile components were removed under vacuum and the resulting mixture was suspended in methanol. After filtration to remove the insoluble solids, the filtrate was evaporated to give Intermediate 200(b) (531 mg, 3 mmol) as pale solids in 54% yield.

LCMS: (M+H$^+$) 178.2.

Step 3. Preparation of Title Compound: 2-(1,3-Dihydro-isoindol-2-yl)-N-(6-oxo-5,6-dihydro-1H-[1,2]diazepino[4,5,6-cd]indol-8-yl)-acetamide Preparation of the title compound from the title compound of Example 2 (118 mg, 0.5 mmol), Intermediate 200(b) (88.5 mg, 0.5 mmol), triethylamine (0.274 mL, 1.98 mmol), O-(7-azabenzotriazol-1-yl)-N,N,N',N'-tetramethyluronium hexafluorophosphate (209 mg, 0.55 mmol) and N,N-dimethylformamide (5 mL) was carried out analogously to Example 11. Following evaporation of the volatile components, the resulting residue was triturated with a small amount of N,N-dimethylformamide and water to give the title compound (121 mg, 0.337 mmol) as a yellow solid in 67% yield.

$^1$H-NMR (d$_6$-DMSO): δ 11.73 (s, 1H), 10.21 (s, 1H), 10.02 (s, 1H), 8.13 (s, 1H), 7.66(s, 1H), 7.55 (s, 1H), 7.46 (s, 1H), 7.22 (d, 4H), 4.07 (s, 4H), 3.56 (s, 2H).

LCMS: (M+H$^+$) 360.4

Example 201

(2-Morpholin-4-yl-6-oxo-5,6-dihydro-1H-[1,2]diazepino[4,5,6-cd]indol-8-yl)-carbamic Acid tert-butyl Ester

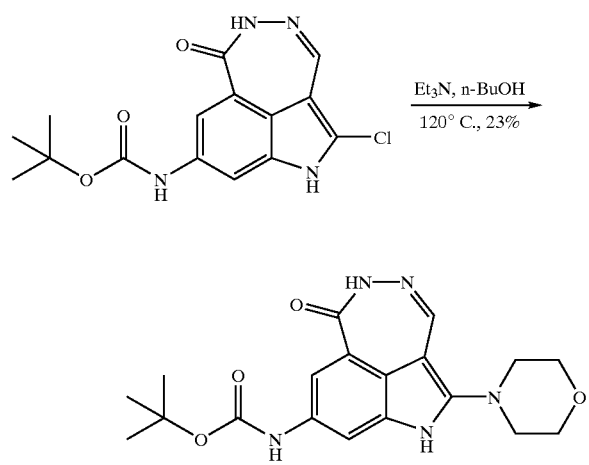

Triethylamine (0.039 mL, 0.28 mmol), the title compound of Example 187 (46 mg, 0.14 mmol), morpholine (96 mg, 1.1 mmol) and n-butanol (5 mL) were stirred in a flask with a condenser at 120° C. overnight. The mixture was allowed to stand at room temperature for two more days. The volatile components were removed under vacuum and the resulting mixture was subjected to silica gel chromatography, eluting with 95:5 dichloromethane:methanol to afford the title compound (12.5 mg, 0.032 mmol) as a yellow solid in 23% yield.

$^1$H-NMR (d$_6$-DMSO): δ 9.53 (s, 1H), 8.47 (s, 1H), 7.80 (s, 1H), 7.28 (s, 1H), 6.06 (s, 2H), 3.74 (s, 8H), 1.48 (s, 9H).

LCMS: (M+H$^+$) 386.4.

Example 202

(1,2-trans)-2-(3-Bromo-phenyl)-cyclopropanecarboxylic Acid (6-oxo-5,6-dihydro-1H-[1,2]diazepino[4,5,6-cd]indol-8-yl)-amide

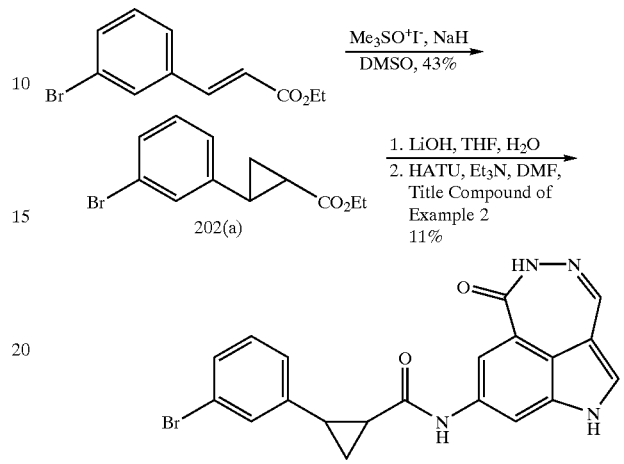

Step 1. Preparation of (1,2-trans)-2-(3-Bromo-phenyl)-cyclopropanecarboxylic Acid Ethyl Ester 202(a)

To a mixture of NaH (186 mg, 4.65 mmol) and trimethylsulfoxonium iodide (1.02 g, 4.65 mmol) was added DMSO (5 mL). After stirring for 30 min, a solution of trans-3-(bromo-phenyl)-acrylic acid ethyl ester (933 mg, 3.57 mmol) in DMSO (2 mL) was added drop-wise. After stirring overnight, the mixture was partitioned between ethyl acetate and water. The aqueous layer was extracted with ethyl acetate. The combined organic layers were dried over Na$_2$SO$_4$, filtered, and concentrated. The residue was subjected to silica gel chromatography, eluting with 10% ethyl acetate/hexane, to furnish Intermediate 202(a) as a colorless oil (408 mg, 1.52 mmol) in 43% yield.

Step 2. Preparation of Title Compound: (1,2-trans)-2-(3-Bromo-phenyl)-cyclopropanecarboxylic Acid (6-oxo-4,6-dihydro-1H-[1,2]diazepino[4,5,6-cd]indol-8-yl)-amide To a stirred solution of Intermediate 202(a) (505 mg, 2.25 mmol) in MeOH (10 mL) was added aqueous 10M LiOH (10 mL). The mixture was stirred at 23° C. for 12 hours, acidified with 1 M HCl to pH 1, and extracted with ethyl acetate. The combined organic layers was then washed with brine and concentrated to give crude (2,3-trans)-3-(3'-bromo-phenyl)-cyclopropanecarboxylic acid (632 mg), which was combined with the title compound of Example 2 (111 mg, 0.49 mmol), triethylamine (0.273 mL, 1.96 mmol), and O-(7-azabenzotriazol-1-yl)-N,N,N',N'-tetramethyluronium hexafluorophosphate (278 mg, 0.73 mmol) in N,N-dimethylformamide (4 mL) in a manner analogous to Example 11. Extractive work-up from ethyl acetate and saturated aqueous NaHCO$_3$ follow by silica gel chromatography afforded the title compound (100 mg, 0.24 mmol) as a yellow solid in 11% yield.

$^1$H NMR (d$_6$-DMSO): 11.85 (d, 1H, J=2.26 Hz), 10.50 (s, 1H), 10.35 (s, 1H), 8.23 (s, 1H), 7.69 (s, 1H), 7.67 (d, 1H, J=4.0 Hz), 7.58 (s, 1H), 7.53–7.51 (m, 2H), 7.40–7.33 (m, 2H), 2.53 (m, 1H), 2.23 (m, 1H), 1.62 (m, 1H), 1.54 (m, 1H).

Example 203

(1,2-trans)-2-(3-Hydroxy-phenyl)-cyclopropanecarboxylic Acid (6-oxo-5,6-dihydro-1H-[1,2]diazepino[4,5,6-cd]indol-8-yl)-amide

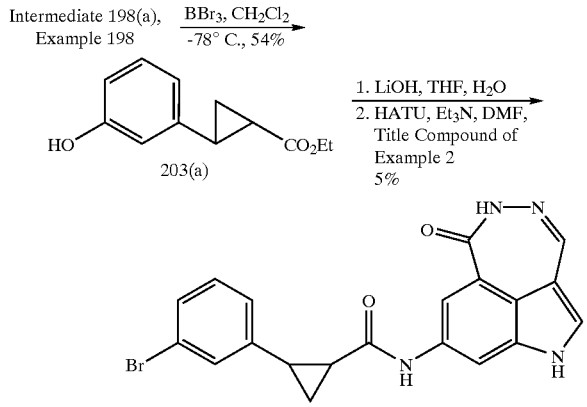

Step 1. Preparation of 2-(3-hydroxy-phenyl)-cyclopropanecarboxylic Acid Ethyl Ester 203(a)

To a stirred solution of Intermediate 196(a) of Example 196 (1.56 g, 7.12 mmol) in $CH_2Cl_2$ at −78° C. was added 1.0M $BBr_3$ in $CH_2Cl_2$ (8.56 ml, 8.56 mmol). The mixture was warmed to room temperature and stirred for 1 hour. Extractive work-up from ethyl acetate and saturated aqueous $NaHCO_3$ followed by silica gel chromatography afforded Intermediate 203(a) as a pale brown solid (795 mg, 3.86 mmol) in 54% yield.

Step 2. Preparation of Title Compound: (1,2-trans)-2-(3-Hydroxy-phenyl)-cyclopropanecarboxylic Acid (6-oxo-5,6-dihydro-1H-[1,2]diazepino[4,5,6-cd]indol-8-yl)-amide To a solution of Intermediate 203(a) (271 mg, 1.32 mmol) in tetrahydrofuran (2 mL) was added aqueous 1M LiOH (6 mL, 6 mmol). The mixture was stirred overnight. After acidifying to pH 2, the mixture was extracted with ethyl acetate. Concentration of the organic layer gave crude 3-(3-hydroxy-phenyl)-cycloprapanecarboxylic acid (235 mg), where a portion (155 mg, 0.57 mmol) was combined with the title compound of Example 2 (137 mg, 0.58 mmol), triethylamine (0.24 mL, 1.72 mmol), and O-(7-azabenzotriazol-1-yl)-N,N,N',N'-tetramethyluronium hexafluorophosphate (331 mg, 0.87 mmol) in N,N-dimethylformamide (3 mL) in a manner analogous to Example 11. Extractive work-up from ethyl acetate and saturated aqueous $NaHCO_3$ followed by silica gel chromatography afforded the title compound (10 mg, 0.028 mmol) as a tan solid in 5% yield.

$^1$H NMR ($d_6$-DMSO): δ 10.35 (s, 1H), 10.27 (s, 1H), 9.35 (s, 1H), 8.12 (s, 1H), 7.67 (dd, 1H, J=3.20, 1.51 Hz), 7.55 (s, 1H), 7.48(s, 1H), 7.15 (t, J=8.0 Hz, 1H), 6.77–0.74 (m, 3H), 2.32 (m, 1H), 2.09 (m, 1H), 1.45 (m, 1H), 1.38 (m, 1H).

LCMS: (M−H$^+$) 359.1

Example 204

2-(3,4-Dihydroisoquinolin-2(1H)-yl)-N-(6-oxo-2-phenyl-5,6-dihydro-1H-[1,2]diazepino[4,5,6-cd]indol-8-yl)acetamide

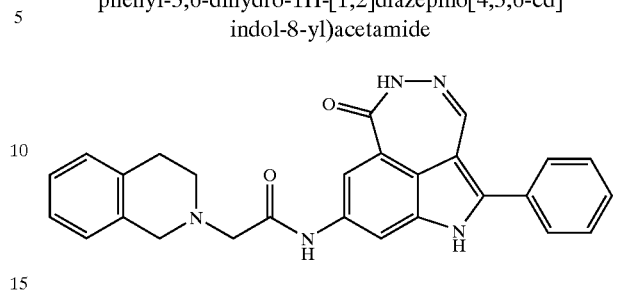

In a manner analogous to that of Example 11, to a stirred solution of 8-amino-1,5-dihydro-6H-[1,2]diazepino[4,5,6-cd]indol-6-one in anhydrous N,N-dimethylformamide (6 mL) was added 3,4-dihydroisoquinolin-2(1H)-ylacetic acid (62 mg, 0.33 mmol) followed by tiethylamine (0.14 mL, 0.98 mmol) and O-(7-azabenzotriazol-1-yl)-N,N,N',N'-tetramethyluronium hexafluorophosphate (372 mg, 0.98 mmol). The reaction was stirred at room temperature for 17 hours. After concentrating, water was added and the precipitated solid was collected by filtration. After preparative HPLC, the title compound (50 mg) was obtained as a yellow powder in 34% yield.

$^1$H NMR (methanol-$d_4$) d: 3.25 (2H, m), 3.72 (2H, bs), 4.27 (2H, s), 4.58 (2H, s), 7.22 (1H, d, J=7.58 Hz), 7.32 (3H, m), 7.52 (4H, m), 7.63 (3H, m), 8.13 (1H, d, J=1.52 Hz).

LCMS: (M+H$^+$) 450.1.

Example 205

(1,2-trans)-2-Pyridin-3-yl-cyclopropanecarboxylic Acid (2-chloro-6-oxo-5,6-dihydro-1H-[1,2]diazepino[4,5,6-cd]indol-8-yl-amide (Hydrochloric Salt)

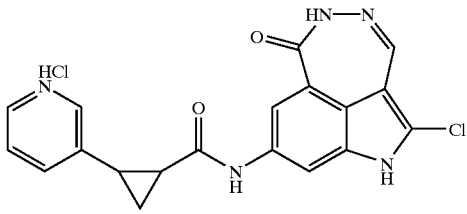

The title compound of Example 191 (20 mg, 0.053 mmol) was converted to an HCl salt in anhydrous $CH_2Cl_2$ (2 mL) with 4.0 M HCl in dioxane (0.026 mL). The mixture was stirred at room temperature for 1 hour. The solid was collected by filtration and washed with $CH_2Cl_2$ and diethyl ether. After drying, the title compound (20.4 mg, 0.049 mmol) was obtained as a yellow powder in 93% yield.

$^1$H NMR ($d_8$-DMSO): δ 12.70 (s, 1H), 10.59 (s, 1H), 10.46 (s, 1H), 8.85 (s, 1H), 8.72 (d, 1H, J=5.84 Hz), 8.25 (d, 1H, J=8.29 Hz), 8.07 (d, 1H, J=1.70 Hz), 7.91 (dd, 1H, J=5.27, 5.27 Hz), 7.63 (d, 1H, J=1.70 Hz), 7.35 (s, 1H), 2.75–2.59 (m, 1H), 2.33–2.21 (m, 1H), 1.67–1.56 (m, 2H).

Example 206

(1R,2R)-2-Phenyl-cyclopropanecarboxylic Acid (2-bromo-6-oxo-5,6-dihydro-1H-[1,2]diazepino[4,5,6-cd]indol-yl)-amide

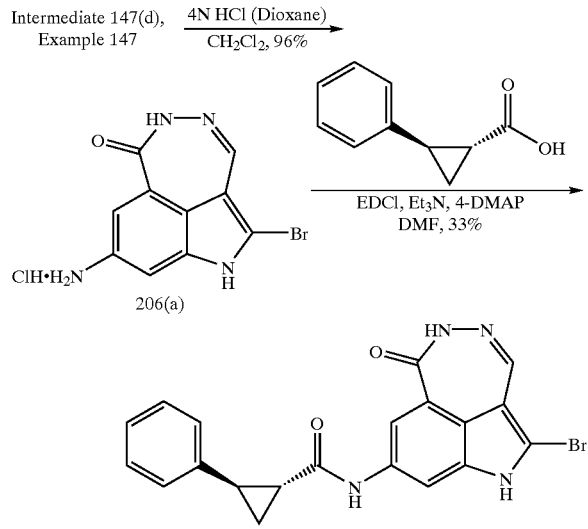

Step 1. Preparation of 8-Amino-2-bromo-1,5-dihydro-[1,2]diazepino[4,5,6-cd]indol-4-one (Hydrochloric Salt) 206(a)

Preparation of intermediate 206(a) from Intermediate 147(d) of Example 147 (2 g, 5.29 mmol) and 4.0 M HCl in dioxane (26.4 mL) was carried out analogously to Example 91. Isolation, also in an analogous manner, afforded Intermediate 206(a) (1.59 g, 5.04 mmol) as a yellow powder in 96% yield.

$^1$H NMR (d$_6$-DMSO): δ 13.13 (s, 1H), 10.67 (s, 1H), 7.52 (s, 1H), 7.51 (s, 1H), 7.35 (s, 1H).

LCMS: (M+H$^+$) 279.0, 281.1, (M+Na$^+$) 401.0, 403.0; (M−H)$^−$ 277.0, 279.0.

Step 2. Preparation of Title Compound: (1R,2R)-2-Phenyl-cyclopropanecarboxylic Acid (2-bromo-6-oxo-5,6-dihydro-1H-[1,2]diazepino[4,5,6-cd]indol-8-yl)-amide Preparation of the title compound from Intermediate 206(a) (120 mg, 0.380 mmol), (1R,2R)-2-phenyl-cyclopropanecarboxylic acid (74.0 mg, 0.457 mmol), (3-dimethylamino-propyl)-ethyl-carbodiimide hydrochloride (88 mg, 0.461 mmol), and 4-dimethylaminopyridine (56 mg, 0.459 mmol) in N,N-dimethylformamide (15.0 mL) was carried out analogously to Example 190, step 2. When the reaction was judged complete, the volatile components were removed in vacuo, and the resulting residue was dissolved in methanol and loaded onto a silica gel plug. The plug was then loaded onto a silica gel column and eluted with 1.2:1 dichloromethane: ethyl acetate to afford the title compound (52.4 mg, 0.124 mmol) as a yellow solid in 33% yield.

$^1$H NMR (d$_6$-DMSO): δ 12.59 (s, 1H), 10.45 (s, 1H), 10.44 (s, 1H), 8.08 (d, 1H, J=1.51 Hz), 7.60 (d, 1H, J=1.70 Hz), 7.33–7.24 (m, 3H), 7.24–7.13 (m, 3H), 2.42–2.32 (m, 1H), 2.11–2.00 (m, 1H), 1.54–1.42 (m, 1H), 1.42–1.30 (m, 1H).

LCMS: (M+H$^+$) 423.0, 425.0, (M+Na$^+$) 445.0, 447.0; (M−H)$^−$ 421.0, 423.0.

HRMS: (M+H$^+$) calcd for C$_{20}$H$_{16}$N$_4$O$_2$Br, 423.0457, found 423.0471.

Example 207

N-Methyl-N-(2-methylprop-2-enyl)-N'-(6-oxo-5,6-dihydro-1H-[1,2]diazepino[4,5,6-cd]indol-8-yl)urea

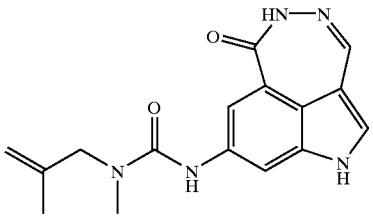

Using a similar route as outlined in Example 192, the title compound of Example 2 (25 mg, 0.11 mmol) and N,N'-disuccinimidyl carbonate (27 mg, 0.11 mmol) were stirred together in N,N-dimethylformamide (1 mL) while N,N-diisopropylethylamine (0.024 mL, 0.21 mmol) was added. After stirring three minutes N-2-dimethylprop-2-en-1-amine (0.046 mL, 0.21 mmol) was added giving the crude product Cation-exchange polystyrene scavenging resin (Argonaut Technologies™, MP-TsOH) was added directly to the mixture. After stirring 2 hours the resin was removed by filtration and washed twice with N,N-dimethylformamide (1 mL). The combined N,N-dimethylformamide solutions were then treated with anion-exchange polystyrene scavenging resin (Argonaut Technologies™, MP-carbonate) and stirred for 2 hours. Again the resin was removed by filtration and washed twice with N,N-dimethylformamide (1 mL). The combined N,N-dimethylformamide solutions were then reduced under vacuum and subjected to preparative RPHPLC (Peeke Scientific HI-Q, C18 reverse-phase, 5 uM, 100A, 150×20 mm column) eluting with 0.1% acetic acid in CH$_3$CN and 0.1% acetic acid in H$_2$O at a flowrate of 20 mL/min using a gradient of 30–70% 0.1% acetic acid in CH$_3$CN over 30 min. Fractions judged pure were pooled, and the volatile components removed in vacuo. After a final trituration with ethyl acetate, the title compound (6 mg, 0.019 mmol) was obtained as brown powder in 18% yield.

$^1$H NMR (CDCl$_3$/methanol-d$_4$): δ 7.90 (s, 1H), 7.42 (s, 1H), 7.30 (s, 1H), 7.28 (s, 1H), 4.98 (s, 1H), 4.90 (s, 1H), 3.95 (s, 2H), 3.03 (s, 3H), 1.77 (s, 3H).

LCMS: (M+H$^+$) 312.2, (M+Na$^+$) 334.1.

Example 208

N-Methyl-N'-(6-oxo-5,6-dihydro-1H-[1,2]diazepino[4,5,6-cd]indol-8-yl)-N-(phenylmethyl)urea

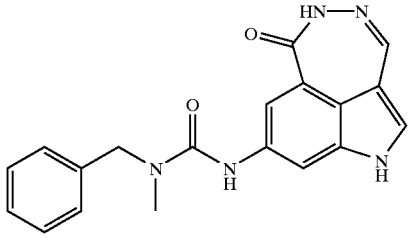

Preparation of example 208 from the title compound of Example 2 (48 mg, 0.20 mmol), N,N'-disuccinimidyl carbonate (52 mg, 0.20 mmol), triethylamine (0.084 mL, 0.60 mmol) and N-methyl-1-phenylmethanamine (0.052 mL, 0.40 mmol) in N,N-dimethylformamide (0.5 mL) was carried out analogously to Example 192. Purification, also in an analogous manner, afforded the title compound (8 mg, 0.023 mmol) was obtained as brown powder in 12% yield.

¹H NMR (CDCl₃/methanol-d₄): δ 7.88 (s, 1H), 7.46–7.23 (m, 8H), 4.64 (s, 2H, obscured), 3.03 (s, 3H).

LCMS: (M+H⁺) 348.4, (M+Na⁺) 370.4.

Example 209

(1,2-trans)-2-(2'-Methoxy-phenyl)-cyclopropanecarboxylic Acid (6-oxo-5,6-dihydro-1H-[1,2]diazepino[4,5,6-cd]indol-8-yl)-amide

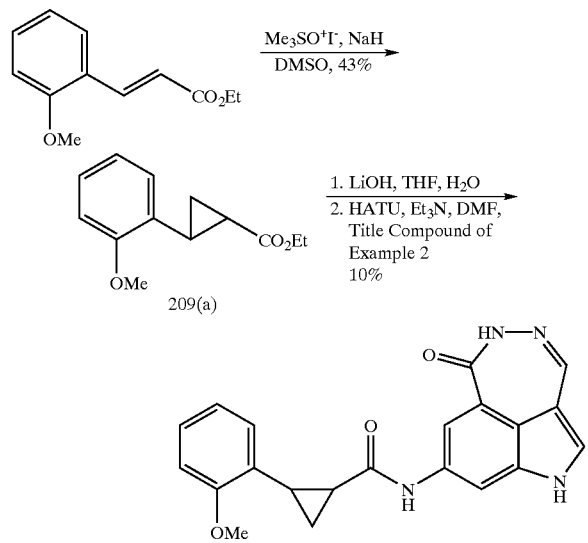

Step 1: Preparation of (1,2-trans)-2-(2'-Methoxy-phenyl)-cyclopropanecarboxylic Acid Ethyl Ester 209(a)

Preparation of intermediate 209(a) from NaH (1.04 g, 26 mmol) and trimethylsulfoxonium iodide (5.72 g, 26 mmol), 2-(methoxy-phenyl)-acrylic acid ethyl ester (4.12 g, 20 mmol) in dimethylsulfoxide (30 mL) was carried out analogously to step 2 of Example 113. Intermediate 209(a) (1.89 g, 8.6 mmol) was obtained in 43% yield.

Step 2: Preparation of Title Compound: (1,2-trans)-2-(2'-Methoxy-phenyl)-cyclopropanecarboxylic Acid (6-oxo-5,6-dihydro-1H-[1,2]diazepino[4,5,6-cd]indol-8-yl)-amide Preparation of the title compound was carried out analogously to step 3 of Example 172 except that Intermediate 209(a) was used instead of Intermediate 172(b). The title compound was obtained in 10% yield.

¹H NMR (d₆-DMSO): δ 11.74 (d, 1H, J=2.26 Hz), 10.35 (s, 1H), 10.24 (s, 1H), 8.14 (s, 1H), 7.57 (dd, 1H, J=3.20, 1.51 Hz), 7.46 (s, 2H), 7.20 (t, J=8.0 Hz, 1H), 6.77–4.74 (m, 3H), 3.80 (s, 3H), 2.36 (m, 1H), 2.02 (m, 1H), 1.44 (m, 1H), 1.34 (m, 1H).

LCMS: (M−H⁺) 373.1.

Example 210

N-cyclohexyl-N-methyl-N'-(6-oxo-5,6-dihydro-1H-[1,2]diazepino[4,5,6-cd]indol-8-yl)urea

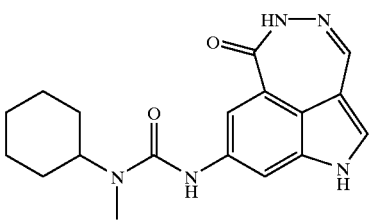

Preparation of example 210 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and N-cyclohexyl-N-methylamine (0.028 mL, 0.021 mmol) in N,N-dimethylformamide (1.0 mL) was carried out analogously to Example 207. Purification, also in an analogous manner, afforded the title compound (7 mg, 0.021 mmol) as yellow powder in 19% yield.

¹H NMR (CDCl₃/methanol-d₄): δ 7.90 (s, 1H), 7.41 (s, 1H), 7.33 (s, 1H), 7.27 (s, 1H), 4.09 (m, 1H), 2.92 (s, 3H), 1.91–1.80 (m, 2H), 1.79–1.65 (m, 3H), 1.56–1.37 (m, 4H), 1.14 (m, 1H).

LCMS: (M+H⁺) 340.2, (M+Na⁺) 362.1.

Example 211

N-Cyclohexyl-N-ethyl-N'-(6-oxo-5,6-dihydro-1H-[1,2]diazepino[4,5,6-cd]indol-8-yl)urea

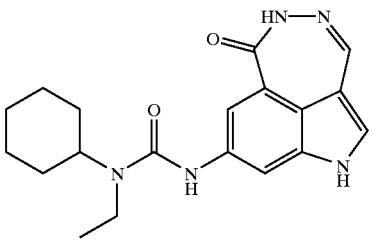

Preparation of example 211 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and N-cyclohexyl-N-methylamine (0.032 mL, 0.021 mmol) in N,N-dimethylformamide (1.0 mL) was carried out analogously to Example 207. Purification, also in an analogous manner, afforded the title compound (7 mg, 0.020 mmol) as yellow powder in 20% yield.

¹H NMR (CDCl₃/methanol-d₄): δ 7.94 (s, 1H), 7.40 (s, 1H, obscured), 7.30 (s, 1H, partially obscured), 7.26 (s, 1H), 4.05 (m, 1H, partially obscured), 3.36 (m, 2H, partially obscured), 1.90–1.74 (m, 4H), 1.71 (m, 1H), 1.58–1.33 (m, 4H), 1.26 (t, 3H, J=7.16 Hz), 1.14 (m, 1H).

LCMS: (M+H⁺) 354.2, (M+Na⁺) 376.1.

Example 212

N,N-Diethyl-N'-(6-oxo-5,6-dihydro-1H-[1,2]diazepino[4,5,6-cd]indol-8-yl)urea

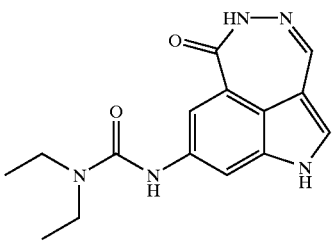

Preparation of example 212 from the title compound of Example 2 (25 mg, 0.11 mmol), N,N' disuccinimidyl carbonate (27 mg, 0.11 mmol), N,N-diisopropylethylamine (0.024 mL, 0.21 mmol) and N,N-diethylamine (0.022 mL, 0.021 mmol) in N,N-dimethylformamide (1.0 mL) was carried out analogously to Example 207. Purification, also in an analogous manner, afforded the title compound (5 mg, 0.016 mmol) as yellow powder in 15% yield.

$^1$H NMR (CDCl$_3$/methanol-d$_4$): δ 7.91 (s, 1H), 7.41 (s, 1H), 7.32 (s, 1H), 7.27 (s, 1H), 3.42 (q, 4H, J=7.16 Hz), 1.24 (t, 6H, J=7.16 Hz).

LCMS: (M+H$^+$) 300.2, (M+Na$^+$) 322.1.

Example 213

N-(6-Oxo-5,6-dihydro-1H-[1,2]diazepino[4,5,6-cd]indol-8-yl)piperidine-1-carboxamide

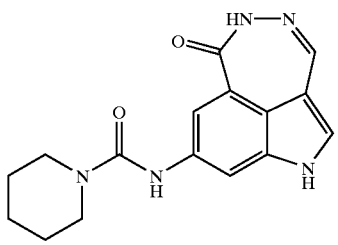

Preparation of example 213 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and piperidine (0.021 mL, 0.021 mmol) in N,N-dimethylformamide (1.0 mL) was carried out analogously to Example 207. Purification, also in an analogous manner, afforded the title compound (7 mg, 0.022 mmol) as yellow powder in 20% yield.

$^1$H NMR (CDCl$_3$/methanol-d$_4$): δ 7.77 (s, 1H), 7.65 (s, 1H), 7.43 (s, 1H, partially obscured), 7.32 (s, 1H), 3.57–3.47 (m, 4H), 1.76–1.56 (m, 6H).

LCMS: (M+H$^+$) 312.1, (M+Na$^+$) 334.1.

Example 214

N-(6-Oxo-5,6-dihydro-1H-[1,2]diazepino[4,5,6-cd]indol-8-yl)-4-(phenylmethyl)piperidine-1-carboxamide

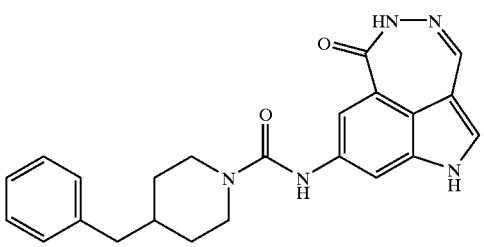

Preparation of example 214 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and 4-(phenylmethyl)piperidine (0.037 mL, 0.021 mmol) in N,N-dimethylformamide (1.0 mL) was carried out analogously to Example 207. Purification, also in an analogous manner, afforded the title compound (7 mg, 0.017 mmol) as yellow powder in 16% yield.

$^1$H NMR (CDCl$_3$/methanol-d$_4$): δ 7.88 (s, 1H), 7.44–7.39 (m, 2H, partially obscured), 7.34–7.12 (m, 6H), 4.16 (d, 2H, J=13.75 Hz), 2.91–2.78 (m, 2H), 2.62–2.57 (m, 2H), 1.80–1.69 (m, 3H), 1.36–1.14 (m, 2H).

LCMS: (M+H$^+$) 402.2, (M+Na$^+$) 424.1.

Example 215

N-Ethyl-N'-(6-oxo-5,6-dihydro-1H-[1,2]diazepino[4,5,6-cd]indol-8-yl)-N-(phenylmethyl)urea

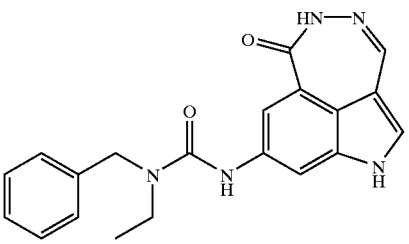

Preparation of example 215 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and N-(phenylmethyl)ethanamine (0.032 mL, 0.021 mmol) in N,N-dimethylformamide (1.0 mL) was carried out analogously to Example 207. Purification, also in an analogous manner, afforded the title compound (7 mg, 0.019 mmol) as yellow powder in 18% yield.

$^1$H NMR (CDCl$_3$/methanol-d$_4$): δ 7.94 (s, 1H), 7.46–7.21 (m, 8H, partially obscured), 4.63 (s, 2H), 3.51–3.34 (m, 2H, partially obscured), 1.28–1.19 (m, 3H).

LCMS: (M+H$^+$) 362.1, (M+Na$^+$) 384.0.

Example 216

N-Butyl-N-methyl-N'-(6-oxo-5,6-dihydro-1H-[1,2]diazepino[4,5,6-cd]indol-8-yl)urea

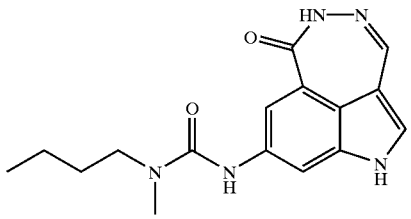

Preparation of example 216 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and N-ethyl-N-propylamine (0.025 mL, 0.021 mmol) in N,N-dimethylformamide (1.0 mL) was carried out analogously to Example 207. Purification, also in an analogous manner, afforded the title compound (4 mg, 0.013 mmol) as yellow powder in 12% yield.

$^1$H NMR (CDCl$_3$/methanol-d$_4$): δ 7.92 (s, 1H), 7.41 (s, 1H, partially obscured), 7.29 (s, 1H), 7.26 (s, 1H), 3.04 (s, 3H), 1.66–1.55 (m, 2H), 1.45–1.21 (m, 4H), 0.97 (t, 3H, J=7.35 Hz).

LCMS: (M+H$^+$) 314.1, (M+Na$^+$) 336.2.

Example 217

N-Methyl-N'-(6-oxo-5,6-dihydro-1H-[1,2]diazepino[4,5,6-cd]indol-8-yl)-N-propylurea

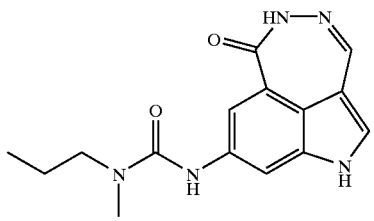

Preparation of example 217 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and N-ethyl-N-propylamine (0.022 mL, 0.021 mmol) in N,N-dimethylformamide (1.0 mL) was carried out analogously to Example 207. Purification, also in an analogous manner, afforded the title compound (4 mg, 0.013 mmol) as yellow powder in 12% yield.

$^1$H NMR (CDCl$_3$/methanol-d$_4$): δ 7.87 (s, 1H), 7.43 (s, 1H), 7.36 (s, 1H), 7.29 (s, 1H), 3.05 (s, 3H), 1.72–1.58 (m, 2H), 1.37–1.21 (m, 2H), 0.96 (t, 3H, J=7.25 Hz)

LCMS: (M+H$^+$) 300.2, (M+Na$^+$) 322.1.

Example 218

(1,2-trans)-2-[3-(2-Dimethylamino-ethoxy)-phenyl]-cyclopropanecarboxylic Acid (6-oxo-5,6-dihydro-1H-[1,2]diazepino[4,5,6-cd]indol-8-yl)-amide

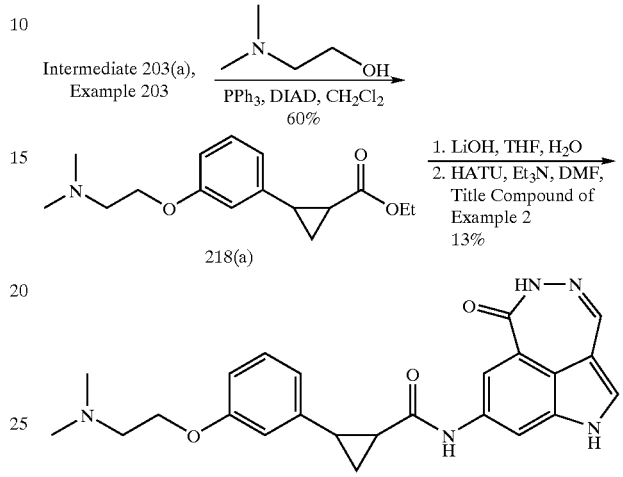

Step 1. Preparation of (1,2-trans)-2-[3-2-Dimethylamino-ethoxy)-phenyl]-cyclopropanecarboxylic Acid 218(a)

To a stirred solution of Intermediate 203(a) of Example 203 (125 mg, 0.607 mmol), 2-dimethylethanol (81 mg, 0.91 mmol) and triphenylphosphine (239 mg, 0.91 mmol) in CH$_2$Cl$_2$ was added diisopropyl azodicarboxylate (184 mg, 0.91 mmol). The mixture was stirred at room temperature for 4 hours, concentrated, and subjected to silica el chromatography, eluting with 20–30% ethyl acetate/hexane, to furnish Intermediate 218(a) as a colorless oil (101 mg, 0.36 mmol) in 60% yield.

Step 2. Preparation of Title Compound: (1,2-trans)-2-[3-2-Dimethylamino-ethoxy)-phenyl]-cyclopropanecarboxylic Acid (6-oxo-5,6-dihydro-1 H-[1,2]diazepino[4,5,6-cd]indol-8-yl)-amide Preparation of the title compound was carried out analogously to step 3 of Example 172 except that Intermediate 218(a) was used instead of Intermediate 172(b). The title compound was obtained in a 13% yield.

$^1$H NMR (d$_6$-DMSO): δ 11.56 (d, 1H, J=2.26 Hz), 10.20 (s, 1H), 10.06 (s, 1H), 7.95 (d, 1H, J=1.88 Hz), 7.38 (dd, 1H, J=3.20, 1.51 Hz), 7.29 (s, 1H), 7.04 (t, 1H, J=8.0 Hz), 6.62–6.58 (m, 3H), 6.36 (s, 1H), 3.96–3.94 (m, 2H), 3.12–3.10 (m, 2H), 2.29 (m, 1H), 1.91 (m, 1H), 1.31 (m, 1H), 1.20 (m, 1H).

LCMS: (M+H$^+$) 432.2.

Example 219

(R)-2-Amino-2-cyclohexyl-N-[6-oxo-2-(1,2,3,6-tetrahydro-pyridin-4-yl)-5,6-dihydro-1H-[1,2]diazepino[4,5,6-cd]indol-8-yl]acetamide; Dihydrochloride

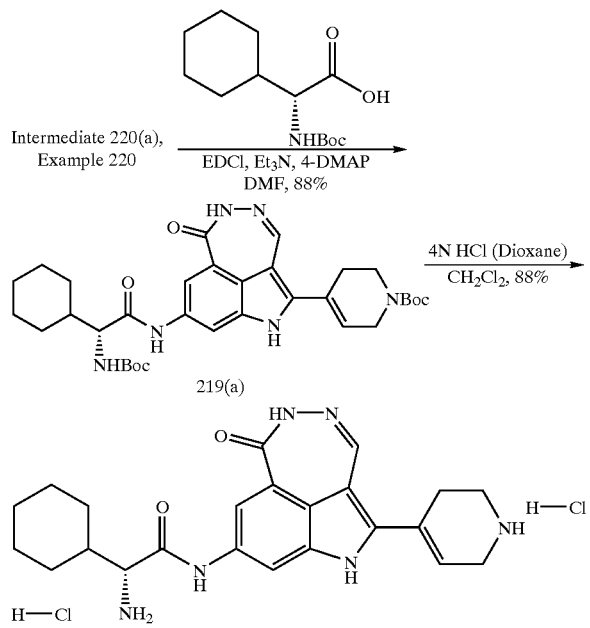

Step 1. Preparation of (R)-4-[8-(2-tert-Butoxycarbonylamino-2-cyclohexyl-acetylamino)-6-oxo-5,6-dihydro-1H-[1,2]diazepino[4,5,6-cd]indol-2-yl]-3,6-dihydro-2H-pyridine-1-carboxylic Acid tert-butyl Ester 219(a)

Preparation of intermediate 219(a) from Intermediate 220(a) of Example 220 (100 mg, 0.262 mmol), (R)-tert-butoxycarbonylamino-cyclohexyl)acetic acid (74.3 mg, 0.289 mmol), (3-dimethylaminopropyl)-ethyl-carbodiimide hydrochloride (55 mg, 0.288 mmol), and 4-dimethylaminopyridine (35.2 mg, 0.288 mmol) in N,N-dimethylformamide (6.0 mL) was carried out analogously to Example 190, step 2. When the reaction was judged complete, the volatile components were removed in vacuo, and the resulting residue was dissolved in methanol and loaded onto a silica gel plug. The plug was then loaded onto a silica gel column and eluted with 1:1 dichloromethane:ethyl acetate to afford Intermediate 219(a) (143 mg, 0.231 mmol) as a yellow solid in 88% yield.

$^1$H NMR (d$_6$-DMSO): δ 11.70 (s, 1H), 10.27 (s, 1H), 10.09 (s, 1H), 8.06 (d, 1H, J=1.51 Hz), 7.59 (s, 1H), 7.51 (s, 1H), 6.88 (d, 1H, J=8.10 Hz), 6.17 (s, 1H), 4.06 (br s, 2H), 3.92 (dd, 1H, J=8.48, 7.72 Hz), 3.55 (t, 2H, J=5.65, 5.27 Hz), 3.32 (m, 2H, obscured), 1.76–1.46 (m, 6H), 1.43 (s, 9H), 1.37 (s, 9H), 1.19–0.94 (m, 5H).

LCMS: (M−H)$^−$ 619.2.

Step 2. Preparation of Title Compound: (R)-2-Amino-2-cyclohexyl-N-[6-oxo-2-(1,2,3,6-tetrahydro-pyridin-4-yl)-5,6-dihydro-1H-[1,2]diazepino[4,5,6-cd]indol-yl]-acetamide; Dihydrochloride Preparation of the title compound from Intermediate 219(a) (143 mg, 0.231 mmol) and 4.0 M HCl in dioxane (2.3 mL) was carried out analogously to Example 91. Isolation, also in an analogous manner, afforded the title compound (100 mg, 0.203 mmol) as a red powder in 88% yield.

$^1$H NMR (d$_6$-DMSO): δ 12.18 (s, 1H), 10.87 (s, 1H), 10.39 (s, 1H), 9.32 (br s, 2H), 8.35 (br s, 3H), 8.07 (d, 1H, J=1.51 Hz), 7.70 (d, 1H, J=1.51 Hz), 7.55 (d, 1H, J=1.51 Hz), 6.19 (s, 1H), 3.87–3.74 (m, 3H), 3.41–3.26 (m, 2H), 2.81–2.69 (m, 2H), 1.90–1.55 (m, 6H), 1.28–0.97 (m, 5H).

LCMS: (M+H$^+$) 421.1, (M+Na$^+$) 443.1; (M−H)$^−$ 419.1.

HRMS: (M+H$^+$) calcd for C$_{23}$H$_{29}$N$_6$O$_2$, 421.2352, found 421.2338.

Example 220

(1R,2R)-2-Phenyl-cyclopropanecarboxylic Acid [6-oxo-2-(1,2,3,6-tetrahydro-pyridin-4-yl)-5,6-dihydro-1H-[1,2]diazepino[4,5,6-cd]indol-8-yl]-amide (Hydrochloric Salt)

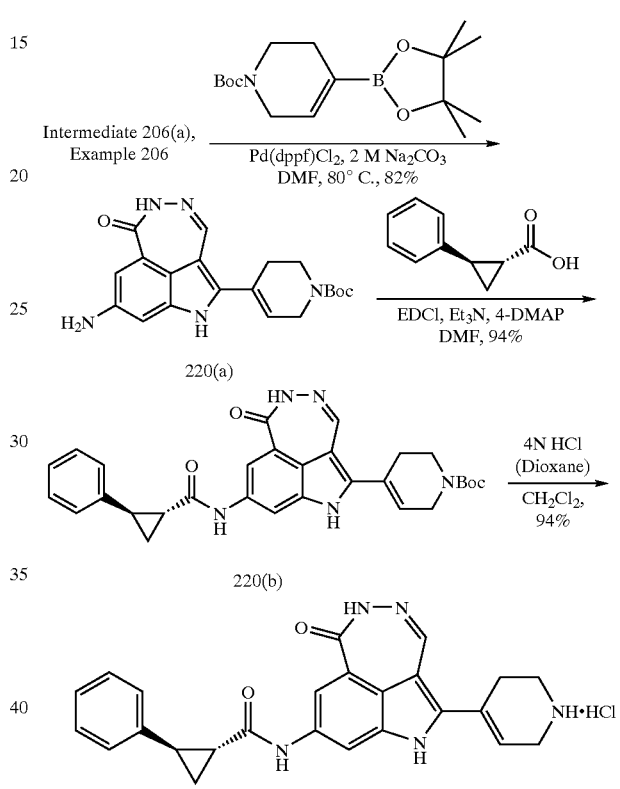

Step 1. Preparation of 4-(8-Amino-6-oxo-5,6-dihydro-1H-[1,2]diazepino[4,5,6-cd]indol-2-yl)-3,6-dihydro-2H-pyridine-1-carboxylic Acid tert-butyl Ester 220(a)

In a manner analogous to that of Example 184, 2.0 M aqueous Na$_2$CO$_3$ (0.66 mL) was added to a mixture of Intermediate 206(a) of Example 206 (1 g, 3.17 mmol), 4-(4,4,5,5-tetramethyl-[1,2]dioxaborolan-2-yl)-3,6-dihydro-2H-pyridine-1-carboxylic acid tert-butyl ester (1.18 g, 3.82 mmol) and [1,1'-bis(diphenylphosphino)ferrocene]dichloropalladium (II) (0.13 g, 0.159 mmol) in anhydrous N,N-dimethylformamide (50 ml), and the reaction was heated at 80° C. for 16 hours. When the reaction was judged complete, the volatile components were removed in vacuo. Ethyl acetate (50 mL), methanol (5 mL) and H$_2$O (500 mL) were added, and the aqueous layer was extracted with ethyl acetate (3×20 mL). The combined ethyl acetate extracts were washed with H$_2$O (2×50 mL) and brine (50 mL) and allowed to dry over Na$_2$SO$_4$. Following filtration, the volatile components were removed in vacuo and CH$_2$Cl$_2$ was added to the residue. The resulting solid was collected by filtration and washed with CH$_2$Cl$_2$ and diethyl ether to afford Intermediate 220(a) (1 g, 2.62 mmol) as a red solid in 82% yield.

235

$^1$H NMR (d$_6$-DMSO): δ 11.15 (s, 1H), 10.04 (s, 1H), 7.42 (s, 1H), 6.92 (d, 1H, J=1.88 Hz), 6.56 (d, 1H, J=1.86 Hz), 6.05 (br s, 1H), 5.17 (s, 2H), 4.03 (s, 2H), 3.53 (t, 2H, J=5.65, 5.27 Hz), 3.36 (m, 2H, partially obscured), 1.42 (s, 9H).

LCMS: (M+H$^+$) 382.1, (M+Na$^+$) 404.3; (M−H)$^−$ 380.1.

Step 2. Preparation of (1R,2R)-4-(6-Oxo-8-[(2-phenyl-cyclopropanecarbonyl)-amino]-5,6-dihydro-1H-[1,2]diazepino[4,5,6-cd]indol-2-yl)-3,6-dihydro-2H-pyridine-1-carboxylic Acid tert-butyl Ester 220(b)

Preparation of intermediate 220(b) from Intermediate 220(a) (100 mg, 0.262 mmol), (1R,2R)-2-phenyl-cyclopropanecarboxylic acid (47.0 mg, 0.290 mmol), (3-dimethylamino-propyl)-ethyl-carbodiimide, hydrochloride (55 mg, 0.288 mmol), and 4-dimethylaminopyridine (35.2 mg, 0.288 mmol) in N,N-dimethylformamide (6.0 mL) was carried out analogously to Example 190, step 2. When the reaction was judged complete, the volatile components were removed in vacuo, and the resulting residue was dissolved in methanol and loaded onto a silica gel plug. The plug was then loaded onto a silica gel column and eluted with 1:1 dichloromethane: ethyl acetate to afford Intermediate 220(b) (130 mg, 0.248 mmol) as a yellow solid in 94% yield.

$^1$H NMR (d$_6$-DMSO): δ 11.71 (s, 1H), 10.39 (s, 1H), 10.26 (s, 1H), 8.07 (d, 1H, J=1.70 Hz), 7.57 (d, 1H, J=1.70 Hz), 7.50 (s, 1H), 7.33–7.25 (m, 2H), 7.23–7.15 (m, 3H), 6.16 (s, 1H), 4.08–4.04 (m, 2H), 3.55 (t, 2H, J=5.65, 5.27 Hz), 3.35 (m, 2H, obscured), 2.41–2.33 (m, 1H), 2.11–2.02 (m, 1H), 1.53–1.46 (m, 1H), 1.43 (s, 9H), 1.40–1.30 (m, 1H).

LCMS: (M−H)$^−$ 524.1.

Step 3. Preparation of Title Compound: (1R,2R)-2-Phenyl-cyclopropanecarboxylic Acid [6-oxo-2-(1,2,3,6-tetrahydro-pyridin-4-yl)-5,6-dihydro-1H-[1,2]diazepino[4,5,6-cd]indol-8-yl]-amide (Hydrochloric Salt)

Preparation of the title compound from Intermediate 220(b) (130 mg, 0.248 mmol) and 4.0 M HCl in dioxane (1.24 mL) was carried out analogously to Example 91. Isolation, also in an analogous manner, afforded the title compound (107 mg, 0.232 mmol) as a red powder in 94% yield.

$^1$H NMR (d$_6$-DMSO): δ 11.97 (s, 1H), 10.47 (s, 1H), 10.33 (s, 1H), 9.31–9.10 (br s, 2H), 8.11 (d, 1H, J=1.70 Hz), 7.61 (d, 2H, J=1.70 Hz), 7.53 (s, 1H), 7.34–7.24 (m, 2H), 7.24–7.12 (m, 3H), 6.17 (s, 1H), 3.87–3.72 (m, 2H), 3.40–3.25 (m, 2H), 2.80–2.66 (m, 2H), 2.42–2.31 (m, 1H), 2.15–2.04 (m, 1H), 1.55–1.42 (m, 1H), 1.42–1.29 (m, 1H).

LCMS: (M+H$^+$) 426.0, (M+Na$^+$) 448.1; (M−H)$^−$ 424.1.

HRMS: (M+H$^+$) calcd for C$_{25}$H$_{24}$N$_5$O$_2$, 426.1930, found 426.1924.

236

Example 221

(1,2-trans)-2-Pyridin-3-yl-cyclopropanecarboxylic Acid [6-oxo-2-(1,2,3,6-tetrahydro-pyridin-4-yl)-5,6-dihydro-1H-[1,2]diazepino[4,5,6-cd]indol-8-yl]-amide; Dihydrochloride

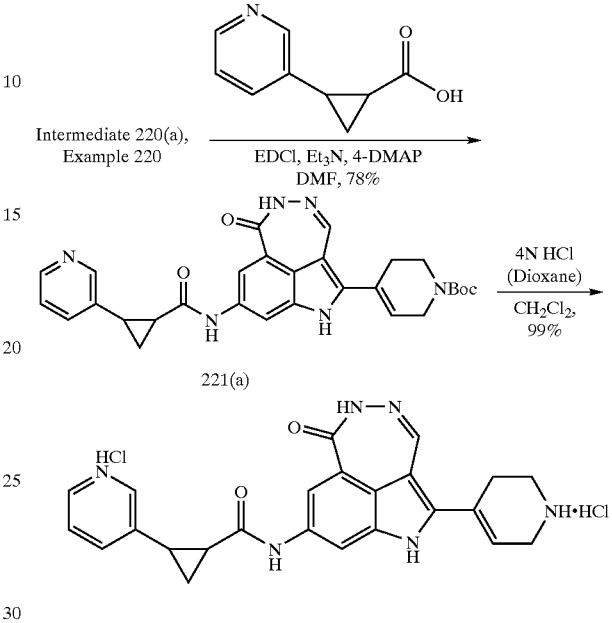

Step 1. Preparation of (1,2-trans)-4-{6-oxo-8-[(2-pyridin-3-yl-cyclopropanecarbonyl)-amino]-5,6-dihydro-1H-[1,2]diazepino[4,5,6-cd]indol-2-yl}-3,6-dihydro-2H-pyridine-1 carboxylic Acid ten-butyl Ester 221(a)

Preparation of intermediate 221(a) from Intermediate 220(a) of Example 220 (100 mg, 0.262 mmol), crude 2-pyridin-3-yl-cyclopropanecarboxylic acid (estimated purity c.a. 75%) (67.3 mg, c.a. 0.289 mmol), (3-dimethylamino-propyl)-ethyl-carbodiimide hydrochloride (55 mg, 0.288 mmol), and 4-dimethylaminopyridine (35.2 mg, 0.288 mmol) in N,N-dimethylformamide (10.0 mL) was carried out analogously to Example 190, step 2. When the reaction was judged complete, the volatile components were removed in vacuo, and the resulting residue was dissolved in methanol and loaded onto a silica gel plug. The plug was then loaded onto a silica gel column and eluted with 20:1 dichloromethane: methanol to afford Intermediate 221(a) (107.6 mg, 0.204 mmol) as a yellow solid in 78% yield.

$^1$H NMR (d$_6$-DMSO): δ 11.72 (s, 1H), 10.42 (s, 1H), 10.26 (s, 1H), 8.50 (s, 1H), 8.40 (d, 1H, J=4.71 Hz), 8.07 (s, 1H), 7.57 (s, 1H), 7.55 (d, 1H, J=7.91 Hz), 7.50 (s, 1H), 7.32 (dd, 1H, J=4.71, 3.77 Hz), 6.16 (s, 1H), 4.05 (br s, 2H), 3.55 (t, 2H, J=4.52, 4.71 Hz), 3.35 (m, 2H, obscured), 2.46–2.37 (m, 1H), 2.16–2.06 (m, 1H), 1.57–1.48 (m, 1H), 1.43 (s, 9H), 1.48–1.38(m, 1H).

LCMS: (M+H$^+$) 527.2; (M−H)$^−$ 525.0.

Step 2. Preparation of Title Compound: (1,2-tans)-2-Pyridin-3-yl-cyclopropanecarboxylic Acid [6-oxo-2-(1,2,3,6-tetrahydro-pyridin-4-yl)-5,6-dihydro-1H-[1,2]diazepino[4,5,6-cd]indol-8-yl]-amide; Dihydrochloride Preparation of the title compound from Intermediate 221(a) (100 mg, 0.190 mmol) and 4.0 M HCl in dioxane (0.95 mL) was carried out analogously to Example 91. Isolation, also in an analogous manner, afforded the title compound (95 mg, 0.190 mmol) as a red powder in 99% yield.

$^1$H NMR (d$_6$-DMSO): δ 12.05 (s, 1H), 10.66 (s, 1H), 10.34 (s, 1H), 9.29 (br s, 2H), 8.89 (d, 1H, J=1.51 Hz), 8.74 (d, 1H, J=5.27 Hz), 8.32 (d, 1H, J=8.48 Hz), 10 (d, 1H, J=1.51 Hz), 7.94 (dd, 1H, J=6.03, 5.65 Hz), 7.65 (d, 1H, J=1.51 Hz), 7.53 (s, 1H), 6.17 (s, 1H), 3.85–3.74 (m, 2H), 3.38–3.25 (m, 2H), 2.80–2.70 (m, 2H), 2.70–2.59 (m, 1H), 2.40–2.29 (m, 1H), 1.69–1.55 (m, 2H).

LCMS: (M+H$^+$) 427.1, (M+Na$^+$) 449.1; (M–H)$^-$ 425.0.

HRMS: (M+H$^+$) calcd for C$_{24}$H$_{23}$N$_6$O$_2$, 427.1882, found 427.1895.

Example 222

(1R,2R)-2-Phenyl-cyclopropanecarboxylic Acid (6-oxo-2-piperidin-4-yl-5,6-dihydro-1H-[1,2]diazepino[4,5,6-cd]indol-8-yl)-amide (Hydrochloric Salt)

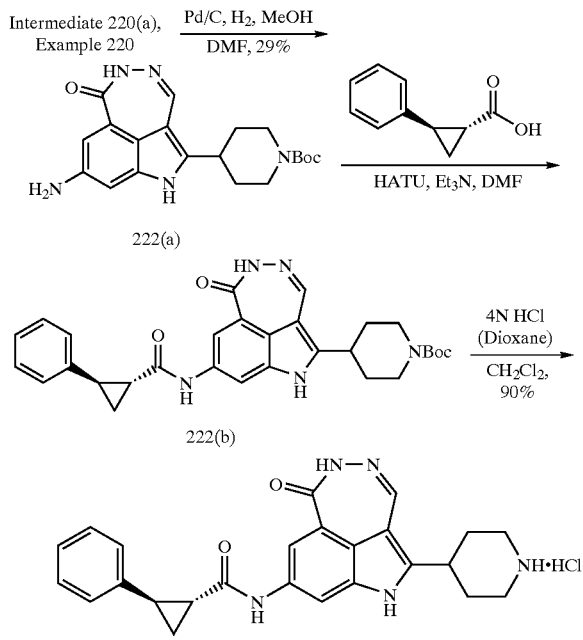

Step 1. Preparation of 4-(8-Amino-6-oxo-5,6-dihydro-1H-[1,2]diazepino[4,5,6-cd]indol-2-yl)-piperidine-1-carboxylic Acid tert-butyl Ester 222(a)

In a manner analogous to that of Example 183, palladium (10% on activated carbon) (0.186 g) was added to a solution of Intermediate 220(a) of Example 220 (0.61 g, 1.60 mmol) in 9:1 methanol:N,N-dimethformamide (50 mL). The reaction mixture was purged with H$_2$ and stirred at room temperature under H$_2$ (1 atm.) for 6.5 hours. The mixture was filtered, and the filtrate evaporated. The resulting residue was dissolved in methanol and loaded onto a silica gel plug. The plug was then loaded onto a silica gel column and eluted with 50:3 dichloromethane:methanol to give Intermediate 222(a) (0.18 g, 0.470 mmol) as a yellow solid in 29% yield.

$^1$H NMR (d$_6$-DMSO): δ 11.03 (s, 1H), 9.88 (s, 1H), 7.43 (s, 1H), 6.86 (s, 1H), 6.54 (s, 1H), 5.04 (br s, 2H), 4.16–3.99 (m, 3H), 2.95–2.67 (m, 2H), 1.73–1.54 (m, 4H), 1.42 (s, 9H).

LCMS: (M+H$^+$) 384.1, (M+Na$^+$) 406.2; (M–H)$^-$ 382.1.

Step 2. Preparation of (1R,2R)-4-{6-Oxo-8-[(2-phenyl-cyclopropanecarbonyl)-amino]-5,6-dihydro-1H-[1,2]diazepino[4,5,6-cd]indol-2-yl}-piperidine-1-carboxylic Acid tert-butyl Ester 222(b)

Preparation of intermediate 222(b) from Intermediate 222(a) (60 mg, 0.157 mmol), (1R,2R)-2-phenyl-cyclopropanecarboxylic acid (27.9 mg, 0.172 mmol), triethylamine (0.086 mL, 0.617 mmol), and O-(7-azabenzotriazol-1-yl)-N,N,N',N'-tetramethyluronium hexafluorophosphate (71.5 mg, 0.188 mmol) in N,N-dimethylformamide (5.0 mL) was carried out analogously to Example 11. The volatile components were removed in vacuo, and the resulting residue was dissolved in methanol and loaded onto a silica gel plug. The plug was then loaded onto a silica gel column and eluted with 1:1 dichloromethane: ethyl acetate to afford Intermediate 222(b) (104 mg) as a yellow solid contaminated with N,N-dimethylformamide which was carried on directly to the next step.

$^1$H NMR (d$_6$-DMSO): δ 11.57 (s, 1H), 10.32 (s, 1H), 10.12 (s, 1H), 7.98 (s, 1H), 7.55 (d, 1H, J=1.32 Hz), 7.54 (s, 1H), 7.33–7.25 (m, 2H), 7.22–7.15 (m, 3H), 4.19–4.00 (m, 3H), 2.92–2.77 (m, 2H), 2.41–2.30 (m, 1H), 2.12–2.00 (m, 1H), 1.80–1.56 (m, 4H), 1.53–1.45 (m, 1H), 1.42 (s, 9H), 1.38–1.29 (m, 1H).

LCMS: (M+H$^+$) 528.2, (M+Na$^+$) 550.1; (M–H)$^-$ 526.1.

Step 3. Preparation of Title Compound: (1R,2R)-2-Phenyl-cyclopropanecarboxylic Acid (6-oxo-2-piperidin-4-yl-5,6-dihydro-1H-[1,2]diazepino[4,5,6-cd]indol-8-yl)-amide (Hydrochloric Salt)

Preparation of the title compound from Intermediate 222(b) (100 mg) and 4.0 M HCl in dioxane (1 mL) was carried out analogously to Example 91. Isolation, also in an analogous manner, afforded the title compound (65.3 mg, 0.141 mmol) as a yellow powder in a combined yield of 90% for steps 2 and 3.

$^1$H NMR (d$_6$-DMSO): δ 11.82 (s, 1H), 10.41 (s, 1H), 10.18 (s, 1H), 9.16–9.00 (m, 1H), 8.93–8.73 (m, 1H), 8.07 (s, 1H), 7.58 (s, 2H), 7.34–7.23 (m, 2H), 7.23–7.09 (m, 3H), 3.46–3.26 (m, 3H), 3.10–2.90 (m, 2H), 2.41–2.29 (m, 1H), 2.15–2.03 (m, 1H), 2.03–1.85 (m, 4H), 1.53–1.40 (m, 1H), 1.40–1.27 (m, 1H).

LCMS: (M+H$^+$) 428.1, (M+Na$^+$) 450.2; (M–H)$^-$ 426.2.

HRMS: (M+H$^+$) calcd for C$_{25}$H$_{26}$N$_5$O$_2$, 428.2087, found 428.2086.

Example 223

(R)-2-Amino-2-cyclohexyl-N-(6-oxo-2-piperidin-4-yl-5,6-dihydro-1H-[1,2]diazepino[4,5,6-cd]indol-8-yl)-acetamide; Dihydrochloride

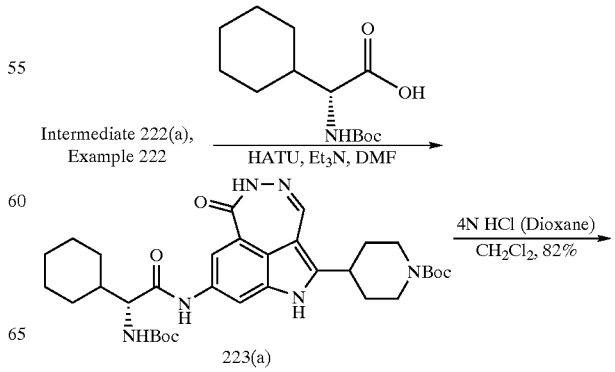

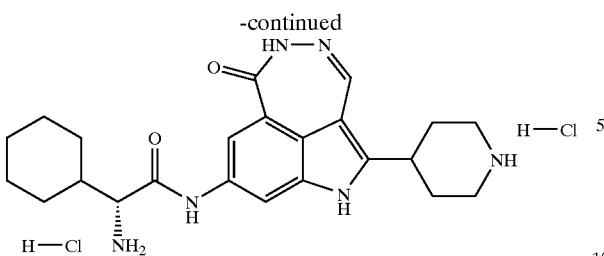

Step 1. Preparation of (R)-4-[8-(2-tert-Butoxycarbonylamino-2-cyclohexyl-acetylamino)-6-oxo-5,6-dihydro-1H-[1,2]diazepino[4,5,6-cd]indol-2-yl]-piperidine-1-carboxylic Acid tert-butyl Ester 223(a)

Preparation of intermediate 223(a) from Intermediate 222(a) of Example 222 (60 mg, 0.157 mmol), (R)-tert-butoxycarbonylamino-cyclohexyl-acetic acid (44.3 mg, 0.172 mmol), triethylamine (0.086 mL, 0.617 mmol), and O-(7-azabenzotriazol-1-yl)-N,N,N',N'-tetramethyluronium hexafluorophosphate (71.5 mg, 0.188 mmol) in N,N-dimethylformamide (8.0 mL) was carried out analogously to Example 11. The volatile components were removed in vacuo, and the resulting residue was dissolved in methanol and loaded onto a silica gel plug. The plug was then loaded onto a silica gel column and eluted with 1:1 dichloromethane: ethyl acetate to afford Intermediate 223(a) (107 mg) as a yellow solid contaminated with N,N-dimethylformamide which was carried on directly to the next step.

$^1$H NMR (d$_6$-DMSO): δ 11.57 (s, 1H), 10.14 (s, 1H), 10.03 (s, 1H), 7.98 (s, 1H), 7.94 (s, 1H), 7.56 (s, 1H), 7.54 (s, 1H), 6.85 (d, 1H, J=8.48 Hz), 4.15–3.99 (m, 2H), 3.99–3.85 (m, 1H), 2.92–2.76 (m, 2H), 1.78–1.45 (m, 10H), 1.42 (s, 9H), 1.37 (s, 9H), 1.22–0.97 (m, 5H).

LCMS: (M+H$^+$) 623.2, (M+Na$^+$) 645.2; (M–H)$^-$ 621.2.

Step 2. Preparation of Title Compound: (R)-2-Amino-2-cyclohexyl-N-(6-oxo-2-piperidin-4-yl-5,6-dihydro-1H-[1,2]diazepino[4,5,6-cd]indol-8-yl)-acetamide; Dihydrochloride Preparation of the title compound from Intermediate 223(a) (100 mg, 0.161 mmol) and 4.0 M HCl in dioxane (1.6 mL) was carried out analogously to Example 91. Isolation, also in an analogous manner, afforded the title compound (63.2 mg, 0.128 mmol) as a yellow powder in a combined yield of 82% for steps 1 and 2.

$^1$H NMR (d$_6$-DMSO): δ 11.98 (s, 1H), 10.82 (s, 1H), 10.24 (s, 1H), 9.21–9.06 (m, 1H), 9.06–8.87 (m, 1H), 8.35 (s, 3H), 8.04 (s, 1H), 7.64 (d, 1H, J=1.70 Hz), 7.60(s, 1H), 3.47–3.28 (m, 4H), 3.10–3.29 (m, 2H), 2.10–1.86 (m, 4H), 1.86–1.52 (m, 6H), 1.28–0.94 (m, 5H).

LCMS: (M+H$^+$) 423.2, (M+Na$^+$) 445.1; (M–H)$^-$ 421.3.

HRMS: (M+H$^+$) calcd for C$_{23}$H$_{31}$N$_5$O$_2$, 423.2508, found 423.2492.

Example 224

(1,2-trans)-2-Pyridin-3-yl-cyclopropanecarboxylic Acid (6-oxo-2-piperidin-4-yl-5,6-dihydro-1H-[1,2]diazepino[4,5,6-cd]indol-8-yl)-amide; Dihydrochloride

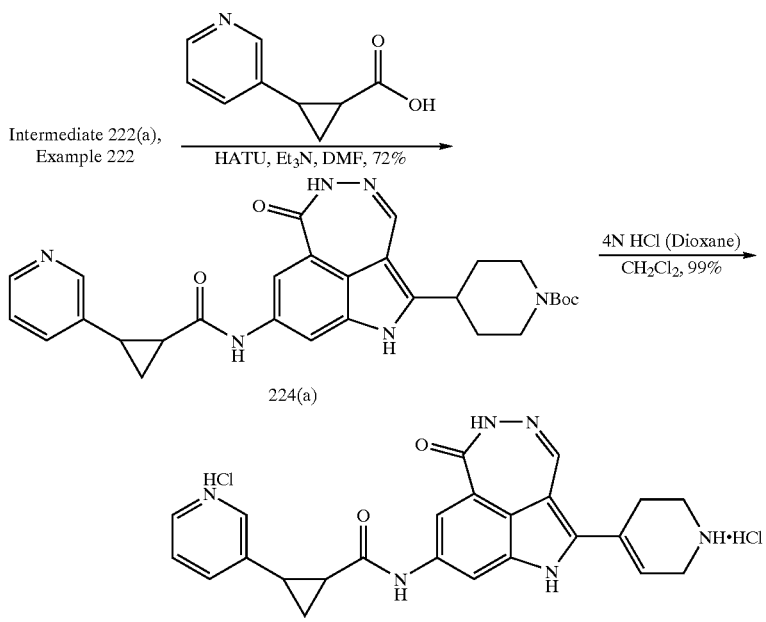

Step 1. Preparation of 4-{6-Oxo-8-[(1,2-trans)-(2-pyridin-3-yl-cyclopropanecarbonyl)-amino]-5,6-dihydro-1H-[1,2]diazepino[4,5,6-cd]indol-2-yl}piperidine-1-carboxylic Acid tert-butyl Ester 224(a)

Preparation of intermediate 224(a) from Intermediate 222(a) of Example 222 (60 mg, 0.157 mmol), (1,2-trans)-2-pyridin-3'-yl-cyclopropanecarboxylic acid (40.2 mg, 75%, 0.172 mmol), triethylamine (0.086 mL, 0.617 mmol), and O-(7-azabenzotriazol-1-yl)-N,N,N',N'-tetramethyluronium hexafluorophosphate (71.5 mg, 0.188 mmol) in N,N-dimethylformamide (8.0 mL) was carried out analogously to Example 11. The volatile components were removed in vacuo, and the resulting residue was dissolved in methanol and loaded onto a silica gel plug. The plug was then loaded onto a silica gel column and eluted with 25:1 dichloromethane: methanol to afford Intermediate 224(a) (59.2 mg, 0.112 mmol) as a yellow solid in 72% yield.

$^1$H NMR (d$_6$-DMSO): δ 11.59(s, 1H), 10.39 (s, 1H), 10.14 (s, 1H), 8.65 (d, 1H, J=2.07 Hz), 8.53 (dd, 1H, J=4.99, 1.41 Hz), 7.98 (d, 1H, J=1.70 Hz), 7.84 (d, 1H, J=7.91 Hz), 7.59–7.53 (m, 3H), 4.16–4.02 (m, 3H), 2.95–2.74 (m, 2H), 2.22–2.13 (m, 1H), 1.78–1.45 (m, 7H), 1.42 (s, 9H).

LCMS: (M+H$^+$) 529.1; (M–H)$^-$ 527.2.

Step 2. Preparation of Title Compound: (1,2-trans)-(2-Pyridin-3-yl-cyclopropanecarboxylic Acid (6-oxo-2-piperidin-4-yl-5,6-dihydro-1H-[1,2]diazepino[4,5,6-cd]indol-8-yl)-amide; Dihydrochloride Preparation of the title compound from Intermediate 224(a) (50 mg, 0.095 mmol) and 4.0 M HCl in dioxane (0.5 mL) was carried out analogously to Example 91. Isolation, also in an analogous manner, afforded the title compound (47.4 mg, 0.095 mmol) as a yellow powder in 99% yield.

$^1$H NMR (d$_6$-DMSO): δ 11.87 (s, 1H), 10.59 (s, 1H), 10.20 (s, 1H), 9.18–9.00 (m, 2H), 8.89 (br s, 2H), 8.72 (d, 1H, J=5.09 Hz), 8.33 (d, 1H, J=8.10 Hz), 8.07 (s, 1H), 7.96 (dd, 1H, J=8.10, 7.72 Hz), 7.60 (d, 2H, J=5.09 Hz), 3.47–3.29 (m, 3H), 3.11–2.84 (m, 2H), 2.75–2.61 (m, 1H), 2.40–2.29 (m, 1H), 2.09–1.84 (m, 4H), 1.70–1.54 (m, 2H).

LCMS: (M+H$^+$) 429.2, (M+Na$^+$) 451.1; (M–H)$^-$ 427.1.

HRMS: (M+H$^+$) calcd for C$_{24}$H$_{25}$N$_6$O$_2$, 429.2039, found 429.2021.

Example 225

(1R,2R)-N-(6-Oxo-2-pyridin-4-yl-5,6-dihydro-1H-[1,2]diazepino[4,5,6-cd]indol-8-yl)-2-phenylcyclopropanecarboxamide

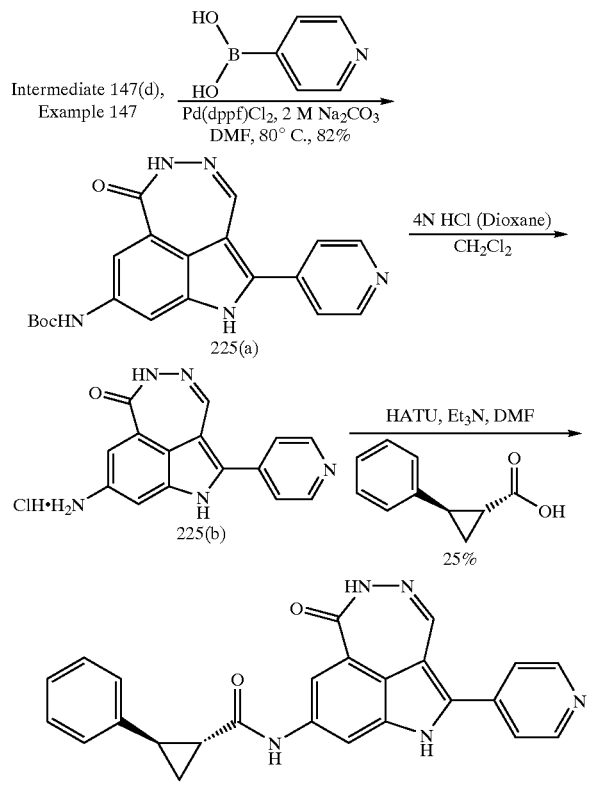

Step 1. Preparation of ten-Butyl 6-oxo-2-pyridin-4-yl-5,6-dihydro-1H-[1,2]diazepino[4,5,6-cd]indol-8-ylcarbamate 225(a)

A mixture of Intermediate 147(d) of Example 147 (0.50 g, 1.3 mmol), 4-pyridyl boronic acid (0.25 g, 2.0 mmol), [1,1'-bis(diphenylphosphino)ferrocene]dichloropalladium (II) (106 mg, 0.13 mmol) and 3.0 M aqueous sodium carbonate (3.3 ml) in N,N-dimethylformamide (20 ml) was stirred at 100° C. for 4 hours. The volatile components were removed in vacuo and the residue was subjected to on silica gel chromatography, eluting with CH$_2$Cl$_2$:methanol (95:5 increasing to 90:10). Intermediate 225(a) (0.41 g) was obtained in 82% yield.

$^1$H NMR (d$_6$-DMSO): δ 12.22 (s, 1H), 10.52 (s, 1H), 9.60 (s, 1H), 8.74 (s, 1H), 8.72 (s, 1H), 7.85 (d, H, J=1.7 Hz), 7.75 (d, 1H, J=1.7 Hz), 7.60–7.72 (m, 3H), 1.51 (s, 9H).

LCMS (M$^+$+1): 378.1

Step 2. Preparation of 8-Amino-2-pyridin-4-yl-1,5-dihydro-6H-[1,2]diazepino[4,5,6-cd]indol-6-one Hydrochloride 225(b)

To a mixture of Intermediate 225(a) (0.38 g, 1.0 mmol) in CH$_2$Cl$_2$ (30 ml), was added 1M HCl in diethyl ether (20 ml). The mixture was then stirred at room temperature for 2 hours. The volatiles were removed in vacuo to provide Intermediate 225(b) which was carried on directly to the next step without further purification.

Step 3. Preparation of Title Compound: (1R,2R)-N-(6-Oxo-2-pyridin-4-yl-5,6-dihydro-1H-[1,2]diazepino[4,5,6-cd]indol-yl)-2-phenylcyclopropanecarboxamide A solution of Intermediate 225(b) (ca. 0.5 mmol), (1R, 2R)-2-phenyl-cyclopropanecarboxylic Acid (113 mg, 0.7 mmol), triethylamine (0.4 ml) and O-(7-azabenzotriazol-1-yl)-N,N,N',N'-tetramethyluronium hexafluorophosphate (0.23 g, 0.6 mmol) in 10 ml of N,N-dimethylformamide was stirred at room temperature for 3 hours. The mixture was subjected to preparative HPLC to afford the title compound (107 mg, 0.25 mmol) in 25% yield for steps 2 and 3.

$^1$H NMR (d$_6$-DMSO): δ 12.25 (s, 1H), 10.49 (s, 1H), 10.44 (s, 1H), 8.67 (s, 1H), 8.65 (s, 1H), 8.16 (s, 1H), 7.48–7.91 (m, 4H), 7.20–7.46 (m, 2H), 6.96–7.20 (m, 3H), 2.26–2.40 (m, 1H), 1.94–2.13 (m, 1H) 1.39–1.60 (m, 1H), 1.22–1.39 (m, 1H).

HRMS calculated for C$_{25}$H$_{19}$N$_5$O$_2$ 422.1617 (M+H), found 422.1626.

Example 226

N-(6-Oxo-2-pyridin-4-yl-5,6-dihydro-1H-[1,2]diazepino[4,5,6-cd]indol-8-yl)-(1,2-trans)-2-pyridin-3-ylcyclopropanecarboxamide

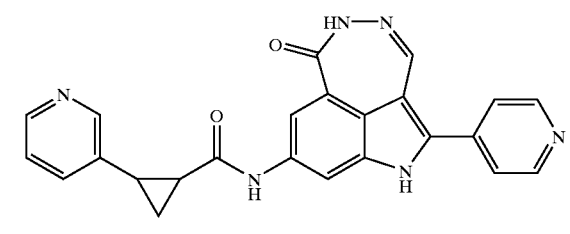

Preparation of example 226 from Intermediate 147(d) of Example 147 (200 mg, 0.529 mmol) was carried out analo gously to the preparation of Example 225 in three steps except that (1,2-trans)-2-pyridin-3-yl-cyclopropanecarboxylic acid was used instead of (1R,2R)-2-phenyl-cyclopropanecarboxylic acid in step 3. Isolation, also in an analogous manner, afforded the title compound (54 mg) as a yellow powder in 25% yield overall.

$^1$H NMR (d$_6$-DMSO): δ 12.26 (s, 1H), 10.49 (s, 1H), 10.47 (s, 1H), 8.67 (s, 1H), 8.65 (s, 1H), 8.46 (s, 1H), 8.30–8.43 (d, 1H, J=4.7 Hz), 8.16 (s, 1H), 7.57–7.88 (m, 4H), 7.45–7.57 (m, 1H), 7.19–7.41 (m, 1H), 2.32–2.42 (m, 1H), 2.01–2.20 (m, 1H), 1.46–1.65 (m, 1H), 1.32–1.46 (m, 1H).

HRMS calculated for C$_{24}$H$_{18}$N$_6$O$_2$ 423.1569 (M+H), found 423.1598.

Example 227

(2,9-Dichloro-6-oxo-5,6-dihydro-1H-[1,2]diazepino[4,5,6-cd]indol-8-yl)-carbamic Acid tert-butyl Ester

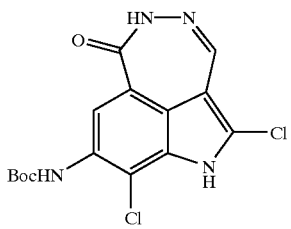

To a solution of Intermediate 147(c) of Example 147 (1.5 g, 5 mmol) in CHCl$_3$ (10 mL) and N,N-dimethylformamide (15 mL), was added N-chlorosuccinimide (701 mg, 5.25 mmol). The mixture was heated to 60° C. and stirred for 3 hours. Chloroform, N,N-dimethylformamide and water were added. Following extractive work-up with chloroform, the organic layer was dried over Na$_2$SO$_4$ and filtered. Evaporation of the volatile components gave a deep brown residue to which methanol was added. Filtration and collection of the solids gave the title compound (648 mg) as deep brown solid whose purity by NMR and HPLC was estimated to be about 70%.

$^1$H-NMR (d$_6$-DMSO): δ 13.15 (s, 1H), 10.62 (s, 1H), 8.90 (s, 1H), 7.65 (s, 1H), 7.39 (s, 1H), 1.47 (s, 9H).

LCMS: (M+H$^+$) 370.2.

Example 228

(R)-8-(2-Amino-2-cyclohexyl-acetylamino)-6-oxo-5,6-dihydro-1H-[1,2]diazepino[4,5,6-cd]indol-2-carboxylic Acid (2-dimethylamino-ethyl)-amide; Dihydrochloride

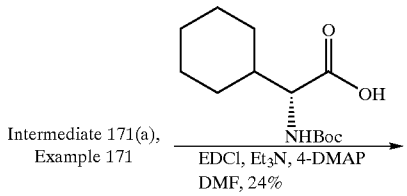

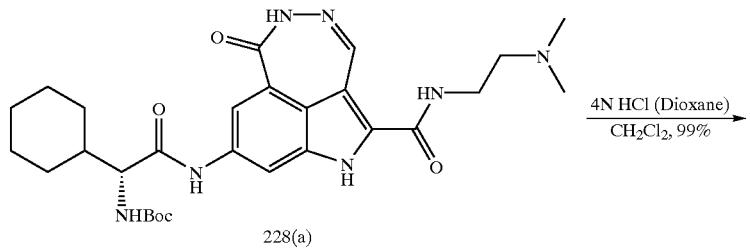

228(a)

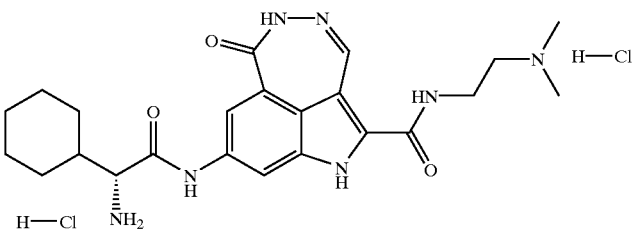

Step 1. Preparation of (R)-(Cyclohexyl-[2-(2-dimethylamino-ethylcarbamoyl)-6-oxo-5,6-dihydro-1H-[1,2]diazepino[4,5,6-cd]indol-ylcarbamoyl]-methyl)-carbamic Acid tert-butyl Ester 228(a)

Preparation of intermediate 228(a) from Intermediate 171(a) of Example 171 (200 mg, 0.571 mmol), (R)-tert-butoxycarbonylamino-cyclohexyl-acetic acid (147 mg, 0.571 mmol), (3-dimethylamino-propyl)-ethyl-carbodiimide hydrochloride (131 mg, 0.686 mmol), and 4-dimethylaminopyridine (84 mg, 0.688 mmol) in N,N-dimethylformamide (8.0 mL) was carried out analogously to Example 190, step 2. When the reaction was judged complete, the volatile components were removed in vacuo, and the resulting residue was dissolved in methanol and loaded onto a silica gel plug. The plug was then loaded onto a silica gel column and eluted with 40:3:0.3 dichloromethane: methanol: ammonium hydroxide to afford Intermediate 228(a) (77 mg, 0.139 mmol) as a yellow solid in 24% yield.

$^1$H NMR ($d_6$-DMSO): δ 12.65 (s, 1H), 10.66 (s, 1H), 10.26 (s, 1H), 9.83 (br s, 1H), 8.98 (br s, 1H), 8.16 (s, 2H), 7.76 (s, 1H), 6.93 (d, 1H, J=9.23 Hz), 4.18–4.03 (m, 1H), 4.01–3.85 (m, 1H), 3.71–3.56 (m, 2H), 2.83 (s, 6H), 1.78–1.45 (m, 6H), 1.37 (s, 9H), 1.21–0.93 (m, 5H). LCMS: (M+H$^+$) 554.2, (M+Na$^+$) 576.1; (M–H)$^-$ 552.2.

Step 2. Preparation of Title Compound: (R)-8-(2-Amino-2-cyclohexyl-acetylamino)-6-oxo-5,6-dihydro-1H-[1,2]diazepino[4,5,6-cd]indole-2-carboxylic Acid (2-dimethylamino-ethyl)-amide; Dihydrochloride Preparation of the title compound from Intermediate 228(a) (75 mg, 0.136 mmol) and 4.0 M HCl in dioxane (1.36 mL) was carried out analogously to Example 91. Isolation, also in an analogous manner, afforded the title compound (71.3 mg, 0.136 mmol) as a yellow powder in 99% yield.

$^1$H NMR ($d_6$-DMSO): δ 12.95 (s, 1H), 10.98 (s, 1H), 10.70 (s, 1H), 10.08 (br s, 1H), 9.16 (s, 1H), 8.37 (s, 3H), 8.21 (s, 1H), 8.13 (d, 1H, J=1.32 Hz), 7.79 (d, 1H, J=1.51 Hz), 3.85–3.74 (m, 1H), 3.65 (d, 2H, J=5.84 Hz), 3.30 (d, 2H, J=6.41 Hz), 2.83 (d, 6H, J=4.71 Hz), 1.93–1.52 (m, 6H), 1.29–0.97 (m, 5H).

LCMS: (M+H$^+$) 454.2, (M+Na$^+$) 476.1; (M–H)$^-$ 452.1.
HRMS: (M+H$^+$) calcd for $C_{23}H_{32}N_7O_3$, 454.2567, found 454.2574.

Example 229

N-(Cyclohexylmethyl)-N-(6-oxo-5,6-dihydro-1H-[1,2]diazepino[4,5,6-cd]indol-8-yl)urea

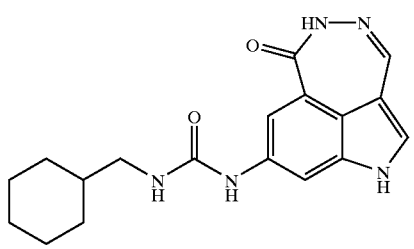

Preparation of example 229 from the title compound of Example 2 (25 mg, 0.11 mmol), N,N'-disuccinimidyl carbonate (27 mg, 0.11 mmol), N,N-diisopropylethylamine (0.024 mL, 0.21 mmol) and 1-cyclohexylmethanamine (0.028 mL, 0.021 mmol) in N,N-dimethylformamide (1.0 mL) was carried out analogously to Example 207. Purification, also in an analogous manner, afforded the title compound (4 mg, 0.009 mmol) as yellow powder in 8% yield.

$^1$H NMR (CDCl$_3$/methanol-$d_4$): δ 8.02 (s, 1H), 7.42 (s, 1H), 7.28 (s, 1H), 7.18 (s, 1H), 3.06 (d, 2H, J=5.84 Hz), 1.82–1.71 (m, 5H), 1.34–1.18 (m, 5H), 0.97 (m, 1H).
LCMS: (M–H)$_-$ 338.1, (M+Na$^+$) 362.1.

Example 230

(1R, 2R)-2-Phenyl-cyclopropanecarboxylic Acid (2-morpholin-4-ylmethyl-6-oxo-5,6-dihydro-1H-[1,2]diazepino[4,5,6-cd]indol-8-yl)-amide Compound with Acetic Acid

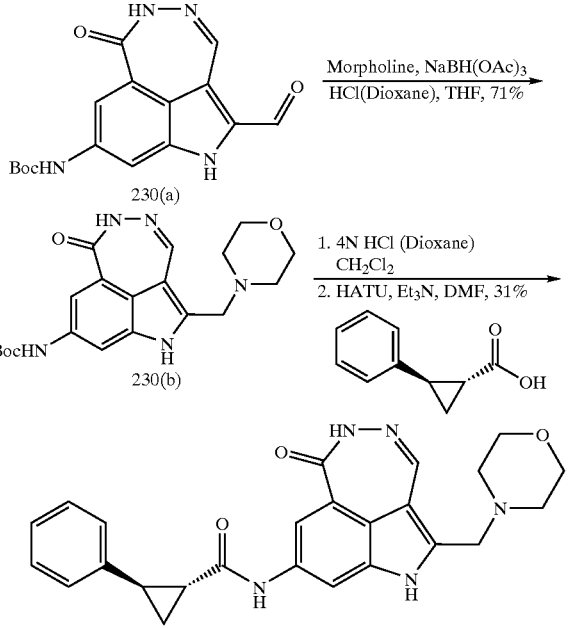

Step 1. Preparation of (2-Formyl-6-oxo-5,6-dihydro-1H-[1,2]diazepino[4,5,6-cd]indol-8-yl)-carbamic Acid tert-butyl Ester 230(a)

To a solution of the title compound of Example 164 (48 mg, 0.146 mmol) in 1:1 tetrahydrofuran:H$_2$O (4 mL) was added K$_2$CO$_3$ (30 mg, 0.219 mmol), K$_2$OsO$_2$(OH)$_4$ (7 mg) and K$_3$Fe(CN)$_6$ (72 mg, 0.219 mmol). The mixture was stirred at room temperature for 2 hours whereupon water and ethyl acetate were added. Following extractive work-up, the organic layer was then dried, filtered, and concentrated. The residue was dissolved in 1:1 tetrahydrofuran:H$_2$O (2 mL) and sodium periodate (156 mg, 50.73 mmol) was added. The mixture was stirred at room temperature for 30 min whereupon water and ethyl acetate were added. Following extractive work-up, the organic layer was then dried, filtered, and concentrated. Silica gel chromatography of the residue, eluting with 30% ethyl acetate in hexane gave Intermediate 230(a) as a pale yellow solid (11 mg, 0.034 mmol) in 22% yield.

Step 2. Preparation of (2-Morpholin-4-ylmethyl-6-oxo-5,6-dihydro-1H-[1,2]diazopino[4,5,6-cd]indol-yl)-carbamic Acid tert-butyl Ester 230(b)

To a solution of morpholine (0.32 mL, 3.64 mmol) and powdered 4A molecular sieves (1.0 g) in tetrahydrofuran (5 mL) was added 4M HCl in dioxane (0.91 mL; 3.64 mmol). After 10 min, a solution of Intermediate 230(a) (199 mg, 0.607 mmol) in tetrahydrofuran (2 mL) was added dropwise followed by NaBH(OAc)₃ (254 mg, 1.2 mmol). The resulting suspension was stirred at room temperature for 24 hours. The mixture was quenched with saturated aqueous sodium bicarbonate and filtered through diatomaceous earth, which was then washed with ethyl acetate. More ethyl acetate was added to the filtrate, and the aqueous layer was extracted. The combined organic layers were dried over Na₂SO₄, filtered, and concentrated. The residue was subjected to silica gel chromatography eluting with 5% MeOH/ethyl acetate to give Intermediate 230(b) as a pale yellow powder (173 mg, 0.43 mmol) in 71% yield.

¹H NMR (d₆-DMSO): 11.71 (s, 1H), 10.21 (s, 1H), 7.73 (s, 1H), 7.62 (s, 2H), 3.74 (s, 2H), 3.63–3.61 (m, 4H), 2.43–2.41 (m, 4H), 1.52 (s, 9H).

LCMS: (M+H⁺) 400.

Step 3. Preparation of Title Compound: (1R, 2R)-2-Phenyl-cyclopropanecarboxylic Acid (2-morpholin-4-ylmethyl-6-oxo-5,6-dihydro-1H-[1,2]diazepino[4,5,6-cd]indol-8-yl)-amide Compound with Acetic Acid Preparation of the title compound from Intermediate 230(b) (173 mg, 0.433 mmol) in CH₂Cl₂ (2 mL) and 4M HCl in dioxane (2 mL) was carried out analogously to the preparation of Example 91. After concentration, the residue was dissolved in N,N-dimethylformamide (5 mL). (1R, 2R)-2-Phenyl-cyclopropanecarboxylic acid (84 mg, 0.52 mmol), triethylamine (0.18 mL, 1.3 mmol), and O-(7-azabenzotriazol-1-yl)-N,N,N',N'-tetramethyluronium hexafluorophosphate (247 mg, 0.65 mmol) were added. After 12 hours, the mixture was concentrated and subjected to preparative HPLC in a manner analogous to Example 146, Step 2. The title compound (59 mg, 0.13 mmol) was obtained as a pale yellow powder in 31% yield.

¹H NMR (d₆-DMSO): 11.84 (s, 1H), 10.42 (s, 1H), 10.28 (s, 1H), 8.10 (s, 1H), 7.67 (s, 1H), 7.64 (s, 1H), 7.39–7.24 (m, 5H), 3.78 (s, 2H), 3.68–3.64 (m, 4H), 2.49–2.47 (m, 4H), 2.14 (m, 1H), 1.56 (m, 1H), 1.42 (m, 1H).

LCMS: (M+H⁺) 444.1

Example 231

N-(6-Oxo-2-pyridin-3-yl-5,6-dihydro-1H-[1,2]diazepino[4,5,6-cd]indol-8-yl)-(1,2-trans)-2-pyridin-3-ylcyclopropanecarboxamide

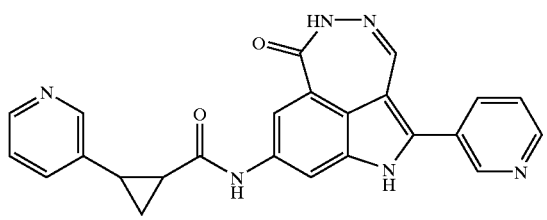

Preparation of example 231 from Intermediate 147(d) of Example 147 was carried out analogously to the preparation of Example 225 in three steps except that 3-pyridyl boronic acid was used instead of 4-pyridyl boronic acid in step 1 and (1,2-trans)-2-pyridin-3-yl-cyclopropanecarboxylic acid was used instead of (1R,2R)-2-phenyl-cyclopropanecarboxylic acid in step 3. Isolation, also in an analogous manner, afforded the title compound (69 mg) as a yellow powder in 33% yield overall.

¹H NMR (d₆-DMSO): δ 12.19 (s, 1H), 10.30–10.50 (m, 2H), 8.81 (m, 1H), 8.60 (m, 1H), 8.46 (m, 1H), 8.36 (m, 1H), 8.13 (m, 1H), 7.93–9.08 (m, 1H), 7.37–7.69 (m, 4H), 7.27 (m, 1H), 2.40 (m, 1H), 2.08 (m, 1H), 1.28–1.60 (m, 2H).

HRMS calculated for C₂₄H₁₈N₆O₂ 423.1569 (M+H), found 423.1590.

Example 232

(1R,2R)-N-(6-Oxo-2-pyridin-3-yl-5,6-dihydro-1H-[1,2]diazepino[4,5,6-cd]indol-8-yl)-2-phenylcyclopropanecarboxamide

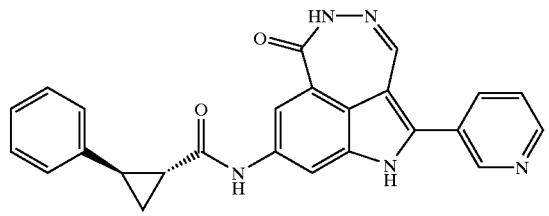

Preparation of example 232 from Intermediate 147(d) of Example 147 was carried out analogously to the preparation of Example 225 in three steps except that 3-pyridyl boronic acid was used instead of 4-pyridyl boronic acid in step 1. Isolation, also in an analogous manner, afforded the title compound (18 mg) as a yellow powder in 8% yield overall.

¹H NMR (d₆-DMSO): δ 12.18 (s, 1H), 10.28–10.54 (m, 2H), 8.81 (m, 1H), 8.60 (m, 1H), 8.13 (m, 1H), 7.95–8.08 (m, 1H), 7.57–7.70 (m, 1H), 7.49–7.57 (m, 1H), 7.38–7.48 (m, 1H), 7.01–7.34 (m, 3H) 4.05 (m, 1H), 2.32 (m, 1H), 2.03 (m, 1H), 1.46 (m, 1H), 1.32 (m, 1H).

HRMS calculated for C₂₅H₁₉N₅O₂ 422.1617 (M+H), found 422.1598.

Example 233

(1R,2R)-2-Phenyl-cyclopropanecarboxylic Acid [2-(3-dimethylamino-prop-1-ynyl)-6-oxo-5,6-dihydro-1H-[1,2]diazepino[4,5,6-cd]indol-8-yl]-amide Intermediate 147(d), Example 147 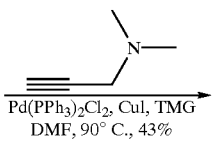 Pd(PPh₃)₂Cl₂, CuI, TMG DMF, 90° C., 43%

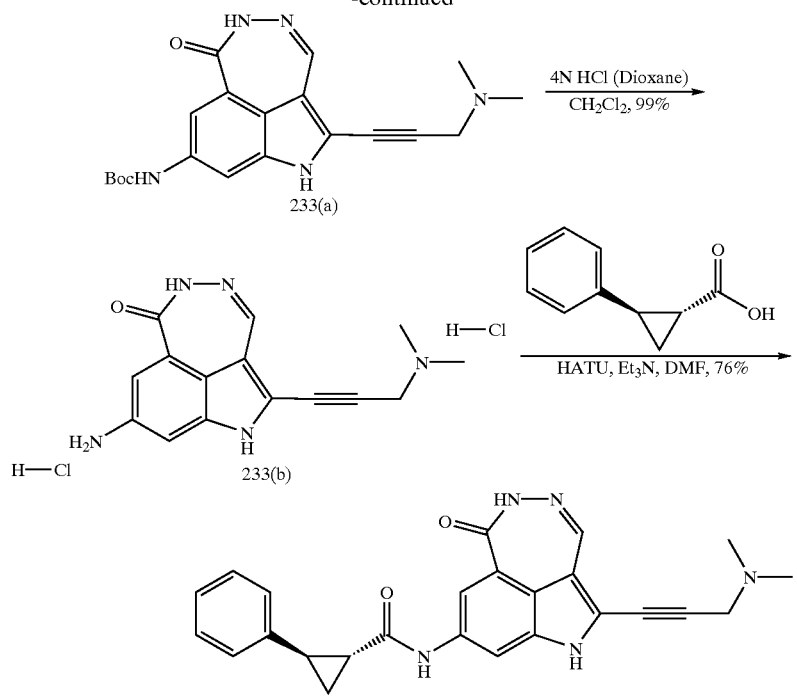

Step 1. Preparation of [2-(3-Dimethylamino-prop-1-ynyl)-6-oxo-5,6-dihydro-1H-[1,2]diazepino[4,5,6-cd]indol-4-yl] carbamic Acid tert-butyl Ester 233(a)

Under argon atmosphere, dimethyl-prop-2-ynyl-amine (198 mg, 2.38 mmol), dichlorobis(triphenylphosphine)palladium(II) (27.6 mg, 0.039 mmol), copperI iodide (7.8 mg, 0.041 mmol) and N,N,N,N-tetramethylguanidine (912 mg, 7.93 mmol) were added to a solution of Intermediate 147(d) from Example 147 (300 mg, 0.794 mmol) in N,N-dimethylformamide (3 mL) and dioxane (12 mL). The reaction was heated at 90° C. for 4 hours at which point the volatile components were removed in vacuo. The resulting residue was dissolved in methanol and loaded onto a silica gel plug. The plug was then loaded onto a silica gel column and eluted with 20:1:0.1 dichloromethane: methanol: ammonium hydroxide to afford Intermediate 233(a) (130 mg, 0.341 mmol) as a yellow solid in 43% yield.

$^1$H NMR (d$_6$-DMSO): δ 12.09 (s, 1H), 10.45 (s, 1H), 9.54 (s, 1H), 7.71 (s, 1H), 7.65 (d, 1H, J=1.51 Hz), 7.40 (s, 1H), 3.61 (s, 2H), 2.27 (s, 6H), 1.47 (s, 9H).

LCMS: (M+H$^+$) 382.1, (M+Na$^+$) 404.1; (M−H)$^-$ 380.1.

Step 2. Preparation of 8-Amino-2-(3-dimethylamino-prop-1-ynyl)-1,5-dihydro-[1,2]diazepino[4,5,6-cd]indol-6-one; Dihydrochloride 233(b)

Preparation of Intermediate 233(b) from Intermediate 233(a) (126 mg, 0.331 mmol) and 4M HCl in dioxane (1.68 mL) was carried out analogously to Example 91. Isolation, also in an analogous manner, afforded Intermediate 233(b) (117 mg, 0.331 mmol) as a yellow powder in 99% yield.

$^1$H NMR (d$_6$-DMSO): δ 12.56 (br s, 1H), 10.68 (s, 1H), 7.58 (s, 1H), 7.36 (s, 1H), 7.24 (s, 1H), 4.46 (s, 2H), 2.88 (s, 6H).

LCMS: (M+Na$^{30}$) 304.1; (M−H)$^-$ 280.1.

Step 3. Preparation of Title Compound: (1R,2R)-2-Phenyl-cyclopropanecarboxylic Acid [2-(3-dimethylamino-prop-1-ynyl)-6-oxo-5,6-dihydro-1H-[1,2]diazepino[4,5,6-cd]indol-8-yl]-amide Preparation of the title compound from Intermediate 233(b) (110 mg, 0.312 mmol), (1R,2R)-2-phenyl-cyclopropanecarboxylic acid (55 mg, 0.339 mmol), triethylamine (0.189 mL, 1.36 mmol), and O-(7-azabenzotriazol-1-yl)-N,N,N',N'-tetramethyluronium hexafluorophosphate (155 mg, 0.408 mmol) in N,N-dimethylformamide (10.0 mL) was carried out analogously to Example 11. The volatile components were removed in vacuo, and the resulting residue was dissolved in methanol and loaded onto a silica gel plug. The plug was then loaded onto a silica gel column and eluted with 40:3:0.3 dichloromethane: methanol: ammonium hydroxide to afford the title compound (100 mg, 0.235 mmol) as a yellow-brown solid in 76% yield.

$^1$H NMR (d$_6$-DMSO): δ 12.24 (s, 1H), 10.53 (s, 1H), 10.47 (s, 1H), 8.10 (d, 1H, J=1.32 Hz), 7.62 (d, 1H, J=1.51 Hz), 7.45 (s, 1H), 7.33–7.25 (m, 2H), 7.23–7.15 (m, 3H), 3.84 (s, 2H), 2.44 (s, 6H), 2.42–2.32 (m, 1H), 2.12–2.02 (m, 1H), 1.55–1.45 (m, 1H), 1.42–1.32 (m, 1H).

LCMS: (M+H$^+$) 426.0, (M+Na$^+$) 448.1; (M−H)$^-$ 424.1.

HRMS: (M+H$^+$) calcd for $C_{25}H_{24}N_5O_2$, 426.1930, found 426.1911.

Example 234

(1R, 2R)-2-Phenyl-cyclopropanecarboxylic Acid [2-(4-methyl-piperazine-1-carbonyl)-6-oxo-5,6-dihydro-1H-[1,2]diazepino[4,5,6-cd]indol-8-yl]-amide (Acetic Acid Salt)

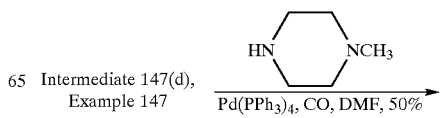

Intermediate 147(d), Example 147

-continued

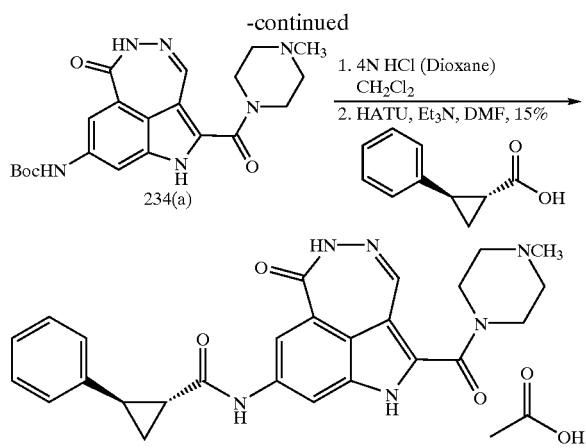

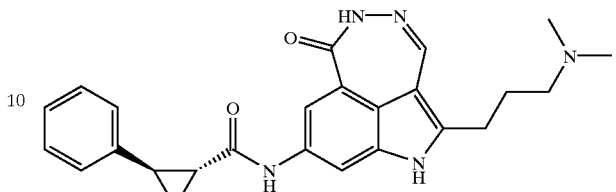

Step 1. Preparation of [2-(4-Methyl-piperazine-1-carbonyl)-6-oxo-5,6-dihydro-1H-[1,2]diazepino[4,5,6-cd]indol-8-yl]-carbamic Acid tert-butyl Ester; Compound with Acetic Acid 234(a)

Preparation of Intermediate 234(a) from Intermediate 147(d) of Example 147 (453 mg, 1.2 mmol), N-methylpiperazine (0.66 mL, 6 mmol), and tetrakis(triphenylphosphine)palladium(0) (105 mg, 0.09 mmol) in N,N-dimethylformamide (7 mL) was carried out analogously to the preparation of Example 161 except that tetrakis(triphenylphosphine)palladium(0) was used as the catalyst instead of bis(diphenylphosphino)ferrocenedichloropalladium (II). After concentration, the residue was subjected to preparative HPLC (Peeke Scientific, HI-Q C18 reverse phase 5u, 100A, 250×21.2 mm column) eluting with $CH_3CN$ and 0.1% acetic acid in water at a flow rate of 20 mL/min using a gradient of 5–95% $CH_3CN$ over 40 min to give Intermediate 234(a) (254 mg, 0.6 mmol) as a pale green powder in 50% yield.

$^1$H NMR ($d_6$-DMSO): 12.06 (s, 1H), 10.46 (s, 1H), 9.52 (s, 1H), 7.74 (s, 1H), 7.64 (s, 1H), 7.37 (s, 1H), 3.49–3.48 (m, 4H), 2.29–2.28 (m, 4H), 2.20 (s, 3H), 1.42 (s, 9H).

LCMS: (M+H$^+$) 426.1

Step 2. Preparation of Title Compound: (1R, 2R)-2-Phenyl-cyclopropanecarboxylic Acid [2-(4-methyl-piperazine-1-carbonyl)-6-oxo-5,6-dihydro-1H-[1,2]diazepino[4,5,6-cd]indol-8-yl]-amide (Acetic Acid Salt)

Preparation of the title compound from Intermediate 234(a) (445 mg, 1.06 mmol) in $CH_2Cl_2$ (5 mL) and 4M HCl in dioxane (5 mL) was carried out analogously to Example 91. After concentration, the residue was dissolved in N,N-dimethylformamide (5 mL). (1R, 2R)-2-Phenyl-cyclopropanecarboxylic acid (162 mg, 1.0 mmol), triethylamine (0.42 mL, 3 mmol), and O-(7-azabenzotriazol-1-yl)-N,N,N',N'-tetramethyluronium hexafluorophosphate (456 mg, 1.2 mmol) was sequentially added. After 12 hours, the mixture was concentrated. The crude product was purified by preparative HPLC in a manner analogous to Example 146, Step 2, to give the title compound as a pale yellow powder (74 mg, 0.16 mmol) in 15% yield.

$^1$H NMR ($d_6$-DMSO): 12.25 (s, 1H), 10.59(s, 1H), 10.51 (s, 1H), 8.18 (s, 1H), 7.69 (s, 1H), 7.49 (s, 1H), 7.34–7.19 (m, 5H), 3.63 (brs, 4H), 2.56 (s, 3H), 2.40–2.30 (m, 4H), 2.11 (m, 1H), 1.56 (m, 1H), 1.42 (m, 1H).

LCMS: (M+H$^+$) 444.1

Example 235

(1R,2R)-2-Phenyl-cyclopropanecarboxylic Acid [2-(3-dimethylamino-propyl)-6-oxo-5,6-dihydro-1H-[1,2]diazepino[4,5,6-cd]indol-8-yl]-amide

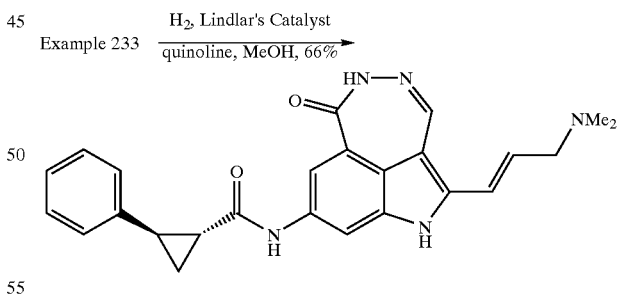

In a manner analogous to that of Example 183, 10% palladium on activated carbon (20 mg) was added to a solution of the title compound of Example 233 (20 mg, 0.047 mmol) in methanol (3 mL). The reaction mixture was purged with $H_2$ and stirred at room temperature under $H_2$ (1 atm.) for 1 hour. The reaction mixture was loaded onto a silica gel plug. The plug was then loaded onto a silica gel column and eluted with 20:1:0.1 dichloromethane: methanol: ammonium hydroxide to afford the title compound (8 mg, 0.0186 mmol) as a yellow solid in 40% yield.

$^1$H NMR ($d_6$-DMSO): δ 11.70 (s, 1H), 10.34 (s, 1H), 10.17 (s, 1H), 8.04 (d, 1H, J=1.51 Hz), 7.52 (d, 1H, J=1.51 Hz), 7.48 (s, 1H), 7.33–7.25 (m, 2H), 7.23–7.14 (m, 3H), 2.98–2.81 (m, 4H), 2.66 (br s, 6H), 2.41–2.31 (m, 1H), 2.11–2.02 (m, 1H), 2.01–1.87 (m, 2H), 1.53–1.43 (m, 1H), 1.41–1.31 (m, 1H).

LCMS: (M+H$^+$) 430.1, (M+Na$^+$) 452.1; (M−H)$^-$ 428.1.

HRMS: (M+H$^+$) calcd for $C_{25}H_{26}N_5O_2$, 430.2243, found 430.2240.

Example 236

(1R,2R)-2-Phenyl-cyclopropanecarboxylic Acid [2-(3-dimethylamino-propenyl)-6-oxo-5,6-dihydro-1H-[1,2]diazepino[4,5,6-cd]indol-8-yl]-amide Example 233 $\xrightarrow{H_2, \text{Lindlar's Catalyst}}_{\text{quinoline, MeOH, 66\%}}$ To a mixture of the title compound from Example 233 (45 mg, 0.106 mmol), Lindlar catalyst (45 mg), and quinoline (4.1 mg, 0.032 mmol) was added anhydrous methanol (3 mL). The reaction mixture was purged with $H_2$ and stirred at room temperature under $H_2$ (1 atm) for 2.5 hours. The reaction mixture was loaded onto a silica gel plug. The plug was then loaded onto a silica gel column and eluted with 20:1:0.1 dichloromethane: methanol: ammonium hydroxide to afford the title compound (30 g, 0.070 mmol) as a yellow solid in 66% yield.

¹H NMR (d₆-DMSO): δ 13.07 (s, 1H), 10.41 (s, 1H), 10.32 (s, 1H), 8.11 (d, 1H, J=1.70 Hz), 7.57 (s, 1H), 7.54 (d, 1H, J=1.70 Hz), 7.33–7.25 (m, 2H), 7.23–7.14 (m, 3H), 6.58 (d, 1H, J=12.25 Hz), 5.91 (dt, 1H, J=12.06, 6.22), 3.16 (d, 2H, J=5.65 Hz), 2.42–2.33 (m, 1H), 2.28 (s, 6H), 2.12–2.03 (m, 1H), 1.53–1.44 (m, 1H), 1.41–1.31 (m, 1H).

LCMS: (M+H⁺) 428.1, (M+Na⁺) 450.0; (M–H)⁻ 426.0.

HRMS: (M+H⁺) calcd for $C_{25}H_{26}N_5O_2$, 428.2087, found 428.2082.

Example 237

(1R,2R)-2-Phenyl-cyclopropanecarboxylic Acid [2-(3-methylamino-prop-1-ynyl)-6-oxo-5,6-dihydro-1H-[1,2]diazepino[4,5,6-cd]indol-8-yl]-amide (Hydrochloric Salt)

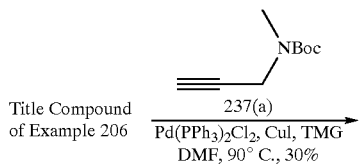

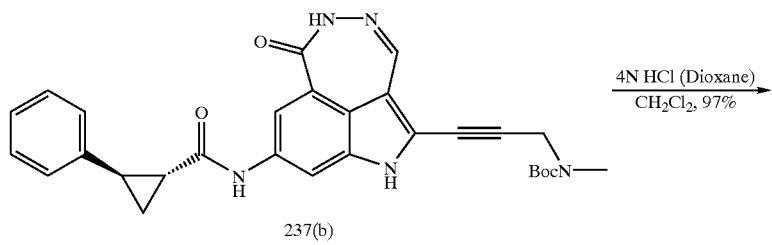

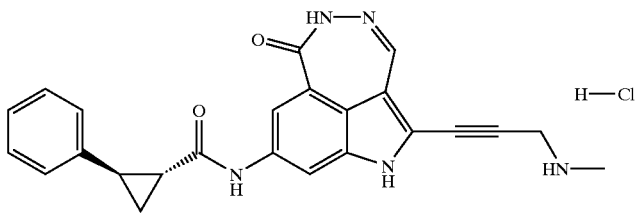

Step 1. Preparation of (1R,2R)-Methyl-(3-{6-oxo-4-[(2-phenyl-cyclopropanecarbonyl)-amino]-5,6-dihydro-1H-[1,2]diazepino[4,5,6-cd]indol-2-yl}-prop-2-ynyl)-carbamic Acid tert-butyl Ester 237(b)

Intermediate 237(a) was prepared by stirring methyl-prop-2-ynyl-amine (0.5 g, 7.23 mmol), di-tert-butyl dicarbonate (1.74 g, 7.97 mmol) and 2,6-dimethyl-pyridine (0.088 g, 0.72 mmol) in anhydrous acetonitrile (10 mL) at room temperature for 16 hours. The solvent was evaporated and the residue was subjected to silica gel chromatography eluting with ethyl acetate to afford Intermediate 237(a) (1 g, 5.91 mmol) as colorless oil in 82% yield. In a manner analogous to that of Example 233, Step 1, under an argon atmosphere, intermediate 237(a) (66 mg, 0.39 mmol), dichlorobis(triphenylphosphine)palladium(II) (4.6 mg, 0.0066 mmol), copperI iodide (1.2 mg, 0.0063 mmol) and N,N,N,N-tetramethylguanidine (150 mg, 1.30 mmol) were added to a solution of the title compound from Example 206 (55 mg, 0.13 mmol) in N,N-dimethylformamide (0.5 mL) and dioxane (2 mL). The reaction was heated at 90° C. for 3 hours at which point the volatile components were removed in vacuo. The resulting residue was dissolved in methanol and loaded onto a silica gel plug. The plug was then loaded onto a silica gel column and eluted with 3:2 dichloromethane:ethyl acetate to afford Intermediate 237(b) (20 mg, 0.039 mmol) as a yellow solid in 30% yield.

¹H NMR (d₆-DMSO): δ 12.22 (s, 1H), 10.51 (s, 1H), 10.46 (s, 1H), 8.08 (d, 1H, J=1.51 Hz), 7.61 (d, 1H, J=1.70 Hz), 7.41 (s, 1H), 7.33–7.25 (m, 2H), 7.22–7.15 (m, 3H), 4.37 (s, 2H), 2.90 (s, 3H), 2.41–2.33 (m, 1H), 2.11–2.02 (m, 1H), 1.54–1.45 (m, 1H), 1.42 (s, 9H), 1.39–1.32 (m, 1H).

LCMS: (M–H)⁻ 510.0.

Step 2. Preparation of Title Compound: (1R,2R)-2-Phenyl-cyclopropanecarboxylic Acid [2-(3-methylamino-prop-1-ynyl)-6-oxo-5,6-dihydro-1H-[1,2]diazepino[4,5,6-cd]indol-8-yl]-amide (Hydrochloric Salt)

Preparation of the title compound from Intermediate 237(b) (20 mg, 0.039 mmol) and 4.0 M HCl in dioxane (0.5 mL) was carried out analogously to Example 91. Isolation, also in an analogous manner afforded the title compound (17 mg, 0.038 mmol) as a yellow powder in 97% yield.

¹H NMR (d₆-DMSO): δ 12.37 (s, 1H), 10.59 (s, 1H), 10.55 (s, 1H), 9.30 (br s, 2H), 8.14 (s, 1H), 7.65 (s, 1H), 7.58 (s, 1H), 7.36–7.24 (m, 2H), 7.24–7.12 (m, 3H), 4.27 (s, 2H), 2.66 (s, 3H), 2.41–2.29 (m, 1H, partial obscured), 2.17–2.03 (m, 1H), 1.56–1.44 (m, 1H), 1.43–1.31 (m, 1H).

LCMS: (M–H)⁻ 410.1.

HRMS: (M+H⁺) calcd for $C_{24}H_{22}N_5O_2$, 412.1774, found 412.1768.

Example 238

(1,2-tans)-2-Pyridin-3-yl-cyclopropanecarboxylic Acid [2-(3-methylamino-prop-1-ynyl)-6-oxo-5,6-dihydro-1H-[1,2]diazepino[4,5,6-cd]indol-8-yl]-amide; Dihydrochloride

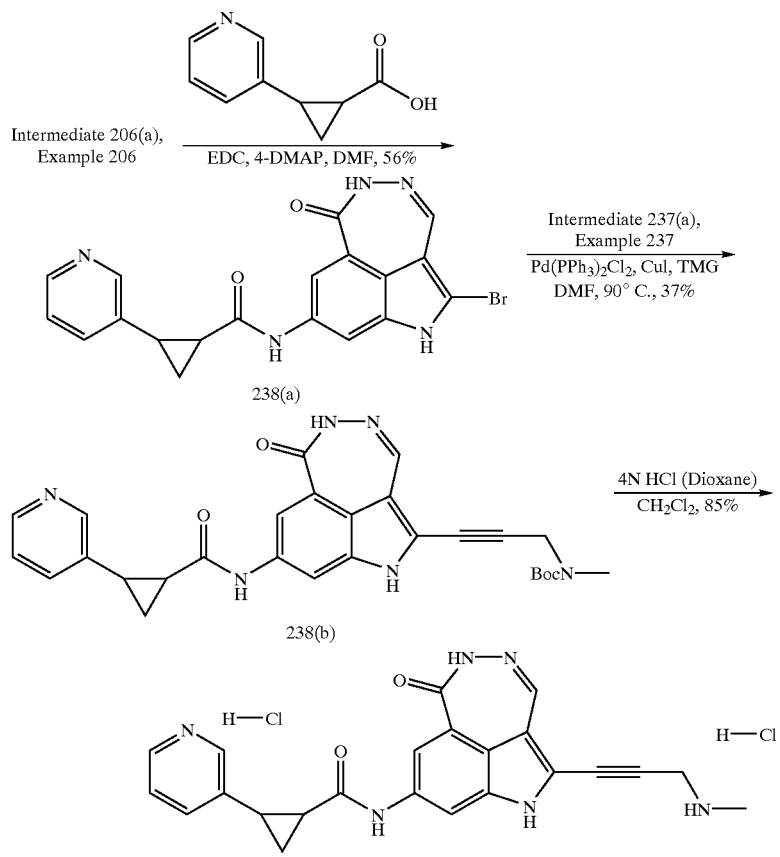

Step 1. Preparation of (1,2-trans)-2-Pyridin-3-yl-cyclopropanecarboxylic Acid (2-bromo-6-oxo-5,6-dihydro-1H-[1,2]diazepino[4,5,6-cd]indol-8-yl)-amide 238(a)

Preparation of Intermediate 238(a) from Intermediate 206(a) of Example 206 (120 mg, 0.38 mmol), (1,2-trans)-2-pyridin-3-yl-cyclopropanecarboxylic acid (106 mg, c.a 0.487 mmol, purity c.a. 75%), (3-dimethylamino-propyl)-ethyl-carbodiimide hydrochloride (88 mg, 0.461 mmol), and 4-dimethylaminopyridine (56 mg, 0.459 mmol) in N,N-dimethylformamide (15.0 mL) was carried out analogously to the preparation of Example 190, step 2. When the reaction was judged complete, the volatile components were removed in vacuo, the resulting residue was dissolved in methanol and loaded onto a silica gel plug. The plug was then loaded onto a silica gel column and eluted with 50:3 dichloromethane:methanol to afford Intermediate 238(a) (90 mg, 0.212 mmol) as a yellow solid in 56% yield.

$^1$H NMR (d$_6$-DMSO): δ 12.60 (s, 1H), 10.46 (s, 1H), 10.45 (s, 1H), 8.50 (d, 1H, J=1.88 Hz), 8.40 (dd, 1H, J=4.62, 1.41 Hz), 8.08 (d, 1H, J=1.70 Hz), 7.60 (d, 1H, J=1.51 Hz), 7.56 (dt, 1H, J=7.96, 1.86 Hz), 7.32 (dd, 1H, J=7.91, 4.90 Hz), 7.27 (s, 1H), 2.45–2.37 (m, 1H), 2.16–2.06 (m, 1H), 1.57–1.49 (m, 1H), 1.49–1.40 (m, 1H).

LCMS: (M–H)⁻ 422.0, 424.0.

Step 2. Preparation of Methyl-(3-{6-oxo-8-[(2-pyridin-3-yl-cyclopropanecarbonyl)-amino]-5,6-dihydro-1H-[1,2]diazepino[4,5,6-cd]indol-2-yl}prop-2-ynyl)-carbamic Acid tert-butyl Ester 238(b)

Under argon in a manner analogous to that of Example 233, step 1, Intermediate 237(a) of Example 237 (54 mg, 0.32 mmol), dichlorobis(triphenylphosphine)palladium(II) (3.7 mg, 0.0053 mmol), copperI iodide (1.0 mg, 0.0053 mmol) and N,N,N,N-tetramethylguanidine (122 mg, 1.06 mmol) were added to a solution of Intermediate 238(a) (45 mg, 0.106 mmol) in N,N-dimethylformamide (1 mL) and dioxane (2 mL). The reaction was heated at 90° C. for 2 hours at which point the volatile components were removed in vacuo. The resulting residue was dissolved in methanol and loaded onto a silica gel plug. The plug was then loaded onto a silica gel column and eluted with 20:1:0.1 dichloromethane: methanol: ammonium hydroxide to afford Intermediate 238(b) (20 mg, 0.039 mmol) as a yellow solid in 37% yield.

$^1$H NMR (d$_6$-DMSO): δ 12.23 (s, 1H), 10.52 (s, 1H), 10.50 (s, 1H), 8.45 (br s, 1H), 8.06 (s, 1H), 7.61 (s, 1H), 7.56 (d, 1H, J=7.91 Hz), 7.41 (s, 1H), 7.35 (br s, 1H), 4.37 (s, 2H), 2.90 (s, 3H), 2.45–2.38 (m, 1H, partial obscured), 2.16–2.07 (m, 1H), 1.59–1.49 (m, 1H), 1.50–1.44 (m, 1H, partial obscured), 1.42 (s, 9H), LCMS: (M+H⁺) 513.2, (M+Na⁺) 535.1; (M–H)⁻ 511.1.

Step 3. Preparation of Title Compound: (1,2-trans)-2-Pyridin-3-yl-cyclopropanecarboxylic Acid [2-(3- methylamino-prop-1-ynyl)-6-oxo-5,6-dihydro-1H-[1,2]
diazepino[4,5,6-cd]indol-yl]-amide; Dihydrochloride Preparation of the title compound from Intermediate 238(b) (20 mg, 0.039 mmol) and 4M HCl in dioxane (0.5 mL) was carried out analogously to Example 91. Isolation, also in an analogous manner afforded the title compound (16 mg, 0.033 mmol) as a dark red solid in 85% yield.

$^1$H NMR (d$_6$-DMSO): δ 12.46 (s, 1H), 10.77 (s, 1H), 10.59 (s, 1H), 9.46 (br s, 2H), 8.90 (s, 1H), 8.76 (d, 1H, J=3.77 Hz), 8.34 (d, 1H, J=7.35 Hz), 8.11 (s, 1H), 8.03–7.90 (m, 1H), 7.69 (s, 1H), 7.59 (s, 1H), 4.25 (s, 2H), 2.65 (s, 3H), 2.49 (m, 1H, obscured), 2.41–2.29 (m, 1H, partial obscured), 1.73–1.55 (m, 2H).

LCMS: (M–H)$^-$ 411.1.

HRMS: (M+H$^+$) calcd for C$_{23}$H$_{21}$N$_6$O$_2$, 413.1726, found 413.1753.

Example 239

(2R)-2-Amino-2-cyclohexyl-N-[2-(3-methylamino-prop-1-ynyl)-6-oxo-5,6-dihydro-1H-[1,2]diazepino[4,5,6-cd]indol-8-yl]-acetamidede; Dihydrochloride

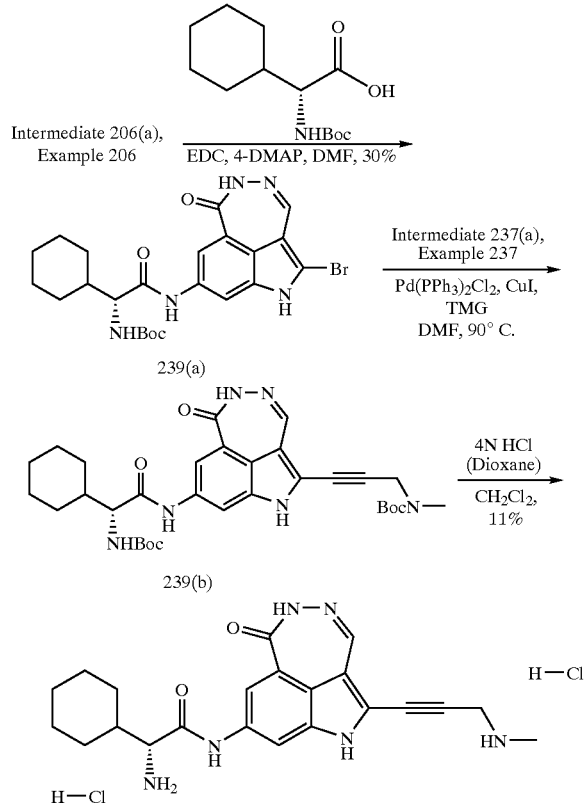

Step 1. Preparation of (R)-[(2-Bromo-6-oxo-5,6-dihydro-1H-[1,2]diazepino[4,5,6-cd]indol-8-ylcarbamoyl)-cyclohexyl-methyl]-carbamic Acid tert-butyl Ester 239(a)

Preparation of intermediate 239(a) from Intermediate 206(a) of Example 206 (120 mg, 0.38 mmol), (R)-tert-butoxycarbonylamino-cyclohexyl-acetic acid (120 mg, 0.466 mmol), (3-dimethylamino-propyl)-ethyl-carbodiimide hydrochloride (87 mg, 0.455 mmol), and 4-dimethylaminopyridine (56 mg, 0.459 mmol) in N,N-dimethylformamide (7.0 mL) was carried out analogously to the preparation of Example 190, step 2. When the reaction was judged complete, the volatile components were removed in vacuo, and the resulting residue was dissolved in methanol and loaded onto a silica gel plug. The plug was then loaded onto a silica gel column and eluted with 1.2:1 dichloromethane: ethyl acetate to afford Intermediate 239(a) (60 mg, 0.116 mmol) as a yellow solid in 30% yield.

$^1$H NMR (d$_6$-DMSO): δ 12.59 (s, 1H), 10.46 (s, 1H), 10.14 (s, 1H), 8.06 (s, 1H), 7.64 (s, 1H), 7.27 (s, 1H), 6.90 (d, 1H, J=8.85 Hz), 3.91 (t, 1H, J=8.29 Hz), 1.76–1.44 (m, 6H), 1.37 (s, 9H), 1.20–0.93 (m, 5H).

LCMS: (M–H)$^-$ 518.0, 516.0.

Step 2. Preparation of (R)-{3-[8-(2-tert-Butoxycarbonylamino-2-cyclohexyl-acetylamino)-6-oxo-5,6-dihydro-1H-[1,2]diazepino[4,5,6-cd]indol-2-yl]-prop-2-ynyl}-methyl-carbamic Acid tert-butyl Ester 239(b)

Under an argon atmosphere in a manner analogous to that of Example 233 step 1, Intermediate 237(a) of Example 237 (65 mg, 0.38 mmol), dichlorobis(triphenylphosphine)palladium(II) (4.5 mg, 0.0064 mmol), copperI iodide (1.2 mg, 0.0063 mmol) and N,N,N,N-tetramethylguanidine (146 mg, 1.27 mmol) were added to a solution of Intermediate 239(a) (66 mg, 0.127 mmol) in N,N-dimethylformamide (0.5 mL) and dioxane (2 mL). The reaction mixture was heated at 90° C. for 3 hours at which point the volatile components were removed in vacuo. The resulting residue was dissolved in methanol and loaded onto a silica gel plug. The plug was then loaded onto a silica gel column and eluted with 4:1 dichloromethane: ethyl acetate to afford Intermediate 239(b) (10 mg) as a yellow solid contaminated with an unknown impurity.

LCMS: (M+H$^+$) 607.2, (M+Na$^+$) 629.3; (M–H)$^-$ 605.2.

Step 3. Preparation of Title Compound: (2R)-2-Amino-2-cyclohexyl-N-[2-(3-methylamino-prop-1-ynyl)-6-oxo-5,6-d hydro-1H-[1,2]diazepino[4,5,6-cd]indol-8-yl]-acetamidede; Dihydrochloride Preparation of the title compound from Intermediate 239(b) (10 mg) and 4 M HCl in dioxane (0.5 mL) was carried out analogously to Example 91. Isolation, also in an analogous manner, included a further trituration with CH$_2$Cl$_2$ which removed the impurity carried along from step 2. The title compound (6 mg, 0.013 mmol) was obtained as a yellow powder in a combined yield of 11% for steps 2 and 3.

$^1$H NMR (d$_6$-DMSO): δ 12.52 (s, 1H), 10.90 (s, 1H), 10.66 (s, 1H), 9.37 (br s, 2H), 8.33 (br s, 3H), 8.08 (s, 1H), 7.73 (d, 1H, J=0.9 Hz), 7.61 (s, 1H), 4.27 (s, 2H), 3.84–3.74 (m, 1H), 2.67 (s, 3H), 1.90–1.54 (m, 6H), 1.27–0.97 (m, 5H).

LCMS: (M+Na$^+$) 429.2; (M–H)$^-$ 405.2.

HRMS: (M+H$^+$) calcd for C$_{22}$H$_{27}$N$_6$O$_2$, 407.2195, found 407.2209.

Example 240

(1,2-trans)-N-[1-(2-Hydroxymethyl)-6-oxo-5,6-dihydro-1H-[1,2]diazepino[4,5,6-cd]indol-8-yl]-2-phenylcyclopropanecarboxamide

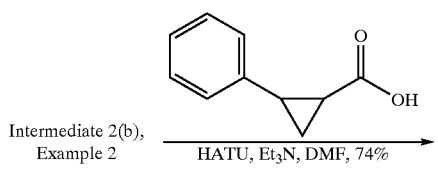

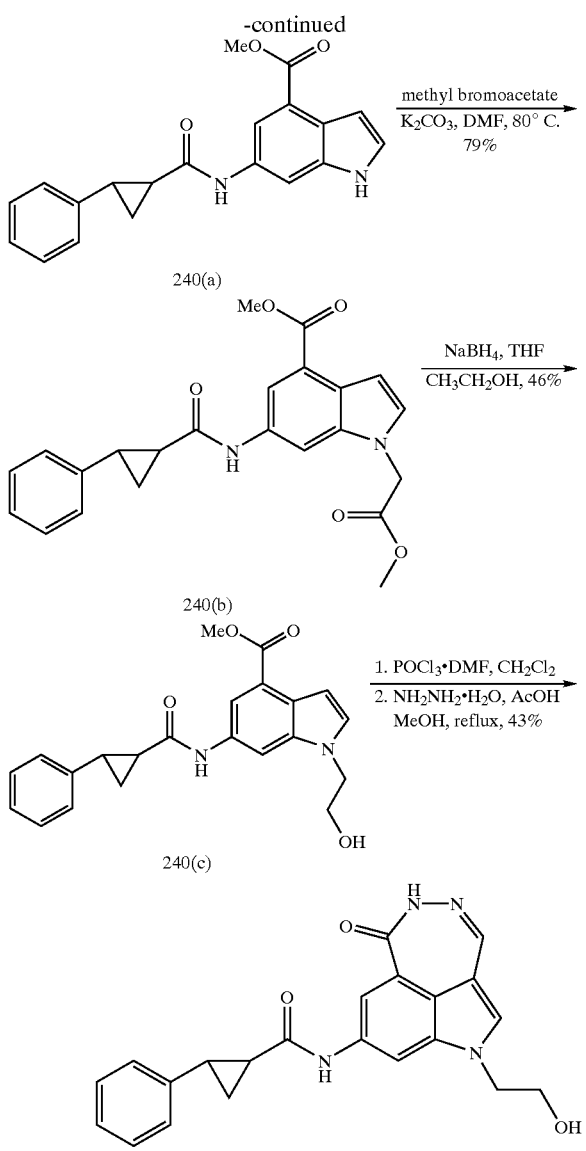

240(a)

240(b)

240(c)

Step 1. Preparation of Methyl 6-{[(2-phenylcyclopropyl)carbonyl]amino}-1H-indole-4-carboxylate 240(a)

Preparation of intermediate 240(a) from Intermediate 2(b) of Example 2 (2.27 g, 10 mmol), (1,2-trans)-2-phenylcyclopropanecarboxylic acid (1.79 g, 11 mmol), triethylamine (3.0 ml, 30 mmol), and O-(7-azabenzotriazol-1-yl)-N,N,N',N'-tetramethyluronium hexafluorophosphate (4.18 g, 11 mmol) in N,N-dimethylformamide (20 mL) was carried out analogously to Example 11.

Extractive work-up from ethyl acetate, followed by purification on silica gel column eluting with CH$_2$Cl$_2$/ethyl acetate afforded Intermediate 240(a) (2.47 g) in 74% yield.

$^1$H NMR (d$_6$-DMSO): δ11.39 (s, 1H), 10.39 (s, 1H), 8.25 (s, 1H), 7.88 (s, 1H), 7.47 (s, 1H), 7.10–7.40 (m, 5H), 6.86 (s, 1H), 3.89 (s, 3H), 2.33–2.48 (m, 1H), 2.04–2.21 (m, 1H), 1.46–1.63 (m, 1H), 1.29–1.45 (m, 1H).

LCMS (M+H): 335.1.

Step 2. Preparation of Methyl 1-(2-methoxy-2-oxoethyl)-6-{[(2-phenylcyclopropyl)carbonyl]amino}-1H-indole-4-carboxylate 240(b)

Intermediate 240(a) (2.40 g, 7.2 mmol), methyl bromoacetate (1.32 g, 8.6 mmol) and K$_2$CO$_3$ (2.0 g, 14.4 mmol) were mixed in N,N-dimethylformamide (25 mL) and stirred at 80° C. for 3 hours. After filtration the filtrate was evaporated, and the residue was subjected to silica gel chromatography eluting with CH$_2$Cl$_2$/ethyl acetate to afford Intermediate 240(b) (2.31 g) in 79% yield.

$^1$H NMR (d$_6$-DMSO): δ 10.50 (s, 1H), 8.09 (s, 1H), 7.95 (s, 1H), 7.48 (m, 1H), 7.10–7.38 (m, 5H), 6.90 (m, 1H), 5.16 (s, 2H), 3.91 (s, 3H), 3.70 (s, 3H), 2.30–2.44 (m, 1H), 2.03–2.21 (m, 1H), 1.44–1.58 (m, 1H), 1.30–1.43 (m, 1H).

LCMS (M+H): 407.1.

Step 3. Preparation of Methyl 1-(2-hydroxyethyl)-6-{[(2-phenylcyclopropyl)carbonyl]amino}-1H-indole-4-carboxylate 240(c)

To Intermediate 240(b) (2.0 g, 49 mmol) in 1:1 ethanol:tetrahydrofuran (80 mL) was added NaBH$_4$ (2.0 g, 53 mmol). The mixture was stirred at room temperature overnight. Purification by silica gel chromatography afforded Intermediate 240(c) (0.85 g) in 46% yield.

$^1$H NMR (d$_6$-DMSO): δ 10.45 (s, 1H), 8.27 (s, 1H), 7.89 (d, 1H, J=1.7 Hz), 7.49 (d, 1H, J=1.5 Hz), 7.15–7.35 (m, 5H), 6.87 (d, 1H, J=3.0 Hz), 4.95 (t, 1H, J=5.2 Hz), 4.20 (t, 2H, J=5.7 Hz), 3.91 (s, 3H), 3.60–3.80 (m, 2H), 2.33–2.46 (m, 1H), 2.05–2.18 (m, 1H), 1.43–1.65 (m, 1H), 1.30–1.43 (m, 1H).

LCMS (M+H): 379.1.

Step 4. Preparation of Title Compound: (1,2-trans)-N-[1-(2-Hydroxyethyl)-6-oxo-5,6-dihydro-1H-[1,2]diazepino[4,5,6-cd]indol-8-yl]-2-phenylcyclopropanecarboxamide With stirring, Intermediate 240(c) in N,N-dimethylformamide (7 ml) was added to a mixture of POCl$_3$ (0.6 ml) and N,N-dimethylformamide (5 mL) at 0° C. After 1 hour, the reaction was quenched with water and extracted with ethyl acetate. The organic phase was dried with Na$_2$SO$_4$ and filtered. After evaporation of the volatile components, the residue was mixed with methanol (50 ml) containing hydrazine (1 mL) and refluxed for 5 hours. After the mixture was cooled to ambient temperature, and the resulting yellow precipitate was collected by filtration and washed with methanol to afford the title compound (0.37 g) in 43% yield.

$^1$H NMR (d$_6$-DMSO): δ 10.41 (s, 1H), d10.25 (s, 1H), 8.12 (d, 1H, J=1.6 Hz), 7.55 (s, 2H), 7.45 (s, 1H), 7.10–7.33 (m, 5H), 4.12 (t, 2H, J=5.1 Hz), 3.67 (t, 2H, J=5.2 Hz), 2.29–2.40 (m, 1H), 1.99–2.10 (m, 1H), 1.41–1.52 (m, 1H), 1.28–1.39 (m, 1H).

HRMS calculated for C$_{22}$H$_{21}$N$_5$O$_3$ 389.1614 (M+H), found 389.1627.

Example 241

(1R, 2R)-2-Phenyl-cyclopropanecarboxylic Acid (2-hydroxymethyl-6-oxo-5,6-dihydro-1H-[1,2-cd]diazepino[4,5,6]indol-8-yl)-amide

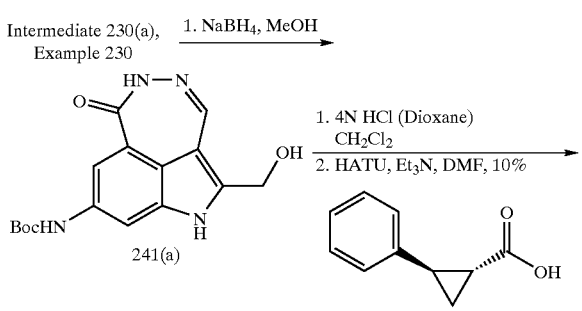

241(a)

261

-continued

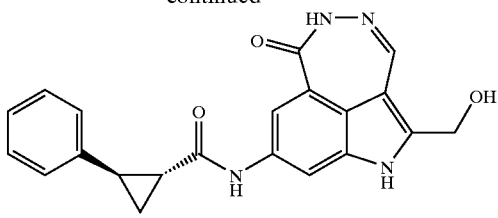

Step 1. Preparation of (2-Hydroxymethyl-6-oxo-5,6-dihydro-1H-[1,2]diazepino[4,5,6-cd]indol-8-yl)carbamic Acid tert-butyl Ester 241(a)

A solution of intermediate 230(a) of Example 230 (26 mg, 0.079 mmol) in methanol (2 mL) was treated with NaBH$_4$ (6 mg, 0.16 mmol) at 0° C. for 15 min. The solution was quenched with saturated aqueous NH$_4$Cl and diluted with ethyl acetate. After extraction, the organic phase was washed with brine, dried (Na$_2$SO$_4$), filtered, and concentrated. Silica gel chromatography of the residue (3:1 ethyl acetate:hexane) gave intermediate 241(a) (13 mg) in 50% yield.

Step 2. Preparation of Title Compound: (1R, 2R)-2-Phenyl-cyclopropanecarboxylic Acid (2-hydroxymethyl-6-oxo-5,6-dihydro-1H-[1,2-cd]diazepino[4,5,6]indol-8-yl)-amide To a suspension of Intermediate 241(a) (76 mg, 0.23 mmol) in CH$_2$Cl$_2$ (2 mL) was added 4M HCl in dioxane (2 mL, 8 mmol). After stirring at room temperature for 2 hours, the mixture was concentrated and the residue was dissolved in N,N-dimethylformamide (2 mL). (1R,2R)-2-Phenyl-cyclopropanecarboxylic acid (33.6 mg, 0.21 mmol), triethylamine (0.1 mL, 0.69 mmol), and O-(7-azabenzotriazol-1-yl)-N,N,N',N'-tetramethyluronium hexafluorophosphate (131 mg, 0.345 mmol) were added. After stirring at room temperature for 2 hours, the mixture was concentrated and the residue was subjected to preparative HPLC in a manner analogous to Example 146, step 2. The title compound was obtained as a pale yellow powder (9 mg, 0.024 mmol) in 10% yield.

$^1$H NMR (d$_6$-DMSO): δ 11.79 (s, 1H), 10.36 (s, 1H), 10.19 (s, 1H), 8.05 (d, 1H, J=1.88 Hz), 7.57 (s, 1H), 7.56 (s, 1H), 7.32–7.19 (m, 5H), 5.70 (t, 1H, J=4.0 Hz), 4.70 (d, 2H, J=5.4 Hz), 2.35 (m, 1H), 2.07 (m, 1H), 1.50 (m, 1H), 1.36 (m, 1H).

LCMS: (M+H$^+$) 375.2

Example 242

(1R,2R)-2-Phenyl-cyclopropanecarboxylic Acid {1-[2-(1,3-dioxo-1,3-dihydro-isoindol-2-yl)-ethyl]-6-oxo-5,6-dihydro-1H-[1,2]diazepino[4,5,6-cd]indol-8-yl}-amide

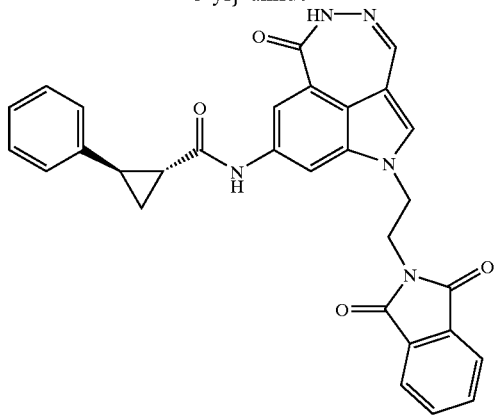

The title compound of Example 100 (130 mg, 0.38 mmol), 2-(2'-bromo-ethyl)-isoindole-1,3-dione (0.48 g, 1.9 mmol) and K$_2$CO$_3$ (0.28 g, 2.0 mmol) were stirred in N,N-dimethylformamide (6 mL) at 80° C. for 20 hours. After evaporation of the volatile components, the residue was subjected to silica gel chromatography eluting with CH$_2$Cl$_2$/MeOH to afford the title compound (130 mg) in 67% yield.

$^1$H NMR (d$_6$-DMSO): δ10.33 (s, 1H), 10.31 (s, 1H), 8.07–8.15 (d, 1H, J=1.5 Hz), 7.72–7.85 (m, 4H), 7.58 (s, 1H), 7.46–7.53 (d, 1H, J=1.5 Hz), 7.40 (s, 1H), 7.27–7.37 (m, 2H), 7.12–7.27 (m, 3H), 4.41 (t, 2H, J=4.7 Hz), 3.95 (t, 2H, J=4.9 Hz), 2.31–2.42 (m, 1H), 1.96–2.07 (m, 1H), 1.43–1.55 (m, 1H), 1.30–1.42 (m, 1H).

HRMS calculated for C$_{30}$H$_{24}$NsO$_4$ 518.1828 (M+H), found 518.1852.

Example 243

(1R,2R)-2-Phenyl-cyclopropanecarboxylic Acid (2-dimethylaminomethyl-6-oxo-5,6-dihydro-1H-[1,2]diazepino[4,5,6-cd]indol-8-yl)-amide

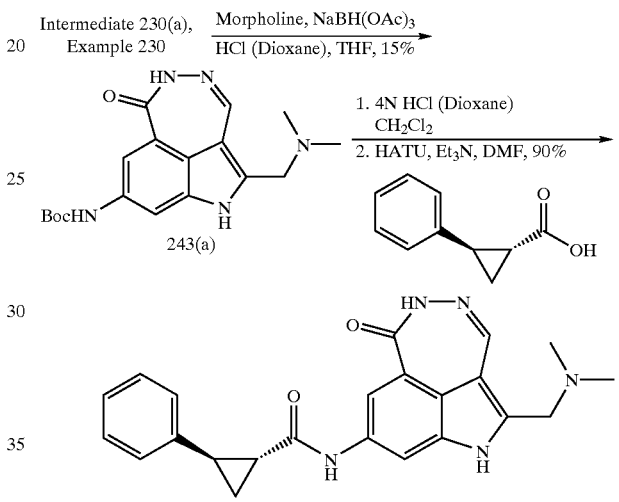

Step 1. Preparation of (2,2-Dimethylaminomethyl-6-oxo-5,6-dihydro-1H-[1,2]diazepino[4,5,6-cd]indol-8-yl)-carbamic Acid tert-butyl Ester 243(a)

Preparation of intermediate 243(a) from Intermediate 230(a) of Example 230 (707 mg, 2.16 mmol), 2M dimethylamine in tetrahydrofuran (5.4 mL, 10.8 mmol), 4M HCl in dioxane (10.8 mL; 10.8 mmol) and NaBH(OAc)$_3$ (2.29 g, 10.8 mmol) in tetrahydrofuran (5 mL) with powdered 4A molecular sieves (400 mg) was carried out analogously to Example 230, step 2. Silica gel chromatography (eluted with 2% methanol in CH$_2$Cl$_2$), also in an analogous manner, afforded Intermediate 243(a) a pale yellow powder (112 mg, 0.31 mmol) in 15% yield.

Step 2. Preparation of Title Compound: (1R,2R)-2-Phenyl-cyclopropanecarboxylic Acid (2-dimethylaminomethyl-6-oxo-5,6-dihydro-1H-[1,2]diazepino[4,5,6-cd]indol-8-yl)-amide Preparation of the title compound from Intermediate 243(a) (112 mg, 0.31 mmol) was carried out analogously to step 3 of Example 230. Silica gel chromatography (eluted with 2% methanol in ethylacetate), also in an analogous manner, afforded the title compound (113 mg, 0.28 mmol) as a yellow powder in 90% yield.

$^1$H NMR (d$_6$-DMSO): 11.84 (s, 1H), 10.38 (s, 1H), 10.28 (s, 1H), 8.75 (d, J=4 Hz, 1H), 8.53 (d, J=4 Hz, 1H), 8.07 (s, 1H), 7.62 (s, 1H), 7.60 (m, 1H), 7.51 (m, 1H), 7.32–7.18 (m, 3H), 3.31 (s, 2H), 2.49 (s, 6H), 2.33 (m, 4H), 2.09 (m, 1H), 1.50 (m, 1H), 1.36 (m, 1H).

LCMS: (M–H)$^-$ 400.

Example 244

(1R,2R)-2-Phenyl-cyclopropanecarboxylic Acid [1-(2-amino-ethyl)-6-oxo-5,6-dihydro-1H-[1,2]diazepino[4,5,6-cd]indol-8-yl]-amide; Compound with Acetic Acid

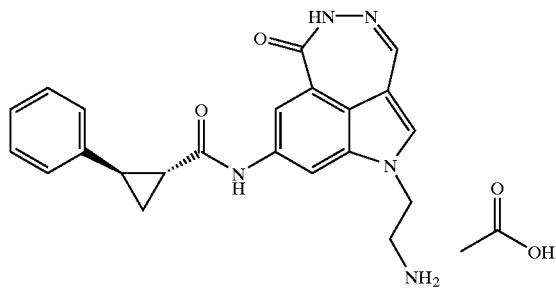

The title compound of Example 242 (92 mg, 0.18 mmol) and hydrazine (0.2 ml) were refluxed together in ethanol (14 mL) 3 hours. After evaporation of the volatile components, the residue was subjected to preparative HPLC which afforded the title compound (71.4 mg) as an acetic acid salt in 89% yield.

$^1$H NMR (d$_6$-DMSO): δ 10.44 (s, 1H), 10.27 (s, 1H), 8.15 (s, 1H), 7.58 (s, 1H), 7.56 (s, 1H), 7.46 (s, 1H), 7.26–7.34 (m, 2H), 7.12–7.23 (m, 3H), 3.99–4.13 (m, 2H), 2.88 (m, 2H), 2.33–2.42 (m, 1H), 2.02–2.12 (m, 1H), 1.43–1.55 (m, 1H), 1.30–1.41 (m, 1H).

HRMS calculated for $C_{22}H_{22}N_5O_2$ 388.1774 (M+H), found 388.1797.

Example 245

2-Naphthalen-1-yl-ethanesulfonic Acid (6-oxo-5,6-dihydro-1H-[1,2]diazepino[4,5,6-cd]indol-8-yl)-amide

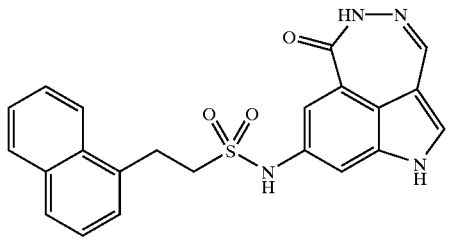

Under nitrogen, the title compound of Example 2 (260 mg, 1.1 mmol), 2-(1-naphthyl)ethanesulphonyl chloride (300 mg, 1.18 mmol), and triethylamine (0.68 mL, 4.89 mmol) were refluxed in tetrahydrofuran (5 mL) for 12 hours. The volatile components were evaporated and silica gel chromatography (eluted with 2% methanol in $CH_2Cl_2$) of the residue afforded the title compound (61 mg, 0.15 mmol) as a yellow powder in 13% yield.

$^1$H NMR (DMSO): δ 11.58 (s, 1H), 10.13 (s, 1H), 9.85 (s, 1H), 7.67 (d, J=8.0 Hz, 1H), 7.56 (dd, J=8.0, 4.0 Hz, 1H), 7.43–7.17 (m, 8H), 7.06 (m, 1H), 3.22–3.15 (m, 4H).

LCMS: (M+H$^+$) 417.0.

Example 246

(1R,2R)-2-Phenyl-cyclopropanecarboxylic Acid [2-(3-morpholin-4-yl-prop-1-ynyl)-6-oxo-5,6-dihydro-1H-[1,2]diazepino[4,5,6-cd]indol-8-yl]-amide

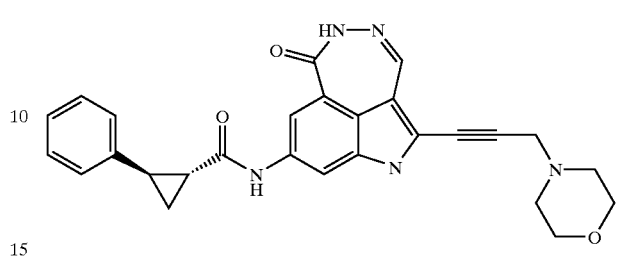

Preparation of example 246 from Intermediate 147(d) of Example 147 (300 mg, 0.794 mmol) was carried out in three steps in a manner similar to that described for the preparation of Example 233 except that 4-prop-2-ynyl-morpholine was used instead of dimethyl-prop-2-ynyl-amine in step 1. 4-Prop-2-ynyl-morpholine was prepared by refluxing 3-bromo-propyne, morpholine and $K_2CO_3$ in tetrahydrofuran for 1 hour. The title compound (34 mg, 0.073 mmol) was obtained as a yellow powder in 18% overall yield.

$^1$H NMR (d$_6$-DMSO): δ 12.21 (s, 1H), 10.49 (s, 1H), 10.46 (s, 1H), 8.08 (s, 1H), 7.61 (s, 1H), 7.41 (s, 1H), 7.33–7.24 (m, 2H), 7.23–7.13 (m, 3H), 3.66 (s, 2H), 3.62 (br s, 4H), 2.54 (br s, 4H), 2.42–2.33 (m, 1H), 2.11–2.02 (m, 1H), 1.54–1.44 (m, 1H), 1.42–1.32 (m, 1H).

LCMS: (M+H$^+$) 468.2, (M+Na$^+$) 490.1; (M−H)$^-$ 466.1.

HRMS: (M+H$^+$) calcd for $C_{27}H_{25}N_5O_3$, 468.2036, found 468.2049.

Example 247

(1R,2R)-2-Phenyl-cyclopropanecarboxylic Acid [6-oxo-2-(3-pyrrolidin-1-yl-prop-1-ynyl)-5,6-dihydro-1H-[1,2]diazepino[4,5,6-cd]indol-8-yl]-amide

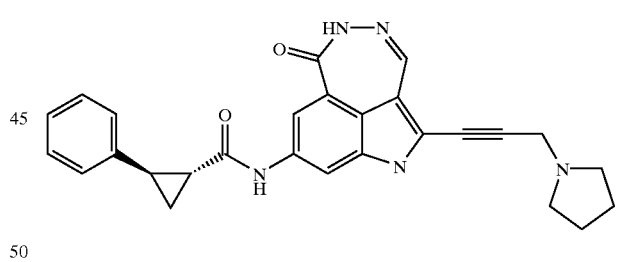

Preparation of example 247 from Intermediate 147(d) of Example 147 (300 mg, 0.794 mmol) was carried out in three steps in a manner similar to that described for the preparation of Example 233 except that 1-prop-2-ynyl-pyrrolidine was used instead of dimethyl-prop-2-ynyl-amine in step 1. 1-Prop-2-ynyl-pyrrolidine was prepared by stirring 3-bromo-propyne, pyrrolidine and triethylamine at room temperature in tetrahydrofuran for 2 hours. The title compound (80 mg, 0.177 mmol) was obtained as a yellow powder in 36% overall yield.

$^1$H NMR (d$_6$-DMSO): δ 12.18 (s, 1H), 10.48 (s, 1H), 10.45 (s, 1H), 8.07 (d, 1H, J=1.77 Hz), 7.61 (d, 1H, J=1.52 Hz), 7.39 (s, 1H), 7.32–7.25 (m, 2H), 7.23–7.14 (m, 3H), 3.75 (s, 2H), 2.60 (br s, 4H), 2.41–2.33 (m, 1H), 2.10–2.03 (m, 1H), 1.73 (br s, 4H), 1.52–1.46 (m, 1H), 1.40–1.33 (m, 1H).

LCMS: (M+H⁺) 452.1, (M+Na⁺) 474.1; (M–H)⁻ 450.2.

HRMS: (M+H⁺) calcd for $C_{27}H_{26}N_5O_2$, 452.2087, found 452.2102.

Example 248

(1R,2R)-2-Phenyl-cyclopropanecarboxylic Acid [1-(2-amino-ethyl)-2-chloro-6-oxo-5,6-dihydro-1H-[1,2]diazepino[4,5,6-cd]indol-8-yl)-amide

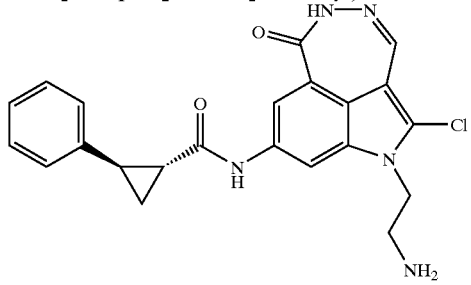

Preparation of example 248 was carried out two steps. The first step was carried out in a manner identical to that described for the preparation of Example 242 except that the title compound of Example 190 was used instead of the title compound of Example 100. This gave the phthaloyl protected intermediate. The second step consisted of phthaloyl deprotection, and the conditions were identical to those described in Example 244. Purification, analogous to that described for Example 244, gave the title compound (0.054 g) as a yellow powder in 49% overall yield.

¹H NMR (d₆-DMSO): δ 10.56 (s, 1H), 10.53 (s, 1H), 8.22 (s, 1H), 8.00–8.18 (br d, 2H), 7.57 (s, 1H), 7.36 (s, 1H), 7.19–7.29 (m, 2H), 7.05–7.18 (m, 3H), 4.39 (t, 2H, J=6.6 Hz), 3.06 (t, 2H, J=6.5 Hz), 2.28–2.37 (m, 1H), 2.00–2.13 (m, 1H), 1.39–1.51 (m, 1H), 1.26–1.38 (m, 1H).

HRMS calculated for $C_{22}H_{22}N_5O_2$ 422.1384 (M+H), found 422.1403.

Example 249

1,2,3,4-Tetrahydro-naphthalene-2-carboxylic Acid (6-oxo-5,6-dihydro-1H-[1,2]diazepino[4,5,6-cd]indol-8-yl)-amide

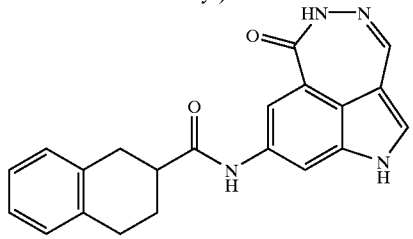

Preparation of example 249 from the title compound of Example 2 (freebase) (100 mg, 0.500 mmol), 1,2,3,4-tetrahydro-naphthalene-2-carboxylic acid (100 mg, 0.567 mmol), triethylamine (0.278 mL, 2.00 mmol), and O-(7-azabenzotriazol-1-yl)-N,N,N',N'-tetramethyluronium hexafluorophosphate (285 mg, 0.750 mmol) in N,N-dimethylformamide (4.0 mL) was carried out analogously to Example 11. Silica gel chromatography (eluted with ethyl acetate), also in an analogous manner, afforded the title compound (87 mg, 0.243 mmol) as a yellow powder in 48% yield.

¹H NMR (d₆-DMSO): δ 11.73 (d, 1H, J=2.26 Hz), 10.23 (s, 1H), 10.11 (s, 1H), 8.16 (d, 1H, J=1.51 Hz), 7.60 (d, 1H, J=1.70 Hz), 7.55 (d, 1H, J=2.64 Hz), 7.46 (s, 1H), 7.14–7.06 (m, 4H), 2.97–2.88 (m, 2H), 2.86–2.70 (m, 3H), 2.14–2.02 (m, 1H), 1.86–1.68 (m, 1H).

LCMS: (M+H⁺) 359.1, (M+Na⁺) 381.0; (M–H)⁻357.2.

HRMS: (M+H⁺) calcd for $C_{21}H_{19}N_4O_2$, 359.1481, found 359.1484.

Anal. Calcd. for $C_{21}H_{18}N_4O_2$: C, 70.38; H, 5.06; N, 15.63.

Found: C, 69.36; H, 5.07; N, 15.21.

Example 250

2-(4-Chloro-phenylsulfanyl)-N-(6-oxo-5,6-dihydro-1H-[1,2]diazepino[4,5,6-cd]indol-8-yl)-acetamide

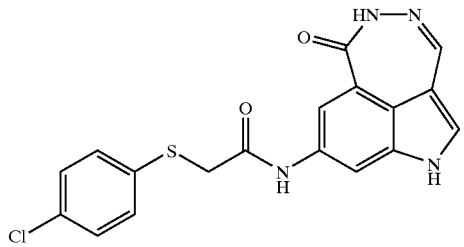

Preparation of example 250 from the title compound of Example 2 (freebase) (100 mg, 0.500 mmol), (4-chlorophenylsulfanyl)-acetic acid (110 mg, 0.543 mmol), triethylamine (0.278 mL, 2.00 mmol), and O-(7-azabenzotriazol-1-yl)-N,N,N',N'-tetramethyluronium hexafluorophosphate (285 mg, 0.750 mmol) in N,N-dimethylformamide (4.0 mL) was carried out analogously to Example 11. When the reaction was judged complete, the N,N-dimethylformamide was evaporated and methanol was added. The mixture was filtered to collect the solids, which were then washed with methanol, dichloromethane and diethyl ether. After drying under vacuum, the title compound (115 mg, 0.321 mmol) was obtained as a yellow powder in 72% yield.

¹H NMR (d₆-DMSO): δ 11.73 (d, 1H, J=1.70 Hz), 10.35 (s, 1H), 10.26 (s, 1H), 8.06 (d, 1H, J=1.51 Hz), 7.56 (d, 1H, J=2.64 Hz), 7.52 (d, 1H, J=1.51 Hz), 7.48–7.34 (m, 5H), 3.86 (s, 2H).

LCMS: (M–H)⁻ 383.0.

HRMS: (M+H⁺) calcd for $C_{18}H_{14}ClN_4O_2S$, 385.0526, found 385.0538.

Anal. Calcd. for $C_{19}H_{13}ClN_4O_2S \cdot 0.25CH_3OH$: C, 55.79; H, 3.59; N, 14.26; Cl, 9.02.

Found: C, 55.49; H, 3.65; N, 14.57, Cl, 8.87.

Example 251

2-(4 Chloro-phenyl)-N-(6-oxo-5,6-dihydro-1H-[1,2]diazepino[4,5,6-cd]indol-yl)-acetamide

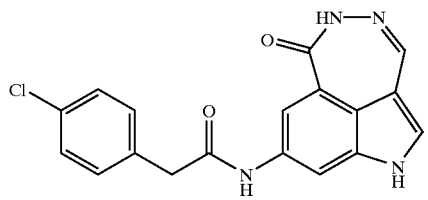

Preparation of example 251 from the title compound of Example 2 (106 mg, 0.448 mmol), (4-chloro-phenyl)-acetic acid (85.0 mg, 0.498 mmol), triethylamine (0.313 mL, 2.25 mmol), and O-(7-azabenzotriazol-1-yl)-N,N,N',N'-tetramethyluronium hexafluorophosphate (257 mg, 0.676 mmol) in N,N-dimethylformamide (4.0 mL) was carried out analogously to Example 11. Silica gel chromatography (eluted with 1:1 ethyl acetate:hexane), also in an analogous manner, afforded the title compound (130 mg, 0.369 mmol) as a yellow powder in 82% yield.

$^1$H NMR (d$_6$-DMSO): δ 11.73 (d, 1H, J=1.70 Hz), 10.31 (s, 1H), 10.24 (s, 1H), 8.10 (d, 1H, J=1.51 Hz), 7.57–7.53 (m, 2H), 7.45 (s, 1H), 7.37 (ddd, 4H, J=8.67, 8.67, 2.64 Hz), 3.64 (s, 2H).

LCMS: (M+H$^+$) 353.2; (M–H)$^-$ 351.2.

Anal. Calcd. for C$_{18}$H$_{13}$ClN$_4$O$_2$: C, 61.28; H, 3.71; N, 15.88; Cl, 10.05.

Found: C, 62.22; H, 3.88; N, 15.80; Cl, 10.13.

Example 252

8-(4-Dimethylamino-pyrimidin-2-ylamino)-1,5-dihydro-[1,2]diazepino[4,5,6-cd]indol-6-one

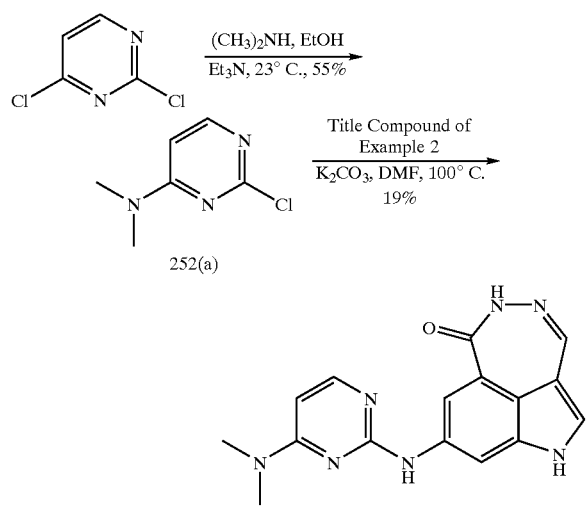

252(a)

Step 1. 2-Chloro 4-Dimethylaminopyridine 252(a)

To a solution of 2,4-dichloropyridine (2.24 g, 15 mmol) in ethanol (45 mL) was added triethylamine (2.1 mL, 15 mmol) followed by dimethylamine (7.5 mL, 1.0 M in THF). The resulting mixture was stirred at 23° C. for 2 h. Extractive work-up from ethyl acetate and saturated aqueous NaHCO$_3$ afforded the crude product, which was purified by silica gel chromatography, eluting with 30% ethyl acetate\hexane to furnish Intermediate 252(a) (1.4 g, 8.2 mmol) in 55% yield.

Step 2. Preparation of Title Compound: 8-(4-Dimethylamino-pyrimidin-2-ylamino)-1,5-dihydro-[1,2]diazepino[4,5,6]indol-6-one A mixture of Intermediate 252(a) (212 mg, 1.35 mmol), the title compound of Example 2 (freebase) (320 mg, 1.6 mmol), K$_2$CO$_3$ (560 mg, 4.05 mmol) in N,N-dimethylformamide (5 mL) was heated at 100° C. for 4 h. Extractive work-up from ethyl acetate and saturated aqueous NaHCO$_3$ afforded the crude product, which was triturated with methanol. The mixture was collected by filtration and washed with methanol to give the title compound as a yellow solid (83 mg, 0.26 mmol) in 19% yield.

$^1$H NMR (d$_6$-DMSO): □ 11.63 (s, 1H), 10.12 (s, 1H), 9.15 (s, 1H), 8.15 (d, 1H, J=1.8 Hz), 7.94 (d, 1H, J=6.1 Hz), 7.92 (d, 1H, J=1.6 Hz), 7.46 (d, 1H, J=2.5 Hz), 7.43 (s, 1H), 6.11 (d, 1H, J=6.1 Hz), 3.08 (s, 6H).

LCMS: (M+H$^+$) 322.3.

Example 253

(1R,2R)-2-Phenyl-cyclopropanecarboxylic Acid [2-(1H-imidazol-2-yl)-6-oxo-5,6-dihydro-1H-[1,2]diazepino[4,5,6-cd]indol-8-yl]-amide

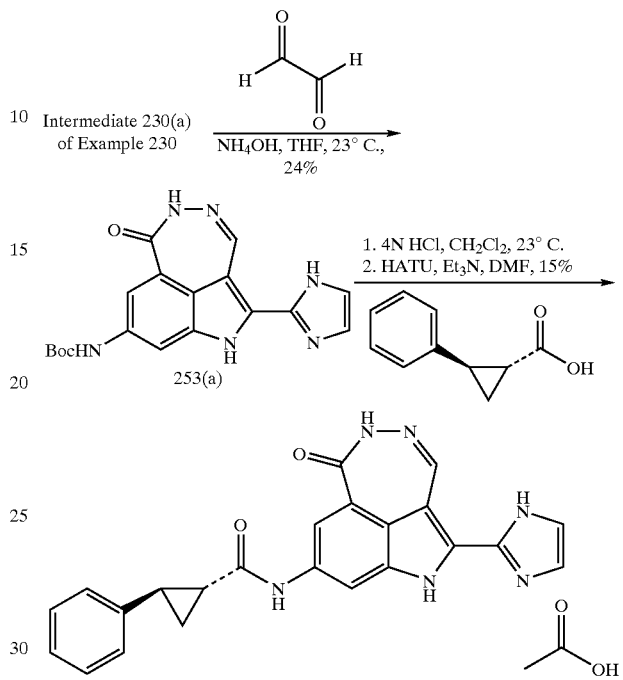

Step 1. [2-(1H-imidazol-2-yl)-6-oxo-5,6-dihydro-1-[1,2]diazopino[4,5,6-]indol-8-yl]-carbamic Acid tert-butyl Ester 253(a)

To a solution of Intermediate 230(a) of Example 230 (274 mg, 0.835 mmol) in tetrahydrofuran (5 mL) and ethanol (1 mL) was added 15N ammonium hydroxide (0.5 mL) followed by 40% glycol in water (0.5 mL). The resulting mixture was stirred at 23° C. overnight. Extractive work-up from ethyl acetate and saturated aqueous NaHCO$_3$ afforded the crude product, which was purified by silica gel chromatography, eluting with 50% ethyl acetate\hexane to furnish the intermediate 253(a) (75 mg, 0.2 mmol) in 24% yield.

Step 2. Preparation of Title Compound: 2-Phenyl-cyclopropanecarboxylic Acid [2-(1H-imidazol-2-yl)-6-oxo-5,6-dihydro-1H-[1,2]diazepino[4,5,6]indol-8-yl]-amide; Compound with Acetic Acid.

Deprotection of Intermediate 253(a) (41 mg, 0.11 mmol) in CH$_2$Cl$_2$ (2 mL) using 4M HCl in dioxane (2 mL) was carried out analogously to Example 91. After concentration, the residue was dissolved in N,N-dimethylformamide (5 mL). (1R, 2R)-2-Phenyl-cyclopropanecarboxylic acid (35.6 mg, 0.22 mmol), triethylamine (0.046 mL, 0.33 mmol), and O-(7-azabenzotriazol-1-yl)-N,N,N',N'-tetramethyluronium hexafluorophosphate (51 mg, 0.13 mmol) were sequentially added. After 12 h, the mixture was concentrated. The crude product was purified by preparative HPLC in a manner analogous to Example 146, Step 2, to give the title compound as a pale yellow powder (7 mg, 0.017 mmol) in 15% yield.

$^1$H NMR (d$_6$-DMSO): 12.27 (s, 1H), 11.79 (s, 1H), 10.25 (s, 1H), 10.21 (s, 1H), 7.93 (d, 1H, J=1.7 Hz), 7.90 (s, 1H), 7.45 (d, 1H, J=1.7 Hz), 7.20 (s, 1H), 7.13–6.99 (m, 5H), 2.19 (m, 1H), 1.89 (m, 1H), 1.31 (m, 1H), 1.18 (m, 1H).

LCMS: (M+H$^+$) 409.

Example 254

(1R,2R)-2-Phenyl-cyclopropanecarboxylic Acid (2-cyano-6-oxo-5,6-dihydro-1H-[1,2]diazepino[4,5,6-cd]indol-8-yl)-amide, Compound with HOAc Salt

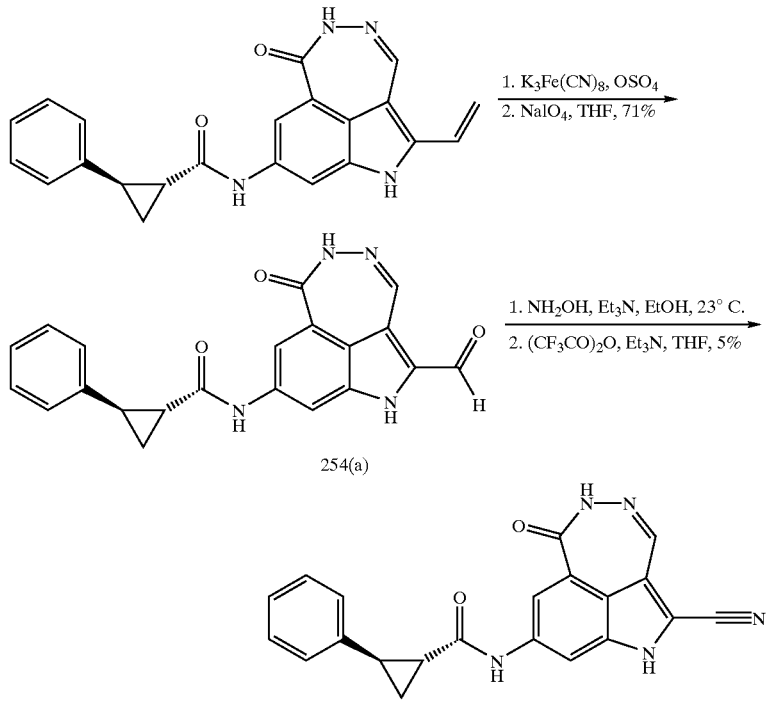

Step 1: 2-Phenyl-cyclopropanecarboxylic Acid (2-formyl-6-oxo-5,6-dihydro-1H-[1,2]diazepino[4,5,6-cd]indol-8-yl)-amide 254(a)

Preparation of starting material, 2-phenyl-cyclopropanecarboxylic acid (6-oxo-2-vinyl-5,6-dihydro-1H-[1,2]diazepino[4,5,6-cd]indol-8-yl)-amide, was carried out by deprotecting the title compound from Example 164 in a manner analogous to Example 91 and then coupling to the amide in a manner analogous to Example 61. The 2-Phenyl-cyclopropanecarboxylic acid (6-oxo-2-vinyl-5,6-dihydro-1H-[1,2]diazepino[4,5,6-cd]indol-8-yl)-amide (542 mg, 1.46 mmol) was then treated with $K_3Fe(CN)_6$ (483 mg, 1.46 mmol) and $NaIO_4$ (1.25 g, 5.84 mmol) in tetrahydrofuran (5 mL) and water (2 mL) analogously to Example 230, step 1. Extractive work-up from ethyl acetate and saturated aqueous $NaHCO_3$ afforded the crude product, which was purified by silica gel chromatography, eluting with 50% ethyl acetate\hexane to furnish intermediate 254(a) (384 mg, 1.17 mmol) in 71% yield.

Step 2. Title Compound: 2-Phenyl-cyclopropanecarboxylic Acid (2-cyano-6-oxo-5,6-dihydro-1H-[1,2]diazepino[4,5,6] indol-8-yl)-amide, Compound with HOAc Salt.

A mixture of Intermediate 254(a) (103 mg, 0.276 mmol), $NH_2OH \cdot HCl$ (38 mg, 0.55 mmol) and triethylamine (0.15 mL, 1.1 mmol) in ethanol (2 mL) was stirred at 23° C. for 1 h. Extractive work-up from ethyl acetate and saturated aqueous $NaHCO_3$ afforded the crude product, which was dissolved in tetrahydrofuran (2 mL) and triethylamine (0.077 mL, 0.55 mmol). Trifluoroacetic anhydride (0.046 mL, 0.33 mL) was then added dropwise. The resulting mixture was stirred overnight. Extractive work-up from ethyl acetate and saturated aqueous $NaHCO_3$ afforded the crude product, which was purified by preparative HPLC in a manner analogous to Example 146, Step 2, to give title compound (5 mg, 0.014 mmol) in 5% yield.

$^1$H NMR ($d_6$-DMSO): 9.05 (s, 1H), 8.74 (s, 1H), 8.09 (s, 1H), 7.58 (s, 1H), 7.47 (s, 1H), 7.24–7.12 (m, 5H), 2.19 (m, 1H), 1.89 (m, 1H), 1.52 (m, 1H), 1.11 (m, 1H).

LCMS: (M+H$^+$) 369.1.

Example 255

(2R)-2-Amino-2-indan-2-yl-N-[2-(1-methyl-1H-pyrazol-4-yl)-6-oxo-5,6-dihydro-1H-[1,2]diazepino[4,5,6-cd]indol-8-yl]-acetamide (Hydrochloric Salt)

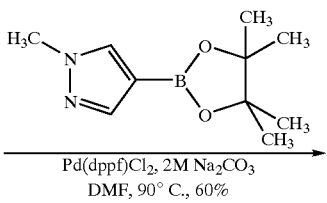

Intermediate 147(d)
Example 147

Pd(dppf)Cl$_2$, 2M Na$_2$CO$_3$
DMF, 90° C., 60%

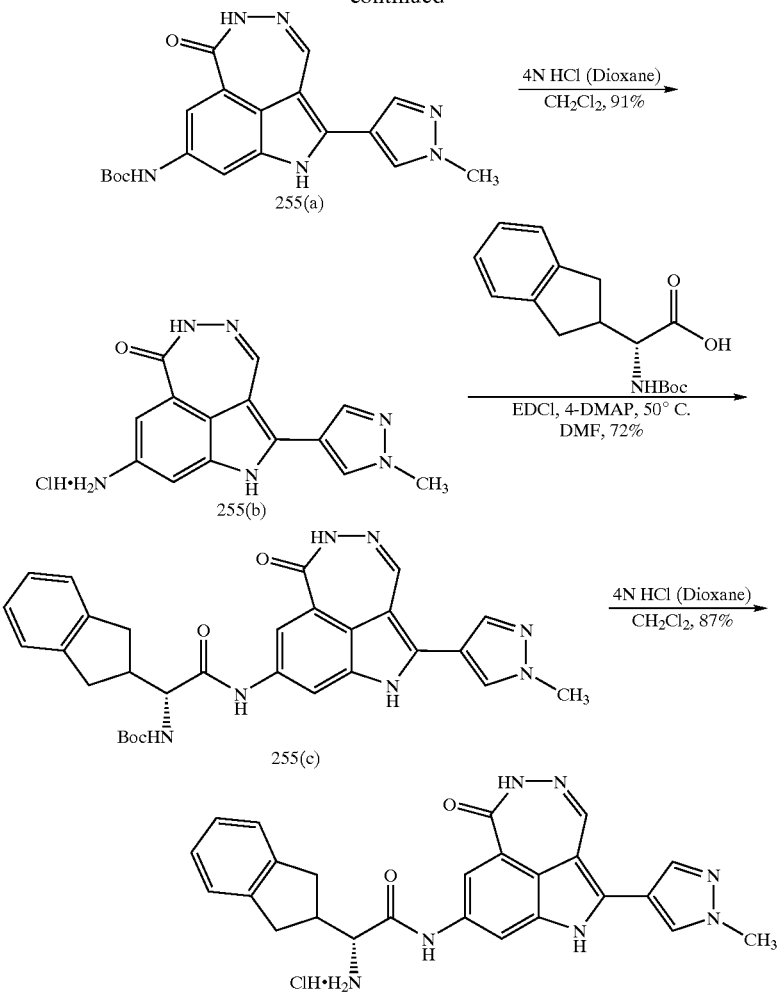

Preparation of Title Compound 255:

Preparation of the title compound from intermediate 255 (c) (2.2 g, 4.07 mmol) and 4N HCl in dioxane (20 mL) was carried out analogously to Example 91. Purification by HPLC afforded the title compound 255 (1.05 g) as a yellow-orange powder (acetic acid salt).

$^1$H NMR (d$_6$-DMSO): δ 12.07 (s, 1H), 10.92 (s, 1H), 10.29 (s, 1H), 8.52 (broad s, 3H) 8.34 (s, 1H), 8.01 (s, 1H), 7.95 (s, 1H), 7.66 (s, 1H), 7.61 (s, 1H), 7.25–7.05 (m, 4H), 4.10 (broad m, 1H), 3.92 (s, 3H), 3.10–2.55 (m, 5H).

LCMS: (M+H$^+$) 454.1.

Preparation of (2R)-{indan-2-yl-[2-1-methyl-1H-pyrazol-4-yl)-6-oxo-5,6-dihydro-1H-[1,2]diazepino[4,5,6-cd]indol-8-ylcarbamoyl]-methyl}-carbamic Acid tert-butyl Ester 255(c)

Intermediate 255(b) (1.5 g), Boc-D-Indanyl glycine (2.25 g), (3-dimethylamino-propyl)-ethyl-carbodiimide hydrochloride (1.85 g, 2 equiv.), and 4-dimethylaminopyridine (1.25 g, 2.2 equiv) were stirred in N,N-dimethylformamide (45 mL) at 50° C. for 2 hours at which point the volatile components were removed in vacuo. The resulting residue was dissolved in THF/methanol (9:1) and loaded onto a silica gel column and eluted with ethyl acetate to afford the title compound (2.2 g) as a yellow solid.

$^1$H NMR (d$_6$-DMSO): δ 11.87 (s, 1H), 10.24 (s, 1H), 10.19 (s, 1H), 8.30 (s, 1H), 8.07 (s, 1H), 7.91 (s, 1H), 7.62 (s, 1H), 7.59 (s, 1H), 7.25–7.05 (m, 5H), 4.17 (broad m, 1H), 3.92 (s, 3H), 3.05–2.60 (m, 5H), 1.39 (s, 9H).

LCMS: (M+H$^+$) 554.1.

Preparation of 8-Amino-2-(1-methyl-1H-pyrazolyl)-11,5-dihydro-[1,2]diazepino[4,5,6-cd]indol-6-one 255(b)

Preparation of intermediate 255(b) from intermediate 255(a) (0.66 g, 1.73 mmol) and 4N HCl in dioxane (8 mL) was carried out analogously to Example 91. Isolation, also in an analogous manner, afforded Intermediate 255(b) (500 mg) as an orange powder in 91% yield.

LCMS: (M+H$^+$) 281.1.

Preparation of [2-(1-Methyl-1H-pyrazol-4-yl)-6-oxo-5,6-dihydro-1H-[1,2]diazepino[4,5,6-cd]indol-8-yl]-carbamic Acid tert-butyl Ester 255(a)

Preparation of intermediate 255(a) from intermediate 147 (d) of Example 147 (1 g, 2.63 mmol) and 1-methyl-4-(4,4,5,5-tetramethyl-1,3,2-dioxaborolan)-1H-pyrazole (648 mg, 3.16 mmol) was carried out analogously to Example 184, except that the mixture was heated at 90° C. instead of 80° C. Isolation, also in an analogous manner, afforded intermediate 255(a) (620 mg) as a yellow-orange powder in 62% yield (Rf 0.35 in 100% ethyl acetate).

$^1$H NMR (d$_6$-DMSO): δ 11.75 (s, 1H), 10.17 (s, 1H), 9.42 (s, 1H), 8.27 (s, 1H), 7.88 (s, 1H), 7.66 (s, 1H), 7.63 (s, 1H), 7.55 (s, 1H), 3.91 (s, 3H), 1.48 (s, 9H).

LCMS: (M+H$^+$) 381.0.

Example 256

(2R)-2-Amino-N-[2-(1-methyl-1H-pyrazol-4-yl)-6-oxo-5,6-dihydro-1H-[1,2]diazepino[4,5,6-cd]indol-8-yl]-4-phenyl-butyramide(Hydrochloric Salt)

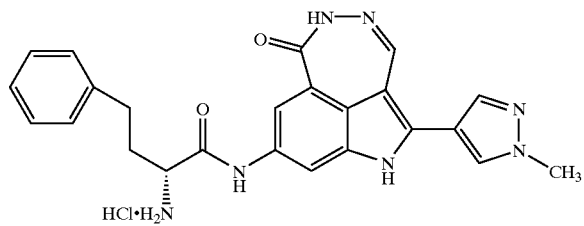

Preparation of example 256 using (2R)-2-tert-Butoxycarbonylamino-4-phenyl-butyric acid as starting material was carried out in two steps. The first step (coupling) was analogous to Example 11, and the second step (deprotection) was analogous to Example 91.

$^1$H NMR ($d_6$-DMSO): δ 12.09 (s, 1H), 10.81 (s, 1H), 10.29 (s, 1H), 8.45 (br s, 3H), 8.34 (s, 1H), 8.03 (s, 1H), 7.95 (s, 1H), 7.65 (s, 1H), 7.61 (s, 1H), 7.32–7.26 (m, 2H), 7.24–7.17 (m, 3H), 4.18 (m, 1H, partially obscured), 3.92 (s, 3H), 2.74–2.65 (m, 2H), 2.19–2.09 (m, 2H).

LCMS: (M+H$^+$) 442.2.

Example 257

(2R)-2-Amino-2-indan-2-yl-N-(6-oxo-5,6-dihydro-1H-[1,2]diazepino[4,5,6-cd]indol-8-yl)-acetamide (Hydrochloric Salt)

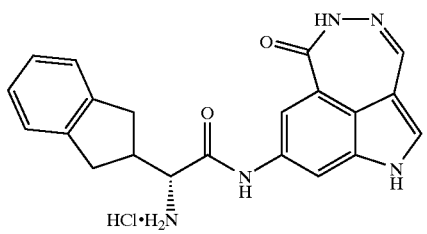

Preparation of example 257 from the title compound of Example 2 (hydrochloride) and (2R)-2-tert-Butoxycarbonylamino-indan-2-yl-acetic acid was carried out in two steps. The first step (coupling) was analogous to Example 11, and the second step (deprotection) was analogous to Example 91.

$^1$H NMR ($d_6$-DMSO): δ 11.91 (s, 1H), 10.95 (s, 1H), 10.32 (s, 1H), 8.56 (br s, 4H), 8.08 (s, 1H), 7.70 (s, 1H), 7.65 (s, 1H), 7.52 (s, 1H), 7.29–7.20 (m, 2H), 7.18–7.10 (m, 2H), 4.15 (m, 1H, partially obscured), 3.12–2.87 (m, 5H).

LCMS: (M+H$^+$) 374.1.

Example 258

(2R)-2-Amino-2-cyclohexyl-#N-!-[2-(1-methyl-1H-pyrazol-4-yl)-6-oxo-5,6-dihydro-1H-[1,2]diazepino[4,5,6-cd]indol-8-yl]-acetamide; (Hydrochloric Salt)

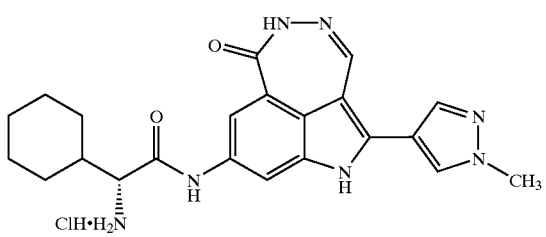

Preparation of example 258 from intermediate 255(b) of Example 255 and Boc-D-cyclohexyl glycine was carried out in two steps in an analogous manner to Example 255.

$^1$H NMR ($d_6$-DMSO): δ 12.09 (s, 1H), 10.76 (s, 1H), 10.30 (s, 1H), 8.35 (broad m, 4H), 8.04 (s, 1H), 7.96 (s, 1H), 7.64 (s, 1H), 7.62 (s, 1H), 3.93 (s, 3H) 3.78 (m, 1H), 1.90–1.50 (m, 7H), 1.30–1.05 (m, 4H).

LCMS: (M+H$^+$) 420.1.

Example 259

(2R)-2-Amino-N-(2-bromo-6-oxo-5,6-dihydro-1H-[1,2]diazepino[4,5,6-cd]indol-8-yl)-4-phenyl-butyramide (Hydrochloric Salt)

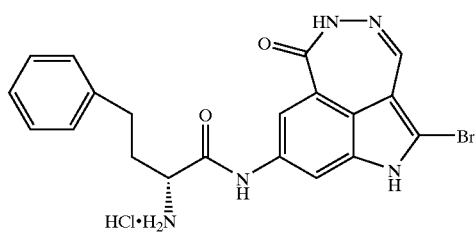

Preparation of example 259 from the title compound of Example 206(a) (hydrochloride) and (2R)-2-tert-Butoxycarbonylamino-4-phenyl-butyric acid was carried out in two steps. The first step (coupling) was analogous to Example 11, and the second step (deprotection) was analogous to Example 91.

$^1$H NMR ($d_4$-methanol): δ 8.05 (s, 1H), 7.65 (s, 1H), 7.37 (s, 1H), 7.30–7.13 (m, 5H), 4.05 (m, 1H), 2.83–2.70 (m, 2H), 2.31–2.18 (m, 2H).

LCMS: (M+H$^+$) 440, 442.

Example 260

(2R)-2-Amino-2-indan-2-yl-N-[2-(6-methyl-pyridin-3-yl)-6-oxo-5,6-dihydro-1H-[1,2]diazepino[4,5,6-cd]indol-8-yl]-acetamide (Hydrochloric Salt)

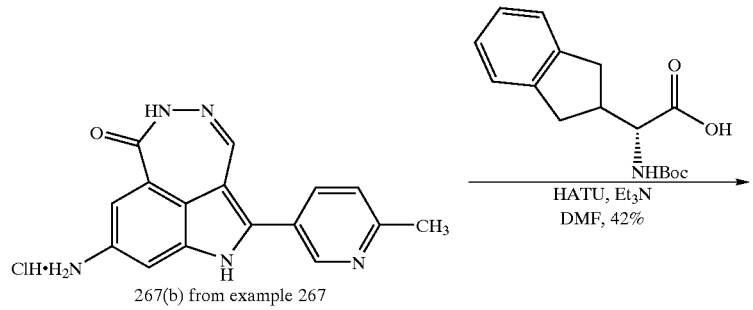

267(b) from example 267

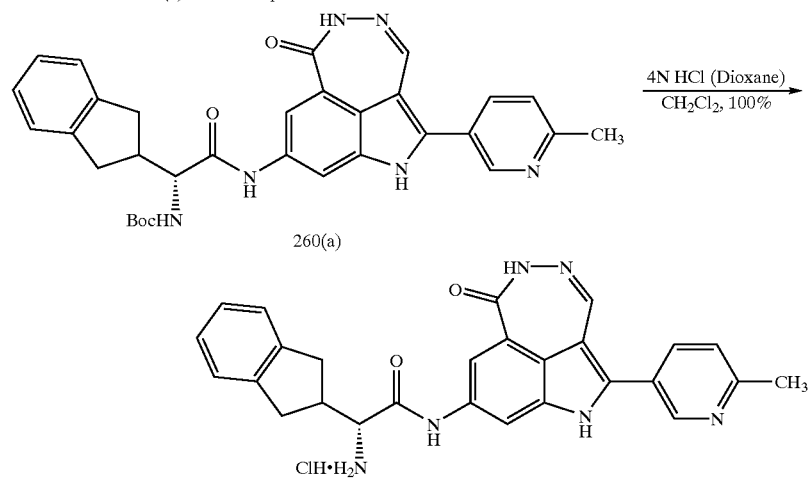

260(a)

Preparation of Title Compound 260

Preparation of title compound from intermediate 260 (a) (58.1 mg, 0.103 mmol) and 4.0 M HCl in dioxane (2 mL) was carried out analogously to Example 91. Isolation, also in an analogous manner, afforded title compound (52 mg, 0.103 mmol) as a yellow powder in 100% yield.

$^1$H NMR (400 MHz, DMSO-D6) d ppm 2.90 (m, 2H) 3.08 (m, 2H) 4.13 (m, 1H) 7.14 (m, 2H) 7.24 (m, 2H) 7.53 (s, 2H) 7.75 (s, 1H) 8.06 (m, 1H) 8.13 (s, 1H) 8.54 (s, 3 H) 8.80 (s, 1 H) 10.51 (s, 1H) 10.99 (s, 1H) 12.40 (s, 1H).

LCMS: (M+H$^+$) 465.1

Preparation of {(R)-Indan-2-yl-[2-(6-methyl-pyridin-3-yl)-6-oxo-5,6-dihydro-1H-[1,2]Diazepino [4,5,6-cd]indol-8-ylcarbamoyl]-methyl}-carbamic Acid tert-butyl Ester 260(a)

Preparation of intermediate 260 (a) from intermediate 267 (b) from Example 267 (96 mg, 0.245 mmol), (R)-tert-Butoxycarbonylamino-indan-2-yl-acetic acid (90 mg, 0.290 mmol), triethylamine (0.11 mL, 0.735 mmol), and O-(7-azabenzotriazol-1-yl)-N,N,N',N'-tetramethyluronium hexafluorophosphate (140 mg, 0.368 mmol) in N,N-dimethylformamide (3.0 mL) was carried out analogously to Example 11. The volatile components were removed in vacuo and the resulting residue was dissolved in methanol and loaded onto a silica gel plug. The plug was then loaded onto a silica gel column and eluted with 1.2:1 dichloromethane: ethyl acetate to afford intermediate 260(a) (58.1 mg, 0.103 mmol) as a yellow solid in 42% yield.

Example 261

(2R)-2-Amino-N-(2-chloro-6-oxo-5,6-dihydro-1H-[1,2]diazepino[4,5,6-cd]indol-8-yl)-4-phenyl-butyramide (Hydrochloric Salt)

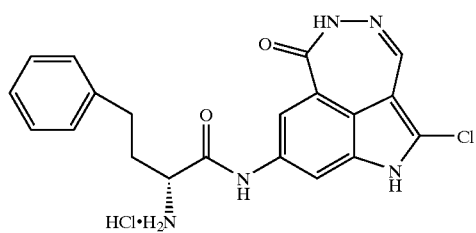

Preparation of example 261 from the title compound of Example 190(a) (hydrochloride) and (2R)-2-tert-Butoxycarbonylamino-4-phenyl-butyric acid was carried out in two steps. The first step (coupling) was analogous to Example 11, and the second step (deprotection) was analogous to Example 91.

$^1$H NMR (d$_6$-DMSO): δ 12.78 (s, 1H), 10.80 (s, 1H), 10.51 (s, 1H), 8.41 (br s, 3H), 8.02 (s, 1H), 7.71 (s, 1H), 7.38 (s, 1H), 7.33–7.26 (m, 2H), 7.23–7.16 (m, 3H), 4.05 (m, 1H), 2.74–2.65 (m, 2H), 2.18–2.09 (m, 2H).

LCMS: (M+H$^+$) 396.1, 398.1, (M+Na$^+$) 418.0, 420.0.

Example 262

(1S,2S)-1-Amino-2-Phenyl-cyclopropanecarboxylic Acid [2-(1-methyl-1H-pyrazol-4-yl)-6-oxo-5,6-dihydro-1H-[1,2]diazepino[4,5,6-cd]indol-8-yl)-amide (Hydrochloric Salt)

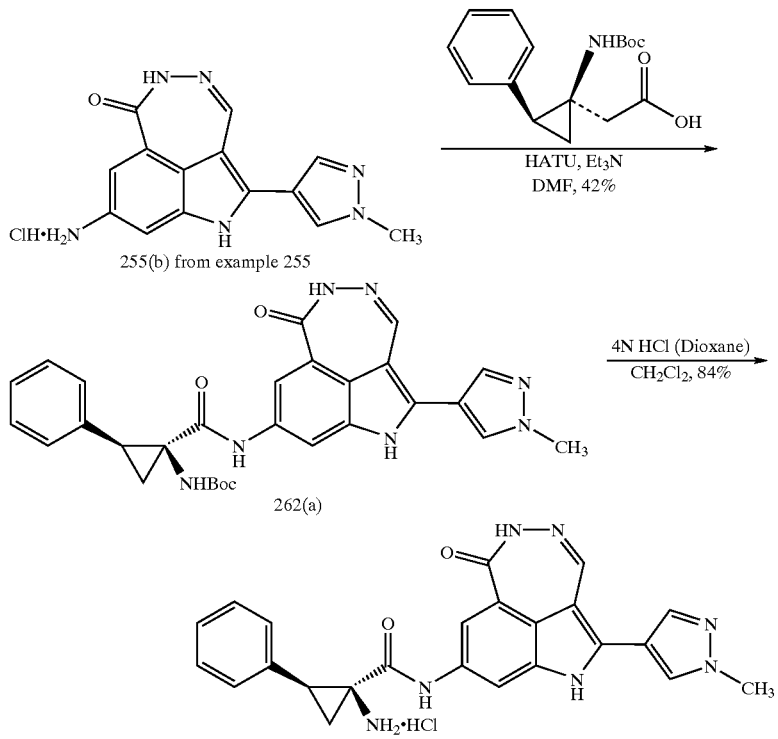

Preparation of Title Compound 262

Preparation of title compound 262 from intermediate 262 (a) (45.4 mg, 0.088 mmol) and 4.0 M HCl in dioxane (2 mL) was carried out analogously to Example 91. Isolation, also in an analogous manner, afforded title compound (35 mg, 0.074 mmol) as a yellow powder in 84% yield.

1H NMR (400 MHz, DMSO-D6) δ 2.34 (m, 1H) 3.48 (m, 1H) 3.69 (m, 1H) 3.93 (s, 3H) 7.40 (m, 5H) 7.62 (s, 2H) 7.76(d, J=1.77 Hz, 2H) 7.96 (s, 2H) 8.03 (d, J=1.77 Hz, 2H) 8.35 (s, 2H) 9.78 (s, 1H) 10.30 (s, 1H) 12.05 (s, 1H).

LCMS: (M+H$^+$) 440.2

Preparation of {(1S,2S)-1-[2-(1-Methyl-1H-pyrazol-4-yl)-6-oxo-5,6-dihydro-1H-[1,2] Diazepino [4,5,6]indol-8-ylcarbamoyl]-2-phenylcyclopropyl}-carbamic Acid tert-butyl Ester 262(a)

Preparation of intermediate 262 (a) by using compound 255 (b) in example 255 (61.7 mg, 0.195 mmol), (1S,2S)-2-phenyl-cyclopropyl)-carbamic acid tert-butyl ester (55 mg, 0.195 mmol), triethylamine (0.11 mL, 0.735 mmol), and O-(7-azabenzotriazol-1-yl)-N,N,N',N'-tetramethyluronium hexafluorophosphate (100 mg, 0.26 mmol) in N,N-dimethylformamide (3.0 mL) as starting materials was carried out analogously to Example 11. The volatile components were removed in vacuo and the resulting residue was dissolved in methanol and loaded onto a silica gel plug. The plug was then loaded onto a silica gel column and eluted with 1.2:1 dichloromethane:ethyl acetate to afford intermediate 262(a) (45.4 mg, 0.088 mmol) as a yellow solid in 42% yield.

Example 263

(2R)-2-Amino-3-(4-fluoro-phenoxy)-N-[2-(1-methyl-1H-pyrazol-4-yl)-6-oxo-5,6-dihydro-1H-[1,2]diazepino[4,5,6-cd]indol-8-yl]-propionamide (Hydrochloric Salt)

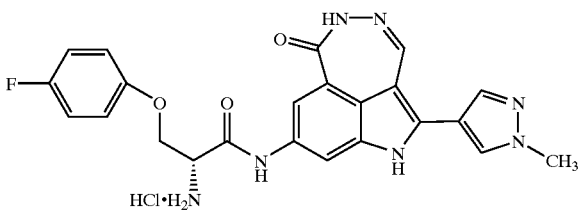

Preparation of Title Compound 263

Preparation of example 263 from intermediate 255 (b) of Example 255 (hydrochloride) and (2R)-2-tert-Butoxycarbonylamino-3-(4-fluoro-phenoxy)-propionic acid was carried out in two steps. The first step (coupling) was analogous to Example 11, and the second step (deprotection) was analogous to Example 91.

¹H NMR (d₆-DMSO): δ 12.04 (s, 1H), 10.82 (s, 1H), 10.29 (s, 1H), 8.57 (s, 3H), 8.33 (s, 1H), 8.01 (s, 1H), 7.94 (s, 1H), 7.63 (d, 1H, J=1.52 Hz), 7.60 (s, 1H), 7.19–7.12 (m, 2H), 7.08–7.01 (m, 2H), 4.51–4.35 (m, 3H), 3.92 (s, 3H).

LCMS: (M+H⁺) 462.1.

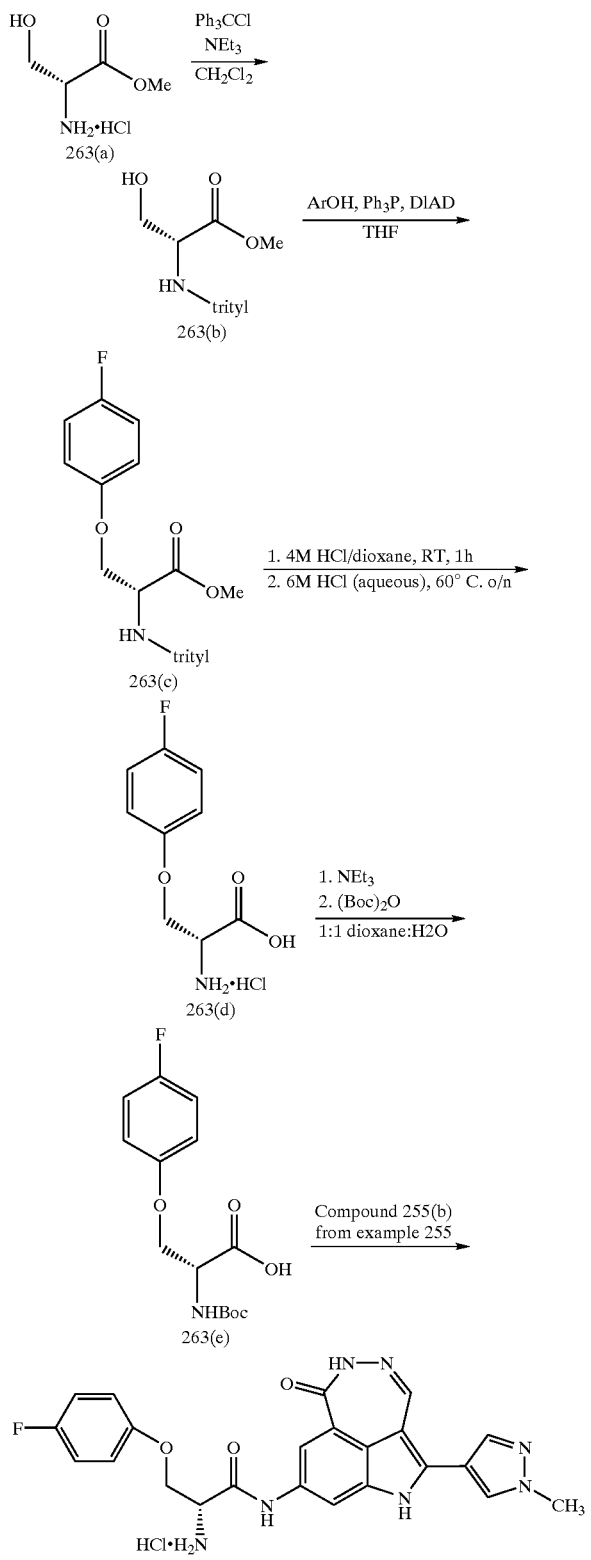

Preparation of (2R)-2-tert-Butoxycarbonylamino-3-(4-fluoro-phenoxy-propionic Acid 263(e)

Compound 263(c) (754 mg, 1.65 mmol) was stirred with 4M HCl in dioxane (c.a. 20 mL) for about 1 hour whereupon the solvent was removed under vacuum and 6M aqueous HCl (10–20 mL) was added. The mixture was capped tightly and stirred at 60° C. overnight. The reaction was checked for completeness. The aqueous layer was extracted with methylene chloride to remove trityl-H by-product and the aqueous layer containing the product was evaporated under vacuum. The resulting solid was dried under high vacuum and 1:1H₂O:dioxane (12 mL) was added to afford compound 263(d), which was not isolated. Triethylamine (2.37 mL, 17 mmol) was added all at once with vigorous stirring at room temperature. After stirring about 15–20 minutes, di-tert-butyl dicarbonate (0.413 mL, 1.8 mmol) is added and the reaction is stirred overnight. After the reaction is checked for completeness, ethyl acetate followed by saturated aqueous potassium hydrogen sulfate are added. The crude product is extracted into ethyl acetate which was then dried over sodium sulfate, filtered, and evaporated to afford 369 mg (75%) of 263(e) as a clear oil which was carried on without further purification.

Preparation of Compound 263(c)

Following a modification of the procedure as described by Cherney and Wang, J. Org. Chem. 61 (1996) 2544–2546, under nitrogen atmosphere, compound 263 (b) (905 mg, 2.51 mmol) was dissolved in dry tetrahydrofuran (29 mL). Triphenylphosphine (711 mg, 2.71 mmol) and 4-fluorophenol were added. The mixture was stirred for approximately 5 minutes and diisopropyl azodicarboxylate (0.534 mL, 2.71 mmol) was added dropwise. The mixture was allowed to stir overnight. The reaction was concentrated and purified on silica gel. The silica was pre-washed with 9:1 hexane:acetone containing 0.3% triethylamine. The column was washed again with 9:1 hexane:acetone followed by hexane. The crude pruduct was then loaded and eluted with 0% to 15% acetone in hexane affording compound 263(c) (754 mg, 66%) as a clear glass.

Preparation of Compound 263(b)

Following a modification of the the procedure as described by C. Gros et. al., Tetrahedron 58 (2002) 2673–2680, D-Serine methyl ester hydrochloride 263(a) (3016 mg, 19.39 mmol) and triethylamine (80.1 mL, 58.17 mmol) were dissolved in dry methylene chloride (60 mL) and cooled in an ice bath. Trityl chloride (5404 mg, 19.39 mmol) in methylene chloride (22 mL) was added dropwise over 15–20 minutes with stirring. The ice bath was removed and the mixture was stirred for 1 hour. The reaction is checked for completeness. The solvent was evaporated and the residue was dissolved in ethyl acetate and washed once with saturated aqueous potassium hydrogen sulfate, twice with saturated aqueous sodium bicarbonate, once with brine, dried over sodium sulfate, filtered and evaporated to afford 6846 mg (97%) of 263(b).

Example 264

(2R)-2-Amino-N-[2-(1-methyl-1H-pyrazol-4-yl)-6-oxo-5,6-dihydro-1H-[1,2]diazepino[4,5,6-cd]indol-8-yl]-3-phenoxy-propionamide (Hydrochloric Salt)

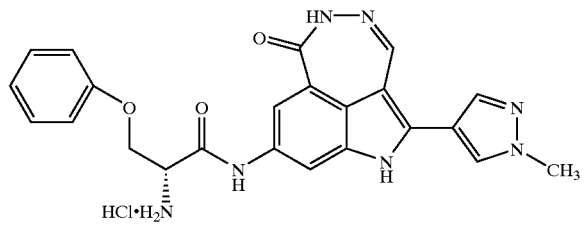

Preparation of example 264 from intermediate 255 (b) of Example 255 and (2R)-2-tert-Butoxycarbonylamino-3-(phenoxy)-propionic acid was carried out in two steps. The first step (coupling) was analogous to Example 11, and the second step (deprotection) was analogous to Example 91.

$^1$H NMR (d$_6$-DMSO): δ 12.03 (s, 1H), 10.79 (s, 1H), 10.29 (s, 1H), 8.56 (s, 3H), 8.33 (s, 1H), 8.01 (s, 1H), 7.93 (s, 1H), 7.63 (d, 1H, J=1.77 Hz), 7.60 (s, 1H), 7.36–7.28 (m, 2H), 7.05–4.96 (m, 3H), 4.52–4.39 (m, 3H), 3.92 (s, 3H).

LCMS: (M+H$^+$) 444.1.

(2R)-2-tert-Butoxycarbonylamino-3-phenoxy)-propionic acid was prepared analogously to (2R)-2-tert-Butoxycarbonylamino-3-(4-fluoro-phenoxy)-propionic acid of example 263 except that phenol was substituted for 4-fluorophenol.

Example 265

(2R)-2-Amino-N-(2-chloro-6-oxo-5,6-dihydro-1H-[1,2]diazepino[4,5,6-cd]indol-8-yl)-2-indan-2-yl-acetamide (Hydrochloric Salt)

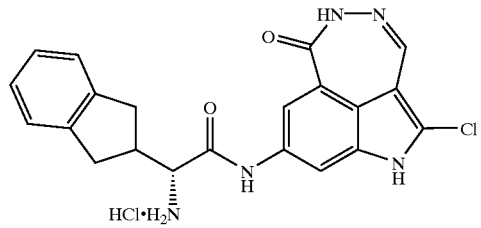

Preparation of example 265 from compound 190(a) of Example 190 (hydrochloride) and (2R)-2-tert-Butoxycarbonylamino-indan-2-yl-acetic acid was carried out in two steps. The first step (coupling) was analogous to Example 11, and the second step (deprotection) was analogous to Example 91.

$^1$H NMR (d$_6$-DMSO): δ 12.78 (s, 1H), 10.90 (s, 1H), 10.51 (s, 1H), 8.49 (br s, 3H), 7.99 (s, 1H), 7.70 (s, 1H), 7.38 (s, 1H), 7.24–7.17 (m, 2H), 7.14–7.07 (m, 2H), 4.07 (m, 1H), 3.07–2.97 (m, 2H), 2.95–2.86 (m, 3H).

LCMS: (M+H$^+$) 408.1, 410.1.

Example 266

(2R)-2-Amino-N-[2-(1-methyl-1H-imidazol-4-yl)-6-oxo-5,6-dihydro-1H-[1,2]diazepino[4,5,6-cd]indol-8-yl]-4-phenyl-butyramide (Hydrochloric Salt)

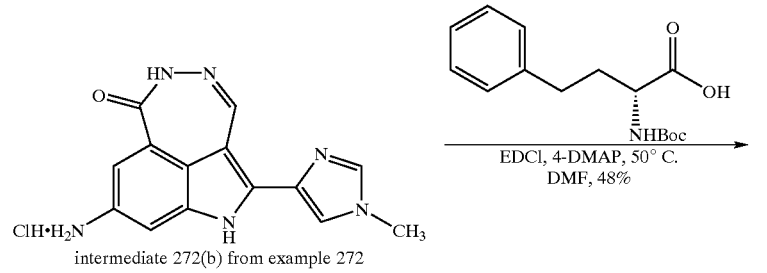

intermediate 272(b) from example 272

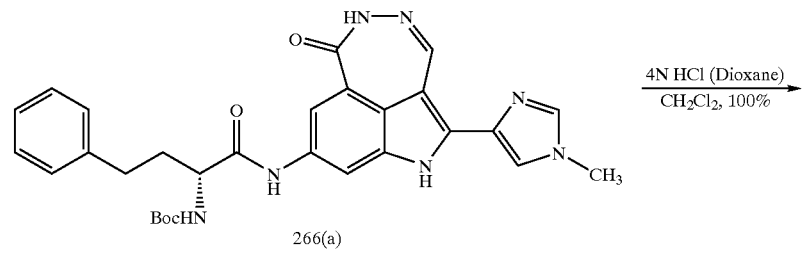

266(a)

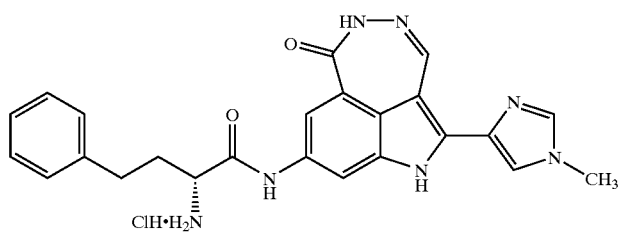

Preparation of title compound from intermediate 266(a) (64.4 mg, 0.119 mmol) and 4.0 M HCl in dioxane (2 mL) was carried out analogously to Example 91. Isolation, also in an analogous manner, afforded title compound (57 mg, 0.119 mmol) as a yellow powder in 100% yield.

1H NMR (400 MHz, DMSO-D6) d ppm 2.13 (m, 2 H) 2.69 (m, 2 H) 4.03 (m, 1 H) 7.22 (m, 3 H) 7.31 (m, 2 H) 7.62 (d, J=1.77 Hz, 1 H) 7.81 (s, 1 H) 7.89 (m, 1 H) 8.02 (d, J=1.52 Hz, 1 H) 8.11 (s, 1 H) 8.36 (s, 3 H) 10.27 (s, 1 H) 10.62 (s, 1 H)

LCMS: (M+H$^+$) 442.1

Preparation of {(R)-1-[2-(1-Methyl-1H-imidazol-4-yl)-6-oxo-5,6-dihydro-1H-1,2]diazepino[4,5,6]indol-8-ylcarbamoyl]-3-phenyl-propyl}-carbamic Acid tert-butyl Ester 266(a)

vacuo and the resulting residue was dissolved in methanol and loaded onto a silica gel plug. The plug was then loaded onto a silica gel column and eluted with 1.2:1 dichloromethane: ethyl acetate to afford intermediate 266(a) (64.4 mg, 0.119 mmol) as a yellow solid in 48% yield.

Example 267

(2R)-2-Amino-N-[2-(6-methyl-pyridin-3-yl)-6-oxo-5,6-dihydro-1H-[1,2]diazepino[4,5,6-cd]indol-8-yl] 4-phenyl-butyramide (Hydrochloric Salt)

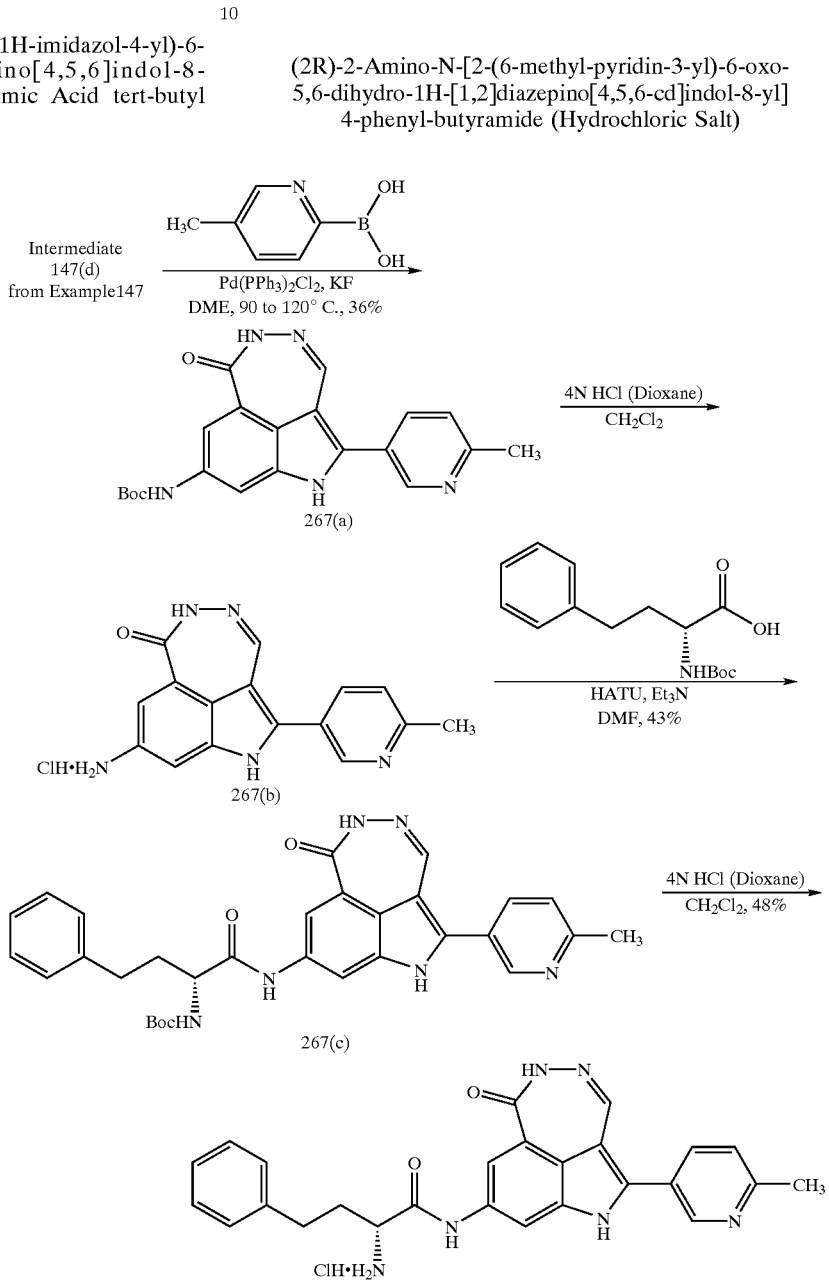

Preparation of intermediate 266(a) from compound 272 (b) of example 272 (94 mg, 0.247 mmol), (R)-2-tert-Butoxycarbonylamino-4-phenyl-butyric acid (71 mg, 0.255 mmol), triethylamine (0.18 mL, 1.24 mmol), and O-(7-azabenzotriazol-1-yl)-N,N,N',N'-tetramethyluronium hexafluorophosphate (113 mg, 0.296 mmol) in N,N-dimethylformamide (4.0 mL) was carried out analogously to Example 11. The volatile components were removed in A suspension of tert-butyl [(1R)-1-({[2-(6-methylpyridin-3-yl)-6-oxo-5,6-dihydro-1H-[1,2]diazepino[4,5,6-cd]indol-8-yl]amino}carbonyl)-3-phenylpropyl]carbamate 267 (c) in 5 mL of 4M HCl in dioxanes was stirred at room temperature for two hours. The mixture was then filtered and the solid material washed thoroughly with ethyl ether. The title compound was obtained as a yellow solid in 48% yield after purification by reverse-phase HPLC.

285

¹H NMR (DMSO-d₆) δ: 1.74 (1H, m), 1.96 (1H, m), 2.55 (3H, s), 2.66 (1H, m), 2.71 (1H, m), 7.23 (5H, bm), 7.45 (1H, d, J=8.45 Hz), 7.47 (1H, s), 7.67 (1H, s), 7.95 (1H, d, J=8.09), 8.21 (1H, s), 8.72 (1H, s), 10.41 (1H, s), 12.18 (1H, s).

LCMS: (M+H⁺) 453.1.

Preparation of tert-butyl [(1R)-1-({[2-(6-methylpyridin-3-yl)-6-oxo-5,6-dihydro-1H-[1,2]diazepino[4,5,6-cd]indol-8-yl]amino}carbonyl)-3-phenylpropyl]carbamate 267 (c)

To a solution of (2R)-2-[(tert-butoxycarbonyl)amino]-4-phenylbutanoic acid and 2-(6-methylpyridin-3-yl)-6-oxo-5,6-dihydro-1H-[1,2]diazepino[4,5,6-cd]indol-8-aminium chloride 267(b) in 8 mL of anhydrous dimethylformamide containing triethylamine (0.3 mL, 2.3 mmol) stirred in an ice/water bath was added HATU (244 mg, 0.64 mmol), portion-wise. The mixture was then stirred overnight at room temperature. The compound 267 (c) was obtained in 43% yield after purification by HPLC.

¹H NMR (DMSO-d₆) δ: 1.35 (9H, s), 1.85–1.93 (3H, bm), 2.50 (4H, s), 4.04 (1H, m), 7.17 (7H, m), 7.39 (1H, d, J=7.83 Hz), 7.42 (1H, s), 7.62 (1H, s), 7.93 (1H, dd, J=8.09 Hz), 8.11 (1H, s), 8.68 (1H, d, J=2.02 Hz), 10.12 (1H, s), 10.37 (1H, s), 12.11 (1H, s).

Preparation of 2-(6-methylpyridin-3-yl)-6-oxo-5,6-dihydro-1H-[1,2]diazepino[4,5,6-cd]indol-6-aminium Chloride 267 (b)

Compound 267 (b) was obtained by reacting tert-butyl [2-(6-methylpyridin-3-yl)-6-oxo-5,6-dihydro-1H-[1,2]diazepino[4,5,6-cd]indol-8-yl]carbamate with 4M HCl in dioxanes. Product 267(b) was isolated in quantitative yield as an orange powder after filtration and ether rinse and was carried on without further purification.

¹H NMR (DMSO-d₆) δ: 2.66 (3H, s), 7.63–7.49 (8H, m), 7.71 (1H, d, J=8.58 Hz), 8.34 (1H, d, J=7.07), 8.92 (1H, s), 10.64 (1H, s), 12.77 (1H, s).

Preparation of 2-(6-methylpyridin-3-yl)-6-oxo-5,6-dihydro-1H-[1,2]diazepino[4,5,6-cd]indol-8-aminium Chloride 267 (a)

Preparation of intermediate 267(a) from intermediate 147 (d) of Example 147 (0.372 g) and the corresponding boronic acid was carried out analogously to Example 184, except that the mixture was heated from 90 to 120° C. instead of 80° C. for 3 hours. Also bistriphenylphosphine dichloro palladium (II) and potassium fluoride was used in DME. Isolation, also in an analogous manner, afforded intermediate 267(a) (133 mg) as a yellow-orange powder in 36% yield.

LCMS: (M+H⁺) 390.4.

Example 268

(2R)-2-Amino-N-[2-(3-methyl-isoxazol-5-yl)-6-oxo-5,6-dihydro-1H-[1,2]diazepino[4,5,6-cd]indol-8-yl]-4-phenyl-butyramide (Hydrochloric Salt)

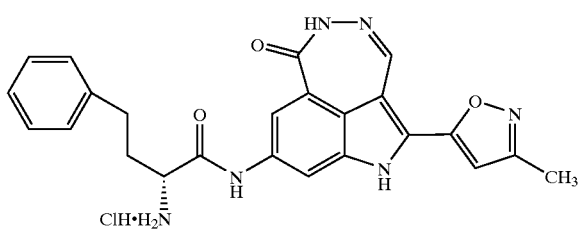

Preparation of Title Compound 268.

Title compound 268 was prepared in an analogous manner to the preparation of 269, in 4 steps.

286

¹H NMR (d₆-DMSO): δ 10.65 (s, 1H), 8.23 (s, 1H), 7.88 (s, 1H), 7.73 (s, 1H), 7.40–7.05 (m, 5H), 6.96 (s, 1H), 2.85–2.55 (m, 2H), 2.33 (s, 3H), 2.10–1.90 (m, 1H), 1.85–1.60 (m, 1H).

LCMS (M⁺+1): 443.2

HRMS calculated for $C_{24}H_{22}N_6O_3$ was 443.1826 (M+H), found 443.1823.

Example 269

(2R)-2-Amino-2-indan-2-yl-N-[2-(3-methyl-isoxazol-5-yl)-6-oxo-5,6-dihydro-1H-[1,2]diazepino[4,5,6-cd]indol-8-yl]-acetamide

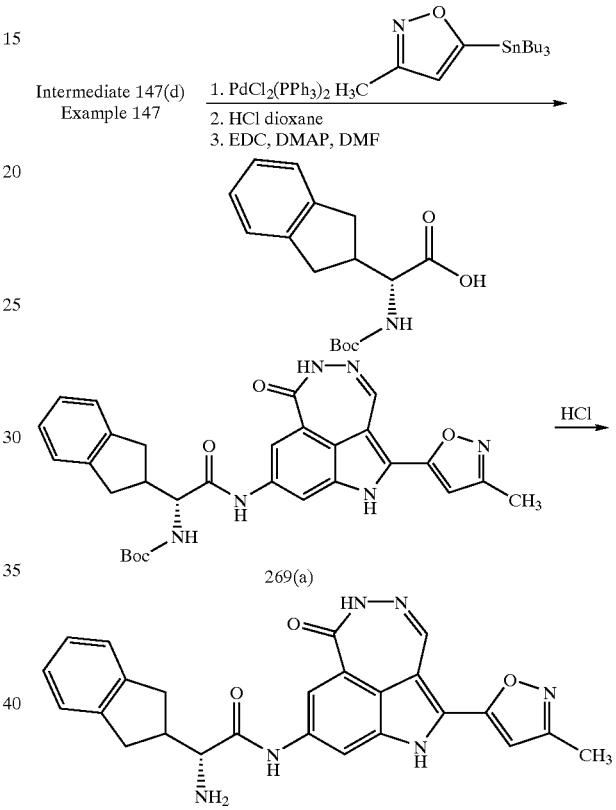

Preparation of Compound 269

Compound 269(a) was reacted with 4 N HCl in 1,4-dioxane, and purified with HPLC to afford 44.8 mg of final product 269.

¹H NMR (d₆-DMSO): δ 10.66 (s, 1H), 8.25 (s, 1H), 7.89 (s, 1H), 7.75 (s, 1H), 7.40–7.00 (m, 4H), 6.97 (s, 1H), 3.05–2.60 (m, 5H), 2.33 (s, 3H).

LCMS (M⁺+1): 455.1

Preparation of Compound 269(a)

A mixture of intermediate 147(b) from example 147 (0.38 g, 1.0 mmol), 5-methyl-3-tributyltin methylisoxazole (0.45 g, 1.2 mmol) and PdCl₂(PPh₃)₂ (50 mg) in 8 ml of 1,4-dioxane was refluxed for 50 minutes. After solvent was removed on Rotavap, the residue was mixed with CH₂Cl₂ and the solid was collected by filtration. 170 mg of crude product 269(a) was obtained. Without further purification, this crude product was reacted with 4 N HCl in 1,4-dioxane and used directly for the next step. Half of the crude product 269(a) was mixed with 76 mg of (2R)-[(tert-butoxycarbonyl)amino](2,3-dihydro-1H-inden-2-yl)acetic acid (76 mg, 0.26 mmol), EDC (51 mg, 0.26 mmol) and DMAP (80 mg, 0.66 mmol) in 7 ml of DMF, stirred at 50°

C. for 2 hours. After removing the solvent, the residue was dissolved in CH$_2$Cl$_2$ and loaded to a short silica gel column, eluting with EtOAc.

HRMS calculated for C$_{25}$H$_{22}$N$_6$O$_3$ 455.1826 (M+H), found 455.1815.

Preparation of 3-methyl-5-(tributylstannyl)isoxazole

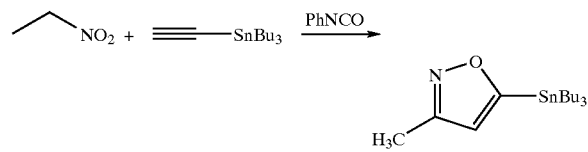

A solution of nitroethane and phenyl isocynate in 8 ml of benzene was stirred at 50° C. for 5 minutes before ethynyltri-n in 8 ml of benzene containing one droplet of Et$_3$N was added. The mixture was stirred at 50° C. for 14 hours. The reaction mixture was then quenched with water and filtered through celite. The filtrate was extracted with EtOAc, dried with Na$_2$SO$_4$. Silica Chromatography using Hexance/EtOAc afforded 3-methyl-5-tributylstannyl) isoxazole, 6.30 g, 85% yield.

Example 270

2-Benzylamino-N-[2-(1-methyl-1H-pyrazol-4-yl)-6-oxo-5,6-dihydro-1H-[1,2]diazepino[4,5,6-cd]indol-8-yl]-acetamide (Hydrochloric Salt)

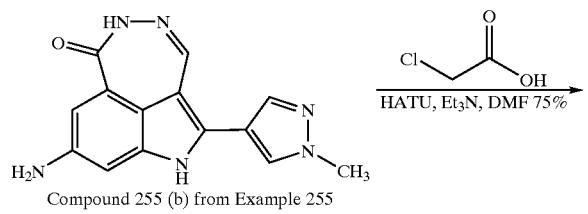

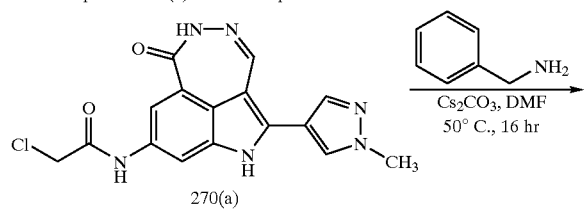

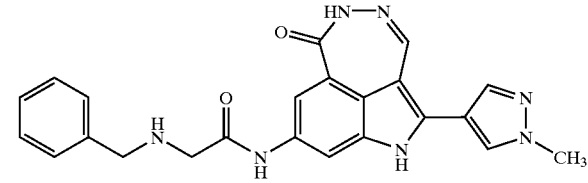

Preparation of Title Compound: 2-Benzylamino-N-[2-1-methyl-1H-pyrazol-4-yl)-6-oxo-5,6-dihydro-1H-[1,2]diazepino[4,5,6-cd]indol-8-yl]-acetamide (270)

To a solution of 2-Chloro-N-[2-(1-methyl-1H-pyrazol-4-yl)-5-oxo-5,6-dihydro-1H-[1,2]diazepino[4,5,6-cd]indol-8-yl]-acetamide 270(a) (100 mg, 0.28 mmol) in DMF (1.5 mL) was added Cs$_2$CO$_3$ (~5 eq.) followed by benzyl amine (33 mg, 0.3 mmoL). The resulting mixture was heated at 50° C. overnight. Excess Cs$_2$CO$_3$ was filtered and the clear dark solution was purified by reverse phase HPLC to afford 15 mg of desired product as yellow solids.

$^1$H-NMR (d$_4$-Methanol): δ 8.06 (s, 1H), 8.04 (d, 1H), 7.84 (s, 1H), 7.53 (s, 1H), 7.48 (d, 1H), 7.41–7.33 (m, 4H), 7.27 (t, 1H), 3.98 (s, 3H), 3.88 (s, 2H), 3.47 (s, 2H);

LCMS: (M+H$^+$) 428.

Preparation of 2-Chloro-N-[2-(1-methyl-1H-pyrazol-4-yl)-6-oxo-5,6-dihydro-1H-[1,2]diazepino[4,5,6-cd]indol-8-yl]-acetamide 270(a)

Preparation of intermediate 270(a) from compound 255 (b) of Example 255 was carried out analogously to Example 11, except that at the end of the reaction, the resulting mixture was poured onto ice water. The resulting tan precipitate was collected by filtration and dried to give the desired product in 75% yield.

$^1$H NMR (d$_6$-DMSO): 811.93 (s, 1H), 11.44 (s, 1H), 10.27 (s, 1H), 8.31 (s, 1H), 8.06 (s, 1H), 7.91 (s, 1H), 7.59 (s, 1H), 7.54 (s, 1H), 4.25 (s, 2H), 3.91 (s, 3H).

LCMS: (M+H$^+$) 358.

Example 271

(2R)-2-Amino-2-cyclohexyl-N-[2-(1-methyl-1H-imidazol-4-yl)-6-oxo-5,6-dihydro-1H-[1,2]diazepino[4,5,6-cd]indol-8-yl]-acetamide (Hydrochloric Salt)

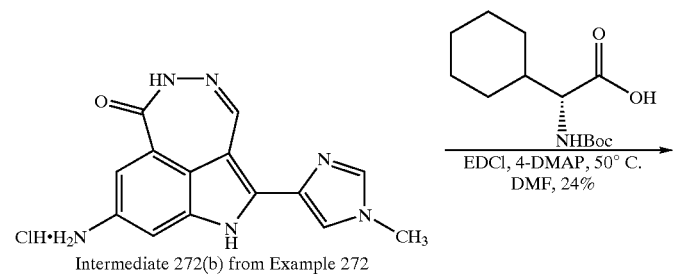

Intermediate 272(b) from Example 272

-continued

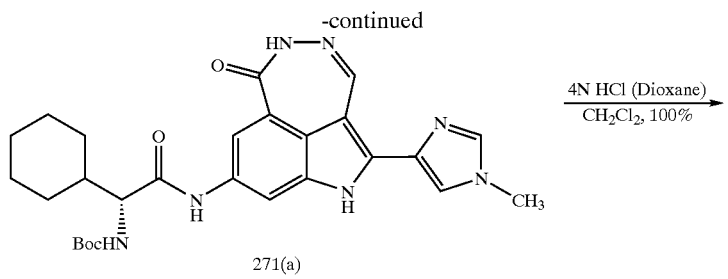
271(a)

4N HCl (Dioxane)
―――――――――
CH₂Cl₂, 100%

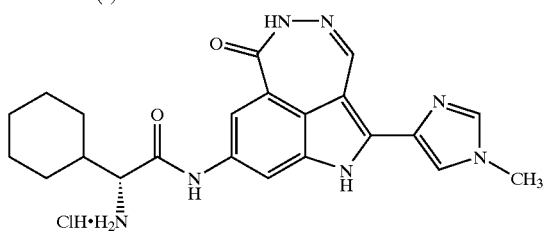

Preparation of Title Compound 271

Preparation of the title compound 271 from intermediate 271 (a) (74 mg, 0.133 mmol) and 4.0 M HCl in dioxane (2 mL) was carried out analogously to Example 91. Isolation, also in an analogous manner, afforded title compound (61 mg, 0.133 mmol) as a yellow powder in 100% yield.

LCMS: (M+H⁺) 418.2.

1H NMR (400 MHz, DMSO-D6) d ppm 1.21 (m, 6H) 1.77 (m, 5H) 3.49 (m, 1H) 7.62 (d, J=1.26 Hz, 1H) 7.82 (s, 1H) 7.90 (m, 1H) 8.03 (d, J=1.26 Hz, 1H) 8.12 (s, 1H) 8.27 (s, 3H) 10.30 (s, 1H) 10.61 (s, 1H) 12.04 (s, 1H).

Preparation of {(R)-Cyclohexyl-[2-(1-methyl-1H-imidazol-4-yl)-6-oxo-5,6-dihydro-1H-[1,2]diazepino[4,5,6]indol-8-ylcarbamoyl]-methyl}-carbamic Acid tert-butyl Ester 271 (a)

Preparation of intermediate 271 (a) from compound 272 (b) (as prepared in Example 272) (170 mg, 0.54 mmol), (R)-tert-Butoxycarbonylamino-cyclohexyl-acetic acid (126.6 mg, 0.435 mmol), (169.0 mg, 0.656 mmol), triethylamine (0.15 mL, 1.1 mmol), and O-(7-azabenzotriazol-1-yl)-N,N,N',N'-tetramethyluronium hexafluorophosphate (312 mg, 0.821 mmol) in N,N-dimethylformamide (4.0 mL) was carried out analogously to Example 11. The volatile components were removed in vacuo and the resulting residue was dissolved in methanol and loaded onto a silica gel plug. The plug was then loaded onto a silica gel column and eluted with 1.2:1 dichloromethane: ethyl acetate to afford intermediate 271(a) (74 mg, 0.133 mmol) as a yellow solid in 24% yield.

Example 272

(2R)-2-Amino-2-indan-2-yl-N-[2-(1-methyl-1H-imidazol-4-yl)-6-oxo-5,6-dihydro-1H-[1,2]diazepino[4,5,6-cd]indol-8-yl]-acetamide (Hydrochloric Salt)

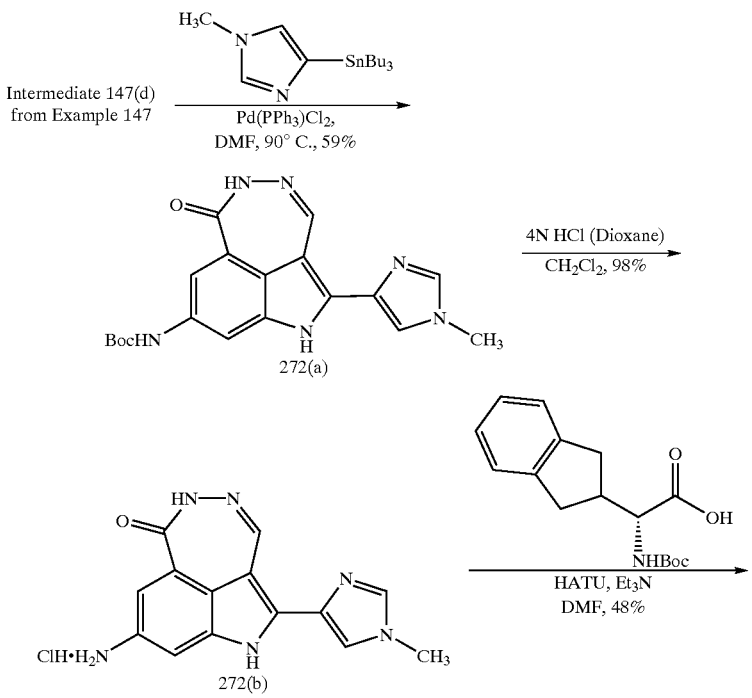

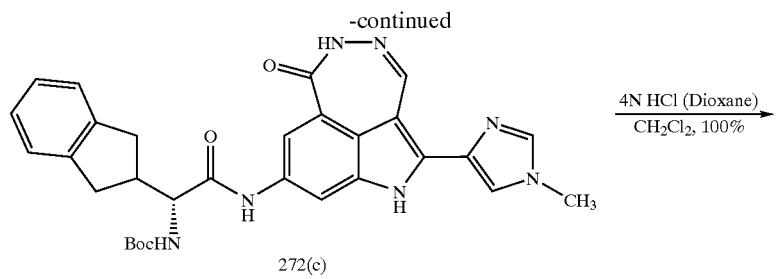

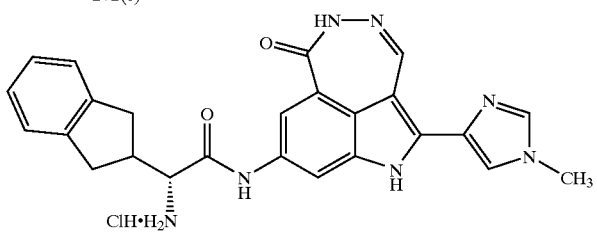

Preparation of Title Compound 272

Preparation of title compound 272 from intermediate 272 (c) (77 mg, 0.141 mmol) and 4.0 M HCl in dioxane (2 mL) was carried out analogously to Example 91. Isolation, also in an analogous manner, afforded title compound (69 mg, 0.14 mmol) as a yellow powder in 100% yield.

1H NMR (400 MHz, DMSO-D6) ppm 2.93 (m, 2H) 3.09 (m, 2H) 3.16 (m, 1H) 3.76 (s, 3H) 7.14 (m, 2H) 7.24 (m, 2H) 7.62 (s, 1H) 7.80 (s, 1H) 7.88 (m, 1H) 8.00 (s, 1H) 8.12 (s, 1H) 8.44 (s, 2H) 10.27 (s, 1H) 10.71 (s, 1H) 12.00 (s, 1H)
LCMS: (M+H$^+$) 454.1.

Preparation of {(R)-Indan-2-yl-[2-(1-methyl-1H-imidazol-4-yl)-6-oxo-5,6-dihydro-1H-[1,2]diazepino[4,5,6-cd)-indol-8-ylcarbamoyl]-methyl}-carbamic Acid tert-butyl Ester 272(c)

Preparation of intermediate 272(c) from Intermediate 272(b) (137 mg, 0.358 mmol), (R)-tert-Butoxycarbonylamino-indan-2-yl-acetic acid (126.6 mg, 0.435 mmol), triethylamine (0.20 mL, 1.432 mmol), and O-(7-azabenzotriazol-1-yl)-N,N,N',N'-tetramethyluronium hexafluorophosphate (206 mg, 0.543 mmol) in N,N-dimethylformamide (4.0 mL) was carried out analogously to Example 11. The volatile components were removed in vacuo and the resulting residue was dissolved in methanol and loaded onto a silica gel plug. The plug was then loaded onto a silica gel column and eluted with 1.2:1 dichloromethane: ethyl acetate to afford the title compound (77 mg, 0.141 mmol) as a yellow solid in 39% yield.

LCMS: (M+H$^+$) 554.1.

Preparation of 8-Amino-2-(1-methyl-1H-pyrazol 4-yl)-1,5-dihydro-[1,2]diazepino[4,5,6-cd]indol-one Hydrochloride 272(b)

Preparation of intermediate 272(b) from the title compound of 272 (a) (208 mg, 0.547 mmol) and 4.0 M HCl in dioxane (3 mL) was carried out analogously to Example 91. Isolation, also in an analogous manner, afforded Intermediate 272(b) (170 mg, 0.54 mmol) as a yellow powder in 98% yield.

Preparation of [2-(1-Methyl-1H-imidazol-4-yl)-6-oxo-5,6-dihydro-1H-[1,2]diazepino[4,5,6-cd]indol-8-yl]-carbamic Acid tert-butyl Ester 272(a)

A mixture of intermediate 147(d) obtained from example 147 (184 mg, 0.5 mmol), 4-(tributylstannyl)-1-methyl-1H-imidazole (223 mg, 0.6 mmol) and Pd(PPh$_3$)Cl$_2$ (35 mg, 0.05 mmol) in THF (3 mL) was heated in a microwave oven (Personal Chemistry) for 2 hours at 130° C. The mixture was concentrated and the residue was purified by silica gel chromatography (5% MeOH/EtOAc) to give the title compound (110 mg, 0.289 mmol) in 59% yield as an orange powder.

LCMS (M$^+$+H): 381.1

Example 273

(2R)-2-Amino-2-(4-fluoro-phenyl)-N-[2-(1-methyl-1H-pyrazol-4-yl)-6-oxo-5,6-dihydro-1H-[1,2]diazepino[4,5,6-cd]indol-8-yl]-acetamide (Hydrochloric Salt)

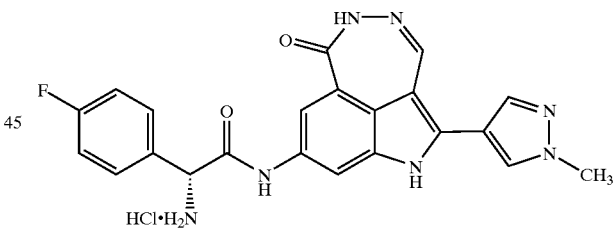

Preparation of example 273 by using (2R)-2-tert-Butoxycarbonylamino-4-fluoro-phenyl)-acetic acid as starting material was carried out in two steps. The first step (coupling) was analogous to Example 11, and the second step (deprotection) was analogous to Example 91.

$^1$H NMR (d$_6$-DMSO): δ 12.03 (s, 1H), 10.93 (s, 1H), 10.28 (s, 1H), 8.80 (br s, 3H), 8.32 (s, 1H), 7.98 (s, 1H), 7.93 (s, 1H), 7.73–7.62 (m, 3H), 7.59 (s, 1H), 7.39–7.30 (m, 2H), 5.19 (m, 1H), 3.1 (s, 3H).

LCMS: (M+H$^+$) 432.1, (M+Na$^+$) 454.0.

Example 274

2-(Benzyl-methyl-amino)-N-[2-(1-methyl-1H-pyrazol-4-yl)-6-oxo-5,6-dihydro-1H-[1,2]diazepino[4,5,6-cd]indol-yl]-acetamide

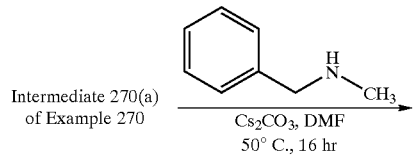

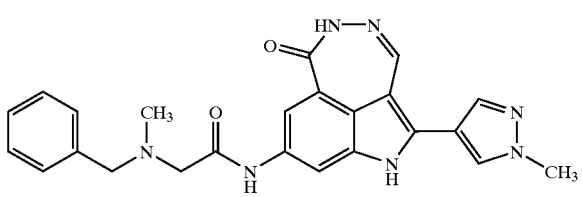

Preparation of Example 274 was carried out analogously to the preparation of Example 270, except that benzyl-methyl amine was used instead of benzyl amine $^1$H-NMR (d$_6$-DMSO): δ 11.88 (s, 1H), 10.24 (s, 1H), 9.89 (s, 1H), 8.30 (s, 1H), 8.07 (d, 1H), 7.91 (s, 1H), 7.62 (d, 1H), 7.58 (s, 1H), 7.40 (d, 2H), 7.33 (t, 2H), 7.25 (t, 1H), 3.91 (s, 3H), 3.64 (s, 2H), 3.18 (s, 2H), 2.26 (s, 3H);

LCMS: (M−) 440.

Example 275

8-[(2-phenylcyclopropyl)methoxy]-1,5-dihydro-6H-[1,2]diazepino[4,5,6-cd]indol-6-one

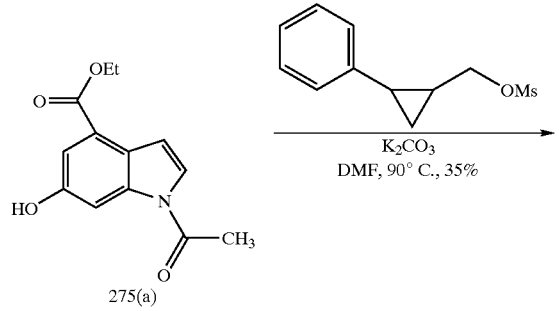

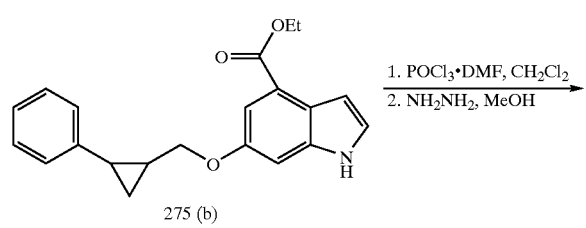

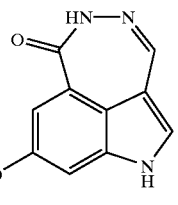

Preparation of the Title Compound 275

Preparation of compound 275 was carried out in two steps analogously to the preparation of Example 3, step 4 and 5 affording 21 mg of desired compound.

$^1$H NMR (d$_6$-DMSO): δ 11.68 (s, 1H), 9.56 (s, 1H), 8.87 (s, 1H), 7.93 (d, 1H, J=2.45 Hz), 7.30–7.20 (m, 2H), 7.19–7.08 (m, 3H), 7.05 (d, 1H, J=2.07 Hz), 6.80 (d, 1H, J=2.07 Hz), 3.96–3.80 (m, 2H), 1.90–1.79 (m, 1H), 1.50–1.37 (m, 1H), 0.96–0.82 (m, 2H).

LCMS: (M+H$^+$) 332.1; (M+Na$^+$) 354.0.

Preparation of 6-(2-Phenyl-cyclopropylmethoxy)-1H-indole-4-carboxylic Acid Ethyl Ester 275(b)

1-Acetyl-6-hydroxy-1H-indole-4-carboxylic acid ethyl ester 275(a) (0.2 g) obtained according to Krutosikova, Aizbeta et al. (Collection of Czechoslovak Chemical Communications (1988), 53(8), 1770–8) was heated with methanesulfonic acid 2-phenyl-cyclopropylmethyl ester (1.5 eq) and potassium carbonate (10 eq) in DMF (2 mL) during 12 h at 90° C. The volatiles were removed in vacuo. Flash Chromatography afforded a white solid (96 mg).

LCMS: (M+) 336.1

Example 276

(2R)-2-Amino-N-(6-oxo-5,6-dihydro-1H-[1,2]diazepino[4,5,6-cd]indol-8-yl)-4-phenyl-butyramide (Hydrochloric Salt)

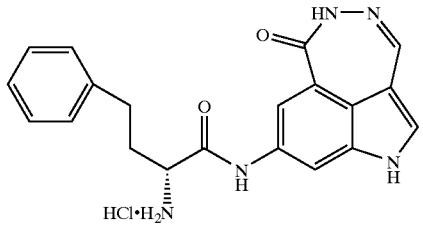

Preparation of example 276 from the title compound of Example 2 (hydrochloride) and (2R)-2-tert-Butoxycarbonylamino-4-phenyl-butyric acid was carried out in two steps. The first step (coupling) was analogous to Example 11, and the second step (deprotection) was analogous to Example 91.

$^1$H NMR (d$_6$-DMSO): δ 11.90 (s, 1H), 10.78 (s, 1H), 10.32 (s, 1H), 8.45 (br s, 4H), 8.11 (s, 1H), 7.69 (s, 1H), 7.65 (s, 1H), 7.53 (s, 1H), 7.36–7.29 (m, 2H), 7.27–7.21 (m, 3H), 4.10 (m, 1H), 2.76–2.69 (m, 2H), 2.23–2.13 (m, 2H).

LCMS: (M+H$^+$) 362.0, (M+Na$^+$) 384.2.

Example 277
(2R)-2-amino-N-(6-oxo-2-pyridin-2-yl-5,6-dihydro-1H-[1,2]diazepino[4,5,6-cd]indol-8-yl)-4-phenylbutanamide
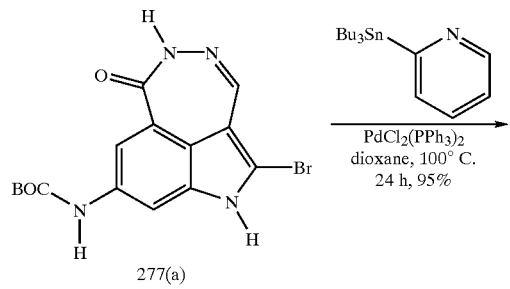
277(a)
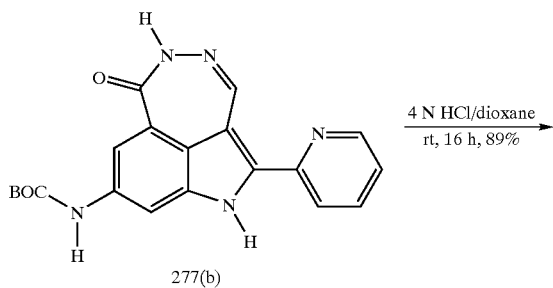
277(b)
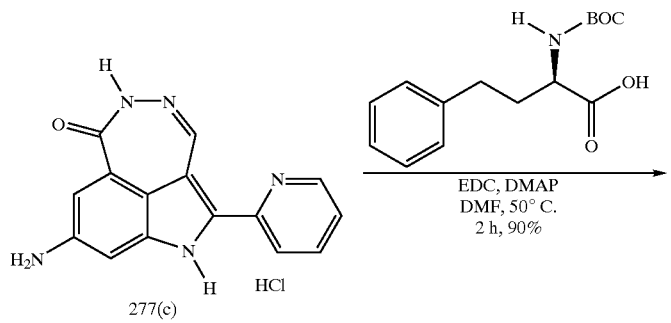
277(c)
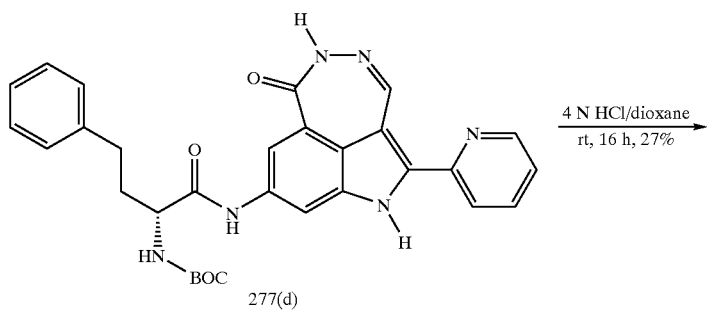
277(d)
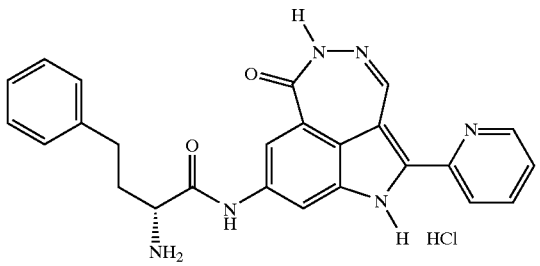

A mixture of tert-butyl ((1R)-1-{[(6-oxo-2-pyridin-2-yl-5,6-dihydro-1H-[1,2]diazepino[4,5,6-cd]indol-8-yl)amino]carbonyl}-3-phenylpropyl)carbamate 277 (d) (0.24 g, 0.46 mmol) in 5 mL of 1,4-dioxane was treated with 10 mL of 4 N HCl in 1,4-dioxane. The mixture was stirred at ambient temperature overnight. The mixture was concentrated and the resulting solid suspended in ether, filtered, washed with ether, and dried under vacuum. Purification via prep HPLC (CH$_3$CN/H$_2$O) gives 0.059 g (27%) of the title compound 277 as a brown solid.

LCMS: (M+) 438.1

Preparation of tert-butyl ((1R)-1-{[(6-oxo-2-pyridin-2-yl-5,6-dihydro-1H-[1,2]diazepino[4,5,6-cd]indol-8-yl]amino]carbonyl}-3-phenylpropyl)carbamate 277(d)

A mixture of 8-amino-2-pyridin-2-yl-1,5-dihydro-6H-[1,2]diazepino[4,5,6-cd]indol-4-one(hydrochloric salt) 277(c) (0.15 g, 0.46 mmol), (2R)-2-amino-4-phenylbutanoic acid (0.15 g, 0.55 mmol), 1-(3-dimethylaminopropyl)-3-ethylcarbodiimide hydrochloride (0.11 g, 0.55 mmol), and 4-(dimethylamino)pyridine (0.17 g, 1.4 mmol) in 15 mL of DMF was stirred at 50° C. for 1.5 hour. After cooling to room temperature, the mixture was concentrated. The resulting residue was dissolved in dichloromethane and loaded onto a silica gel plug. The plug was eluted with EtOAc (100 mL) and the filtrate concentrated to give 0.24 g (96%) of the title compound as brown oil.

LCMS: (M+) 538.1

Preparation of 8-amino-2-pyridin-2-yl-1,5-dihydro-6H-[1,2]diazepino[4,5,6-cd]indol-6-one(Hydrochloric Salt) 277(c)

A mixture of tert-butyl (6-oxo-2-pyridin-2-yl-5,6-dihydro-1H-[1,2]diazepino[4,5,6-cd]indol-8-yl)carbamate (0.6 g, 1.6 mmol) 277(b) in 8 mL of 1,4-dioxane was treated with 30 mL of 4 N HCl in 1,4-dioxane. The mixture was stirred at room temperature overnight. The mixture was concentrated and the resulting solid suspended in ether, filtered, washed with ether, and dried under vacuum to give 0.45 g (89%) of compound 277(c) as a brown solid.

LCMS: (M+) 277.1

Preparation of tert-butyl (6-oxo-2-pyridin-2-yl-5,6-dihydro-1H-[1,2]diazepino[4,5,6-cd]indol-8-yl)carbamate 277(b)

A mixture of tert-butyl (2-bromo-6-oxo-5,6-dihydro-1H-[1,2]diazepino[4,5,6-cd]indol-8-yl)carbamate 277(a) (0.50 g, 1.3 mmol) and 2-tributylstannylpyridine (1.4 g, 4.0 mmol) in 25 mL of 1.4-dioxane was stirred at 60° C. for 0.5 hour. After cooling to room temperature, [1,1'-Bis(diphenylphosphino)ferrocene]dichloro palladium (II) (0.15 g, 0.13 mmol)was added and the mixture stirred at 100° C. overnight. After cooling to room temperature, the mixture was filtered through celite and concentrated. Purification via flash column chromatography (25% EtOAc/hexane) gives 0.47 g (95%) of compound 277(b) as a brown oil.

LCMS: (M+) 377.1

Example 278

(2R)-2-amino-2-(2,3-dihydro-1H-inden-2-yl)-N-(6-oxo-2-pyridin-2-yl-5,6-dihydro-1H-[1,2]diazepino[4,5,6-cd]indol-8-yl)acetamide(Hydrochloric Salt)

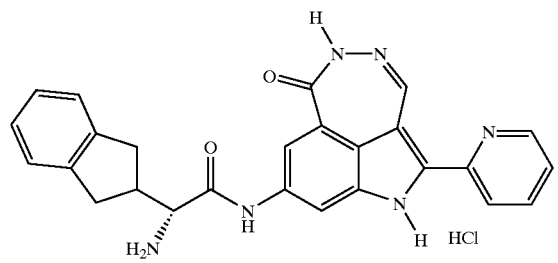

Following the general procedure of Example 277, tert-butyl (2-bromo-6-oxo-5,6-dihydro-1H-1,2]diazepino[4,5,6-cd]indol-8-yl)carbamate was converted to the title compound 278.

LCMS: (M+) 450.1

Example 279

Preparation of (2R)-2-amino-2-cyclohexyl-N-6-oxo-2-pyridin-2-yl-5,6-dihydro-1H-[1,2]diazepino[4,5,6-cd]indol-8-yl)acetamide(Hydrochloric Salt)

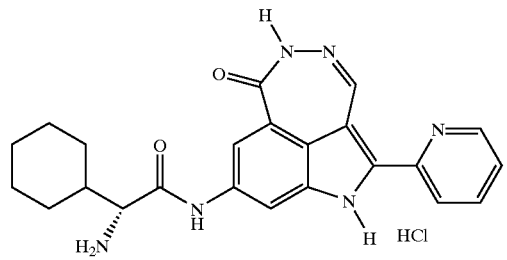

Following the general procedure of Example 277, tert-butyl (2-bromo-6-oxo-5,6-dihydro-1H-[1,2]diazepino[4,5,6-cd]indol-8-yl)carbamate was converted to the title compound 279.

LCMS: (M+) 416.2

Example 280

In Vitro Combination Studies

Cancer cells can be incubated with an antineoplastic agent either alone or in combination with a CHK-1 inhibitor of formula 1. Cell growth data from a combination study (antineoplastic agent together with a fixed concentration of test compound) can be compared to corresponding data obtained from a single agent study (antineoplastic agent without test compound). The concentration of antineoplastic agent causing 50% cell growth inhibition (IC$_{50}$) can be determined for both single agent treatment and combination treatment. IC$_{50}$ values can be calculated using the linear portion of a semi-log plot of antineoplastic agent concentration versus percent cell growth inhibition. The ratio between the IC$_{50}$ of the antineoplastic agent alone and the IC$_{50}$ of the antineoplastic agent in combination with test compound represents the Potentiation Factor 50 (PF$_{50}$). The PF$_{50}$ can be used to measure the effectiveness of the combination treatment. Combination treatment with an antineoplastic agent and test compounds of formula I can provide $PF_{50}$ values ranging from 2 to 8 in cancer cells.

Cancer cell viability and proliferation can be evaluated using a tetrazolium salt reduction assay (MTT assay). In viable cells, this colorimetric assay can measure mitochondrial reduction of a tetrazolium component into an insoluble formazan product. Conversely, this assay can be used to determine whether or not mitochondrial function is impaired, for instance, by the metabolic events leading to apoptosis or necrosis. Cancer cell lines can be grown in 96-well plates and can be plated in the appropriate medium at a volume of 100 ul/well. Plates can be incubated for four hours before the addition of test compounds. On the bottom part of the 96 well-plate, cells can be treated with increasing concentrations of antineoplastic agent. On the top part of the plate, cells can be treated with increasing concentrations of antineoplastic agent combined with a fixed concentration of test compound. Cells can be incubated at 37° C. (5% $CO_2$) for four to six days (depending on cell type). At the end of the incubation, the tetrazolium component can be added to a final concentration of 0.2 mg/ml, and cells can be incubated for 4 hours at 37° C. After centrifugation of the plates and removal of medium, the absorbance of the formazan (solubilized in dimethylsulfoxide) can be measured at 540 nm.

Antineoplastic agents can include cisplatin, hydroxyurea, gemcitibine, carboplatin, 7-ethyl-10-hydroxycamptothecin (SN-38), and cytosine β-D-arabinoside.

Cancer cells can refer to the following:

| Cell Line | Cancer Type |
| --- | --- |
| CA-46 | (human) lymphoma |
| HT-29 | (human) colon |
| Colo205 | (human) colon |
| MV522 | (human) lung |
| SW620 | (human) colon |
| L1210 | (murine) leukemia |
| PANC-1 | (human) pancreas |
| BXPC-3 | (human) pancreas |
| MCF-7 | (human) breast |
| HCT116 | (human) colon |
| H23 | (human) lung |

Example 281

In Vivo Tumor Models

To assess the ability of CHK-1 inhibitors of formula I to augment reduction in tumor volume in combination with gemcitibine in mice, xenograft tumor models using HT-29, MV522 or Colo205 tumor cell lines can be established.

Mice can be randomized (12 mice/group) into treatment groups and used when tumors reach a volume of 150–200 $mm^3$. Mice can undergo a course of intraperitoneal (i.p) injections consisting of vehicle alone, gemcitibine alone or gemcitibine in combination with the test compound of formula 1. Tumor volumes can be measured at times ranging from 2 to 25 days. Control can consist of i.p. injection of vehicle at appropriate intervals. Parallel control can consist of i.p. injection of gemcitibine alone at 15 mg/kg to 240 mg/kg at appropriate intervals. Treatment can consist of i.p. injection of gemcitibine (5 mg/kg to 240 mg/kg) at appropriate intervals in combination with i.p. injection of the test compound of formula I (1 mg/kg to 100 mg/kg) at appropriate intervals. At the end of the study, tumor volume ($mm^3$) can be measured. An enhancement in the delay of tumor growth can be observed in the mice treated with gemcitibine in combination with the test compound of formula I versus gemcitibine treatment alone.

While the invention has been illustrated by reference to specific and preferred embodiments, those skilled in the art will recognize that variations and modifications may be made through routine experimentation and practice of the invention. Thus, the invention is intended not to be limited by the foregoing description, but to be defined by the appended claims and their equivalents.

We claim:

1. A compound of the formula:

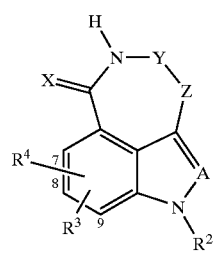

I wherein:

X is =O or =S;

A is $=CR^1—$ or $=N—$;

The group —Y—Z— has the formula —O—$CH_2$— or —N=CH—;

$R^1$ is:

(a) $(C_1-C_8)$alkyl;

(b) —C(=O)—$R^5$;

(c) —C(=O)—$NR^6R^7$; or (d) $R^{35}$, or $R^{36}$, $(C_2-C_8)$alkenyl, or $(C_2-C_8)$alkynyl {wherein each of said $(C_2-C_8)$alkenyl or $(C_2-C_8)$ alkynyl is unsubstituted or substituted with one to four substituents independently selected from the group consisting of F, Cl, OH, —$NH_2$, $R^{40}$, and $R^{42}$};

$R^2$ is (a) H, OH, or $(C_1-C_8)$alkyl;

(b) —C(=O)—$R^8$;

(c) —(C=S)—$R^9$ or —(C=S)—$NR^{10}R^{11}$; or (d) $R^{38}$ or $R^{39}$;

$R^3$ is (a) $R^{38}$;

(b) —C(=O)—$R^{12}$;

(c) —C(=O)—$NR^{13}R^{14}$;

(d) —$NR^{15}$—C(=O)—$R^{16}$;

(e) —$NR^{17}$—$SO_2R^{18}$;

(f) —$NR^{19}$—$SO_n$—$NR^{20}R^{21}$ {wherein n is 1 or 2};

(g) —$NR^{22}$—(C=S)—$R^{23}$ or —$NR^{22}$—(C=S)—$NR^{23}R^{24}$;

(h) $R^{36}$, $(C_2-C_8)$alkenyl, or $(C_2-C_8)$alkynyl {wherein each of said $R^3$ $(C_2-C_8)$alkenyl or $(C_2-C_8)$alkynyl is unsubstituted or substituted with one to four substituents independently selected from the group consisting of —(C=O)—O—$(C_1-C_8)$alkyl, —O—(C=O)—$(C_1-C_8)$alkyl, —(C=O)—$(C_1-C_8)$alkyl, $R^{40}$, $R^{41}$, and $R^{42}$}; or (i) $R^{37}$, —$NH_2$, —NH(($C_2-C_8$)alkenyl), —NH(($C_2-C_8$) alkynyl), —N(($C_1-C_8$)alkyl)(($C_2-C_8$)alkenyl), or —N(($C_1$–$C_8$)alkyl)(($C_2$–$C_8$)alkynyl) {wherein each of said $R^{26}$ ($C_2$–$C_8$)alkenyl or ($C_2$–$C_8$)alkynyl is unsubstituted or substituted with one to four substituents independently selected from the group consisting of $R^{40}$, $R^{41}$, and $R^{42}$};

$R^4$ is selected from the group consisting of H, F, Br, Cl, and ($C_1$–$C_8$)alkyl;

$R^5$ is selected from the group consisting of H, ($C_1$–$C_8$)alkyl, ($C_1$–$C_8$)alkyl—O—, and $R^{36}$;

Each $R^6$ and $R^7$ are independently selected from the group consisting of H, ($C_1$–$C_8$)alkyl, and $R^{36}$;

$R^8$ is selected from the group consisting of ($C_1$–$C_8$)alkyl, ($C_2$–$C_8$)alkenyl, ($C_2$–$C_8$)alkynyl, —$NH_2$, $R^{36}$, and $R^{37}$;

Each of $R^9$, $R^{10}$ and $R^{11}$ are independently selected from the group consisting of H, ($C_1$–$C_8$)alkyl, and $R^{36}$;

$R^{12}$ is selected from the group consisting of H, OH, ($C_1$–$C_8$)alkyl, ($C_1$–$C_8$)alkyl—O—, and $R^{36}$;

$R^{13}$ is H or ($C_1$–$C_8$)alkyl;

$R^{14}$ is selected from the group consisting of H, ($C_1$–$C_8$)alkyl, —$CH_2$—(C=O)—O—($C_1$–$C_8$)alkyl, and $R^{36}$;

$R^{15}$ is H or ($C_1$–$C_8$)alkyl;

$R^{16}$ is selected from the group consisting of H, ($C_1$–$C_8$)alkyl, ($C_2$–$C_8$)alkenyl, ($C_2$–$C_8$)alkynyl, —$NH_2$, $R^{36}$, and $R^{37}$;

wherein said $R^{16}$ ($C_2$–$C_8$)alkenyl or ($C_2$–$C_8$)alkynyl is unsubstituted or substituted with one to four substituents independently selected from the group consisting of $R^{40}$;

$R^{17}$ is selected from the group consisting of H, ($C_1$–$C_8$)alkyl, and $R^{36}$;

$R^{18}$ is ($C_1$–$C_8$)alkyl or $R^{36}$;

$R^{19}$, $R^{20}$, and $R^{21}$ are independently selected from the group consisting of H, ($C_1$–$C_8$)alkyl, and $R^{36}$;

$R^{22}$, $R^{23}$ and $R^{24}$ are independently selected from the group consisting of H, ($C_1$–$C_8$)alkyl, and $R^{36}$;

$R^{25}$ is H or ($C_1$–$C_8$)alkyl;

$R^{26}$ is selected from the group consisting of —C(=O)—O—C($CH_3$)$_3$, ($C_1$–$C_8$)alkyl, —($CR^{13}R^{15}$)$_t$($C_3$–$C_{10}$)cycloalkyl, —($CR^{13}R^{15}$)$_t$($C_2$–$C_{10}$)heterocyclyl, —($CR^{13}R^{15}$)$_t$($C_6$–$C_{10}$)aryl, and —($CR^{13}R^{15}$)$_t$($C_1$–$C_{10}$)heteroaryl; wherein t is an integer from 0 to 2;

or $R^{25}$ and $R^{26}$ may optionally be taken together with the nitrogen to which they are attached to form a 5 to 8-membered heteroaryl or heterocyclyl ring;

$R^{27}$ is selected from the group consisting of ($C_1$–$C_8$)alkyl, ($C_3$–$C_{10}$)cycloalkyl, ($C_2$–$C_{10}$)heterocyclyl, ($C_6$–$C_{10}$)aryl, and ($C_1$–$C_{10}$)heteroaryl;

$R^{28}$ is selected from the group consisting of ($C_1$–$C_8$)alkyl, ($C_3$–$C_{10}$)cycloalkyl, ($C_2$–$C_{10}$)heterocyclyl, ($C_6$–$C_{10}$)aryl, and ($C_1$–$C_{10}$)heteroaryl;

$R^{29}$ is H or ($C_1$–$C_8$)alkyl;

$R^{30}$ is ($C_1$–$C_8$)alkyl, ($C_3$–$C_{10}$)cycloalkyl, ($C_2$–$C_{10}$)heterocyclyl, ($C_6$–$C_{10}$)aryl, or ($C_1$–$C_{10}$)heteroaryl;

or $R^{29}$ and $R^{30}$ may optionally be taken together with the nitrogen to which they are attached to form a 5 to 8-membered heteroaryl or heterocyclyl ring;

$R^{31}$ is H or ($C_1$–$C_8$)alkyl;

$R^{32}$ is independently selected from the group consisting of ($C_1$–$C_8$)alkyl, ($C_3$–$C_{10}$)cycloalkyl, ($C_2$–$C_{10}$)heterocyclyl, ($C_6$–$C_{10}$)aryl, and ($C_1$–$C_{10}$)heteroaryl;

or $R^{31}$ and $R^{32}$ may optionally be taken together with the nitrogen to which they are attached to form a 5 to 8-membered heteroaryl or heterocyclyl ring;

$R^{33}$ is ($C_1$–$C_8$)alkyl, —($CR^{13}R^{15}$)$_q$($C_3$–$C_{10}$)cycloalkyl, —($CR^{13}R^{15}$)$_q$($C_2$–$C_{10}$)heterocyclyl, —($CR^{13}R^{15}$)$_q$($C_6$–$C_{10}$)aryl, or —($CR^{13}R^{15}$)$_q$($C_1$–$C_{10}$)heteroaryl; wherein q is an integer from 0 to 2;

$R^{34}$ is ($C_1$–$C_8$)alkyl, —($CR^{13}R^{15}$)$_p$($C_3$–$C_{10}$)cycloalkyl, —($CR^{13}R^{15}$)$_p$($C_2$–$C_{10}$)heterocyclyl, —($CR^{13}R^{15}$)$_p$($C_6$–$C_{10}$)aryl, or —($CR^{13}R^{15}$)$_p$($C_1$–$C_{10}$)heteroaryl; wherein p is an integer from 0 to 2;

Each $R^{35}$ is independently selected from the group consisting of H, F, Cl, Br, I, CN, OH, $NO_2$, —$NH_2$, —NH—C(=O)—O—C($CH_3$)$_3$, and $CF_3$;

Each $R^{36}$ is independently selected from the group consisting of ($C_3$–$C_{10}$)cycloalkyl, ($C_2$–$C_{10}$)heterocyclyl, ($C_6$–$C_{10}$)aryl, and ($C_1$–$C_{10}$)heteroaryl;

Each $R^{37}$ is independently selected from the group consisting of —$NR^{25}R^{26}$ and $R^{27}$—O—;

$R^{38}$ is $R^{28}$—$SO_n$—; wherein n is 0, 1, or 2 when —$SO_n$— is bonded to $R^{28}$ via an $R^{28}$ carbon atom, or wherein n is 1 or 2 when —$SO_n$— is bonded to $R^{28}$ via an $R^{28}$ ring nitrogen atom;

$R^{39}$ is $R^{29}R^{30}$N—$SO_n$—; wherein n is 1 or 2;

wherein each of said ($C_1$–$C_8$)alkyl, wherever it occurs in any of said $R^1$(a)–(d), $R^2$(a)–(d), $R^3$(a)–(i), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{37}$, $R^{38}$, and $R^{39}$ is unsubstituted or substituted with one to four substituents independently selected from the group consisting of ($C_2$–$C_8$)alkenyl and $R^{40}$;

wherein each of said ($C_3$–$C_{10}$)cycloalkyl, ($C_2$–$C_{10}$)heterocyclyl, ($C_6$–$C_{10}$)aryl, or ($C_1$–$C_{10}$)heteroaryl, wherever it occurs in said $R^1$(b)–(d), $R^2$(b)–(d), $R^3$(a)–(i), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$, $R^{32}$, $R^{33}$, $R^{34}$, $R^{36}$, $R^{37}$, $R^{38}$, and $R^{39}$ is independently unsubstituted or substituted with one to four substituents independently selected from $R^{40}$;

$R^{40}$ is selected from the group consisting of ($C_1$–$C_8$)alkyl, $R^{41}$, $R^{42}$, and $R^{43}$;

Each $R^{41}$ is independently selected from the group consisting of F, Cl, Br, I, CN, OH, $NO_2$, —$NH_2$, —NH—C(=O)—O—C($CH_3$)$_3$, COOH, —C(=O)($C_1$–$C_8$)alkyl, —C(=O)—O—($C_1$–$C_8$)alkyl, —NH—$SO_2$—($C_1$–$C_8$)alkyl, —NH—$SO_2$—($C_6$–$C_{10}$)aryl, and $CF_3$;

Each $R^{42}$ is independently selected from the group consisting of ($C_3$–$C_{10}$)cycloalkyl, ($C_2$–$C_{10}$)heterocyclyl, ($C_6$–$C_{10}$)aryl, and ($C_1$–$C_{10}$)heteroaryl;

Each $R^{43}$ is independently selected from the group consisting of:

—$NR^{31}R^{32}$; $R^{33}$—O—; and $R^{34}$—$SO_n$—; wherein n is 0, 1, or 2 when —$SO_n$— is bonded to $R^{34}$ via an $R^{34}$ carbon atom, or wherein n is 1 or 2 when —$SO_n$— is bonded to $R^{34}$ via an $R^{34}$ ring nitrogen atom;

wherein each of said ($C_1$–$C_8$)alkyl, wherever it occurs in any of $R^{40}$ and $R^{41}$ is independently unsubstituted or substituted with one to four substituents independently selected from the group consisting of $R^{44}$ and $R^{45}$;

wherein each of said ($C_3$–$C_{10}$)cycloalkyl, ($C_2$–$C_{10}$)heterocyclyl, ($C_6$–$C_{10}$)aryl, or ($C_1$–$C_{10}$)heteroaryl, wherever it occurs in any of said $R^{42}$ or $R^{43}$, is independently unsubstituted or substituted with one to four substituents independently selected from the group consisting of $R^{47}$ selected from the group consisting of ($C_1$–$C_8$)alkyl, $R^{44}$, and $R^{45}$;

Each $R^{44}$ is independently selected from the group consisting of F, Cl, Br, I, CN, OH, $NO_2$, $-NH_2$, $-CF_3$, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N<[(C_1-C_8)$alkyl$]_2$, $-NH-(C=O)-(C_1-C_8)$alkyl, $R^{37}$, and $R^{38}$;

Each $R^{45}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

wherein each of said $(C_1-C_8)$alkyl wherever it occurs in any of said $R^{44}$ or $R^{45}$ is independently unsubstituted or substituted with one to four substituents independently selected from the group consisting of $R^{46}$ and $R^{47}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{43}$ or $R^{44}$ is independently unsubstituted or substituted with one to four substituents independently selected from the group consisting of $(C_1-C_8)$alkyl, $R^{46}$ and $R^{47}$;

Each $R^{46}$ is independently selected from the group consisting of F, Cl, Br, I, CN, OH, $NO_2$, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N<[(C_1-C_8)$alkyl$]_2$, $-NH-(C=O)-(C_1-C_8)$alkyl, $-C(=NH)-NH_2$, $-C(=NH)-NH-OH$, $-C(=NH)-NH-O-(C_1-C_8)$alkyl, $-(C=O)-O-(C_1-C_8)$alkyl, $-O-(C=O)-(C_1-C_8)$alkyl, $-(C=O)-(C_1-C_8)$alkyl, $-(C=O)-NH_2$, $-(C=O)-NH(C_1-C_8)$alkyl, $-(C=O)-N>[(C_1-C_8)$alkyl$]_2$, $-NH-(C=O)-(C_1-C_8)$alkyl, $R^{37}$, and $R^{38}$; and Each $R^{47}$ is independently selected from the group consisting of $(C_3-C_{10})$cycloalkyl; $(C_2-C_{10})$heterocyclyl, $(C_6-C_{10})$aryl, and $(C_1-C_{10})$heteroaryl;

or a pharmaceutically acceptable salt thereof.

2. The compound according to claim 1 wherein $R^3$ is selected from the group consisting of $(C_2-C_8)$alkenyl, $(C_2-C_8)$alkynyl, $(C_3-C_6)$cycloalkyl, $(C_2-C_{10})$heterocyclyl, phenyl, and $(C_1-C_{10})$heteroaryl; wherein each of said $(C_2-C_8)$alkenyl or $(C_2-C_8)$alkynyl is unsubstituted or substituted with one to three substituents independently selected from the group consisting of F, OH, $-NH_2$, $(C_1-C_8)$alkyl-NH—, $[(C_1-C_8)$alkyl$]_2$>N—, $(C_3-C_{10})$cycloalkyl, $(C_2-C_{10})$heterocyclyl, $(C_6-C_{10})$aryl, and $(C_1-C_{10})$heteroaryl; and wherein each of said $(C_3-C_6)$cycloalkyl, $(C_2-C_{10})$heterocyclyl, phenyl, or $(C_1-C_{10})$heteroaryl is unsubstituted or substituted with one to four substituents independently selected from the group consisting of $(C_1-C_8)$alkyl, F, OH, $-NH_2$, $(C_1-C_8)$alkyl-NH—, $[(C_1-C_8)$alkyl$]_2$>N—, $(C_3-C_{10})$cycloalkyl, $(C_2-C_{10})$heterocyclyl, $(C_6-C_{10})$aryl, and $(C_1-C_{10})$heteroaryl.

3. The compound according to claim 1 wherein $R^3$ is $-C(=O)-NR^{13}R^{14}$ {wherein $R^{13}$ is H or $(C_1-C_8)$alkyl}, wherein said $R^{13}$ $(C_1-C_4)$alkyl is unsubstituted or substituted with one to four substituents independently selected from the group consisting of F, OH, $-NH_2$, $R^{41}$, and $R^{42}$; wherein each of said $R^{38}$ is unsubstituted or substituted with one or two substituents independently selected from the group consisting of $(C_6-C_{10})$aryl, $(C_1-C_{10})$heteroaryl, $(C_2-C_{10})$heterocyclyl, $(C_1-C_8)$alkyl-NH—, and $[(C_1-C_8)$alkyl$]_2$N—; and wherein each of said $(C_6-C_{10})$aryl substituent is unsubstituted or substituted with one to three substituents independently selected from the group consisting of $(C_1-C_8)$alkyl, F, Cl, $-CF_3$, and OH.

4. The compound according to claim 1 wherein $R^3$ is $-NR^{15}-C(=O)-R^{16}$; wherein $R^{16}$ is $(C_1-C_8)$alkyl unsubstituted or substituted with one to four substituents independently selected from the group consisting of OH, $R^{33}-O-$, CN, $-NH_2$, $(C_1-C_8)$alkyl-N H—, $-NH-(CR^{13}R^{15})_t(C_3-C_{10})$cycloalkyl, $-NH-(CR^{13}R^{15})_t(C_2-C_{10})$heterocyclyl, $-NH-(CR^{13}R^{15})_t(C_6-C_{10})$aryl, or $-NH-(CR^{13}R^{15})_t(C_1-C_{10})$heteroaryl-NH— {wherein t is an integer from 0 to 2}, $[(C_1-C_8)$alkyl$]_2$>N—, $[(C_1-C_8)$alkyl$][(C_3-C_{10})$cycloalkyl$]$>N—, $(C_3-C_{10})$cycloalkyl, $(C_2-C_{10})$heterocyclyl, $(C_6-C_{10})$aryl, and $(C_1-C_{10})$heteroaryl; wherein said $R^{33}$ is $(C_1-C_8)$alkyl, $-(CR^{13}R^{15})_q(C_3-C_{10})$cycloalkyl, $-(CR^{13}R^{15})_q(C_2-C_{10})$heterocyclyl, $-(CR^{13}R^{15})_q(C_8-C_{10})$aryl, or $-(CR^{13}R^{15})_q(C_1-C_{10})$heteroaryl; and wherein q is an integer from 0 to 2.

5. The compound according to claim 4 wherein said $(C_3-C_{10})$cycloalkyl substituent wherever it occurs is unsubstituted or substituted with one to four substituents independently selected from the group consisting of $(C_3-C_{10})$cycloalkyl, $(C_2-C_{10})$heterocyclyl, $(C_6-C_{10})$aryl, and $(C_1-C_{10})$heteroaryl.

6. The compound according to claim 4 wherein said $(C_8-C_{10})$aryl substituent wherever it occurs is unsubstituted or substituted with one to four substituents independently selected from the group consisting of $(C_1-C_8)$alkyl, F, Cl, Br, CN, OH, and $CF_3$.

7. The compound according to claim 4 wherein said $(C_2-C_{10})$heterocyclyl substituent wherever it occurs is unsubstituted or substituted with one or two substituents independently selected from the group consisting of $(C_1-C_8)$alkyl, $-(C=O)-(C_1-C_8)$alkyl, $-(C=O)-O-(C_1-C_8)$alkyl, $-S-(C_1-C_8)$alkyl, F, Br, OH, and $CF_3$.

8. The compound according to claim 1 wherein $R^3$ is $-NR^{15}-C(=O)-R^{16}$; wherein $R^{16}$ is $(C_2-C_8)$alkenyl unsubstituted or substituted with one to four substituents independently selected from the group consisting of $(C_3-C_{10})$cycloalkyl, $(C_2-C_{10})$heterocyclyl, $(C_6-C_{10})$aryl, and $(C_1-C_{10})$heteroaryl; wherein said $(C_6-C_{10})$aryl substituent is unsubstituted or substituted with one to four substituents independently selected from the group consisting of $(C_1-C_8)$alkyl, F, Cl, Br, CN, OH, and $CF_3$; and wherein said $(C_2-C_{10})$heterocyclyl substituent is unsubstituted or substituted with one or two substituents independently selected from the group consisting of $(C_1-C_8)$alkyl, $-(C=O)-(C_1-C_8)$alkyl, $-(C=O)-O-(C_1-C_8)$alkyl, $-S-(C_1-C_8)$alkyl, F, Br, OH, and $CF_3$.

9. The compound according to claim 1 wherein $R^3$ is $-NR^{15}-C(=O)-R^{16}$; wherein $R^{16}$ is $(C_1-C_{10})$heteroaryl unsubstituted or substituted with one or two substituents independently selected from the group consisting of $(C_1-C_8)$alkyl, $-(C=O)-(C_1-C_8)$alkyl, $-S-(C_1-C_8)$alkyl, F, Cl, CN, OH, and $CF_3$.

10. The compound according to claim 9 wherein said $R^{16}$ is pyridinyl.

11. The compound according to claim 1 wherein $R^3$ is $-NR^{15}-C(=O)-R^{16}$; wherein $R^{16}$ is $(C_3-C_{10})$cycloalkyl unsubstituted or substituted with one or two substituents independently selected from the group consisting of $(C_1-C_8)$alkyl, F, Cl, CN, OH, $NH_2$, $CF_3$, $(C_2-C_{10})$heterocyclyl, $(C_6-C_{10})$aryl, and $(C_1-C_{10})$heteroaryl; wherein said $(C_6-C_{10})$aryl substituent is unsubstituted or substituted with one to four substituents independently selected from the group consisting of $(C_1-C_8)$alkyl, F, Cl, Br, CN, OH, and $CF_3$; and wherein said $(C_2-C_{10})$heterocyclyl substituent is unsubstituted or substituted with one or two substituents independently selected from the group consisting of $(C_1-C_8)$ alkyl, —(C=O)—$(C_1-C_8)$alkyl, —(C=O)—O—$(C_1-C_8)$ alkyl, —S—$(C_1-C_8)$alkyl, F, Br, OH, and $CF_3$.

12. The compound according to claim 11 wherein said $R^{16}$ $(C_{3-C10})$cycloalkyl is selected from the group consisting of cyclopropyl and cyclohexyl.

13. The compound according to claim 11 wherein said $(C_6-C_{10})$aryl substituent is unsubstituted.

14. The compound according to claim 1 wherein $R^3$ is —$NR^{15}$—C(=O)—$R^{16}$; wherein $R^{16}$ is $(C_2-C_{10})$ heterocyclyl unsubstituted or substituted with one to four substituents independently selected from the group consisting of $(C_1-C_8)$alkyl, —(C=O)—$(C_1-C_8)$alkyl, —(C=O)—O—$(C_1-C_8)$alkyl, F, Cl, CN, OH, and $CF_3$.

15. The compound according to claim 14 wherein said $R^{16}$ $(C_{2-C10})$heterocyclyl is selected from the group consisting of piperazinyl, piperidinyl, pyrrolidinyl, pyrrolidinonyl, thiadiazolyl, tetrahydroisoquinolinyl, tetrahydronaphthalenyl, and indanyl.

16. The compound according to claim 1 wherein $R^3$ is —$NR^{15}$—C(=O)—$R^{16}$; wherein $R^{16}$ is phenyl unsubstituted or substituted with one to three substituents independently selected from the group consisting of $(C_1-C_8)$alkyl, $(C_1-C_8)$alkyl-O—, F, Cl, Br, CN, OH, and $CF_3$.

17. The compound according to claim 1 wherein $R^1$ is $(C_1-C_8)$alkyl substituted with one to two substituents independently selected from the group consisting of F, Cl —OH, —$NH_2$, $(C_1-C_8)$alkyl-NH—, $[(C_1-C_8)$alkyl$]_2$N—, and $(C_1-C_8)$alkyl-O—; wherein each of said $(C_1-C_8)$alkyl substituent, wherever it occurs, is independently unsubstituted or substituted with one to three substituents independently selected from the group consisting of —$NH_2$, $(C_1-C_8)$alkyl-NH—, $[(C_1-C_8)$alkyl$]_2$N—, —O—(C=O)—$(C_1-C_8)$alkyl, $(C_2-C_{10})$heterocycyl, $(C_6-C_{10})$ aryl, and $(C_1-C_{10})$heteroaryl.

18. The compound according to claim 1 wherein $R^1$ is $(C_2-C_8)$alkenyl or $(C_2-C_8)$alkynyl; wherein each of said $(C_2-C_8)$alkenyl or $(C_2-C_{10})$alkynyl is unsubstituted or substituted with one to two substituents independently selected from the group consisting of —$NH_2$, $(C_1-C_8)$alkyl-NH—, $[(C_1-C_8)$alkyl$]_2$N—, $(C_2-C_{10})$heterocyclyl, and $(C_1-C_{10})$ heteroaryl; wherein each of said $(C_1-C_8)$alkyl substituent, wherever it occurs, is independently unsubstituted or substituted with one to three substituents independently selected from the group consisting of —$NH_2$, $(C_1-C_8)$alkyl-NH—, $[(C_1-C_8)$alkyl$]_2$N—, —O(C=O)—$(C_1-C_8)$alkyl, $(C_2-C_{10})$heterocyclyl, $(C_6-C_{10})$aryl, and $(C_1-C_{10})$ heteroaryl.

19. The compound according to claim 1 wherein $R^1$ is $R^{36}$ selected from the group consisting of H, Cl, and Br.

20. The compound according to claim 1 wherein $R^1$ is selected from the group consisting of $(C_3-C_6)$cycloalkyl, $(C_2-C_{10})$heterocyclyl, phenyl, and $(C_1-C_{10})$heteroaryl; wherein each of said $(C_2-C_{10})$heterocyclyl, phenyl, or $(C_1-C_{10})$heteroaryl is unsubstituted or substituted with one to three substituents independently selected from the group consisting of $(C_1-C_8)$alkyl, F, Cl, —$NH_2$, —OH, $(C_1-C_8)$ alkyl-NH—, and $[(C_1-C_8)$alkyl$]_2$N—; wherein each of said $(C_1-C_8)$alkyl substituent, wherever it occurs, is unsubstituted or substituted with one to three substituents selected from —$NH_2$, $(C_1-C_8)$alkyl-NH—, $[(C_1-C_8)$alkyl$]_2$N—, —O—(C=O)—$(C_1-C_8)$alkyl, $(C_2-C_{10})$heterocyclyl, $(C_6-C_{10})$aryl, and $(C_1-C_{10})$heteroaryl.

21. The compound according to claim 1 wherein $R^1$ is —C(=O)—$R^5$, wherein $R^5$ is $(C_1-C_8)$alkyl-O— or $(C_2-C_{10})$heterocyclyl.

22. The compound according to claim 1 wherein $R^1$ is —C(=O)—$NR^6R^7$; wherein each of said $R^6$ and $R^7$ are independently H or $(C_1-C_8)$alkyl; and wherein each of said $R^6$ and $R^7$ $(C_1-C_8)$alkyl are unsubstituted or substituted with one to three substituents independently selected from the group consisting of OH, —$NH_2$, $(C_1-C_8)$alkyl-NH—, $[(C_1-C_8)$alkyl$]_2$>N—, $(C_2-C_{10})$heterocyclyl, and $(C_1-C_{10})$ heteroaryl.

23. The compound according to claim 1 wherein $R^2$ is H or $(C_1-C_8)$alkyl unsubstituted or substituted with one to four substituents independently selected from the group consisting of OH, —$NH_2$, $(C_1-C_8)$alkyl-NH—, $[(C_1-C_8)$alkyl$]_2$>N—, $(C_2-C_{10})$heterocyclyl, and $(C_1-C_{10})$ heteroaryl.

24. The compound according to claim 1 wherein $R^2$ is —C(=O)—$R^8$, wherein $R^8$ is selected from the group consisting of $(C_1-C_8)$alkyl, $(C_2-C_{10})$alkenyl, $(C_2-C_8)$ alkynyl, —$NH_2$, and $R^{37}$ selected from the group consisting of $(C_1-C_8)$alkyl-NH—, $[(C_1-C_8)$alkyl]>N—, and $(C_1-C_8)$ alkyl-O—; wherein each of said $R^8$ and $R^{37}$ $(C_1-C_8)$alkyl, wherever it occurs, is independently unsubstituted or substituted with one to four substituents independently selected from $R^{40}$ selected from the group consisting of F, OH, —$NH_2$, $(C_3-C_{10})$cycloalkyl, $(C_2-C_{10})$heterocyclyl, $(C_6-C_{10})$aryl, $(C_1-C_{10})$heteroaryl; $(C_1-C_8)$alkyl-NH— and $[(C_1-C_8)$alkyl$]_2$>N—;

wherein each of said $R^{40}$ $(C_1-C_8)$alkyl, wherever it occurs, is independently unsubstituted or substituted with one to four substituents independently selected from $R^{44}$ independently selected from the group consisting of OH, —$NH_2$, $(C_1-C_8)$alkyl-NH—, $[(C_1-C_8)$ alkyl$]_2$>N—, and $(C_3-C_{10})$cycloalkyl-NH—;

wherein each of said each of said $R^{40}$ $(C_3-C_{10})$cycloalkyl, $(C_2-C_{10})$heterocycyl, $(C_6-C_{10})$aryl, or $(C_1-C_{10})$ heteroaryl, wherever it occurs, is independently unsubstituted or substituted with one to four substituents independently selected from $R^{47}$ selected from the group consisting of $(C_1-C_8)$alkyl, OH, —$NH_2$, $(C_1-C_8)$ alkyl-NH—, $[(C_1-C_8)$alkyl$]_2$>N—, and $(C_3-C_{10})$ cycloalkyl-NH—; and wherein each of said $R^{47}$ $(C_1-C_8)$alkyl, wherever it occurs, is independently unsubstituted or substituted with one to four substituents independently selected from the group consisting of OH, —$NH_2$, $(C_1-C_8)$ alkyl-NH—, $[(C_1-C_8)$alkyl]2>N—, and $(C_3-C_{10})$ cycloalkyl-NH.

25. The compound according to claim 1 wherein $R^2$ is —C(=O)—$R^8$, wherein $R^8$ is selected from the group consisting of $(C_3-C_5)$cycloalkyl, $(C_2-C_{10})$heterocyclyl, phenyl, or $(C_1-C_{10})$heteroaryl; wherein each of said $R^8$ $(C_3-C_6)$cycloalkyl, $(C_2-C_{10})$heterocyclyl, phenyl, or $(C_1-C_{10})$heteroaryl is unsubstituted or substituted with one to four substituents independently selected from $R^{40}$ selected from the group consisting of $(C_1-C_8)$alkyl, F, OH, —$NH_2$, $(C_1-C_8)$alkyl-NH—, $[(C_1-C_8)$alkyl$]_2$>N—, $(C_3-C_{10})$cycloalkyl, $(C_2-C_{10})$heterocyclyl, $(C_6-C_{10})$aryl, and $(C_1-C_{10})$heteroaryl; wherein each of said $R^{40}$ $(C_1-C_8)$ alkyl, wherever it occurs, is independently unsubstituted or substituted with one to four substituents independently selected from $R^{44}$ independently selected from the group consisting OH, —$NH_2$, $(C_1-C_8)$alkyl-NH—, $[(C_1-C_8)$alkyl$]_2$>N—, and $(C_3-C_{10})$cycloalkyl-NH—, wherein each of said $R^{40}$ $(C_3-C_{10})$cycloalkyl, $(C_2-C_{10})$ heterocyclyl $(C_8-C_{10})$aryl, or $(C_1-C_{10})$heteroaryl is unsubstituted or substituted with one to four substituents independently selected from $R^{47}$ selected from the group consisting of $(C_1-C_8)$alkyl, OH, —$NH_2$, $(C_1-C_8)$alkyl-NH—, $[(C_1-C_8)$alkyl$]_2$>N—, and $(C_3-C_{10})$cycloalkyl-NH—; wherein each of said $R^{47}$ ($C_1$–$C_8$)alkyl, wherever it occurs, is unsubstituted or substituted with one to four substituents independently selected from the group consisting of OH, —$NH_2$, ($C_1$–$C_8$)alkyl-NH—, [($C_1$–$C_8$)alkyl]$_2$>N—, and ($C_3$–$C_{10}$)cycloalkyl-NH.

26. The compound according to claim 1 wherein said $R^3$ is on position 8 of said compound of the formula I.

27. The compound according to claim 1 wherein said $R^4$ is on position 7 of said compound of the formula I.

28. The compound according to claim 1 wherein said $R^4$ is H on position 7 of said compound of the formula I.

29. The compound according to claim 1 wherein X is =O.

30. The compound according to claim 1 wherein the group —Y—Z— has the formula —N=CH—.

31. The compound according to claim 1 selected from the group consisting of:

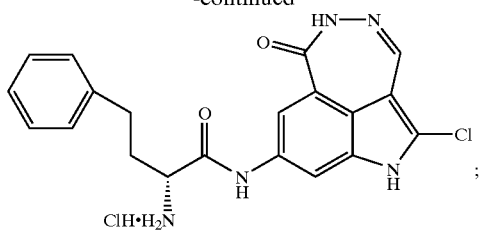

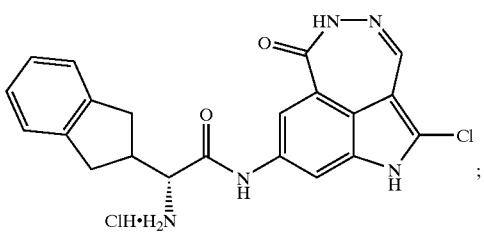

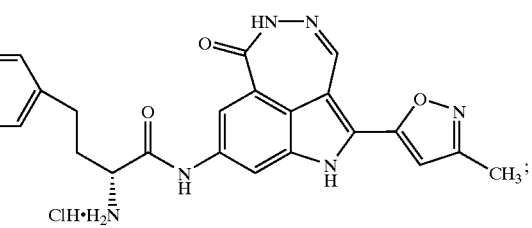

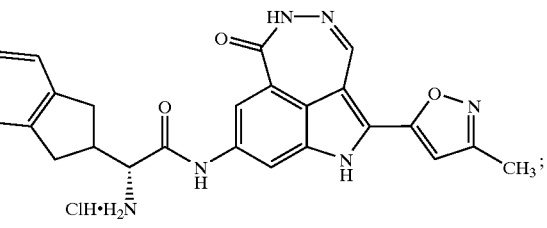

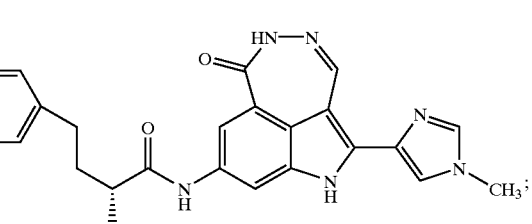

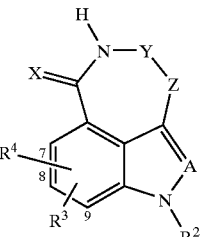

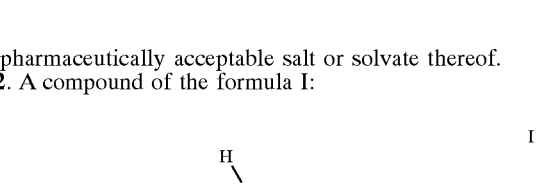

and

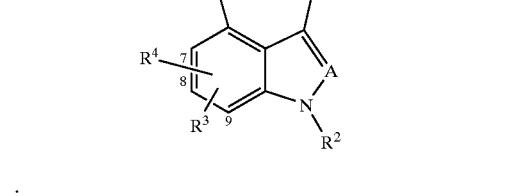

or a pharmaceutically acceptable salt or solvate thereof.

32. A compound of the formula I:

wherein:
X is =O or =S;

A is $=CR^1—$ or $=N—$;

The group $—Y—Z—$ has the formula $—O—CH_2—$ or $—N=CH—$;

$R^1$ is:
(a) $(C_1-C_8)$ alkyl;
(b) $—C(=O)—R^5$;
(c) $—C(=O)—NR^6R^7$; or
(d) $R^{35}$, or $R^{36}$, $(C_2-C_8)$alkenyl, or $(C_2-C_8)$alkynyl {wherein each of said $(C_2-C_8)$alkenyl or $(C_2-C_8)$ alkynyl is unsubstituted or substituted with one to four substituents independently selected from the group consisting of F, Cl, OH, $—NH_2$, $R^{40}$, and $R^{42}$};

$R^2$ is
(a) H, OH, or $(C_1-C_8)$alkyl;
(b) $—C(=O)—R^8$;
(c) $—(C=S)—R^9$ or $(C=S)—NR^{10}R^{11}$; or
(d) $R^{38}$ or $R^{39}$;

$R^3$ is $—NR^{15}—C(=O)—R^{16}$;

$R^4$ is selected from the group consisting of H, F, Br, Cl, and $(C_1-C_8)$alkyl;

$R^5$ is selected from the group consisting of H, $(C_1-C_8)$ alkyl, $(C_1-C_8)$alkyl—O—, and $R^{36}$;

Each $R^6$ and $R^7$ are independently selected from the group consisting of H, $(C_1-C_8)$alkyl, and $R^{36}$;

$R^8$ is selected from the group consisting of $(C_1-C_8)$alkyl, $(C_2-C_8)$alkenyl, $(C_2-C_8)$alkynyl, $—NH_2$, $R^{36}$, and $R^{37}$;

Each of $R^9$, $R^{10}$ and $R^{11}$ are independently selected from the group consisting of H, $(C_1-C_8)$alkyl, and $R^{36}$;

$R^{13}$ is H or $(C_1-C_8)$alkyl;

$R^{15}$ is H or $(C_1-C_8)$alkyl;

$R^{16}$ is $(C_1-C_8)$alkyl unsubstituted or substituted with one to four substituents independently selected from the group consisting of OH, $R^{33}—O—$, CN, $—NH_2$, $(C_1-C_8)$alkyl—NH—, $—NH—(CR^{13}R^{15})_t(C_3-C_{10})$cycloalkyl, $—NH—(CR^{13}R^{15})_t(C_2-C_{10})$heterocyclyl, $—NH—(CR^{13}R^{15})_t(C_6-C_{10})$aryl, or $—NH—(CR^{13}R^{15})_t(C_1-C_{10})$heteroaryl—NH— {wherein t is an integer from 0 to 2}, $[((C_1-C_8)alkyl]_2>N—$, $[(C_1-C_8)$alkyl][$(C_3-C_{10})$cycloalkyl]>N—, $(C_3-C_{10})$cycloalkyl, $(C_2-C_{10})$heterocyclyl, $(C_6-C_{10})$aryl, and $(C_1-C_{10})$heteroaryl; wherein said $R^{33}$ is $(C_1-C_8)$alkyl, $—(CR^{13}R^{15})_q(C_3-C_{10})$cycloalkyl, $—(CR^{13}R^{15})_q(C_2-C_{10})$heterocyclyl, $—(CR^{13}R^{15})_q(C_1-C_{10})$heteroaryl; and wherein q is an integer from 0 to 2;

$R^{25}$ is H or $(C_1-C_8)$alkyl;

$R^{26}$ is selected from the group consisting of $—C(=O)—O—C(CH_3)_3$, $(C_1-C_8)$alkyl, $—(CR^{13}R^{15})_t(C_3-C_{10})$cycloalkyl, $—(CR^{13}R^{15})_t(C_2-C_{10})$heterocyclyl, $—(CR^{13}R^{15})_t(C_6-C_{10})$aryl, and $—(CR^{13}R^{15})_t(C_1-C_{10})$heteroaryl; wherein t is an integer from 0 to 2;

or $R^{25}$ and $R^{26}$ may optionally be taken together with the nitrogen to which they are attached to form a 5 to 8-membered heteroaryl or heterocyclyl ring;

$R^{27}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{28}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{29}$ is H or $(C_1-C_8)$alkyl;

$R^{30}$ is $(C_1-C_8)$alkyl, $(C_3-C_{10})$cycloalkyl, $(C_2-C_{10})$heterocyclyl, $(C_6-C_{10})$aryl, or $(C_1-C_{10})$heteroaryl;

or $R^{29}$ and $R^{30}$ may optionally be taken together with the nitrogen to which they are attached to form a 5 to 8-membered heteroaryl or heterocyclyl ring;

$R^{31}$ is H or $(C_1-C_8)$alkyl;

$R^{32}$ is independently selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

or $R^{31}$ and $R^{32}$ may optionally be taken together with the nitrogen to which they are attached to form a 5 to 8-membered heteroaryl or heterocyclyl ring;

$R^{33}$ is $(C_1-C_8)$alkyl, $—(CR^{13}R^{15})_q(C_3-C_{10})$cycloalkyl, $—(CR^{13}R^{15})_q(C_2-C_{10})$heterocyclyl, $—(CR^{13}R^{15})_q(C_6-C_{10})$aryl, or $—(CR^{13}R^{15})_q(C_1-C_{10})$heteroaryl; wherein q is an integer from 0 to 2;

$R^{34}$ is $(C_1-C_8)$alkyl, $—(CR^{13}R^{15})_p(C_3-C_{10})$cycloalkyl, $—(CR^{13}R^{15})_p(C_2-C_{10})$heterocyclyl, $—(CR^{13}R^{15})_p(C_6-C_{10})$aryl, or $—(CR^{13}R^{15})_p(C_1-C_{10})$heteroaryl; wherein p is an integer from 0 to 2;

Each $R^{35}$ is independently selected from the group consisting of H, F, Cl, Br, I, CN, OH, $NO_2$, $—NH_2$, $—NH—C(=O)—O—C(CH_3)_3$, and $CF_3$;

Each $R^{36}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{37}$ is independently selected from the group consisting of $—NR^{25}R^{26}$ and $R^{27}—O—$;

$R^{38}$ is $R^{28}—SO_n—$; wherein n is 0, 1, or 2 when $—SO_n—$ is bonded to $R^{28}$ via an $R^{28}$ carbon atom, or wherein n is 1 or 2 when $—SO_n—$ is bonded to $R^{28}$ via an $R^{28}$ ring nitrogen atom;

$R^{39}$ is $R^{29}R^{30}N—SO_n—$; wherein n is 1 or 2;

wherein each of said $(C_1-C_8)$alkyl, wherever it occurs in any of said $R^1$(a)–(d), $R^2$(a)–(d), $R^3$, $R^4$, $R^5$, $R^6$, $R^7$, $R^8$, $R^9$, $R^{10}$, $R^{11}$, $R^{13}$, $R^{15}$, $R^{25}$, $R^{26}$, $R^{27}$, $R^{28}$, $R^{29}$, $R^{30}$, $R^{31}$, $R^{32}$, $R^{33}$, $R^{34}$, $R^{37}$, $R^{38}$, and $R^{39}$ is unsubstituted or substituted with one to four substituents independently selected from the group consisting of $(C_2-C_8)$ alkenyl and $R^{40}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in said $R^1$(b)–(d), $R^2$(b)–(d), $R^3$, $R^4$, $R^5$, $R^6$, $R^7$, $R^8$, $R^9$, $R^{10}$, $R^{11}$, $R^{13}$, $R^{15}$, $R^{25}$, $R^{26}$, $R^{27}$, $R^{28}$, $R^{30}$, $R^{32}$, $R^{33}$, $R^{34}$, $R^{36}$, $R^{37}$, $R^{38}$, and $R^{39}$ is independently unsubstituted or substituted with one to four substituents independently selected from $R^{40}$;

$R^{40}$ is selected from the group consisting of $(C_1-C_8)$alkyl, $R^{41}$, $R^{42}$, and $R^{43}$;

Each $R^{41}$ is independently selected from the group consisting of F, Cl, Br, I, CN, OH, $NO_2$, $—NH_2$, $—NH—C(=O)—O—C(CH_3)_3$, COOH, $—C(=O)(C_1-C_8)$ alkyl, $—C(=O)—O—(C_1-C_8)$alkyl, $—NH—SO_2—(C_1-C_8)$alkyl, $—NH—SO_2—(C_6-C_{10})$aryl, and $CF_3$;

Each $R^{42}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{43}$ is independently selected from the group consisting of:

$—NR^{31}R^{32}$; $R^{33}—O—$; and $R^{34}—SO_n—$; wherein n is 0, 1, or 2 when $—SO_n—$ is bonded to $R^{34}$ via an $R^{34}$ carbon atom, or wherein n is 1 or 2 when $—SO_n—$ is bonded to $R^{34}$ via an $R^{34}$ ring nitrogen atom;

wherein each of said $(C_1-C_8)$alkyl, wherever it occurs in any of $R^{40}$ and $R^{41}$ is independently unsubstituted or substituted with one to four substituents independently selected from the group consisting of $R^{44}$ and $R^{45}$;

wherein each of said (C$_3$–C$_{10}$)cycloalkyl, (C$_2$–C$_{10}$) heterocyclyl, (C$_6$–C$_{10}$)aryl, or (C$_1$–C$_{10}$)heteroaryl, wherever it occurs in any of said R$^{42}$ or R$^{43}$, is independently unsubstituted or substituted with one to four substituents independently selected from the group consisting of R$^{47}$ selected from the group consisting of (C$_1$–C$_8$)alkyl, R$^{44}$, and R$^{45}$;

Each R$^{44}$ is independently selected from the group consisting of F, Cl, Br, I, CN, OH, NO$_2$, —NH$_2$, —CF$_3$, —C(=NH)—NH$_2$, —C(=NH)—NH—OH, —C(=NH)—NH—O—(C$_1$–C$_8$)alkyl, —(C=O)—O—(C$_1$–C$_8$)alkyl, —O—(C=O)—(C$_1$–C$_8$)alkyl, —(C=O)—(C$_1$–C$_8$)alkyl, —(C=O)—NH$_2$, —(C=O)—NH(C$_1$–C$_8$)alkyl, —(C=O)—N<[(C$_1$–C$_8$)alkyl]$_2$, —NH—(C=O)—(C$_1$–C$_8$)alkyl, R$^{37}$, and R$^{38}$;

Each R$^{45}$ is independently selected from the group consisting of (C$_3$–C$_{10}$)cycloalkyl, (C$_2$–C$_{10}$)heterocyclyl, (C$_6$–C$_{10}$)aryl, and (C$_1$–C$_{10}$)heteroaryl;

wherein each of said (C$_1$–C$_8$)alkyl wherever it occurs in any of said R$^{44}$ or R$^{45}$ is independently unsubstituted or substituted with one to four substituents independently selected from the group consisting of R$^{46}$ and R$^{47}$;

wherein each of said (C$_3$–C$_{10}$)cycloalkyl, (C$_2$–C$_{10}$) heterocyclyl, (C$_6$–C$_{10}$)aryl, or (C$_1$–C$_{10}$)heteroaryl, wherever it occurs in any of said R$^{43}$ or R$^{44}$ is independently unsubstituted or substituted with one to four substituents independently selected from the group consisting of (C$_1$–C$_8$)alkyl, R$^{46}$ and R$^{47}$;

Each R$^{46}$ is independently selected from the group consisting of F, Cl, Br, I, CN, OH, NO$_2$, —C(=NH)—NH$_2$, —C(=NH)—NH—OH, —C(=NH)—NH—O—(C$_1$–C$_8$)alkyl, —(C=O)—O—(C$_1$–C$_8$)alkyl, —O—(C=O)—(C$_1$–C$_8$)alkyl, —(C=O)—(C$_1$–C$_8$)alkyl, —(C=O)—NH$_2$, —(C=O)—NH(C$_1$–C$_8$)alkyl, —(C=O)—N<[(C$_1$–C$_8$)alkyl]$_2$, —NH—(C=O)—(C$_1$–C$_8$)alkyl, —C(=NH)—NH$_2$, —C(=NH)—NH—OH, —C(=NH)—NH—O—(C$_1$–C$_8$)alkyl, —(C=O)—O—(C$_1$–C$_8$)alkyl, —O—(C=O)—(C$_1$–C$_8$)alkyl, —(C=O)—(C$_1$–C$_8$)alkyl, —(C=O)—NH$_2$, —(C=O)—NH(C$_1$–C$_8$)alkyl, —(C=O)—N>[(C$_1$–C$_8$)alkyl]$_2$, —NH—(C=O)—(C$_1$–C$_8$)alkyl, R$^{37}$, and R$^{38}$; and Each R$^{47}$ is independently selected from the group consisting of (C$_3$–C$_{10}$)cycloalkyl; (C$_2$–C$_{10}$)heterocyclyl, (C$_6$–C$_{10}$)aryl, and (C$_1$–C$_{10}$)heteroaryl;

or a pharmaceutically acceptable salt thereof.

33. The compound according to claim 32 wherein said (C$_3$–C$_{10}$)cycloalkyl substituent wherever it occurs is unsubstituted or substituted with one to four substituents independently selected from the group consisting of (C$_3$–C$_{10}$) cycloalkyl, (C$_2$–C$_{10}$)heterocyclyl, (C$_6$–C$_{10}$)aryl, and (C$_1$–C$_{10}$)heteroaryl.

34. The compound according to claim 32 wherein said (C$_6$–C$_{10}$)aryl substituent wherever it occurs is unsubstituted or substituted with one to four substituents independently selected from the group consisting of (C$_1$–C$_8$)alkyl, F, Cl, Br, CN, OH, and CF$_3$.

35. The compound according to claim 32 wherein said (C$_2$–C$_{10}$)heterocyclyl substituent wherever it occurs is unsubstituted or substituted with one or two substituents independently selected from the group consisting of (C$_1$–C$_8$) alkyl, —(C=O)—(C$_1$–C$_8$)alkyl, —(C=O)—O—(C$_1$–C$_8$) alkyl, —S—(C$_1$–C$_8$)alkyl, F, Br, OH, and CF$_3$.

36. A compound of formula I,

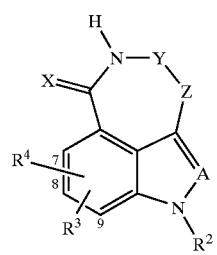

I wherein:

X is =O or =S;

A is =CR$^1$— or =N—;

The group —Y—Z— has the formula —O—CH$_2$— or —N=CH—;

R$^1$ is selected from the group consisting of (C$_3$–C$_6$) cycloalkyl, (C$_2$–C$_{10}$)heterocyclyl, phenyl, and (C$_1$–C$_{10}$)heteroaryl; wherein each of said (C$_2$–C$_{10}$) heterocyclyl, phenyl, or (C$_1$–C$_{10}$)heterocyclyl, phenyl, or (C$_1$–C$_{10}$)heteroaryl is unsubstituted or susbstituted with one to three substituents independently selected from the group consisting of (C$_1$–C$_8$)alkyl, F, Cl, —NH$_2$, —OH, (C$_1$–C$_8$)alkyl—NH—, and [(C$_1$–C$_8$) alkyl]$_2$>N—; wherein each of said (C$_1$–C$_8$)alkyl substituent, wherever it occurs, is unsubstituted or substituted with one to three substituents selected from —NH$_2$, (C$_1$–C$_8$)alkyl—NH—, [(C$_1$–C$_8$)alkyl]$_2$>N—, —O—(C=O)—(C$_1$–C$_8$)alkyl, (C$_2$–C$_{10}$)heterocyclyl, (C$_6$–C$_{10}$)aryl, and (C$_1$–C$_{10}$)heteroaryl;

R$^2$ is (a) H, OH, or (C$_1$–C$_8$)alkyl;

(b) —C(=O)—R$^8$;

(c) —C(=S)—R$^9$ or —C(=S)—NR$^{10}$R$^{11}$; or (d) R$^{38}$ or R$^{39}$,

R$^3$ is (a) R$^{38}$;

(b) —C(=O)—R$^{12}$;

(c) —C(=O)—NR$^{13}$R$^{14}$;

(d) —NR$^{15}$—C(=O)—R$^{16}$;

(e) —NR$^{17}$—SO$_2$R$^{18}$;

(f) —NR$^{19}$—SO$_n$—NR$^{20}$R$^{21}$ {wherein n is 1 or 2};

(g) —NR$^{22}$—(C=S)—R$^{23}$ or —NR$^{22}$—(C=S)—NR$^{23}$R$^{24}$;

(h) R$^{36}$, (C$_2$–C$_8$)alkenyl, or (C$_2$–C$_8$)alkynyl {wherein each of said R$^3$ (C$_2$–C$_8$)alkenyl or (C$_2$–C$_8$)alkynyl is unsubstituted or substituted with one to four substituents independently selected from the group consisting of —(C=O)—O—(C$_1$–C$_8$)alkyl, —O—(C=O)—(C$_1$–C$_8$)alkyl, —(C=O)—(C$_1$–C$_8$)alkyl, R$^{40}$, R$^{41}$, and R$^{42}$}; or (i) R$^{37}$, —NH$_2$, —NH((C$_2$–C$_8$)alkenyl), —NH((C$_2$–C$_8$)alkynyl), —N((C$_1$–C$_8$)alkyl)((C$_2$–C$_8$)alkenyl), or —N((C$_1$–C$_8$)alkyl)((C$_2$–C$_8$)alkynyl) {wherein each of said R$^{26}$ (C$_2$–C$_8$)alkenyl or (C$_2$–C$_8$)alkynyl is unsubstituted or substituted with one to four substituents independently selected from the group consisting of R$^{40}$, R$^{41}$, and R$^{42}$};

R$^4$ is selected from the group consisting of H, F, Br, Cl, and (C$_1$–C$_8$)alkyl;

R$^8$ is selected from the group consisting of (C$_1$–C$_8$)alkyl, (C$_2$–C$_8$)alkenyl, (C$_2$–C$_8$)alkynyl, —NH$_2$, R$^{36}$, and R$^{37}$;

Each of $R^9$, $R^{10}$ and $R^{11}$ are independently selected from the group consisting of H, $(C_1-C_8)$alkyl, and $R^{36}$;

$R^{12}$ is selected from the group consisting of H, OH, $(C_1-C_8)$alkyl, $(C_1-C_8)$alkyl—O—, and $R^{36}$;

$R^{13}$ is H or $(C_1-C_8)$alkyl;

$R^{14}$ is selected from the group consisting of H, $(C_1-C_8)$alkyl, —$CH_2$—(C=O)—O—$(C_1-C_8)$alkyl, and $R^{36}$;

$R^{15}$ is H or $(C_1-C_8)$alkyl;

$R^{16}$ is selected from the group consisting of H, $(C_1-C_8)$alkyl, $(C_2-C_8)$alkenyl, $(C_2-C_8)$alkynyl, —$NH_2$, $R^{36}$, and $R^{37}$;

wherein said $R^{16}$ $(C_2-C_8)$alkenyl or $(C_2-C_8)$alkynyl is unsubstituted or substituted with one to four substituents independently selected from the group consisting of $R^{40}$;

$R^{17}$ is selected from the group consisting of H, $(C_1-C_8)$alkyl, and $R^{36}$;

$R^{18}$ is $(C_1-C_8)$alkyl or $R^{36}$;

$R^{19}$, $R^{20}$, and $R^{21}$ are independently selected from the group consisting of H, $(C_1-C_8)$alkyl, and $R^{36}$;

$R^{22}$, $R^{23}$ and $R^{24}$ are independently selected from the group consisting of H, $(C_1-C_8)$alkyl, and $R^{36}$;

$R^{25}$ is H or $(C_1-C_8)$alkyl;

$R^{26}$ is selected from the group consisting of —C(=O)—O—$C(CH_3)_3$, $(C_1-C_8)$alkyl, —$(CR^{13}R^{15})_t(C_3-C_{10})$cycloalkyl, —$(CR^{13}R^{15})_t(C_2-C_{10})$heterocyclyl, —$(CR^{13}R^{15})_t(C_6-C_{10})$aryl, and —$(CR^{13}R^{15})_t(C_1-C_{10})$heteroaryl; wherein t is an integer from 0 to 2;

or $R^{25}$ and $R^{26}$ may optionally be taken together with the nitrogen to which they are attached to form a 5 to 8-membered heteroaryl or heterocyclyl ring;

$R^{27}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{28}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{29}$ is H or $(C_1-C_8)$alkyl;

$R^{30}$ is $(C_1-C_8)$alkyl, $(C_3-C_{10})$cycloalkyl, $(C_2-C_{10})$heterocyclyl, $(C_6-C_{10})$aryl, or $(C_1-C_{10})$heteroaryl;

or $R^{29}$ and $R^{30}$ may optionally be taken together with the nitrogen to which they are attached to form a 5 to 8-membered heteroaryl or heterocyclyl ring;

$R^{31}$ is H or $(C_1-C_8)$alkyl;

$R^{32}$ is independently selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

or $R^{31}$ and $R^{32}$ may optionally be taken together with the nitrogen to which they are attached to form a 5 to 8-membered heteroaryl or heterocyclyl ring;

$R^{33}$ is $(C_1-C_8)$alkyl, —$(CR^{13}R^{15})_q(C_3-C_{10})$cycloalkyl, —$(CR^{13}R^{15})_q(C_2-C_{10})$heterocyclyl, —$(CR^{13}R^{15})_q(C_6-C_{10})$aryl, or —$(CR^{13}R^{15})_q(C_1-C_{10})$heteroaryl; wherein q is an integer from 0 to 2;

$R^{34}$ is $(C_1-C_8)$alkyl, —$(CR^{13}R^{15})_p(C_3-C_{10})$cycloalkyl, —$(CR^{13}R^{15})_p(C_2-C_{10})$heterocyclyl, —$(CR^{13}R^{15})_p(C_6-C_{10})$aryl, or —$(CR^{13}R^{15})_p(C_1-C_{10})$heteroaryl; wherein p is an integer from 0 to 2;

Each $R^{35}$ is independently selected from the group consisting of H, F, Cl, Br, I, CN, OH, $NO_2$, —$NH_2$, —NH—C(=O)—O—$C(CH_3)_3$, and $CF_3$;

Each $R^{36}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{37}$ is independently selected from the group consisting of —$NR^{25}R^{26}$ and $R^{27}$—O—;

$R^{38}$ is $R^{28}$—$SO_n$—; wherein n is 0, 1, or 2 when —$SO_n$— is bonded to $R^{28}$ via an $R^{28}$ carbon atom, or wherein n is 1 or 2 when —$SO_n$— is bonded to $R^{28}$ via an $R^{28}$ ring nitrogen atom;

$R^{39}$ is $R^{29}R^{30}$N—$SO_n$—; wherein n is 1 or 2;

wherein each of said $(C_1-C_8)$alkyl, wherever it occurs in any of said $R^1$(a)–(d), $R^2$(a)–(d), $R^3$(a)–(i), $R^4$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{37}$, $R^{38}$, and $R^{39}$ is unsubstituted or substituted with one to four substituents independently selected from the group consisting of $(C_2-C_8)$alkenyl and $R^{40}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in said $R^1$(b)–(d), $R^2$(b)–(d), $R^3$(a)–(i), $R^4$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$, $R^{32}$, $R^{33}$, $R^{34}$, $R^{36}$, $R^{37}$, $R^{38}$, and $R^{39}$ is independently unsubstituted or substituted with one to four substituents independently selected from $R^{40}$;

$R^{40}$ is selected from the group consisting of $(C_1-C_8)$alkyl, $R^{41}$, $R^{42}$, and $R^{43}$;

Each $R^{41}$ is independently selected from the group consisting of F, Cl, Br, I, CN, OH, $NO_2$, —$NH_2$, —NH—C(=O)—O—$C(CH_3)_3$, COOH, —C(=O)$(C_1-C_8)$alkyl, —C(=O)—O—$(C_1-C_8)$alkyl, —NH—$SO_2$—$(C_1-C_8)$alkyl, —NH—$SO_2$—$(C_6-C_{10})$aryl, and $CF_3$;

Each $R^{42}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{43}$ is independently selected from the group consisting of:

—$NR^{31}R^{32}$; $R^{33}$—O—; and $R^{34}$—$SO_n$—; wherein n is 0, 1, or 2 when —$SO_n$— is bonded to $R^{34}$ via an $R^{34}$ carbon atom, or wherein n is 1 or 2 when —$SO_n$— is bonded to $R^{34}$ via an $R^{34}$ ring nitrogen atom;

wherein each of said $(C_1-C_8)$alkyl, wherever it occurs in any of $R^{40}$ and $R^{41}$ is independently unsubstituted or substituted with one to four substituents independently selected from the group consisting of $R^{44}$ and $R^{45}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{42}$ or $R^{43}$, is independently unsubstituted or substituted with one to four substituents independently selected from the group consisting of $R^{47}$ selected from the group consisting of $(C_1-C_8)$alkyl, $R^{44}$, and $R^{45}$;

Each $R^{44}$ is independently selected from the group consisting of F, Cl, Br, I, CN, OH, $NO_2$, —$NH_2$, —$CF_3$, —C(=NH)—$NH_2$, —C(=NH)—NH—OH, —C(=NH)—NH—O—$(C_1-C_8)$alkyl, —(C=O)—O—$(C_1-C_8)$alkyl, —O—(C=O)—$(C_1-C_8)$alkyl, —(C=O)—$(C_1-C_8)$alkyl, —(C=O)—$NH_2$, —(C=O)—NH$(C_1-C_8)$alkyl, —(C=O)—N<$[(C_1-C_8)$alkyl$]_2$, —NH—(C=O)—$(C_1-C_8)$alkyl, $R^{37}$, and $R^{38}$;

Each $R^{45}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

wherein each of said $(C_1-C_8)$alkyl wherever it occurs in any of said $R^{44}$ or $R^{45}$ is independently unsubstituted or substituted with one to four substituents independently selected from the group consisting of $R^{46}$ and $R^{47}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{43}$ or $R^{44}$ is independently unsubstituted or substituted with one to four substituents independently selected from the group consisting of $(C_1-C_8)$alkyl, $R^{46}$ and $R^{47}$;

Each $R^{46}$ is independently selected from the group consisting of F, Cl, Br, I, CN, OH, $NO_2$, —C(=NH)—$NH_2$, —C(=NH)—NH—OH, —C(=NH)—NH—O—$(C_1-C_8)$alkyl, —(C=O)—O—$(C_1-C_8)$alkyl, —O—(C=O)—$(C_1-C_8)$alkyl, —(C=O)—$(C_1-C_8)$alkyl, —(C=O)—$NH_2$, —(C=O)—NH$(C_1-C_8)$alkyl, —(C=O)—N<[$(C_1-C_8)$alkyl]$_2$, —NH—(C=O)—$(C_1-C_8)$alkyl, —C(=NH)—$NH_2$, —C(=NH)—NH—OH, —C(=NH)—NH—O—$(C_1-C_8)$alkyl, —(C=O)—O—$(C_1-C_8)$alkyl, —O—(C=O)—$(C_1-C_8)$alkyl, —(C=O)—$(C_1-C_8)$alkyl, —(C=O)—$NH_2$, —(C=O)—NH$(C_1-C_8)$alkyl, —(C=O)—N>[$(C_1-C_8)$alkyl]$_2$, —NH—(C=O)—$(C_1-C_8)$alkyl, $R^{37}$, and $R^{38}$; and Each $R^{47}$ is independently selected from the group consisting of $(C_3-C_{10})$cycloalkyl; $(C_2-C_{10})$heterocyclyl, $(C_6-C_{10})$aryl, and $(C_1-C_{10})$heteroaryl;

or a pharmaceutically acceptable salt thereof.

37. A compound of formula I

I wherein:

X is =O or =S;

A is =CR$^1$— or =N—;

The group —Y—Z— has the formula —N=CH—;

$R^1$ is:

(a) $(C_1-C_8)$alkyl;
(b) —C(=O)—$R^5$;
(c) —C(=O)—NR$^6$R$^7$; or
(d) $R^{35}$, or $R^{36}$, $(C_2-C_8)$alkenyl, or $(C_2-C_8)$alkynyl {wherein each of said $(C_2-C_8)$alkenyl or $(C_2-C_8)$alkynyl is unsubstituted or substituted with one to four substituents independently selected from the group consisting of F, Cl, OH, —$NH_2$, $R^{40}$, and $R^{42}$};

$R^2$ is (a) H, OH, or $(C_1-C_8)$alkyl;
(b) —C(=O)—$R^8$;
(c) —(C=S)—$R^9$ or —(C=S)—NR$^{10}$R$^{11}$; or
(d) $R^{38}$ or $R^{39}$;

$R^3$ is (a) $R^{38}$;
(b) —C(=O)—$R^{12}$;
(c) —C(=O)—NR$^{13}$R$^{14}$;
(d) —NR$^{15}$—C(=O)—$R^{16}$;
(e) —NR$^{17}$—SO$_2$R$^{18}$;
(f) —NR$^{19}$—SO$_n$—NR$^{20}$R$^{21}$ {wherein n is 1 or 2};
(g) —NR$^{22}$—(C=S)—$R^{23}$ or —NR$^{22}$—(C=S)—NR$^{23}$R$^{24}$;
(h) $R^{36}$, $(C_2-C_8)$alkenyl, or $(C_2-C_8)$alkynyl {wherein each of said $R^3$ $(C_2-C_8)$alkenyl or $(C_2-C_8)$alkynyl is unsubstituted or substituted with one to four substituents independently selected from the group consisting of —(C=O)—O—$(C_1-C_8)$alkyl, —O—(C=O)—$(C_1-C_8)$alkyl, —(C=O)—$(C_1-C_8)$alkyl, $R^{40}$, $R^{41}$, and $R^{42}$}; or
(i) $R^{37}$, —$NH_2$, —NH(($C_2-C_8$)alkenyl), —NH(($C_2-C_8$)alkynyl), —N(($C_1-C_8$)alkyl)(($C_2-C_8$)alkenyl), or —N(($C_1-C_8$)alkyl)(($C_2-C_8$)alkynyl) {wherein each of said $R^{26}$ $(C_2-C_8)$alkenyl or $(C_2-C_8)$alkynyl is unsubstituted or substituted with one to four substituents independently selected from the group consisting of $R^{40}$, $R^{41}$, and $R^{42}$};

$R^4$ is selected from the group consisting of H, F, Br, Cl, and $(C_1-C_8)$alkyl;

$R^5$ is selected from the group consisting of H, $(C_1-C_8)$alkyl, $(C_1-C_8)$alkyl—O—, and $R^{36}$;

Each $R^6$ and $R^7$ are independently selected from the group consisting of H, $(C_1-C_8)$alkyl, and $R^{36}$;

$R^8$ is selected from the group consisting of $(C_1-C_8)$alkyl, $(C_2-C_8)$alkenyl, $(C_2-C_8)$alkynyl, —$NH_2$, $R^{36}$, and $R^{37}$;

Each of $R^9$, $R^{10}$ and $R^{11}$ are independently selected from the group consisting of H, $(C_1-C_8)$alkyl, and $R^{36}$;

$R^{12}$ is selected from the group consisting of H, OH, $(C_1-C_8)$alkyl, $(C_1-C_8)$alkyl—O—, and $R^{36}$;

$R^{13}$ is H or $(C_1-C_8)$alkyl;

$R^{14}$ is selected from the group consisting of H, $(C_1-C_8)$alkyl, —CH$_2$—(C=O)—O—$(C_1-C_8)$alkyl, and $R^{36}$;

$R^{15}$ is H or $(C_1-C_8)$alkyl;

$R^{16}$ is selected from the group consisting of H, $(C_1-C_8)$alkyl, $(C_2-C_8)$alkenyl, $(C_2-C_8)$alkynyl, —$NH_2$, $R^{36}$, and $R^{37}$;

wherein said $R^{16}$ $(C_2-C_8)$alkenyl or $(C_2-C_8)$alkynyl is unsubstituted or substituted with one to four substituents independently selected from the group consisting of $R^{40}$;

$R^{17}$ is selected from the group consisting of H, $(C_1-C_8)$alkyl, and $R^{36}$;

$R^{18}$ is $(C_1-C_8)$alkyl or $R^{36}$;

$R^{19}$, $R^{20}$, and $R^{21}$ are independently selected from the group consisting of H, $(C_1-C_8)$alkyl, and $R^{36}$;

$R^{22}$, $R^{23}$ and $R^{24}$ are independently selected from the group consisting of H, $(C_1-C_8)$alkyl, and $R^{36}$;

$R^{25}$ is H or $(C_1-C_8)$alkyl;

$R^{26}$ is selected from the group consisting of —C(=O)—O—C(CH$_3$)$_3$, $(C_1-C_8)$alkyl, —(CR$^{13}$R$^{15}$)$_t$($C_3-C_{10}$)cycloalkyl, —(CR$^{13}$R$^{15}$)$_t$($C_2-C_{10}$)heterocyclyl, —(CR$^{13}$R$^{15}$)$_t$($C_6-C_{10}$)aryl, and —(CR$^{13}$R$^{15}$)$_t$($C_1-C_{10}$)heteroaryl; wherein t is an integer from 0 to 2;

or $R^{25}$ and $R^{26}$ may optionally be taken together with the nitrogen to which they are attached to form a 5 to 8-membered heteroaryl or heterocyclyl ring;

$R^{27}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{28}$ is selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

$R^{29}$ is H or $(C_1-C_8)$alkyl;

$R^{30}$ is $(C_1-C_8)$alkyl, $(C_3-C_{10})$cycloalkyl, $(C_2-C_{10})$heterocyclyl, $(C_6-C_{10})$aryl, or $(C_1-C_{10})$heteroaryl;

or $R^{29}$ and $R^{30}$ may optionally be taken together with the nitrogen to which they are attached to form a 5 to 8-membered heteroaryl or heterocyclyl ring;

$R^{31}$ is H or $(C_1-C_8)$alkyl;

$R^{32}$ is independently selected from the group consisting of $(C_1-C_8)$alkyl, $(C_3-C_{10})$cycloalkyl, $(C_2-C_{10})$heterocyclyl, $(C_6-C_{10})$aryl, and $(C_1-C_{10})$heteroaryl;

or $R^{31}$ and $R^{32}$ may optionally be taken together with the nitrogen to which they are attached to form a 5 to 8-membered heteroaryl or heterocyclyl ring;

$R^{33}$ is $(C_1-C_8)$alkyl, $—(CR^{13}R^{15})_q(C_3-C_{10})$cycloalkyl, $—(CR^{13}R^{15})_q(C_2-C_{10})$heterocyclyl, $—(CR^{13}R^{15})_q(C_6-C_{10})$aryl, or $—(CR^{13}R^{15})_q(C_1-C_{10})$heteroaryl; wherein q is an integer from 0 to 2;

$R^{34}$ is $(C_1-C_8)$alkyl, $—(CR^{13}R^{15})_p(C_3-C_{10})$cycloalkyl, $—(CR^{13}R^{15})_p(C_2-C_{10})$heterocyclyl, $—(CR^{13}R^{15})_p(C_6-C_{10})$aryl, or $—(CR^{13}R^{15})_p(C_1-C_{10})$heteroaryl; wherein p is an integer from 0 to 2;

Each $R^{35}$ is independently selected from the group consisting of H, F, Cl, Br, I, CN, OH, $NO_2$, $—NH_2$, $—NH—C(=O)—O—C(CH_3)_3$, and $CF_3$;

Each $R^{36}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{37}$ is independently selected from the group consisting of $—NR^{25}R^{26}$ and $R^{27}—O—$;

$R^{38}$ is $R^{28}—SO_n—$; wherein n is 0, 1, or 2 when $—SO_n—$ is bonded to $R^{28}$ via an $R^{28}$ carbon atom, or wherein n is 1 or 2 when $—SO_n—$ is bonded to $R^{28}$ via an $R^{28}$ ring nitrogen atom;

$R^{39}$ is $R^{29}R^{30}N—SO_n—$; wherein n is 1 or 2;

wherein each of said $(C_1-C_8)$alkyl, wherever it occurs in any of said $R^1$(a)–(d), $R^2$(a)–(d), $R^3$(a)–(i), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{37}$, $R^{38}$, and $R^{39}$ is unsubstituted or substituted with one to four substituents independently selected from the group consisting of $(C_2-C_8)$alkenyl and $R^{40}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in said $R^1$(b)–(d), $R^2$(b)–(d), $R^3$(a)–(i), $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{30}$, $R^{32}$, $R^{33}$, $R^{34}$, $R^{36}$, $R^{37}$, $R^{38}$, and $R^{39}$ is independently unsubstituted or substituted with one to four substituents independently selected from $R^{40}$;

$R^{40}$ is selected from the group consisting of $(C_1-C_8)$alkyl, $R^{41}$, $R^{42}$, and $R^{43}$;

Each $R^{41}$ is independently selected from the group consisting of F, Cl, Br, I, CN, OH, $NO_2$, $—NH_2$, $—NH—C(=O)—O—C(CH_3)_3$, COOH, $—C(=O)(C_1-C_8)$alkyl, $—C(=O)—O—(C_1-C_8)$alkyl, $—NH—SO_2—(C_1-C_8)$alkyl, $—NH—SO_2—(C_6-C_{10})$aryl, and $CF_3$;

Each $R^{42}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

Each $R^{43}$ is independently selected from the group consisting of:

$—NR^{31}R^{32}$; $R^{33}—O—$; and $R^{34}—SO_n—$; wherein n is 0, 1, or 2 when $—SO_n—$ is bonded to $R^{34}$ via an $R^{34}$ carbon atom, or wherein n is 1 or 2 when $—SO_n—$ is bonded to $R^{34}$ via an $R^{34}$ ring nitrogen atom;

wherein each of said $(C_1-C_8)$alkyl, wherever it occurs in any of $R^{40}$ and $R^{41}$ is independently unsubstituted or substituted with one to four substituents independently selected from the group consisting of $R^{44}$ and $R^{45}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{42}$ or $R^{43}$, is independently unsubstituted or substituted with one to four substituents independently selected from the group consisting of $R^{47}$ selected from the group consisting of $(C_1-C_8)$alkyl, $R^{44}$, and $R^{45}$;

Each $R^{44}$ is independently selected from the group consisting of F, Cl, Br, I, CN, OH, $NO_2$, $—NH_2$, $—CF_3$, $—C(=NH)—NH_2$, $—C(=NH)—NH—OH$, $—C(=NH)—NH—O—(C_1-C_8)$alkyl, $—(C=O)—O—(C_1-C_8)$alkyl, $—O—(C=O)—(C_1-C_8)$alkyl, $—(C=O)—(C_1-C_8)$alkyl, $—(C=O)—NH_2$, $—(C=O)—NH(C_1-C_8)$alkyl, $—(C=O)—N<[(C_1-C_8)$alkyl$]_2$, $—NH—(C=O)—(C_1-C_8)$alkyl, $R^{37}$, and $R^{38}$;

Each $R^{45}$ is independently selected from the group consisting of $(C_3-C_{10})$cycloalkyl, $(C_2-C_{10})$heterocyclyl, $(C_6-C_{10})$aryl, and $(C_1-C_{10})$heteroaryl;

wherein each of said $(C_1-C_8)$alkyl wherever it occurs in any of said $R^{44}$ or $R^{45}$ is independently unsubstituted or substituted with one to four substituents independently selected from the group consisting of $R^{46}$ and $R^{47}$;

wherein each of said $(C_3-C_{10})$cycloalkyl, $(C_2-C_{10})$heterocyclyl, $(C_6-C_{10})$aryl, or $(C_1-C_{10})$heteroaryl, wherever it occurs in any of said $R^{43}$ or $R^{44}$ is independently unsubstituted or substituted with one to four substituents independently selected from the group consisting of $(C_1-C_8)$alkyl, $R^{46}$ and $R^{47}$;

Each $R^{46}$ is independently selected from the group consisting of F, Cl, Br, I, CN, OH, $NO_2$, $—C(=NH)—NH_2$, $—C(=NH)—NH—OH$, $—C(=NH)—NH—O—(C_1-C_8)$alkyl, $—(C=O)—O—(C_1-C_8)$alkyl, $—O—(C=O)—(C_1-C_8)$alkyl, $—(C=O)—(C_1-C_8)$alkyl, $—(C=O)—NH_2$, $—(C=O)—NH(C_1-C_8)$alkyl, $—(C=O)—N<[(C_1-C_8)$alkyl$]_2$, $—NH—(C=O)—(C_1-C_8)$alkyl, $—C(=NH)—NH_2$, $—C(=NH)—NH—OH$, $—C(=NH)—NH—O—(C_1-C_8)$alkyl, $—(C=O)—O—(C_1-C_8)$alkyl, $—O—(C=O)—(C_1-C_8)$alkyl, $—(C=O)—(C_1-C_8)$alkyl, $—(C=O)—NH_2$, $—(C=O)—NH(C_1-C_8)$alkyl, $—(C=O)—N>[(C_1-C_8)$alkyl$]_2$, $—NH—(C=O)—(C_1-C_8)$alkyl, $R^{37}$, and $R^{38}$; and Each $R^{47}$ is independently selected from the group consisting of $(C_3-C_{10})$cycloalkyl; $(C_2-C_{10})$heterocyclyl, $(C_6-C_{10})$aryl, and $(C_1-C_{10})$heteroaryl;

or a pharmaceutically acceptable salt thereof.

* * * * *